United States Patent
Trzoss et al.

(10) Patent No.: US 12,139,479 B2
(45) Date of Patent: *Nov. 12, 2024

(54) HETEROCYCLE SUBSTITUTED PYRIDINE DERIVATIVE ANTIFUNGAL AGENTS

(71) Applicant: Basilea Pharmaceutica International AG, Allschwil, Allschwil (CH)

(72) Inventors: Michael Trzoss, San Diego, CA (US); Jonathan Covel, San Diego, CA (US); Karen Joy Shaw, Poway, CA (US); Peter Webb, San Diego, CA (US)

(73) Assignee: Basilea Pharmaceutica International AG, Allschwil, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,629

(22) Filed: Sep. 23, 2022

(65) Prior Publication Data

US 2023/0065881 A1    Mar. 2, 2023

Related U.S. Application Data

(63) Continuation of application No. 16/770,476, filed as application No. PCT/US2018/064609 on Dec. 7, 2018, now Pat. No. 11,512,079.

(60) Provisional application No. 62/649,225, filed on Mar. 28, 2018, provisional application No. 62/595,894, filed on Dec. 7, 2017.

(51) Int. Cl.
| | |
|---|---|
| *C07D 413/14* | (2006.01) |
| *A61P 31/10* | (2006.01) |
| *C07D 401/14* | (2006.01) |
| *C07D 413/04* | (2006.01) |
| *C07D 417/14* | (2006.01) |
| *C07D 471/04* | (2006.01) |
| *C07F 9/6558* | (2006.01) |

(52) U.S. Cl.
CPC ............ *C07D 413/14* (2013.01); *A61P 31/10* (2018.01); *C07D 401/14* (2013.01); *C07D 413/04* (2013.01); *C07D 417/14* (2013.01); *C07D 471/04* (2013.01); *C07F 9/65583* (2013.01)

(58) Field of Classification Search
CPC .. C07D 413/14; C07D 413/04; C07D 401/14; C07D 417/14; C07D 471/04; A61P 31/10; C07F 9/65583
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,340,690 B1 | 1/2002 | Bachand et al. |
| 7,691,882 B2* | 4/2010 | Tanaka ..................... A61P 31/00 546/256 |
| 8,058,444 B2 | 11/2011 | Niijima et al. |
| 8,153,662 B2* | 4/2012 | Tanaka ................. C07D 401/04 546/256 |
| 8,158,657 B2 | 4/2012 | Tanaka et al. |
| 8,188,119 B2 | 5/2012 | Tanaka |
| 8,507,530 B2 | 8/2013 | Tanaka et al. |
| 8,513,287 B2 | 8/2013 | Masukura |
| 8,841,327 B2* | 9/2014 | Tanaka ................. C07D 401/04 546/275.4 |
| 11,512,079 B2* | 11/2022 | Trzoss ................. C07D 417/14 |
| 2003/0045554 A1 | 3/2003 | Sankaranarayanan |
| 2006/0247237 A1 | 11/2006 | Freyne et al. |
| 2007/0105904 A1 | 5/2007 | Tanaka et al. |
| 2009/0082403 A1 | 3/2009 | Tanaka et al. |
| 2009/0233883 A1 | 9/2009 | Matsukura |
| 2010/0004235 A1 | 1/2010 | Schirok et al. |
| 2010/0168173 A1 | 7/2010 | Tanaka et al. |
| 2010/0331282 A1 | 12/2010 | Matsukura |
| 2011/0201649 A1 | 8/2011 | Matsuzaki |
| 2011/0263845 A1 | 10/2011 | Niijima et al. |
| 2012/0029023 A1 | 2/2012 | Tanaka et al. |

FOREIGN PATENT DOCUMENTS

| | | |
|---|---|---|
| WO | 2011051198 A2 | 5/2011 |
| WO | 2019113542 | 6/2019 |
| WO | 2020005860 | 1/2020 |
| WO | 2020247804 | 12/2020 |

OTHER PUBLICATIONS

Trzoss, Bioorganic & Med Chem Lett, vol. 29, 2019, 12613, pp. 1-5. (Year: 2019).*
Viriyakosol, Antimicobial Agents and CHemotherapy, Experimetal Therapeutics, Feb. 2019, vol. 63(2), e01715-18, pp. 1-14. (Year: 2019).*
Tanaka, Chem Lett, 2010, vol. 39, 1033-1035. (Year: 2010).*
Miyazaki, Am Soc for Microbiology, Antimicrobial Agents and Chemotherapy, vol. 55(10), Oct. 2011, 4652-4658. (Year: 2011).*
Hata, Am Soc for Micribio, Antimicrobial Agents and Chemotherapy, vol. 55 (10), Oct. 2011, 4543-4551. (Year: 2011).*
Trzoss, Bioorg & Med Chem Lett, vol. 29, 2019, 12613, pp. 1-5. (Year: 2019).*
Viriyakosol, Antimicrobial Agents and Chemotherapy, Experimental Therapeutics, Feb. 2019, vol. 63(2), e01715-18. (Year: 2019).*
PCT/US2020/036400 International Search Report and Written Opinion dated Sep. 23, 2020.
Al-Muhammed et al. In-vivo studies on dexamethasone sodium phosphate liposomes. J Microencapsul 13(3):293-306 (1996).
Berge et al. Pharmaceutical Salts. Journal of Pharmaceutical Sciences 66(1):1-19(Jan. 1977).

(Continued)

*Primary Examiner* — D Margaret M Seaman

(57) ABSTRACT

Described herein are heterocycle substituted pyridine derivative antifungal agents and pharmaceutical compositions comprising said compounds. The subject compounds and compositions are useful for the treatment of fungal diseases and infections.

8 Claims, 3 Drawing Sheets

(56) References Cited

OTHER PUBLICATIONS

Chonn et al. Recent Advances in liposomal drug-delivery systems. Curr Opin Biotechnol. 6(6):698-709(1995).
Covel et al. Chapter 12: The Discovery of Manogepix/ Fosmanogepix and Other GWT1 Inhibitors for the Treatment of Invasive Fungal Infections. 2019 Medicinal Chemistry Reviews vol. 54 (18 pgs).
Eyles et al. Oral delivery and fate of poly(lactic acid) microsphere-encapsulated interferon in rats. J Pharm Pharmacol. 49(7):669-74 (1997).
Gao et al. Controlled release of a contraceptive steroid from biodegradable and injectable gel formulations: in vitro evaluation. Pharm Res 12(6):857-63 (1995).
Gebremariam et al. galactomannan Is a Biomarker of Fosmanogepix (APX001) Efficacy in Treating Experimental Invasive Pulmonary Aspergillosis. Antimicrob Agents Chemother 64(1):e10966-19 (2019).
Hata, Antimicrobial Agents and Chemotherapy, Oct. 2011, vol. 55(10), p. 4543-4551 (2011).
Kapoor et al. Evaluation of Resistance Development to the Gwt1 Inhibitor Manogepix (APX001A) in *Candida* Species. Antimicrob Agents Chemother 64(1):e01387-19 (2019).
McGuigan et al. Application of phosphoramidate pronucleotide technology to abacavir leads to a significant enhancement of anti-viral potency. J. Med. Chem. 48:3504-3515 (2005).
Ostro et al. Use of Liposomes as Injectable-Drug Delivery Systems. Am J Hosp Pharm 56(8):1576-1587 (Aug. 1989).
PCT/US2019/038780 International Search Report and Written Opinion dated Nov. 21, 2019.
PCT/US2019/038780 Invitation to Pay Additional Fees dated Sep. 23, 2019.
PubChem CID 68452548 Entry for [3-[3-[[4-(Pyridin-2-yloxymethyl)phenyl]methyl]-1,2-oxazol-5-yl]pyridin-2-yl]carbamic acid; https://pubchem.ncbi.nlm.nih.gov/compound/ 68452548 Entry created Nov. 30, 2012.
Rao. Recent developments of collagen-based materials for medical applications and drug delivery systems. J Biomater Sci Polym Ed. 7(7):623-45 (1995).
Shaw et al. Fosmanogepix: A Review of the First-in-Class Broad Spectrum Agent for the Treatment of Invasive Fungal Infections. J Fungi (Basel) 6(4):239 (2020).
Silverman. Chapter 8. Prodrugs and Drug Delivery Systems. The Organic Chemistry of Drug Design and Drug Action, Academic Press, Inc., San Diego (pp. 352-401) (1992).
Tanaka. Chem Lett, 2010, vol. 39, p. 1033-1035 (2010).
Thomas et al. Synthesis and biological evaluation of glucuronide prodrugs of the histone deacetylase inhibitor CI-994 for application in selective cancer chemotherapy. Bioorg. Med. Chem. 16:8109-16 (2018).
Trzoss et al. Synthesis of analogs of the Gwt1 inhibitor manogepix (APX001A) and in vitro evaluation against *Cryptococcus* spp. Bioorg Med Chem Lett 29(23):126713 (2019).
Arendrup et al. APX001A In Vitro Activity against Contemporary Blood Isolates and Candida auris Determined by the EUCAST Reference Method. Antimicrob Agents Chemother 62(10):e01225-18 (2018).
Berkow et al. Activity of novel antifungal compound APX001A against a large collection of Candida auris. J Antimicrob Chemother 73(11):3060-3062 (2018).
Bundgard, H. Design of Prodrugs. 1985; pp. 7-9, 21-24 (Elsevier, Amsterdam).
Gebremariam et al. APX001 is Effective in the Treatment of Murine Invasive Pulmonary Aspergillosis. Antimicrob Agents Chemother 63(2):e01713-18 (2019).
Hager et al. In Vitro and In Vivo Evaluation of the Antifungal Activity of APX001A/APX001 against Candida Auris. Antimicrob Agents Chemother 62(3):e02319-17 (2018).
Hata et al. Efficacy of Oral E1210, a New Broad-Spectrum Antifungal with a Novel Mechanism of Action, In Murine Models of Candidiasis, Aspergillosis, and Fusariosis. Antimicrob Agents Chemother 55(1):4543-4551 (2011).
Miyazaki et al. In Vitro Activity of E1210, A Novel Antifungal, against Clinically Important Yeasts and Molds. Antimicrob Agents Chemother 55(10):4652-4658 (2011).
PCT/US2018/064609 International Preliminary Report on Patentability dated Jul. 9, 2020.
PCT/US2018/064609 Invitation to Pay Additional Fees dated Jan. 16, 2019.
PCT/US2018/064609 International Search Report and Written Opinion dated Mar. 14, 2019.
Pfaller et al. In Vitro Activity of a Novel Broad-Spectrum Antifungal, E1210, Tested against Aspergillus spp. Determined by CLSI and EUCAST Broth Microdilution Methods. Antimicrob Agents Chemother 55(11):5155-8 (2011).
Pfaller et al. In Vitro Activity of APX001A (Manogepix) and Comparator Agents against 1,706 Fungal Isolates Collected during an International Surveillance Program in 2017. Antimicrob Agents Chemother 63(8):e00840-19 (2019).
Rivero-Menendez et al. In vitro activity of APX001A against rare moulds using EUCAST and CLSI methodologies. J Antimicrob Chemother 74(5):1295-1299 (2019).
Shaw et al. In Vitro and In Vivo Evaluation of APX001A/APX001 and Other Gwt1 Inhibitors against Cryptococcus. Antimicrob Agents Chemother 62(8):e00523-18 (2018).
Viriyakosol et al. APX001 and Other Gwt1 Inhibitor Prodrugs Are Effective in Experimental Coccidioides immitis Pneumonia. Antimicrob Agents Chemother 63(2):e 10715-18 (2019).
Watanabe et al. E1210, a new broad-spectrum antifungal, suppresses Candida albicans hyphal growth through inhibition of glycosylphosphatidylinositol biosynthesis. Antimicrob Agents Chemother 56(2):960-971 (2012).
Wiederhold et al. Efficacy of Delayed Therapy with Fosmanogepix (APX001) in a Murine Model of Candida auris Invasive candidiasis. Antimicrob Agents Chemother 63(11):e01120-19 (2019).
Wiederhold et al. The Investigational Agent E1210 is Effective in Treatment of Experimental Invasive Candidiasis Caused by Resistant Candida albicans. Antimicrob Agents Chemother 59(1):690-692 (2015).
Zhao et al. APX001 Pharmacokinetic/Pharmacodynamic Target Determination against Aspergillus fumigatus in an In Vivo Model of Invasive Pulmonary Aspergillosis. Antimicrob Agents Chemother 63(4):e02372-18 (2019).
Zhao et al. In Vivo Pharmacokinetics and Pharmacodynamics of APX001 against *Candida* spp. in a Netropenic Cisseminated Candidiasis Mouse Model. Antimicrob Agents Chemother 62(4):e02542-17 (2019).
Zhao et al. Significantly Improved Pharmacokinetics Enhances In Vivo Efficacy of APX001 against Echinocandin- and Multidrug-Resistant Candida Isolates in a Mouse Model of Invasive Candidiasis. Antimicrob Agents Chemother 62(10):e00425-18 (2018).

* cited by examiner

HETEROCYCLE SUBSTITUTED PYRIDINE DERIVATIVE ANTIFUNGAL AGENTS

CROSS REFERENCE TO RELATED APPLICATIONS

This application is a continuation of U.S. application Ser. No. 16/770,476, filed Jun. 5, 2020, which is the National Stage Entry of International Application No. PCT/US2018/064609, filed on Dec. 7, 2018, which claims the benefit of U.S. Provisional Application No. 62/595,894, filed Dec. 7, 2017, and U.S. Provisional Application No. 62/649,225, filed Mar. 28, 2018; the disclosure of each of the prior applications is considered part of and is incorporated by reference in the disclosure of this application.

BACKGROUND

A need exists in the art for an effective treatment of fungal diseases.

BRIEF SUMMARY OF THE INVENTION

Provided herein are compounds of Formula (I), (Ia), (II), (IIa), (IIb), (IIc), (II'), (II"), (III), (IIIa), or (III-B) or a pharmaceutically acceptable salt, solvate, hydrate tautomer, a stereoisomer, mixture of stereoisomers, or an isotopic variant thereof, and pharmaceutical compositions comprising said compounds. The subject compounds and compositions are useful for treating fungal diseases. Furthermore, the subject compounds and compositions are useful for the treatment of cryptococcosis.

Provided herein are compounds having the structure of Formula (III), or a pharmaceutically acceptable salt, solvate, hydrate, tautomer, a stereoisomer mixture of stereoisomers, or an isotopic variant thereof:

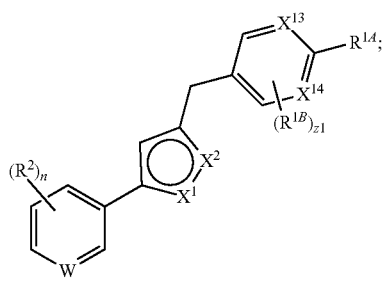

Formula (III)

wherein:

$R^{1A}$ is —OH, substituted or unsubstituted $C_{1-6}$alkyl, —$(CH_2)_2S(CH_{23})_2OC(O)H$, —$X^{15}$-L-C≡N, -L-$X^{15}$—$(CH_2)_{x2}$C≡N, —$X^{15}$-L-CH=$CR^{20}R^{30}$,

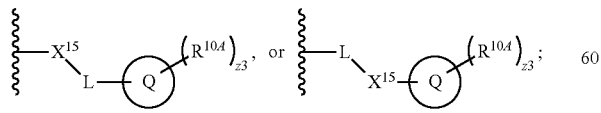

one of $X^1$ and $X^2$ is N while the other is O;
$X^{13}$ and $X^{14}$ are independently N or $C(R^{1B})$;
$X^{15}$ is a bond, —NH—, —O—, —S—, or —$SO_2$—;
L is a bond or substituted or unsubstituted $C_{1-6}$alkylene;
W is N or $N^+$—$OPO_3H^-$;
Ring Q is cycloalkyl, heterocycloalky, aryl, or heteroaryl;
each $R^2$ is independently hydrogen, —$NH_2$, or halogen;
each $R^{1B}$ and $R^{10A}$ is independently hydrogen, halogen, —$CF_3$, —CN, —$CH_2$—OH, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O)$NR^cR^d$, —$NR^aC$(=O)$R^b$, —$NR^aC$(=O)$OR^a$, substituted or unsubstituted $C_{1-6}$ alkyl, substituted or unsubstituted, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^{29}$ and $R^{30}$ are independently hydrogen, halogen, substituted or unsubstituted $C_{1-6}$ alkyl, substituted or unsubstituted aryl, substituted or unsubstituted heteroaryl, substituted or unsubstituted cycloalkyl, or substituted or unsubstituted heterocycloalkyl;
$R^a$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^b$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^c$ and $R^d$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
n is 0-3;
z1 is 0-2;
z2 is 0-3; and
z3 is 1-3.

In some embodiments of a compound of Formula (III), if $R^{1A}$ is

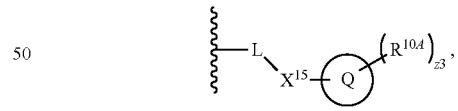

$R^2$ is —$NH_2$, Ring Q is 2-pyridinyl, L is methylene, $R^{10A}$ is hydrogen, $X^1$ is O, $X^2$ is N, $X^{13}$ is CH, $X^{14}$ is CH, n is 1, and Z1 is 0, then $X^{15}$ is a bond, —NH—, —S—, or —$SO_2$—.

In some embodiments of a compound of Formula (III), if $R^{1A}$ is

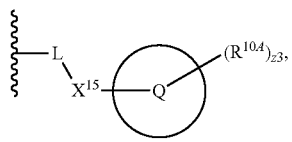

$R^2$ is 2-amino, Ring Q is 2-pyridinyl, L is methylene, $R^{10A}$ is hydrogen, $X^1$ is O, $X^2$ is N, $X^{13}$ is CH, $X^{14}$ is CH, n is 1, and Z1 is 0, then $X^{15}$ is a bond, —NH—, —S—, or —SO$_2$—.

In some embodiments, the compound of Formula (III) is of Formula (IIIa), or a pharmaceutically acceptable salt, solvate, hydrate, tautomer, a stereoisomer, mixture of stereoisomers, or an isotopic variant thereof:

Formula (IIIa)

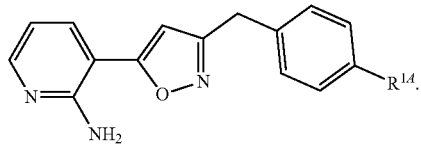

Provided herein are compounds having the structure of Formula (II), or a pharmaceutically acceptable salt, solvate, or stereoisomer thereof:

Formula (II)

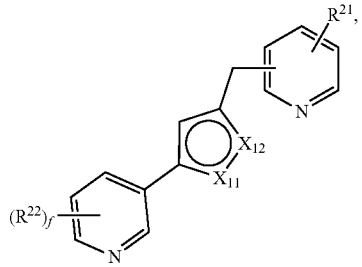

wherein:

$R^{23}$ is halogen

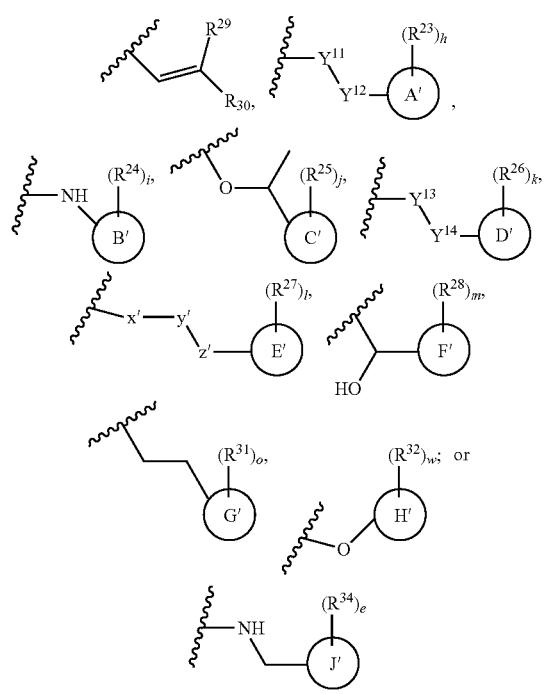

one of $X_{11}$ and $X_{12}$ is N while the other is O;
one or $Y^{11}$ and $Y^{12}$ is —NH— or —O— while the other is —CH$_2$—;
one of $Y^{13}$ and $Y^{14}$ is —S— while the other is —CH$_2$—;
one of x'y' and z' is —O— while the others are —CH$_2$—;
Ring A' is heteroaryl, cycloalkyl, or heterocycloalkyl;
Ring B' is aryl, heteroaryl, cycloalkyl, or heterocycloalkyl;
Ring C' is aryl, heteroaryl, cycloalkyl, or heterocycloalkyl;
Ring D' is aryl, heteroaryl, cycloalkyl, or heterocycloalkyl;
Ring E' is aryl, heteroaryl, cycloalkyl, or heterocycloalkyl;
Ring F' is aryl, heteroaryl, cycloalkyl, or heterocycloalkyl;
Ring G' is aryl, heteroaryl, cycloalkyl, or heterocycloalkyl;
Ring H' is bicyclic aryl, heteroaryl, cycloalkyl, or heterocycloalkyl;
Ring J' is aryl;
$R^{22}$ is hydrogen, —NH$_2$, or halogen;
$R^{29}$ and $R^{30}$ are independently hydrogen, halogen, C$_{1-6}$ alkyl, aryl, heteroaryl, cycloalkyl, heterocycloalkyl;
each $R^{23}$, $R^{24}$, $R^{25}$, $R^{26}$, $R^{27}$, $R^{28}$, $R^{31}$, and $R^{32}$ is independently hydrogen, halogen, —CF$_3$, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^a$ is hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^b$ is substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{1-6}$ heteroalkyl, substituted or unsubstituted cycloalkyl, substituted or unsubstituted heterocycloalkyl, substituted or unsubstituted aryl, or substituted or unsubstituted heteroaryl;
each R$^c$ and R$^d$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{1-6}$ heteroalkyl, substituted or unsubstituted cycloalkyl, substituted or unsubstituted heterocycloalkyl, substituted or unsubstituted aryl, or substituted or unsubstituted heteroaryl;
or R$^c$ or R$^d$, together with the nitrogen atom to which they are attached, form an substituted or unsubstituted heterocycloalkyl or substituted or unsubstituted heteroaryl;
f is 1;
h is 1-3;
i is 1-3;
j is 1-3;
k is 1-3;
l is 1-3;

m is 1-3;
o is 1-3;
w is 1-3; and
e is 1-3.

In some embodiments provided herein are compounds compound having the structure of Formula (II') or Formula (II'') or a pharmaceutically acceptable salt, solvate, or stereoisomer thereof.

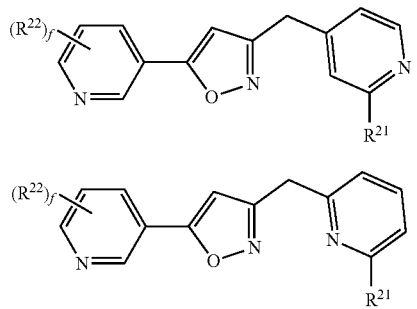

Formula (II')

Formula (II'')

wherein:
$R^{21}$ is halogen,

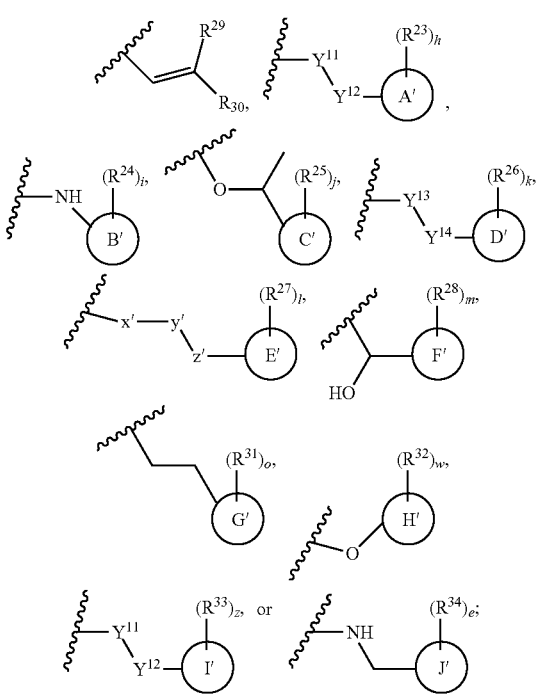

one of $X_{11}$ and $X_{12}$ is N while the other is O;
one or $Y^{11}$ and $Y^{12}$ is —NH— or —O— while the other is —CH$_2$—;
one of $Y^{13}$ and $Y^{14}$ is —S— while the other is —CH$_2$—;
one of x'y' and z' is —O— while the others are —CH$_2$—;
Ring A' is heteroaryl, cycloalkyl, or heterocycloalkyl;
Ring B' is aryl, heteroaryl, cycloalkyl, or heterocycloalkyl;
Ring C' is aryl, heteroaryl, cycloalkyl, or heterocycloalkyl;
Ring D' is aryl, heteroaryl, cycloalkyl, or heterocycloalkyl;

Ring E' is aryl, heteroaryl, cycloalkyl, or heterocycloalkyl;
Ring F' is aryl, heteroaryl, cycloalkyl, or heterocycloalkyl;
Ring G' is aryl, heteroaryl, cycloalkyl, or heterocycloalkyl;
Ring H' is bicyclic aryl, heteroaryl, cycloalkyl, or heterocycloalkyl;
Ring I' is aryl,
Ring J' is aryl,
$R^{22}$ is hydrogen, —NH$_2$, or halogen;
$R^{29}$ and $R^{30}$ are independently hydrogen, halogen, $C_{1-6}$ alkyl, aryl, heteroaryl, cycloalkyl, heterocycloalkyl;
each $R^{23}$, $R^{24}$, $R^{25}$, $R^{26}$, $R^{27}$, $R^{28}$, $R^{31}$, $R^{32}$, $R^{33}$, $R^{34}$ is independently hydrogen, halogen, —CF$_3$, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^a$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^b$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
each $R^c$ and $R^d$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
or $R^c$ and $R^d$, together with the nitrogen atom to which they are attached, form an substituted or unsubstituted heterocycloalkyl or substituted or unsubstituted heteroaryl;
f is 1;
h is 1-3;
i is 1-3;
j is 1-3;
k is 1-3;
l is 1-3;
m is 1-3;
o is 1-3;
w is 1-3;
z is 1-3; and
e is 1-3.

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIa):

Formula (IIa)

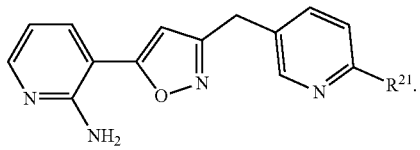

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIb):

Formula (IIb)

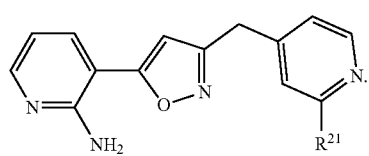

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIc):

Formula (IIc)

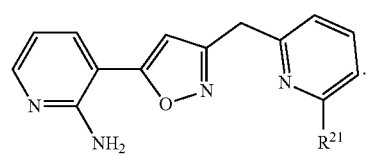

DETAILED DESCRIPTION OF THE INVENTION

Figure 1:
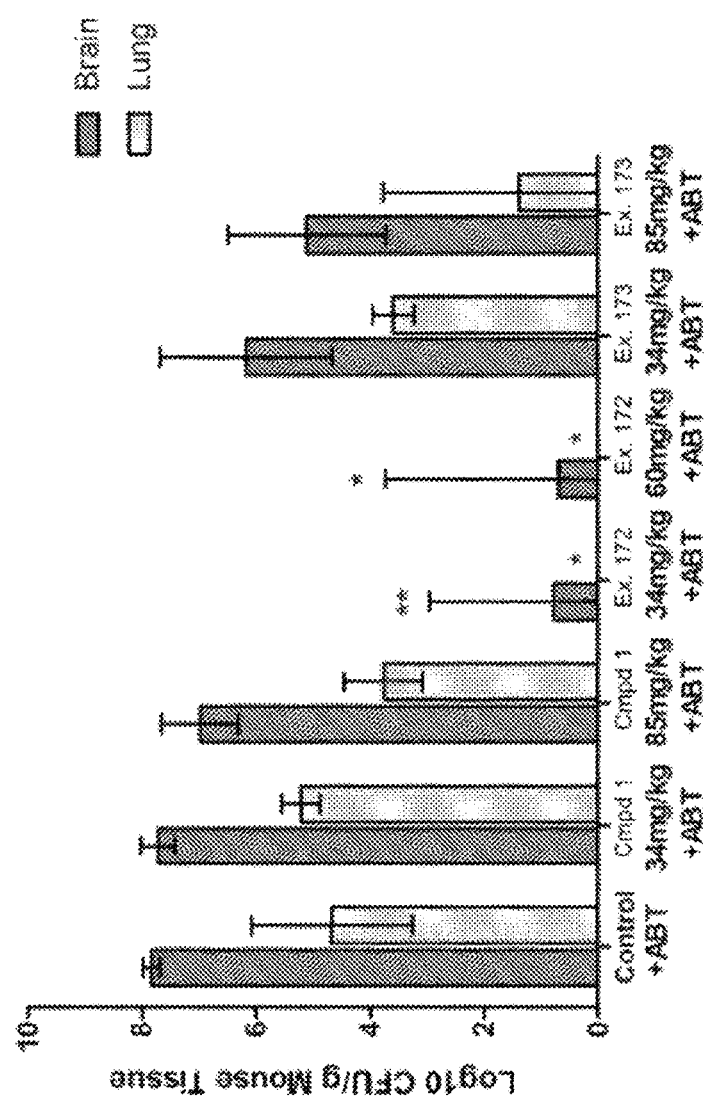
FIG. 1 shows the efficacy of certain compounds of the present disclosure in a murine model of cryptococcal meningitis when dosed in the presence of the pan-CYP inhibitor 1-aminobenzotriazole (ABT).

The incidence of fungal infections has increased over the last few decades. Such infections have risen in the last few decades in part due to an increase in individuals that are immunocompromised. Immunocompromised individuals, include, for example, elderly individuals, individuals with HIV/AIDS, or individuals undergoing chemotherapy treatment or immunosuppressive therapy after a transplant.

Current antifungal therapies exploit differences between mammalian cells and fungal cells to kill the fungi. However, because fungi and mammals are both eukaryotes, many antifungal therapies cause side effects in the host mammal. Additionally, many fungal organisms have developed resistance to front line antifungal treatments. Thus, there exists a need for new compositions and methods for treating fungal diseases.

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to an substituted or unsubstituted straight-chain, or substituted or unsubstituted branched-chain saturated hydrocarbon monoradical having from one to about ten carbon atoms, or from one to six carbon atoms, wherein a sp3-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, test-amyl and hexyl, and longer alkyl groups, such as heptyl, octyl, and the like. Whenever it appears herein, a numerical range such as "$C_1$-$C_6$alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or amethyl. Unless stated otherwise specifically in the specification, an alkyl group is substituted or unsubstituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is substituted or unsubstituted with oxo, halogen, —CN, —$CF_3$, —OH, —OMe, —$NH_2$, or —$NO_2$.

In some embodiments, the alkyl is substituted or unsubstituted with oxo, halogen, —CN, —CF$_3$, —OH, or —OMe.

"Alkenyl" refers to a7 substituted or unsubstituted straight-chain, or substituted or unsubstituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the doable bond(s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein a numerical range such as "C$_2$-C$_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a C$_2$-C$_{10}$ alkenyl, a C$_2$-C$_9$ alkenyl, a C$_2$-C$_8$ alkenyl, a C$_2$-C$_7$ alkenyl, a C$_2$-C$_6$ alkenyl, a C$_2$-C$_5$ alkenyl, a C$_2$-C$_4$ alkenyl, a C$_2$-C$_3$ alkenyl, or a C$_2$ alkenyl. Unless stated otherwise specifically in the specification, an alkenyl group is substituted or unsubstituted as described below, for example, with oxo, halogen, amino, nitrite, nitro, hydroxyl, haloalkyl, alkoxy, aryl, cycloalkyl, heterocycloalkyl, heteroaryl, and the like. In some embodiments, an alkenyl is substituted or unsubstituted with oxo, halogen, —CN, —CF$_3$, —OH, —OMe, —NH$_2$, or —NO$_2$. In some embodiments, an alkenyl is substituted or unsubstituted with oxo, halogen, —CN, —CF$_3$, —OH, or —OMe.

"Alkynyl" refers to a substituted or unsubstituted straight-chain or substituted or unsubstituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a C$_2$-C$_{10}$ alkynyl, a C$_2$-C$_9$ alkynyl, C$_2$-C$_8$ alkynyl, C$_2$-C$_7$ alkynyl, a C$_2$-C$_6$ alkynyl, C$_2$-C$_5$ alkynyl, a C$_2$-C$_4$ alkynyl, a C$_2$-C$_3$ alkynyl, or a C$_2$ alkynyl. Unless stated otherwise specifically in the specification, an alkynyl group is substituted or unsubstituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is substituted or unsubstituted with oxo, halogen, —CN, —CF$_3$, —OH, —OMe, —NH$_2$, or —NO$_2$. In some embodiments, an alkynyl is substituted or unsubstituted with oxo, halogen, —CN, —CF$_3$, —OH, or —OMe.

"Alkylene" refers to a straight or branched divalent hydrocarbon chain. Unless stated otherwise specifically in the specification, an alkylene group may be substituted or unsubstituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is substituted or unsubstituted with oxo, halogen, —CN, —CF$_3$, —OH, —OMe, —NH$_2$, or —NO$_2$. In some embodiments, an alkylene is substituted or unsubstituted with oxo, halogen, —CN, —CF$_3$, —OH, or —OMe.

"Alkoxy" refers to a radical of the formula —OR$_a$ where R$_a$ is an alkyl radical as defined. Unless stated otherwise specifically in the specification, an alkoxy group may be substituted or unsubstituted as described below, for example, with oxo, halogen, amino, nitrite, nitro, hydroxyl, haloalkyl, alkoxy, aryl, cycloalkyl, heterocycloalkyl, heteroaryl, and the like. In some embodiments, an alkoxy is substituted or unsubstituted with oxo, halogen, —CN, —CF$_3$, —OH, —OMe, —NH$_2$, or —NO$_2$. In some embodiments, an alkoxy is substituted or unsubstituted with oxo, halogen, —CN, —CF$_3$, —OH, or —OMe.

"Aryl" refers to a radical derived from a hydrocarbon ring system comprising hydrogen, 6 to 30 carbon atoms and at least one aromatic ring. the aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be substituted or unsubstituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is substituted or unsubstituted with halogen, methyl, ethyl, —CN, —CF$_3$, —OH, —OMe, —NH$_2$, or —NO$_2$. In some embodiments, an aryl is substituted or unsubstituted with halogen, methyl, ethyl, —CN, —CF$_3$, —OH, or —OMe.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cylcoalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is substituted or unsubstituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is substituted or unsubstituted with oxo, halogen, methyl, ethyl, —CN, —CF$_3$, —OH, —OMe, —NH$_2$, or —NO$_2$. In some embodiments, a cycloalkyl is substituted or unsubstituted with oxo, halogen, methyl, ethyl, —CN, —CF$_3$, —OH, or —OMe.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, 1,1-dioxo-thiomorpholinyl, 1,3-dihydroisobenzofuran-1-yl, 3-oxo-1,3-dihydroisobenzouran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalky (i.e. skeletal atoms of the heterocycloalkyl ring). Unless stated otherwise specifically in the specification, a heterocycloalkyl is substituted or unsubstituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is substituted or unsubstituted with oxo, halogen, methyl, ethyl, —CN, —CF$_3$, —OH, —OMe, —NH$_2$, or —NO$_2$. In some embodiments, a heterocycloalkyl is substituted or unsubstituted with oxo, halogen, methyl, ethyl, —CN, —CF$_3$, —OH, or —OMe.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl. Unless stated otherwise specifically in the specification, a Heteroalkyl is substituted or unsubstituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is substituted or unsubstituted with oxo, halogen, methyl, ethyl, —CN, —CF$_3$, —OH, —OMe, —NH$_2$, or —NO$_2$. In some embodiments a heteroalkyl is substituted or unsubstituted with oxo, halogen, methyl, ethyl, —CN, —CF$_3$, —OH, or —OMe.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]-imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadizolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is substituted or unsubstituted as described below, for example, with halogen, amino nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is substituted or unsubstituted with halogen, methyl, ethyl, —CN, —CF$_3$, —OH, —OMe, —NH$_2$, or —NO$_2$. In some embodiments, a heteroaryl is substituted or unsubstituted with halogen, methyl, ethyl, —CN, —CF$_3$, —OH, or —OMe.

All the above groups may be either substituted or unsubstituted. The term "substituted" as used herein means any of the above groups (e.g., alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl, or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups, and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be substituted or unsubstituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "substituted or unsubstituted alkyl" means either "alkyl" or "substituted alkyl" as defined above. Further, a substituted or unsubstituted group may be unsubstituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes substituted or unsubstituted cycloalkyl groups, which in turn are defined as including substituted or unsubstituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The terms "inhibit," "block," "suppress," and grammatical variants thereof are used interchangeably herein and refer to any statistically significant decrease in biological activity, including full blocking of the activity. In some embodiments, "inhibition" refers to a decrease of about 10%, about 20%, about 30%, about 40%, about 50%, about 60%, about 70%, about 80%, about 90% or about 100% in biological activity.

As used herein "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptom of a disease, even though a diagnosis of this disease has not been made.

Compounds

Described herein are compounds of Formula (I), (Ia), (II), (IIa), (IIb), (IIc), (II'), (II''), (III), (IIIa), and (III-B). These compounds, and compositions comprising these compounds, are useful for the treatment of fungal diseases in humans and in animals.

In an aspect, provided herein is a compound having the structure of Formula (III), of a pharmaceutically acceptable salt, solvate, hydrate, tautomer, a stereoisomer, mixture stereoisomers, or an isotopic variant thereof:

Formula (III)

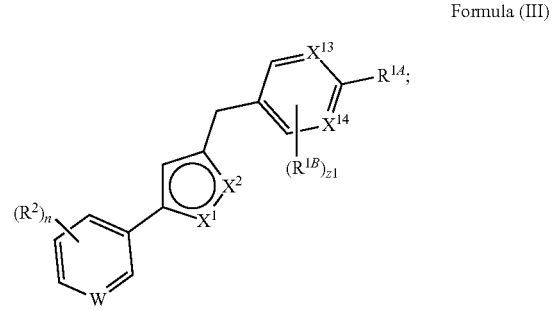

wherein:

R$^{14}$ is —OH, substituted or unsubstituted C$_3$-C$_6$alkyl, —(CH$_2$)$_2$S(CH$_2$)$_2$OC(O)H, —X$^{15}$-L-C≡N, -L-X$^{15}$—(CH$_2$)$_{x2}$C≡N, —X$^{15}$-L-CH=CR$^{29}$R$^{30}$,

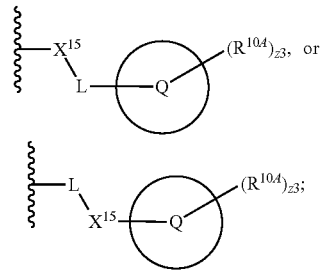

one of X$^1$ and X$^2$ is N while the other is O;
X$^{13}$ and X$^{14}$ are independently N or C(R$^{1B}$);
X$^{15}$ is a bond, —NH—, —O—, —S—, or —SO$_2$—;
L is a bond or substituted or unsubstituted C$_1$-C$_6$alkylene;
W is N or N$^+$—OPO$_3$H$^-$;
Ring Q is cycloalkyl, heterocycloalky, aryl, or heteroaryl;
R$^2$ is independently hydrogen, —NH$_2$, or halogen;
each R$^{1B}$ and R$^{10A}$ is independently hydrogen, halogen, —CF$_3$, —CN, —CH$_2$—OH, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, substituted or unsubstituted cycloalkyl, substituted or unsubstituted heterocycloalkyl, substituted or unsubstituted aryl, or substituted or unsubstituted heteroaryl;
R$^{29}$ and R$^{30}$ are independently hydrogen, halogen, substituted or unsubstituted C$_{1-6}$ alkyl, substituted or unsubstituted aryl, substituted or unsubstituted heteroaryl, substituted or unsubstituted cycloalkyl, or substituted or unsubstituted heterocycloalkyl;

$R^a$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;

$R^b$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;

$R^c$ and $R^d$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;

n is 0-3;

z1 is 0-2;

z2 is 0-3; and z3 is 1-3.

In some embodiments of a compound of Formula (III), if $R^{1A}$ is

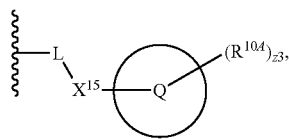

$R^2$ is —$NH_2$, Ring Q is 2-pyridinyl, L is methylene, $R^{10A}$ is hydrogen, $X^1$ is O, $X^2$ is N, $X^{13}$ is CH, $X^{14}$ is CH, n is 1, and z1 is 0, and then $X^{15}$ is a bond, —NH—, —S—, or —$SO_2$—.

In some embodiments of a compound of Formula (III), if $R^{1A}$ is

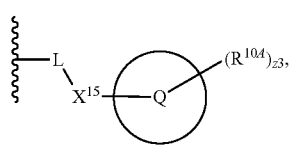

$R^2$ is 2-amino, Ring Q is 2-pyridinyl, L is methylene, $R^{10A}$ is hydrogen, $X^1$ is O, $X^2$ is N, $X^{13}$ is CH, $X^{14}$ is CH, n is 1, and z1 is 0, and then $X^{15}$ is a bond, —NH—, —S—, or —$SO_2$—.

In some embodiments, $R^2$ is 2-amino and $R^2$ is —$NH_2$ are synonymous and refer to an amino group (i.e., —$NH_2$ group) on the 2-position of the pyridinyl or pyridinium ring of a compound of Formula (III) as shown in Formula (IV):

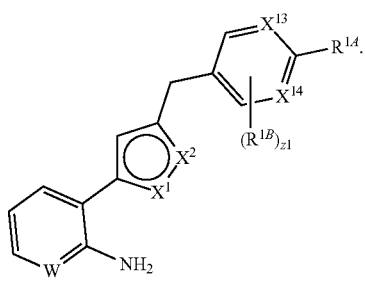

Formula (IV)

In some embodiments of a compound of Formula (III), or a pharmaceutically acceptable salt, solvate, hydrate, tautomer, a stereoisomer, mixture of stereoisomers, or an isotopic variant thereof, the compound of Formula (III) is of Formula (III'):

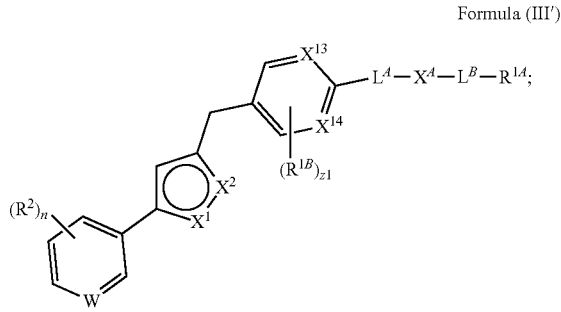

Formula (III')

wherein:
$R^2$, W, $X^1$, $X^2$, $R^{1B}$, $X^{13}$, $X^{14}$, $R^{1A}$, z1, z2, z3, and n are as described herein, including embodiments.

$L^A$ and $L^B$ are independently a bond or substituted or unsubstituted $C_1$-$C_6$ alkylene; and $X^A$ is a bond, —NH—, —O—, —S—, or —$SO_2$—.

In some embodiments, the compound is not hydrogen (2-(2-amino-3-(3-(4-((pyridin-2-yloxy)methylbenzyl)isoxazol-5-yl)pyridin-1-ium-1-yl)ethyl)phosphonate or 3-(3-(4-((pyridin-2-yloxy)methyl)benzyl)(isoxazol-5-yl)pyridin-2-amine.

In some embodiments of the compounds disclosed W is N. In some embodiments of the compounds disclosed herein, $N^+$—$OPO_3H^-$.

In some embodiments of the compounds disclosed herein, $X^1$ is —O—; and $X^2$ is N.

In some embodiments of the compounds disclosed herein, $R^2$ is —$NH_2$. In some embodiments of the compounds disclosed herein, $R^{10A}$ is hydrogen or halogen. In some embodiments of the compounds disclosed herein, z3 is 0. In some embodiments of the compounds disclosed herein, z3 is 1. In some embodiments of the compounds disclosed herein, z3 is 2. In some embodiments of the compounds disclosed herein, z3 is 3.

In some embodiments of the compounds disclosed herein. z3 is 1-2.

In some embodiments of the compounds disclosed herein, z2 is 0. In some embodiments of the compounds disclosed herein, z2 is 1. In some embodiments of the compounds disclosed herein, z2 is 2. In some embodiments of the compounds disclosed herein, z2 is 3.

In some embodiments of the compounds disclosed herein, z1 is 0. In some embodiments of the compounds disclosed herein, z1 is 1. In some embodiments of the compounds disclosed herein, z1 is 2.

In some embodiments of the compounds disclosed herein, the compound of Formula (III) is of Formula (IIIa), or a pharmaceutically acceptable salt, solvate, hydrate, tautomer, a stereoisomer, mixture of stereoisomers, or an isotopic variant thereof.

Formula (IIIa)

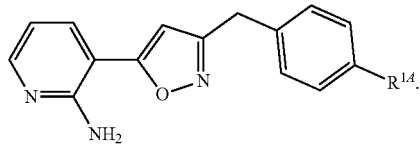

In some embodiments of the compounds disclosed herein, $R^{1A}$ is

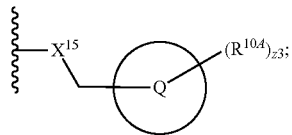

and Ring Q is bicyclic aryl, bicyclic heteroaryl, monocylic heteroaryl containing at least 2N atoms in the ring, or oxazolyl.

In some embodiments of the compounds disclosed herein, $R^{1A}$ is

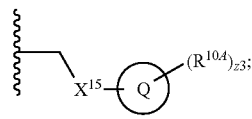

and Ring Q is bicyclic aryl, bicyclic heteroaryl, monocylic 5-membered heteroaryl, or cycloalkyl.

In some embodiments of the compounds disclosed herein, $X^{15}$ is —O—.

In some embodiments of the compounds disclosed herein, Ring Q is bicyclic aryl or bicyclic heteroaryl.

In some embodiments of the compounds disclosed herein, Ring Q is bicyclic heteroaryl selected from the group consisting of indolizinyl, indolyl, benzofuranyl, benzothiophenyl, indazolyl, benzimidazolyl, purinyl, quinolizinyl, quinolinyl, isoquinolinyl, cinnolinyl, phthalazinyl, quinazolinyl, quinoxalinyl, 1,8-naphthyridinyl, and pteridinyl In some embodiments of the compounds disclosed herein, Ring Q is quinolinyl or quinoxalinyl.

In some embodiments of the compounds disclosed herein, Ring Q is monocylic heteroaryl containing at least 2 N atoms in the ring.

In some embodiments of the compounds disclosed herein, Ring Q is monocylic heteroaryl containing at least 2 N atoms in the ring is selected from the group consisting of pyridazinyl, pyrimidinyl, pyrazinyl, and triazinyl.

In some embodiments of the compounds disclosed herein, Ring Q is pyrimidinyl.

In some embodiments of the compounds disclosed herein, Ring Q is monocylic 5-membered heteroaryl.

In some embodiments of the compounds disclosed herein, Ring Q is monocylic 5-membered heteroaryl selected from the group consisting of imidazolyl, triazolyl, furyl, thienyl, isoxazolyl, thiazolyl, oxazolyl, isothiazolyl, pyrrolyl, and thiadiazolyl.

In some embodiments of the compounds disclosed herein, Ring Q is imidazolyl or oxazolyl.

In some embodiments of the compounds disclosed herein, Ring Q is cycloalkyl.

In some embodiments of the compounds disclosed herein, Ring Q is cyclohexyl.

In some embodiments of the compounds disclosed herein, $X^{15}$ is —NH—.

In some embodiments of the compounds disclosed herein, Ring Q is heteroaryl or cycloalkyl.

In some embodiments of the compounds disclosed herein, Ring Q is heteroaryl selected from the group consisting of azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadizolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of the compounds disclosed herein, Ring Q is pyridinyl, thiadiazolyl, pyrimidinyl, azaindolyl, benzimidazolyl, or thiazolyl.

In some embodiments of the compounds disclosed herein, $R^{1A}$ is

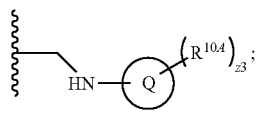

and Ring Q is heteroaryl or cycloalkyl.

In some embodiments of compounds disclosed herein, Ring Q is heteroaryl.

In some embodiments of the compounds disclosed herein, Ring Q is heteroaryl selected from the group consisting of azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadizolyl, thiadiazolyl, furazanyl, benzofurazanyl, benzothiophenyl, benzothiazolyl, benzoxazolyl, quinazolinyl, quinoxalinyl, naphthyridinyl, and furopyidinyl.

In some embodiments of the compounds disclosed herein, Ring Q is pyridinyl, thiadiazolyl, pyrimidinyl, azaindolyl, benzimidazolyl, or thiazolyl.

In some embodiments of the compounds disclosed herein, Ring Q is cycloalkyl.

In some embodiments of the compounds disclosed herein, $R^{1A}$ is

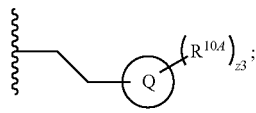

and Ring Q is aryl, bicyclic heteroaryl, or cycloalkyl.

In some embodiments of the compounds disclosed herein, Ring Q is aryl selected from phenyl and naphthyl.

In some embodiments of the compounds disclosed herein, Ring Q is bicyclic heteroaryl selected from the group consisting of indolizinyl, indolyl, benzofuranyl, benzothiophenyl, indazolyl, benzimidazolyl, purinyl, quinolizinyl, quinolinyl, isoquinolinyl phthalazinyl, quinazolinyl, quinoxalinyl, 1,8-naphthyridinyl, and pteridinyl.

In some embodiments of the compounds disclosed herein, Ring Q is $C_3$-$C_6$ cycloalkyl.

In some embodiments of the compounds disclosed herein, z3 is 1. In some embodiments of the compounds disclosed herein, z3 is 2.

In some embodiments of the compounds disclosed herein, $R^{10A}$ is hydrogen, —$CF_3$, halogen, or methyl.

In some embodiments of the compounds disclosed herein, $R^{1A}$ is

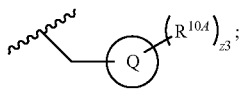

and Ring Q is aryl, heteroaryl, heterocycloalkyl, or cycloalkyl.

In some embodiments of the compounds disclosed herein, $R^{1A}$ is

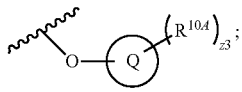

and Ring Q is aryl, heteroaryl, heterocycloalkyl, or cycloalkyl.

In some embodiments of the compounds disclosed herein, $R^{1A}$ is

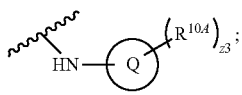

and Ring Q is aryl, heteroaryl, heterocycloalkyl, or cycloalkyl.

In some embodiments of the compounds disclosed herein, $R^{1A}$ is

and Ring Q is aryl, heteroaryl, heterocycloalkyl, or cycloalkyl.

In some embodiments of the compounds disclosed here n, $R^{1A}$ is

and Ring Q is aryl, heteroaryl, heterocycloalkyl, or cycloalkyl.

In some embodiments of the compounds disclosed herein, $R^{1A}$ is

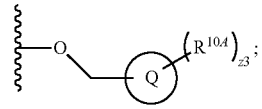

and Ring Q is aryl, heteroaryl, heterocycloalkyl, or cycloalkyl.

In some embodiments of the compounds disclosed herein, Ring Q is aryl selected from phenyl and naphthyl. In some embodiments of the compounds disclosed herein, Ring Q is substituted or unsubstituted phenyl. In some embodiments of the compounds disclosed herein, Ring Q is substituted or unsubstituted heteroaryl. In some embodiments of the compounds disclosed herein, Ring Q is substituted or unsubstituted 5- or 6-membered heteroaryl. In some embodiments of the compounds disclosed herein, Ring Q is substituted or unsubstituted pyridinyl. In some embodiments of the compounds disclosed herein, Ring Q is substituted or unsubstituted furanyl.

In some embodiments of the compounds disclosed herein, Ring Q is heteroaryl containing at least 1 N atom in the ring.

In some embodiments of the compounds disclosed herein, Ring Q is selected from

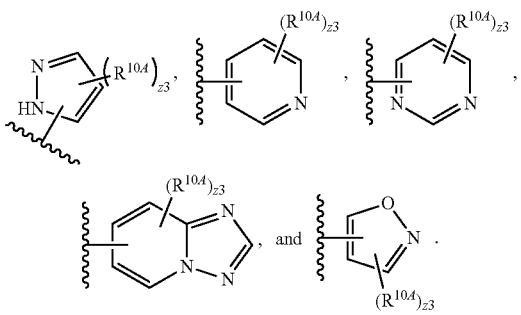

In some embodiments of the compounds disclosed herein, Ring Q is

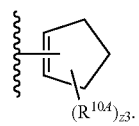

In some embodiments of the compounds disclosed herein, $R^{10A}$ is selected from the group consisting of hydrogen, —CN, halogen, —$CH_2$—OH, —$CF_3$, methyl, ethyl, isobutyl, and butyl.

In some embodiments of the compounds disclosed herein, $R^{10A}$ is —F, isobutyl, or —$CH_2$—OH.

In some embodiments of the compounds disclosed herein, $R^{10A}$ is —F.

In some embodiments of the compounds disclosed herein, $R^{1A}$ is

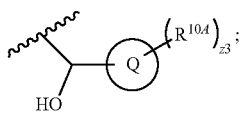

and Ring Q is aryl, heteroaryl, cycloalkyl, or heterocycloalkyl.

In some embodiments of the compounds disclosed herein, $R^{1A}$ is substituted or unsubstituted aryl, substituted or unsubstituted heteroaryl, or substituted or unsubstituted cycloalkyl. In some embodiments of the compounds disclosed herein, $R^{1A}$ is substituted or unsubstituted phenyl, substituted or unsubstituted 5-membered heteroaryl, or substituted or unsubstituted 6-membered heteroaryl. In some embodiments of the compounds disclosed herein, $R^{1A}$ is heteroaryl selected from pyridinyl and furanyl.

In some embodiments of the compounds disclosed herein, Ring Q is heteroaryl selected from the group consisting of azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of the compounds disclosed herein, Ring Q is heteroaryl selected from furyl and benzofuranyl.

In some embodiments of the compounds disclosed herein, Ring Q is cycloalkyl selected from $C_3$-$C_6$ cycloalkyl.

In some embodiments of the compounds disclosed herein, Ring Q is heterocycloalkyl that the heterocycloalkyl contains at least one O atom.

In some embodiments of the compounds disclosed herein, Ring Q is heterocycloalkyl that contains at least one O atom selected from the group consisting of

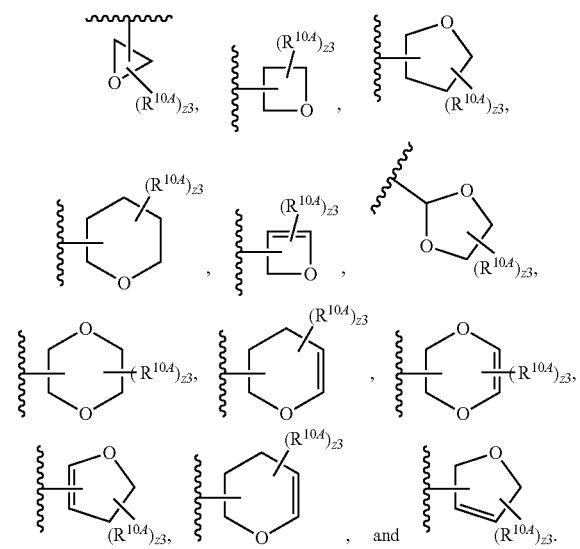

In some embodiments of the compounds disclosed herein, $R^{10A}$ is hydrogen, methyl, —$CF_3$, or halogen.

In some embodiments of the compounds disclosed herein, is $R^{1A}$ is —$CClR^5R^6$; and $R^5$ and $R^6$ are is independently hydrogen, halogen, or $C_1$-$C_6$ alkyl.

In some embodiments of compounds disclosed herein, $R^5$ and $R^6$ are hydrogen.

In some embodiments of the compounds disclosed herein, $R^{1A}$ is

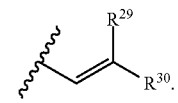

In some embodiments of the compounds disclosed herein, $R^{29}$ and $R^{30}$ are hydrogen.

In some embodiments of the compounds disclosed herein, $R^{29}$ is hydrogen and $R^{30}$ is cyclohexyl.

In some embodiments of the compounds disclosed herein, L is —$CH_2$—; and Ring Q is bicyclic aryl, bicyclic heteroaryl, monocylic heteroaryl containing at least 2 N atoms in the ring, or oxazolyl.

In some embodiments of the compounds disclosed herein, $X^{15}$ is a bond; L is —$CH_2$—; and Ring Q is aryl, heteroaryl containing at least 1 N atom in the ring, or cycloalkyl.

In some embodiments of the compounds disclosed herein, $X^{15}$ is a bond; L is —$(CH_2)_2$—; and Ring Q is aryl, bicyclic heteroaryl, cycloalkyl.

In some embodiments of the compounds disclosed herein, $X^{15}$ is a bond: L is —CH(OH)—; and Ring Q is aryl, heteroaryl, cycloalkyl, or heterocycloalkyl.

In some embodiments of the compounds disclosed herein, $X^{15}$ is a bond; L is —NH—; and Ring Q is heteroaryl or cycloalkyl.

In some embodiments of the compounds disclosed herein, $X^{15}$ is —NH—; L is —$CH_2$—; and Ring Q is heteroaryl or cycloalkyl.

In some embodiments of the compounds disclosed herein, $X^{15}$ is —O— or —S—; L is —$CH_2$—; and Ring Q is bicyclic aryl, bicyclic heteroaryl, monocylic 5-membered heteroaryl, or cycloalkyl.

In some embodiments of the compounds disclosed herein, $X^{13}$ is CH. In some embodiments of the compounds disclosed herein, $X^{13}$ is N. In some embodiments of the compounds disclosed herein, $X^{14}$ is CH. In some embodiments of the compounds disclosed herein, $X^{14}$ is N.

In some embodiments of the compounds disclosed herein, $X^{13}$ and $X^{14}$ are CH. In some embodiments of the compounds disclosed herein, $X^3$ is CH; and $X^{14}$ is N.

In an aspect provided herein, is a compound of Formula (III-B), or a pharmaceutically acceptable salt, solvate, hydrate, tautomer, a stereoisomer, mixture of stereoisomers, or an isotopic variant thereof:

Formula (III-B)

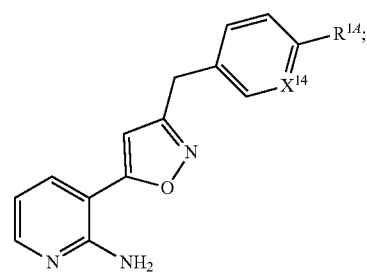

wherein:
R[14] is

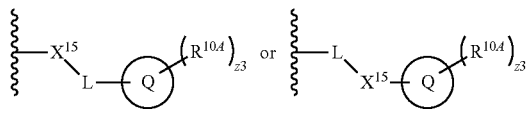

In some embodiments of the compounds of Formula (III-B), $X^{14}$ is N or CH;
$X^{15}$ is a bond, —NH— or —O—;
L is a bond or unsubstituted $C_1$-$C_2$ alkylene;
Ring Q is cycloalkyl, aryl, or heteroaryl,
$R^{10A}$ is hydrogen or halogen; and
z3 is 1-2.

In some embodiments of the compounds of Formula (III-B), $X^{14}$ is N.

In some embodiments of the compounds of Formula (III-B), $X^{14}$ is CH. In some embodiments of the compounds disclosed herein, $X^{15}$ is a bond; and L is —CH$_2$—. In some embodiments of the compounds disclosed herein, $X^{15}$ is a bond; and L is —(CH$_2$)$_2$—.

In some embodiments of the compounds of Formula (III-B), $X^{15}$ is —O— or —NH—; and L is a bond.

In some embodiments of the compounds disclosed herein, —$X^{15}$-L- is -#-$X^{15}$-L-* or #-$X^{15}$-L-*, wherein # is the attachment point to Ring Q and * is the attachment point to the rest of the molecule.

In some embodiments of the compounds disclosed herein, $X^{15}$-L is —CH$_2$—O— or —CH$_2$—NH—. In some embodiments of the compounds disclosed herein, $X^{15}$-L is #-CH$_2$—O—* or #-CH$_2$—NH—*, wherein # is the attachment point to Ring Q and * is the attachment point to the rest of the molecule. In other embodiments of the compounds disclosed herein, $X^{15}$-L is *-CH$_2$—O-# or *-CH$_2$—NH-#, wherein # is the attachment point to Ring Q and * is the attachment point to the rest of the molecule.

In some embodiments of the compounds disclosed herein, $X^{15}$-L is —(CH$_2$)$_2$—O— or —(CH$_2$)$_2$—NH—.

In an aspect provided herein, is a compound selected from the compounds in Table 1.

In an aspect provided herein, is a compound selected from the compounds in Table 2.

In an aspect provided herein, is a compound selected from:
3-(3-(4-((6-fluoropyridin-2-yl)oxy)benzyl)isoxazol-5-yl)pyridin-2-amine;
3-(3-(4-((6-chloropyridin-2-yl)oxy)benzyl)isoxazol-5-yl)pyridin-2-amine;
3-(3-(4-((3-fluoropyridin-2-yl)oxy)benzyl)isoxazol-5-yl)pyridin-2-amine;
3-(3-(4-((3,5-fluoropyridin-2-yl)oxy)benzyl)isoxazol-5-yl)pyridin-2-amine;
3-(3-((6-(3-fluorophenoxy)pyridin-3-yl)methyl)isoxazol-5-yl)pyridin-2-amine;
3-(3-(4-((5-fluorofuran-2-yl)methyl)benzyl)isoxazol-5-yl)pyridin-2-amine;
3-(3-((6-phenoxypyridin-3-yl)methyl)isoxazol-5-yl)pyridin-2-amine;
3-(3-((6-fluorobenzyl)oxy)pyridin-3-yl)methyl)isoxazol-5-yl)pyridin-2-amine;
5-((5-(2-aminopyridin-3-yl)isoxazol-3-yl)methyl)-N-(2-fluorophenyl)pyridin-2-amine;
5-((5-(2-aminopyridin-3-yl)isoxazol-3-yl)methyl)-N-(2,6-difluorophenyl)pyridin-2-amine;
3-(3-(4-benzylbenzyl)isoxazol-5-yl)pyridin-2-amine;
3-(3-(4-((6-fluoropyridin-2-yl)methyl)benzyl)isoxazol-5-yl)pyridin-2-amine;
3-(3-(4-((6-(2-fluorophenoxy)pyridin-3-yl)methyl)isoxazol-5-yl)pyridin-2-amine;
3-(3-((6-(3,5-difluorophenoxy)pyridin-3-yl)methyl)isoxazol-5-yl)pyridin-2-amine;
3-(3-((6-(cyclopropylmethoxy)pyridin-3-yl)methyl)isoxazol-5-yl)pyridin-2-amine;
3-(3-(4-((3,5-difluorobenzyl)benzyl)isoxazol-5-yl)pyridin-2-amine;
3-(3-((2-((3-fluorobenzyl)oxy)pyridin-4-yl)methyl)isoxazol-5-yl)pyridin-2-amine;
3-(3-(4-(3-fluorobenzyl)benzyl)isoxazol-5-yl)pyridin-2-amine; and
3-(3-(4-((3-fluorophenyl)amino)methyl)benzyl)isoxazol-5-yl)pyridin-2-amine, or a pharmaceutically acceptable salt, solvate, hydrate, tautomer, a stereoisomer, mixture of stereoisomers, or an isotopic variant thereof.

In some embodiments provided herein is a compound having the structure of Formula (I), or a pharmaceutically acceptable salt, solvate, or stereoisomer thereof:

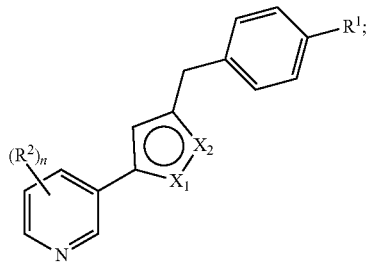

Formula (I)

wherein:
R[1] is

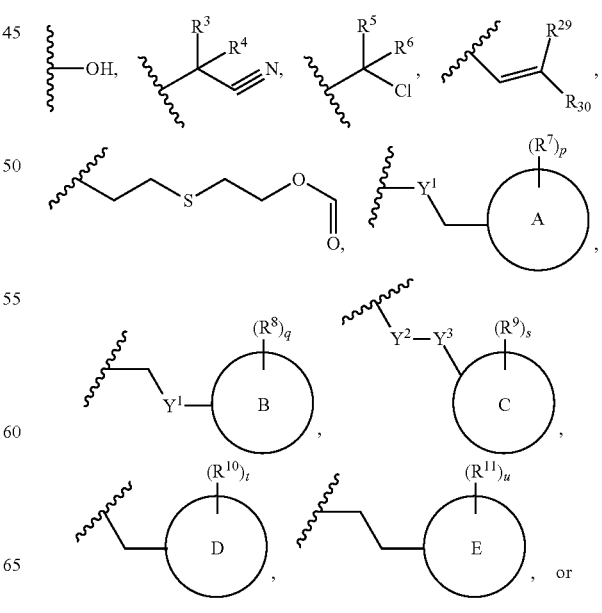

-continued

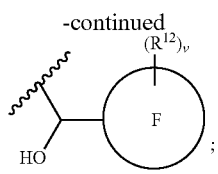

one of $X_1$ and $X_2$ is N while the other is O;
$Y^1$ is —O— or —S—;
one of $Y^2$ and $Y^3$ is —NH— while the other is —CH$_2$—;
Ring A is bicyclic aryl, bicyclic heteroaryl, monocylic heteroaryl containing at least 2 N atoms in the ring, or oxazolyl;
Ring B is bicyclic aryl, bicyclic heteroaryl, monocylic 5-membered heteroaryl, or cycloalkyl;
Ring C is heteroaryl or cycloalkyl;
Ring D is aryl, heteroaryl containing at least 1 N atom in the ring, or cycloalkyl;
Ring E is aryl, bicyclic heteroaryl, cycloalkyl;
Ring F is aryl, heteroaryl, cycloalkyl, or heterocycloalkyl;
each $R^2$ is independently hydrogen, —NH$_2$, or halogen;
each $R^3$, $R^4$, $R^5$, and $R^6$ are independently hydrogen, halogen, or $C_1$-$C_6$ alkyl;
each $R^7$, $R^8$, $R^9$, $R^{10}$, $R^{11}$, and $R^{12}$ is independently hydrogen, halogen, —CF$_3$, —CN, —CH$_2$—OH, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
each $R^{29}$ and $R^{30}$ is independently hydrogen, halogen, $C_1$-$C_6$ alkyl, aryl, heteroaryl, cycloalkyl, heterocycloalkyl;
$R^a$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted cycloalkyl, optionally substituted heterocycloalkyl, optionally substituted aryl, or optionally substituted heteroaryl;
$R^b$ is optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted cycloalkyl, optionally substituted heterocycloalkyl, optionally substituted aryl, or optionally substituted heteroaryl;
each $R^c$ and $R^d$ is independently hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted cycloalkyl, optionally substituted heterocycloalkyl, optionally substituted aryl, or optionally substituted heteroaryl;
$R^c$ and $R^d$, together with the nitrogen atom to which they are attached, form an optionally substituted heterocycloalkyl or optionally substituted heteroaryl;
n is 1-3;
p is 1-3;
q is 1-3;
s is 1-3;
t is 1-3;
u is 1-3; and
y is 1-3.

In some embodiments of a compound of Formula (I), or a pharmaceutically acceptable salt, solvate, hydrate, tautomer, a stereoisomer, mixture of stereoisomers, or an isotopic variant thereof, $X^1$ is O and $X^2$ is N. In some embodiments of a compound of Formula (I), or a pharmaceutically acceptable salt, solvate, hydrate, tautomer, a stereoisomer, mixture of stereoisomers, or an isotopic variant thereof, $X^1$ is N and $X^2$ is O. In some embodiments of a compound of Formula (I), or a pharmaceutically acceptable salt, solvate, hydrate, tautomer, a stereoisomer, mixture of stereoisomers, or an isotopic variant thereof, $R^2$ is —NH$_2$. In some embodiments of a compound of Formula (I), or a pharmaceutically acceptable salt, solvate, hydrate, tautomer, a stereoisomer, mixture of stereoisomers, or an isotopic variant thereof, $R^2$ is hydrogen. In some embodiments of a compound of Formula (I), or a pharmaceutically acceptable salt, solvate, hydrate, tautomer, a stereoisomer, mixture of stereoisomers, or an isotopic variant thereof, $R^2$ is a halogen. In some embodiments of a compound of Formula (I), or a pharmaceutically acceptable salt, solvate, hydrate, tautomer, a stereoisomer, mixture of stereoisomers, or an isotopic variant thereof, $R^2$ is —F, —Cl, or —Br.

In some embodiments of a compound of Formula (I), or a pharmaceutically acceptable salt, solvate, hydrate, tautomer, stereoisomer, mixture of stereoisomers, or an isotopic variant thereof, n is 1. In some embodiments of a compound of Formula (I), or a pharmaceutically acceptable salt, solvate, hydrate, tautomer, stereoisomer, mixture of stereoisomers, or an isotopic variant thereof, n is 2. In some embodiments of a compound of Formula (I), or a pharmaceutically acceptable salt, solvate, hydrate, tautomer, a stereoisomer, mixture of stereoisomers, or an isotopic variant thereof, n is 3.

In some embodiments of a compound of Formula (I), or a pharmaceutically acceptable salt, solvate, hydrate, tautomer, a stereoisomer, mixture of stereoisomers, or an isotopic variant thereof, the compound of Formula (I) is of Formula (Ia):

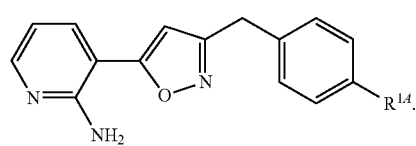

Formula (Ia)

In some embodiments of a compound of Formula (I) or (Ia), or a pharmaceutically acceptable salt, solvate, hydrate, tautomer, a stereoisomer, mixture of stereoisomers, or an isotopic variant thereof, $R^1$ is

In some embodiments of a compound of Formula (I) or (Ia), or a pharmaceutically acceptable salt, solvate, hydrate, tautomer, a stereoisomer, mixture of stereoisomers, or an isotopic variant thereof, $R^1$ is $$\text{\Large $\underset{\substack{\phantom{R^3}\\\phantom{R^4}}}{\overset{R^3\quad R^4}{\diagdown\diagup}}$N.}$$

In some embodiments of a compound of Formula (I) or (Ia), or a pharmaceutically acceptable salt, solvate, hydrate, tautomer, a stereoisomer, mixture of stereoisomers, or an isotopic variant thereof, $R^3$ is hydrogen and $R^4$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof, $R^3$ is hydrogen and $R^4$ is halogen. In some embodiments of a compound of Formula (I) or (Ia), or a pharmaceutically acceptable salt, solvate, hydrate, tautomer, a stereoisomer, mixture of stereoisomers, or an isotopic variant thereof, $R^3$ is halogen and $R^4$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^3$ is $C_1$-$C_6$ alkyl and $R^4$ is hydrogen. In some embodiments of a compound of Formula (I) or (Ia), $R^3$ is methyl. In some embodiments or a compound of Formula (I) or (Ia), $R^3$ is ethyl. In some embodiments of a compound of Formula (I) or (Ia), $R^3$ is propyl. In some embodiments of a compound of Formula (I) or (Ia), $R^3$ is butyl. In some embodiments of a compound Formula (I) or (Ia), $R^3$ is pentyl. In some embodiments of a compound of Formula (I) or (Ia). $R^3$ is hexyl. In some embodiments of a compound Formula (I) or (Ia), or a pharmaceutically acceptable salt, solvate, hydrate, tautomer, a stereoisomer, mixture of stereoisomers, or an isotopic variant thereof $R^3$ is hydrogen and $R^4$ is $C_1$-$C_6$ alkyl. In some embodiments of a compound of Formula (I) or (Ia), $R^4$ is methyl. In some embodiments of a compound of Formula (I) or (Ia), $R^4$ is ethyl. In some embodiments of a compound of Formula (I) or (Ia), $R^4$ is propyl. In some embodiments of a compound of Formula (I) or (Ia), $R^4$ is butyl. In some embodiments of a compound of Formula (I) or (Ia), $R^4$ is pentyl. In some embodiments of a compound of Formula (I) or (Ia), $R^4$ is hexyl.

In some embodiments of a compound of Formula (I) or (Ia), or a pharmaceutically acceptable salt, solvate hydrate, tautomer, a stereoisomer, mixture of stereoisomers, or an isotopic variant thereof $R^3$ is $$\text{\Large $\underset{\substack{\phantom{R^5}\\\phantom{R^6}}}{\overset{R^5\quad R^6}{\diagdown\diagup}}$Cl.}$$

In some embodiments of a compound of Formula (I) or (Ia), or a pharmaceutically acceptable salt, solvate, hydrate, tautomer, a stereoisomer, mixture of stereoisomers, or an isotopic variant thereof, $R^5$ is hydrogen and $R^6$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^5$ is hydrogen and $R^6$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^5$ is $C_1$-$C_6$ alkyl and $R^6$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^5$ is $C_1$-$C_6$ alkyl and $R^6$ is $C_1$-$C_6$ alkyl. In some embodiments of a compound of Formula (I) or (Ia), or a pharmaceutically acceptable salt, solvate, hydrate, tautomer, a stereoisomer, mixture of stereoisomers, or an isotopic variant thereof $R^5$ is hydrogen and $R^6$ is $C_1$-$C_6$ alkyl. In some embodiments of a compound of Formula (I) or (Ia), $R^5$ is methyl. In some embodiments of a compound of Formula (I) or (Ia), $R^5$ is ethyl. In some embodiments of a compound of Formula (I) or (Ia), $R^5$ is propyl. In some embodiments of a compound of Formula (I) or (Ia), $R^5$ is butyl. In some embodiments of a compound of Formula (I) or (Ia), $R^5$ is pentyl. In some embodiments of a compound of Formula (I) or (Ia), $R^5$ is hexyl. In some embodiments of a compound of Formula (I) or (Ia), $R^6$ is methyl. In some embodiments of a compound of Formula (I) or (Ia), $R^6$ is ethyl. In some embodiments of a compound of Formula (I) or (Ia), $R^6$ is propyl. In some embodiments of a compound of Formula (I) or (Ia), $R^6$ is butyl. In some embodiments of a compound of Formula (I) or (Ia), $R^6$ is pentyl. In some embodiments of a compound of Formula (I) or (Ia), $R^6$ is hexyl.

In some embodiments of a compound of Formula (I) or (Ia), or a pharmaceutically acceptable salt, solvate, hydrate, tautomer, a stereoisomer, mixture of stereoisomers, or an isotopic variant thereof $R^1$ is $$\text{\Large $\underset{R_{30}.}{\overset{R^{29}}{\diagdown\diagup}}$}$$

In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is hydrogen and $R^{30}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is hydrogen and $R^{30}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is $C_1$-$C_6$ alkyl and $R^{30}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is $C_3$-$C_6$ alkyl and $R^{30}$ is $C_1$-$C_6$ alkyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is hydrogen and $R^{30}$ is $C_1$-$C_6$ alkyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is hydrogen and $R^{30}$ is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{29}$ is hydrogen and $R^{30}$ is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{30}$ hydrogen and $R^{29}$ is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{30}$ is hydrogen and $R^{29}$ is cyclopropyl, cyclobutyl, cyclopentyl, or cyclohexyl.

In some embodiments of a compound of Formula (I) or (Ia), or a pharmaceutically acceptable salt, solvate, hydrate, tautomer, a stereoisomer, mixture of stereoisomers, or an isotopic variant thereof $R^3$ is —(CH$_2$)$_2$S(CH$_2$)$_2$OC(O)H.

In some embodiments of a compound of Formula (I) or (Ia), or a pharmaceutically acceptable salt, solvate, hydrate, tautomer, a stereoisomer, mixture of stereoisomers, or an isotopic variant thereof $R^3$ is

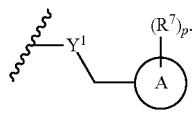

In some embodiments of a compound of Formula (I) or (Ia), or a pharmaceutically acceptable salt, solvate, hydrate, tautomer, a stereoisomer, mixture of stereoisomers, or an isotopic variant thereof $Y^1$ is —O—. In some embodiments of a compound of Formula (I) or (Ia), or a pharmaceutically acceptable salt, solvate, hydrate, tautomer, a stereoisomer, mixture of stereoisomers, or an isotopic variant thereof $Y^1$ is —S—.

In some embodiments of a compound of Formula (I) or (Ia), or a pharmaceutically acceptable salt, solvate, hydrate, tautomer, a stereoisomer, mixture of stereoisomers, or an isotopic variant thereof Ring A is bicyclic aryl. In some embodiments of a compound of Formula (I) or (Ia), or a pharmaceutically acceptable salt, solvate, hydrate, tautomer, a stereoisomer, mixture of stereoisomers, or an isotopic variant thereof Ring A is naphthyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring A is bicyclic heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof Ring A is bicyclic heteroaryl selected from indolizinyl, indolyl, benzofuranyl, benzothiophenyl, indazolyl, benzimidazolyl, purinyl, quinolizinyl, quinolinyl, isoquinolinyl, cinnolinyl, phthalazinyl, quinazolinyl, quinoxalinyl, 1,8-naphthyridinyl, and pteridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring A is quinolinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring A is quinoxalinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring A is monocylic heteroaryl containing at least 2 N atoms in the ring. In some embodiments of a compound of Formula (I) or (Ia), or a pharmaceutically acceptable salt, solvate, hydrate, tautomer, a stereoisomer, mixture of stereoisomers, or an isotopic variant thereof Ring A is pyridazinyl, pyrimidinyl, pyrazinyl, and triazinyl. In some embodiments of a compound of Formula (I) or (Ia), or a pharmaceutically acceptable salt, solvate, hydrate, tautomer a stereoisomer mixture of stereoisomers, or an isotopic variant thereof Ring A is pyrimidinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring A is oxazolyl.

In some embodiments of a compound of Formula (I) or (Ia), or a pharmaceutically acceptable salt, solvate, hydrate, tautomer, a stereoisomer, mixture of stereoisomers, or an isotopic variant thereof p is 1. In some embodiments of a compound of Formula (I) or (Ia), or a pharmaceutically acceptable salt, solvate, hydrate, tautomer, a stereoisomer, mixture of stereoisomers, or an isotopic variant thereof p is 2. In some embodiments of a compound of Formula (I) or (Ia), or a pharmaceutically acceptable salt, solvate, hydrate, tautomer, a stereoisomer, mixture of stereoisomers, or an isotopic variant thereof p 3. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted $C_1$-$C_6$ unsubstituted cycloalkyl, substituted or unsubstituted heterocycloalkyl, substituted or unsubstituted or substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is hydrogen, —CF$_3$, or methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is —CF$_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is a halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is —F. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is —Cl. In some embodiments of a compound of Formula (I) or (Ia), or a pharmaceutically acceptable salt, solvate, hydrate, tautomer, a stereoisomer, mixture of stereoisomers, or an isotopic variant thereof $R^7$ is —Br.

In some embodiments of a compound of Formula (I) or (Ia), or a pharmaceutically acceptable salt, solvate, hydrate, tautomer, a stereoisomer, mixture of stereoisomers, or an isotopic variant thereof $R^3$ is

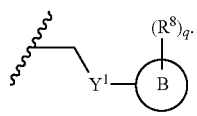

In some embodiments of a compound of Formula (I) or (Ia), or a pharmaceutically acceptable salt, solvate, hydrate, tautomer, stereoisomer, mixture of stereoisomers, of an isotopic variant thereof $Y^1$ is —O—. In some embodiments of a compound of Formula (I) or (Ia), or a pharmaceutically acceptable salt, solvate, hydrate, tautomer, a stereoisomer, mixture of stereoisomers, or an isotopic variant thereof $Y^1$ is —S—.

In some embodiments of a compound of Formula (I) or (Ia), or a pharmaceutically acceptable salt, solvate, hydrate, tautomer, a stereoisomer, mixture of stereoisomers, or an isotopic variant thereof Ring B is bicyclic aryl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is naphthyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring B is bicyclic heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is bicyclic heteroaryl selected from indolizinyl, indolyl, benzofuranyl, benzothiophenyl, indazolyl, benzimidazolyl, purinyl, quinolizinyl, quinolinyl, isoquinolinyl, cinnolinyl, phthalazinyl, quinazolinyl, quinoxalinyl, 1,8-naphthyridinyl, and pteridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is bicyclic heteroaryl selected from indolyl, indazolyl, benzimidazolyl, quinolizinyl, quinolinyl, isoquinolinyl, cinnolinyl, quinazolinyl, quinoxalinyl, and pteridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is quinolinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is quinoxalinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring B is monocylic heteroaryl containing at least 2 N atoms in the ring. In some embodiments of a compound of Formula (I) or (Ia), or a pharmaceutically acceptable salt, solvate, hydrate, tautomer, stereoisomer, mixture of stereoisomers, or an isotopic variant thereof Ring B is monocyclic heteroaryl containing at least 2N atoms in the ring selected from pyridazinyl, pyrimidinyl, pyrazinyl, and triazinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is pyrimidinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring B is oxazolyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring B is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is cyclopropyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is cyclobutyl. In some embodiments of a compound of Formula (I) or (Ia), or a pharmaceutically acceptable salt, solvate, hydrate, tautomer, a stereoisomer, mixture of stereoisomers, or an isotopic variant thereof Ring B is cyclopentyl.

In some embodiments of a compound of Formula (I) or (Ia), or a pharmaceutically acceptable salt, solvate, hydrate, tautomer, a stereoisomer, mixture of stereoisomers, or an isotopic variant thereof q is 1. In some embodiments of a compound of Formula (I) or (Ia), or a pharmaceutically acceptable salt, solvate, hydrate, tautomer, a stereoisomer, mixture of stereoisomers, or an isotopic variant thereof q is 2. In some embodiments of a compound of Formula (I) or (Ia), or a pharmaceutically acceptable salt, solvate, hydrate, tautomer, a stereoisomer, mixture of stereoisomers, or an isotopic variant thereof q is 3.

In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is hydrogen, methyl, —$CF_3$, or halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is —Cl. In some embodiments of a compound of Formula (I) or (Ia), or a pharmaceutically acceptable salt, solvate, hydrate, tautomer, a stereoisomer, mixture of stereoisomers, or an isotopic variant thereof $R^8$ is —F.

In some embodiments of a compound of Formula (I) or (Ia), or a pharmaceutically acceptable salt, solvate, hydrate, tautomer, a stereoisomer, mixture of stereoisomers, or an isotopic variant thereof $R^1$ is

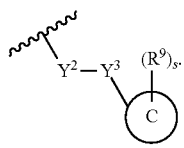

In some embodiments of a compound of Formula (I) or (Ia), or a pharmaceutically acceptable salt, solvate, hydrate, tautomer, a stereoisomer, mixture of stereoisomers, or an isotopic variant thereof $Y^2$ is —CH$_2$— and $Y^3$ is —NH—. In some embodiments of a compound of Formula (I) or (Ia), or a pharmaceutically acceptable salt, solvate, hydrate, tautomer, a stereoisomer, mixture of stereoisomers, or an isotopic variant thereof $Y^2$ is —NH— and $Y^3$ is —CH$_2$—.

In some embodiments of a compound of Formula (I) or (Ia), or a pharmaceutically acceptable salt, solvate, hydrate, tautomer, a stereoisomer, mixture of stereoisomers, or an isotopic variant thereof Ring C is heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is pyridinyl, thiadiazolyl, pyrimidinyl, azaindolyl, or thiazolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is pyridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is thiadiazolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is pyrimidinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is azaindolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is thiazolyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring C is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is cyclopropyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is cyclobutyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is cyclopentyl.

In some embodiments of a compound of Formula (I) or (Ia), or a pharmaceutically acceptable salt, solvate, hydrate, tautomer, a stereoisomer, mixture of stereoisomers, or an isotopic variant thereof s is 1. In some embodiments of a compound of Formula (I) or (Ia), or a pharmaceutically acceptable salt, solvate, hydrate, tautomer, a stereoisomer, mixture of stereoisomers, or an isotopic variant thereof s is 2. In some embodiments of a compound of Formula (I) or (Ia), or a pharmaceutically acceptable salt, solvate, hydrate, tautomer, a stereoisomer, mixture of stereoisomers, or an isotopic variant thereof s is 3.

In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is hydrogen, methyl, —CF$_3$, or halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is —CF. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is —Cl. In some embodiments of a compound of Formula (I) or (Ia), or a pharmaceutically acceptable salt, solvate, hydrate, tautomer, a stereoisomer, mixture of stereoisomers, or an isotopic variant thereof $R^9$ is —F.

In some embodiments of a compound of Formula (I) or (Ia), or a pharmaceutically acceptable salt, solvate, hydrate, tautomer, a stereoisomer, mixture of stereoisomers, or an isotopic variant thereof $R^1$ is

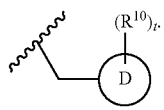

In some embodiments of a compound of Formula (I) or (Ia), or a pharmaceutically acceptable salt, solvate, hydrate, tautomer, a stereoisomer, mixture of stereoisomers, or an isotopic variant thereof Ring D is aryl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is phenyl. In some embodiments of a compound of Formula (I) or (Ia), or a pharmaceutically acceptable salt, solvate, hydrate, tautomer, a stereoisomer, mixture of stereoisomers, or an isotopic variant thereof Ring C is naphthyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring D is heteroaryl containing at least 1 N atom in the ring. In some embodiments of a compound of Formula (I) or (Ia), or a pharmaceutically acceptable salt, solvate, hydrate, tautomer, a stereoisomer, mixture of stereoisomers, or an isotopic variant thereof Ring D is heteroaryl containing at least 1 N atom in the ring including but not limited to azaindolyl, pyridinyl, imidazolyl, pyrimidinyl, pyrazolyl, triazolyl, pyrazinyl, tetrazolyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiazolyl, benzoxazolyl, quinazolinyl, quinoxalinyl, naphthyridinyl, and furopyridinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is selected from,

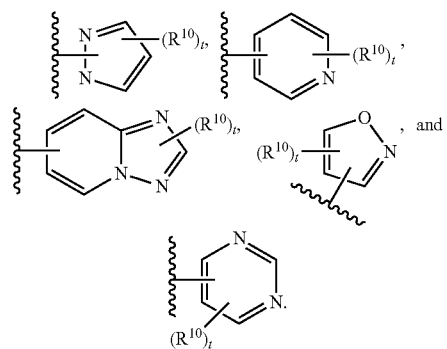

In some embodiments of a compound of Formula (I) or (Ia), or a pharmaceutically acceptable salt, solvate, hydrate, tautomer, a stereoisomer, mixture of stereoisomers, or an isotopic variant thereof Ring D is

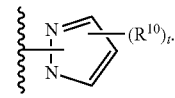

In some embodiments of a compound of Formula (I) or (Ia), or a pharmaceutically acceptable salt, solvate, hydrate, tautomer, a stereoisomer, mixture of stereoisomers, or an isotopic variant thereof Ring D is

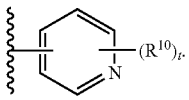

In some embodiments of a compound of Formula (I) or (Ia), or a pharmaceutically acceptable salt, solvate, hydrate, tautomer, a stereoisomer, mixture of stereoisomers, or an isotopic variant thereof Ring D is

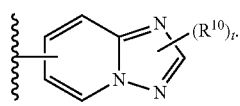

In some embodiments of a compound of Formula (I) or (Ia), or a pharmaceutically acceptable salt, solvate, hydrate, tautomer, a stereoisomer, mixture of stereoisomers, or an isotopic variant thereof Ring D is

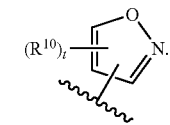

In some embodiments of a compound of Formula (I) or (Ia), or a pharmaceutically acceptable salt, solvate, hydrate, tautomer, a stereoisomer, mixture of stereoisomers, or an isotopic variant thereof Ring D is

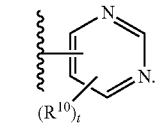

In some embodiments of a compound of Formula (I) or (Ia), or a pharmaceutically acceptable salt, solvate, hydrate, tautomer, a stereoisomer, mixture of stereoisomers, or an isotopic variant thereof Ring D is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is cyclopropyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is cyclobutyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is cyclopentyl. In some embodiments of a compound of Formula (I) or (Ia), or a pharmaceutically acceptable salt, solvate, hydrate, tautomer, a stereoisomer, mixture of stereoisomers, or an isotopic variant thereof Ring D is partially saturated. In some embodiments of a compound of Formula (I) or (Ia), or a pharmaceutically acceptable salt, solvate, hydrate, tautomer, a stereoisomer, mixture of stereoisomers, or an isotopic variant thereof Ring D is In some embodiments of a compound of Formula (I) or (Ia), or a pharmaceutically acceptable salt, solvate, hydrate, tautomer, a stereoisomer, mixture of stereoisomers, or an isotopic variant thereof t is 1. In some embodiments of a compound of Formula (I) or (Ia), or a pharmaceutically acceptable salt, solvate, hydrate, tautomer, a stereoisomer, mixture of stereoisomers, or an isotopic variant thereof t is 2. In some embodiments of a compound of Formula (I) or (Ia), or a pharmaceutically acceptable salt, solvate, hydrate, tautomer, a stereoisomer, mixture of stereoisomers, or an isotopic variant thereof t is 3.

In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is hydrogen, —CN, halogen, —$CF_3$, methyl, ethyl, and butyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is —CN. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is —F. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is ethyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is propyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is butyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is pentyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is hexyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is heptyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is octyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is nonyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is decyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is isobutyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{10}$ is isopentyl.

In some embodiments of a compound of Formula (I) or (Ia), or a pharmaceutically acceptable salt, solvate, hydrate, tautomer, a stereoisomer, mixture of stereoisomers, or an isotopic variant thereof $R^1$ is In some embodiments of a compound of Formula (I) or (Ia), or a pharmaceutically acceptable salt, solvate, hydrate, tautomer, a stereoisomer, mixture of stereoisomers, or an isotopic variant thereof Ring E is aryl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is phenyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is naphthyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring E is bicyclic heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is bicyclic heteroaryl selected from indolizinyl, indolyl, benzofuranyl, benzothiophenyl, indazolyl, benzimidazolyl, purinyl, quinolizinyl, quinolinyl, isoquinolinyl, cinnolinyl, phthalazinyl, quinazolinyl, quinoxalinyl, 1,8-naphthyridinyl, and pteridinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring E is indolyl, indazolyl, benzimidazolyl, quinazolinyl, or quinolinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is indolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is indazolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is benzimidazolyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is quinazolinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is quinolinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring E is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is cyclopropyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is cyclobutyl. In some embodiments of a compound of Formula (I) or (Ia), or a pharmaceutically acceptable salt, solvate, hydrate, tautomer, a stereoisomer, mixture of stereoisomers, or an isotopic variant thereof Ring E is cyclopentyl.

In some embodiments of a compound of Formula (I) or (Ia), or a pharmaceutically acceptable salt, solvate, hydrate, tautomer, a stereoisomer, mixture of stereoisomers, or an isotopic variant thereof u is 1. In some embodiments of a compound of Formula (I) or (Ia), or a pharmaceutically acceptable salt, solvate, hydrate, tautomer, a stereoisomer, mixture of stereoisomers, or an isotopic variant thereof u is 2. In some embodiments of a compound of Formula (I) or (Ia), or a pharmaceutically acceptable salt, solvate, hydrate, tautomer, a stereoisomer, mixture of stereoisomers, or an isotopic variant thereof u is 3.

In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is hydrogen or —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is —F. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is —Cl. In some embodiments of a compound of Formula (I) or (Ia), or a pharmaceutically acceptable salt, solvate, hydrate, tautomer, a stereoisomer, mixture of stereoisomers, or an isotopic variant thereof $R^{11}$ is —Br.

In some embodiments of a compound of Formula (I) or (Ia), or a pharmaceutically acceptable salt, solvate, hydrate, tautomer, a stereoisomer, mixture of stereoisomers, or an isotopic variant thereof $R^1$ is In some embodiments of a compound of Formula (I) or (Ia), or a pharmaceutically acceptable salt, solvate, hydrate, tautomer, a stereoisomer, mixture of stereoisomers, or an isotopic variant thereof Ring F is aryl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is phenyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is naphthyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring F is heteroaryl.

In some embodiments of a compound of Formula (I) or (Ia), or a pharmaceutically acceptable salt, solvate, hydrate, tautomer, a stereoisomer, mixture of stereoisomers, or an isotopic variant thereof Ring F is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring F is imidazolyl, triazolyl, pyrazinyl furyl, quinolinyl, benzofuranyl, quinazolinyl, or pyridazinyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is furyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is benzofuranyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring F is cycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is cyclopropyl, cyclobutyl, cyclopentyl, or cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is cyclohexyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is cyclopropyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is cyclobutyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is cyclopentyl.

In some embodiments of a compound of Formula (I) or (Ia), or a pharmaceutically acceptable salt, solvate, hydrate, tautomer, a stereoisomer, mixture of stereoisomers, or an isotopic variant thereof Ring F is heterocycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is a 5-membered heterocycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is a 6-membered heterocycloalkyl. In some embodiments of a compound of Formula (I) or (Ia), or a pharmaceutically acceptable salt, solvate, hydrate, tautomer, a stereoisomer, mixture of stereoisomers, or an isotopic variant thereof Ring F is heterocycloalkyl that contains at least one O atom. In some embodiments of a compound of Formula (I) or (Ia), or a pharmaceutically acceptable salt, solvate, hydrate, tautomer, a stereoisomer, mixture of stereoisomers, or an isotopic variant thereof Ring F is heterocycloalkyl that contains at least one O atom selected from

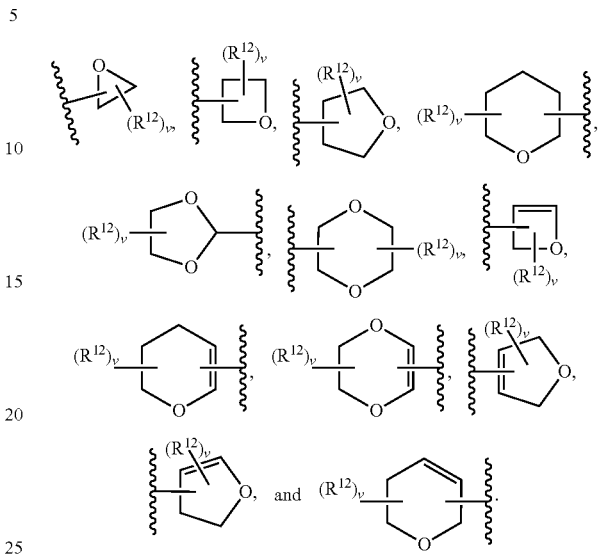

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

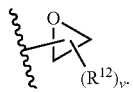

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

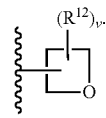

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

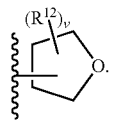

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

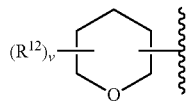

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

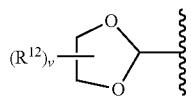

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

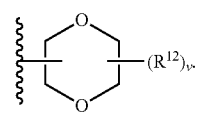

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

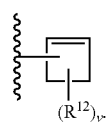

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

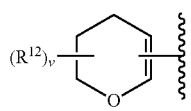

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

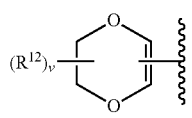

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

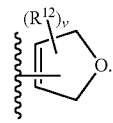

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

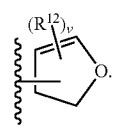

In some embodiments of a compound of Formula (I) or (Ia), or a pharmaceutically acceptable salt, solvate, hydrate, tautomer, a stereoisomer, mixture of stereoisomers, or an isotopic variant thereof Ring F is

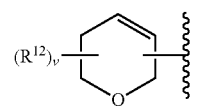

In some embodiments of a compound of Formula (I) or (Ia), or a pharmaceutically acceptable salt, solvate, hydrate, tautomer, a stereoisomer, mixture of stereoisomers, or an isotopic variant thereof v is 1. In some embodiments of a compound of Formula (I) or (Ia), or a pharmaceutically acceptable salt, solvate, hydrate, tautomer, a stereoisomer, mixture of stereoisomers, or an isotopic variant thereof v is 2. In some embodiments of a compound of Formula (I) or (Ia), or a pharmaceutically acceptable salt, solvate, hydrate, tautomer, a stereoisomer, mixture of stereoisomers, or an isotopic variant thereof v is 3.

In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is hydrogen, —$CF_3$, methyl, or hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is hydrogen or —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is hydrogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is —$CF_3$. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is methyl. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is halogen. In some embodiments of a compound of Formula (I) or (Ia), or a pharmaceutically acceptable salt, solvate, hydrate, tautomer, a stereoisomer, mixture of stereoisomers, or an isotopic variant thereof $R^{12}$ is —F.

In some embodiments provided herein is a compound having the structure of Formula (II), or a pharmaceutically acceptable salt, solvate, or stereoisomer thereof:

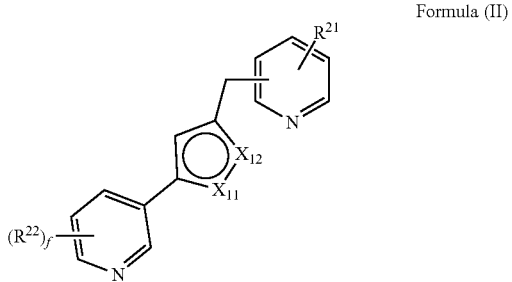

Formula (II)

wherein
$R^{21}$ is halogen,

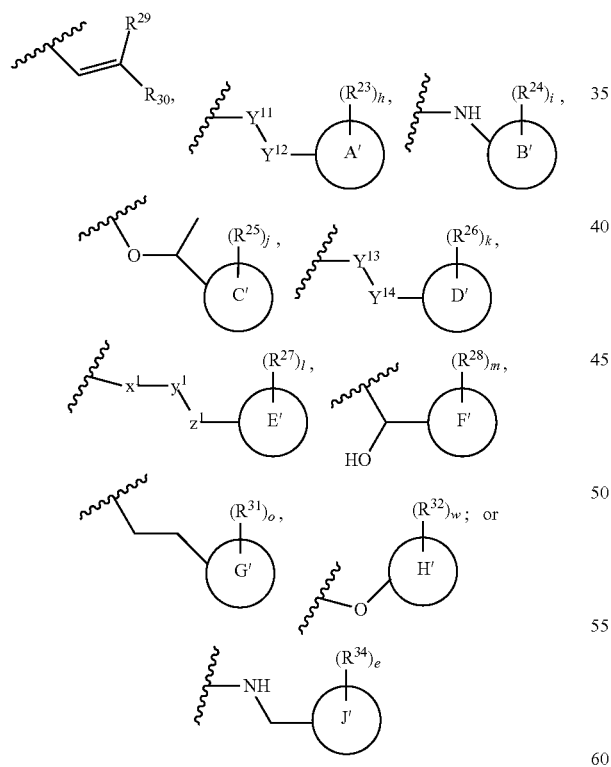

one of $X_{11}$ and $X_{12}$ is N while the other is O;
one or $Y^{11}$ and $Y^{12}$ is —NH— or —O— while the other is —CH$_2$—;
one of $Y^{13}$ and $Y^{14}$ is —S— while the other is —CH$_2$—;
one of x'y' and z' is —O— while the others are —CH$_2$—;
Ring A' is heteroaryl, cycloalkyl, or heterocycloalkyl;

Ring B' is aryl, heteroaryl, cycloalkyl, or heterocycloalkyl;
Ring C' is aryl, heteroaryl, cycloalkyl, or heterocycloalkyl;
Ring D' is aryl, heteroaryl, cycloalkyl, or heterocycloalkyl;
Ring E' is aryl, heteroaryl, cycloalkyl, or heterocycloalkyl;
Ring F' is aryl, heteroaryl, cycloalkyl, or heterocycloalkyl;
Ring G' is aryl, heteroaryl, cycloalkyl, or heterocycloalkyl;
Ring H' is bicyclic aryl, heteroaryl, cycloalkyl, or heterocycloalkyl;
Ring J' is aryl;
$R^{22}$ is hydrogen, —NH$_2$, or halogen;
$R^{29}$ and $R^{30}$ are independently hydrogen, halogen, $C_{1-6}$ alkyl, aryl, heteroaryl, cycloalkyl, heterocycloalkyl;
each $R^{23}$, $R^{24}$, $R^{25}$, $R^{26}$, $R^{27}$, $R^{28}$, $R^{31}$, and $R^{32}$ is independently hydrogen, halogen, —CF$_3$, —CN, —OR$^a$, —SR$^a$, —S(=O)R$^b$, —NO$_2$, —NR$^cR^d$, —S(=O)$_2$R$^d$, —NR$^a$S(=O)$_2$R$^d$, —S(=O)$_2$NR$^cR^d$, —C(=O)R$^b$, —OC(=O)R$^b$, —CO$_2$R$^a$, —OCO$_2$R$^a$, —C(=O)NR$^cR^d$, —OC(=O)NR$^cR^d$, —NR$^a$C(=O) NR$^cR^d$, —NR$^a$C(=O)R$^b$, —NR$^a$C(=O)OR$^a$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^a$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^b$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
each $R^c$ and $R^d$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
or $R^c$ or $R^d$, together with the nitrogen atom to which they are attached, form an substituted or unsubstituted heterocycloalkyl or substituted or unsubstituted heteroaryl;
f is 1;
h is 1-3;
i is 1-3;
j is 1-3;
k is 1-3;
l is 1-3;
m is 1-3;
o is 1-3;
w is 1-3; and
e is 1-3.

In some embodiments provided herein is a compound having the structure of Formula (II') or Formula (II"), or a pharmaceutically acceptable salt, solvate, or stereoisomer thereof:

Formula (II')

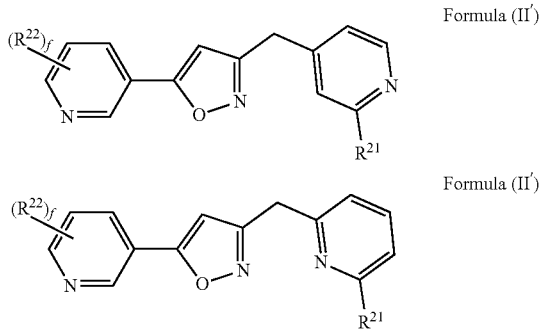

Formula (II")

wherein
$R^{23}$ is halogen,

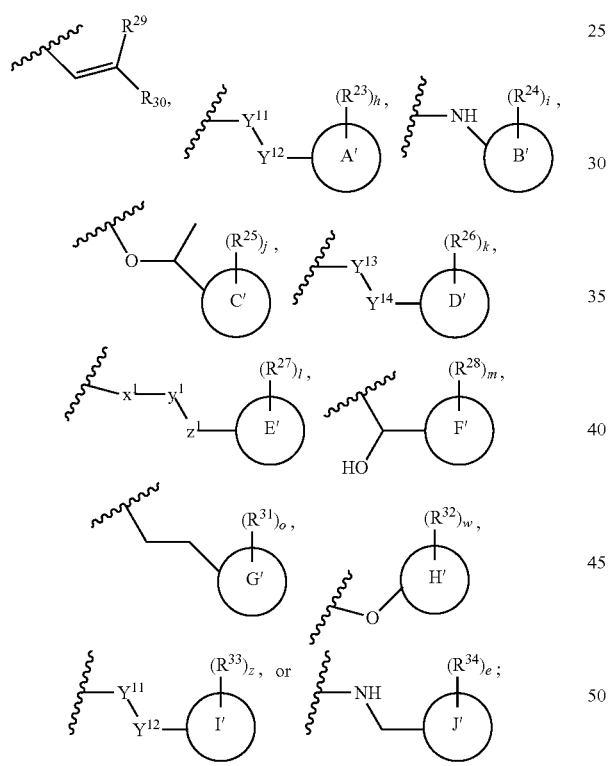

one of $X_{11}$ and $X_{12}$ is N while the other is O;
one or $Y^{11}$ and $Y^{12}$ is —NH— or —O— while the other is —CH$_2$—;
one of $Y^{13}$ and $Y^{14}$ is —S— while the other is —CH$_2$—;
one of x'y' and z' is —O— while the others are —CH$_2$—;
Ring A' is heteroaryl, cycloalkyl, or heterocycloalkyl;
Ring B' is aryl, heteroaryl, cycloalkyl, or heterocycloalkyl;
Ring C' is aryl, heteroaryl, cycloalkyl, or heterocycloalkyl;
Ring D' is aryl, heteroaryl, cycloalkyl, or heterocycloalkyl;
Ring E' is aryl, heteroaryl, cycloalkyl, or heterocycloalkyl;

Ring F' is aryl, heteroaryl, cycloalkyl, or heterocycloalkyl;
Ring G' is aryl, heteroaryl, cycloalkyl, or heterocycloalkyl;
Ring H' is bicyclic aryl, heteroaryl, cycloalkyl, or heterocycloalkyl;
Ring I' is aryl,
Ring J' is aryl,
$R^{22}$ is hydrogen, —NH$_2$, or halogen;
$R^{29}$ and $R^{30}$ are independently hydrogen, halogen, $C_{1-6}$ alkyl, aryl, heteroaryl, cycloalkyl, heterocycloalkyl;
each $R^{23}$, $R^{24}$, $R^{25}$, $R^{26}$, $R^{27}$, $R^{28}$, $R^{31}$, and $R^{32}$ is independently hydrogen, halogen, —CF$_3$, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^a$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
$R^b$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
each $R^c$ and $R^d$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{1-6}$ heteroalkyl, substituted or unsubstituted cycloalkyl, substituted or unsubstituted heterocycloalkyl, substituted or unsubstituted aryl, or substituted or unsubstituted heteroaryl;
or $R^c$ or $R^d$, together with the nitrogen atom to which they are attached, form an substituted or unsubstituted heterocycloalkyl or substituted or unsubstituted heteroaryl;
f is 1;
h is 1-3;
i is 1-3;
j is 1-3;
k is 1-3;
l is 1-3;
m is 1-3;
o is 1-3;
w is 1-3; and
e is 1-3.

In some embodiments of a compound of Formula (II), (II'), (II"), or a pharmaceutically acceptable salt, solvate, hydrate, tautomer, a stereoisomer, mixture of stereoisomers, or an isotopic variant thereof, $X_{11}$ is O and $X_{12}$ is N.

In some embodiments of a compound of Formula (II), or a pharmaceutically acceptable salt, solvate, hydrate, tautomer, a stereoisomer, mixture of stereoisomers, or an isotopic variant thereof, $X_{11}$ is N and $X_{12}$ is O.

In some embodiments of a compound of Formula (II), (II'), (II"), or a pharmaceutically acceptable salt, solvate, hydrate, tautomer, a stereoisomer, mixture of stereoisomers, or an isotopic variant thereof $R^{22}$ is —NH$_2$. In some embodiments of a compound of Formula (I), or a pharmaceutically acceptable salt, solvate, hydrate, tautomer, a stereoisomer, mixture of stereoisomers, or an isotopic variant thereof $R^{22}$ is hydrogen. In some embodiments of a compound of Formula (II), (II'), (II"), or a pharmaceutically acceptable salt, solvate, hydrate, tautomer, a stereoisomer, mixture of stereoisomers, or an isotopic variant thereof, $R^{22}$ is a halogen. In some embodiments of a compound of Formula (II), (II'), (II"), or a pharmaceutically acceptable salt, solvate, hydrate, tautomer, a stereoisomer, mixture of stereoisomers, or an isotopic variant thereof, $R^{22}$ is —F, —Cl, or —Br.

In some embodiments of a compound of Formula (II), (II'), (II"), or a pharmaceutically acceptable salt, solvate, hydrate, tautomer, a stereoisomer, mixture of stereoisomers, or an isotopic variant thereof, f is 1.

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIa):

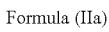
Formula (IIa)

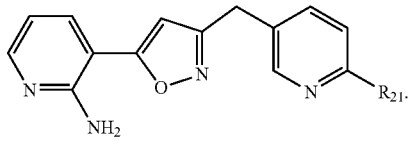

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIb):

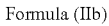
Formula (IIb)

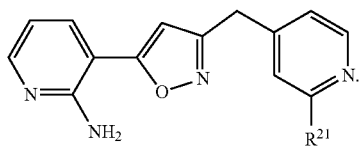

In some embodiments of a compound of Formula (II), or a pharmaceutically acceptable salt, solvate, hydrate, tautomer, a stereoisomer, mixture of stereoisomers, or an isotopic variant thereof, the compound of Formula (II) is of Formula (IIc):

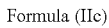
Formula (IIc)

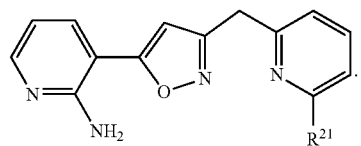

In some embodiments of a compound of Formula (II') or (II"), or a pharmaceutically acceptable salt, solvate, hydrate, tautomer, a stereoisomer, mixture of stereoisomers, or an isotopic variant thereof $R^{21}$ is

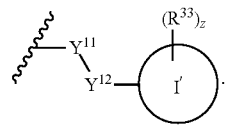

In some embodiments of a compound of Formula (II'), (II"), or a pharmaceutically acceptable salt, solvate, hydrate, tautomer, a stereoisomer, mixture of stereoisomers, or an isotopic variant thereof $Y^{11}$ is —O— and $Y^{12}$ is —CH$_2$—. In some embodiments of a compound of Formula (II') or (II"), or a pharmaceutically acceptable salt, solvate, hydrate, tautomer, a stereoisomer, mixture of stereoisomers, or an isotopic variant thereof $Y^{11}$ is —NH— and $Y^{12}$ is —CH$_2$—. In some embodiments of a compound of Formula (II') or (II"), or a pharmaceutically acceptable salt, solvate, hydrate, tautomer, a stereoisomer, mixture of stereoisomers, or an isotopic variant thereof $Y^{12}$ is —O— and $Y^{11}$ is —CH$_2$—. In some embodiments of a compound of Formula (II') or (II"), or a pharmaceutically acceptable salt, solvate, hydrate, tautomer, a stereoisomer, mixture of stereoisomers, or an isotopic variant thereof $Y^{12}$ is —NH— and $Y^{11}$ is —CH$_2$—.

In some embodiments of a compound of Formula (II') or (II"), or a pharmaceutically acceptable salt, solvate, hydrate, tautomer, a stereoisomer, mixture of stereoisomers, or an isotopic variant thereof Ring I' is aryl. In some embodiments of a compound of Formula (II') or (II"), or a pharmaceutically acceptable salt, solvate, hydrate, tautomer, a stereoisomer, mixture of stereoisomers, or an isotopic variant thereof Ring I' is phenyl. In some embodiments of a compound of Formula (II') or (II"), or a pharmaceutically acceptable salt, solvate, hydrate, tautomer, a stereoisomer, mixture of stereoisomers, or an isotopic variant thereof Ring I' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof z is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof z is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof z is 3. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is hydrogen, methyl, or —F. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is hydrogen. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is methyl. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is a halogen. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is —Cl. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is —F. In some embodiments of a compound of Formula (II') or (II"), or a pharmaceutically acceptable salt, solvate, hydrate, tautomer, a stereoisomer, mixture of stereoisomers, or an isotopic variant thereof $R^{33}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{21}$ is —F. In some embodiments of a compound of Formula (II), (IIa), (IIb), (IIc), (II') or (II"), or a pharmaceutically acceptable salt, solvate, hydrate, tautomer, a stereoisomer, or an isotopic variant thereof $R^{21}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{21}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{21}$ is In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $Y^{11}$ is —O— and $Y^{12}$ is —CH$_2$—. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $Y^{11}$ is —NH— and $Y^{12}$ is —CH$_2$—. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $Y^{12}$ is —O— and $Y^{11}$ is —CH$_2$—. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $Y^{12}$ is —NH— and $Y^{11}$ is —CH$_2$—.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is furyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is oxazolyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cyclopropyl and cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cyclohexyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is cyclopentyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring A' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof h is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof h is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof h is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{23}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is

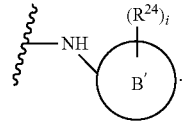

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is aryl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is phenyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof i is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof i is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof i is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{21}$ is In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is aryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is phenyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring C' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring C' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring C' is oxetanyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof j is 1. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof j is 2. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof j is 3. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{23}$ is hydrogen, methyl, or —F. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is hydrogen. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is methyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is halogen. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is —Cl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is —F. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{25}$ is —Br.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{21}$ is

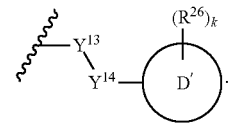

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof wherein $Y^{13}$ is S and $Y^{14}$ is —$CH_2$—. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof wherein $Y^{13}$ is —$CH_2$— and $Y^{14}$ is —S—.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is aryl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is phenyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is naphthyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is heteroaryl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring D' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring D' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof k is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof k is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof k is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{26}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²³ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁶ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²¹ is In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof x' is O; y' is —CH₂—; and z' is —CH₂—. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof x' is —CH₂—; y' is —O—; and z' is —CH₂—. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof x' is —CH₂—; y' is —CH₂—; and z' is —O—.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is aryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is phenyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring E' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof l is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof l is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof l is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is a halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{27}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is

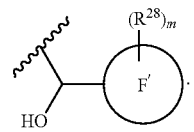

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof wherein Ring F' is aryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof wherein Ring F' is phenyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring B' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring F' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof m is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof m is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof m is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{24}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is —Br.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof $R^{21}$ is

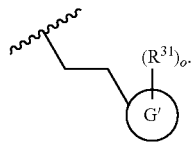

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is aryl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is phenyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is naphthyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heteroaryl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is pyridinyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is isoxazolyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is thienyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is thiazolyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is pyrazolyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is pyrimidinyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is furyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is cycloalkyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is $C_3$-$C_6$ cycloalkyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is cyclopropyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is cyclobutyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is cyclopentyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is cyclohexyl.

In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heterocycloalkyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II''), or a pharmaceutically acceptable salt, solvate, hydrate, tautomer, a stereoisomer, mixture of stereoisomers, or an isotopic variant thereof Ring G' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring G' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof o is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof o is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof o is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{31}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{21}$ is

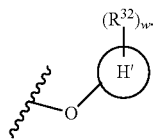

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is aryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heteroaryl selected from azaindolyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heteroaryl selected from pyridinyl, isoxazolyl, thienyl, thiazolyl, pyrazolyl, pyrimidinyl, furyl, and oxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is pyridinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is isoxazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is thienyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is thiazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is pyrazolyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is pyrimidinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is furyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is $C_3$-$C_6$ cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is cyclopropyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is cyclobutyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is cyclopentyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heterocycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is heterocycloalkyl selected from tetrahydrofuranyl, piperazinyl, oxetanyl, indolinyl, 2H-pyranyl, 4H-pyranyl, dioxanyl, 1,3-dioxolanyl, pyrazolinyl, imidazolinyl, and quinolizinyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring H' is oxetanyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof w is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof w is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof w is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ heteroalkyl, substituted or unsubstituted cycloalkyl, substituted or unsubstituted heterocycloalkyl, substituted or unsubstituted aryl, or substituted or unsubstituted heteroaryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is -halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{32}$ is —Br.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{28}$ is

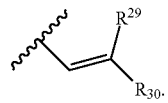

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof wherein $R^{29}$ is hydrogen and $R^{30}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{29}$ is hydrogen and $R^{30}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof $R^{29}$ is $C_1$-$C_6$ alkyl and $R^{30}$ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁹ is alkyl and R³⁰ is C₁-C₆ alkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁹ is hydrogen and R³⁰ is C₁-C₆ alkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁹ is hydrogen and R³⁰ is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁹ is hydrogen and R³⁰ is cyclopropyl, cyclobutyl, cyclopentyl, or cyclohexyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁰ is hydrogen and R²⁹ is cycloalkyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R²⁹ is hydrogen and R³⁰ is cyclopropyl, cyclobutyl, cyclopentyl, or cyclohexyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof acceptable salt, solvate, tautomer, or stereoisomer thereof R²¹ is

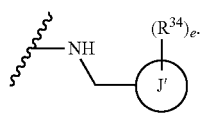

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring J' is aryl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring J' is phenyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof Ring J' is naphthyl.

In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof e is 1. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof e is 2. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof e is 3. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is hydrogen, methyl, or —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is hydrogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is methyl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is a halogen. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is —Cl. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is —F. In some embodiments of a compound of Formula (II), (IIa), (IIb), (IIc), (II') or (II"), or a pharmaceutically acceptable salt, solvate, hydrate, tautomer, a stereoisomer, mixture of stereoisomers, or an isotopic variant thereof R³⁴ is —Br.

In some embodiments of a compound of Formula (III) is not hydrogen (2-(2-amino-3-(3-(4-((pyridin-2-yloxy) methyl)benzyl)isoxazol-5-yl)pyridin-1-ium-1-yl)ethyl) phosphonate or a compound having structural formula:

Compound 1

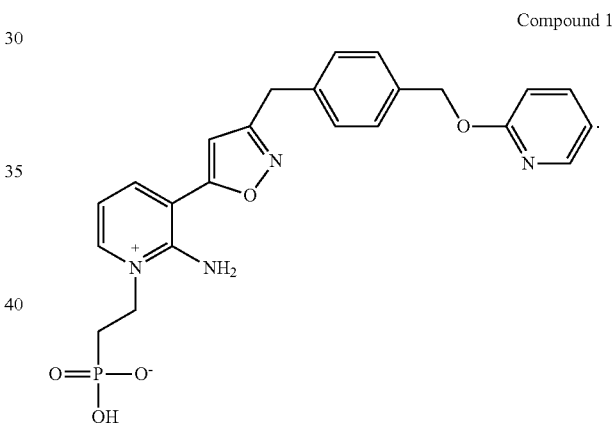

In some embodiments of a compound of Formula (III) is not 3-(3-(4-((pyridin-2-yloxy)methyl)benzyl)isoxazol-5-yl) pyridin-2-amine or a compound having structural formula:

Compound 2

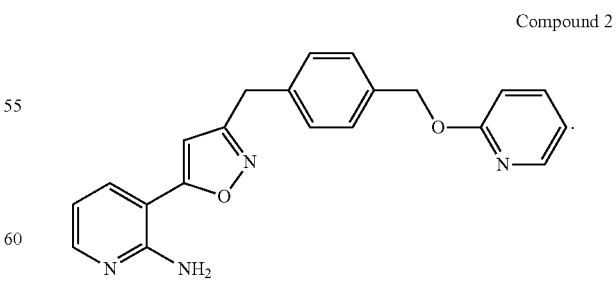

In some embodiments, there is a compound, or a pharmaceutically acceptable salt, solvate or stereoisomer thereof, having a structure selected from the compounds in Table 1.

TABLE 1

| Ex. | Structure | Name |
|---|---|---|
| B | 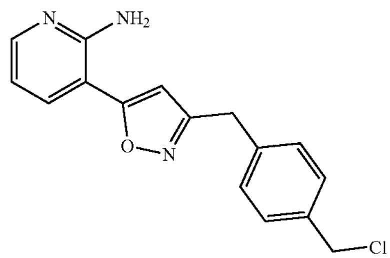 [SMILES: Nc1ncccc1-c1cc(Cc2ccc(CCl)cc2)no1] | 3-(3-(4-(chloromethyl)benzyl)isoxazol-5-yl)pyridin-2-amine |
| C | 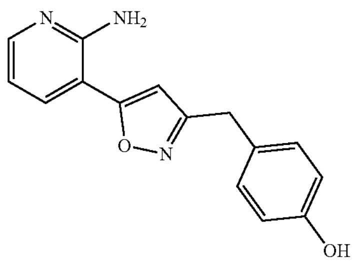 [SMILES: Nc1ncccc1-c1cc(Cc2ccc(O)cc2)no1] | 4-((5-(2-aminopyridin-3-yl)isoxazol-3-yl)methyl)phenol |
| E | 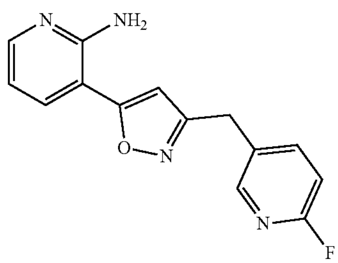 [SMILES: Nc1ncccc1-c1cc(Cc2ccc(F)nc2)no1] | 3-(3-((6-fluoropyridin-3-yl)methyl)isoxazol-5-yl)pyridin-2-amine |
| 1 | 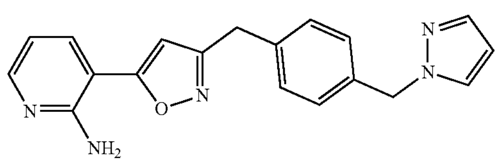 [SMILES: Nc1ncccc1-c1cc(Cc2ccc(Cn3cccn3)cc2)no1] | 3-(3-(4-((1H-pyrazol-1-yl)methy)benzyl)isoxazol-5-yl)pyridin-2-amine |
| 2 | 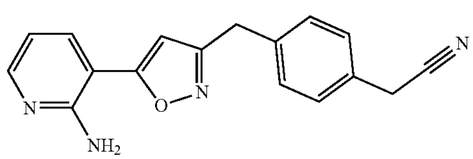 [SMILES: N#CCc1ccc(Cc2cc(-c3cccnc3N)on2)cc1] | 2-(4-((5-(2-aminopyridin-3-yl)isoxazol-3-yl)methyl)phenyl)acetonitrile |
| 3 | 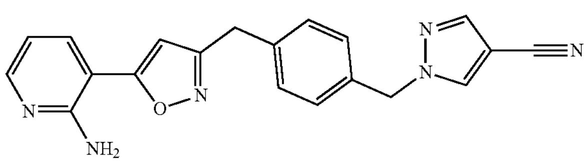 [SMILES: N#Cc1cnn(Cc2ccc(Cc3cc(-c4cccnc4N)on3)cc2)c1] | 1-(4-((5-(2-aminopyridin-3-yl)isoxazol-3-yl)methy)benzyl)-1H-pyrazole-4-carbonitrile |
| 4 | 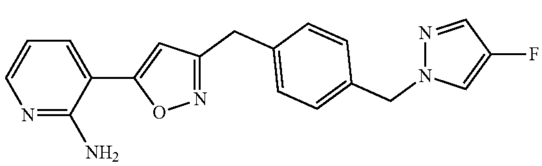 [SMILES: Nc1ncccc1-c1cc(Cc2ccc(Cn3cc(F)cn3)cc2)no1] | 3-(3-(4-((4-fluoro-1H-pyrazol-1-yl)methyl)benzyl)isoxazol-5-yl)pyridin-2-amine |

TABLE 1-continued

| Ex. | Structure | Name |
|---|---|---|
| 5 | 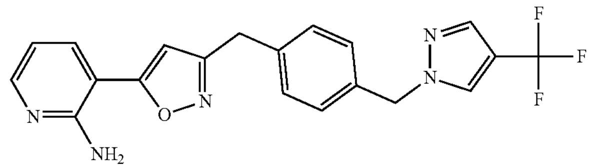 [SMILES: Nc1ncccc1-c1cc(Cc2ccc(Cn3cc(C(F)(F)F)cn3)cc2)no1] | 3-(3-(4-((4-(trifloromethyl)-1H-pyrazol-1-yl)methyl)benzyl)isoxazol-5-yl)pyridin-2-amine |
| 6 | 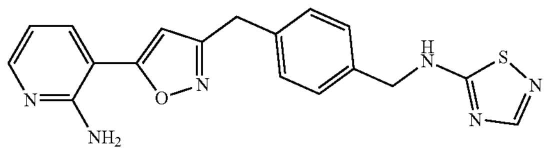 [SMILES: Nc1ncccc1-c1cc(Cc2ccc(CNc3ncns3)cc2)no1] | N-(4-((5-(2-aminopyridin-3-yl)isoxazol-3-yl)methyl)benzyl)-1,2,4-thiadiazol-5-amine |
| 7 | 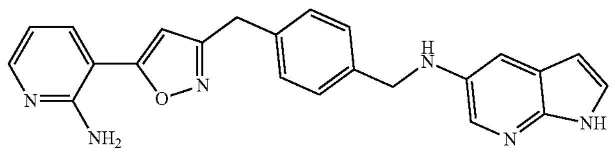 [SMILES: Nc1ncccc1-c1cc(Cc2ccc(CNc3cnc4[nH]ccc4c3)cc2)no1] | N-(4-((5-(2-aminopyridin-3-yl)isoxazol-3-yl)methyl)benzyl)-1H-pyrrolo[2,3-b]pyridin-5-amine |
| 8 | 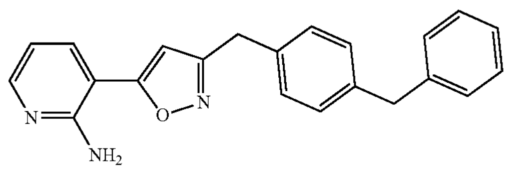 | 3-(3-(4-benzylbenzyl)isoxazol-5-yl)pyridin-2-amine |
| 9 | 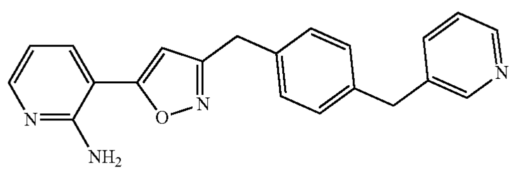 | 3-(3-(4-(pyridin-3-ylmethyl)benzyl)isoxazol-5-yl)pyridin-2-amine |
| 10 | 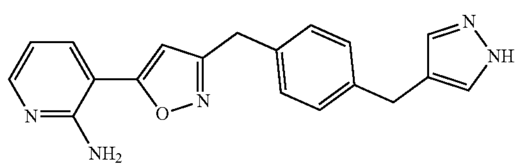 [SMILES: Nc1ncccc1-c1cc(Cc2ccc(Cc3cn[nH]c3)cc2)no1] | 3-(3-(4-((1H-pyrazol-4-yl)methyl)benzyl)isoxazol-5-yl)pyridin-2-amine |
| 11 | 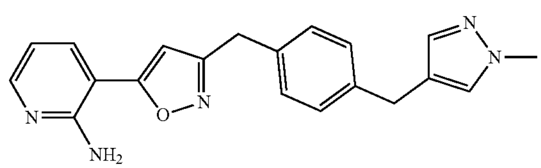 [SMILES: Cn1cc(Cc2ccc(Cc3cc(-c4cccnc4N)on3)cc2)cn1] | 3-(3-(4-((1-methyl-1H-pyrazol-4-yl)methyl)benzyl)isoxazol-5-yl)pyridin-2-amine |
| 12 | 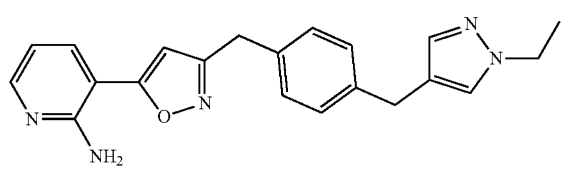 [SMILES: CCn1cc(Cc2ccc(Cc3cc(-c4cccnc4N)on3)cc2)cn1] | 3-(3-(4-((1-ethyl-1H-pyrazol-4-yl)methyl)benzyl)isoxazol-5-yl)pyridin-2-amine |
| 13 | 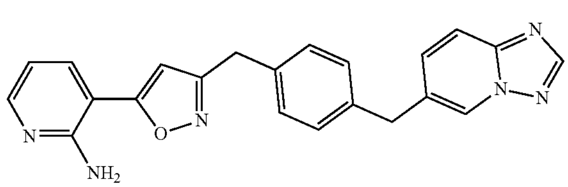 [SMILES: Nc1ncccc1-c1cc(Cc2ccc(Cc3ccc4ncnn4c3)cc2)no1] | 3-(3-(4-([1,2,4]triazolo[1,5-a]pyridin-6-ylmethyl)benzyl)isoxazol-5-yl)pyridin-2-amine |

TABLE 1-continued

| Ex. | Structure | Name |
|---|---|---|
| 14 | 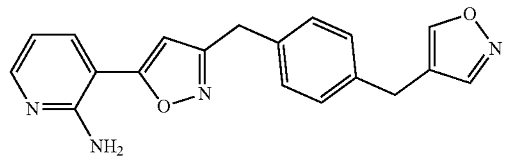 | 3-(3-(4-(isoxazol-4-ylmethyl)benzyl)isoxazol-5-yl)pyridin-2-amine |
| 15 | 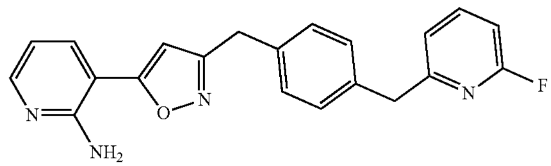 | 3-(3(4-((6-fluoropyridin-2-yl)methyl)benzyl)isoxazol-5-yl)pyridin-2-amine |
| 16 | 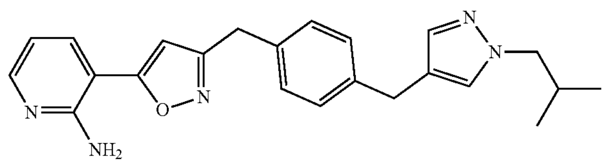 [SMILES: CC(C)Cn1cc(Cc2ccc(Cc3cc(-c4cccnc4N)on3)cc2)cn1] | 3-(3-(4-((1-isobutyl-1H-pyrazol-4-yl)methyl)benzyl)isoxazol-5-yl)pyridin-2-amine |
| 17 | 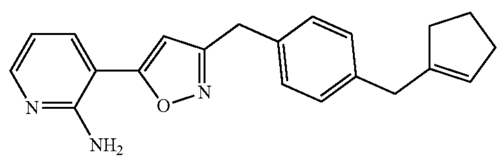 [SMILES: Nc1ncccc1-c1cc(Cc2ccc(CC3=CCCC3)cc2)no1] | 3-(3-(4-(cyclopent-1-en-1-ylmethyl)benzyl)isoxazol-5-y)pyridin-2-amine |
| 18 | 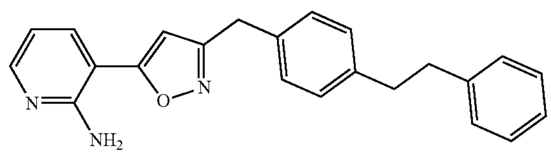 | 3-(3-(4-phenethylbenzyl)isoxazol-5-yl)pyridin-2-amine |
| 19 | 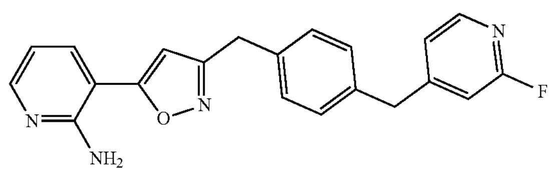 | 3-(3-(4-((2-fluoropyridin-4-yl)methyl)benzyl)isoxazol-5-yl)pyridin-2-amine |
| 20 | 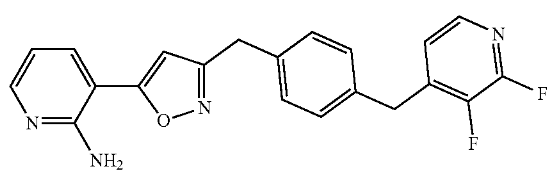 | 3-(3-(4-((2,3-difluoropyridin-4-yl)methyl)benzyl)isoxazol-5-yl)pyridin-2-amine |
| 21 | 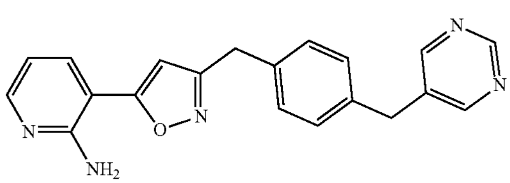 [SMILES: Nc1ncccc1-c1cc(Cc2ccc(Cc3cncnc3)cc2)no1] | 3-(3-(4-(pyrimidin-5-ylmethyl)benzyl)isoxazol-5-y)pyridin-2-amine |
| 22 | 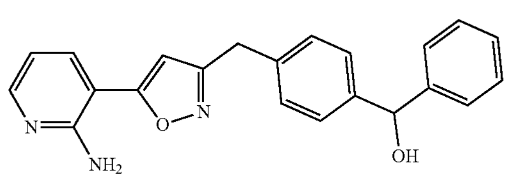 [SMILES: Nc1ncccc1-c1cc(Cc2ccc(C(O)c3ccccc3)cc2)no1] | (4-((5-(2-aminopyridin-3-yl)isoxazol-3-yl)methyl)phenyl)(phenyl)methanol |

TABLE 1-continued

| Ex. | Structure | Name |
|---|---|---|
| 23 | 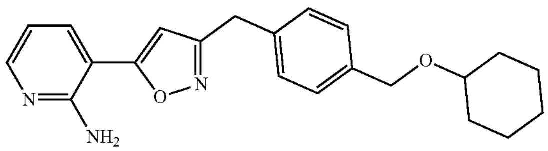 | 3-(3-(4-((cyclohexyloxy)methyl)benzyl)isoxazol-5-yl)pyridin-2-amine |
| 24 | 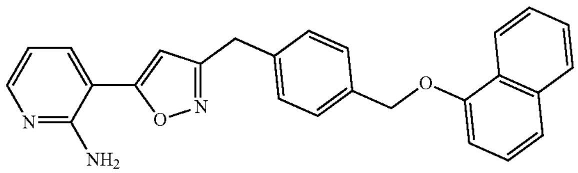 [SMILES: Nc1ncccc1-c1cc(Cc2ccc(COc3cccc4ccccc34)cc2)no1] | 3-(3-(4-((naphthalen-1-yloxy)methyl)benzyl)isoxazol-5-yl)pyridin-2-amine |
| 25 | 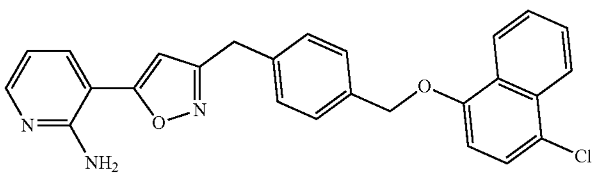 [SMILES: Nc1ncccc1-c1cc(Cc2ccc(COc3ccc(Cl)c4ccccc34)cc2)no1] | 3-(3-(4-(((4-chloronaphthalen-1-yl)oxy)methyl)benzyl)isoxazol-5-yl)pyridin-2-amine |
| 26 | 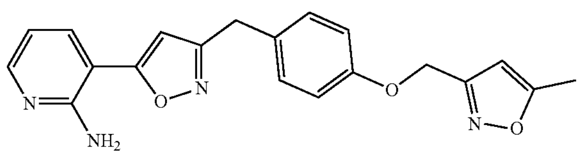 [SMILES: Cc1cc(COc2ccc(Cc3cc(-c4cccnc4N)on3)cc2)no1] | 3-(3-(4-((5-methylisoxazol-3-yl)methoxy)benzyl)isoxazol-5-yl)pyridin-2-amine |
| 27 | 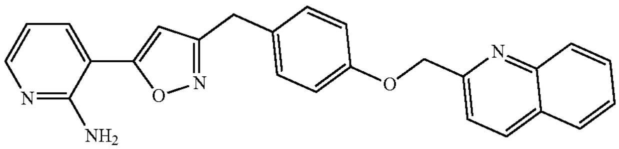 [SMILES: Nc1ncccc1-c1cc(Cc2ccc(OCc3ccc4ccccc4n3)cc2)no1] | 3-(3-(4-(quinolin-2-ylmethoxy)benzyl)isoxazol-5-yl)pyridin-2-amine |
| 28 | 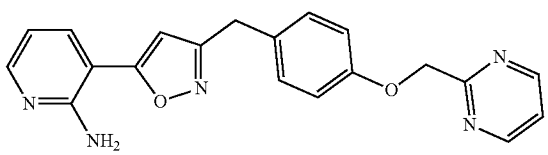 | 3-(3-(4-(pyrimidin-2-ylmethoxy)benzyl)isoxazol-5-yl)pyridin-2-amine |
| 29 | 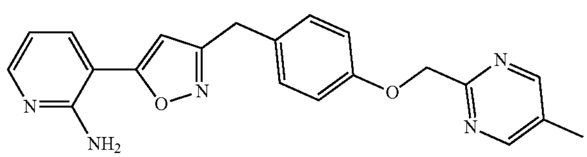 [SMILES: Cc1cnc(COc2ccc(Cc3cc(-c4cccnc4N)on3)cc2)nc1] | 3-(3-(4-((5-methylpyrimidin-2-yl)methoxy)benzyl)isoxazol-5-yl)pyridin-2-amine |
| 30 | 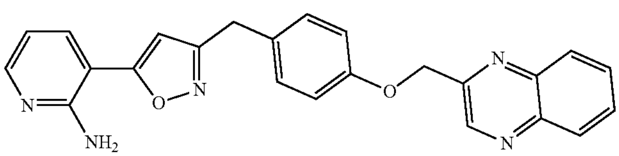 [SMILES: Nc1ncccc1-c1cc(Cc2ccc(OCc3cnc4ccccc4n3)cc2)no1] | 3-(3-(4-(quinoxalin-2-ylmethoxy)benzyl)isoxazol-5-yl)pyridin-2-amine |
| 31 | 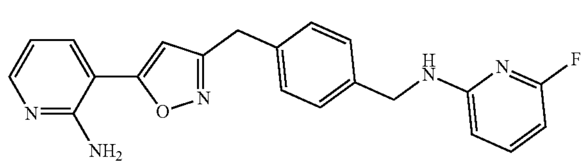 | N-(4-((5-(2-aminopyridin-3-yl)isoxazol-3-yl)methyl)benzyl)-6-fluoropyridin-2-amine |

TABLE 1-continued

| Ex. | Structure | Name |
|---|---|---|
| 32 | 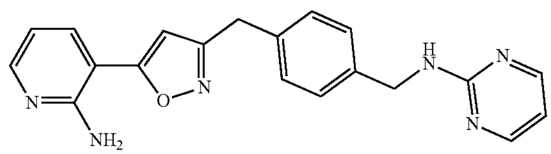 [SMILES: Nc1ncccc1-c1cc(Cc2ccc(CNc3ncccn3)cc2)no1] | N-(4-((5-(2-aminopyridin-3-yl)isoxazol-3-yl)methyl)benzyl)pyrimidin-2-amine |
| 33 | 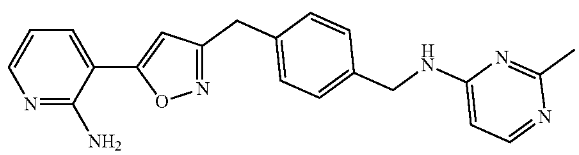 | N-(4-((5-(2-aminopyridin-3-yl)isoxazol-3-yl)methyl)benzyl)-2-methylpyrimidin-4-amine |
| 34 | 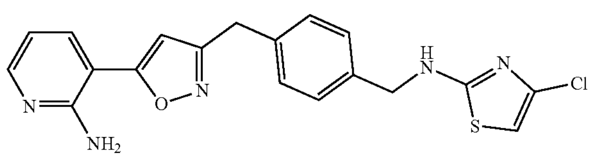 [SMILES: Nc1ncccc1-c1cc(Cc2ccc(CNc3nc(Cl)cs3)cc2)no1] | N-(4-((5-(2-aminopyridin-3-yl)isoxazol-3-yl)methyl)benzyl)-4-chlorothiazol-2-amine |
| 35 | 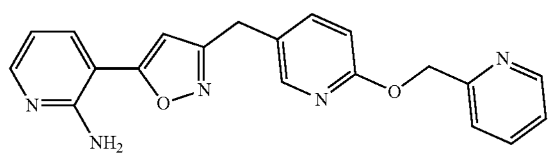 | 3-(3-((6-(pyridin-2-ylmethoxy)pyridin-3-yl)methyl)isoxazol-5-yl)pyridin-2-amine |
| 36 | 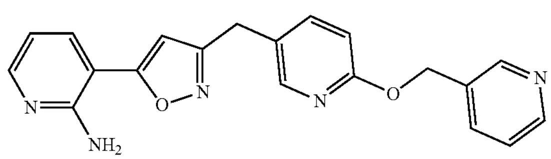 | 3-(3-((6-(pyridin-3-ylmethoxy)pyridin-3-yl)methyl)isoxazol-5-yl)pyridin-2-amine |
| 37 | 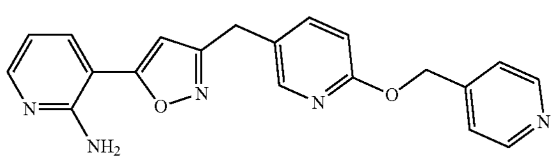 | 3-(3-((6-(pyridin-4-ylmethoxy)pyridin-3-yl)methyl)isoxazol-5-yl)pyridin-2-amine |
| 38 | 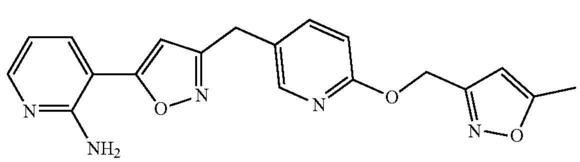 [SMILES: Cc1cc(COc2ccc(Cc3cc(-c4cccnc4N)on3)cn2)no1] | 3-(3-((6-((5-methylisoxazol-3-yl)methoxy)pyridin-3-yl)methyl)isoxazol-5-yl)pyridin-2-amine |
| 39 | 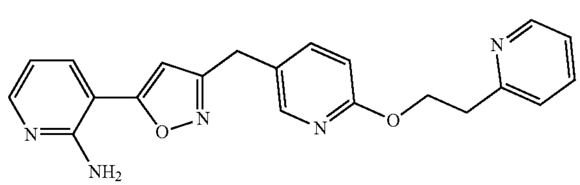 [SMILES: Nc1ncccc1-c1cc(Cc2ccc(OCCc3ccccn3)nc2)no1] | 3-(3-((6-(2-(pyridin-2-yl)ethoxy)pyridin-3-yl)methyl)isoxazol-5-yl)pyridin-2-amine |
| 40 | 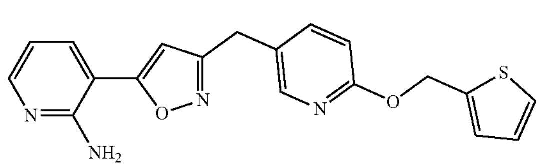 | 3-(3-((6-(thiophen-2-ylmethoxy)pyridin-3-yl)methyl)isoxazol-5-yl)pyridin-2-amine |

TABLE 1-continued

| Ex. | Structure | Name |
|---|---|---|
| 41 | 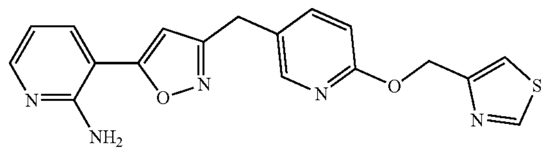 [SMILES: Nc1ncccc1-c1cc(Cc2ccc(OCc3cscn3)nc2)no1] | 3-(3-((6-(thiazol-4-ylmethoxy)pyridin-3-yl)methyl)isoxazol-5-yl)pyridin-2-amine |
| 42 | 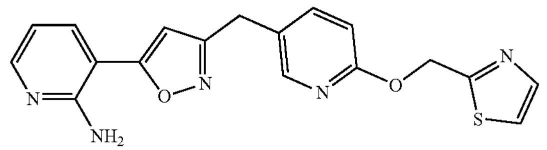 | 3-(3-((6-(thiazol-2-ylmethoxy)pyridin-3-yl)methyl)isoxazol-5-yl)pyridin-2-amine |
| 43 | 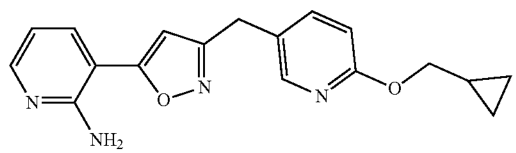 [SMILES: Nc1ncccc1-c1cc(Cc2ccc(OCC3CC3)nc2)no1] | 3-(3-((6-(cyclopropylmethoxy)pyridin-3-yl)methyl)isoxazol-5-yl)pyridin-2-amine |
| 44 | 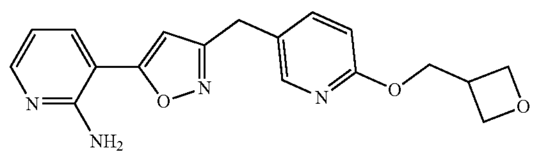 [SMILES: Nc1ncccc1-c1cc(Cc2ccc(OCC3COC3)nc2)no1] | 3-(3-((6-(oxetan-3-ylmethoxy)pyridin-3-yl)methyl)isoxazol-5-yl)pyridin-2-amine |
| 45 | 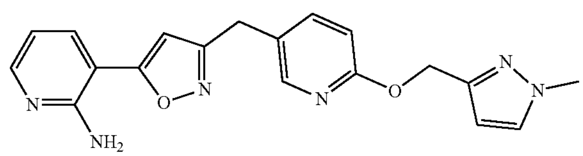 [SMILES: Cn1ccc(COc2ccc(Cc3cc(-c4cccnc4N)on3)cn2)n1] | 3-(3-((6-((1-methyl-1H-pyrazol-3-yl)methoxy)pyridin-3-yl)methyl)isoxazol-5-yl)pyridin-2-amine |
| 46 | 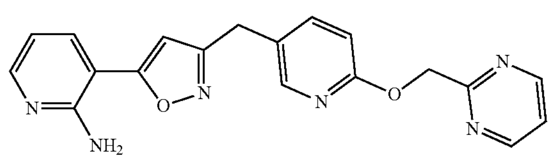 | 3-(3-((6-(pyrimidin-2-ylmethoxy)pyridin-3-yl)methyl)isoxazol-5-yl)pyridin-2-amine |
| 47 | 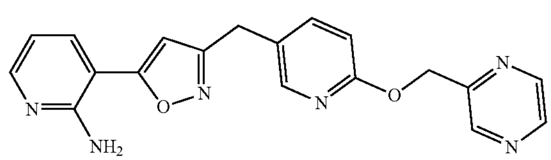 | 3-(3-((6-(pyrazin-2-ylmethoxy)pyridin-3-yl)methyl)isoxazol-5-yl)pyridin-2-amine |
| 48 | 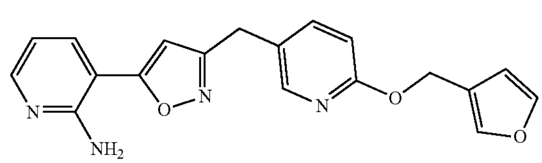 [SMILES: Nc1ncccc1-c1cc(Cc2ccc(OCc3ccoc3)nc2)no1] | 3-(3-((6-(furan-3-ylmethoxy)pyridin-3-yl)methyl)isoxazol-5-yl)pyridin-2-amine |
| 49 | 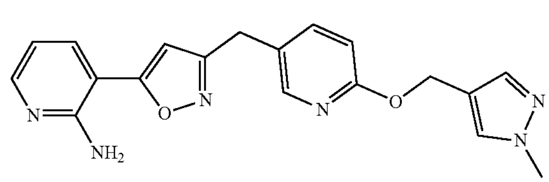 [SMILES: Cn1cc(COc2ccc(Cc3cc(-c4cccnc4N)on3)cn2)cn1] | 3-(3-((6-((1-methyl-1H-pyrazol-4-yl)methoxy)pyridin-3-yl)methyl)isoxazol-5-yl)pyridin-2-amine |

TABLE 1-continued

| Ex. | Structure | Name |
|---|---|---|
| 50 | 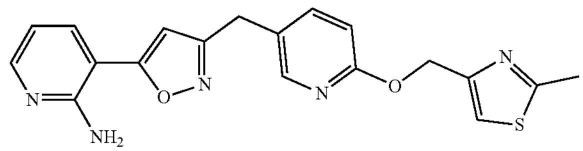 [SMILES: Cc1nc(COc2ccc(Cc3cc(-c4cccnc4N)on3)cn2)cs1] | 3-(3-((6-((2-methylthiazol-4-yl)methoxy)pyridin-3-yl)methyl)isoxazol-5-yl)pyridin-2-amine |
| 51 | 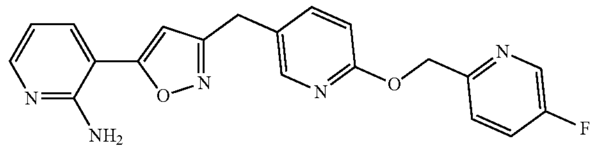 | 3-(3-((6-((5-fluoropyridin-2-yl)methoxy)pyridin-3-yl)methyl)isoxazol-5-yl)pyridin-2-amine |
| 52 | 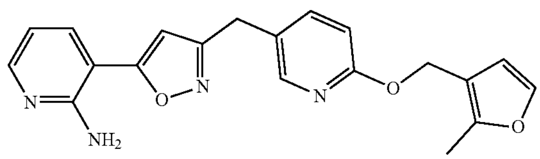 [SMILES: Cc1occc1COc1ccc(Cc2cc(-c3cccnc3N)on2)cn1] | 3-(3-((6-((2-methylfuran-3-yl)methoxy)pyridin-3-yl)methyl)isoxazol-5-yl)pyridin-2-amine |
| 53 | 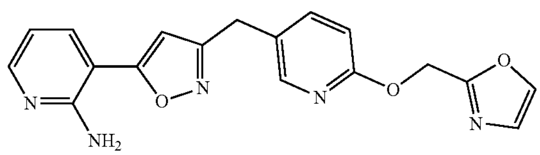 | 3-(3-((6-(oxazol-2-ylmethoxy)pyridin-3-yl)methyl)isoxazol-5-yl)pyridin-2-amine |
| 54 | 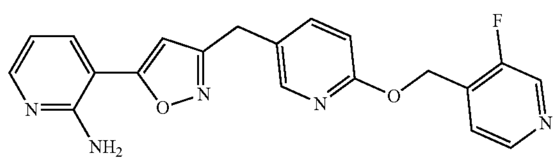 [SMILES: Nc1ncccc1-c1cc(Cc2ccc(OCc3ccncc3F)nc2)no1] | 3-(3-((6-((3-fluoropyridin-4-yl)methoxy)pyridin-3-yl)methyl)isoxazol-5-yl)pyridin-2-amine |
| 55 | 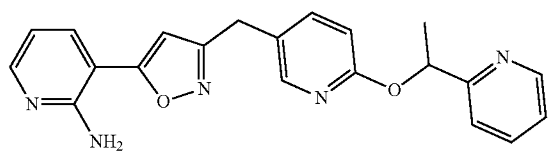 | 3-(3-((6-(1-(pyridin-2-yl)ethoxy)pyridin-3-yl)methyl)isoxazol-3-yl)pyridin-2-amine |
| 56 | 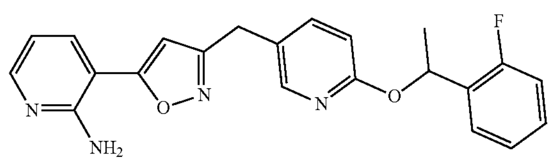 [SMILES: CC(Oc1ccc(Cc2cc(-c3cccnc3N)on2)cn1)c1ccccc1F] | 3-(3-((6-(1-(2-fluorophenyl)ethoxy)pyridin-3-yl)methyl)isoxazol-5-yl)pyridin-2-amine |
| 57 | 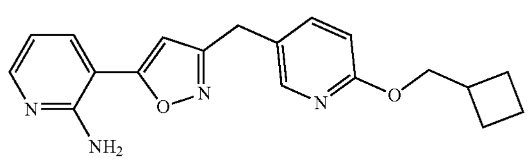 [SMILES: Nc1ncccc1-c1cc(Cc2ccc(OCC3CCC3)nc2)no1] | 3-(3-((6-(cyclobutylmethoxy)pyridin-3-yl)methyl)isoxazol-5-yl)pyridin-2-amine |
| 58 | 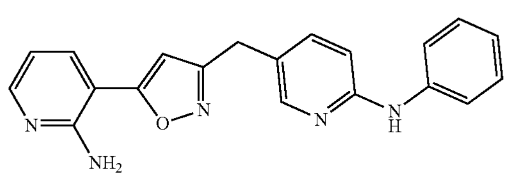 | 5-((5-(2-aminopyridin-3-yl)isoxazol-3-yl)methyl)-N-phenylpyridin-2-amine |

TABLE 1-continued

| Ex. | Structure | Name |
|---|---|---|
| 59 | 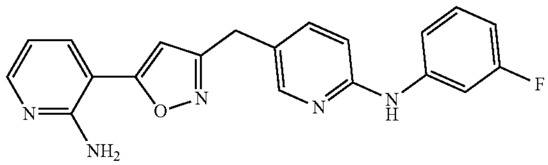 | 5-((5-(2-aminopyridin-3-yl)isoxazol-3-yl)methyl)-N-(3-fluorophenyl)pyridin-2-amine |
| 60 | 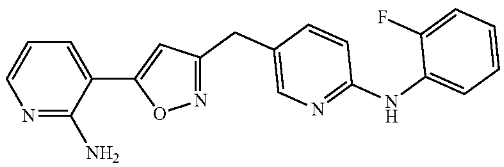 | 5-((5-(2-aminopyridin-3-yl)isoxazol-3-yl)methyl)-N-(2-fluorophenyl)pyridin-2-amine |
| 61 | 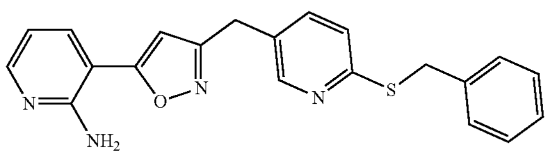 [SMILES: Nc1ncccc1-c1cc(Cc2ccc(SCc3ccccc3)nc2)no1] | 3-(3-((6-(benzylthio)pyridin-3-yl)methyl)isoxazol-5-yl)pyridin-2-amine |
| 62 | 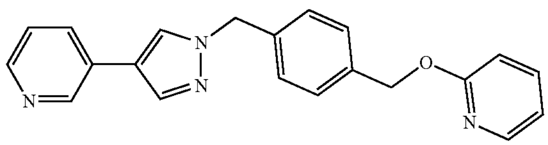 [SMILES: c1ccc(OCc2ccc(Cn3cc(-c4cccnc4)cn3)cc2)nc1] | 2-((4-((4-(pyridin-3-yl)-1H-pyrazol-1-yl)methyl)benzyl)oxy)pyridine |
| 63 | 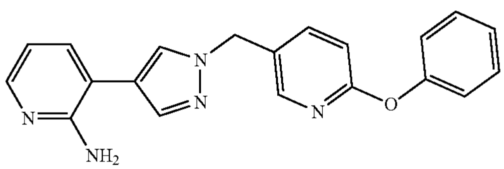 | 3-(1-((6-phenoxypyridin-3-yl)methyl)-1H-pyrazol-4-yl)pyridin-2-amine |
| 64 | 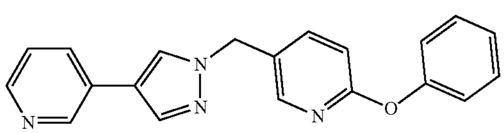 [SMILES: c1ccc(Oc2ccc(Cn3cc(-c4cccnc4)cn3)cn2)cc1] | 2-phenoxy-5-((4-(pyridin-3-yl)-1H-pyrazol-1-yl)methyl)pyridine |
| 65 | 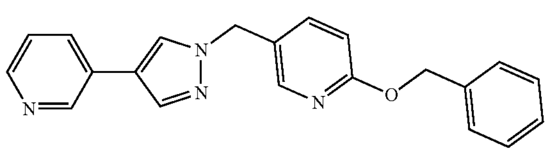 [SMILES: c1ccc(COc2ccc(Cn3cc(-c4cccnc4)cn3)cn2)cc1] | 2-(benzyloxy)-5-((4-(pyridin-3-yl)-1H-pyrazol-1-yl)methyl)pyridine |
| 66 | 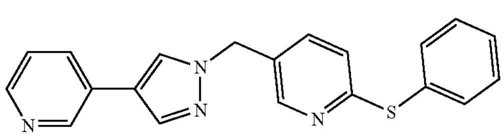 | 2-(phenylthio)-5-((4-(pyridin-3-yl)-1H-pyrazol-1-yl)methyl)pyridine |
| 67 | 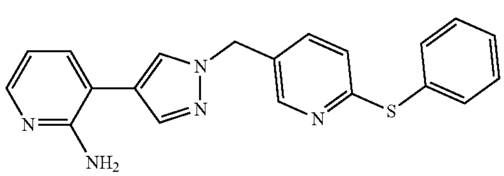 [SMILES: Nc1ncccc1-c1cnn(Cc2ccc(Sc3ccccc3)nc2)c1] | 3-(1-((6-(phenylthio)pyridin-3-yl)methyl)-1H-pyrazol-4-yl)pyridin-2-amine |
| 68 | 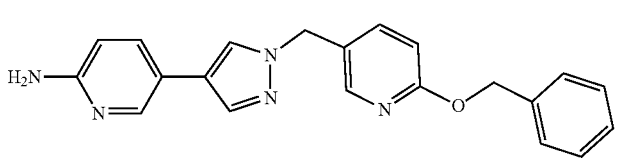 [SMILES: Nc1ccc(-c2cnn(Cc3ccc(OCc4ccccc4)nc3)c2)cn1] | 5-(1-((6-(benzyloxy)pyridin-3-yl)methyl)-1H-pyrazol-4-yl)pyridin-2-amine |

TABLE 1-continued

| Ex. | Structure | Name |
|---|---|---|
| 69 | 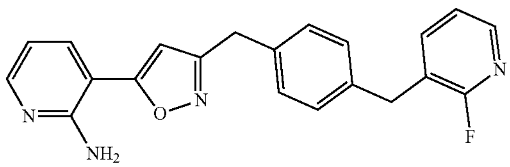 [SMILES: Nc1ncccc1-c1cc(Cc2ccc(Cc3cccnc3F)cc2)no1] | 3-(3-(4-((2-fluoropyridin-3-yl)methyl)benzyl)isoxazol-5-yl)pyridin-2-amine |
| 70 | 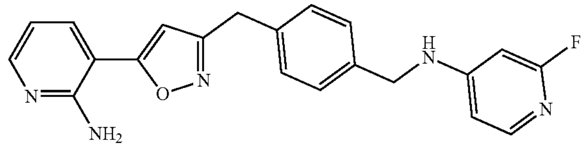 [SMILES: Nc1ncccc1-c1cc(Cc2ccc(CNc3ccnc(F)c3)cc2)no1] | 3-(3-(4-(((2-fluoropyridin-4-yl)amino)methyl)benzyl)isoxazol-5-yl)pyridin-2-amine |
| 71 | 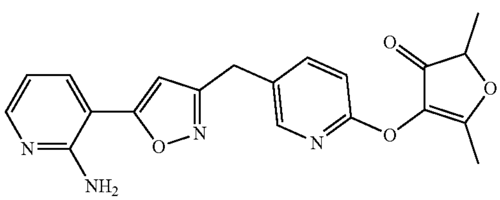 [SMILES: CC1=C(Oc2ccc(Cc3cc(-c4cccnc4N)on3)cn2)C(=O)C(C)O1] | 4-((5-((5-(2-aminopyridin-3-yl)isoxazol-3-yl)methyl)pyridin-2-yl)oxy)-2,5-dimethylfuran-3(2H)-one |
| 72 | 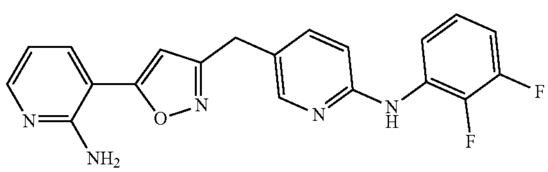 [SMILES: Nc1ncccc1-c1cc(Cc2ccc(Nc3cccc(F)c3F)nc2)no1] | 5-((5-(2-aminopyridin-3-yl)isoxazol-3-yl)methyl)-N-(2,3-difluorophenyl)pyridin-2-amine |
| 73 | 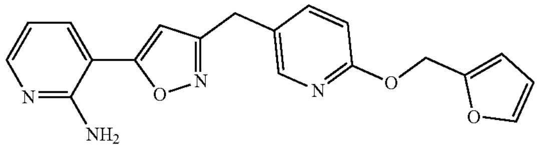 [SMILES: Nc1ncccc1-c1cc(Cc2ccc(OCc3ccco3)nc2)no1] | 3-(3-((6-(furan-2-ylmethoxy)pyridin-3-yl)methyl)isoxazol-5-yl)pyridin-2-amine |
| 74 | 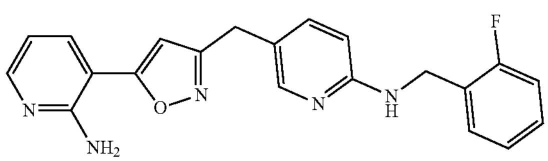 [SMILES: Nc1ncccc1-c1cc(Cc2ccc(NCc3ccccc3F)nc2)no1] | 5-((5-(2-aminopyridin-3-yl)isoxazol-3-yl)methyl)-N-(2-fluorobenzyl)pyridin-2-amine |
| 75 | 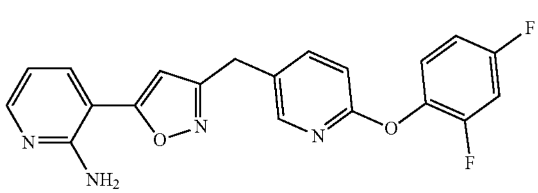 [SMILES: Nc1ncccc1-c1cc(Cc2ccc(Oc3ccc(F)cc3F)nc2)no1] | 3-(3-((6-(2,4-difluorophenoxy)pyridin-3-yl)methyl)isoxazol-5-yl)pyridin-2-amine |
| 76 | 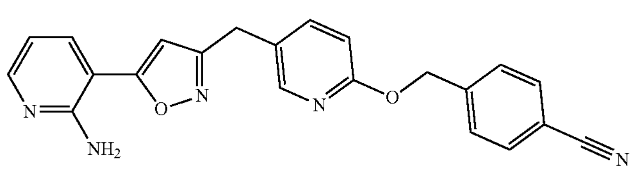 | 4-(((3-((5-(2-aminopyridin-3-yl)isoxazol-3-yl)methyl)pyridin-2-yl)oxy)methyl)benzonitrile |
| 77 | 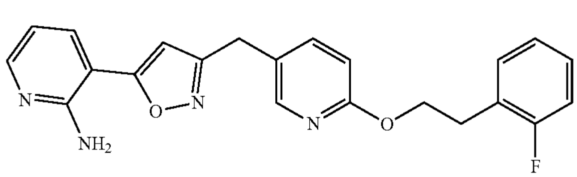 [SMILES: Nc1ncccc1-c1cc(Cc2ccc(OCCc3ccccc3F)nc2)no1] | 3-(3-((6-(2-fluorophenethoxy)pyridin-3-yl)methyl)isoxazol-5-yl)pyridin-2-amine |

TABLE 1-continued

| Ex. | Structure | Name |
|---|---|---|
| 78 | 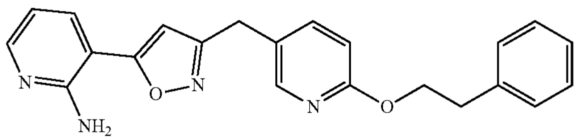 [SMILES: Nc1ncccc1-c1cc(Cc2ccc(OCCc3ccccc3)nc2)no1] | 3-(3-((6-phenethoxypyridin-3-yl)methyl)isoxazol-5-yl)pyridin-2-amine |
| 79 | 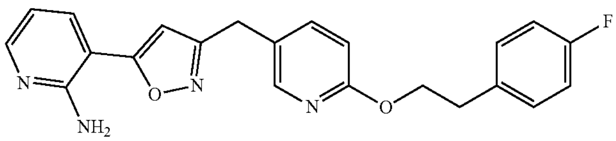 [SMILES: Nc1ncccc1-c1cc(Cc2ccc(OCCc3ccc(F)cc3)nc2)no1] | 3-(3-((6-(4-fluorophenethoxy)pyridin-3-yl)methyl)isoxazol-5-yl)pyridin-2-amine |
| 80 | 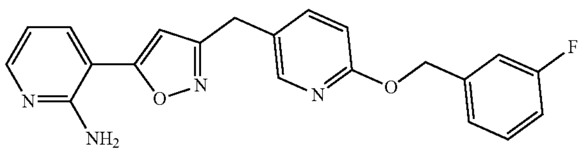 [SMILES: Nc1ncccc1-c1cc(Cc2ccc(OCc3cccc(F)c3)nc2)no1] | 3-(3-((6-((3-fluorobenzyl)oxy)pyridin-3-yl)methyl)isoxazol-5-yl)pyridin-2-amine |
| 81 | 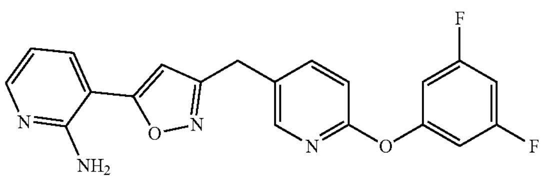 [SMILES: Nc1ncccc1-c1cc(Cc2ccc(Oc3cc(F)cc(F)c3)nc2)no1] | 3-(3-((6-(3,5-difluorophenoxy)pyridin-3-yl)methyl)isoxazol-5-yl)pyridin-2-amine |
| 82 | 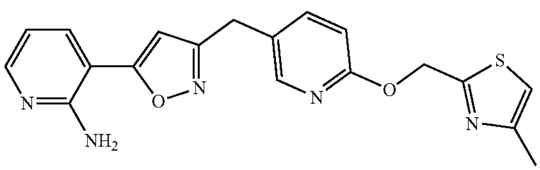 [SMILES: Cc1csc(COc2ccc(Cc3cc(-c4cccnc4N)on3)cn2)n1] | 3-(3-((6-((4-methylthiazol-2-yl)methoxy)pyridin-3-yl)methyl)isoxazol-5-ypyridin-2-amine |
| 83 | 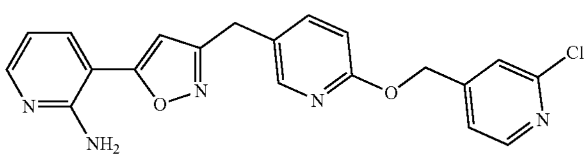 [SMILES: Nc1ncccc1-c1cc(Cc2ccc(OCc3ccnc(Cl)c3)nc2)no1] | 3-(3-((6-((2-chloropyridin-4-yl)methoxy)pyridin-3-yl)methyl)isoxazol-5-yl)pyridin-2-amine |
| 84 | 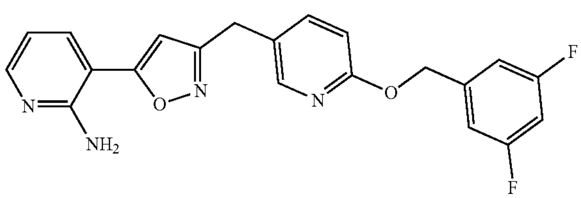 [SMILES: Nc1ncccc1-c1cc(Cc2ccc(OCc3cc(F)cc(F)c3)nc2)no1] | 3-(3-((6-(3,5-difluorobenzyl)oxy)pyridin-3-yl)methyl)isoxazol-5-yl)pyridin-2-amine |
| 85 | 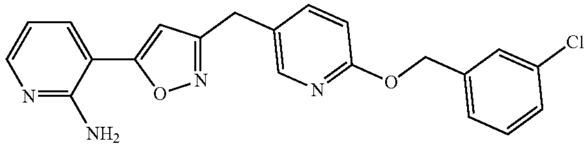 [SMILES: Nc1ncccc1-c1cc(Cc2ccc(OCc3cccc(Cl)c3)nc2)no1] | 3-(3-((6-((3-chlorobenzyl)oxy)pyridin-3-yl)methyl)isoxazol-5-yl)pyridin-2-amine |
| 86 | 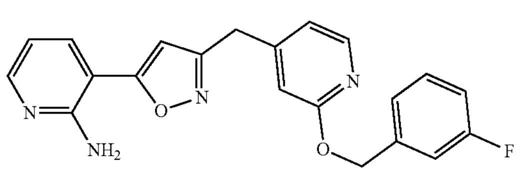 [SMILES: Nc1ncccc1-c1cc(Cc2ccnc(OCc3cccc(F)c3)c2)no1] | 3-(3-((2-((3-fluorobenzyl)oxy)pyridin-4-yl)methyl)isoxazol-5-yl)pyridin-2-amine |

TABLE 1-continued

| Ex. | Structure | Name |
|---|---|---|
| 87 | 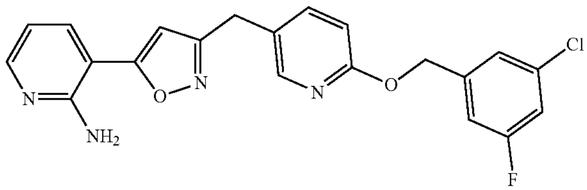 [SMILES: Nc1ncccc1-c1cc(Cc2ccc(OCc3cc(F)cc(Cl)c3)nc2)no1] | 3-(3-((6-((3-chloro-5-fluorobenzyl)oxy)pyridin-3-yl)methyl)isoxazol-5-yl)pyridin-2-amine |
| 88 | 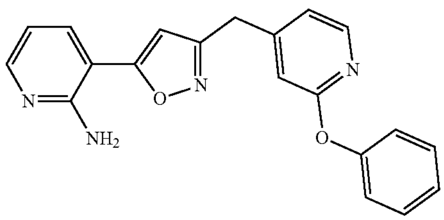 [SMILES: Nc1ncccc1-c1cc(Cc2ccnc(Oc3ccccc3)c2)no1] | 3-3-((2-((phenoxypyridin-4-yl)methyl)isoxazol-5-yl)pyridin-2-amine |
| 89 | 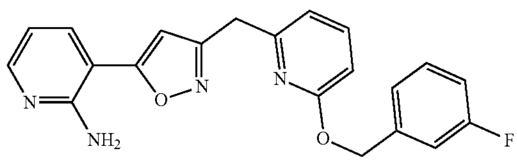 [SMILES: Nc1ncccc1-c1cc(Cc2cccc(OCc3cccc(F)c3)n2)no1] | 3-(3-((6-((3-fluorobenzyl)oxy)pyridin-2-yl)methyl)isoxazol-5-yl)pyridin-2-amine |
| 90 | 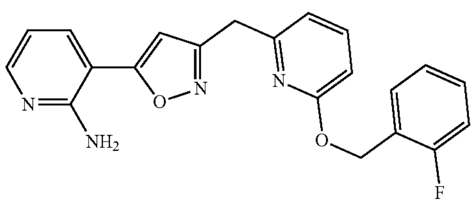 [SMILES: Nc1ncccc1-c1cc(Cc2cccc(OCc3ccccc3F)n2)no1] | 3-(3-((6-((2-fluorobenzyl)oxy)pyridin-2-yl)methyl)isoxazol-5-yl)pyridin-2-amine |
| 91 | 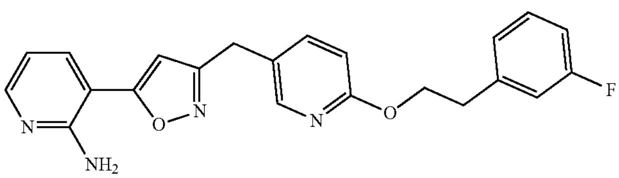 [SMILES: Nc1ncccc1-c1cc(Cc2ccc(OCCc3cccc(F)c3)nc2)no1] | 3-(3-((6-(3-fluorophenethoxy)pyridin-3-yl)methyl)isoxazol-5-yl)pyridin-2-amine |
| 92 | 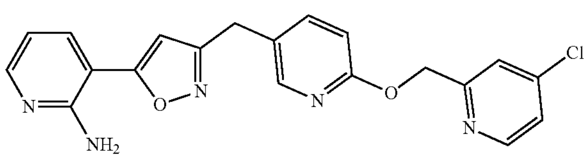 [SMILES: Nc1ncccc1-c1cc(Cc2ccc(OCc3cc(Cl)ccn3)nc2)no1] | 3-(3-(6-((4-chloropyridin-2-yl)methoxy)pyridin-3-yl)methyl)isoxazol-5-yl)pyridin-2-amine |
| 93 | 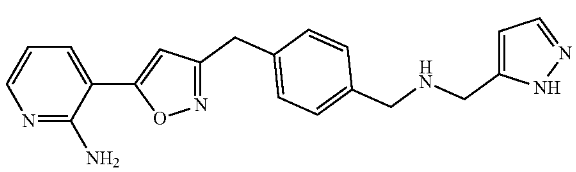 [SMILES: Nc1ncccc1-c1cc(Cc2ccc(CNCc3ccn[nH]3)cc2)no1] | 3-(3-(4-((((1H-pyrazol-5-yl)methyl)amino)methyl)benzyl)isoxazol-5-yl)pyridin-2-amine |
| 94 | 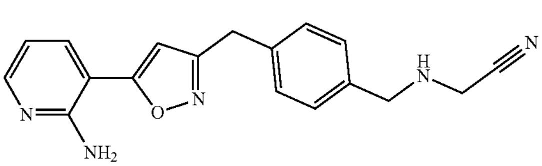 [SMILES: N#CCNCc1ccc(Cc2cc(-c3cccnc3N)on2)cc1] | 2-((4-((5-(2-aminopyridin-3-yl)isoxazol-3-yl)methyl)benzyl)amino)acetonitrile |

TABLE 1-continued

| Ex. | Structure | Name |
|---|---|---|
| 95 | 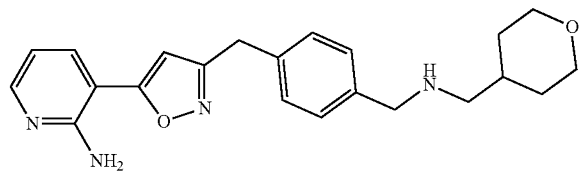 [SMILES: Nc1ncccc1-c1cc(Cc2ccc(CNCC3CCOCC3)cc2)no1] | 3-(3-(4-((((tetrahydro-2H-pyran-4-yl)methyl)amino)methyl)benzyl)isoxazol-5-yl)pyridin-2-amine |
| 96 | 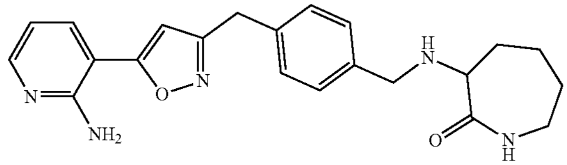 [SMILES: Nc1ncccc1-c1cc(Cc2ccc(CNC3CCCCNC3=O)cc2)no1] | 3-((4-((5-(2-aminopyridin-3-yl)isoxazol-3-yl)methyl)benzyl)amino)azepan-2-one |
| 97 | 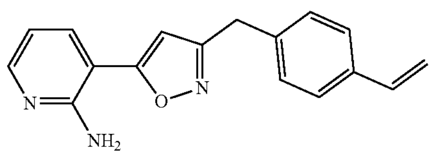 [SMILES: C=Cc1ccc(Cc2cc(-c3cccnc3N)on2)cc1] | 3-(3-(4-Vinylbenzyl)isoxazol-5-yl)pyridin-2-amine |
| 98 | 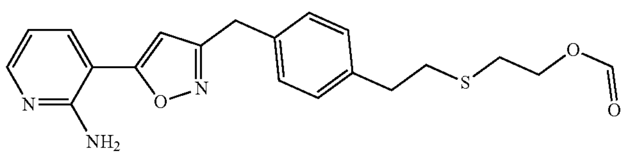 [SMILES: Nc1ncccc1-c1cc(Cc2ccc(CCSCCOC=O)cc2)no1] | 2-((4-((5-(2-aminopyridin-3-yl)isoxazol-3-yl)methyl)phenethyl)thio)ethyl formate |
| 99 | 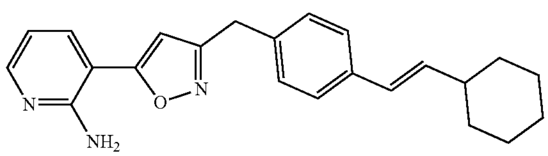 [SMILES: Nc1ncccc1-c1cc(Cc2ccc(/C=C/C3CCCCC3)cc2)no1] | (E)-3-(3-(4-(2-cyclohexylvinyl)benzyl)isoxazol-5-yl)pyridin-2-anime |
| 100 | 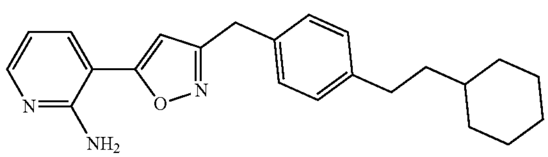 [SMILES: Nc1ncccc1-c1cc(Cc2ccc(CCC3CCCCC3)cc2)no1] | 3-(3-(4-(2-cyclohexylethyl)benzyl)isoxazol-5-yl)pyridin-2-amme |
| 101 | 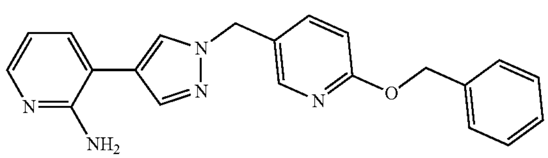 [SMILES: Nc1ncccc1-c1cnn(Cc2ccc(OCc3ccccc3)nc2)c1] | 3-(1-((6-(benzyloxy)pyridin-3-yl)methyl)-1H-pyrazol-4-yl)pyridin-2-amine |
| 102 | 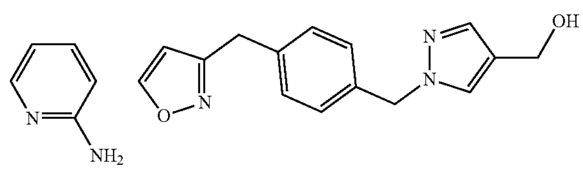 | (1-(4-((5-(2-aminopyridin-3-yl)isoxazol-3-yl)methyl)benzyl)-1H-pyrazol-4-yl)methanol |
| 103 | 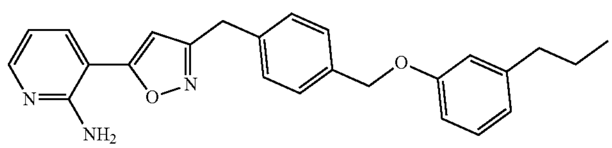 | 3-(3-(4-((3-propylphenoxy)methyl)benzyl)isoxazol-5-yl)pyridin-2-amine |

TABLE 1-continued

| Ex. | Structure | Name |
|---|---|---|
| 104 | 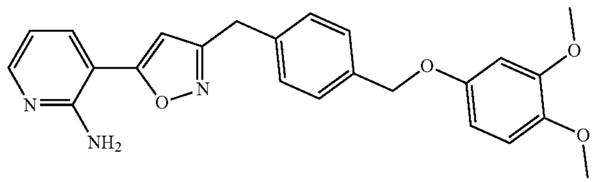 [SMILES: COc1ccc(OCc2ccc(Cc3cc(-c4cccnc4N)on3)cc2)cc1OC] | 3-(3-(4-((3,4-dimethoxyphenoxy)methyl)benzyl)isoxazol-5-yl)pyridin-2-amine |
| 105 | 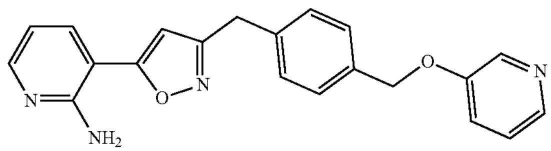 [SMILES: Nc1ncccc1-c1cc(Cc2ccc(COc3cccnc3)cc2)no1] | 3-(3-(4-((pyridin-3-yloxy)methyl)benzyl)isoxazol-5-yl)pyridin-2-amine |
| 106 | 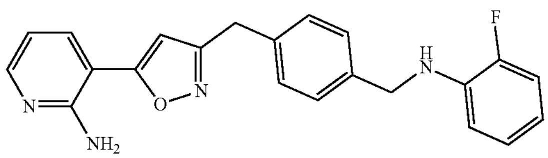 [SMILES: Nc1ncccc1-c1cc(Cc2ccc(CNc3ccccc3F)cc2)no1] | 3-(3-(4-(((2-fluorophenyl)amino)methyl)benzyl)isoxazol-5-yl)pyridin-2-amine |
| 107 | 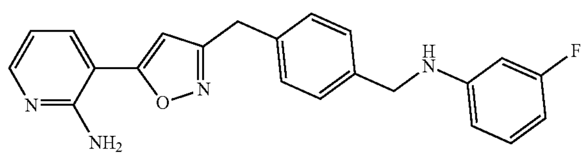 [SMILES: Nc1ncccc1-c1cc(Cc2ccc(CNc3cccc(F)c3)cc2)no1] | 3-(3-(4-(((3-fluorophenyl)amino)methyl)benzyl)isoxazol-5-yl)pyridin-2-amine |
| 108 | 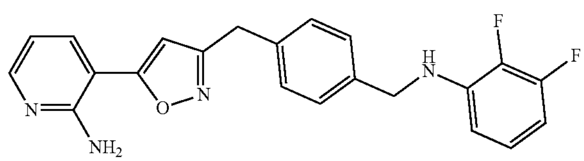 [SMILES: Nc1ncccc1-c1cc(Cc2ccc(CNc3cccc(F)c3F)cc2)no1] | 3-(3-(4-(((2,3-difluorophenyl)amino)methyl)benzyl)isoxazol-5-yl)pyridin-2-amine |
| 109 | 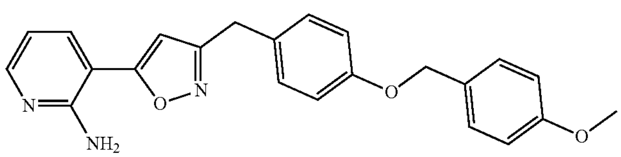 [SMILES: COc1ccc(COc2ccc(Cc3cc(-c4cccnc4N)on3)cc2)cc1] | 3-(3-(4-((4-methoxybenzyl)oxy)benzyl)isoxazol-5-yl)pyridin-2-amine |
| 110 | 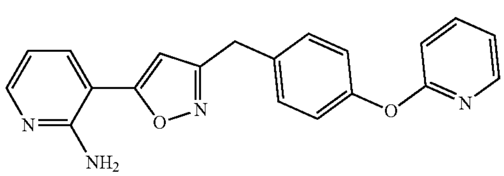 [SMILES: Nc1ncccc1-c1cc(Cc2ccc(Oc3ccccn3)cc2)no1] | 3-(3-(4-(pyridia-2-yloxy)benzyl)isoxazol-5-yl)pyridin-2-amine |
| 111 | 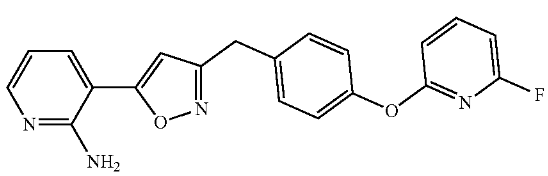 [SMILES: Nc1ncccc1-c1cc(Cc2ccc(Oc3cccc(F)n3)cc2)no1] | 3-(3-(4-((6-fluoropyridin-2-yl)oxy)benzyl)isoxazol-5-yl)pyridin-2-amine |
| 112 | 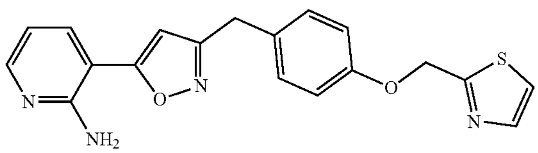 [SMILES: Nc1ncccc1-c1cc(Cc2ccc(OCc3nccs3)cc2)no1] | 3-(3-(4-(thiazol-2-ylmethoxy)benzyl)isoxazol-5-yl)pyridin-2-amine |

TABLE 1-continued

| Ex. | Structure | Name |
|---|---|---|
| 113 | 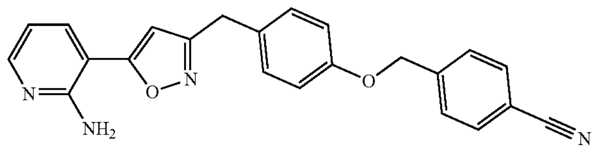 [SMILES: N#Cc1ccc(COc2ccc(Cc3cc(-c4cccnc4N)on3)cc2)cc1] | 4-((4-((5-(2-aminopyridin-3-yl)isoxazol-3-yl)methyl)phenoxy)methyl)benzonitrile |
| 114 | 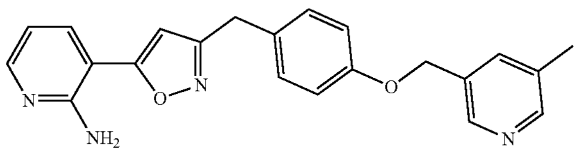 [SMILES: Cc1cncc(COc2ccc(Cc3cc(-c4cccnc4N)on3)cc2)c1] | 3-(3-(4-((5-methylpyridin-3-yl)methoxy)benzyl)isoxazol-5-yl)pyridin-2-amine |
| 115 | 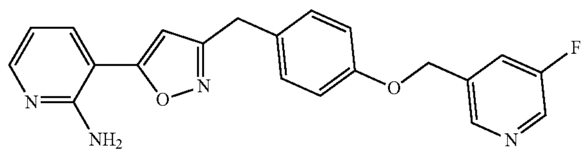 [SMILES: Nc1ncccc1-c1cc(Cc2ccc(OCc3cncc(F)c3)cc2)no1] | 3-(3-(4-((5-fluoropyridin-3-yl)methoxy)benzyl)isoxazol-5-yl)pyridin-2-amine |
| 116 | 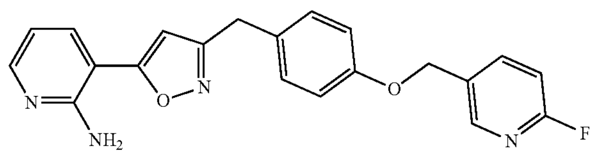 [SMILES: Nc1ncccc1-c1cc(Cc2ccc(OCc3ccc(F)nc3)cc2)no1] | 3-(3-(4-((6-fluoropyridin-3-yl)methoxy)benzyl)isoxazol-5-yl)pyridin-2-amine |
| 117 | 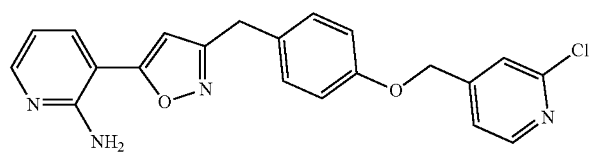 [SMILES: Nc1ncccc1-c1cc(Cc2ccc(OCc3ccnc(Cl)c3)cc2)no1] | 3-(3-(4-((2-chloropyridin-4-yl)methoxy)benzyl)isoxazol-5-yl)pyridin-2-amine |
| 118 | 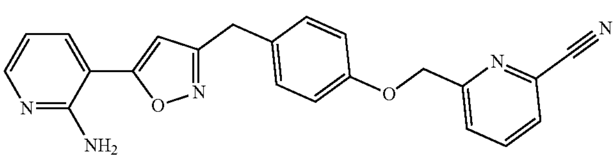 [SMILES: N#Cc1cccc(COc2ccc(Cc3cc(-c4cccnc4N)on3)cc2)n1] | 6-((4-((5-(2-aminopyridin-3-yl)isoxazol-3-yl)methyl)phenoxy)methyl)picolinonitrile |
| 119 | 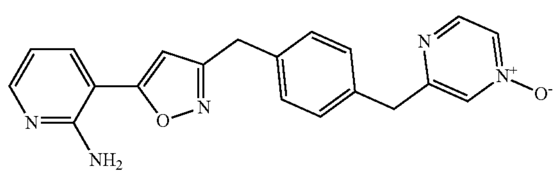 [SMILES: Nc1ncccc1-c1cc(Cc2ccc(Cc3c[n+]([O-])ccn3)cc2)no1] | 3-(4-((5-(2-aminopyridin-3-yl)isoxazol-3-yl)methyl)phenoxy)pyrazine 1-oxide |
| 120 | 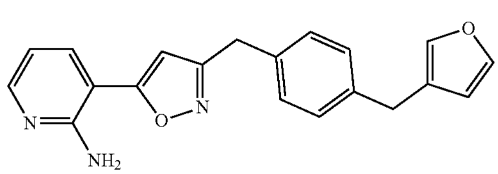 [SMILES: Nc1ncccc1-c1cc(Cc2ccc(Cc3ccoc3)cc2)no1] | 3-(3-(4-(furan-3-ylmethyl)benzyl)isoxazol-5-yl)pyridin-2-amine |
| 121 | 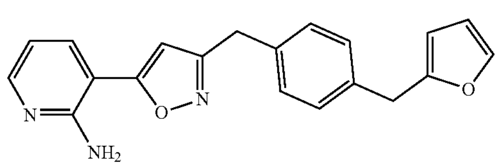 [SMILES: Nc1ncccc1-c1cc(Cc2ccc(Cc3ccco3)cc2)no1] | 3-(3-(4-(furan-2-yl)methyl)benzyl)isoxazol-5-yl)pyridin-2-amine |

TABLE 1-continued

| Ex. | Structure | Name |
|---|---|---|
| 122 | 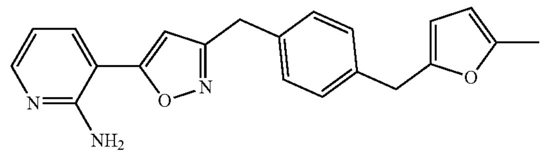 [SMILES: Cc1ccc(Cc2ccc(Cc3cc(-c4cccnc4N)on3)cc2)o1] | 3-(3-(4-((5-methylfuran-2-yl)methyl)benzyl)isoxazol-5-yl)pyridin-2-amine |
| 123 | 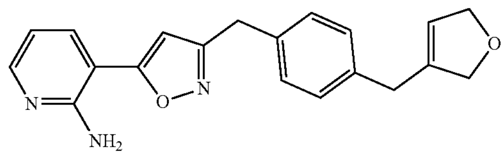 [SMILES: Nc1ncccc1-c1cc(Cc2ccc(CC3=CCOC3)cc2)no1] | 3-(3-(4-((2,5-dihydrofuran-3-yl)methyl)benzyl)isoxazol-5-yl)pyridin-2-amine |
| 124 | 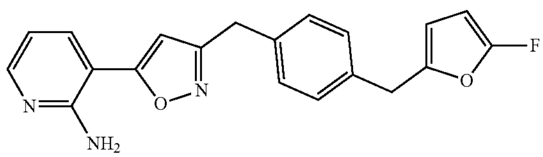 [SMILES: Nc1ncccc1-c1cc(Cc2ccc(Cc3ccc(F)o3)cc2)no1] | 3-(3-(4-((5-fluorofuran-2-yl)methyl)benzyl)isoxazol-5-yl)pyridin-2-amine |
| 125 | 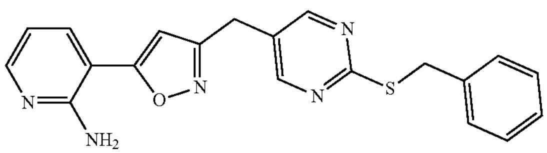 [SMILES: Nc1ncccc1-c1cc(Cc2cnc(SCc3ccccc3)nc2)no1] | 3-(3-((2-(benzylthio)pyrimidin-5-yl)methyl)isoxazol-5-yl)pyridin-2-amine |
| 126 | 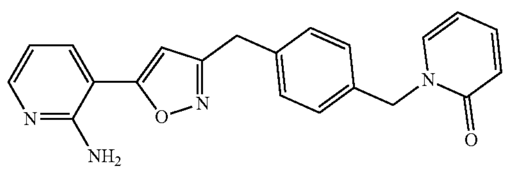 [SMILES: Nc1ncccc1-c1cc(Cc2ccc(Cn3ccccc3=O)cc2)no1] | 1-(4-((5-(2-aminopyridin-3-yl)isoxazol-3-yl)methyl)benzyl)pyridin-2(1H)-one |
| 127 | 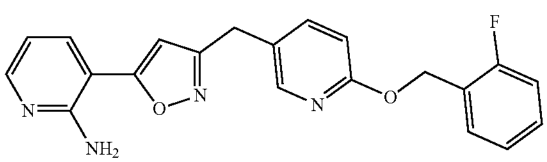 [SMILES: Nc1ncccc1-c1cc(Cc2ccc(OCc3ccccc3F)nc2)no1] | 3-(3-((6-((2-fluorobenzyl)oxy)pyridin-3-yl)methyl)isoxazol-5-yl)pyridin-2-amine |
| 128 | 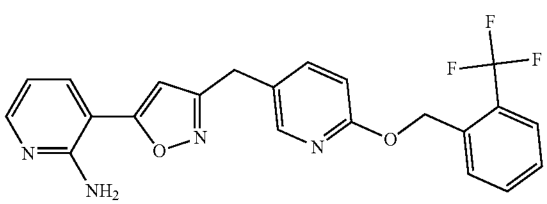 [SMILES: Nc1ncccc1-c1cc(Cc2ccc(OCc3ccccc3C(F)(F)F)nc2)no1] | 3-(3-((6-((2-(trifluoromethyl)benzyl)oxy)pyridin-3-yl)methyl)isoxazol-5-yl)pyridin-2-amine |
| 129 | 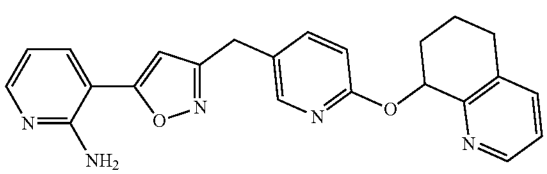 [SMILES: Nc1ncccc1-c1cc(Cc2ccc(OC3CCCc4cccnc43)nc2)no1] | 3-(3-((6-((5,6,7,8-tetrahydroquinolin-8-yl)oxy)pyridin-3-yl)methyl)isoxazol-5-yl)pyridin-2-amine |
| 130 | 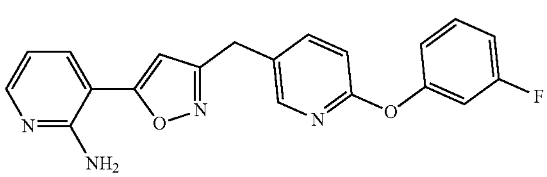 [SMILES: Nc1ncccc1-c1cc(Cc2ccc(Oc3cccc(F)c3)nc2)no1] | 3-(3-((6-(3-fluorophenoxy)pyridin-3-yl)methyl)isoxazol-5-yl)pyridin-2-amine |

TABLE 1-continued

| Ex. | Structure | Name |
|---|---|---|
| 131 | 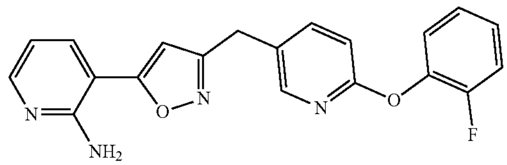 [SMILES: Nc1ncccc1-c1cc(Cc2ccc(Oc3ccccc3F)nc2)no1] | 3-(3-((6-(2-fluorophenoxy)pyridin-3-yl)methyl)isoxazol-5-yl)pyridin-2-amine |
| 132 | 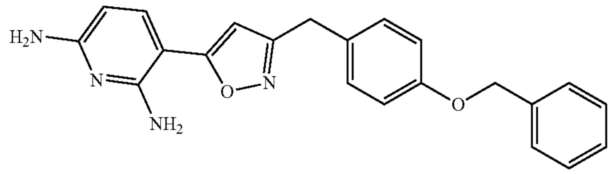 [SMILES: Nc1ccc(-c2cc(Cc3ccc(OCc4ccccc4)cc3)no2)c(N)n1] | 3-(3-(4-(benzyloxy)benzyl)isoxazol-5-yl)pyridine-2,6-diamine |
| 133 | 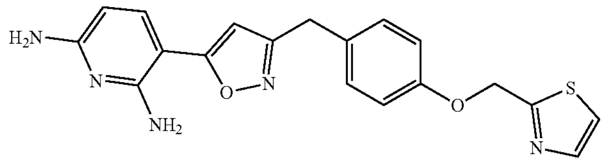 [SMILES: Nc1ccc(-c2cc(Cc3ccc(OCc4nccs4)cc3)no2)c(N)n1] | 3-(3-(4-(thiazol-2-ylmethoxy)benzyl)isoxazol-5-yl)pyridine-2,6-diamine |
| 134 | 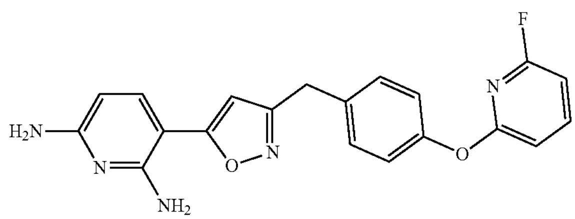 [SMILES: Nc1ccc(-c2cc(Cc3ccc(Oc4cccc(F)n4)cc3)no2)c(N)n1] | 3-(3-(4-((6-fluropyridin-2-yl)oxy)benzyl)isoxazol-5-yl)pyridine-2,6-diamine |
| 135 | 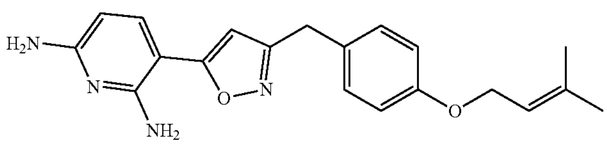 [SMILES: CC(C)=CCOc1ccc(Cc2cc(-c3ccc(N)nc3N)on2)cc1] | 3-(3-(4-((3-methylbut-2-en-1-yl)oxy)benzyl)isoxazol-5-yl)pyridine-2,6-diamine |
| 136 | 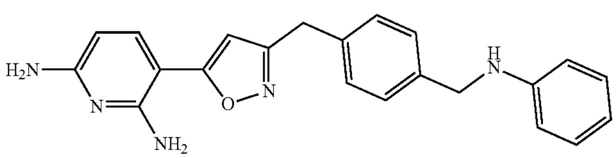 [SMILES: Nc1ccc(-c2cc(Cc3ccc(CNc4ccccc4)cc3)no2)c(N)n1] | 3-(3-(4-((phenylamino)methyl)benzyl)isoxazol-5-yl)pyridine-2,6-diamine |
| 137 | 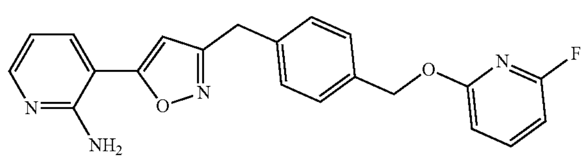 [SMILES: Nc1ncccc1-c1cc(Cc2ccc(COc3cccc(F)n3)cc2)no1] | 3-(3-(4-(((6-fluoropyridin-2-yl)oxy)methyl)benzyl)isoxazol-5-yl)pyridin-2-amine |
| 138 | 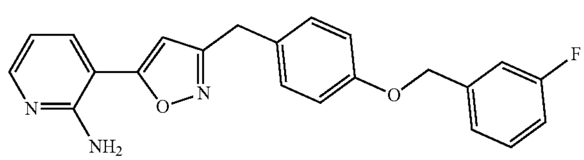 [SMILES: Nc1ncccc1-c1cc(Cc2ccc(OCc3cccc(F)c3)cc2)no1] | 3-(3-(4-((3-fluorobenzyl)oxy)benzyl)isoxazol-5-yl)pyridin-2-amine |
| 139 | 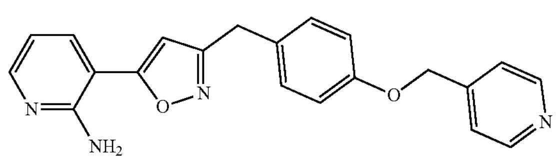 [SMILES: Nc1ncccc1-c1cc(Cc2ccc(OCc3ccncc3)cc2)no1] | 3-(3-(4-(pyridin-4-ylmethoxy)benzyl)isoxazol-5-yl)pyridin-2-amine |

TABLE 1-continued

| Ex. | Structure | Name |
|---|---|---|
| 140 | 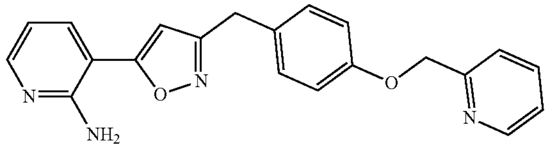 [SMILES: Nc1ncccc1-c1cc(Cc2ccc(OCc3ccccn3)cc2)no1] | 3-(3-(4-(pyridin-2-ylmethoxy)benzyl)isoxazol-5-yl)pyridin-2-amine |
| 141 | 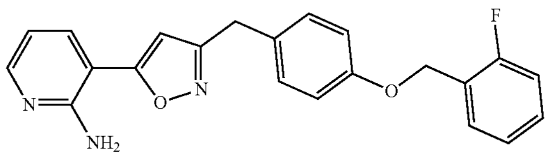 [SMILES: Nc1ncccc1-c1cc(Cc2ccc(OCc3ccccc3F)cc2)no1] | 3-(3-(4-((2-fluorobenzyloxy)benzyl)isoxazol-5-yl)pyridin-2-amine |
| 142 | 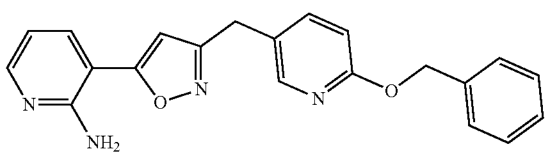 [SMILES: Nc1ncccc1-c1cc(Cc2ccc(OCc3ccccc3)nc2)no1] | 3-(3-((6-(benzyloxy)pyridin-3-yl)methyl)isoxazol-5-yl)pyridin-2-amine |
| 143 | 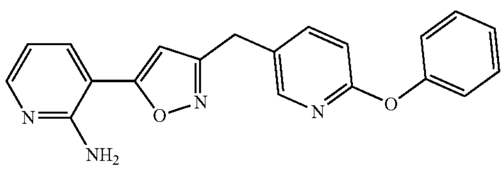 [SMILES: Nc1ncccc1-c1cc(Cc2ccc(Oc3ccccc3)nc2)no1] | 3-(3-((6-phenoxypyridin-3-yl)methyl)isoxazol-5-yl)pyridin-2-amine |
| 144 | 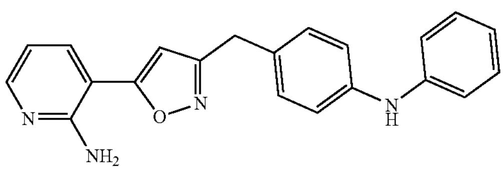 [SMILES: Nc1ncccc1-c1cc(Cc2ccc(Nc3ccccc3)cc2)no1] | 3-(3-(4-(phenylamino)benzyl)isoxazol-5-yl)pyridin-2-amine |
| 145 | 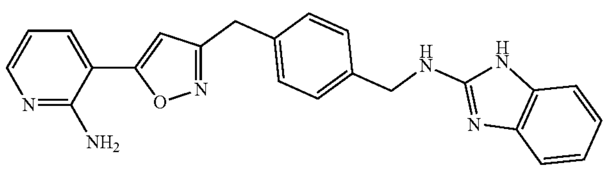 [SMILES: Nc1ncccc1-c1cc(Cc2ccc(CNc3nc4ccccc4[nH]3)cc2)no1] | N-(4-((5-(2-aminopyridin-3-yl)isoxazol-3-yl)methyl)benzyl)-1H-benzo[d]imidazol-2-amine |
| 146 | 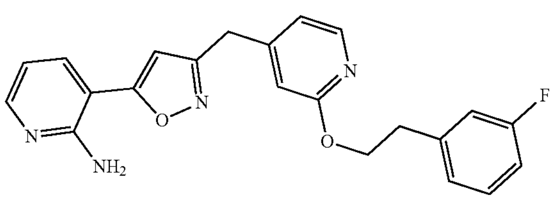 [SMILES: Nc1ncccc1-c1cc(Cc2ccnc(OCCc3cccc(F)c3)c2)no1] | 3-(3-((2-(3-fluorophenethoxy)pyridin-4-yl)methyl)isoxazol-5-yl)pyridin-2-amine |
| 147 | 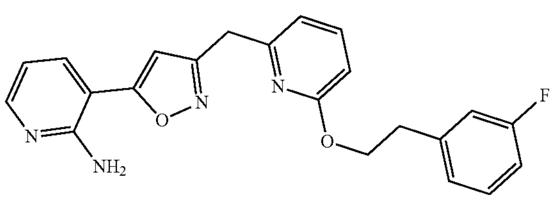 [SMILES: Nc1ncccc1-c1cc(Cc2cccc(OCCc3cccc(F)c3)n2)no1] | 3-(3-((6-(3-fluorophenethoxy)pyridin-2-yl)methyl)isoxazol-5-yl)pyridin-2-amine |
| 148 | 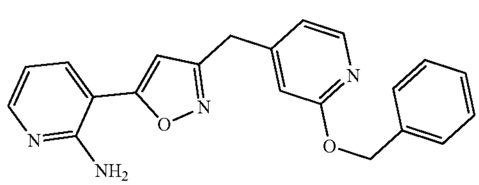 [SMILES: Nc1ncccc1-c1cc(Cc2ccnc(OCc3ccccc3)c2)no1] | 3-(3-((2-(benzyloxy)pyridin-4-yl)methyl)sisoxazol-5-yl)pyridin-2-amine |

TABLE 1-continued

| Ex. | Structure | Name |
|---|---|---|
| 149 | 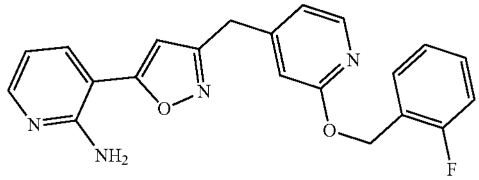 [SMILES: Nc1ncccc1-c1cc(Cc2ccnc(OCc3ccccc3F)c2)no1] | 3-(3-((2-((2-fluorobenzyl)oxy)pyridin-4-yl)methyl)isoxazol-5-yl)pyridin-2-amine |
| 150 | 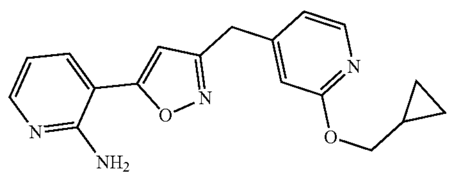 [SMILES: Nc1ncccc1-c1cc(Cc2ccnc(OCC3CC3)c2)no1] | 3-(3-((2-(cyclopropylmethoxy)pyridin-4-yl)methyl)isoxazol-5-yl)pyridin-2-amine |
| 151 | 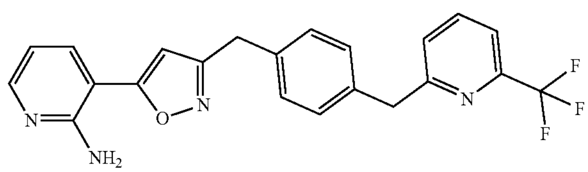 [SMILES: Nc1ncccc1-c1cc(Cc2ccc(Cc3cccc(C(F)(F)F)n3)cc2)no1] | 3-(3-(4-((6-(trifluoromethyl)pyridin-2-yl)methyl)benzyl)isoxazol-5-yl)pyridin-2-amine |
| 152 | 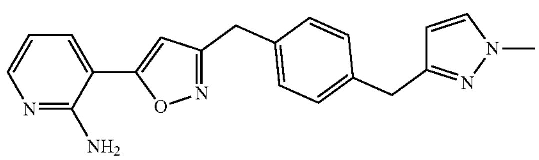 [SMILES: Cn1ccc(Cc2ccc(Cc3cc(-c4cccnc4N)on3)cc2)n1] | 3-(3-(4-((1-methyl-1H-pyrazol-3-yl)methyl)benzyl)isoxazol-5-yl)pyridin-2-amine |
| 153 | 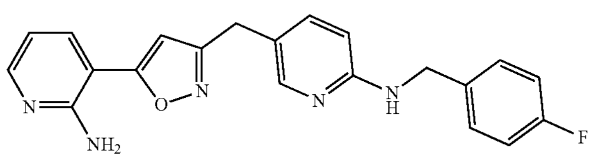 [SMILES: Nc1ncccc1-c1cc(Cc2ccc(NCc3ccc(F)cc3)nc2)no1] | 5-((5-(2-aminopyridin-3-yl)isoxazol-3-yl)methyl)-N-(4-fuorobenzyl)pyridin-2-amine |
| 154 | 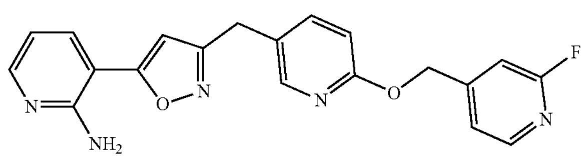 [SMILES: Nc1ncccc1-c1cc(Cc2ccc(OCc3ccnc(F)c3)nc2)no1] | 3-(3-((6-((2-fluoropyridin-4-yl)methoxy)pyridin-3-yl)methyl)isoxazol-5-yl)pyridin-2-amine |
| 155 | 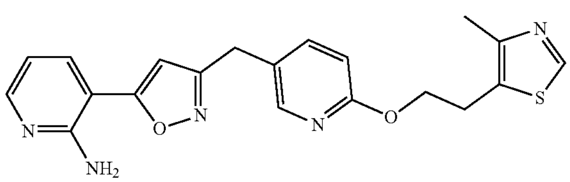 [SMILES: Cc1ncsc1CCOc1ccc(Cc2cc(-c3cccnc3N)on2)cn1] | 3-(3-((6-(2-(4-methylthiazol-5-yl)ethoxy)pyridin-3-yl)methyl)isoxazol-5-yl)pyridin-2-amine |
| 156 | 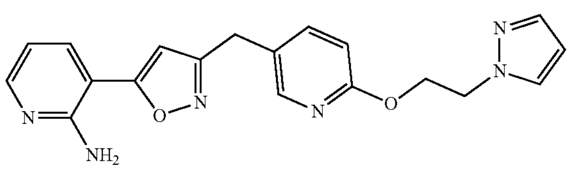 [SMILES: Nc1ncccc1-c1cc(Cc2ccc(OCCn3cccn3)nc2)no1] | 3-(3-((6-(2-(1H-pyrazol-1-yl)ethoxy)pyridin-3-yl)methyl)isoxazol-5-yl)pyridin-2-amine |
| 157 | 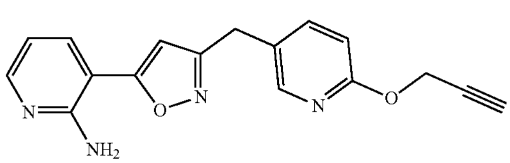 [SMILES: C#CCOc1ccc(Cc2cc(-c3cccnc3N)on2)cn1] | 3-(3-((6-(prop-2-yn-1-yloxy)pyridin-3-yl)methyl)isoxazol-5-yl)pyridin-2-amine |

TABLE 1-continued

| Ex. | Structure | Name |
|---|---|---|
| 158 | 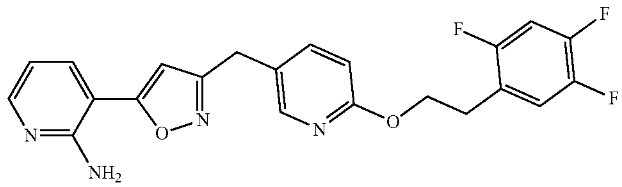 [SMILES: Nc1ncccc1-c1cc(Cc2ccc(OCCc3cc(F)c(F)cc3F)nc2)no1] | 3-(3-((6-(2,4,5-trifluorophenethoxy)pyridin-3-yl)methyl)isoxazol-5-yl)pyridin-2-amine |
| 159 | 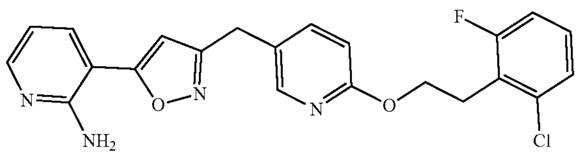 [SMILES: Nc1ncccc1-c1cc(Cc2ccc(OCCc3c(F)cccc3Cl)nc2)no1] | 3-(3-((6-(2-chloro-6-fluorophenethoxy)pyridin-3-yl)methyl)isoxazol-5-yl)pyridin-2-amine |
| 160 | 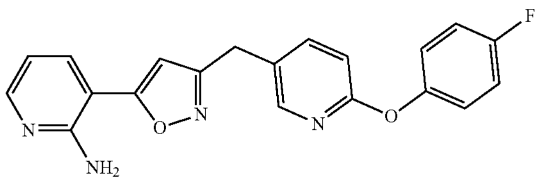 [SMILES: Nc1ncccc1-c1cc(Cc2ccc(Oc3ccc(F)cc3)nc2)no1] | 3-(3-((6-(4-fluorophenoxy)pyridin-3-yl)methyl)isoxazol-5-yl)pyridin-2-amine |
| 161 | 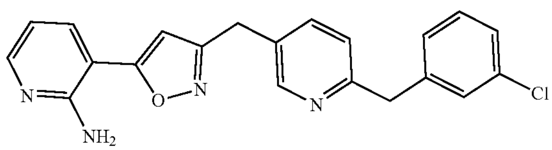 [SMILES: Nc1ncccc1-c1cc(Cc2ccc(Cc3cccc(Cl)c3)nc2)no1] | 3-(3-((6-(3-chlorophenoxy)pyridin-3-yl)methyl)isoxazol-5-yl)pyridin-2-amine |
| 162 | 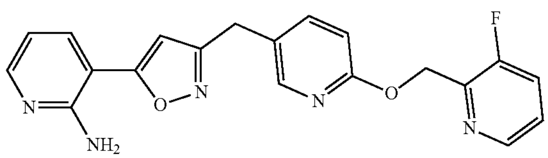 | 3-(3-((6-((3-fluoropyridin-2-yl)methoxy)pyridin-3-yl)methyl)isoxazol-5-yl)pyridin-2-amine |
| 163 | 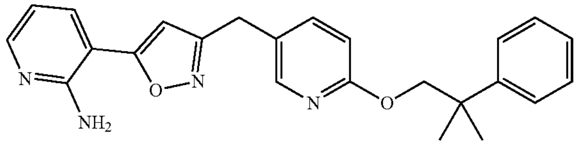 [SMILES: CC(C)(COc1ccc(Cc2cc(-c3cccnc3N)on2)cn1)c1ccccc1] | 3-(3-((6-(2-methyl-2-phenylpropoxy)pyridin-3-yl)methyl)isoxazol-5-yl)pyridin-2-amine |
| 164 | 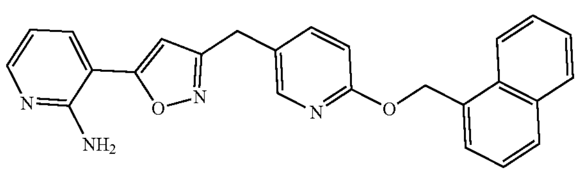 [SMILES: Nc1ncccc1-c1cc(Cc2ccc(OCc3cccc4ccccc34)nc2)no1] | 3-(3-((6-(naphthalen-1-ylmethoxy)pyridin-3-yl)methyl)isoxazol-5-yl)pyridin-2-amine |
| 165 | 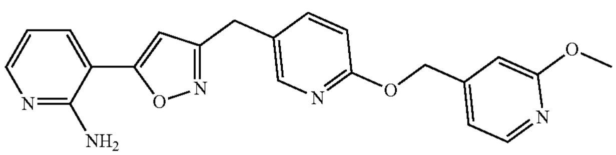 [SMILES: COc1cc(COc2ccc(Cc3cc(-c4cccnc4N)on3)cn2)ccn1] | 3-(3-((6-((2-methoxypyridin-4-yl)methoxy)pyridin-3-yl)methyl)isoxazol-5-yl)pyridin-2-amine |
| 166 | 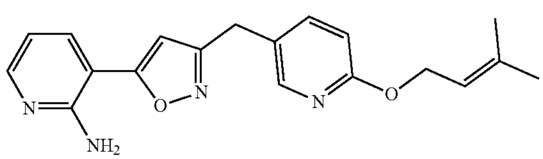 [SMILES: CC(C)=CCOc1ccc(Cc2cc(-c3cccnc3N)on2)cn1] | 3-(3-((6-((3-methylbut-2-en-1-yl)oxy)pyridin-3-yl)methyl)isoxazol-5-yl)pyridin-2-amine |

TABLE 1-continued

| Ex. | Structure | Name |
| --- | --- | --- |
| 167 | 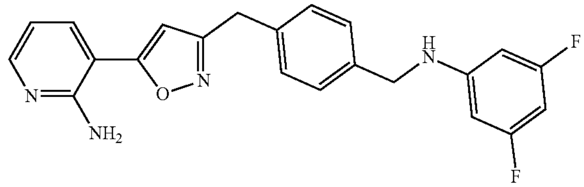 [SMILES: Nc1ncccc1-c1cc(Cc2ccc(CNc3cc(F)cc(F)c3)cc2)no1] | 3-(3-(4-(((3,5-difluorophenyl)amino)methyl)benzyl)isoxazol-5-yl)pyridin-2-amine |
| 168 | 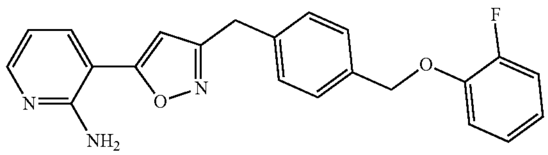 [SMILES: Nc1ncccc1-c1cc(Cc2ccc(COc3ccccc3F)cc2)no1] | 3-(3-(4-((2-fluorophenoxy)methyl)benzyl)isoxazol-5-yl)pyridin-2-amine |
| 169 | 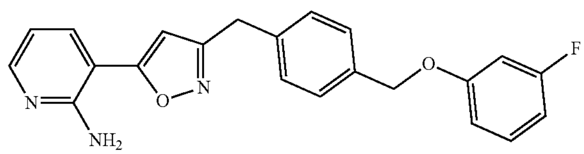 [SMILES: Nc1ncccc1-c1cc(Cc2ccc(COc3cccc(F)c3)cc2)no1] | 3-(3-(4-((3-fluorophenoxy)methyl)benzyl)isoxazol-5-yl)pyridin-2-amine |
| 170 | 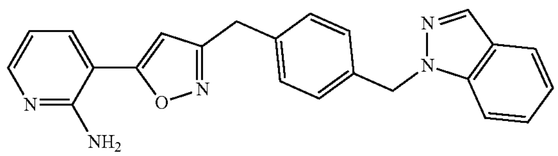 [SMILES: Nc1ncccc1-c1cc(Cc2ccc(Cn3ncc4ccccc43)cc2)no1] | 3-(3-(4-((1H-indazol-1-yl)methyl)benzyl)isoxazol-5-yl)pyridin-2-amine |
| 171 | 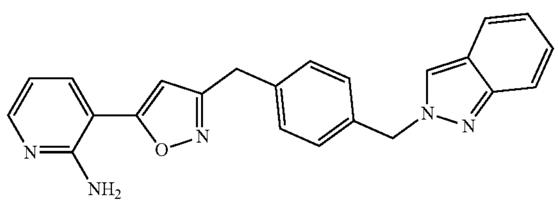 [SMILES: Nc1ncccc1-c1cc(Cc2ccc(Cn3cc4ccccc4n3)cc2)no1] | 3-(3-(4-((2H-indazol-2-yl)methyl)benzyl)isoxazol-5-yl)pyridin-2-amine |
| 172 | 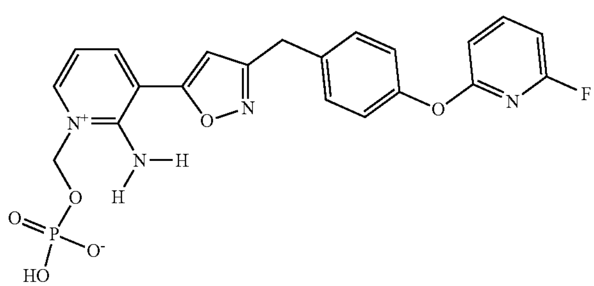 [SMILES: Nc1c(-c2cc(Cc3ccc(Oc4cccc(F)n4)cc3)no2)ccc[n+]1COP(=O)([O-])O] | (2-amino-3-(3-(4-((6-fluoropyridin-2-yl)oxy)benzyl)isoxazol-5-yl)pyridin-1-ium-1-yl)methyl hydrogen phosphate |
| 173 | 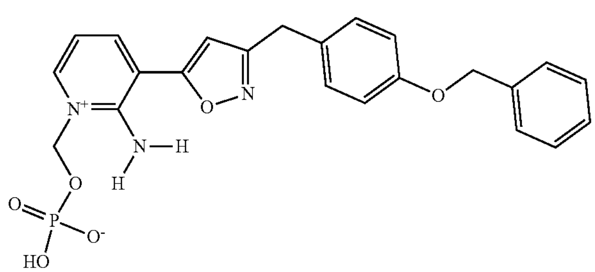 [SMILES: Nc1c(-c2cc(Cc3ccc(OCc4ccccc4)cc3)no2)ccc[n+]1COP(=O)([O-])O] | (2-amino-3-(3-(4-(benzyloxy)benzyl)isoxazol-5-yl)pyridin-1-ium-1-yl)methyl hydrogen phosphate |

TABLE 1-continued

| Ex. | Structure | Name |
|---|---|---|
| 174 | 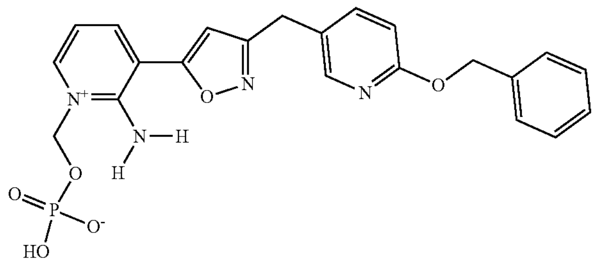 [SMILES: Nc1c(-c2cc(Cc3ccc(OCc4ccccc4)nc3)no2)ccc[n+]1COP(=O)([O-])O] | (2-amino-3-(3-((6-(benzyloxy)pyridin-3-yl)methyl)isoxazol-5-yl)pyridin-1-ium-1-yl)methyl hydrogen phosphate |
| 175 | 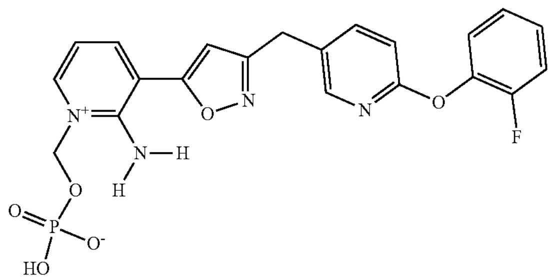 [SMILES: Nc1c(-c2cc(Cc3ccc(Oc4ccccc4F)nc3)no2)ccc[n+]1COP(=O)([O-])O] | (2-amino-3-(3-((6-(2-fluorophenoxy)pyridin-3-yl)methyl)isoxazol-5-yl)pyridin-1-ium-1-yl)methyl hydrogen phosphate |
| 176 | 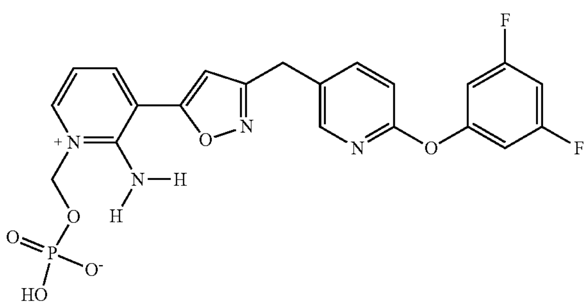 | (2-amino-3-(3-((6-(3,5-difluorophenoxy)pyridin-3-yl)methyl)isoxazol-5-yl)pyridin-1-ium-1-yl)methyl hydrogen phosphate |
| 177 | 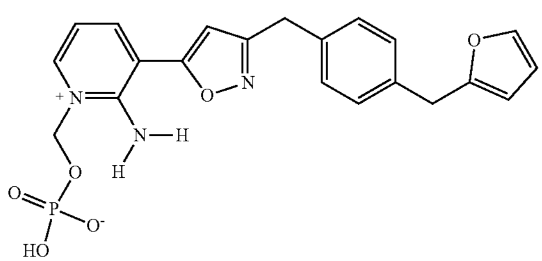 | (2-amino-3-(3-(4-(furan-2-ylmethyl)benzyl)isoxazol-5-yl)pyridin-1-ium-1-yl)methyl hydrogen phosphate |
| 178 | 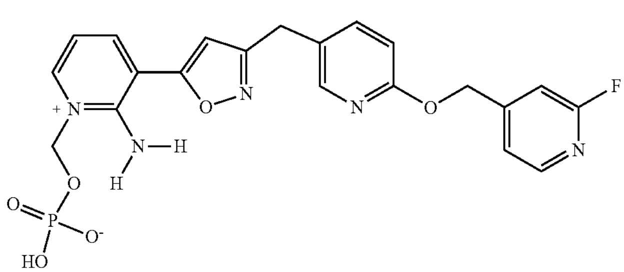 | (2-amino-3-(3-((6-((2-fluoropyridin-4-yl)methoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 179 | 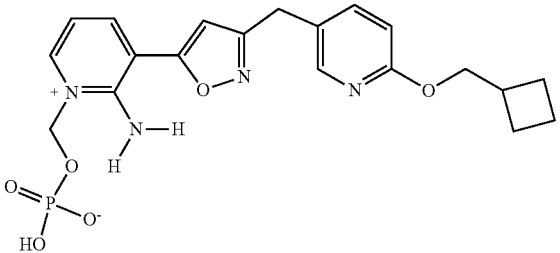 | (2-amino-3-(3-((6-(cyclobutylmethoxy)pyridin-3-yl)methyl)isoxazol-5-yl)pyridin-1-ium-1-yl)methyl hydrogen phosphate |
| 180 | 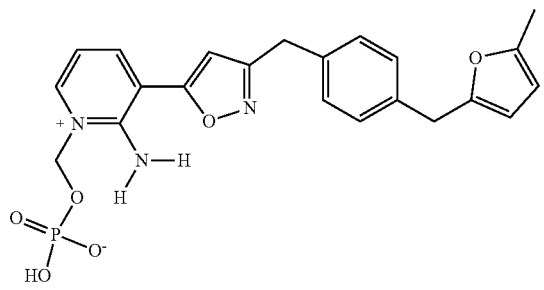 | (2-amino-3-(3-(4-((5-methylfuran-2-yl)methyl)benzyl)isoxazol-5-yl)pyridin-1-ium-1-yl)methyl hydrogen phosphate |
| 181 | 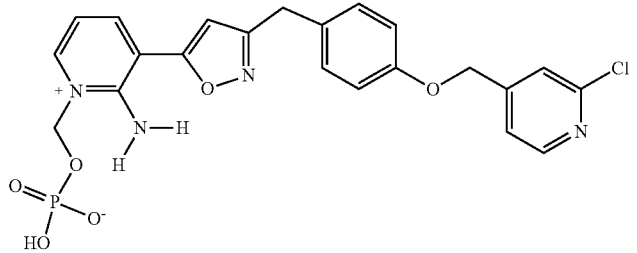 | (2-amino-3-(3-(4-((2-chloropyrdin-4-yl)methoxy)benzyl)isoxazol-5-yl)pyridin-1-ium-1-yl)methyl hydrogen phosphate |
| 182 | 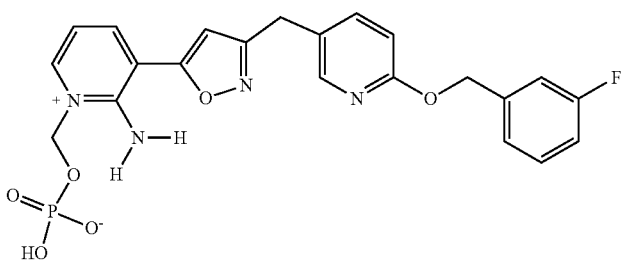 | (2-amino-3-(3-((6-((3-fluorobenzyl)oxy)pyridin-3-yl)methyl)isoxazol-5-yl)pyridin-1-ium-1-yl)methyl hydrogen phosphate |
| 183 | 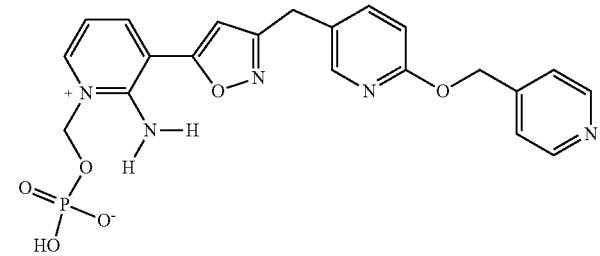 | (2-amino-3-(3-((6-(pyridin-4-ylmethoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 184 | 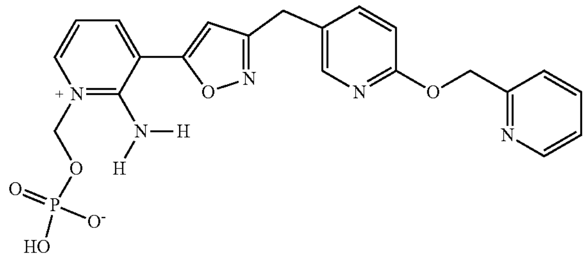 | (2-amino-3-(3-((6-(pyridin-2-ylmethoxy)pyridin-3-yl)methyl)isoxazol-5-yl)pyridin-1-ium-1-yl)methyl hydrogen phosphate |
| 185 | 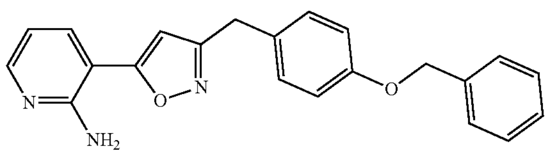 | 3-(3-(4-(benzyloxy)benzyl)isoxazol-5-yl)pyridin-2-amine |
| 186 | 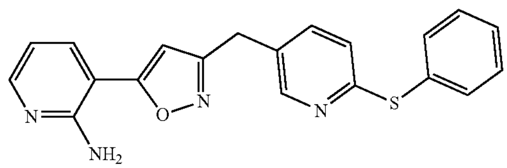 | 3-(3-((6-(phenylthio)pyridin-3-yl)methyl)isoxazol-5-yl)pyridin-2-amine |
| 187 | 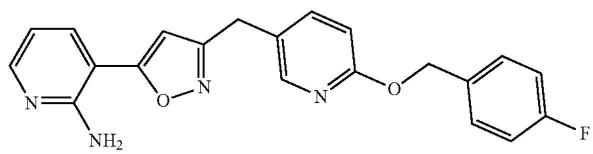 [SMILES: Nc1ncccc1-c1cc(Cc2ccc(OCc3ccc(F)cc3)nc2)no1] | 3-(3-((6-((4-fluorobenzyl)oxy)pyridin-3-yl)methyl)isoxazol-5-yl)pyridin-2-amine |
| 188 | 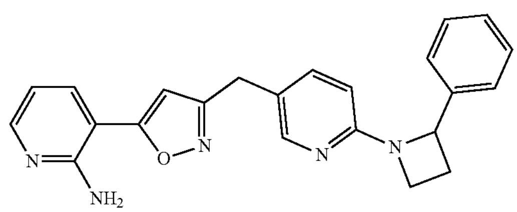 [SMILES: Nc1ncccc1-c1cc(Cc2ccc(N3CCC3c3ccccc3)nc2)no1] | 3-(3-((6-(2-phenylazetidin-1-yl)pyridin-3-yl)methyl)isoxazol-5yl)pyridin-2-amine |
| 189 | 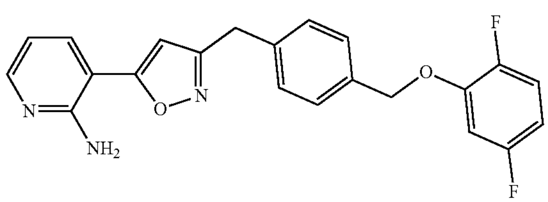 [SMILES: Nc1ncccc1-c1cc(Cc2ccc(COc3cc(F)ccc3F)cc2)no1] | 3-(3-(4-((2,5-difluorophenoxy)methyl)benzyl)isoxazol-5-yl)pyridin-2-amine |
| 190 | 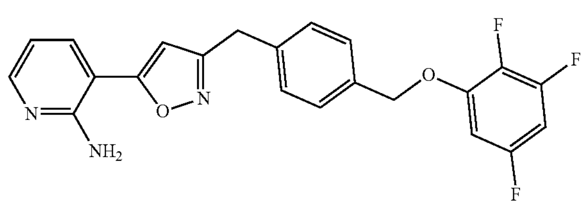 [SMILES: Nc1ncccc1-c1cc(Cc2ccc(COc3cc(F)cc(F)c3F)cc2)no1] | 3-(3-(4-((2,3,5-trifluorophenoxy)methyl)benzyl)isoxazol-5-yl)pyridin-2-amine |
| 191 | 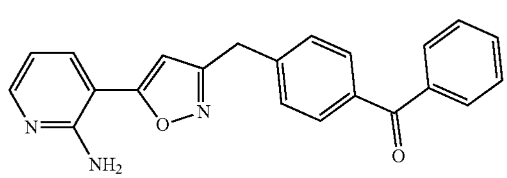 [SMILES: Nc1ncccc1-c1cc(Cc2ccc(C(=O)c3ccccc3)cc2)no1] | (4-((5-(2-aminopyridin-3-yl)isoxazol-3-yl)methyl)phenyl)(phenyl)methanone |

TABLE 1-continued

| Ex. | Structure | Name |
|---|---|---|
| 192 | 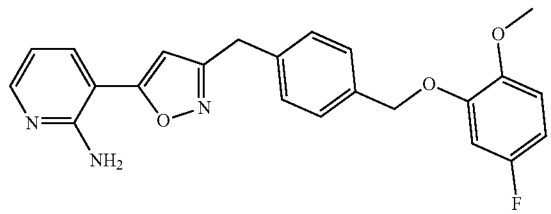 [SMILES: COc1ccc(F)cc1OCc1ccc(Cc2cc(-c3cccnc3N)on2)cc1] | 3-(3-(4-((5-fluoro-2-methosyphenoxy)methyl)benzyl)isoxazol-5-yl)pyridin-2-amine |
| 193 | 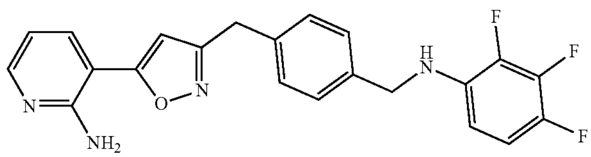 [SMILES: Nc1ncccc1-c1cc(Cc2ccc(CNc3ccc(F)c(F)c3F)cc2)no1] | 3-(3-(4-(((2,3,4-trifluorophenyl)amino)methyl)benzyl)isoxazol-5-yl)pyridin-2-amine |
| 194 | 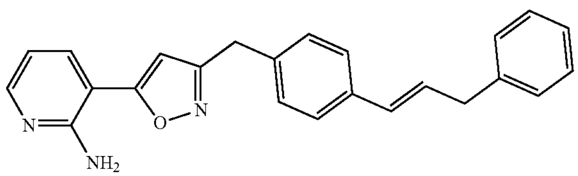 [SMILES: Nc1ncccc1-c1cc(Cc2ccc(/C=C/Cc3ccccc3)cc2)no1] | (E)-3-(3-(4-(3-phenylprop-1-en-1-yl)benzyl)isoxazol-5-yl)pyridin-2-amine |
| 195 | 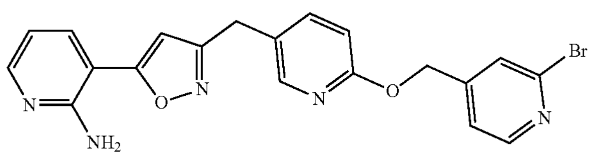 | 3-(3-((6-((2-bromopyridin-4-yl)methoxy)pyridin-3-yl)methyl)isoxazol-5-yl)pyridin-2-amine |
| 196 | 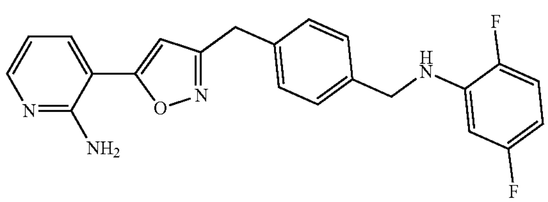 [SMILES: Nc1ncccc1-c1cc(Cc2ccc(CNc3cc(F)ccc3F)cc2)no1] | 3-(3-(4-(((2,5-difluorophenyl)amino)methyl)benzyl)isoxazol-5-yl)pyridin-2-amine |
| 197 | 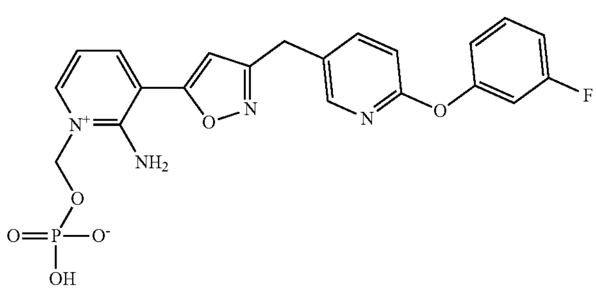 [SMILES: Nc1c(-c2cc(Cc3ccc(Oc4cccc(F)c4)nc3)no2)ccc[n+]1COP(=O)([O-])O] | (2-amino-3-(3-((6-(3-fluorophenoxy)pyridin-3-yl)methyl)isoxazol-5-yl)pyridin-1-ium-1-yl)methyl hydrogen phosphate |
| 198 | 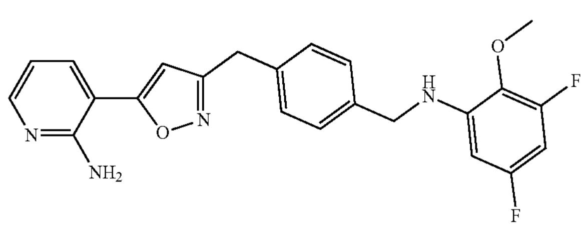 [SMILES: COc1c(F)cc(F)cc1NCc1ccc(Cc2cc(-c3cccnc3N)on2)cc1] | 3-(3-(4-(((3,5-difluoro-2-methoxyphenyl)amino)methyl)benzyl)isoxazol5-yl)pyridin-2-amine |
| 199 | 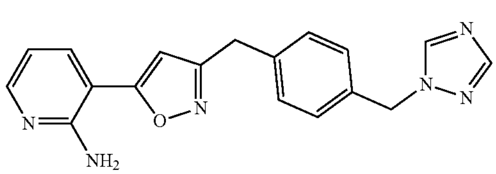 [SMILES: Nc1ncccc1-c1cc(Cc2ccc(Cn3cncn3)cc2)no1] | 3-(3-(4-((1H-1,2,4-triazol-1-yl)methyl)benzyl)isoxazol-5-yl)pyridin-2-amine |

TABLE 1-continued

| Ex. | Structure | Name |
|---|---|---|
| 200 | 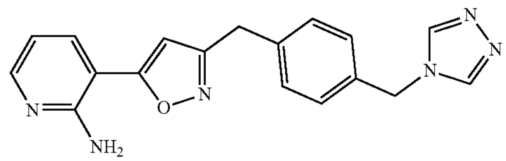 [SMILES: Nc1ncccc1-c1cc(Cc2ccc(Cn3cnnc3)cc2)no1] | 3-(3-(4-((4H-1,2,4-triazol-4-yl)methyl)benzyl)isoxazol-5-yl)pyridin-2-amine |
| 201 | 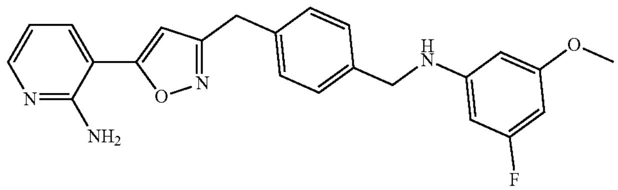 [SMILES: COc1cc(F)cc(NCc2ccc(Cc3cc(-c4cccnc4N)on3)cc2)c1] | 3-(3-(4-(((3-fluoro-5-methoxyphenyl)amino)methyl)benzyl)isoxazol-5-yl)pyridin-2-amine |
| 202 | 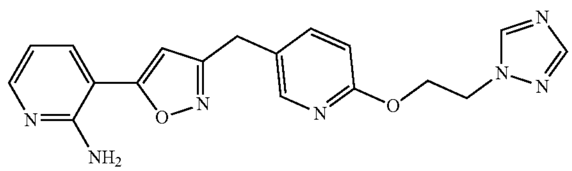 [SMILES: Nc1ncccc1-c1cc(Cc2ccc(OCCn3cncn3)nc2)no1] | 3-(3-((6-(2-(1H-1,2,4-triazol-1-yl)ethoxy)pyridin-3-yl)methyl)isoxazol-5-yl)pyridin-2-amine |
| 203 | 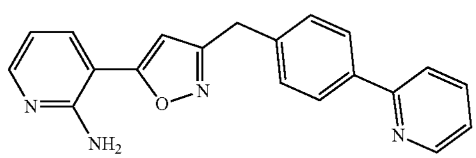 [SMILES: Nc1ncccc1-c1cc(Cc2ccc(-c3ccccn3)cc2)no1] | 3-(3-(4-(pyridin-2-yl)benzyl)isoxazol-5-yl)pyridin-2-amine |
| 204 | 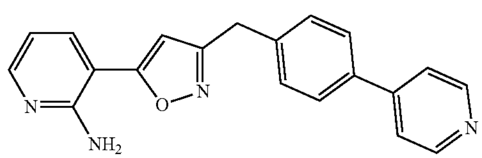 [SMILES: Nc1ncccc1-c1cc(Cc2ccc(-c3ccncc3)cc2)no1] | 3-(3-(4-(pyridin-4-yl)benzyl)isoxazol-5-yl)pyridin-2-amine |
| 205 | 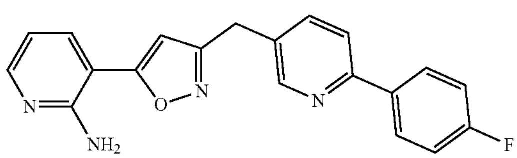 [SMILES: Nc1ncccc1-c1cc(Cc2ccc(-c3ccc(F)cc3)nc2)no1] | 3-(3-((6-(4-fluorophenyl)pyridin-3-yl)methyl)isoxazol-5-yl)pyridin-2-amine |
| 206 | 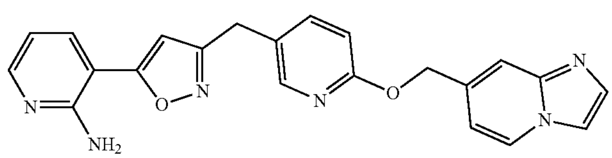 [SMILES: Nc1ncccc1-c1cc(Cc2ccc(OCc3ccn4ccnc4c3)nc2)no1] | 3-(3-((6-(imidazo[1,2-a]pyridin-7-ylmethoxy)pyridin-3-yl)methyl)isoxazol-5-yl)pyridin-2-amine |
| 207 | 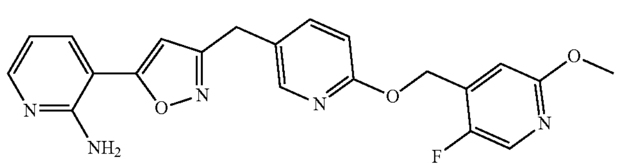 [SMILES: COc1cc(COc2ccc(Cc3cc(-c4cccnc4N)on3)cn2)c(F)cn1] | 3-(3-((6-((5-fluoro-2-methoxypyridin-4-yl)methoxy)pyridin-3-yl)methyl)isoxazol-5-yl)pyridin-2-amine |
| 208 | 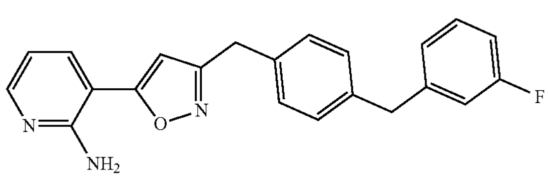 [SMILES: Nc1ncccc1-c1cc(Cc2ccc(Cc3cccc(F)c3)cc2)no1] | 3-(3-(4-(3-fluorobenzyl)benzyl)isoxazol-5-yl)pyridin-2-amine |

TABLE 1-continued

| Ex. | Structure | Name |
|---|---|---|
| 209 | 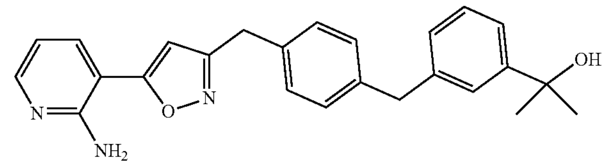 [SMILES: CC(C)(O)c1cccc(Cc2ccc(Cc3cc(-c4cccnc4N)on3)cc2)c1] | 2-(3-(4-((5-(2-aminopyridin-3-yl)isoxazol-3-yl)methyl)benzyl)phenyl)propan-2-ol |
| 210 | 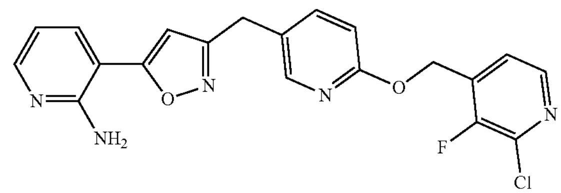 [SMILES: Nc1ncccc1-c1cc(Cc2ccc(OCc3ccnc(Cl)c3F)nc2)no1] | 3-(3-((6-((2-chloro-3-fluoropyridin-4-yl)methoxy)pyridin-3-yl)methyl)isoxazol-5-yl)pyridin-2-amine |
| 211 | 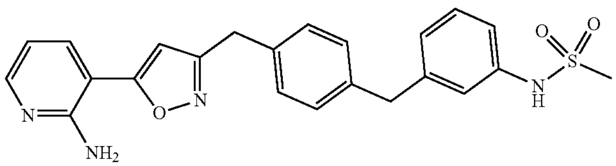 [SMILES: CS(=O)(=O)Nc1cccc(Cc2ccc(Cc3cc(-c4cccnc4N)on3)cc2)c1] | N-(3-(4-((5-(2-aminopyridin-3-yl)isoxazol-3-yl)methyl)benzyl)phenyl)methanesulfonamide |
| 212 | 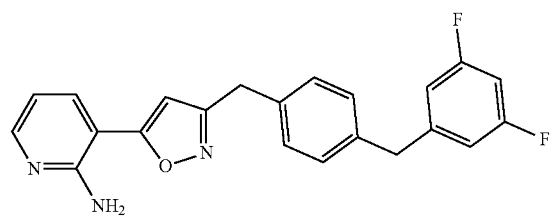 [SMILES: Nc1ncccc1-c1cc(Cc2ccc(Cc3cc(F)cc(F)c3)cc2)no1] | 3-(3-(4-(3,5-difluorobenzyl)benzyl)isoxazol-5-yl)pyridin-2-amine |
| 213 | 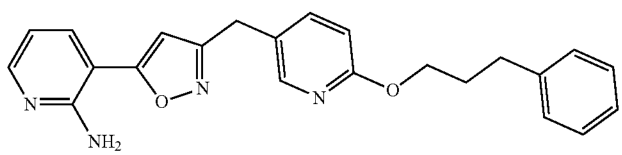 [SMILES: Nc1ncccc1-c1cc(Cc2ccc(OCCCc3ccccc3)nc2)no1] | 3-(3-((6-(3-phenylpropoxy)pyridin-3-yl)methyl)isoxazol-5-yl)pyridin-2-amine |
| 214 | 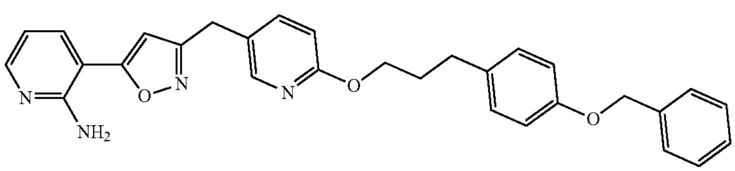 [SMILES: Nc1ncccc1-c1cc(Cc2ccc(OCCCc3ccc(OCc4ccccc4)cc3)nc2)no1] | 3-(3-((6-(3-(4-(benzyloxy)phenyl)propoxy)pyridin-3-yl)methyl)isoxazol-5-yl)pyridin-2-amine |
| 215 | 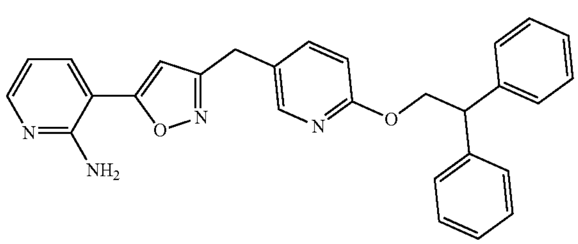 [SMILES: Nc1ncccc1-c1cc(Cc2ccc(OCC(c3ccccc3)c3ccccc3)nc2)no1] | 3-(3-((6-(2,2-diphenylethoxy)pyridin-3-yl)methyl)isoxazol-5-yl)pyridin-2-amine |
| 216 | 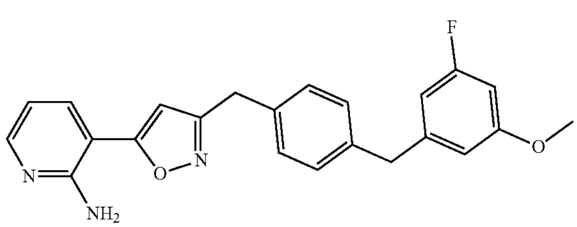 [SMILES: COc1cc(F)cc(Cc2ccc(Cc3cc(-c4cccnc4N)on3)cc2)c1] | 3-(3-(4-(3-fluoro-5-methoxybenzyl)benzyl)isoxazol-5-yl)pyridin-2-amine |

TABLE 1-continued

| Ex. | Structure | Name |
|---|---|---|
| 217 | 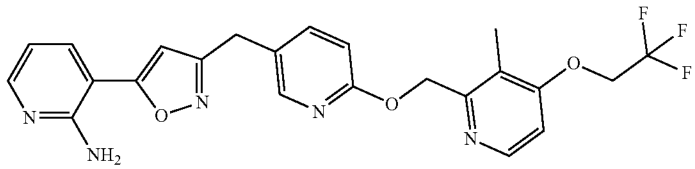 [SMILES: Cc1c(OCC(F)(F)F)ccnc1COc1ccc(Cc2cc(-c3cccnc3N)on2)cn1] | 3-(3-((6-((3-methyl-4-(2,2,2-trifluoroethoxy)pyridin-2-yl)methoxyl)pyridin-3-yl)methyl)isoxazol-5-yl)pyridin-2-amine |
| 218 | 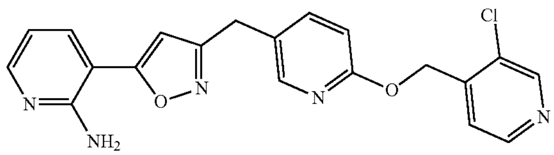 [SMILES: Nc1ncccc1-c1cc(Cc2ccc(OCc3ccncc3Cl)nc2)no1] | 3-(3-((6-((3-chloropyridin-4-yl)methoxy)pyridin-3-yl)methyl)isoxazol-5-yl)pyridin-2-amine |
| 219 | 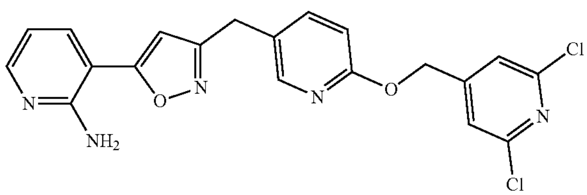 | 3-(3-((6-((2,6-dichloropyridin-4-yl)methoxy)pyridin-3-yl)methyl)isoxazol-5-yl)pyridin-2-amine |
| 220 | 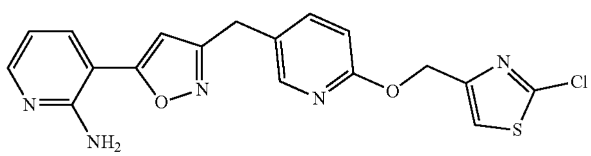 [SMILES: Nc1ncccc1-c1cc(Cc2ccc(OCc3csc(Cl)n3)nc2)no1] | 3-(3-((6-((2-chlorothiazol-4-yl)methoxy)pyridin-3-yl)methyl)isoxazol-5-yl)pyridin-2-amine |
| 221 | 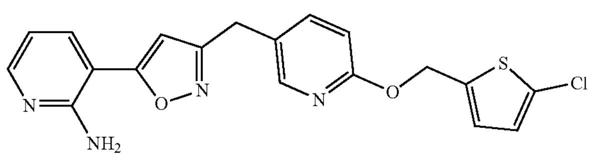 [SMILES: Nc1ncccc1-c1cc(Cc2ccc(OCc3ccc(Cl)s3)nc2)no1] | 3-(3-((6-((5-chlorothiophen-2-yl)methoxy)pyridin-3-yl)methyl)isoxazol-5-yl)pyridin-2-amine |
| 222 | 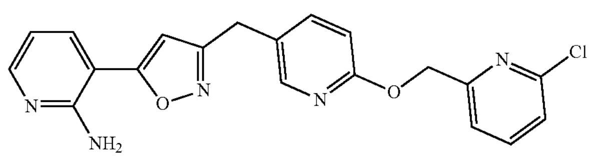 | 3-3-((6-((6-chloropyridin-2-ylmethoxy)pyridin-3-yl)methyl)isoxazol-5-yl)pyridin-2-amine |
| 223 | 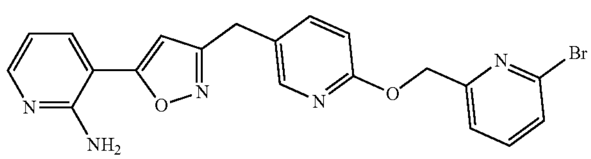 | 3-(3-((6-((6-bromopyridin-2-yl)methoxy)pyridin-3-yl)methyl)isoxazol-5-yl)pyridin-2-amine |
| 224 | 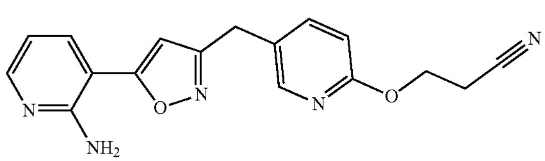 | 3-((5-((5-(2-aminopyridin)-3-yl)isoxazol-3-yl)methyl)pyridin-2-yl)oxy)propanenitrile |
| 225 | 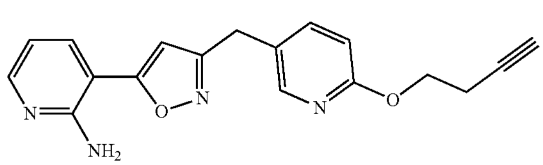 [SMILES: C#CCCOc1ccc(Cc2cc(-c3cccnc3N)on2)cn1] | 3-(3-((6-(but-3-yn-1-yloxy)pyridin-3-yl)methyl)isoxazol-5-yl)pyridin-2-amine |

TABLE 1-continued

| Ex. | Structure | Name |
|---|---|---|
| 226 | 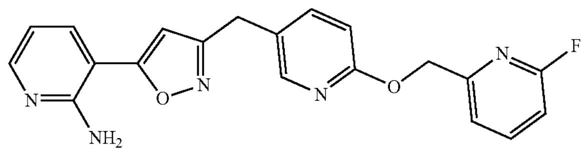 | 3-(3-((6-((6-fluoropyridin-2-yl)methoxy)pyridin-3-yl)methyl)isoxazol-5-yl)pyridin-2-amine |
| 227 | 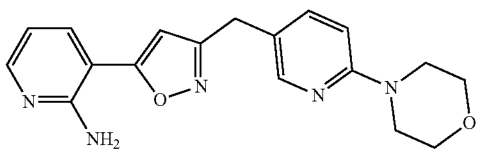 [SMILES: Nc1ncccc1-c1cc(Cc2ccc(N3CCOCC3)nc2)no1] | 3-(3-((6-morpholinopyridin-3-yl)methyl)isoxazol-5-yl)pyridin-2-amine |
| 228 | 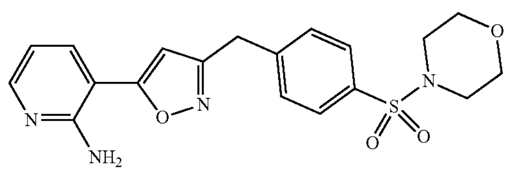 [SMILES: Nc1ncccc1-c1cc(Cc2ccc(S(=O)(=O)N3CCOCC3)cc2)no1] | 3-(3-(4-(morpholinosulfonyl)benzyl)isoxazol-5-yl)pyridin-2-amine |
| 229 | 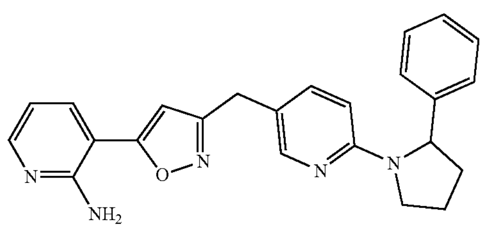 [SMILES: Nc1ncccc1-c1cc(Cc2ccc(N3CCCC3c3ccccc3)nc2)no1] | 3-(3-((6-(2-phenylpyrrolidin-1-yl)pyridin-3-yl)methyl)isoxazol-5-yl)pyridin-2-amine |
| 230 | 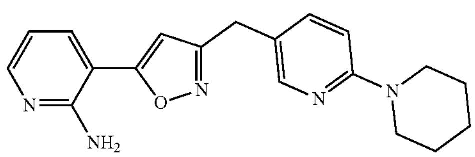 [SMILES: Nc1ncccc1-c1cc(Cc2ccc(N3CCCCC3)nc2)no1] | 3-(3-((6-(piperidin-1-yl)pyridin-3-yl)methyl)isoxazol-5-yl)pyridin-2-amine |
| 231 | 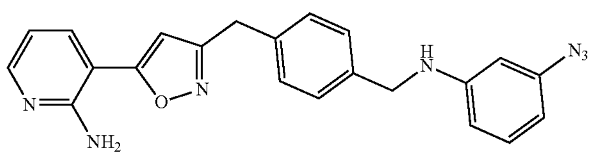 [SMILES: [N-]=[N+]=Nc1cccc(NCc2ccc(Cc3cc(-c4cccnc4N)on3)cc2)c1] | 3-(3-(4-(((3-azidophenyl)amino)methyl)benzyl)isoxazol-5-yl)pyridin-2-amine |
| 232 | 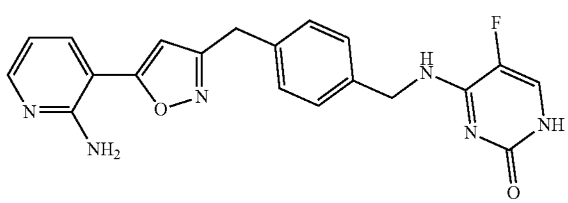 [SMILES: Nc1ncccc1-c1cc(Cc2ccc(CNc3nc(=O)[nH]cc3F)cc2)no1] | 4-((4-((5-(2-aminopyridin-3-yl)isoxazol-3-yl)methyl)benzyl)amino)-5-fluoropyrimidin-2(1H)-one |
| 233 | 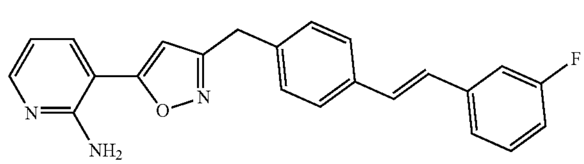 | (E)-3-(3-(4-(3-fluorostyryl)benzyl)isoxazol-5-yl)pyridin-2-amine |
| 234 | 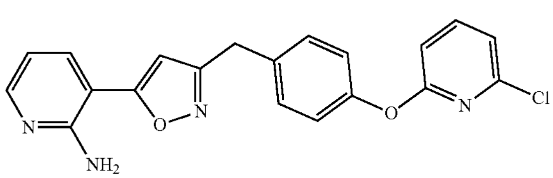 | 3-(3-(4-((6-chloropyridin-2-yl)oxy)benzyl)isoxazol-5-yl)pyridin-2-amine |

TABLE 1-continued

| Ex. | Structure | Name |
|---|---|---|
| 235 | 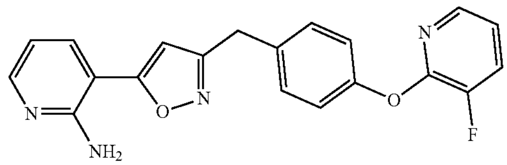 | 3-(3-(4-((3-fluoropyridin-2-yl)oxy)benzyl)isoxazol-yl)pyridin-2-amine |
| 236 | 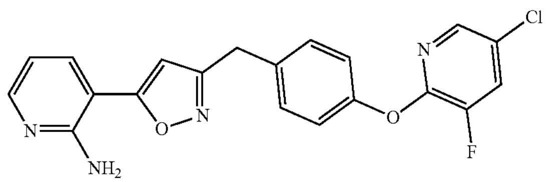 [SMILES: Nc1ncccc1-c1cc(Cc2ccc(Oc3ncc(Cl)cc3F)cc2)no1] | 3-(3-(4-((5-chloro-3-fluoropyridin-2-yl)oxy)benzyl)isoxazol-5-yl)pyridin-2-amine |
| 237 | 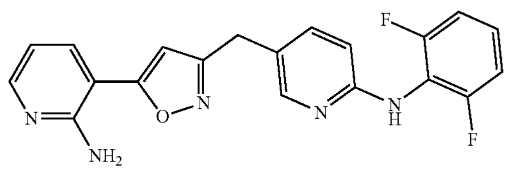 [SMILES: Nc1ncccc1-c1cc(Cc2ccc(Nc3c(F)cccc3F)nc2)no1] | 5-((5-(2-aminopyridin-3-yl)isoxazol-3-yl)methyl)-N-(2,6-difluorophenyl)pyridin-2-amine |
| 238 | 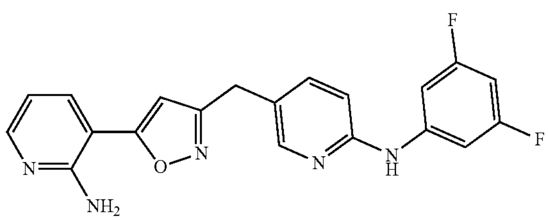 | 5-((5-(2-aminopyridin-3-yl)isoxazol-3-yl)methyl)-N-(3,5-difluorophenyl)pyridin-2-amine |
| 239 | 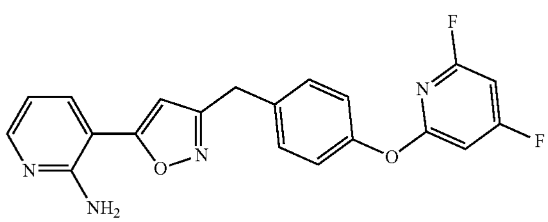 [SMILES: Nc1ncccc1-c1cc(Cc2ccc(Oc3cc(F)cc(F)n3)cc2)no1] | 3-(3-(4-((4,6-difluoropyridin-2-yl)oxy)benzyl)isoxazol-5-yl)pyridin-2-amine |
| 240 | 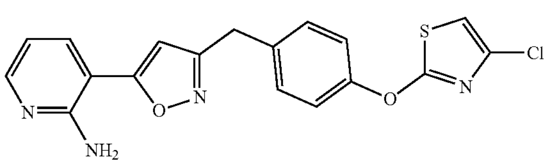 [SMILES: Nc1ncccc1-c1cc(Cc2ccc(Oc3nc(Cl)cs3)cc2)no1] | 3-(3-(4-((4-chlorothiazol-2-yl)oxy)benzyl)isoxazol-5-yl)pyridin-2-amine |
| 241 | 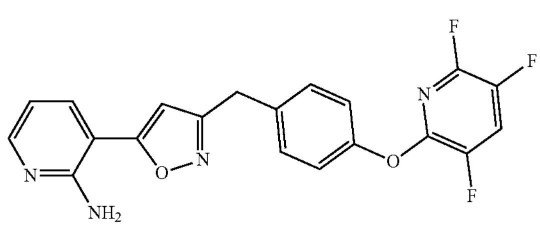 [SMILES: Nc1ncccc1-c1cc(Cc2ccc(Oc3nc(F)c(F)cc3F)cc2)no1] | 3-(3-(4-((3,5,6-trifluoropyridin-2-yl)oxy)benzyl)isoxazol-5-yl)pyridin-2-amine |
| 242 | 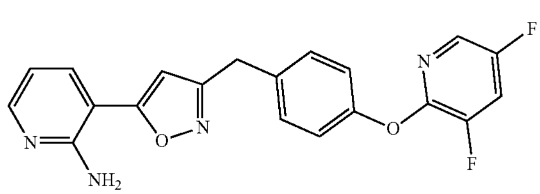 [SMILES: Nc1ncccc1-c1cc(Cc2ccc(Oc3ncc(F)cc3F)cc2)no1] | 3-(3-(4-((3,5-difluoropyridin-2-yl)oxy)benzyl)isoxazol-5-yl)pyridin-2-amine |

TABLE 1-continued

| Ex. | Structure | Name |
|---|---|---|
| 243 | 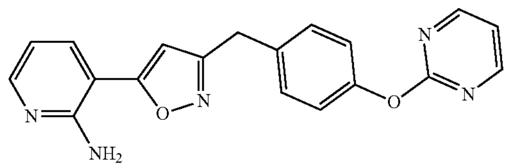 | 3-(3-(4-(pyrimidin-2-yloxy)benzyl)isoxazol-5-yl)pyridin-2-amine |
| 244 | 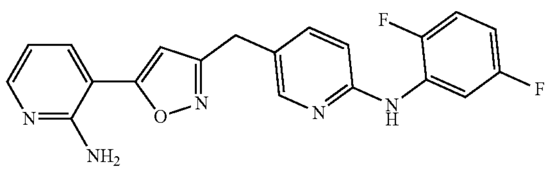 [SMILES: Nc1ncccc1-c1cc(Cc2ccc(Nc3cc(F)ccc3F)nc2)no1] | 5-((5-(2-aminopyridin-3-yl)isoxazol-3-yl)methyl)-N-(2,5-difluorophenyl)pyridin-2-amine |
| 245 | 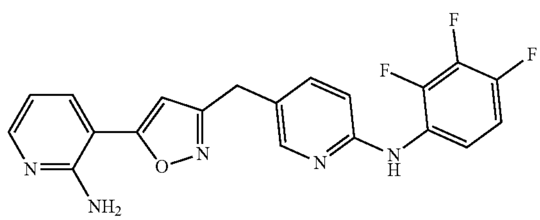 [SMILES: Nc1ncccc1-c1cc(Cc2ccc(Nc3ccc(F)c(F)c3F)nc2)no1] | 5-((5-(2-aminopyridin-3-yl)isoxazol-3-yl)methyl)-N-(2,3,4-trifluorophenyl)pyridin-2-amine |
| 246 | 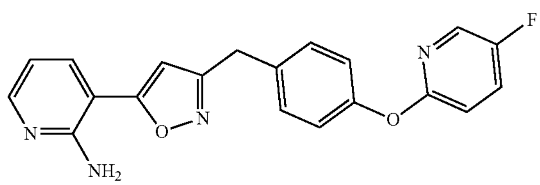 [SMILES: Nc1ncccc1-c1cc(Cc2ccc(Oc3ccc(F)cn3)cc2)no1] | 3-(3-(4-((5-fluoropyridin-2-yl)oxy)benzyl)isoxazol-5-yl)pyridin-2-amine |
| 247 | 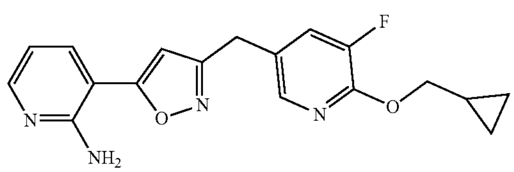 [SMILES: Nc1ncccc1-c1cc(Cc2cnc(OCC3CC3)c(F)c2)no1] | 3-(3-((6-(cyclopropylmethoxy)-5-fluoropyridin-3-yl)methyl)isoxazol-5-yl)pyridin-2-amine |
| 248 | 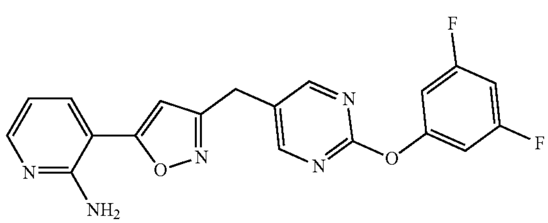 | 3-(3-((2-(3,5-difluorophenoxy)pyrimidin-5-yl)methyl)isoxazol-5-yl)pyridin-2-amine |
| 249 | 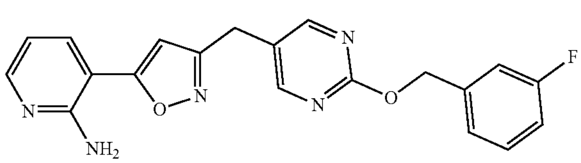 | 3-(3-((2-((3-fluorobenzyl)oxy)pyrimidin-5-yl)methyl)isoxazol-5-yl)pyridin-2-amine |
| 250 | 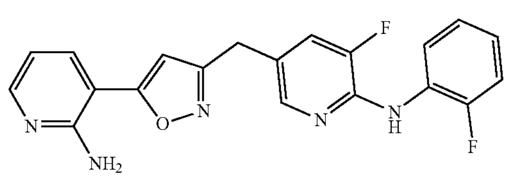 [SMILES: Nc1ncccc1-c1cc(Cc2cnc(Nc3ccccc3F)c(F)c2)no1] | 5-(((5-(2-aminopyridin-3-yl)isoxazol-3-yl)methyl)-3-fluoro-N-(2-fluorophenyl)pyridin-2-amine |

TABLE 1-continued

| Ex. | Structure | Name |
|---|---|---|
| 251 | 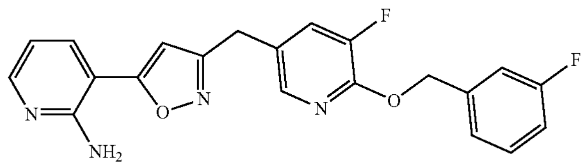 [SMILES: Nc1ncccc1-c1cc(Cc2cnc(OCc3cccc(F)c3)c(F)c2)no1] | 3-(3-((5-fluoro-6-((3-fluorobenzyl)oxy)pyridin-3-yl)methyl)isoxazol-5-yl)pyridin-2-amine |
| 252 | 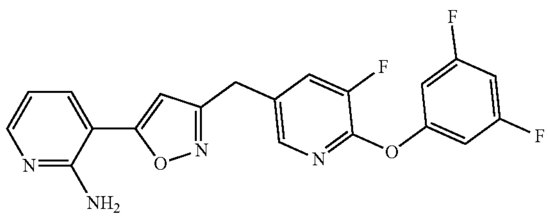 [SMILES: Nc1ncccc1-c1cc(Cc2cnc(Oc3cc(F)cc(F)c3)c(F)c2)no1] | 3-(3-((6-(3,5-difluorophenoxy)-5-fluoropyridin-3-yl)methyl)isoxazol-5-yl)pyridin-2-amine |
| 253 | 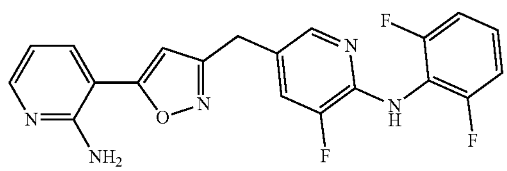 [SMILES: Nc1ncccc1-c1cc(Cc2cnc(Nc3c(F)cccc3F)c(F)c2)no1] | 5-((5-(2-aminopyridin-3-yl)isoxazol-3-yl)methyl)-N-(2,6-difluorophenyl)-3-fluoropyridin-2-amine |
| 254 | 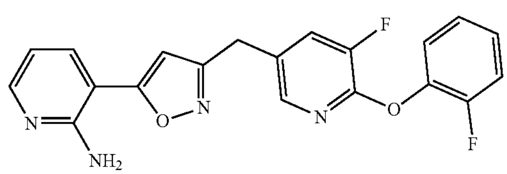 [SMILES: Nc1ncccc1-c1cc(Cc2cnc(Oc3ccccc3F)c(F)c2)no1] | 3-(3-((5-fluoro-6-(2-fluorophenoxy)pyridin-3-yl)methyl)isoxazol-5-yl)pyridin-2-amine |
| 255 | 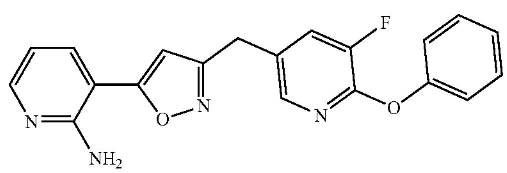 [SMILES: Nc1ncccc1-c1cc(Cc2cnc(Oc3ccccc3)c(F)c2)no1] | 3-(3-((5-fluoro-6-phenoxypyridin-3-yl)methyl)isoxazol-5-yl)pyridin-2-amine |
| 256 | 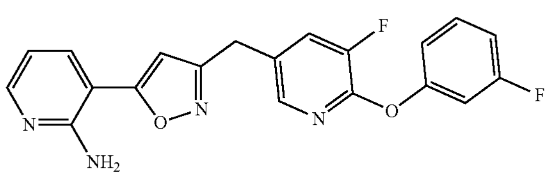 [SMILES: Nc1ncccc1-c1cc(Cc2cnc(Oc3cccc(F)c3)c(F)c2)no1] | 3-(3-((5-fluoro-6-(3-fluorophenoxy)pyridin-3-yl)methyl)isoxazol-5-yl)pyridin-2-amine |
| 257 | 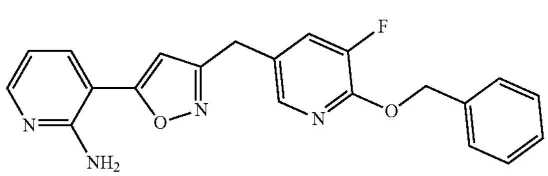 [SMILES: Nc1ncccc1-c1cc(Cc2cnc(OCc3ccccc3)c(F)c2)no1] | 3-(3-((6-(benzyloxy)-5-fluoropyridin-3-yl)methyl)isoxazol-5-yl)pyridin-2-amine |
| 258 | 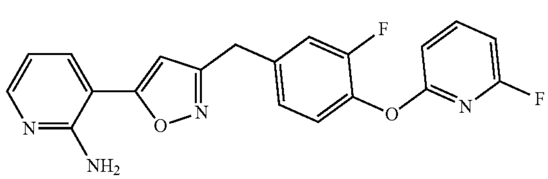 [SMILES: Nc1ncccc1-c1cc(Cc2ccc(Oc3cccc(F)n3)c(F)c2)no1] | 3-(3-(3-fluoro-4-((6-fluoropyridin-2-yl)oxy)benzyl)isoxazol-5-yl)pyridin-2-amine |

TABLE 1-continued

| Ex. | Structure | Name |
|---|---|---|
| 259 | 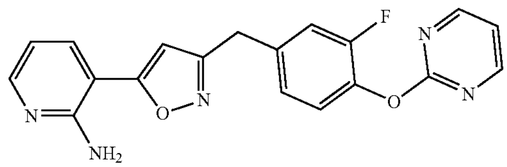 [SMILES: Nc1ncccc1-c1cc(Cc2ccc(Oc3ncccn3)c(F)c2)no1] | 3-(3-(3-fluoro-4-(pyrimidin-2-yloxy)benzyl)isoxazol-5-yl)pyridin-2-amine |
| 260 | 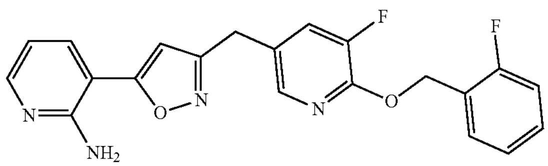 [SMILES: Nc1ncccc1-c1cc(Cc2cnc(OCc3ccccc3F)c(F)c2)no1] | 3-(3-((5-fluoro-6-((2-fluorobenzyl)oxy)pyridin-3-yl)methyl)isoxazol-5-yl)pyridin-2-amine |
| 261 | 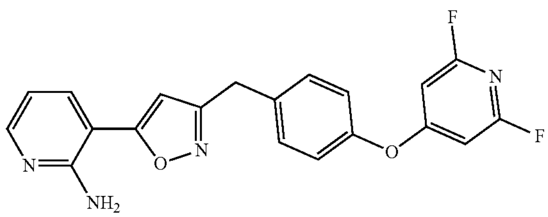 [SMILES: Nc1ncccc1-c1cc(Cc2ccc(Oc3cc(F)nc(F)c3)cc2)no1] | 3-(3-(4-((2,6-difluoropyridin-4-yl)methyl)benzyl)isoxazol-5-yl)pyridin-2-amine |
| 262 | 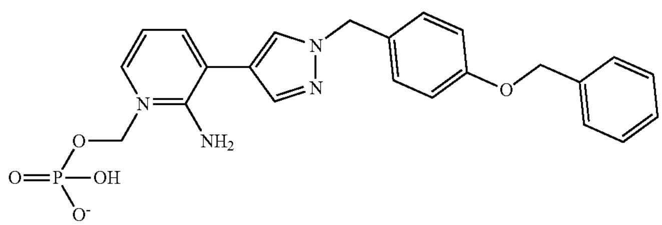 | (2-amino-3-(1-(4-(benzyloxy)benzyl)-1H-pyrazol-4-yl)pyridin-1-ium-1-yl)methyl hydrogen phosphate |
| 263 | 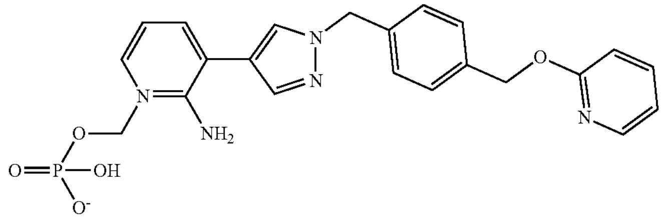 | (3-(1-(4-((pyridin-2-yloxy)methyl)benzyl)-1H-pyrazol-4-yl)pyridin-1-ium-yl)methyl hydrogen phosphate |
| 264 | 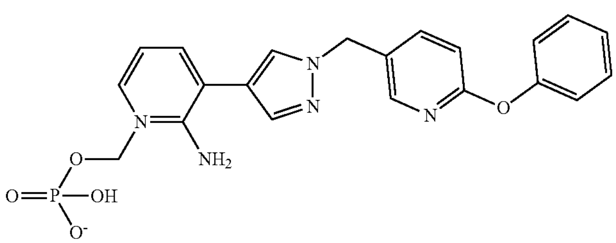 | (2-amino-3-(1-((6-phenoxypyridin-3-yl)methyl)-1H-pyrazol-4-yl)pyridin-1-ium-1-yl)methyl hydrogen phosphate |
| 265 | 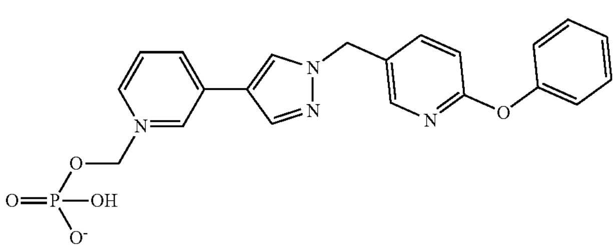 | (3-(1-((6-phenoxypyridin-3-yl)methyl)-1H-pyrazol-4-yl)pyridin-1-ium-1-yl)methyl hydrogen phosphate |

TABLE 1-continued

| Ex. | Structure | Name |
|---|---|---|
| 266 | 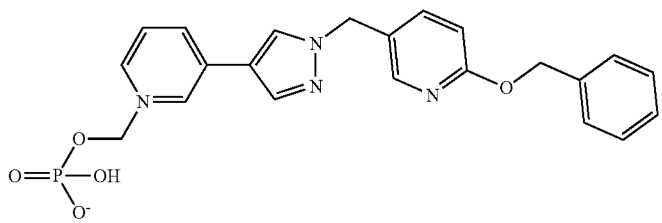 | (3-(1-((6-(benzyloxy)pyridin-3-yl)methyl)-1H-pyrazol-4-yl)pyridin-1-ium-1-yl)methyl hydrogen phosphate |
| 267 | 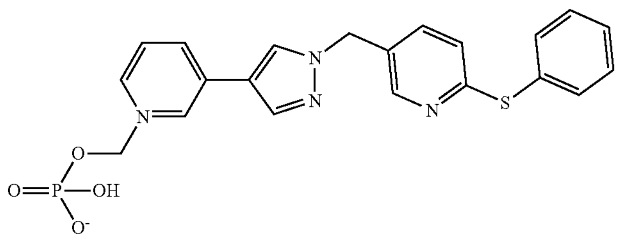 | (3-(1-((6-(phenylthio)pyridin-3-yl)methyl)-1H-pyrazol-4-yl)pyridin-1-ium-1-yl)methyl hydrogen phosphate |
| 268 | 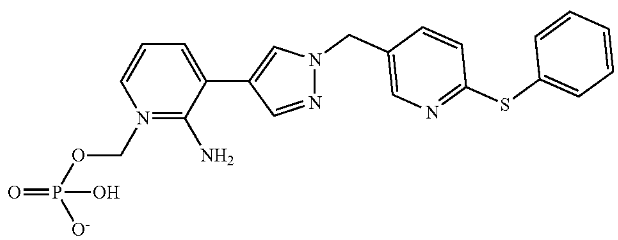 | (2-amino-3-(1-((6-(phenylthio)pyridin-3-yl)methyl)-1H-pyrazol-4-yl)pyridin-1-ium-1-yl)methyl hydrogen phosphate |
| 269 | 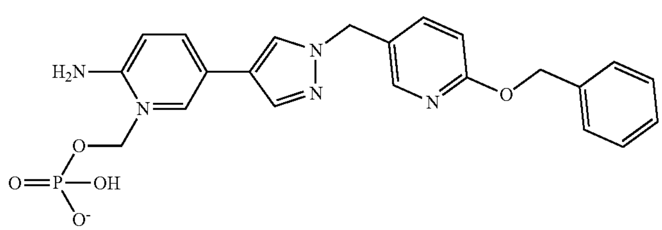 | (2-amino-5-(1-((6-(benzyloxy)pyridin-3-yl)methyl)-1H-pyrazol-4-yl)pyridin-1-ium-1-yl)methyl hydrogen phosphate |
| 270 | 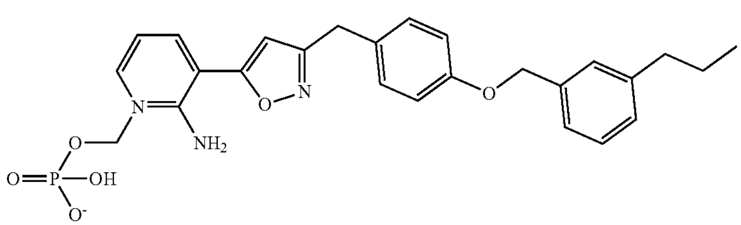 | (2-amino-3-(3-(4-((3-propylphenoxy)methyl)benzyl)isoxazol-5-yl)pyridin-1-ium-1-yl)methyl hydrogen phosphate |
| 271 | 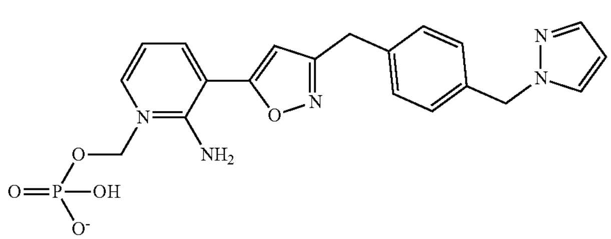 | (3-(3-(4-((1H-pyrazol-1-yl)methyl)benzyl)isoxazol-5-yl)-2-aminopyridin-1-ium-1-yl)methyl hydrogenphosphate |

TABLE 1-continued

| Ex. | Structure | Name |
|---|---|---|
| 272 | 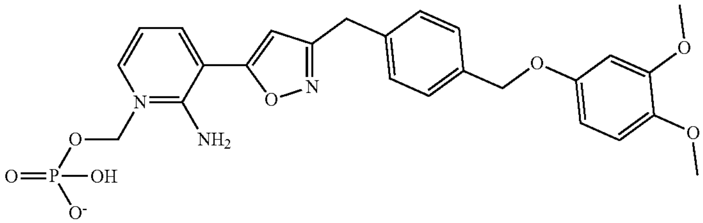 | (2-amino-3-(3-(4-((3,4-dimethoxyphenoxy)methyl)benzyl)isoxazol-5-yl)pyridin-1-ium-1-yl)methyl hydrogen phosphate |
| 273 | 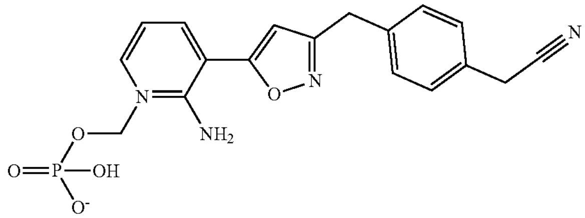 | (2-amino-3-(3-(4-(cyanomethyl)benzyl)isoxazol-5-yl)pyridin-1-ium-1-yl)methyl hydrogen phosphate |
| 274 | 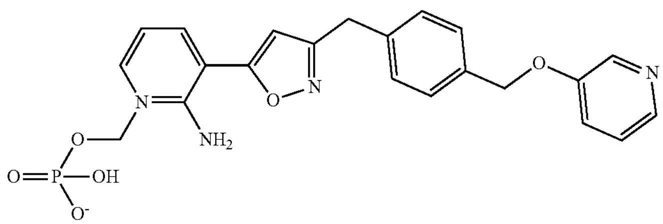 | (2-amino-3-(3-(4-((pyridin-3-yloxy)methyl)benzyl)isoxazol-5-yl)pyridin-1-ium-1-yl)methyl hydrogen phosphate |
| 275 | 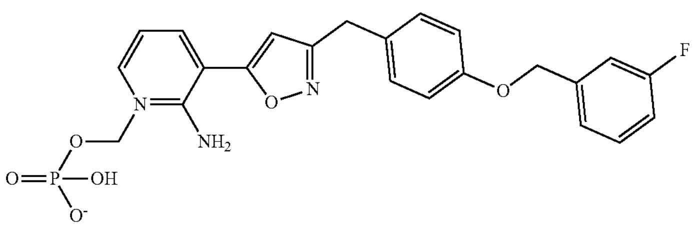 | (2-amino-3-(3-(4-((3-fluorobenzyl)oxy)benzyl)isoxazol-5-yl)pyridin-1-ium-1-yl)methyl hydrogen phosphate |
| 276 | 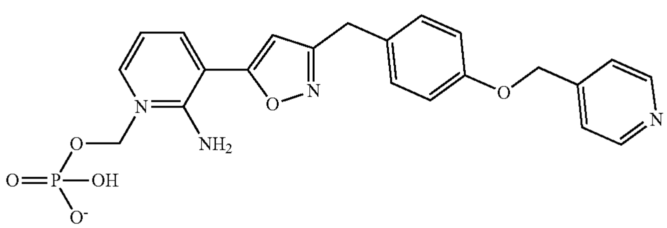 | (2-amino-3-(3-(4-(pyridin-4-ylmethoxy)benzyl)isoxazol-5-yl)pyridin-1-ium-1-yl)methyl hydrogen phosphate |
| 277 | 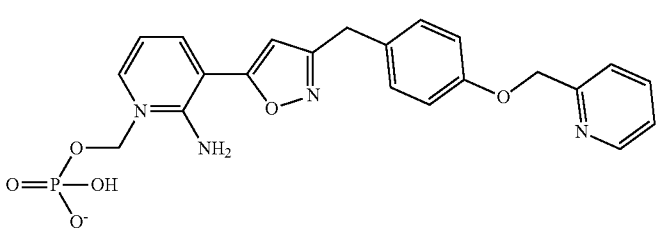 | (2-amino-3-(3-(4-(pyridin-2-ylmethoxy)benzyl)isoxazol-5-yl)pyridin-1-ium-1-yl)methyl hydrogen phosphate |
| 278 | 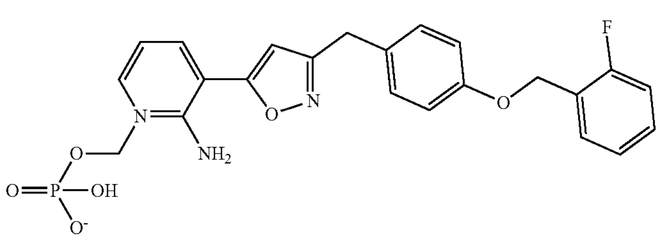 | (2-amino-3-(3-(4-((2-fluorobenzyl)oxy)benzyl)isoxazol-5-yl)pyridin-1-ium-1-yl)methyl hydrogen phosphate |

TABLE 1-continued

| Ex. | Structure | Name |
|---|---|---|
| 279 | 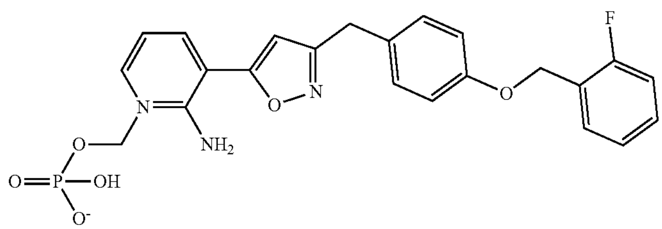 | (2-amino-3-(3-(4-((4-methoxybenzyl)oxy)benzyl)isoxazol-5-yl)pyridin-1-ium-1-yl)methyl hydrogen phosphate |
| 280 | 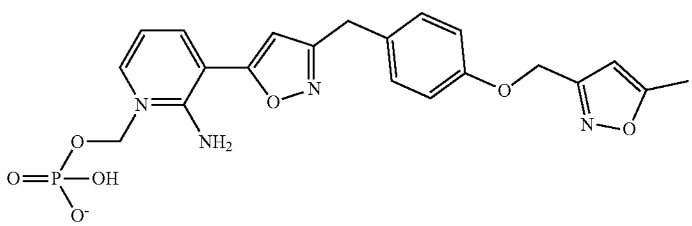 | (2-amino-3-(3-(4-((5-methylisoxazol-3-yl)methoxy)benzyl)isoxazol-5yl)pyridin-1-ium-1-yl)methyl hydrogen phosphate |
| 281 | 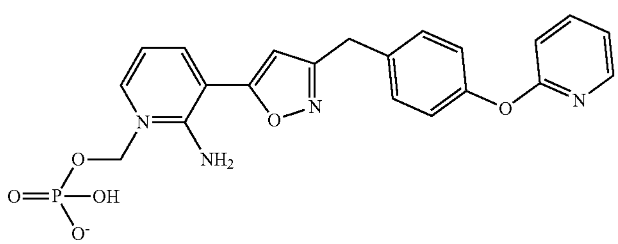 | (2-amino-3-(3-(4-(pyridin-2-yloxy)benzyl)isoxazol-5-yl)pyridin-1-ium-1-yl)methyl hydrogen phosphate |
| 282 | 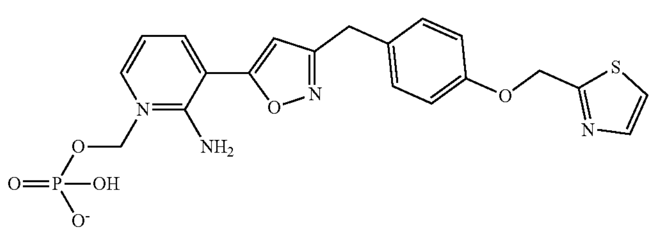 | (2-amino-3-(3-(4-(thiazol-2-ylmethoxy)benzyl)isoxazol-5-yl)pyridin-1-ium-1-yl)methyl hydrogen phosphate |
| 283 | 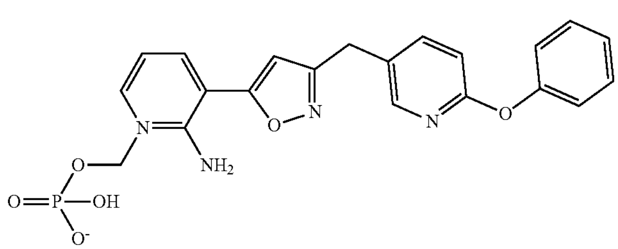 | (2-amino-3-(3-((6-phenoxypyridin-3-yl)methyl)isoxazol-5-yl)pyridin-1-ium-1-yl)methyl hydrogen phosphate |
| 284 | 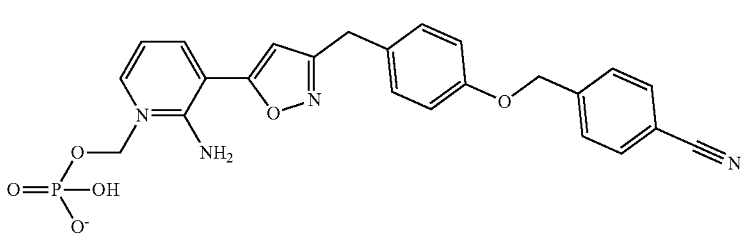 | (2-amino-3-(3-(4-((4-cyanobenzyl)oxy)benzyl)isoxazol-5-yl)pyridin-1-ium-1-yl)methyl hydrogen phosphate |

| Ex. | Structure | Name |
|---|---|---|
| 285 | 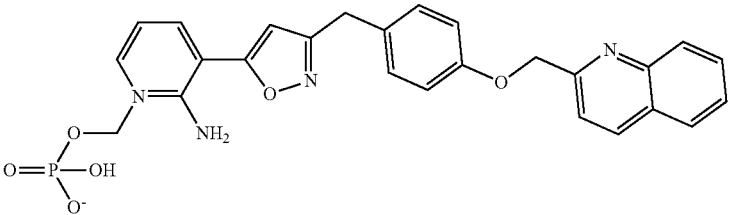 | (2-amino-3-(3-(4-(quinolin-2-ylmethoxy)benzyl)isoxazol-5-yl)pyridin-1-ium-1-yl)methyl hydrogen phosphate |
| 286 | 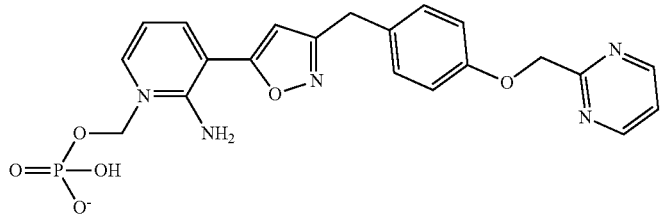 | (2-amino-3-(3-(4-(pyrimidin-2-ylmethoxy)benzyl)isoxazol-5-yl)pyridin-1-ium-1-yl)methyl hydrogen phosphate |
| 287 | 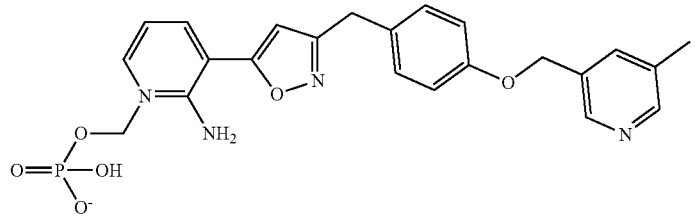 | (2-amino-3-(3-(4-((5-methylpyridin-3-yl)methoxy)benzyl)isoxazol-5-yl)pyridin-1-ium-1-yl)methyl hydrogen phosphate |
| 288 | 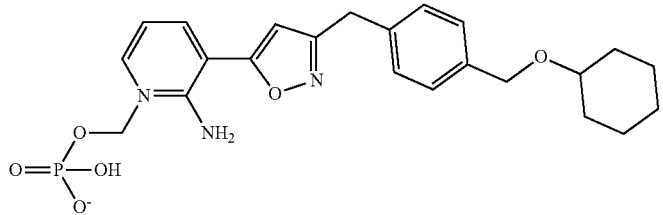 | (2-amino-3-(3-(4-((cyclohexyloxy)methyl)benzyl)isoxazol-5-yl)pyridin-1-ium-1-yl)methyl hydrogen phosphate |
| 289 | 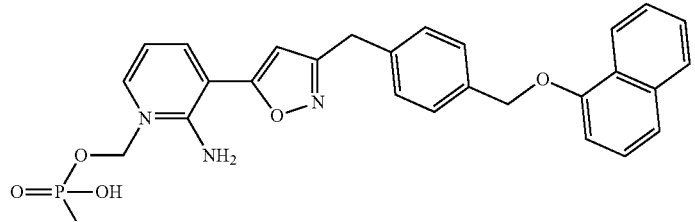 | (2-amino-3-(3-(4-((naphthalen-1-yloxy)methyl)benzyl)isoxazol-5-yl)pyridin-1-ium-1-yl)methyl hydrogen phosphate |
| 290 | 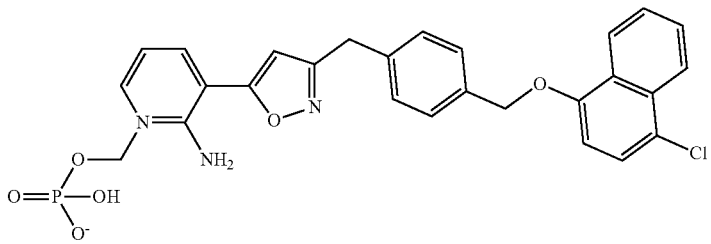 | (2-amino-3-(3-(4-(((4-chloronaphthalen-1-yl)oxy)methyl)benzyl)isoxazol-5-yl)pyridin-1-ium-1-yl)methyl hydrogen phosphate |

TABLE 1-continued

| Ex. | Structure | Name |
|---|---|---|
| 291 | 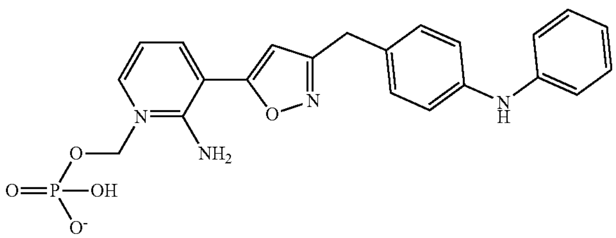 | (2-amino-3-(3-(4-(phenylamino)benzyl)isoxazol-5-yl)pyridin-1-ium-1-yl)methyl hydrogen phosphate |
| 292 | 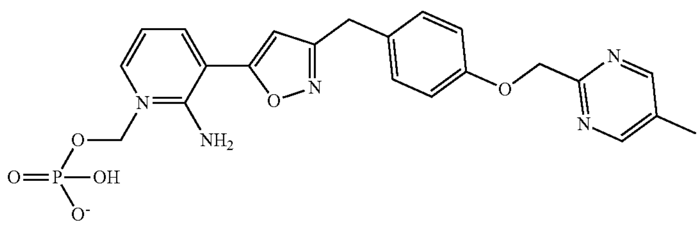 | (2-amino-3-(3-(4-((5-methylpyrimidin-2-yl)methoxy)benzyl)isoxazol-5-yl)pyridin-1-ium-1-yl)methyl hydrogen phosphate |
| 293 | 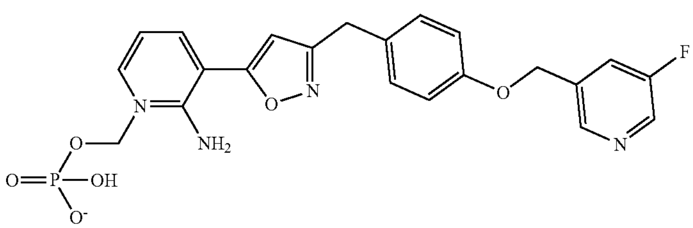 | (2-amino-3-(3-(4-((5-fluoropyridin-3-yl)methoxy)benzyl)isoxazol-5-yl)pyridin-1-ium-1-yl)methyl hydrogen phosphate |
| 294 | 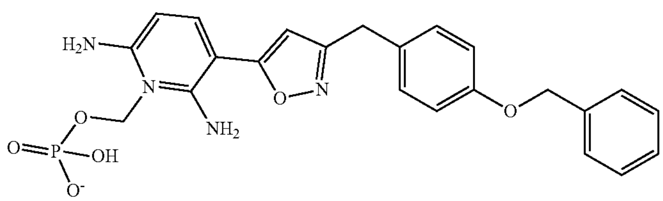 | (2,6-diamino-3-(3-(4-(benzyloxy)benzyl)isoxazol-5-yl)pyridin-1-ium-1-yl)methyl hydrogen phosphate |
| 295 | 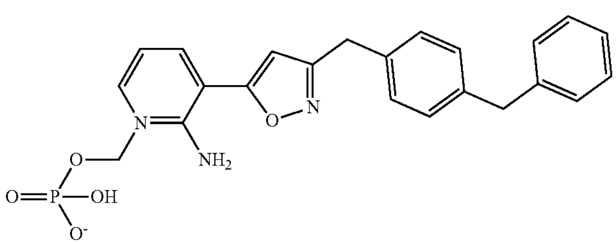 | (2-amino-3-(3-(4-benzylbenzyl)isoxazol-5-yl)pyridin-1-ium-1-yl)methyl hydrogen phosphate |
| 296 | 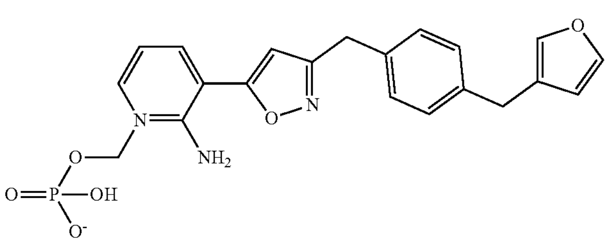 | (2-amino-3-(3-(4-(furan-3-ylmethyl)benzyl)isoxazol-5-yl)pyridin-1-ium-1-yl)methyl hydrogen phosphate |

TABLE 1-continued

| Ex. | Structure | Name |
|---|---|---|
| 297 | 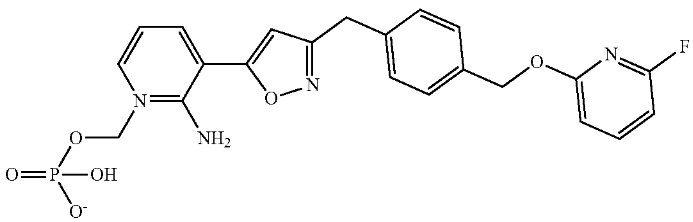 | (2-amino-3-(3-(4-(((6-fluoropyridin-2-yl)oxy)methyl)benzyl)isoxazol-5-yl)pyridin-1-ium-1-yl)methyl hydrogen phosphate |
| 298 | 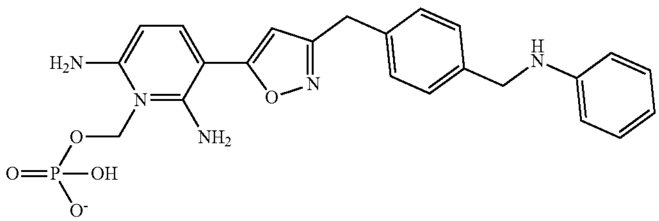 | (2,6-diamino-3-(3-(4-((phenylamino)methyl)benzyl)isoxazol-5-yl)pyridin-1-ium-1-yl)methyl hydrogen phosphate |
| 299 | 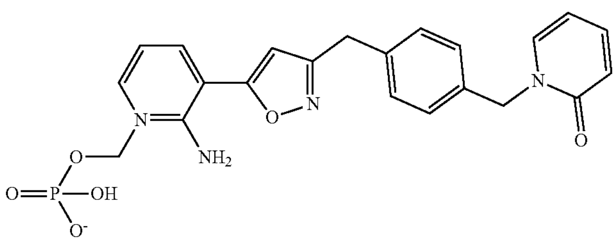 | (2-amino-3-(3-(4-((2-oxopyridin-1(2H)-yl)methyl)benzyl)isoxazol-5-yl)pyridin-1-ium-1-yl)methyl hydrogen phosphate |
| 300 | 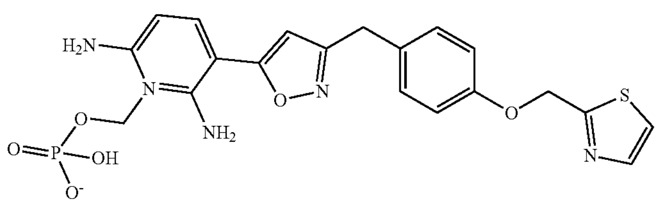 | (2,6-diamino-3-(3-(4-(thiazol-2-ylmethoxy)benzyl)isoxazol-5-yl)pyridin-1-ium-1-yl)methyl hydrogen phosphate |
| 301 | 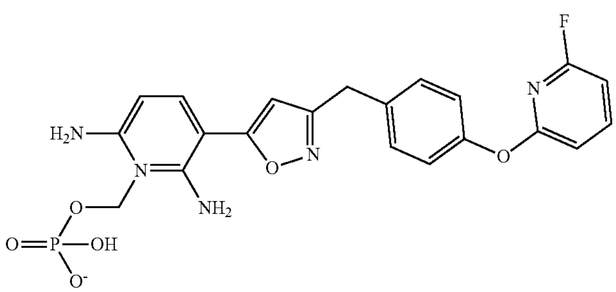 | (2,6-diamino-3-(3-(4-((6-fluoropyridin-2-yl)oxy)benzyl)isoxazol-5-yl)pyridin-1-ium-1-yl)methyl hydrogen phosphate |
| 302 | 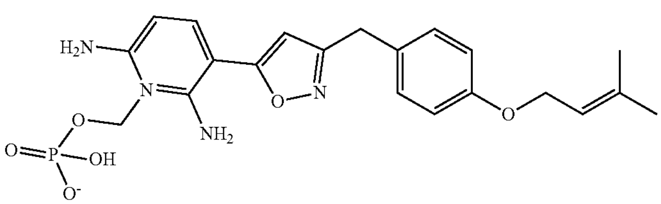 | (2,6-diamino-3-(3-(4-((3-methylbut-2-en-1-yl)oxy)benzyl)isoxazol-5-yl)pyridin-1-ium-1-yl)methyl hydrogen phosphate |

TABLE 1-continued

| Ex. | Structure | Name |
|---|---|---|
| 303 | 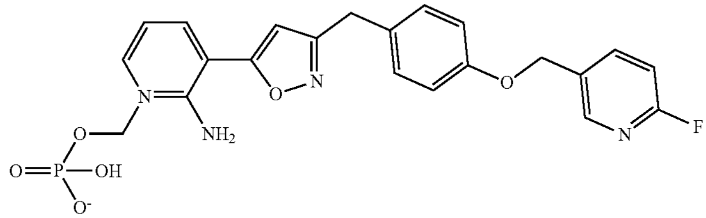 | (2-amino-3-(3-(4-((6-fluoropyridin-3-yl)methoxy)benzyl)isoxazol-5-yl)pyridin-1-ium-1-yl)methyl hydrogen phosphate |
| 304 | 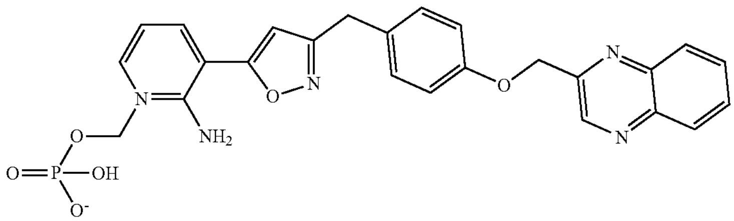 | (2-amino-3-(3-(4-(quinoxalin-2-ylmethoxy)benzyl)isoxazol-5-yl)pyridin-1-ium-1-yl)methyl hydrogen phosphate |
| 305 | 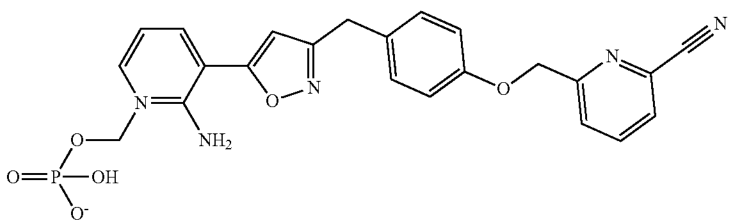 | (2-amino-3-(3-(4-((6-cyanopyridin-2-yl)methoxy)benzyl)isoxazol-5-yl)pyridin-1-ium-1-yl)methyl hydrogen phosphate |
| 306 | 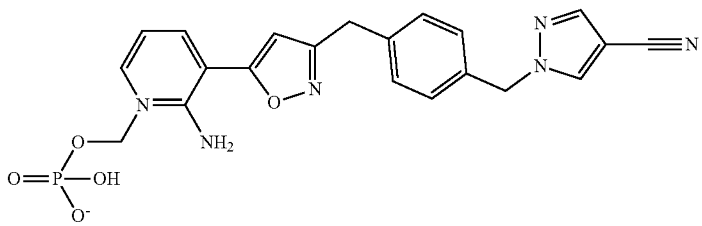 | (2-amino-3-(3-(4-((4-cyano-1H-pyrazol-1-yl)methyl)benzyl)isoxazol-5-yl)pyridin-1-ium-1-yl)methyl hydrogen phosphate |
| 307 | 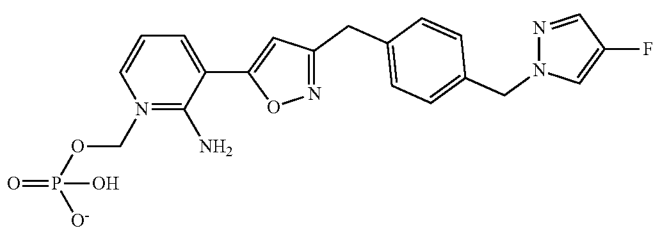 | (2-amino-3-(3-(4-((4-fluoro-1H-pyrazol-1-yl)methyl)benzyl)isoxazol-5-yl)pyridin-1-ium-1-yl)methyl hydrogen phosphate |
| 308 | 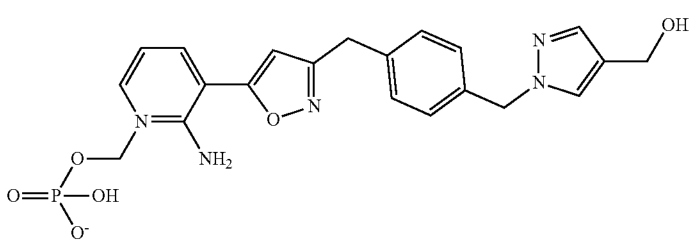 | (2-amino-3-(3-(4-((4-(hydroxymethyl)-1H-pyrazol-1-yl)methyl)benzyl)isoxazol-5-yl)pyridin-1-ium-1-yl)methyl hydrogen phosphate |

TABLE 1-continued

| Ex. | Structure | Name |
|---|---|---|
| 309 | 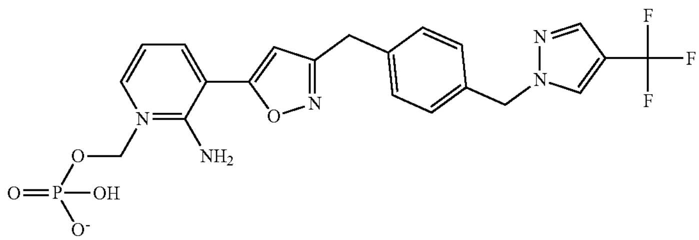 | (2-amino-3-(3-(4-((4-(trifluoromethyl)-1H-pyrazol-1-yl)methyl)benzyl)isoxazol-5-yl)pyridin-1-ium-1-yl)methyl hydrogen phosphate |
| 310 | 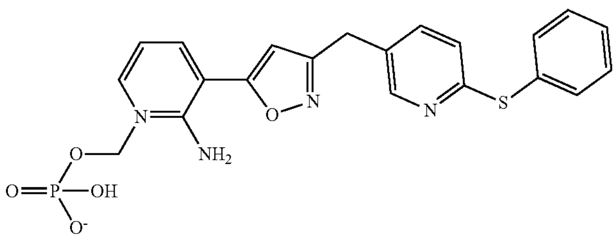 | (2-amino-3-(3-((6-(phenylthio)pyridin-3-yl)methyl)isoxazol-5-yl)pyridin-1-ium-1-yl)methyl hydrogen phosphate |
| 311 | 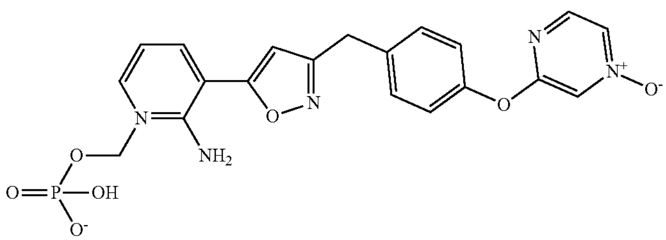 | (2-amino-3-(3-(4-((1-oxidopyrazin-3-yl)oxy)benzyl)isoxazol-5-yl)pyridin-1-ium-1-yl)methyl hydrogen phosphate |
| 312 | 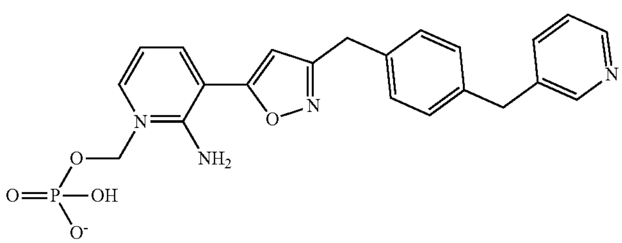 | (2-amino-3-(3-(4-(pyridin-3-ylmethyl)benzyl)isoxazol-5-yl)pyridin-1-ium-1-yl)methyl hydrogen phosphate |
| 313 | 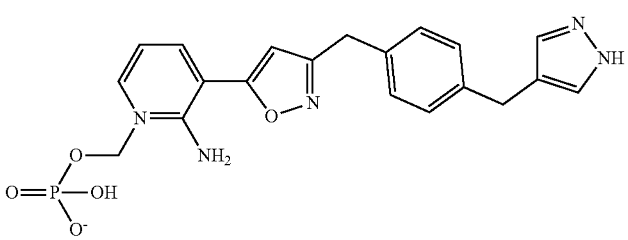 | (3-(3-(4-((1H-pyrazol-4-yl)methyl)benzyl)isoxazol-5-yl)-2-aminopyridin-1-ium-1-yl)methyl hydrogen phosphate |
| 314 | 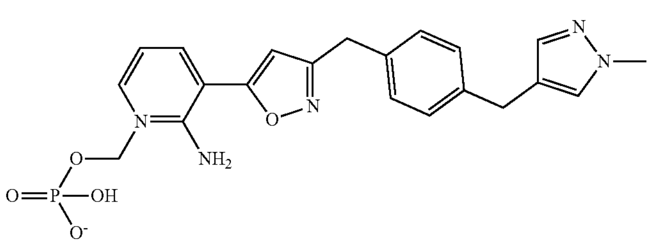 | (2-amino-3-(3-(4-((1-methyl-1H-pyrazol-4-yl)methyl)benzyl)isoxazol-5-yl)pyridin-1-ium-1-yl)methyl hydrogen phosphate |

TABLE 1-continued

| Ex. | Structure | Name |
|---|---|---|
| 315 | 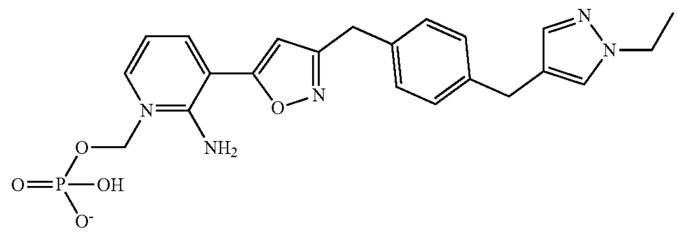 | (2-amino-3-(3-(4-((1-ethyl-1H-pyrazol-4-yl)methyl)benzyl)isoxazol-5-yl)pyridin-1-ium-1-yl)methyl hydrogen phosphate |
| 316 | 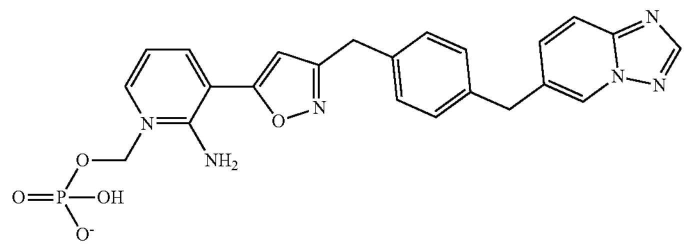 | (3-(3-(4-([1,2,4]triazolo[1,5-a]pyridin-6-ylmethyl)benzyl)isoxazol-5-yl)-2-aminopyridin-1-ium-1-yl)methyl hydrogenphosphate |
| 317 | 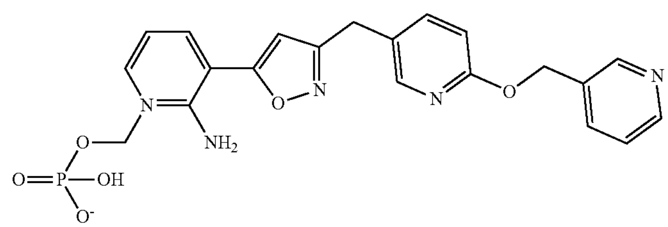 | (2-amino-3-(3-((6-(pyridin-3-ylmethoxy)pyridin-3-yl)methyl)isoxazol-5-yl)pyridin-1-ium-1-yl)methyl hydrogen phosphate |
| 318 | 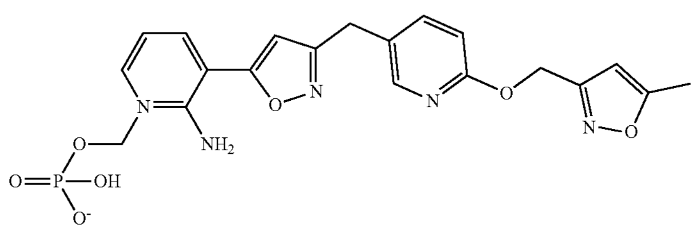 | (2-amino-3-(3-((6-((5-methylisoxazol-3-yl)methoxy)pyridin-3-yl)methyl)isoxazol-5-yl)pyridin-1-ium-1-yl)methyl hydrogen phosphate |
| 319 | 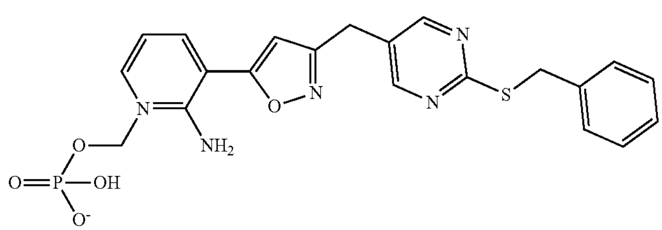 | (2-amino-3-(3-((2-(benzylthio)pyrimidin-5-yl)methyl)isoxazol-5-yl)pyridin-1-ium-1-yl)methyl hydrogen phosphate |
| 320 | 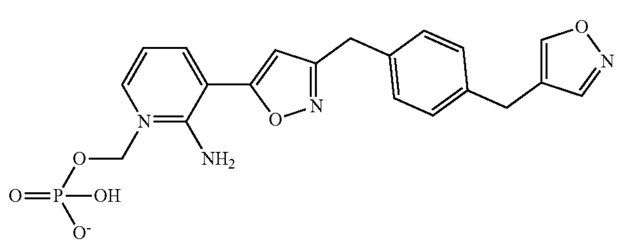 | (2-amino-3-(3-(4-(isoxazol-4-ylmethyl)benzyl)isoxazol-5-yl)pyridin-1-ium-1-yl)methyl hydrogen phosphate |

TABLE 1-continued

| Ex. | Structure | Name |
| --- | --- | --- |
| 321 | 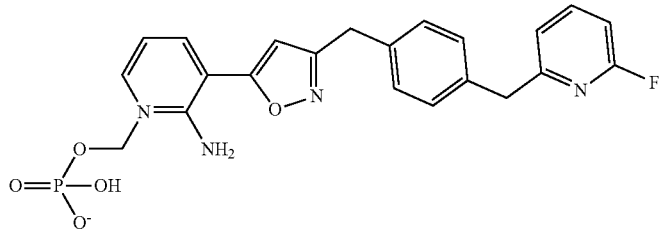 | (2-amino-3-(3-(4-((6-fluoropyridin-2-yl)methyl)benzyl)isoxazol-5-yl)pyridin-1-ium-1-yl)methyl hydrogen phosphate |
| 322 | 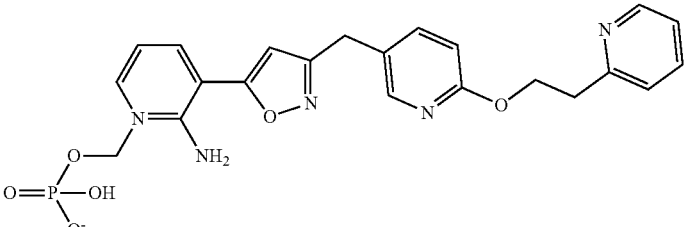 | (2-amino-3-(3-((6-(2-(pyridin-2-yl)ethoxy)pyridin-3-yl)methyl)isoxazol-5-yl)pyridin-1-ium-1-yl)methyl hydrogen phosphate |
| 323 | 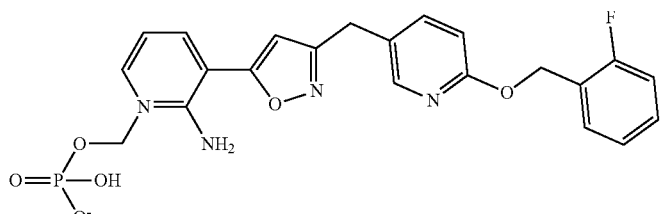 | (2-amino-3-(3-((6-((2-fluorobenzyl)oxy)pyridin-3-yl)methyl)isoxazol-5-yl)pyridin-1-ium-1-yl)methyl hydrogen phosphate |
| 324 | 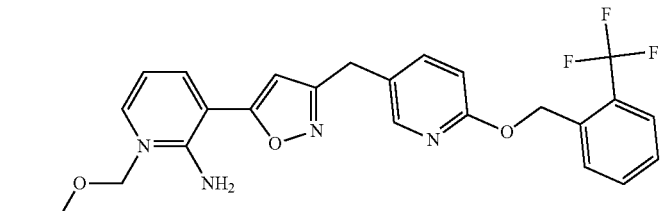 | (2-amino-3-(3-((6-((2-(trifluoromethyl)benzyl)oxy)pyridin-3-yl)methyl)isoxazol-5-yl)pyridin-1-ium-1-yl)methyl hydrogen phosphate |
| 325 | 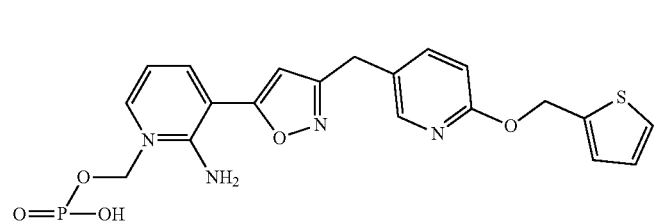 | (2-amino-3-(3-((6-(thiophen-2-ylmethoxy)pyridin-3-yl)methyl)isoxazol-5-yl)pyridin-1-ium-1-yl)methyl hydrogen phosphate |
| 326 | 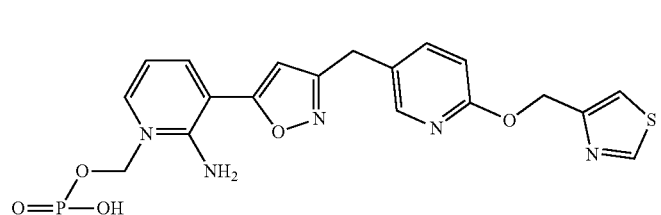 | (2-amino-3-(3-((6-(thiazol-4-ylmethoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 327 | 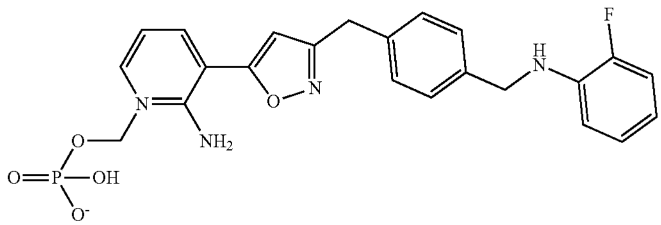 | (2-amino-3-(3-(4-(((2-fluorophenyl)amino)methyl)benzyl)isoxazol-5-yl)pyridin-1-ium-1-yl)methyl hydrogen phosphate |
| 328 | 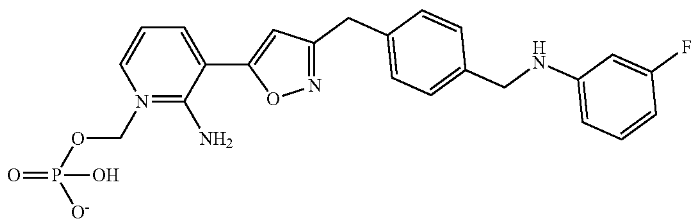 | (2-amino-3-(3-(4-(((3-fluorophenyl)amino)methyl)benzyl)isoxazol-5-yl)pyridin-1-ium-1-yl)methyl hydrogen phosphate |
| 329 | 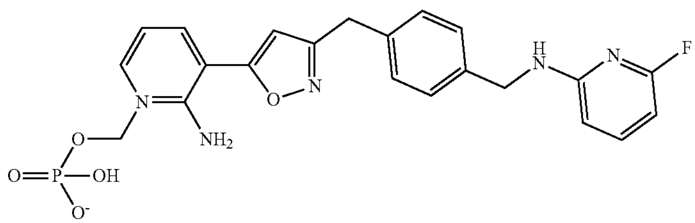 | (2-amino-3-(3-(4-(((6-fluoropyridin-2-yl)amino)methyl)benzyl)isoxazol-5-yl)pyridin-1-ium-1-yl)methyl hydrogen phosphate |
| 330 | 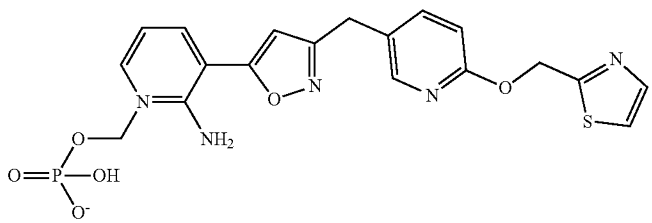 | (2-amino-3-(3-((6-(thiazol-2-ylmethoxy)pyridin-3-yl)methyl)isoxazol-5-yl)pyridin-1-ium-1-yl)methyl hydrogen phosphate |
| 331 | 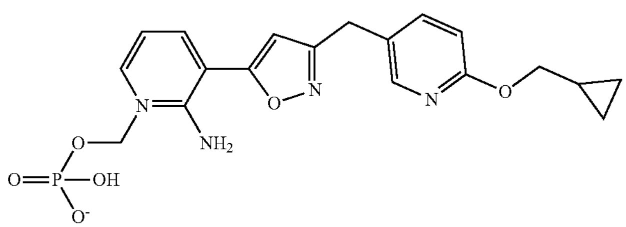 | (2-amino-3-(3-((6-(cyclopropylmethoxy)pyridin-3-yl)methyl)isoxazol-5-yl)pyridin-1-ium-1-yl)methyl hydrogen phosphate |
| 332 | 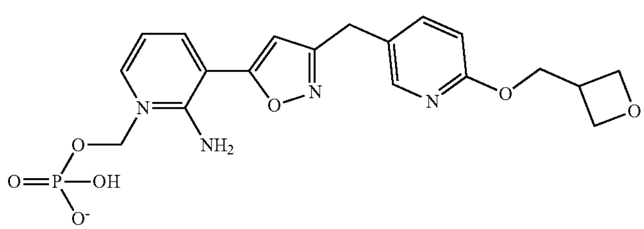 | (2-amino-3-(3-((6-(oxetan-3-ylmethoxy)pyridin-3-yl)methyl)isoxazol-5-yl)pyrdin-1-ium-1-yl)methyl hydrogen phosphate |
| 333 | 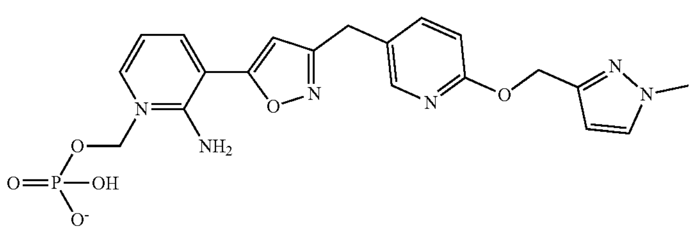 | (2-amino-3-(3-((6-((1-methyl-1H-pyrazol-3-yl)methoxy)pyridin-3-yl)methyl)isoxazol-5-yl)pyridin-1-ium-1-yl)methyl hydrogen phosphate |

TABLE 1-continued

| Ex. | Structure | Name |
| --- | --- | --- |
| 334 | 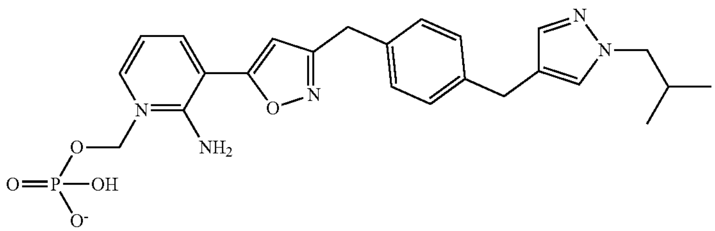 | (2-amino-3-(3-(4-((1-isobutyl-1H-pyrazol-4-yl)methyl)benzyl)isoxazol-5-yl)pyridin-1-ium1-yl)methyl hydrogen phosphate |
| 335 | 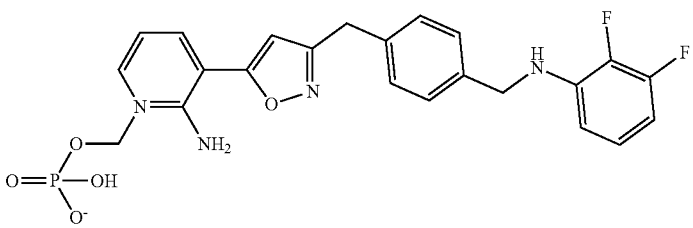 | (2-amino-3-(3-(4-(((2,3-difluorophenyl)amino)methyl)benzyl)isoxazol-5-yl)pyridin-1-ium-1-yl)methyl hydrogen phosphate |
| 336 | 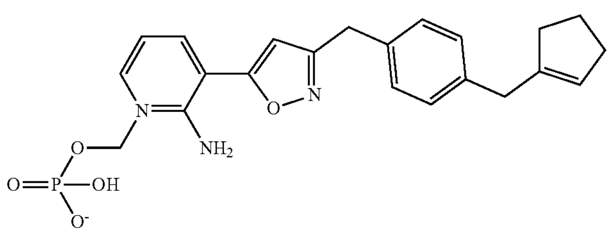 | (2-amino-3-(3-(4-(cyclopent-1-en-1-ylmethyl)benzyl)isoxazol-5-yl)pyridin-1-ium-1-yl)methyl hydrogen phosphate |
| 337 | 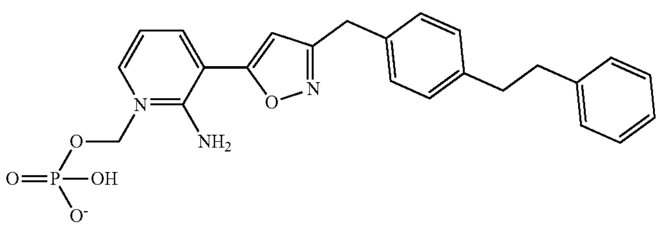 | (2-amino-3-(3-(4-phenethylbenzyl)isoxazol-5-yl)pyridin-1-ium-1-yl)methyl hydrogen phosphate |
| 338 | 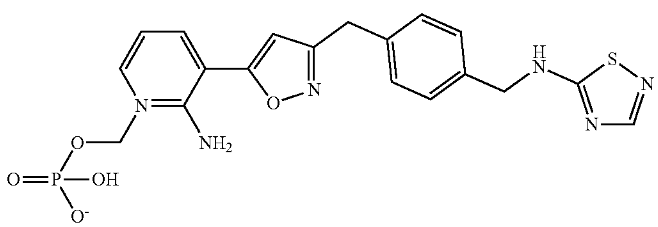 | (3-(3-(4-(((1,2,4-thiadiazol-5-yl)amino)methyl)benzyl)isoxazol-5-yl)-2-aminopyridin-1-ium-1-yl)methyl hydrogen phosphate |
| 339 | 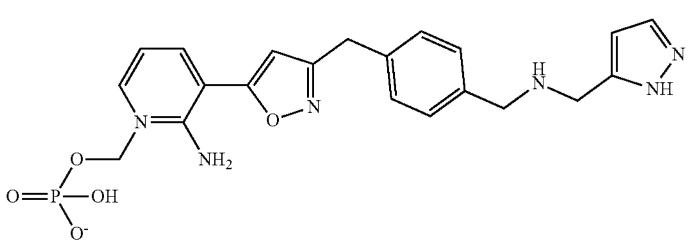 | (3-(3-(4-((((1H-pyrazol-5-yl)methyl)amino)methyl)benzyl)isoxazol-5-yl)-2-aminopyridin-1-ium-1-yl)methyl hydrogen phosphate |

TABLE 1-continued

| Ex. | Structure | Name |
|---|---|---|
| 340 | 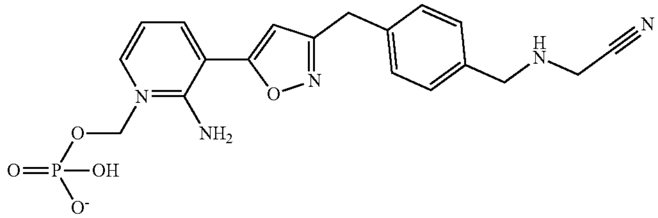 | (2-amino-3-(3-(4-(((cyanomethyl)amino)methyl)benzyl)isoxazol-5-yl)pyridin-1-ium-1-yl)methyl hydrogen phosphate |
| 341 | 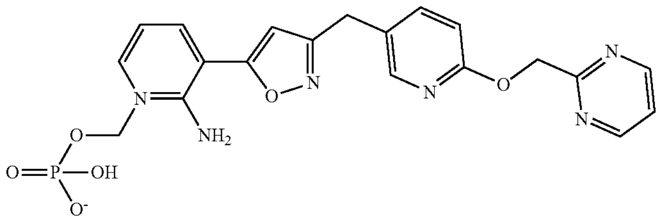 | (2-amino-3-(3-((6-(pyrimidin-2-ylmethoxy)pyridin-3-yl)methyl)isoxazol-5-yl)pyridin-1-ium-1-yl)methyl hydrogen phosphate |
| 342 | 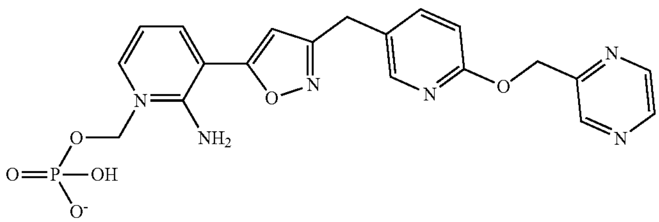 | (2-amino-3-(3-((6-(pyrazin-2-ylmethoxy)pyridin-3-yl)methyl)isoxazol-5-yl)pyridin-1-ium-1-yl)methyl hydrogen phosphate |
| 343 | 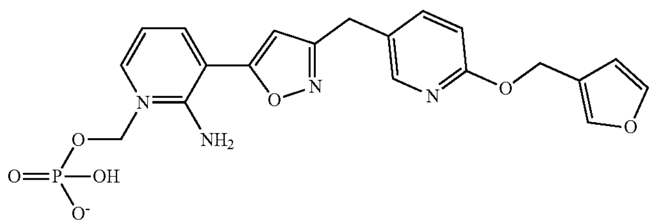 | (2-amino-3-(3-((6-(furan-3-ylmethoxy)pyridin-3-yl)methyl)isoxazol-5-yl)pyridin-1-ium-1-yl)methyl hydrogen phosphate |
| 344 | 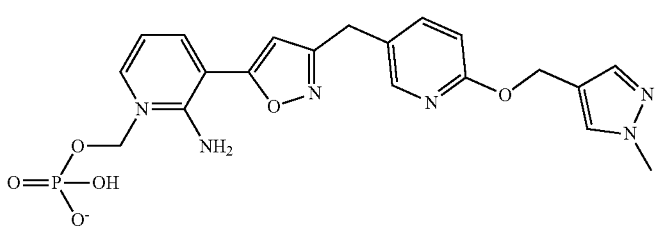 | (2-amino-3-(3-((6-((1-methyl-1H-pyrazol-4-yl)methoxy)pyridin-3-yl)methyl)isoxazol-5-yl)pyridin-1-ium-1-yl)methyl hydrogen phosphate |
| 345 | 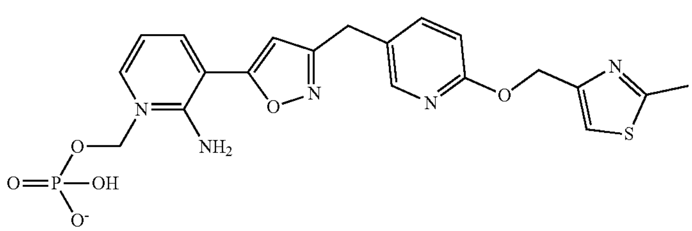 | (2-amino-3-(3-((6-((2-methylthiazol-4-yl)methoxy)pyridin-3-yl)methyl)isoxazol-5-yl)pyridin-1-ium-1-yl)methyl hydrogen phosphate |
| 346 | 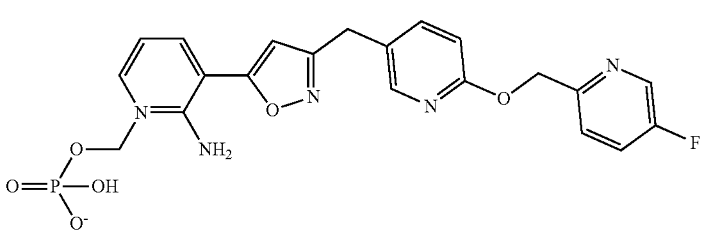 | (2-amino-3-(3-((6-((5-fluoropyridin-2-yl)methoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 347 | 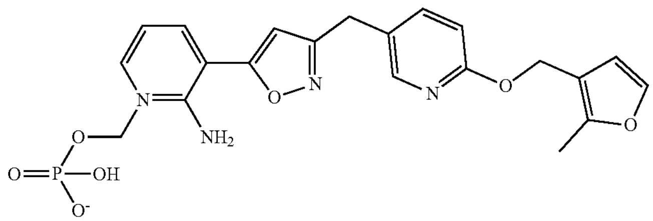 | (2-amino-3-(3-((6-((2-methylfuran-3-yl)methoxy)pyridin-3-yl)methyl)isoxazol-5-yl)pyridin-1-ium-1-yl)methyl hydrogen phosphate |
| 348 | 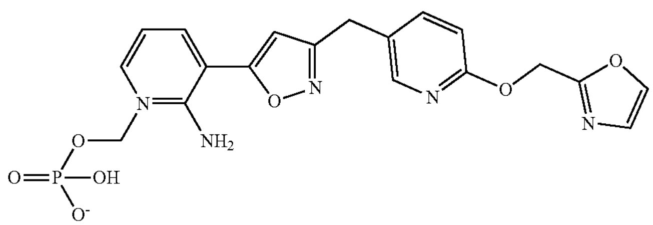 | (2-amino-3-(3-((6-(oxazol-2-ylmethoxy)pyridin-3-yl)methyl)isoxazol-5-yl)pyridin-1-ium-1-yl)methyl hydrogen phosphate |
| 349 | 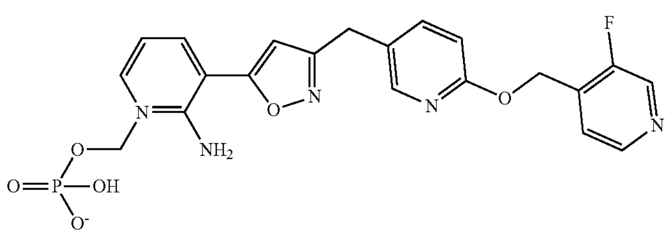 | (2-amino-3-(3-((6-((3-fluoropyridin-4-yl)methoxy)pyridin-3-yl)methyl)isoxazol-5-yl)pyridin-1-ium-1-yl)methyl hydrogen phosphate |
| 350 | 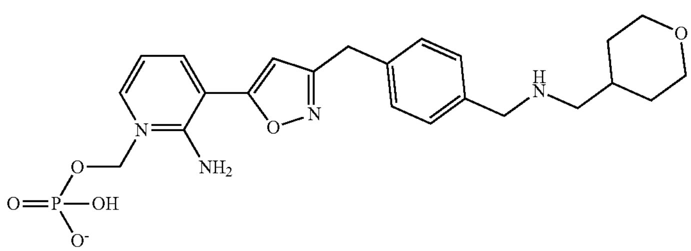 | (2-amino-3-(3-(4-((((tetrahydro-2H-pyran-4-yl)methyl)amino)methyl)benzyl)isoxazol-5-yl)pyridin-1-ium-1-yl) methyl hydrogen phosphate |
| 351 | 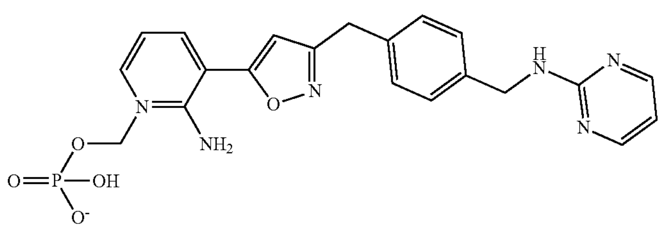 | (2-amino-3-(3-(4-((pyrimidin-2-ylamino)methyl)benzyl)isoxazol-5-yl)pyridin-1-ium-1-yl)methyl hydrogen phosphate |
| 352 | 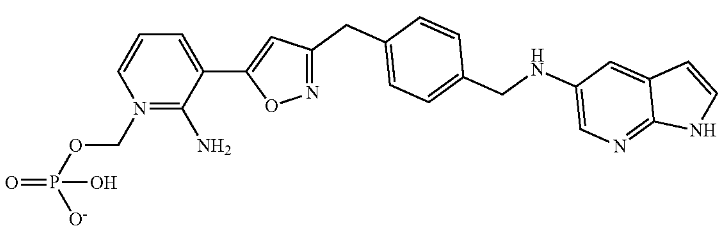 | (3-(3-(4-(((1H-pyrrolo[2,3-b]pyridin-5-yl)amino)methyl)benzyl)isoxazol-5-yl)-2-aminopyridin-1-ium-1-yl)methyl hydrogen phosphate |

TABLE 1-continued

| Ex. | Structure | Name |
|---|---|---|
| 353 | 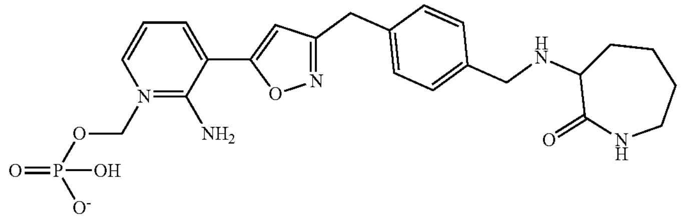 | (2-amino-3-(3-(4-(((2-oxoazepan-3-yl)amino)methyl)benzyl)isoxazol-5-yl)pyridin-1-ium-1-yl)methyl hydrogen phosphate |
| 354 | 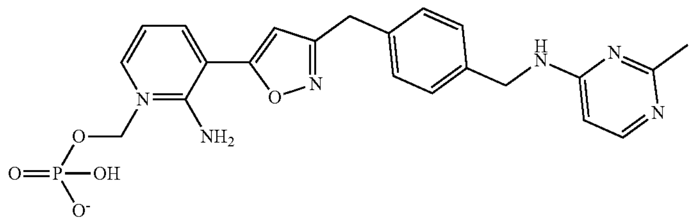 | (2-amino-3-(3-(4-(((2-methylpyrimidin-4-yl)amino)methyl)benzyl)isoxazol-5-yl)pyridin-1-ium-1-yl)methyl hydrogen phosphate |
| 355 | 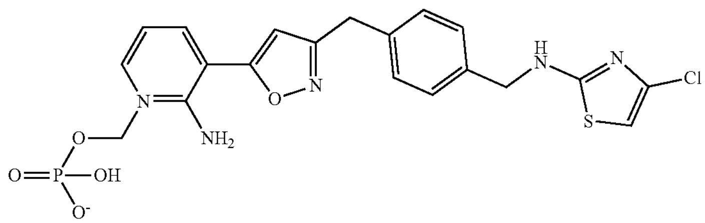 | (2-amino-3-(3-(4-(((4-chlorothiazol-2-yl)amino)methyl)benzyl)isoxazol-5-yl)pyridin-1-ium-1-yl)methyl hydrogen phosphate |
| 356 | 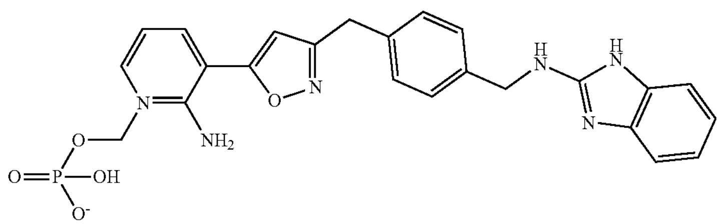 | (3-(3-(4-(((1H-benzo[d]imidazol-2-yl)amino)methyl)benzyl)isoxazol-5-yl)-2-aminopyridin-1-ium-1-yl)methyl hydrogen phosphate |
| 357 | 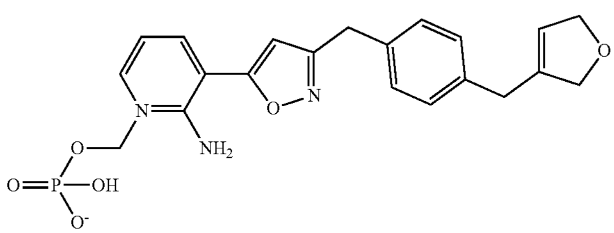 | (2-amino-3-(3-(4-((2,5-dihydrofuran-3-yl)methyl)benzyl)isoxazol-5-yl)pyridin-1-ium-1-yl)methyl hydrogen phosphate |
| 358 | 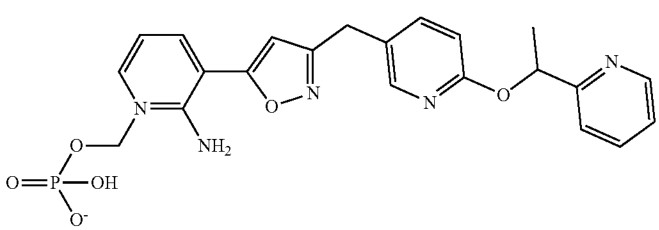 | (2-amino-3-(3-((6-(1-(pyridin-2-yl)ethoxy)pyridin-3-yl)methyl)isoxazol-5-yl)pyridin-1-ium-1-yl)methyl hydrogen phosphate |
| 359 | 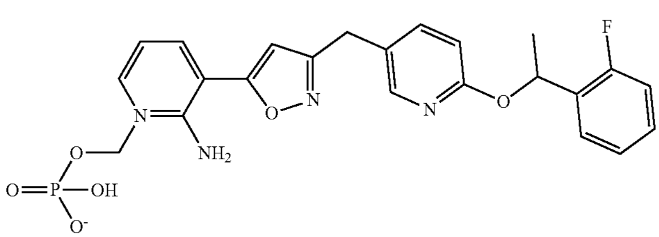 | (2-amino-3-(3-((6-(1-(2-fluorophenyl)ethoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 360 | 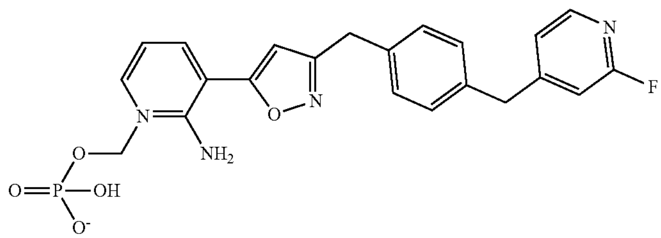 | (2-amino-3-(3-(4-((2-fluoropyridin-4-yl)methyl)benzyl)isoxazol-5-yl)pyridin-1-ium-1-yl)methyl hydrogen phosphate |
| 361 | 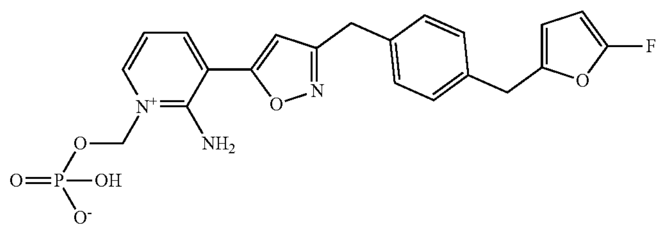 [SMILES: Nc1c(-c2cc(Cc3ccc(Cc4ccc(F)o4)cc3)no2)ccc[n+]1COP(=O)([O-])O] | (2-amino-3-(3-(4-((5-fluorofuran-2-yl)methyl)benzyl)isoxazol-5-yl)pyridin-1-ium-1-yl)methyl hydrogen phosphate |
| 362 | 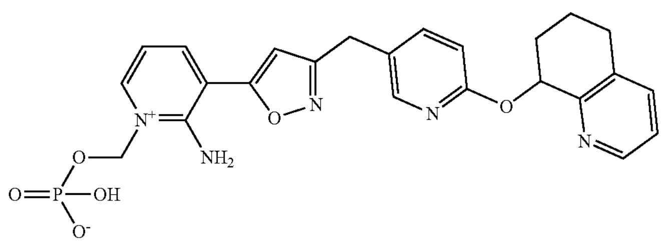 [SMILES: Nc1c(-c2cc(Cc3ccc(OC4CCCc5cccnc54)nc3)no2)ccc[n+]1COP(=O)([O-])O] | (2-amino-3-(3-((6-((5,6,7,8-tetrahydroquinolin-8-yl)oxy)pyridin-3-yl)methyl)isoxazol-5-yl)pyridin-1-ium-1-yl)methyl hydrogen phosphate |
| 363 | 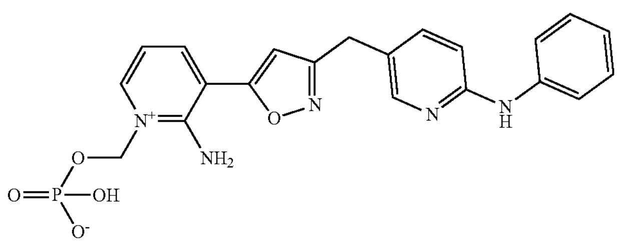 [SMILES: Nc1c(-c2cc(Cc3ccc(Nc4ccccc4)nc3)no2)ccc[n+]1COP(=O)([O-])O] | (2-amino-3-(3-((6-(phenylamino)pyridin-3-yl)methyl)isoxazol-5-yl)pyridin-1-ium-1-yl)methyl hydrogen phosphate |
| 364 | 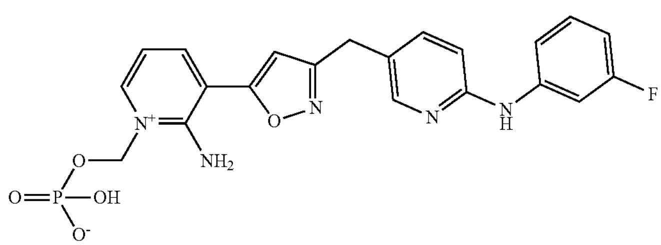 [SMILES: Nc1c(-c2cc(Cc3ccc(Nc4cccc(F)c4)nc3)no2)ccc[n+]1COP(=O)([O-])O] | (2-amino-3-(3-((6-((3-fluorophenyl)amino)pyridin-3-yl)methyl)isoxazol-5-yl)pyridin-1-ium-1-yl)methyl hydrogen phosphate |
| 365 | 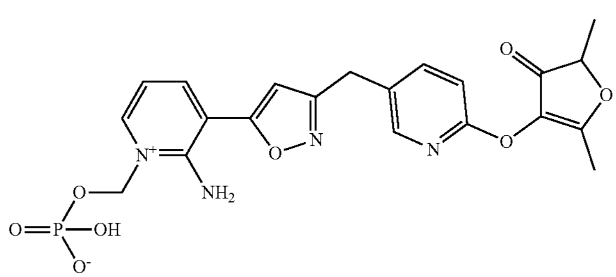 [SMILES: CC1=C(Oc2ccc(Cc3cc(-c4ccc[n+](COP(=O)([O-])O)c4N)on3)cn2)C(=O)C(C)O1] | (2-amino-3-(3-((6-((2,5-dimethyl-4-oxo-4,5-dihydrofuran-3-yl)oxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 366 | 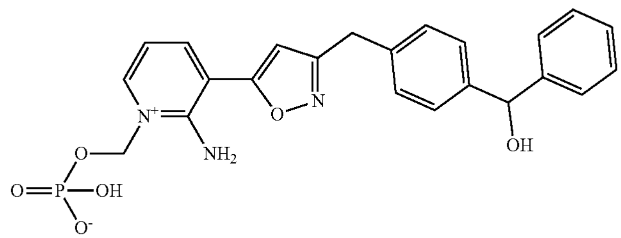 [SMILES: Nc1c(-c2cc(Cc3ccc(C(O)c4ccccc4)cc3)no2)ccc[n+]1COP(=O)([O-])O] | (2-amino-3-(3-(4-(hydroxy(phenyl)methyl)benzyl)isoxazol-5-yl)pyridin-1-ium-1-yl)methyl hydrogen phosphate |
| 367 | 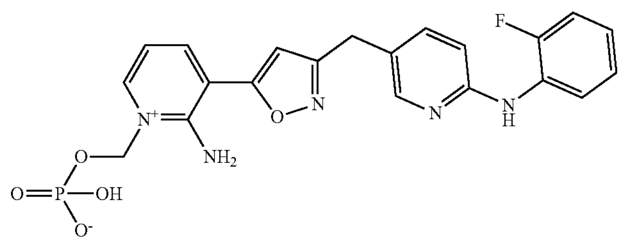 [SMILES: Nc1c(-c2cc(Cc3ccc(Nc4ccccc4F)nc3)no2)ccc[n+]1COP(=O)([O-])O] | (2-amino-3-(3-((6-((2-fluorophenyl)amino)pyridin-3-yl)methyl)isoxazol-5-yl)pyridin-1-ium-1-yl)methyl hydrogen phosphate |
| 368 | 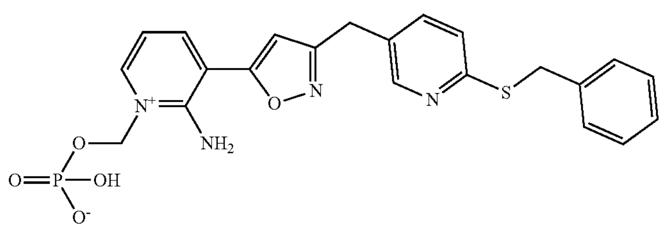 [SMILES: Nc1c(-c2cc(Cc3ccc(SCc4ccccc4)nc3)no2)ccc[n+]1COP(=O)([O-])O] | (2-amino-3-(3-((6-(benzylthio)pyridin-3-yl)methyl)isoxazol-5-yl)pyridin-1-ium-1-yl)methyl hydrogen phosphate |
| 369 | 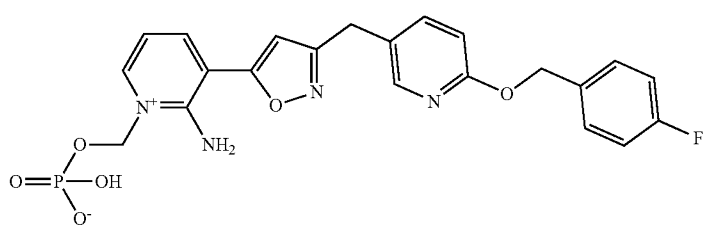 [SMILES: Nc1c(-c2cc(Cc3ccc(OCc4ccc(F)cc4)nc3)no2)ccc[n+]1COP(=O)([O-])O] | (2-amino-3-(3-((6-((4-fluorobenzyl)oxy)pyridin-3-yl)methyl)isoxazol-5-yl)pyridin-1-ium-1-yl)methyl hydrogen phosphate |
| 370 | 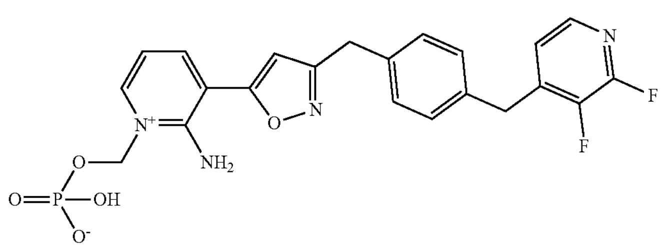 [SMILES: Nc1c(-c2cc(Cc3ccc(Cc4ccnc(F)c4F)cc3)no2)ccc[n+]1COP(=O)([O-])O] | (2-amino-3-(3-(4-((2,3-difluoropyridin-4-yl)methyl)benzyl)isoxazol-5-yl)pyridin-1-ium-1-yl)methyl hydrogen phosphate |
| 371 | 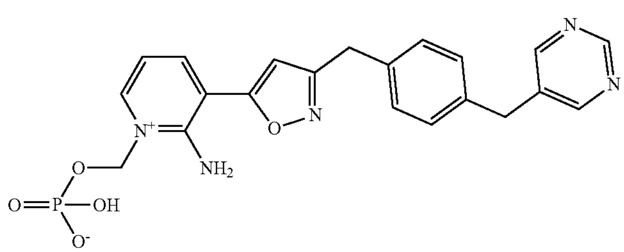 [SMILES: Nc1c(-c2cc(Cc3ccc(Cc4cncnc4)cc3)no2)ccc[n+]1COP(=O)([O-])O] | (2-amino-3-(3-(4-(pyrimidin-5-ylmethyl)benzyl)isoxazol-5yl)pyridin-1-ium-1-yl)methyl hydrogen phosphate |

TABLE 1-continued

| Ex. | Structure | Name |
|---|---|---|
| 372 | 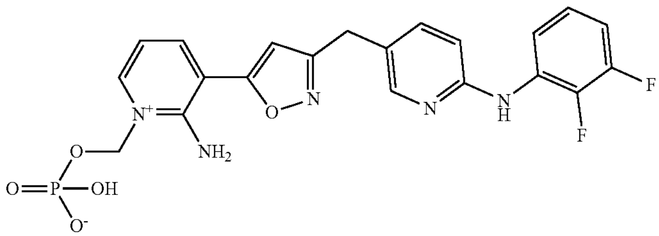 [SMILES: Nc1c(-c2cc(Cc3ccc(Nc4cccc(F)c4F)nc3)no2)ccc[n+]1COP(=O)([O-])O] | (2-amino-3-(3-((6-((2,3-difluorophenyl)amino)pyridin-3-yl)methyl)isoxazol-5-yl)pyridin-1-ium-1-yl)methyl hydrogen phosphate |
| 373 | 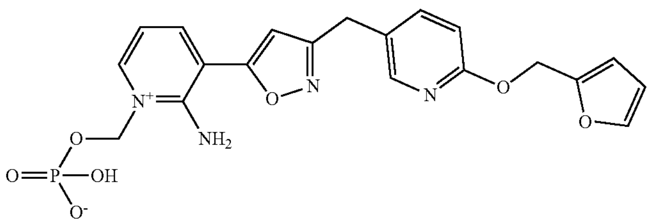 [SMILES: Nc1c(-c2cc(Cc3ccc(OCc4ccco4)nc3)no2)ccc[n+]1COP(=O)([O-])O] | (2-amino-3-(3-((6-(furan-2-ylmethoxy)pyridin-3-yl)methyl)isoxazol-5-yl)pyridin-1-ium-1-yl)methyl hydrogen phosphate |
| 374 | 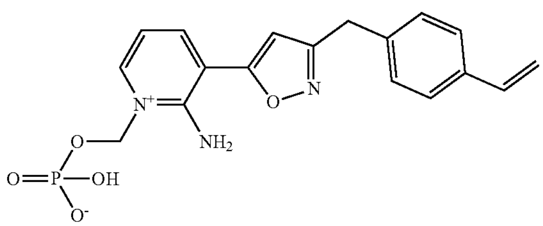 [SMILES: C=Cc1ccc(Cc2cc(-c3ccc[n+](COP(=O)([O-])O)c3N)on2)cc1] | (2-amino-3-(3-(4-vinylbenzyl)isoxazol-5-yl)pyridin-1-ium-1-yl)methyl hydrogen phosphate |
| 375 | 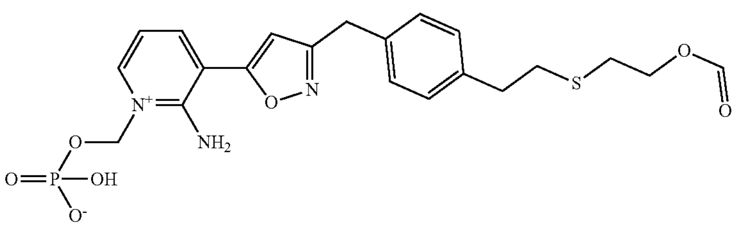 [SMILES: Nc1c(-c2cc(Cc3ccc(CCSCCOC=O)cc3)no2)ccc[n+]1COP(=O)([O-])O] | (2-amino-3-(3-(4-(2-((2-(formyloxy)ethyl)thio)ethyl)benzyl)isoxazol-5-yl)pyridin-1-ium-1-yl)methyl hydrogen phosphate |
| 376 | 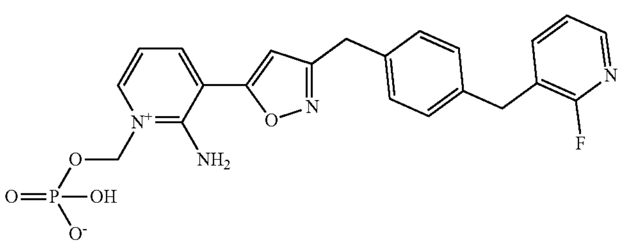 [SMILES: Nc1c(-c2cc(Cc3ccc(Cc4cccnc4F)cc3)no2)ccc[n+]1COP(=O)([O-])O] | (2-amino-3-(3-(4-((2-fluoropyridin-3-yl)methyl)benzyl)isoxazol-5-yl)pyridin-1-ium-1-yl)methyl hydrogen phosphate |
| 377 | 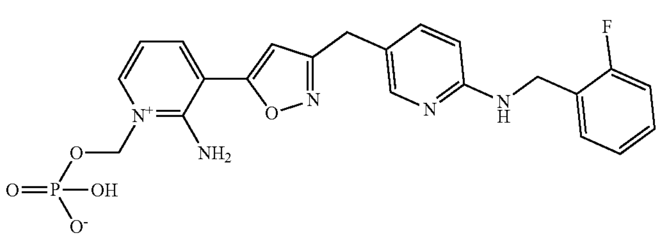 [SMILES: Nc1c(-c2cc(Cc3ccc(NCc4ccccc4F)nc3)no2)ccc[n+]1COP(=O)([O-])O] | (2-amino-3-(3-((6-((2-fluorobenzyl)amino)pyridin-3-yl)methyl)isoxazol-5-yl)pyridin-1-ium-1-yl)methyl hydrogen phosphate |

TABLE 1-continued

| Ex. | Structure | Name |
|---|---|---|
| 378 | 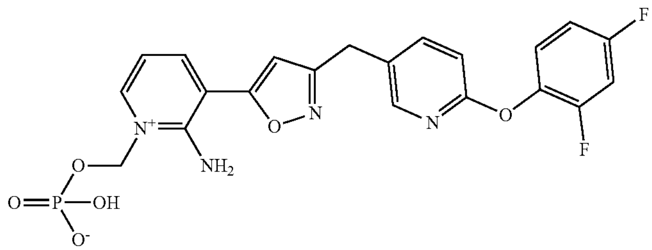 [SMILES: Nc1c(-c2cc(Cc3ccc(Oc4ccc(F)cc4F)nc3)no2)ccc[n+]1COP(=O)([O-])O] | (2-amino-3-(3-((6-(2,4-difluorophenoxy)pyridin-3-yl)methyl)isoxazol-5-yl)pyridin-1-ium-1-yl)methyl hydrogen phosphate |
| 379 | 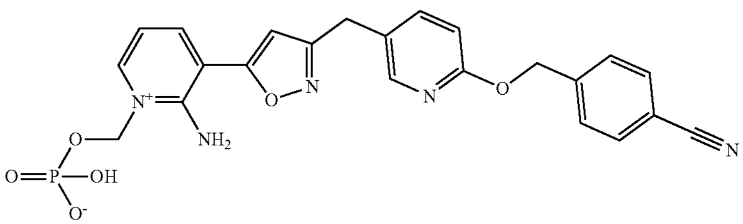 [SMILES: N#Cc1ccc(COc2ccc(Cc3cc(-c4ccc[n+](COP(=O)([O-])O)c4N)on3)cn2)cc1] | (2-amino-3-(3-((6-((5-cyanobenzyl)oxy)pyridin-3-yl)methyl)isoxazol-5-yl)pyridin-1-ium-1-yl)methyl hydrogen phosphate |
| 380 | 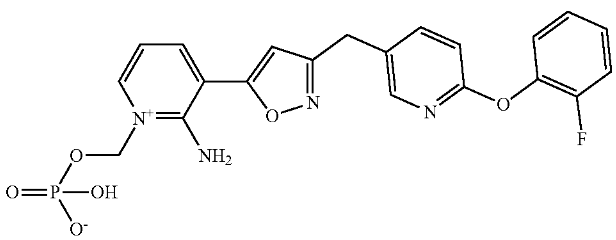 [SMILES: Nc1c(-c2cc(Cc3ccc(Oc4ccccc4F)nc3)no2)ccc[n+]1COP(=O)([O-])O] | (2-amino-3-(3-((6-(2-fluorophenoxy)pyridin-3-yl)methyl)isoxazol-5-yl)pyridin-1-ium-1-yl)methyl hydrogen phosphate |
| 381 | 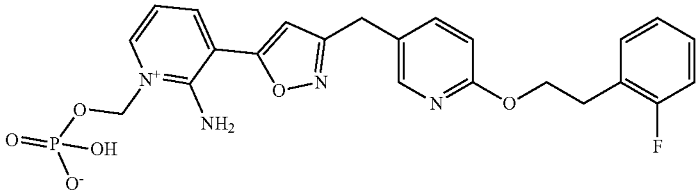 [SMILES: Nc1c(-c2cc(Cc3ccc(OCCc4ccccc4F)nc3)no2)ccc[n+]1COP(=O)([O-])O] | (2-amino-3-(3-((6-(2-fluorophenethoxy)pyridin-3-yl)methyl)isoxazol-5-yl)pyridin-1-ium-1-yl)methyl hydrogen phosphate |
| 382 | 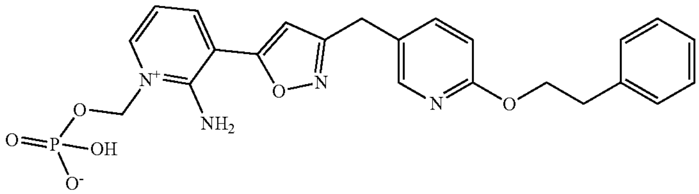 [SMILES: Nc1c(-c2cc(Cc3ccc(OCCc4ccccc4)nc3)no2)ccc[n+]1COP(=O)([O-])O] | (2-amino-3-(3-((6-phenethoxypyridin-3-yl)methyl)isoxazol-5-yl)pyridin-1-ium-1-yl)methyl hydrogen phosphate |
| 383 | 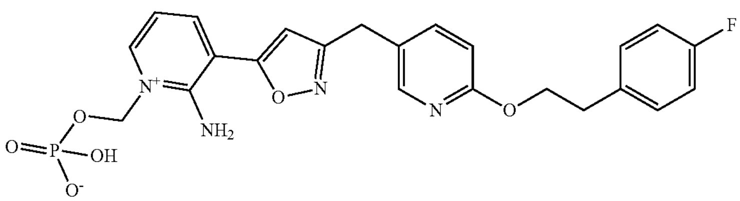 [SMILES: Nc1c(-c2cc(Cc3ccc(OCCc4ccc(F)cc4)nc3)no2)ccc[n+]1COP(=O)([O-])O] | (2-amino-3-(3-((6-(4-fluorophenethoxy)pyridin-3-yl)methyl)isoxazol-5-yl)pyridin-1-ium-1-yl)methyl hydrogen phosphate |
| 384 | 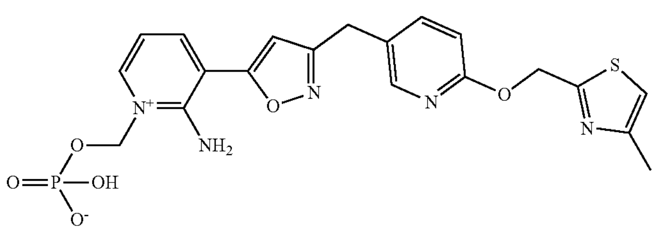 [SMILES: Cc1csc(COc2ccc(Cc3cc(-c4ccc[n+](COP(=O)([O-])O)c4N)on3)cn2)n1] | (2-amino-3-(3-((6-((4-methylthiazol-2-yl)methoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 385 | 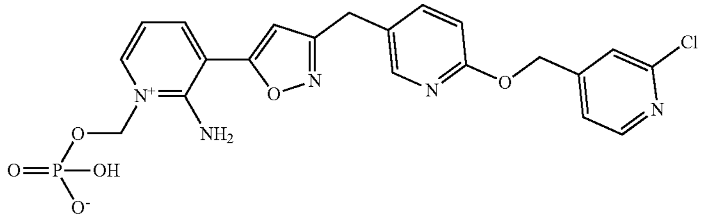 | (2-amino-3-(3-((6-((2-chloropyridin-4-yl)methoxy)pyridin-3-yl)methyl)isoxazol-5-yl)pyridin-1-ium-1-yl)methyl hydrogen phosphate |
| 386 | 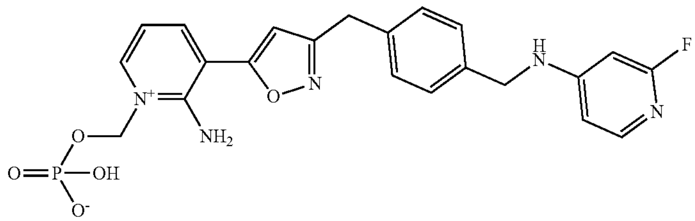 [SMILES: Nc1c(-c2cc(Cc3ccc(CNc4ccnc(F)c4)cc3)no2)ccc[n+]1COP(=O)([O-])O] | (2-amino-3-(3-(4-(((2-fluoropyridin-4-yl)amino)methyl)benzyl)isoxazol-5-yl)pyridin-1-ium-1-yl)methyl hydrogen phosphate |
| 387 | 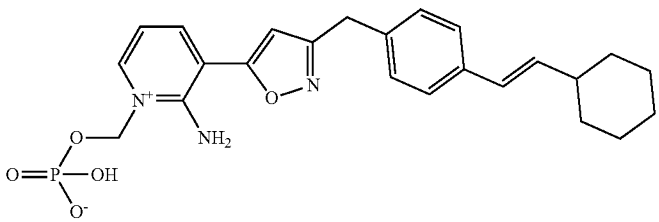 [SMILES: Nc1c(-c2cc(Cc3ccc(/C=C/C4CCCCC4)cc3)no2)ccc[n+]1COP(=O)([O-])O] | (E)-(2-amino-3-(3-(4-(2-cyclohexylvinyl)benzyl)isoxazol-5-yl)pyridin-1-ium-1-yl)methyl hydrogen phosphate |
| 388 | 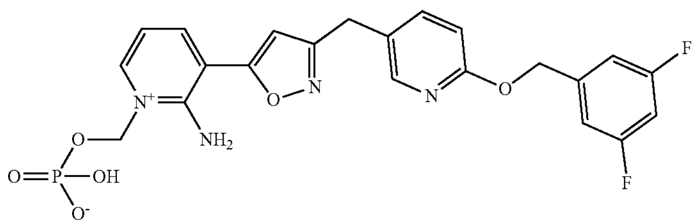 [SMILES: Nc1c(-c2cc(Cc3ccc(OCc4cc(F)cc(F)c4)nc3)no2)ccc[n+]1COP(=O)([O-])O] | (2-amino-3-(3-((6-((3,5-difluorobenzyl)oxy)pyridin-3-yl)methyl)isoxazol-5-yl)pyridin-1-ium-1-yl)methyl hydrogen phosphate |
| 389 | 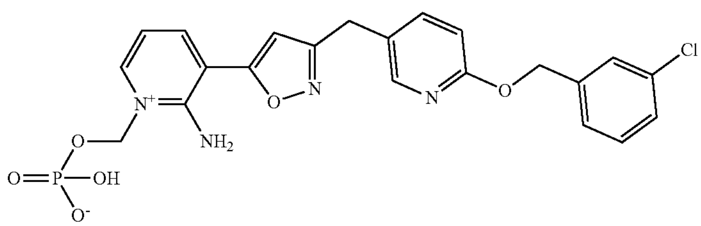 [SMILES: Nc1c(-c2cc(Cc3ccc(OCc4cccc(Cl)c4)nc3)no2)ccc[n+]1COP(=O)([O-])O] | (2-amino-3-(3-((6-((3-chlorobenzyl)oxy)pyridin-3-yl)methyl)isoxazol-5-yl)pyridin-1-ium-1-yl)methyl hydrogen phosphate |
| 390 | 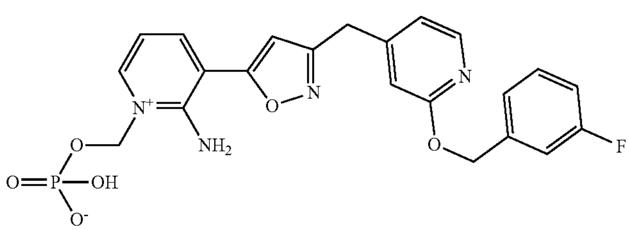 [SMILES: Nc1c(-c2cc(Cc3ccnc(OCc4cccc(F)c4)c3)no2)ccc[n+]1COP(=O)([O-])O] | (2-amino-3-(3-((2-((3-fluorobenzyl)oxy)pyridin-4-yl)methyl)isoxazol-5-yl)pyridin-1-ium-1-yl)methyl hydrogen phosphate |
| 391 | 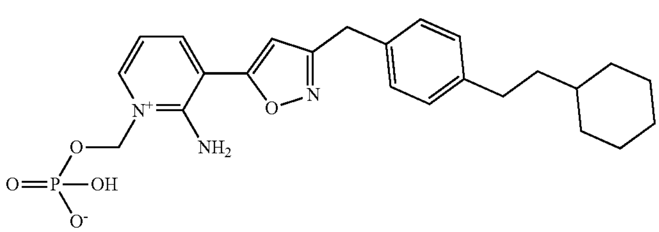 [SMILES: Nc1c(-c2cc(Cc3ccc(CCC4CCCCC4)cc3)no2)ccc[n+]1COP(=O)([O-])O] | (2-amino-3-(3-(4-(2-cyclohexylethyl)benzyl)isoxazol-5-yl)pyridin-1-ium-1-yl)methyl hydrogen phosphate |

TABLE 1-continued

| Ex. | Structure | Name |
|---|---|---|
| 392 | 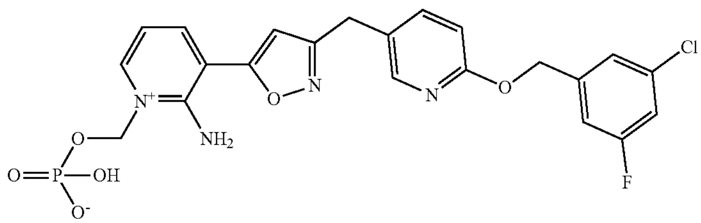 [SMILES: Nc1c(-c2cc(Cc3ccc(OCc4cc(F)cc(Cl)c4)nc3)no2)ccc[n+]1COP(=O)([O-])O] | (2-amino-3-(3-((6-((3-chloro-5-fluorobenzyl)oxy)pyridin-3-yl)methyl)isoxazol-5-yl)pyridin-1-ium-1-yl)methyl hydrogen phosphate |
| 393 | 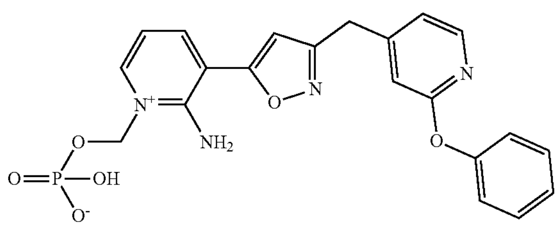 [SMILES: Nc1c(-c2cc(Cc3ccnc(Oc4ccccc4)c3)no2)ccc[n+]1COP(=O)([O-])O] | (2-amino-3-(3-((2-phenoxypyridin-4-yl)methyl)isoxazol-5-yl)pyridin-1-ium-1-yl)methyl hydrogen phosphate |
| 394 | 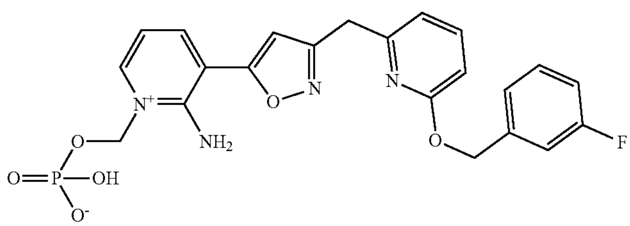 [SMILES: Nc1c(-c2cc(Cc3cccc(OCc4cccc(F)c4)n3)no2)ccc[n+]1COP(=O)([O-])O] | (2-amino-3-(3-((6-((3-fluorobenzyl)oxy)pyridin-2-yl)methyl)isoxazol-5-yl)pyridin-1-ium-1-yl)methyl hydrogen phosphate |
| 395 | 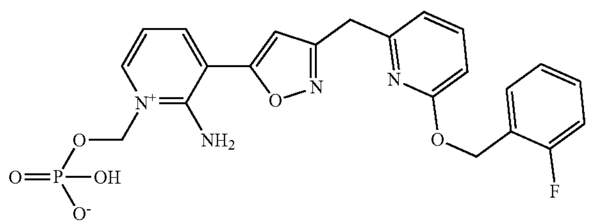 [SMILES: Nc1c(-c2cc(Cc3cccc(OCc4ccccc4F)n3)no2)ccc[n+]1COP(=O)([O-])O] | (2-amino-3-(3-((6-((2-fluorobenzyl)oxy)pyridin-2-yl)methyl)isoxazol-5-yl)pyridin-1-ium-1-yl)methyl hydrogen phosphate |
| 396 | 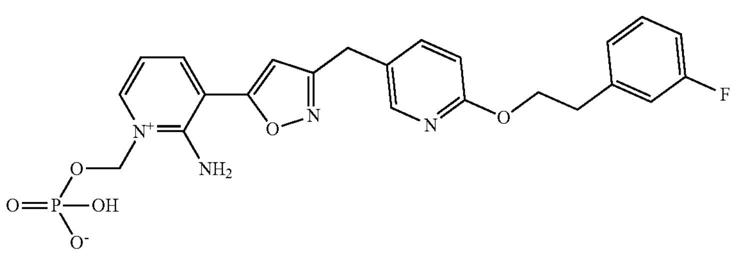 [SMILES: Nc1c(-c2cc(Cc3ccc(OCCc4cccc(F)c4)nc3)no2)ccc[n+]1COP(=O)([O-])O] | (2-amino-3-(3-((6-(3-fluorophenethoxy)pyridin-3-yl)methyl)isoxazol-5-yl)pyridin-1-ium-1-yl)methyl hydrogen phosphate |
| 397 | 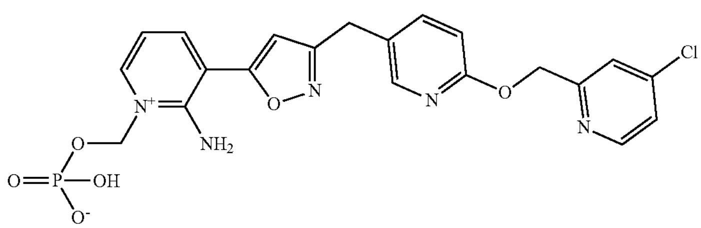 [SMILES: Nc1c(-c2cc(Cc3ccc(OCc4cc(Cl)ccn4)nc3)no2)ccc[n+]1COP(=O)([O-])O] | (2-amino-3-(3-((6-((4-chloropyridin-2-yl)methoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 398 | 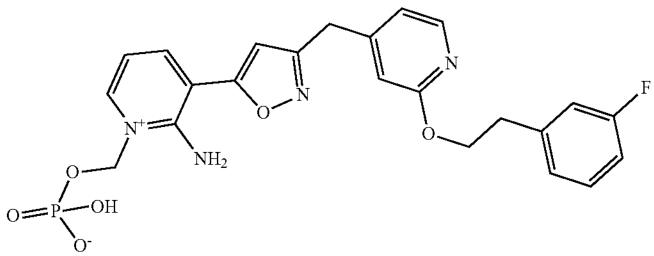 [SMILES: Nc1c(-c2cc(Cc3ccnc(OCCc4cccc(F)c4)c3)no2)ccc[n+]1COP(=O)([O-])O] | (2-amino-3-(3-((2-(3-fluorophenethoxy)pyridin-4-yl)methyl)isoxazol-5-yl)pyridinn-1-ium-1-yl)methyl hydrogen phosphate |
| 399 | 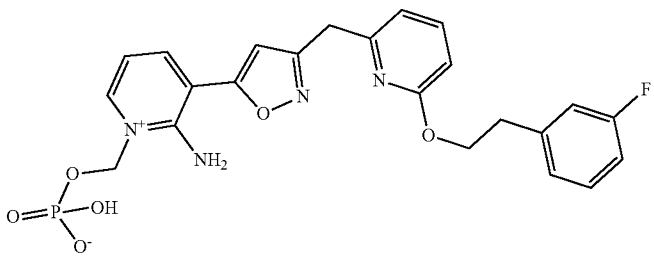 [SMILES: Nc1c(-c2cc(Cc3cccc(OCCc4cccc(F)c4)n3)no2)ccc[n+]1COP(=O)([O-])O] | (2-amino-3-(3-((6-(3-fluorophenethoxy)pyridin-2-yl)methyl)isoxazol-5-yl)pyridin-1-ium-1-yl)methyl hydrogen phosphate |
| 400 | 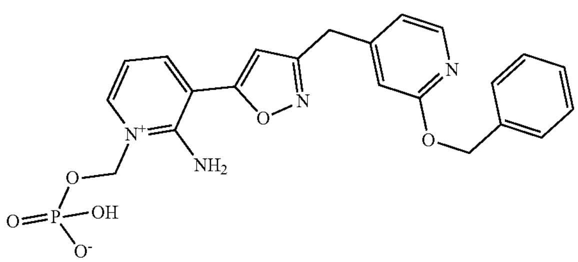 [SMILES: Nc1c(-c2cc(Cc3ccnc(OCc4ccccc4)c3)no2)ccc[n+]1COP(=O)([O-])O] | (2-amino-3-(3-((2-(benzyloxy)pyridin-4-yl)methyl)isoxazol-5-yl)pyridin-1-ium-1-yl)methyl hydrogen phosphate |
| 401 | 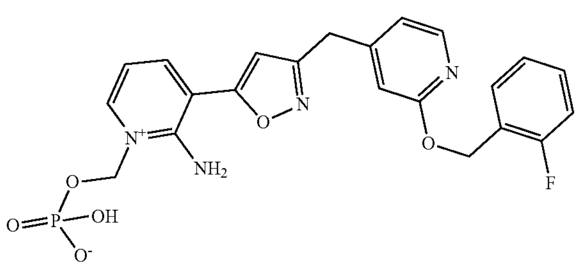 [SMILES: Nc1c(-c2cc(Cc3ccnc(OCc4ccccc4F)c3)no2)ccc[n+]1COP(=O)([O-])O] | (2-amino-3-(3-((2-((2-fluorobenzyl)oxy)pyridin-4-yl)methyl)isoxazol-5-yl)pyridin-1-ium-1-yl)methyl hydrogen phosphate |
| 402 | 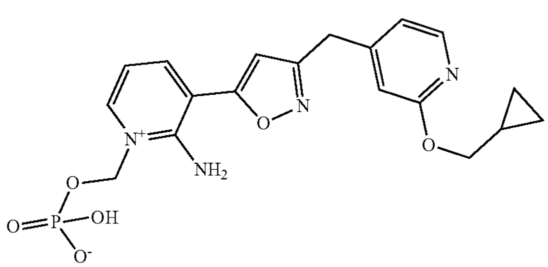 [SMILES: Nc1c(-c2cc(Cc3ccnc(OCC4CC4)c3)no2)ccc[n+]1COP(=O)([O-])O] | (2-amino-3-(3-((2-(cyclopropylmethoxy)pyridin-4-yl)methyl)isoxazol-5-yl)pyridin-1-ium-1-yl)methyl hydrogen phosphate |
| 403 | 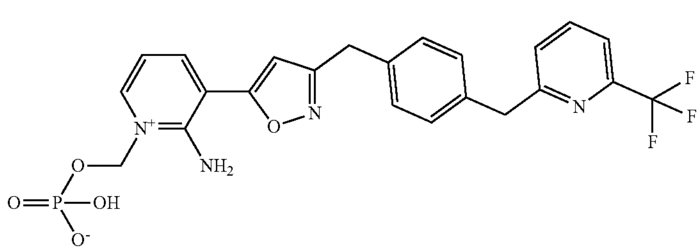 [SMILES: Nc1c(-c2cc(Cc3ccc(Cc4cccc(C(F)(F)F)n4)cc3)no2)ccc[n+]1COP(=O)([O-])O] | (2-amino-3-(3-(4-((6-(trifluoromethyl)pyridin-2-yl)methyl)benzyl)isoxazol-5-yl)pyridin-1-ium-1-yl)methyl hydrogen phosphate |

TABLE 1-continued

| Ex. | Structure | Name |
|---|---|---|
| 404 | 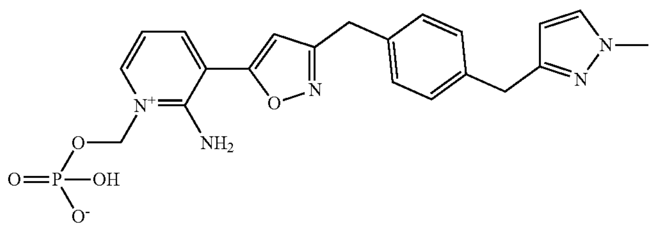 [SMILES: Cn1ccc(Cc2ccc(Cc3cc(-c4ccc[n+](COP(=O)([O-])O)c4N)on3)cc2)n1] | (2-amino-3-(3-(4-((1-methyl-1H-pyrazol-3-yl)methyl)benzyl)isoxazol-5-yl)pyridin-1-ium-1-yl)methyl hydrogen phosphate |
| 405 | 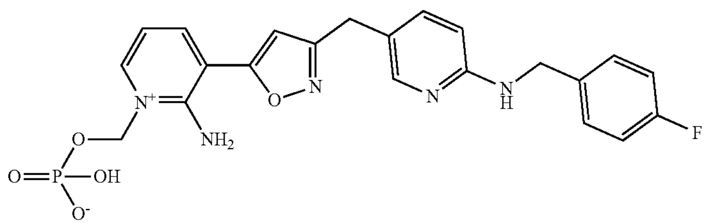 [SMILES: Nc1c(-c2cc(Cc3ccc(NCc4ccc(F)cc4)nc3)no2)ccc[n+]1COP(=O)([O-])O] | (2-amino-3-(3-((6-((4-fluorobenzyl)amino)pyridin-3-yl)methyl)isoxazol-5-yl)pyridin-1-ium-1-yl)methyl hydrogen phosphate |
| 406 | 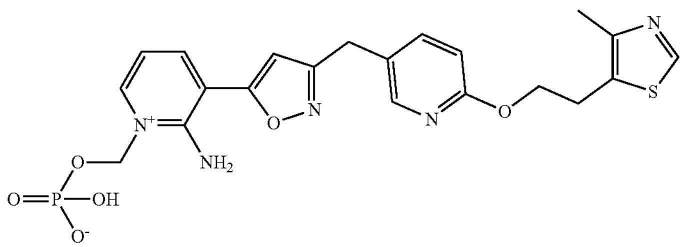 [SMILES: Cc1ncsc1CCOc1ccc(Cc2cc(-c3ccc[n+](COP(=O)([O-])O)c3N)on2)cn1] | (2-amino-3-(3-((6-(2-(4-methylthiazol-5-yl)ethoxy)pyridin-3-yl)methyl)isoxazol-5-yl)pyridin-1-ium-1-yl)methyl hydrogen phosphate |
| 407 | 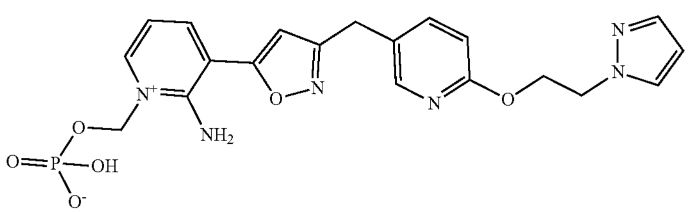 [SMILES: Nc1c(-c2cc(Cc3ccc(OCCn4cccn4)nc3)no2)ccc[n+]1COP(=O)([O-])O] | (3-(3-((6-(2-(1H-pyrazol-1-yl)ethoxy)pyridin-3-yl)methyl)isoxazol-5-yl)-2-aminopyridin-1-ium-1-yl)methyl hydrogen phosphate |
| 408 | 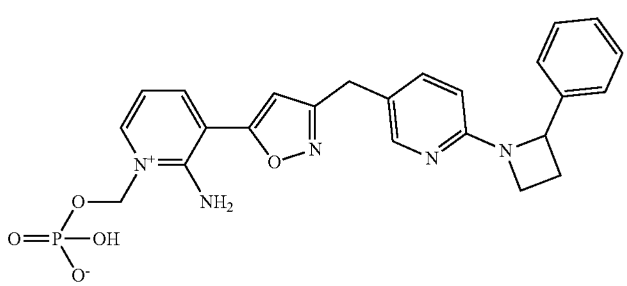 [SMILES: Nc1c(-c2cc(Cc3ccc(N4CCC4c4ccccc4)nc3)no2)ccc[n+]1COP(=O)([O-])O] | (2-amino-3-(3-((6-(2-phenylazetidin-1-yl)pyridin-3-yl)methyl)isoxazol-5-yl)pyridin-1-ium-1-yl)methyl hydrogen phosphate |
| 409 | 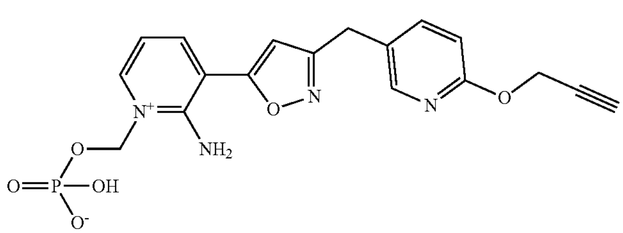 [SMILES: C#CCOc1ccc(Cc2cc(-c3ccc[n+](COP(=O)([O-])O)c3N)on2)cn1] | (2-amino-3-(3-((6-(prop-2-yn-1-yloxy)pyridin-3-yl)methyl)isoxazol-5-yl)pyridiii-1-ium-1-yl)methyl hydrogen phosphate |

TABLE 1-continued

| Ex. | Structure | Name |
|---|---|---|
| 410 | 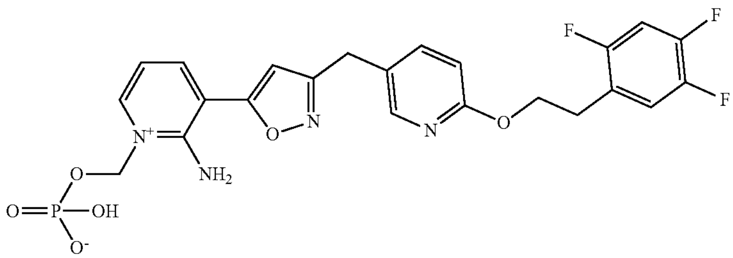 [SMILES: Nc1c(-c2cc(Cc3ccc(OCCc4cc(F)c(F)cc4F)nc3)no2)ccc[n+]1COP(=O)([O-])O] | (2-amino-3-(3-((6-(2,4,5-trifluorophenethoxy)pyridin-3-yl)methyl)isoxazol-5-yl)pyridin-1-ium-1-yl)methyl hydrogen phosphate |
| 411 | 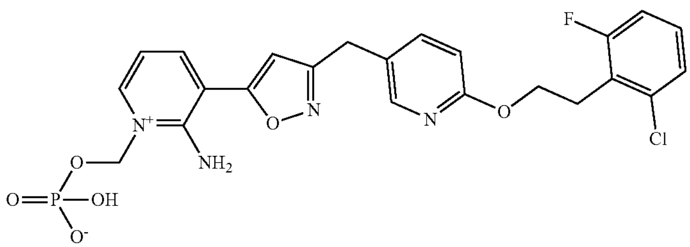 [SMILES: Nc1c(-c2cc(Cc3ccc(OCCc4c(F)cccc4Cl)nc3)no2)ccc[n+]1COP(=O)([O-])O] | (2-amino-3-(3-((6-(2-chloro-6-fluorophenothoxy)pyridin-3-yl)methyl)isoxazol-5-yl)pyridin-1-ium-1-yl)methyl hydrogen phosphate |
| 412 | 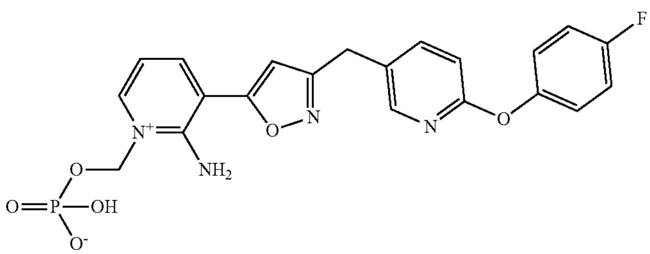 [SMILES: Nc1c(-c2cc(Cc3ccc(Oc4ccc(F)cc4)nc3)no2)ccc[n+]1COP(=O)([O-])O] | (2-amino-3-(3-((6-(4-fluorophenoxy)pyridin-3-yl)methyl)isoxazol-5-yl)pyridin-1-ium-1-yl)methyl hydrogen phosphate |
| 413 | 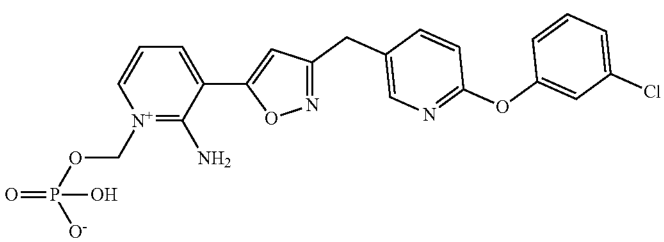 [SMILES: Nc1c(-c2cc(Cc3ccc(Oc4cccc(Cl)c4)nc3)no2)ccc[n+]1COP(=O)([O-])O] | (2-amino-3-(3-((6-(3-chlorophenoxy)pyridin-3-yl)methyl)isoxazol-5-yl)pyridin-1-ium-1-yl)methyl hydrogen phosphate |
| 414 | 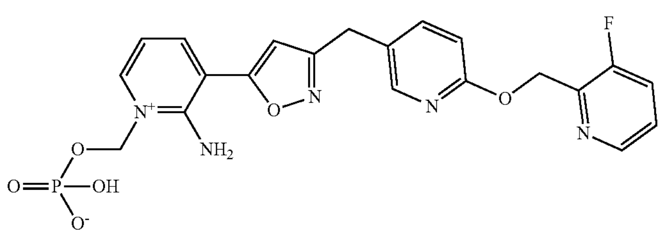 | (2-amino-3-(3-((6-((3-fluoropyridin-2-yl)methoxy)pyridin-3-yl)methyl)isoxazol-5-yl)pyridin-1-ium-1-yl)methyl hydrogen phosphate |
| 415 | 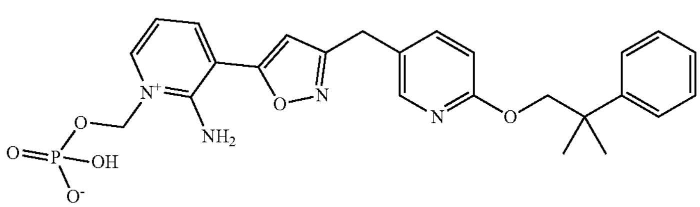 [SMILES: CC(C)(COc1ccc(Cc2cc(-c3ccc[n+](COP(=O)([O-])O)c3N)on2)cn1)c1ccccc1] | (2-amino-3-(3-((6-(2-methyl-2-phenylpropoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 416 | 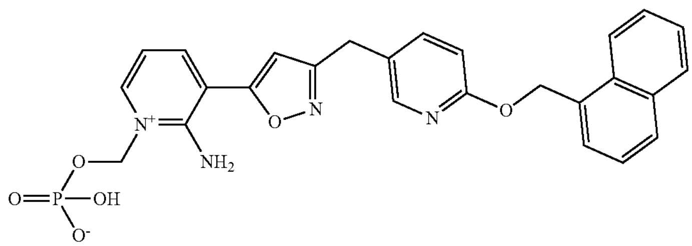 [SMILES: Nc1c(-c2cc(Cc3ccc(OCc4cccc5ccccc45)nc3)no2)ccc[n+]1COP(=O)([O-])O] | (2-amino-3-(3-((6-(naphthalen-1-ylmethoxy)pyridin-3-yl)methyl)isoxazol-5-yl)pyridin-1-ium-1-yl)methyl hydrogen phosphate |
| 417 | 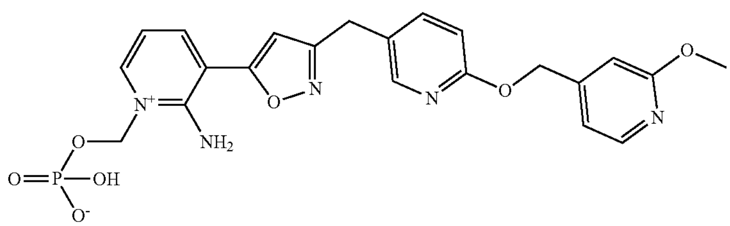 [SMILES: COc1cc(COc2ccc(Cc3cc(-c4ccc[n+](COP(=O)([O-])O)c4N)on3)cn2)ccn1] | (2-amino-3-(3-((6-((2-methoxypyridin-4-yl)methoxy)pyridin-3-yl)methyl)isoxazol-5-yl)pyridin-1-ium-1-yl)methyl hydrogen phosphate |
| 418 | 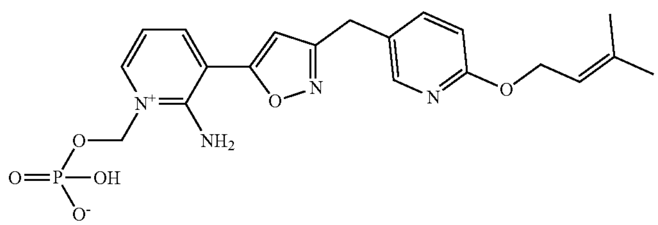 [SMILES: CC(C)=CCOc1ccc(Cc2cc(-c3ccc[n+](COP(=O)([O-])O)c3N)on2)cn1] | (2-amino-3-(3-((6-((3-methylbut-2-en-1-yl)oxy)pyridin-3-yl)methyl)isoxazol-5-yl)pyridin-1-ium-1-yl)methyl hydrogen phosphate |
| 419 | 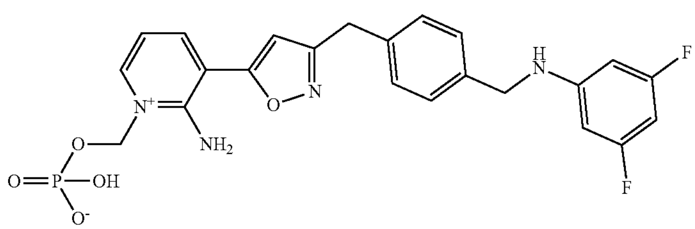 [SMILES: Nc1c(-c2cc(Cc3ccc(CNc4cc(F)cc(F)c4)cc3)no2)ccc[n+]1COP(=O)([O-])O] | (2-amino-3-(3-(4-(((3,5-difluorophenyl)amino)methyl)benzyl)isoxazol-5-yl)pyridin-1-ium-1-yl)methyl hydrogen phosphate |
| 420 | 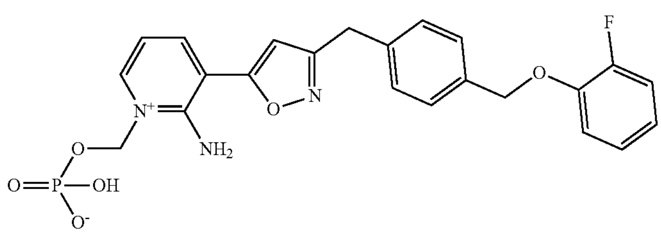 [SMILES: Nc1c(-c2cc(Cc3ccc(COc4ccccc4F)cc3)no2)ccc[n+]1COP(=O)([O-])O] | (2-amino-3-(3-(4-((2-fluorophenoxy)methyl)benzyl)isoxazol-5-yl)pyridin-1-ium-1-yl)methyl hydrogen phosphate |
| 421 | 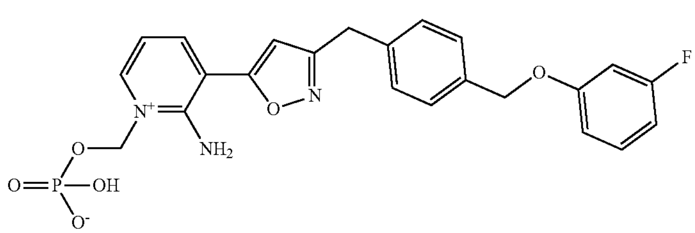 [SMILES: Nc1c(-c2cc(Cc3ccc(COc4cccc(F)c4)cc3)no2)ccc[n+]1COP(=O)([O-])O] | (2-amino-3-(3-(4-((3-fluorophenoxy)methyl)benzyl)isoxazol-5-yl)pyridin-1-ium-1-yl)methyl hydrogen phosphate |

TABLE 1-continued

| Ex. | Structure | Name |
|---|---|---|
| 422 | 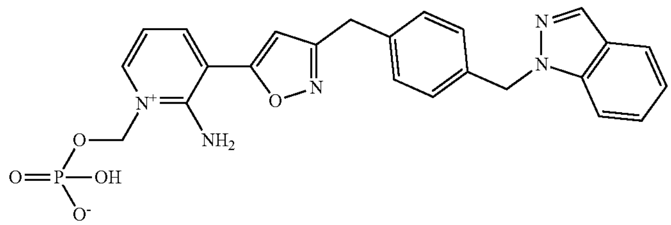 [SMILES: Nc1c(-c2cc(Cc3ccc(Cn4ncc5ccccc54)cc3)no2)ccc[n+]1COP(=O)([O-])O] | (3-(3-(4-((1H-indazol-1-yl)methyl)benzyl)isoxazol-5-yl)-2-aminopyridin-1-ium-1-yl)methyl hydrogen phosphate |
| 423 | 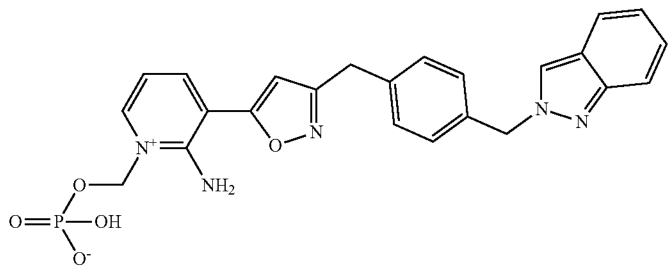 [SMILES: Nc1c(-c2cc(Cc3ccc(Cn4cc5ccccc5n4)cc3)no2)ccc[n+]1COP(=O)([O-])O] | (3-(3-(4-((2H-indazol-2-yl)methyl)benzyl)isoxazol-5-yl)-2-aminopyridin-1-ium-1-yl)methyl hydrogen phosphate |
| 424 | 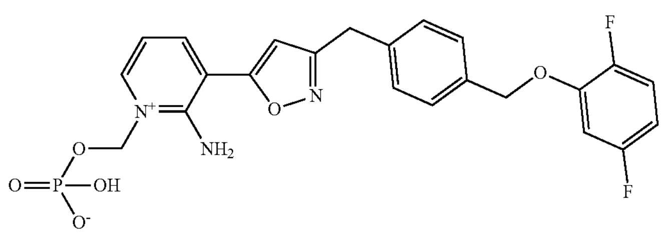 | (2-amino-3-(3-(4-((2,5-difluorophenoxy)methyl)benzyl)isoxazol-5-yl)pyridin-1-ium-1-yl)methyl hydrogen phosphate |
| 425 | 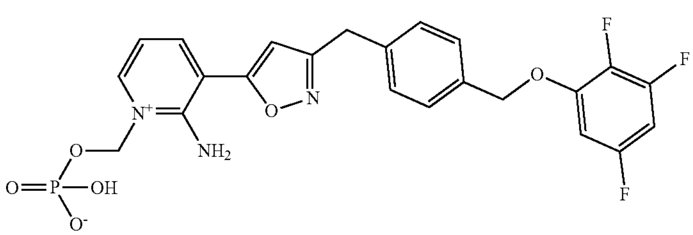 [SMILES: Nc1c(-c2cc(Cc3ccc(COc4cc(F)cc(F)c4F)cc3)no2)ccc[n+]1COP(=O)([O-])O] | (2-amino-3-(3-(4-((2,3,5-trifluorophenoxy)methyl)benzyl)isoxazol-5-yl)pyridin-1-ium-1-yl)methyl hydrogen phosphate |
| 426 | 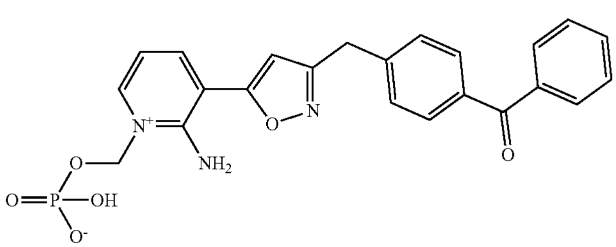 | (2-amino-3-(3-(4-benzoylbenzyl)isoxazol-5-yl)pyridin-1-ium-1-yl)methyl hydrogen phosphate |
| 427 | 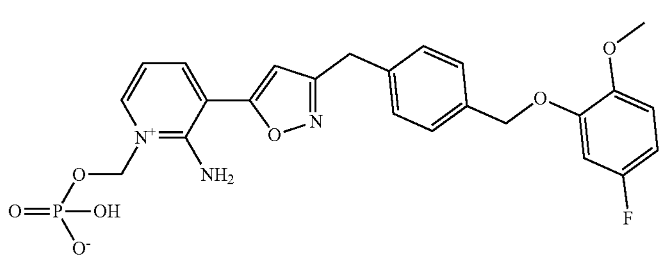 [SMILES: COc1ccc(F)cc1OCc1ccc(Cc2cc(-c3ccc[n+](COP(=O)([O-])O)c3N)on2)cc1] | (2-amino-3-(3-(4-((5-fluoro-2-methoxyphenoxy)methyl)benzyl)isoxazol-5-yl)pyridin-1-ium-1-yl)methyl hydrogen phosphate |

TABLE 1-continued

| Ex. | Structure | Name |
|---|---|---|
| 428 | 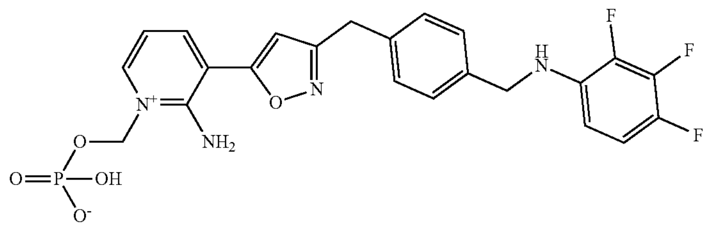 [SMILES: Nc1c(-c2cc(Cc3ccc(CNc4ccc(F)c(F)c4F)cc3)no2)ccc[n+]1COP(=O)([O-])O] | (2-amino-3-(3-(4-(((2,3,4-trifluorophenyl)amino)methyl)benzyl)isoxazol-5-yl)pyridin-1-ium-1-yl)methyl hydrogen phosphate |
| 429 | 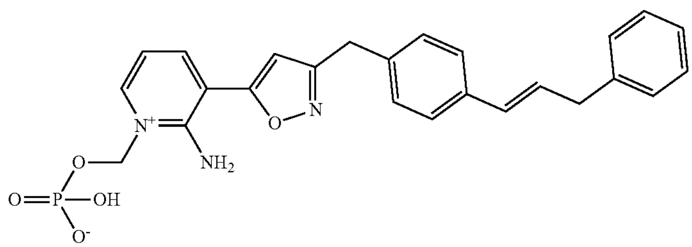 [SMILES: Nc1c(-c2cc(Cc3ccc(/C=C/Cc4ccccc4)cc3)no2)ccc[n+]1COP(=O)([O-])O] | (E)-(2-amino-3-(3-(4-(3-phenylprop-1-en-1-yl)benzyl)isoxazol-5-yl)pyridin-1-ium-1-yl)methyl hydrogen phosphate |
| 430 | 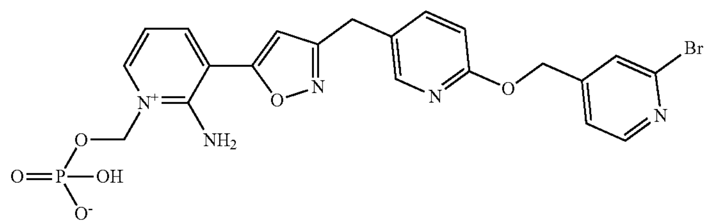 | (2-amino-3-(3-((6-((2-bromopyridin-4-yl)methoxy)pyridin-3-yl)methyl)isoxazol-5-yl)pyridin-1-ium-1-yl)methyl hydrogen phosphate |
| 431 | 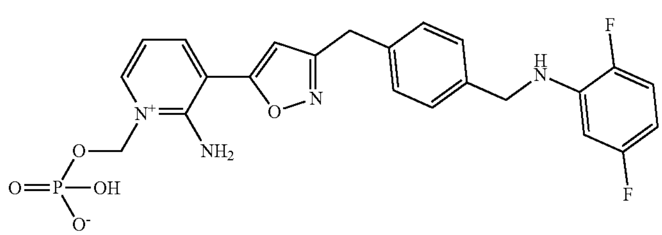 | (2-amino-3-(3-(4-(((2,5-difluorophenyl)amino)methyl)benzyl)isoxazol-5-yl)pyridin-ium-1-yl)methyl hydrogen phosphate |
| 432 | 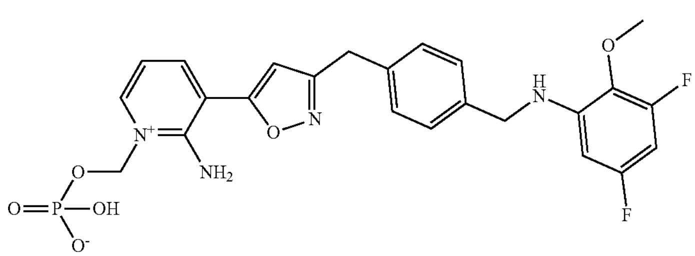 [SMILES: COc1c(F)cc(F)cc1NCc1ccc(Cc2cc(-c3ccc[n+](COP(=O)([O-])O)c3N)on2)cc1] | (2-amino-3-(3-(4-(((3,3-difluoro-2-methoxyphenyl)amino)methyl)benzyl)isoxazol-5-yl)pyridin-1-ium-1-yl)methyl hydrogen phosphate |
| 433 | 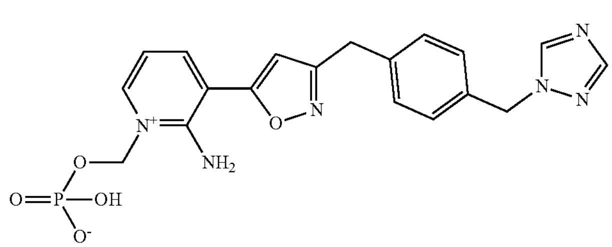 [SMILES: Nc1c(-c2cc(Cc3ccc(Cn4cncn4)cc3)no2)ccc[n+]1COP(=O)([O-])O] | (3-(3-(4-((1H-1,2,4-triazol-1-yl)methyl)benzyl)isoxazol-5-yl)-2-aminopyridin-1-ium-1-yl)methyl hydrogen phosphate |

TABLE 1-continued

| Ex. | Structure | Name |
|---|---|---|
| 434 | 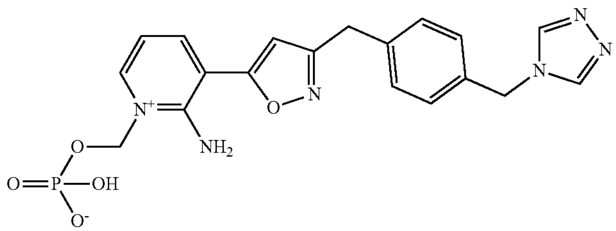 [SMILES: Nc1c(-c2cc(Cc3ccc(Cn4cnnc4)cc3)no2)ccc[n+]1COP(=O)([O-])O] | (3-(3-(4-((4H-1,2,4-triazol-4-yl)methyl)benzyl)isoxazol-5-yl)-2-aminopyridin-1-ium-1-yl)methyl hydrogen phosphate |
| 435 | 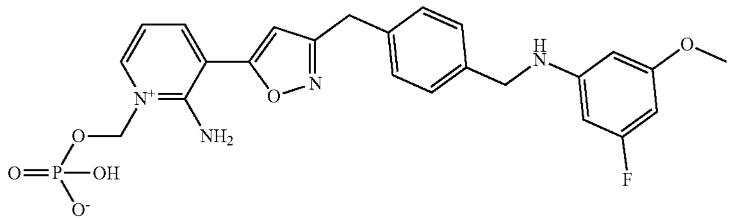 [SMILES: COc1cc(F)cc(NCc2ccc(Cc3cc(-c4ccc[n+](COP(=O)([O-])O)c4N)on3)cc2)c1] | (2-amino-3-(3-(4-(((3-fluoro-5-methoxyphenyl)amino)methyl)benzyl)isoxazol-5-yl)pyridin-1-ium-1-yl)methyl hydrogen phosphate |
| 436 | 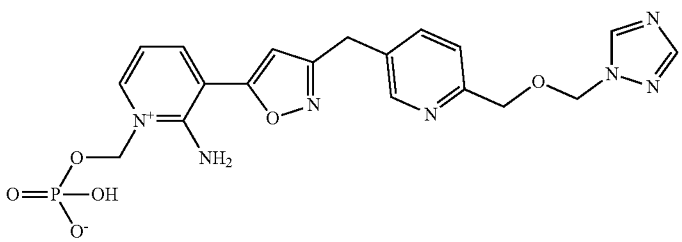 [SMILES: Nc1c(-c2cc(Cc3ccc(COCn4cncn4)nc3)no2)ccc[n+]1COP(=O)([O-])O] | (3-(3-((6-(2-(1H-1,2,4-triazol-1-yl)ethoxy)pyridin-3-yl)methyl)isoxazol-5-yl)-2-aminopyridin-1-ium-1-yl)methyl hydrogen phosphate |
| 437 | 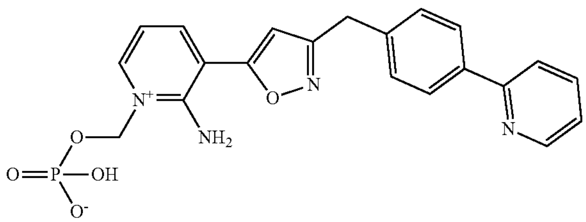 [SMILES: Nc1c(-c2cc(Cc3ccc(-c4ccccn4)cc3)no2)ccc[n+]1COP(=O)([O-])O] | (2-amino-3-(3-(4-(pyridin-2-yl)benzyl)isoxazol-5-yl)pyridin-1-ium-1-yl)methyl hydrogen phosphate |
| 438 | 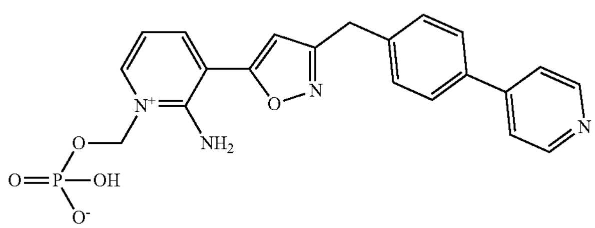 [SMILES: Nc1c(-c2cc(Cc3ccc(-c4ccncc4)cc3)no2)ccc[n+]1COP(=O)([O-])O] | (2-amino-3-(3-(4-(pyridin-4-yl)benzyl)isoxazol-5-yl)pyridin-1-ium-1-yl)methyl hydrogen phosphate |
| 439 | 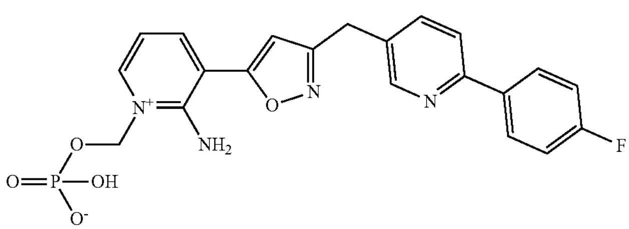 [SMILES: Nc1c(-c2cc(Cc3ccc(-c4ccc(F)cc4)nc3)no2)ccc[n+]1COP(=O)([O-])O] | (2-amino-3-(3-((6-(4-fluorophenyl)pyridin-3-yl)methyl)isoxazol-5-yl)pyridin-1-ium-1-yl)methyl hydrogen phosphate |

TABLE 1-continued

| Ex. | Structure | Name |
|---|---|---|
| 440 | 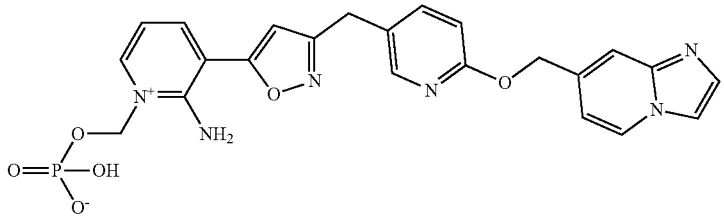 [SMILES: Nc1c(-c2cc(Cc3ccc(OCc4ccn5ccnc5c4)nc3)no2)ccc[n+]1COP(=O)([O-])O] | (2-amino-3-(3-((6-(imidazo[1,2-a]pyridin-7-ylmethoxy)pyridin-3-yl)methyl)isoxazol-5-yl)pyridin-1-ium-1-yl)methyl hydrogen phosphate |
| 441 | 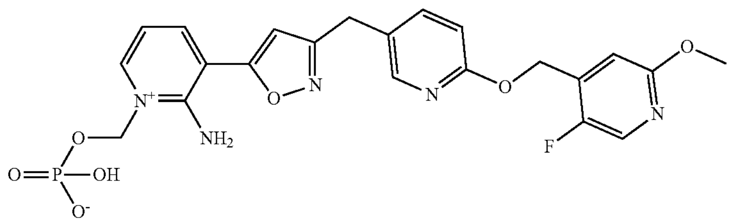 [SMILES: COc1cc(COc2ccc(Cc3cc(-c4ccc[n+](COP(=O)([O-])O)c4N)on3)cn2)c(F)cn1] | (2-amino-3-(3-((6-((5-fluoro-2-methoxypyridin-4-yl)methoxy)pyridin-3-yl)methyl)isoxazol-5-yl)pyridin-1-ium-1-yl)methyl hydrogen phosphate |
| 442 | 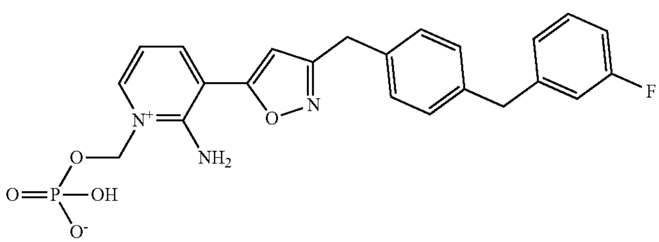 | (2-amino-3-(3-(4-(3-fluorobenzyl)benzyl)isoxazol-5-yl)pyridin-1-ium-1-yl)methyl hydrogen phosphate |
| 443 | 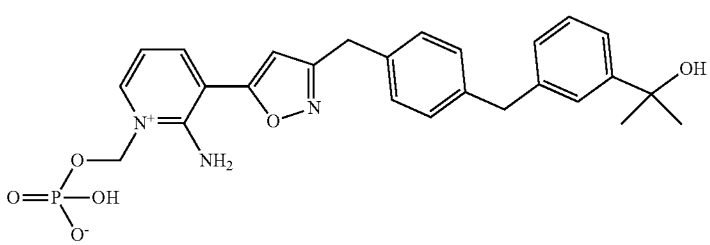 [SMILES: CC(C)(O)c1cccc(Cc2ccc(Cc3cc(-c4ccc[n+](COP(=O)([O-])O)c4N)on3)cc2)c1] | (2-amino-3-(3-(4-(3-(2-hydroxypropan-2-yl)benzyl)benzyl)isoxazol-5-yl)pyridin-1-ium-1-yl)methyl hydrogen phosphate |
| 444 | 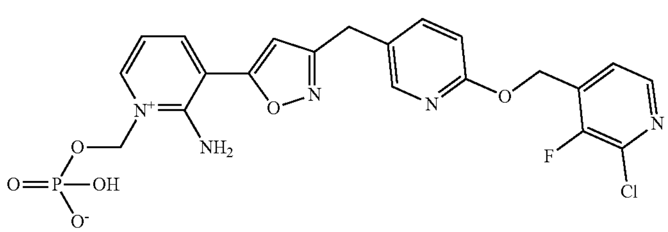 [SMILES: Nc1c(-c2cc(Cc3ccc(OCc4ccnc(Cl)c4F)nc3)no2)ccc[n+]1COP(=O)([O-])O] | (2-amino-3-(3-((6-((2-chloro-3-fluoropyridin-4-yl)methoxy)pyridin-3-yl)methyl)isoxazol-5-yl)pyridin-1-ium-1-yl)methyl hydrogen phosphate |
| 445 | 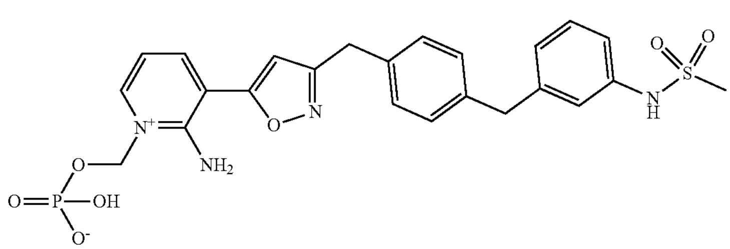 [SMILES: CS(=O)(=O)Nc1cccc(Cc2ccc(Cc3cc(-c4ccc[n+](COP(=O)([O-])O)c4N)on3)cc2)c1] | (2-amino-3-(3-(4-(3-(methylsulfonamido)benzyl)benzyl)isoxazol-5-yl)pyridin-1-ium-1-yl)methyl hydrogen phosphate |

TABLE 1-continued

| Ex. | Structure | Name |
|---|---|---|
| 446 | 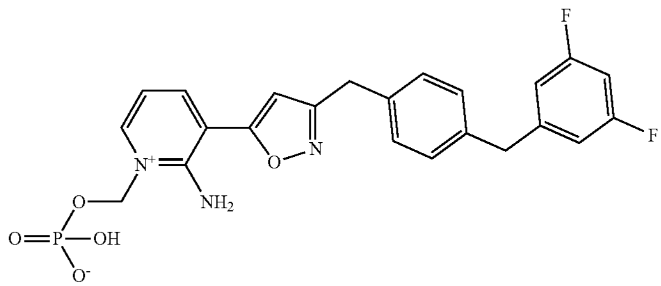 [SMILES: Nc1c(-c2cc(Cc3ccc(Cc4cc(F)cc(F)c4)cc3)no2)ccc[n+]1COP(=O)([O-])O] | (2-amino-3-(3-(4-(3,5-difluorobenzyl)benzyl)isoxazol-5-yl)pyridin-1-ium-1-yl)methyl hydrogen phosphate |
| 447 | 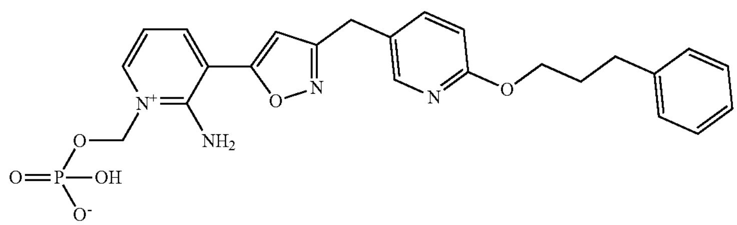 [SMILES: Nc1c(-c2cc(Cc3ccc(OCCCc4ccccc4)nc3)no2)ccc[n+]1COP(=O)([O-])O] | (2-amino-3-(3-((6-(3-phenylpropoxy)pyridin-3-yl)methyl)isoxazol-5-yl)pyridin-1-ium-1-yl)methyl hydrogen phosphate |
| 448 | 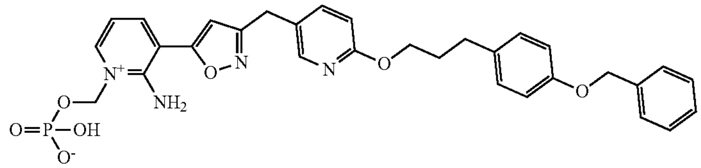 [SMILES: Nc1c(-c2cc(Cc3ccc(OCCCc4ccc(OCc5ccccc5)cc4)nc3)no2)ccc[n+]1COP(=O)([O-])O] | (2-amino-3-(3-((6-(3-(4-(benzyloxy)phenyl)propoxy)pyridin-3-yl)methyl)isoxazol-5-yl)pyridin-1-ium-1-yl)methyl hydrogen phosphate |
| 449 | 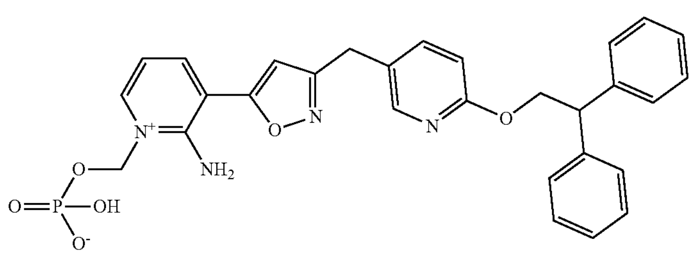 [SMILES: Nc1c(-c2cc(Cc3ccc(OCC(c4ccccc4)c4ccccc4)nc3)no2)ccc[n+]1COP(=O)([O-])O] | (2-amino-3-(3-((6-(2,2-diphenylethoxy)pyridin-3-yl)methyl)isoxazol-5-yl)pyridin-1-ium-1-yl)methyl hydrogen phosphate |
| 450 | 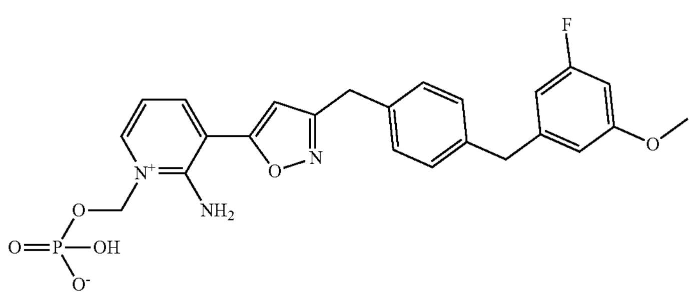 [SMILES: COc1cc(F)cc(Cc2ccc(Cc3cc(-c4ccc[n+](COP(=O)([O-])O)c4N)on3)cc2)c1] | (2-amino-3-(3-(4-(3-fluoro-5-methoxybenzyl)benzyl)isoxazol-5-yl)pyridin-1-ium-1-yl)methyl hydrogen phosphate |
| 451 | 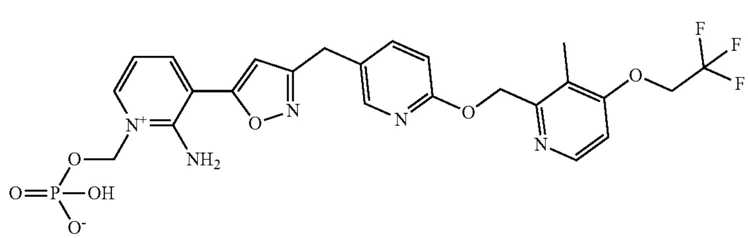 [SMILES: Cc1c(OCC(F)(F)F)ccnc1COc1ccc(Cc2cc(-c3ccc[n+](COP(=O)([O-])O)c3N)on2)cn1] | (2-amino-3-(3-((6-((3-methyl-4-(2,2,2-trifluoroethoxy)pyridin-2-yl)methoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 452 | 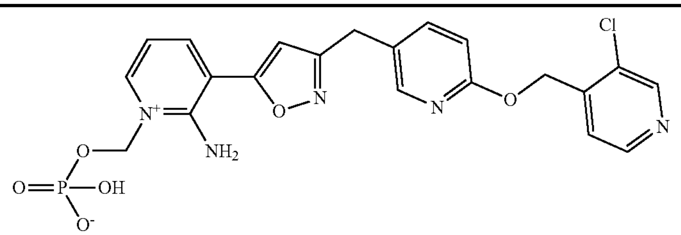 | (2-amino-3-(3-((6-((3-chloropyridin-4-yl)methoxy)pyridin-3-yl)methyl)isoxazol-5-yl)pyridin-1-ium-1-yl)methyl hydrogen phosphate |
| 453 | 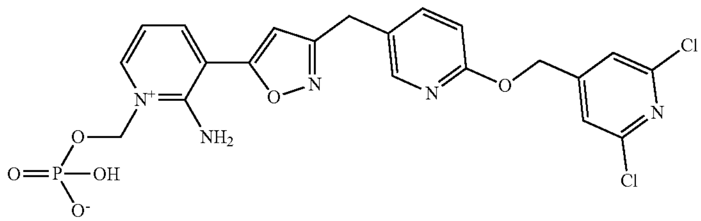 | (2-amino-3-(3-((6-((2,6-dichloropyridin-4-yl)methoxy)pyridin-3-yl)methyl)isoxazol-5-yl)pyridin-1-ium-1-yl)methyl hydrogen phosphate |
| 454 | 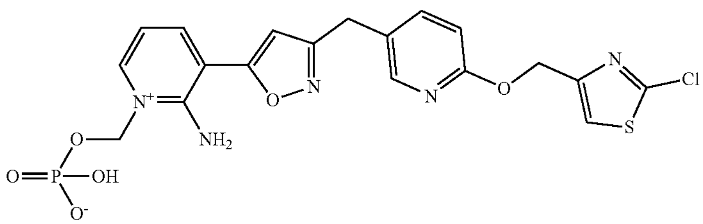 [SMILES: Nc1c(-c2cc(Cc3ccc(OCc4csc(Cl)n4)nc3)no2)ccc[n+]1COP(=O)([O-])O] | (2-amino-3-(3-((6-((2-chlorothiazol-4-yl)methoxy)pyridin-3-yl)methyl)isoxazol-5-yl)pyridin-1-ium-1-yl)methyl hydrogen phosphate |
| 455 | 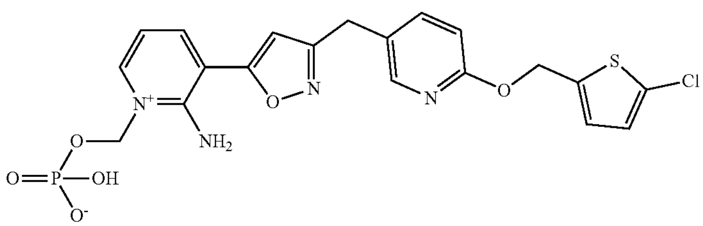 [SMILES: Nc1c(-c2cc(Cc3ccc(OCc4ccc(Cl)s4)nc3)no2)ccc[n+]1COP(=O)([O-])O] | (2-amino-3-(3-((6-((5-chlorothiophen-2-yl)methoxy)pyridin-3-yl)methyl)isoxazol-5-yl)pyridin-1-ium-1-yl)methyl hydrogen phosphate |
| 456 | 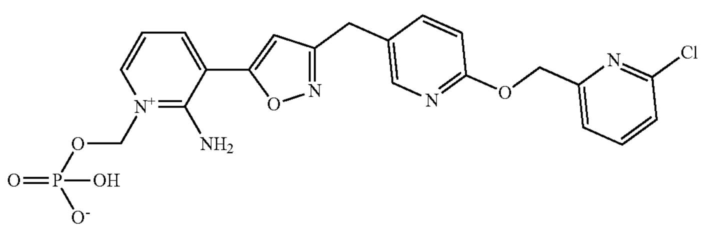 | (2-amino-3-(3-((6-((6-chloropyridin-2-yl)methoxy)pyridin-3-yl)methyl)isoxazol-5-yl)pyridin-1-ium-1-yl)methyl hydrogen phosphate |
| 457 | 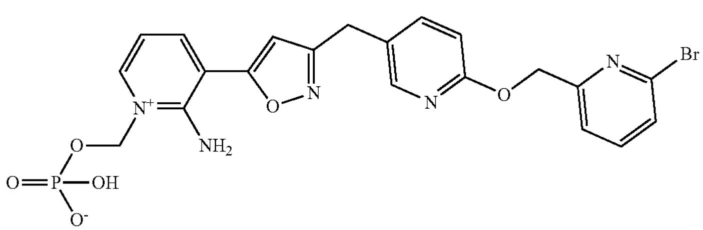 [SMILES: Nc1c(-c2cc(Cc3ccc(OCc4cccc(Br)n4)nc3)no2)ccc[n+]1COP(=O)([O-])O] | (2-amino-3-(3-((6-((6-bromopyridin-2-yl)methoxy)pyridin-3-yl)methyl)isoxazol-5-yl)pyridin-1-ium-1-yl)methyl hydrogen phosphate |
| 458 | 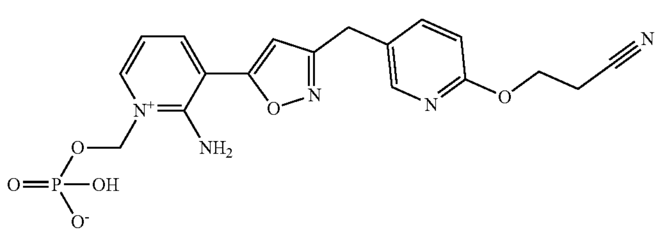 [SMILES: N#CCCOc1ccc(Cc2cc(-c3ccc[n+](COP(=O)([O-])O)c3N)on2)cn1] | (2-amino-3-(3-((6-(2-cyanoethoxy)pyridin-3-yl)methyl)isoxazol-5yl)pyridin-1-ium-1-yl)methyl hydrogen phosphate |

TABLE 1-continued

| Ex. | Structure | Name |
|---|---|---|
| 459 | 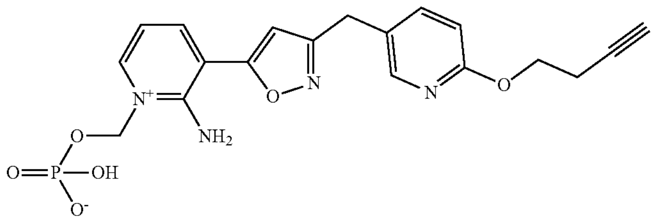 [SMILES: C#CCCOc1ccc(Cc2cc(-c3ccc[n+](COP(=O)([O-])O)c3N)on2)cn1] | (2-amino-3-(3-((6-(but-3-yn-1-yloxy)pyridin-3-yl)methyl)isoxazol-5-yl)pyridin-1-ium-1-yl)methyl hydrogen phosphate |
| 460 | 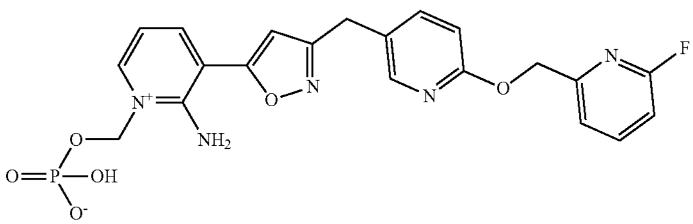 [SMILES: Nc1c(-c2cc(Cc3ccc(OCc4cccc(F)n4)nc3)no2)ccc[n+]1COP(=O)([O-])O] | (2-amino-3-(3-((6-((6-fluoropyridin-2-yl)methoxy)pyridin-3-yl)methyl)isoxazol-5-yl)pyridin-1-ium-1-yl)methyl hydrogen phosphate |
| 461 | 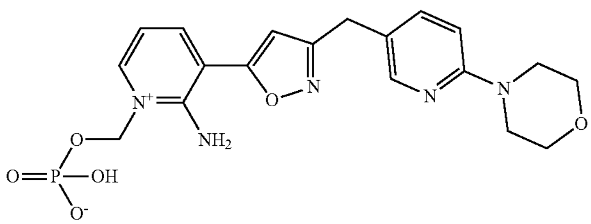 [SMILES: Nc1c(-c2cc(Cc3ccc(N4CCOCC4)nc3)no2)ccc[n+]1COP(=O)([O-])O] | (2-amino-3-(3-((6-morpholinopyridin-3-yl)methyl)isoxazol-5-yl)pyridin-1-ium-1-yl)methyl hydrogen phosphate |
| 462 | 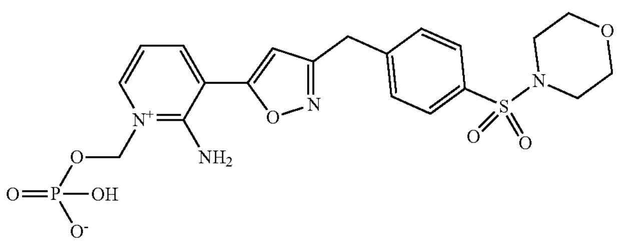 [SMILES: Nc1c(-c2cc(Cc3ccc(S(=O)(=O)N4CCOCC4)cc3)no2)ccc[n+]1COP(=O)([O-])O] | (2-amino-3-(3-(4-(morpholinosulfonyl)benzyl)isoxazol-5-yl)pyridin-1-ium-1-yl)methyl hydrogen phosphate |
| 463 | 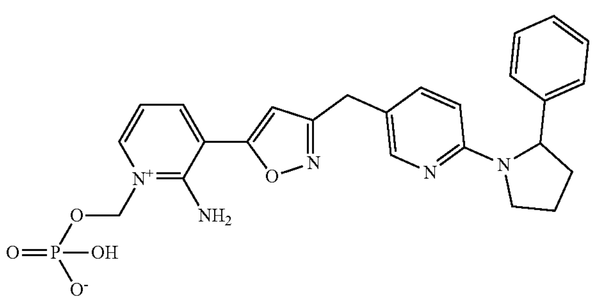 [SMILES: Nc1c(-c2cc(Cc3ccc(N4CCCC4c4ccccc4)nc3)no2)ccc[n+]1COP(=O)([O-])O] | (2-amino-3-(3-((6-(2-phenylpyrrolidin-1-yl)pyridin-3-yl)methyl)isoxazol-5-yl)pyridin-1-ium-1-yl)methyl hydrogen phosphate |
| 464 | 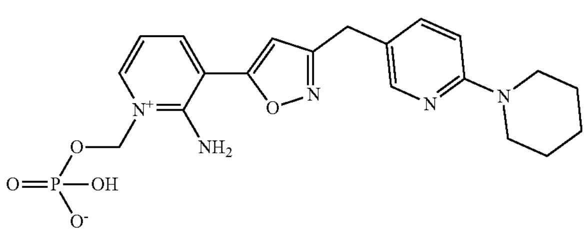 [SMILES: Nc1c(-c2cc(Cc3ccc(N4CCCCC4)nc3)no2)ccc[n+]1COP(=O)([O-])O] | (2-amino-3-(3-((6-(piperidin-1-yl)pyridin-3-yl)methyl)isoxazol-5-yl)pyridin-1-ium-1-yl)methyl hydrogen phosphate |

TABLE 1-continued

| Ex. | Structure | Name |
|---|---|---|
| 465 | 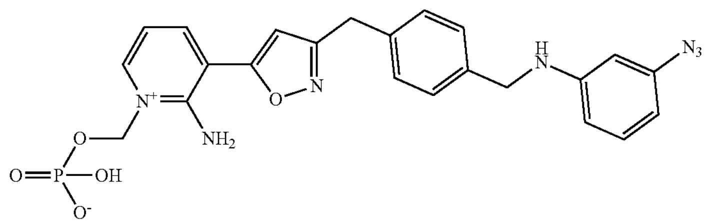 [SMILES: [N-]=[N+]=Nc1cccc(NCc2ccc(Cc3cc(-c4ccc[n+](COP(=O)([O-])O)c4N)on3)cc2)c1] | (2-amino-3-(3-(4-(((3-azidophenyl)amino)methyl)benzyl)isoxazol-5-yl)pyridin-1-ium-1-yl)methyl hydrogen phosphate |
| 466 | 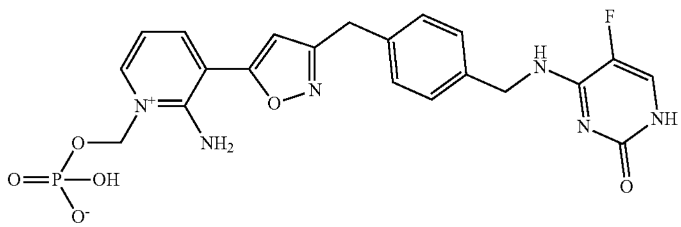 [SMILES: Nc1c(-c2cc(Cc3ccc(CNc4nc(=O)[nH]cc4F)cc3)no2)ccc[n+]1COP(=O)([O-])O] | (2-amino-3-(3-(4-(((5-fluoro-2-oxo-1,2-dihydropyrimidin-4-yl)amino)methyl)benzyl)isoxazol-5-yl)pyridin-1-ium-1-yl)methyl hydrogen phosphate |
| 467 | 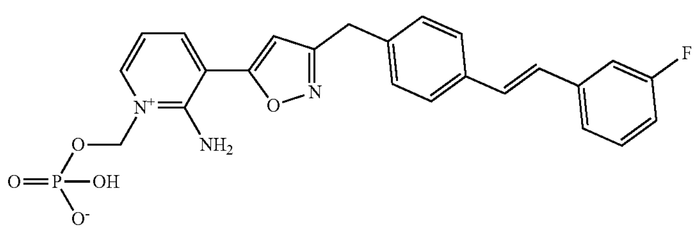 [SMILES: Nc1c(-c2cc(Cc3ccc(/C=C/c4cccc(F)c4)cc3)no2)ccc[n+]1COP(=O)([O-])O] | (E)-(2-amino-3-(3-(4-(3-fluorostyryl)benzyl)isoxazol-5-yl)pyridin-1-ium-1-yl)methyl hydrogen phosphate |
| 468 | 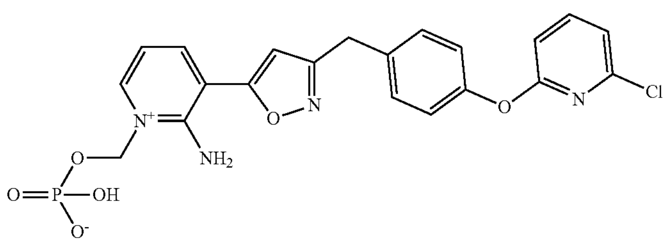 [SMILES: Nc1c(-c2cc(Cc3ccc(Oc4cccc(Cl)n4)cc3)no2)ccc[n+]1COP(=O)([O-])O] | (2-amino-3-(3-(4-((6-chloropyridin-2-yl)oxy)benzyl)isoxazol-5-yl)pyridin-1-ium-1-yl)methyl hydrogen phosphate |
| 469 | 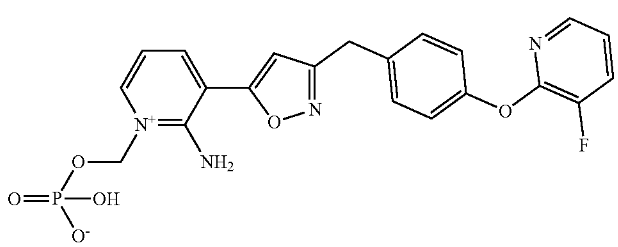 [SMILES: Nc1c(-c2cc(Cc3ccc(Oc4ncccc4F)cc3)no2)ccc[n+]1COP(=O)([O-])O] | (2-amino-3-(3-(4-((3-fluoropyridin-2-yl)oxy)benzyl)isoxazol-5-yl)pyridin-1-ium-1-yl)methyl hydrogen phosphate |
| 470 | 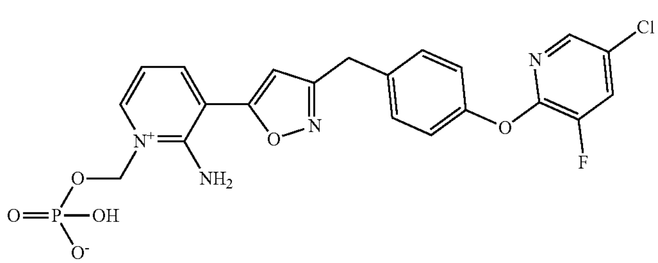 [SMILES: Nc1c(-c2cc(Cc3ccc(Oc4ncc(Cl)cc4F)cc3)no2)ccc[n+]1COP(=O)([O-])O] | (2-amino-3-(3-(4-((5-chloro-3-fluoropyridin-2-yl)oxy)benzyl)isoxazol-5-yl)pyridin-1-ium-1-yl)methyl hydrogen phosphate |

TABLE 1-continued

| Ex. | Structure | Name |
|---|---|---|
| 471 | 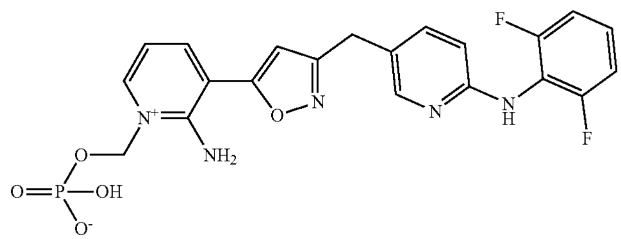 [SMILES: Nc1c(-c2cc(Cc3ccc(Nc4c(F)cccc4F)nc3)no2)ccc[n+]1COP(=O)([O-])O] | (2-amino-3-(3-((6-((2,6-difluorophenyl)amino)pyridin-3-yl)methyl)isoxazol-5-yl)pyridin-1-ium-1-yl)methyl hydrogen phosphate |
| 472 | 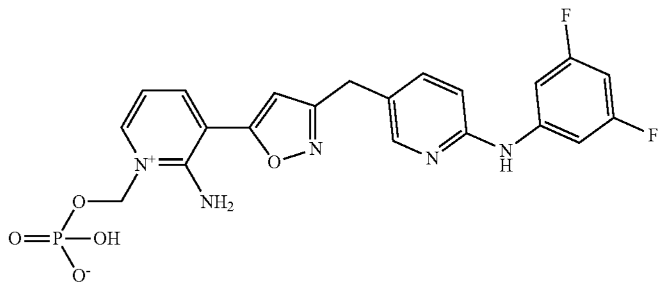 [SMILES: Nc1c(-c2cc(Cc3ccc(Nc4cc(F)cc(F)c4)nc3)no2)ccc[n+]1COP(=O)([O-])O] | (2-amino-3-(3-((6-((3,5-difluorophenyl)amino)pyridin-3-yl)methyl)isoxazol-5-yl)pyridin-1-ium-1-yl)methyl hydrogen phosphate |
| 473 | 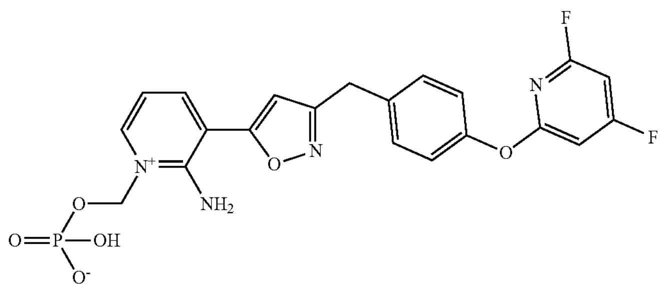 [SMILES: Nc1c(-c2cc(Cc3ccc(Oc4cc(F)cc(F)n4)cc3)no2)ccc[n+]1COP(=O)([O-])O] | (2-amino-3-(3-(4-((4,6-difluoropyridin-2-yl)oxy)benzyl)isoxazol-5-yl)pyridin-1-ium-1-yl)methyl hydrogen phosphate |
| 474 | 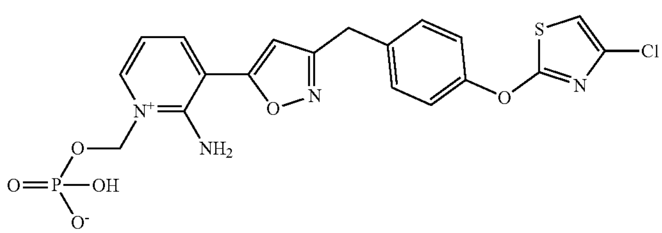 [SMILES: Nc1c(-c2cc(Cc3ccc(Oc4nc(Cl)cs4)cc3)no2)ccc[n+]1COP(=O)([O-])O] | (2-amino-3-(3-(4-((4-chlorothiazol-2-yl)oxy)benzyl)isoxazol-5-yl)pyridin-1-ium-1-yl)methyl hydrogen phosphate |
| 475 | 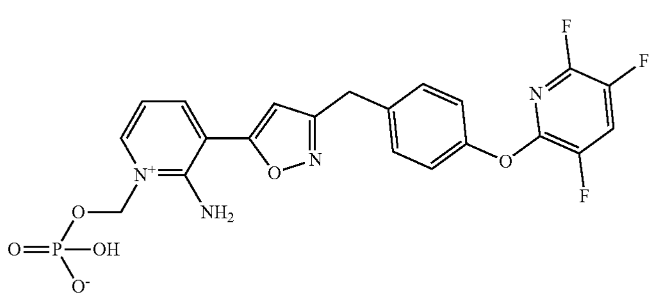 [SMILES: Nc1c(-c2cc(Cc3ccc(Oc4nc(F)c(F)cc4F)cc3)no2)ccc[n+]1COP(=O)([O-])O] | (2-amino-3-(3-(4-((3,5,6-trifluoropyridin-2-yl)oxy)benzyl)isoxazol-3-yl)pyridin-1-ium-1-yl)methyl hydrogen phosphate |
| 476 | 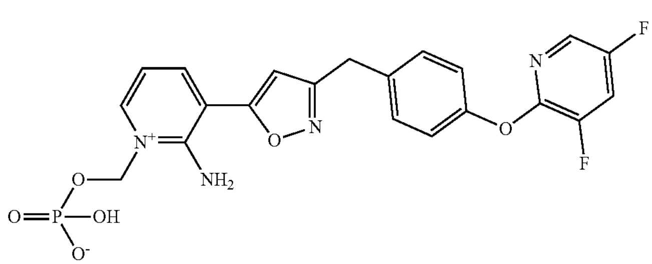 [SMILES: Nc1c(-c2cc(Cc3ccc(Oc4ncc(F)cc4F)cc3)no2)ccc[n+]1COP(=O)([O-])O] | (2-amino-3-(3-(4-((3,5-difluoropyridin-2-yl)oxy)benzyl)isoxazol-5-yl)pyridin-1-ium-1-yl)methyl hydrogen phosphate |

TABLE 1-continued

| Ex. | Structure | Name |
| --- | --- | --- |
| 477 | 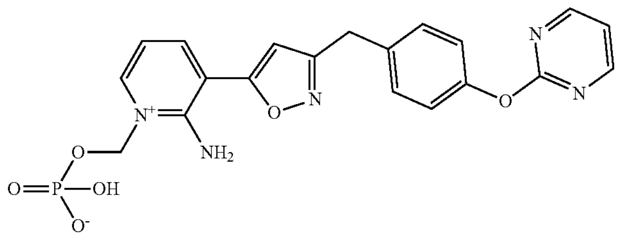 [SMILES: Nc1c(-c2cc(Cc3ccc(Oc4ncccn4)cc3)no2)ccc[n+]1COP(=O)([O-])O] | (2-amino-3-(3-(4-(pyrimidin-2-yloxy)benzyl)isoxazol-5-yl)pyridin-1-ium-1-yl)methyl hydrogen phosphate |
| 478 | 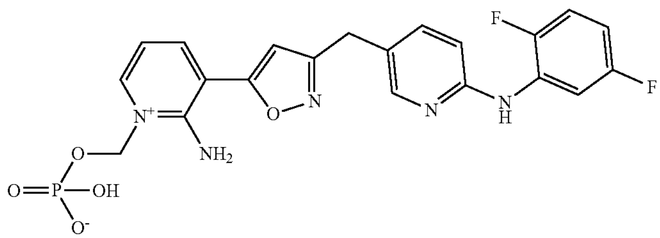 [SMILES: Nc1c(-c2cc(Cc3ccc(Nc4cc(F)ccc4F)nc3)no2)ccc[n+]1COP(=O)([O-])O] | (2-amino-3-(3-((6-((2,5-difluorophenyl)amino)pyridin-3-yl)methyl)isoxazol-5-yl)pyridin-1-ium-1-yl)methyl hydrogen phosphate |
| 479 | 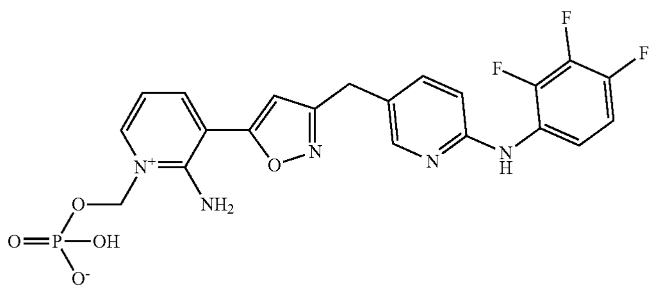 [SMILES: Nc1c(-c2cc(Cc3ccc(Nc4ccc(F)c(F)c4F)nc3)no2)ccc[n+]1COP(=O)([O-])O] | (2-amino-3-(3-((6-((2,3,4-trifluorophenyl)amino)pyridin-3-yl)methyl)isoxazol-5-yl)pyridin-1-ium-1-yl)methyl hydrogen phosphate |
| 480 | 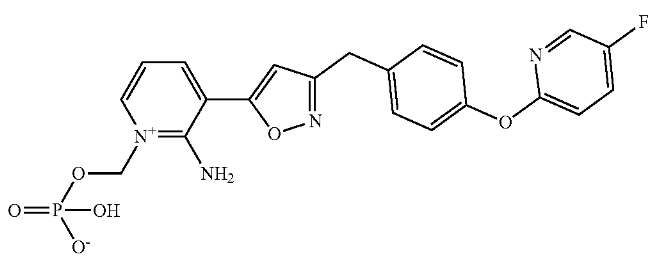 | (2-amino-3-(3-(4-((5-fluoropyridin-2-yl)oxy)benzyl)isoxazol-5-yl)pyridin-1-ium-1-yl)methyl hydrogen phosphate |
| 481 | 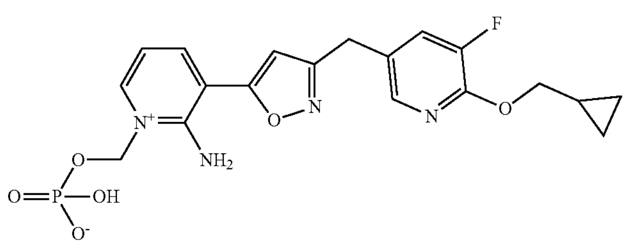 [SMILES: Nc1c(-c2cc(Cc3cnc(OCC4CC4)c(F)c3)no2)ccc[n+]1COP(=O)([O-])O] | (2-amino-3-(3-((6-(cyclopropylmethoxy)-5-fluoropyridin-3-yl)methyl)isoxazol-5-yl)pyridin-1-ium-1-yl)methyl hydrogen phosphate |
| 482 | 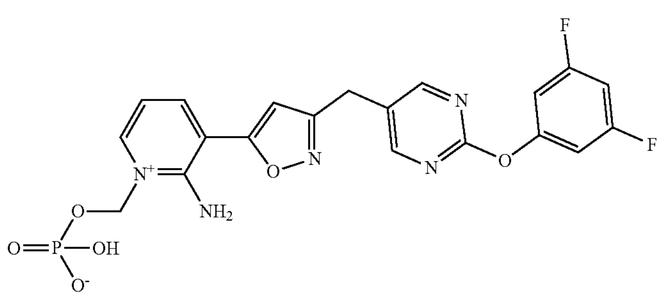 [SMILES: Nc1c(-c2cc(Cc3cnc(Oc4cc(F)cc(F)c4)nc3)no2)ccc[n+]1COP(=O)([O-])O] | (2-amino-3-(3-((2-(3,5-difluorophenoxy)pyrimidin-5-yl)methyl)isoxazol-5-yl)pyridin-1-ium-1-yl)methyl hydrogen phosphate |

| Ex. | Structure | Name |
| --- | --- | --- |
| 483 | 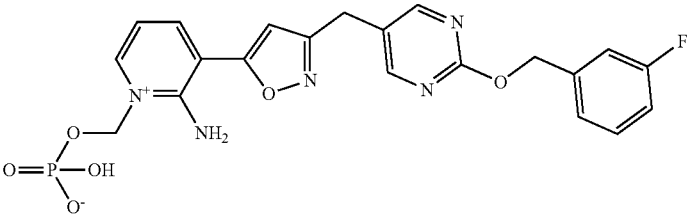 | (2-amino-3-(3-((2-((3-fluorobenzyl)oxy)pyrimidin-5-yl)methyl)isoxazol-5-yl)pyridin-1-ium-1-yl)methyl hydrogen phosphate |
| 484 | 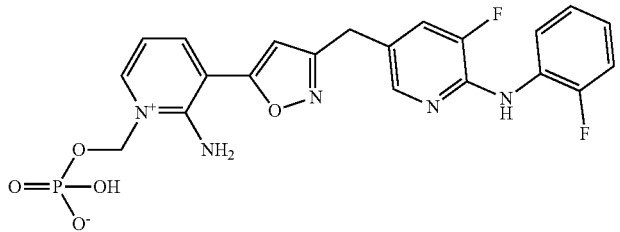 [SMILES: Nc1c(-c2cc(Cc3cnc(Nc4ccccc4F)c(F)c3)no2)ccc[n+]1COP(=O)([O-])O] | (2-amino-3-(3-((5-fluoro-6-((2-fluorophenyl)amino)pyridin-3-yl)methyl)isoxazol-5-yl)pyridin-1-ium-1-yl)methyl hydrogen phosphate |
| 485 | 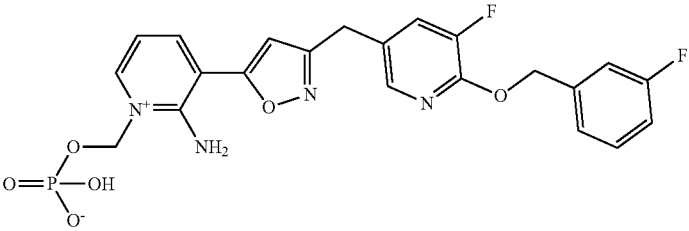 [SMILES: Nc1c(-c2cc(Cc3cnc(OCc4cccc(F)c4)c(F)c3)no2)ccc[n+]1COP(=O)([O-])O] | (2-amino-3-(3-((5-fluoro-6-((3-fluorobenzyl)oxy)pyridin-3-yl)methyl)isoxazol-5-yl)pyridin-1-ium-1-yl)methyl hydrogen phosphate |
| 486 | 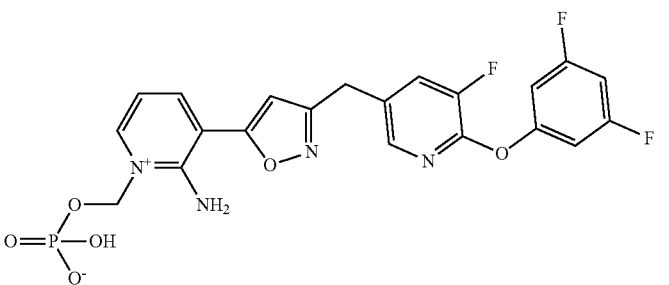 [SMILES: Nc1c(-c2cc(Cc3cnc(Oc4cc(F)cc(F)c4)c(F)c3)no2)ccc[n+]1COP(=O)([O-])O] | (2-amino-3-(3-((6-(3,5-difluorophenoxy)-5-fluoropyridin-3-yl)methyl)isoxazol-5-yl)pyridin-1-ium-1-yl)methyl hydrogen phosphate |
| 487 | 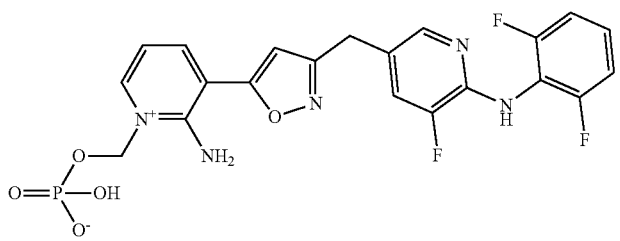 [SMILES: Nc1c(-c2cc(Cc3cnc(Nc4c(F)cccc4F)c(F)c3)no2)ccc[n+]1COP(=O)([O-])O] | (2-amino-3-(3-((6-((2,6-difluorophenyl)amino)-5-fluoropyridin-3-yl)methyl)isoxazol-5-yl)pyridin-1-ium-1-yl)methyl hydrogen phosphate |
| 488 | 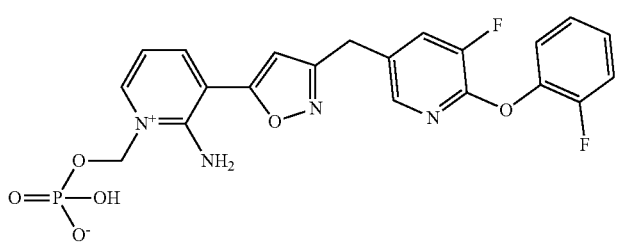 [SMILES: Nc1c(-c2cc(Cc3cnc(Oc4ccccc4F)c(F)c3)no2)ccc[n+]1COP(=O)([O-])O] | (2-amino-3-(3-((5-fluoro-6-(2-fluorophenoxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 489 | 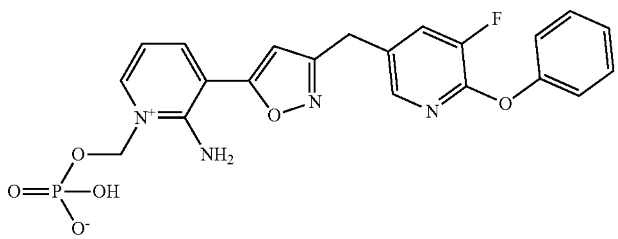 [SMILES: Nc1c(-c2cc(Cc3cnc(Oc4ccccc4)c(F)c3)no2)ccc[n+]1COP(=O)([O-])O] | (2-amino-3-(3-((5-fluoro-6-phenoxypyridin-3-yl)methyl)isoxazol-5-yl)pyridin-1-ium-1-yl)methyl hydrogen phosphate |
| 490 | 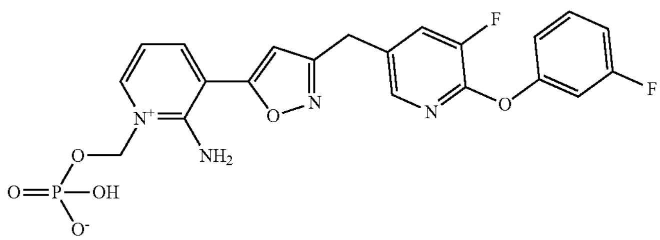 [SMILES: Nc1c(-c2cc(Cc3cnc(Oc4cccc(F)c4)c(F)c3)no2)ccc[n+]1COP(=O)([O-])O] | (2-amino-3-(3-((5-fluoro-6-(3-fluorophenoxy)pyridin-3-yl)methyl)isoxazol-5-yl)pyridin-1-ium-1-yl)methyl hydrogen phosphate |
| 491 | 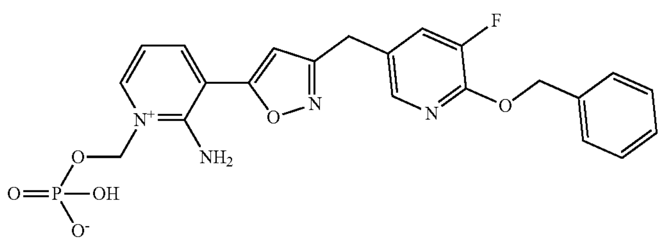 [SMILES: Nc1c(-c2cc(Cc3cnc(OCc4ccccc4)c(F)c3)no2)ccc[n+]1COP(=O)([O-])O] | (2-amino-3-(3-((6-(benzyloxy)-5-fluoropyridin-3-yl)methyl)isoxazol-5-yl)pyridin-1-ium-1-yl)methyl hydrogen phosphate |
| 492 | 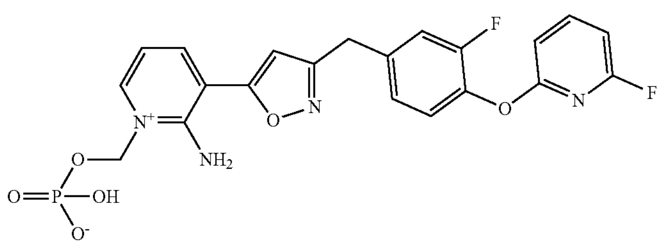 [SMILES: Nc1c(-c2cc(Cc3ccc(Oc4cccc(F)n4)c(F)c3)no2)ccc[n+]1COP(=O)([O-])O] | (2-amino-3-(3-(3-fluoro-4-((6-fluoropyridin-2-yl)oxy)benzyl)isoxazol-5-yl)pyridin-1-ium-1-yl)methyl hydrogen phosphate |
| 493 | 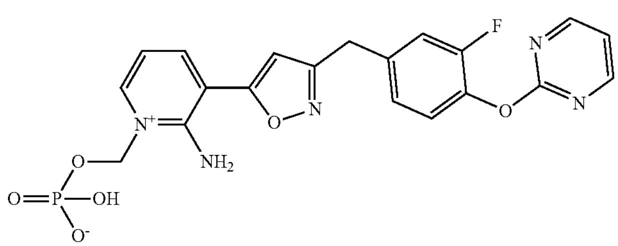 [SMILES: Nc1c(-c2cc(Cc3ccc(Oc4ncccn4)c(F)c3)no2)ccc[n+]1COP(=O)([O-])O] | (2-amino-3-(3-(3-fluoro-4-(pyrimidin-2-yloxy)benzyl)isoxazol-5-yl)pyridin-1-ium-1-yl)methyl hydrogen phosphate |
| 494 | 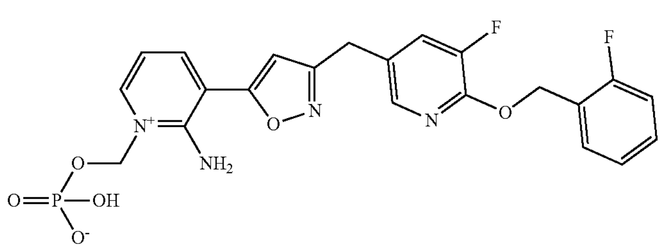 [SMILES: Nc1c(-c2cc(Cc3cnc(OCc4ccccc4F)c(F)c3)no2)ccc[n+]1COP(=O)([O-])O] | (2-amino-3-(3-((5-fluoro-6-((2-fluorobenzyl)oxy)pyridin-3-yl)methyl)isoxazol-5-yl)pyridin-1-ium-1-yl)methyl hydrogen phosphate |

TABLE 1-continued

| Ex. | Structure | Name |
|---|---|---|
| 495 | 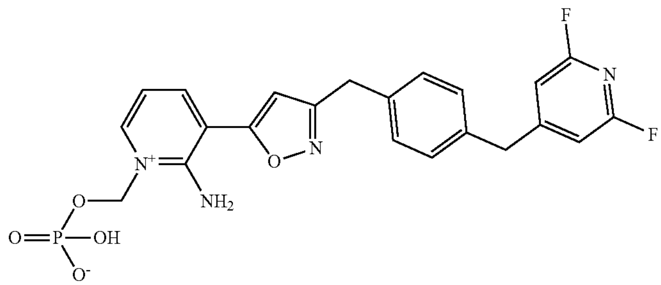 [SMILES: Nc1c(-c2cc(Cc3ccc(Cc4cc(F)nc(F)c4)cc3)no2)ccc[n+]1COP(=O)([O-])O] | (2-amino-3-(3-(4-((2,6-difluoropyridin-4-yl)methyl)benzyl)isoxazol-5-yl)pyridin-1-ium-1-yl)methyl hydrogen phosphate |

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers, as well as the corresponding mixtures thereof. In some situations, the compounds described herein possess one or more chiral centers and each center exists in the R configuration, or S configuration. The compounds described herein include all diastereomeric, enantiomeric and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of Formula (I), (II), or (III), or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{34}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Prodrugs

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). Prodrugs are delivered through any known methods described herein, including but not limited to orally, intravenously, intraperitoneal, or other method of administration known by those skilled in the art.

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. In some embodiments, prodrugs include any group bound to a heteroatom, such as the nitrogen of a pyridine which is cleaved in-vivo to form the active compound or metabolite thereof. Examples of prodrugs include, but are not limited to, acetate, formate phosphate, and benzoate derivatives of alcohol or amine functional groups in the active compounds and the like.

In some embodiments, a prodrug is a salt. In some embodiments, a prodrug is a phosphate salt. In some embodiments, the prodrug is an alkyl phosphate salt. In some embodiments, the prodrug is an alkylated heteroaromatic salt. In some embodiments, the prodrug is a pyridinium salt. In some embodiments, the prodrug is pyridinium alkylphosphate salt. In some embodiments, the prodrug is a pyridinium methylphosphate salt. In some embodiments, a prodrug comprises an alkyl phosphate bound to a heteroatom. In some embodiments, a prodrug comprises an alkyl phosphate bound to a heteroatom of a heterocycle.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, for example, or any carbon can be $^{13}C$, for example, or any nitrogen can be $^{15}N$, for example, or any oxygen can be $^{18}O$, for example, where feasible according to the judgment of one of skill. In certain embodiments, an "isotopic variant" of a compound contains unnatural proportions of deuterium (D).

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compound described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limiting to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary buylacetic acid, lauryl sulfuric acid, gluconic acid, glutamic acid, hydroxynaphthoic acid, salicyclic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

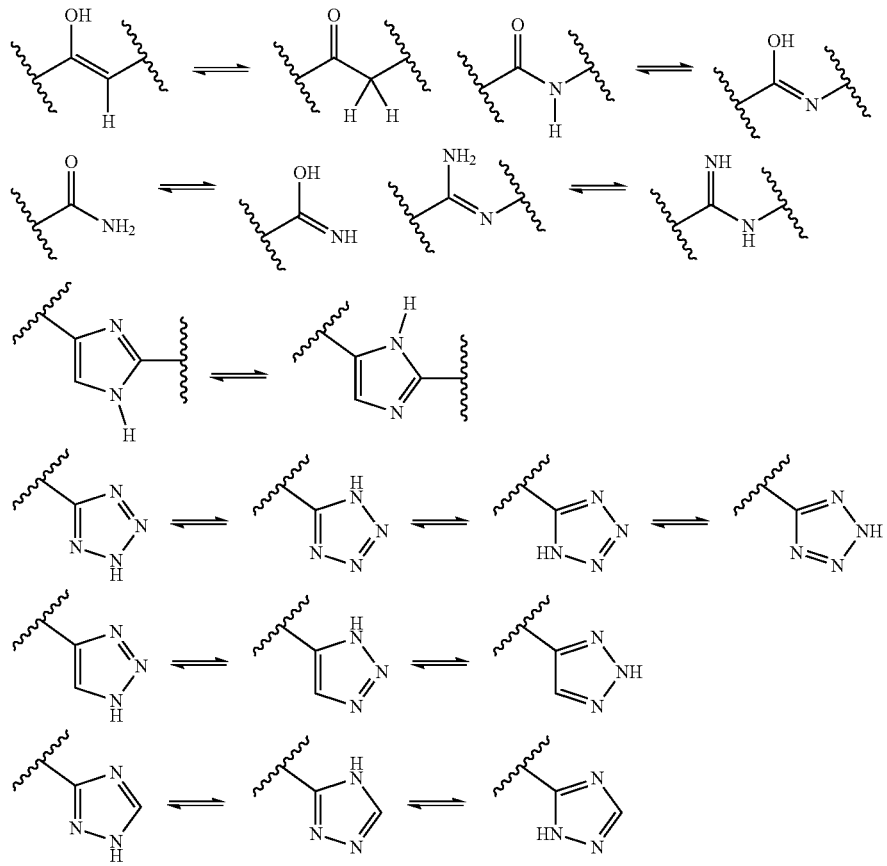

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein.

Pharmaceutical Compositions

In certain embodiments, the compound of Formula (I), (Ia), (II), (IIa), (IIb), (IIc), (II'), (II''), (III), (IIIa), or (III-B) as described herein is administered as a pure chemical. In some embodiments, the compound of Formula (I), (Ia), (II), (IIa), (IIb), (IIc), (II'), (II''), (III), (IIIa), or (III-B) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Accordingly, provided herein is a pharmaceutical composition comprising at least one compound of Formula (I), (Ia), (II), (IIa), (IIb), (IIc), (II'), (II"), (III), (IIIa), or (III-B) described herein, or a pharmaceutically acceptable salt, solvate, or stereoisomer thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), (Ia), (II), (IIa), (IIb), (IIc), (II'), (II"), (III), (IIIa), or (III-B) or a pharmaceutically acceptable salt, solvate, or stereoisomer thereof.

In certain embodiments, the compound of Formula (I), (Ia), (II), (IIa), (IIb), (IIc), (II'), (II"), (III), (IIIa), or (III-B) provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, sex, age, renal status, hepatic status, or blood volume of the patient.

Oral doses typically range from about 1.0 mg to about 1000 mg, one to four times, or more, per day, or one to four times per week.

In some embodiments, the compounds contemplated by the present disclosure may be administered (e.g., orally) at dosage levels of about 0.01 mg/kg to about 1000 mg/kg, or about 1 mg/kg to about 50 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. Pharmaceutically acceptable carrier(s), diluent(s) and/or excipient(s) may be present in an amount of from about 0.1 g to about 2.0 g.

Methods of Treatment

Disclosed herein, in certain embodiments, are methods for treating a fungal disease in a subject in need thereof, comprising administering to the subject a therapeutically effective amount of a compound of Formula (I), (Ia), (II), (IIa), (IIb), (IIc), (II'), (II"), (III), (IIIa), or (III-B) at a frequency and for a duration sufficient to provide a beneficial effect to the subject.

Disclosed herein, in certain embodiments, are methods for treating a fungal disease in a subject in need thereof, comprising administering to the subject a therapeutically effective amount of a pharmaceutical composition, comprising compound of Formula (I), (Ia), (II), (IIa), (IIb), (IIc), (II'), (II"), (III), (IIIa), or (III-B), and at least one pharmaceutically acceptable excipient, at a frequency and for a duration sufficient to provide a beneficial effect to the subject.

Fungal Diseases

In some embodiments, the fungal disease is selected from the group consisting of aspergillosis, blastomycosis, candidiasis, coccidioidomycosis (Valley Fever), cryptococcosis, fungal eye infection, histoplasmosis, mucormycosis, *Pneumocystis* pneumonia (PCP), ringworm, sporotrichosis, and talaromycosis.

In some embodiments, the fungal disease is aspergillosis. In some embodiments, asperigllosis is allergic bronchopulmonary aspergillosis (abpa), allergic *Aspergillus* sinusitis, chronic pulmonary aspergillosis, invasive aspergillosis or cutaneous (skin) aspergillosis. In some embodiments, the subject has an aspergilloma.

In some embodiments, the fungal disease is blastomycosis.

In some embodiments, the fungal disease is candidiasis. In some embodiments, candidiasis is oropharyngeal candidiasis (thrush), vulvovaginal candidiasis (vaginal candidiasis), fungemia, or invasive candidiasis.

In some embodiments, the fungal disease is coccidioidomycosis (Valley Fever). In some embodiments, cocidioidomycosis is acute coccidioidomycosis (primary pulmonary coccidioidomycosis), chronic coccidioidomycosis, or disseminated coccidioidomycosis, including primary cutaneous coccidioidomycosis.

In some embodiments, the fungal disease is cryptococcosis. In some embodiments, cryptococcosis is wound or cutaneous cryptococcosis, pulmonary cryptococcosis, or cryptococcal meningitis.

In some embodiments, the fungal disease is a fungal eye infection. In some embodiments, the fungal eye infection is fungal keratitis, fungal exogenous endophthalmitis, or fungal endogenous endophthalmitis.

In some embodiments, the fungal disease is histoplasmosis. In some embodiments, histoplasmosis is acute histoplamosis. In some embodiments, histoplamosis is chronic histoplamosis.

In some embodiments, the fungal disease is mucormycosis. In some embodiments, mucormycosis is rhinocerebral (sinus and brain) mucormycosis, pulmonary (lung) mucormycosis, gastrointestinal mucormycosis, cutaneous (skin) mucormycosis, or disseminated mucormycosis.

In some embodiments, the fungal disease is *Pneumocystis* pneumonia (PCP).

In some embodiments, the fungal disease is ringworm. In some embodiments, the ringworm is tinea pedis, tinea cruris, tinea capitis, tinea barbae, tinea manuum, tinea unguium, or tinum corporis. In some embodiments, the ringworm is caused by a type of fungi including *Trichophyton, Microsporum*, or *Epidermorphyton*.

In some embodiments, the fungal disease is sporotrichosis. In some embodiments, sporotrichosis is cutaneous (skin) sporotrichosis, pulmonary (lung) sporotrichosis, or disseminated sporotrichosis.

In some embodiments, the fungal disease is talaromycosis.

In some embodiments, the fungal disease is caused by a fungal species including, but not limited to, *Aspergillus fumigatus, Aspergillus flavus, Aspergillus niger, Aspergillus terreus. Blastomyces dermatitidis, Ajcliomyces dermatitidis, Candida albicans, Candida auris, Candida glabrata, Candida parapsilosis, Candida rugosa, Candida tropicalis, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia species, Saksenaea species, Rhizomucor pusillus, Entomophthora species, Conidiabolus species, Basidiobolus species, Sporothrix schenckii, Pneumocystis firovecil, Talaomyces marneffei, Asclepias albicans, Fusarium solani, Scedosporium apiospermum*, and *Rhizomucor pusillus*. In some embodiments, the fungal disease is caused by the fungal species *Aspergillus fumigatus*. In some embodiments, the fungal disease is caused by the fungal species *Candida albicans*. In some embodiments, the fungal disease is caused by the fungal species *Fusarium solani*. In some embodiments, the fungal disease is caused by the fungal species *Mucor indicus*. In some embodiments, the fungal disease is caused by the fungal species *Scedosporium apiosperman*. In some embodiments, the fungal disease is caused by the fungal species *Cryptococcus neoformans*. In some embodiments, the fungal disease is caused by the fungal species *Cryptococcus gattii*. In some embodiments, the fungal disease is caused by the fungal species *Candida auris*.

In an aspect provided herein, there is a method of treating a fungal disease in a subject in need thereof, comprising administering to the subject a therapeutically effective amount of a compound of Formula (I), (Ia), (II), (IIa), (IIb), (IIc), (II'), (II''), (III), (IIIa), or (III-B). In an aspect provided herein, there is a method of treating a fungal disease in a subject in need thereof, comprising administering to the subject a therapeutically effective amount of a pharmaceutical composition comprising compound of Formula (I), (Ia), (II), (IIa), (IIb), (IIc), (II'), (II''), (III), (IIIa), or (III-B) and at least one pharmaceutically acceptable excipient.

In some embodiments of the methods disclosed herein the fungal disease is selected from the group consisting of aspergillosis, blastomycosis, candidiasis, coccidioidomycosis (Valley Fever), cryptococcosis, fungal eye infection, histoplasmosis, mucormycosis, *Pneumocystis* pneumonia (PCP), ringworm, sporotrichosis, and talaromycosis.

In some embodiments of the methods disclosed herein, the fungal disease is caused by a fungal species selected the group consisting of *Aspergillus fumigatus, Aspergillus flavus, Blastomyces dermatitidis, Ajeliomyces dermatitidis, Candida albicans, Candida glabrata, Candida rugosa, Candida auris, Coccidioides immitis, Coccidioides posadasii, Cryptococcus neoformans, Cryptococcus gattii, Histoplasma capsulatum, Rhizopus stolonifer, Rhizopus arrhizus, Mucor indicus, Cunninghamella bertholletiae, Apophysomyces elegans, Absidia species, Saksenaea species, Rhizomucor pusillus, Entomophthora species, Conidiabolus species, Basidiobolus species, Sporothrix schenckii, Pneumocystis firovecii, Talaromyces marneffei, Asclepias albicans, Fusarium solani, Scedosporium apiospermum*, and *Rhizomucor pusillus*.

In some embodiments of the methods disclosed herein, the subject is immunocompromised.

In some embodiments of the methods disclosed herein, the subject has received chemotherapy treatment.

In some embodiments of the methods disclosed herein, the subject is infect with HIV/AIDS.

In some embodiments of the methods disclosed herein, the fungal disease is caused by *Cryptococcus neoformans* or *Cryptococcus gattii*.

In some embodiments of the methods disclosed herein, the compound is selected from the compounds in Table 1. In some embodiments of the methods disclosed herein, the compound is selected from the compounds in Table 2.

In some embodiments of the methods disclosed herein, the compound is selected from:

3-(3-(4-((6-fluoropyridin-2-yl)oxy)benzyl)isoxazol-5-yl)pyridin-2-amine;

3-(3-(4-((6-chloropyridin-2-yl)oxy)benzyl)isoxazol-5-yl)pyridin-2-amine;

3-(3-(4-((3-fluoropyridin-2-yl)oxy)benzyl)isoxazol-5-yl)pyridin-2-amine;

3-(3-(4-((3,5-difluoropyridin-2-yl)oxy)benzyl)isoxazol-5-yl)pyridin-2-amine;

3-(3-((6-((3-fluorophenoxy)pyridin-3-yl)methyl)isoxazol-5-yl)pyridin-2-amine;

3-(3-(4-((5-fluorofuran-2-yl)methyl)benzyl)isoxazol-5-yl)pyridin-2-amine;

3-(3-((6-phenoxypyridin-3-yl)methyl)isoxazol-5-yl)pyridin-2-amine;

3-(3-((6-((3-fluorobenzyl)oxy)pyridin-3-yl)methyl)isoxazol-5-yl)pyridin-2-amine;

5-((5-(2-aminopyridin-3-yl)isoxazol-3-yl)methyl)-N-(2-fluorophenyl)pyridin-2-amine;

5-((5-(2-aminopyridin-3-yl)isoxazol-3-yl)methyl)-N-(2,6-difluorophenyl)pyridin-2-amine;

3-(3-(4-benzylbenzyl)isoxazol-5-yl)pyridin-2-amine;

3-(3-(4-((6-fluoropyridin-2-yl)methyl)benzyl)isoxazol-5-yl)pyridin-2-amine;

3-(3-((6-(2-fluorophenoxy)pyridin-3-yl)methyl)isoxazol-5-yl)pyridin-2-amine;

3-(3-((6-(3,5-difluorophenoxy)pyridin-3-yl)methyl)isoxazol-5-yl)pyridin-2-amine;

3-(3-((6-(cyclopropylmethoxy)pyridin-3-yl)methyl)isoxazol-5-yl)pyridin-2-amine;

3-(3-(4-(3,5-difluorobenzyl)benzyl)isoxazol-5-yl)pyridin-2-amine;

3-(3-((2-(3-fluorobenzyl)oxy)pyridin-4-yl)methyl)isoxazol-5-yl)pyridin-2-amine;

3-(3-((4-(3-fluorobenzyl)benzyl)isoxazol-5-yl)pyridin-2-amine; and 3-(3-(4-(((3-fluorophenyl)amino)methyl)benzyl)isoxazol-5-yl)pyridin-2-amine, or a pharmaceutically acceptable salt, solvate, hydrate, tautomer, a stereoisomer, mixture of stereoisomers, or an isotopic variant thereof.

In some embodiments, a compound described herein is active against the fungal Gwt1 protein. This conserved enzyme catalyzes the glycosylphosphatidyl inositol (GPI) post-translational modification that anchors eukaryotic cell surface proteins to the cell membrane. In yeasts, GPI mediates cross-linking of cell wall mannoproteins to β-1,6-glucan. Inhibition of this enzyme in both *Candida albicans* and *Saccharomyces cerevisiae* has been shown to result in inhibition of maturation and localization of GPI-anchored mannoproteins thus demonstrating pleiotropic effects that include inhibition of fungal adherence to surfaces, inhibition of biofilm formation, inhibition of germ tube formation, severe growth defects, or lethality.

Subjects

In some embodiments, the subject is immunocompromised. In some embodiments, the subject is an immunocompromised human subject. In some embodiments, the human subject is under the age of 1 year. In some embodiments, the human subject is an infant under 1 month old. In some embodiments, the human subject is over the age of 70 years. In some embodiments, the subject is infected with HIV/AIDS. In some embodiments, the subject is undergoing or has undergone cancer chemotherapy treatment. In some embodiments, the subject is undergoing or has undergone corticosteroid treatment. In some embodiments, the subject is undergoing or has undergone TNF inhibitor treatment. In some embodiments, the subject is a transplant recipient. In some embodiments, the subject is a recipient of a hematopoietic stem-cell transplant, bone marrow transplant, lung transplant, liver transplant, heart transplant, kidney transplant, pancreas transplant or a combination thereof. In some embodiments, the subject is a recipient of a hematopoietic stem-cell transplant. In some embodiments, the subject is a recipient of a bone marrow transplant. In some embodiments, the subject is a recipient of a lung transplant. In some embodiments, the subject is a recipient of a liver transplant. In some embodiments, the subject is a recipient of a heart transplant. In some embodiments, the subject is a recipient of a kidney transplant. In some embodiments, the subject is a recipient of a pancreas transplant.

In some embodiments, the subject is a vertebrate. In some embodiments, the vertebrate is a fish, an amphibian, a reptile, a bird, a marsupial, or a mammal. In some embodiments, the subject is a fish. In some embodiments, the subject is a mammal. In some embodiments, the mammal is a human. In some embodiments, the mammal is a dog. In some embodiments, the mammal is a cat. In some embodiments, the mammal is livestock. In some embodiments, the livestock is selected from the group consisting of cattle, sheep, goats, swine, poultry, bovine, and equine animals. In some embodiments, the subject is an invertebrate. In some embodiments, the invertebrate is an insect. In some embodiments, the invertebrate is a plant.

Combination Therapy

In certain instances, the compound of Formula (I), (Ia), (II), (IIa), (IIb), (IIc), (II'), (II"), (III), (IIIa), or (III-B) or a pharmaceutically acceptable salt, solvate, or stereoisomer thereof, is administered in combination with a second therapeutic agent.

In some embodiments, the benefit experienced by a subject is increased by administering one of the compounds described herein with a second therapeutic agent (which also includes a therapeutic regimen) that also has therapeutic benefit.

In one specific embodiment, a compound of Formula (I), (Ia), (II), (IIa), (IIb), (IIc), (II'), (II"), (III), (IIIa), or (III-B) or a pharmaceutically acceptable salt, solvate, or stereoisomer thereof, is co-administered with a second therapeutic agent, wherein the compound of Formula (I), (Ia), (II), (IIa), (IIb), (IIc), (II'), (II"), (III), (IIIa), or (III-B) or a pharmaceutically acceptable salt, solvate, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the subject is simply additive of the two therapeutic agents or the subject experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (Ia), (II), (IIa), (IIb), (IIc), (II'), (II"), (III), (IIIa), or (III-B) or a pharmaceutically acceptable salt, solvate, or stereoisomer thereof, is initiated prior to, during, or after treatment with a second agent described herein, and continues until any time during treatment with the second agent or after termination of treatment with the second agent. It also includes treatments in which a compound of Formula (I), (Ia), (II), (IIa), (IIb), (IIc), (II'), (II"), (III), (IIIa), or (III-B) or a pharmaceutically acceptable salt, solvate or stereoisomer thereof, and the second agent being use din combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), (Ia), (II), (IIa), (IIb), (IIc), (II'), (II"), (III), (IIIa), or (III-B) or a pharmaceutically acceptable salt, solvate, or stereoisomer thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In certain embodiments, the second therapeutic agent is antifungal agent. In some embodiments, the second therapeutic agent is an antifungal agent selected from the group consisting of: a polyene antifungal agent, an azole antifungal agent, an allylamine antifungal agent, and an echinocandin antifungal agent.

In some embodiments, the polyene antifungal agent is selected from the group consisting of: Amphotericin B, Candicidin, Filipin, Hamycin, Natamycin, Nystatin, and Rimocidin.

In some embodiments, the azole antifungal agent is selected from the group consisting of: an imidazole, a triazole, and a thiazole. In some embodiments, the imidazole is selected from the group consisting of: Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, and Tioconazole. In some embodiments, the triazole is selected from the group consisting of: Albaconazole, Efinaconazole, Epoxiconazole, Fluconazole, Isavuconazole, Itraconazole, Posaconazole, Propiconazole, Ravuconazole, Terconazole, and Voriconazole. In some embodiments, the thiazole is Abafungin.

In some embodiments, the allylamine antifungal agent is selected from the group consisting of: Amorolfin, Butenafine, Nafufine, and Terbinafine.

In some embodiments, the echinocandin antifungal agent is selected from the group consisting of: Anidulafungin, Caspofungin, Micafungin and Rezafungin.

In some embodiments, are methods for treating a subject with a fungal disease comprising administering to the subject a combination treatment of a compound of Formula (I), (Ia), (II), (IIa), (IIb), (IIc), (II'), (II''), (III), (IIIa), or (III-B) or a pharmaceutically acceptable salt, solvate, or stereoisomer thereof, and fluconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), (Ia), (II), (IIa), (IIb), (IIc), (II'), (II''), (III), (IIIa), or (III-B) or a pharmaceutically acceptable salt, solvate, or stereoisomer thereof, and ketoconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), (Ia), (II), (IIa), (IIb), (IIc), (II'), (II''), (III), (IIIa), or (III-B) or a pharmaceutically acceptable salt, solvate, or stereoisomer thereof, and itraconazole, wherein the subject is selected from the group consisting of cattle, sheep, goats, swine, poultry, bovine, and equine animals.

EXAMPLES

Example 1: Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Intermediate A: Synthesis of di-tert-butyl [3-(3-chloromethyl-1,2-oxazol-5-yl)pyridin-2-yl]imidodicarbonate

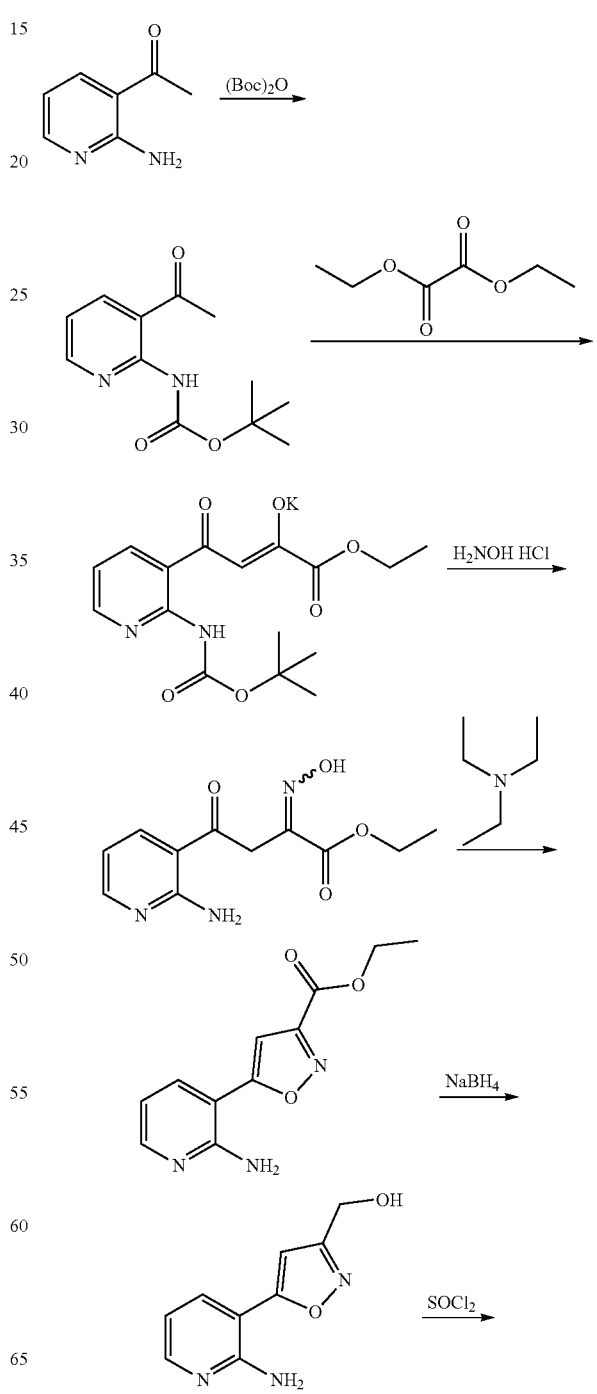

-continued

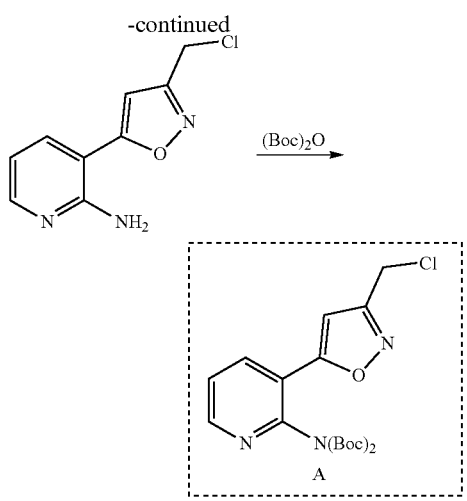

Step 1: tert-butyl (3-acetylpyridin-2-yl)carbamate 1-(2-Aminopyridin-3-yl)ethan-1-one (5 g, 37 mmol) was dissolved in tert-butyl alcohol (20 mL), and then di-tert-butyl dicarbonate (12 g) was added. The mixture was heated to 90° C. for 3 hours. The mixture was cooled to room temperature and evaporated under reduced pressure to give a dark-tan solid. The crude material was washed with a mixture of heptane and hexane, and then filtered. The solid was manually crushed, and again washed with heptane hexane. The solid was air-dried, then extensively vacuum-dried to give the title compound as a tan solid (7.8 g, 90%). This material was taken forward without further purification.

Step 2: Ethyl 5-(2-aminopyridin-3-yl)isoxazole-3-carboxylate

To a solution of tert-butyl (3-acetylpyridin-2-yl)carbamate (7.7 g, 33 mmol) and diethyl oxalate (8.9 mL, 65 mmol) in toluene (65 mL) was added potassium tert-butoxide (7.3 g, 65 mmol) portion-wise at room temperature. The dark-purple heterogeneous mixture was stirred under nitrogen and began to form a thick precipitate. An additional 65 mL of toluene was added, and the mixture was stirred for another 2 hours before adding an additional 3.7 g of potassium tert-butoxide. After stirring another 1 hour, ethanol (130 mL) was added followed by hydroxylamine hydrochloride (6.8 g, 98 mmol). The resulting burnt-orange-colored mixture was stirred for 2 hours, and then water (13 mL) was added. The solution briefly cleared somewhat, and then became a thick caramel-color. The mixture was stirred for 16 hours and gradually became a yellowish color. Another 400 mL of water was added and 500 mL of ethyl acetate. The layers were separated. The organic phase was washed with water (2×150 mL). The combined aqueous phase was extracted with ethyl acetate (2×250 mL). The combined organic phase was washed with brine, dried over sodium sulfate, and evaporated under reduced pressure to give an orange solid. To the solid product was added DMF (65 mL) and triethylamine (4.5 mL, 33 mmol). The solution was stirred at 80° C. for 6 hours, and then allowed to gradually reach room temperature overnight. Water (300 mL) was added and the solution was extracted with ethyl acetate, and then evaporated to give an orange oily solid. The crude material was treated with warm hexane/acetone (15:1) which resulted in a deep orange solution over a solid material. The solid was collected by filtering through a sintered glass funnel and washed with copious amounts of hexane. This gave the title compound as a free-flowing tannish pale-orange solid (4 g, 53%) which was taken forward without further purification.

Step 3: (5-(2-Aminopyridin-3-yl)isoxazol-3-yl)methanol

To a suspension of ethyl 5-(2-aminopyridin-3-yl)isoxazole-3-carboxylate (0.50 g, 2.1 mmol) in a 1:1 mixture of THF/ethanol (10 mL) at 0° C. was added sodium borohydride (0.24 g, 6.4 mmol) in portions. The cold bath was removed, and the mixture was stirred at room temperature for 19 hours with occasional monitoring by TLC. Another 0.5 equivalents of sodium borohydride (0.040 g, 1.0 mmol) was added to the mixture. After stirring briefly the mixture was quenched by pouring into ice followed by slow cautious addition of aqueous 5N HCl solution (2 mL)—vigorous reaction. The acidic solution (pH 3) was stirred for 10 min, then basified to pH 9 was aqueous 5N NaOH solution. The basic mixture was extracted three times with ethyl acetate. The combined organic phase was washed with brine, dried over sodium sulfate, and evaporated under reduced pressure to give the title compound as a yellow solid (0.32 g, 77%). This material was taken forward without further purification.

Step 4: 3-(3-Chloromethyl)isoxazol-5-yl)pyridin-2-amine

To a mixture of (5-(2-aminopyridin-3-yl)isoxazol-3-yl)methanol (0.31 g, 1.6 mmol) in N,N-dimethylacetamide (1.6 mL) at 0° C. was added a cold mixture of thionyl chloride (0.24 mL, 3.3 mmol) and benzotriazole (0.43 g, 3.6 mmol) in tetrahydrofuran. The cold bath was removed, and the mixture was stirred at room temperature. TLC after 30 min indicated complete reaction. The mixture was quenched by pouring into ice followed by basification to pH 8 with aqueous 5N NaOH. The mixture was then extracted three times with ethyl acetate. The combined organic phase was washed with brine, dried over sodium sulfate, and evaporated under reduced pressure to give the title compound as an oil which will be taken forward without further purification.

Step 5: Di-tert-butyl [3-(3-(chloromethyl)-1,2-oxazol-5-yl)pyridin-2-yl]imidodicarbonate To a solution of 3-(3-(chloromethyl)isoxazol-5-yl)pyridin-2-amine (0.34 g, 1.6 mmol, based on theoretical yield of previous reaction) in tetrahydrofuran was added N,N-dimethylaminopyridine (0.020 g, 0.16 mmol) and di-tert-butyl dicarbonate (0.75 g, 3.4 mmol). The homogeneous solution was stirred at room temperature and gradually changed color from orange to red. LCMS and TLC after 2 h suggested only partially completed conversion, and there was little improvement after 19 h. Another 0.6 equivalents of di-tert-butyl dicarbonate (0.20 g, 0.92 mmol) was added and the mixture stirred for another 2 h. The reaction was quenched with water and extracted three times with toluene. The combined organic phase was washed with diluted brine, dried over sodium sulfate, and evaporated under reduced pressure to give a red oil. The oil was further purified using Biotage normal-phase flash chromatography (50 g SNAP Ultra, 2-40% ethyl acetate in hexanes). The desired fractions were combined and evaporated to give the title compound as a white solid (0.53 g, 80% yield over two steps). 400 MHz $^1$H NMR (CDCl$_3$) δ 8.50 (dd, J=4.8, 1.8 Hz, 1H), 8.18 (dd, J=7.9, 1.8 Hz, 1H), 7.36 (dd, J=7.9, 4.8 Hz, 1H), 6.56 (s, 1H), 4.52 (s, 2H), 1.21 (s, 18H); 125 MHz $^{13}$C NMR (CDCl$_3$) δ 165.7, 161.6, 150.2, 150.0, 148.5, 136.6, 123.6, 121.5, 102.4, 83.5, 35.2, 27.6 ppm MS: 410.5 [M+H]$^+$.

Intermediate B: Synthesis of 3-(3-(4-(chloromethyl) benzyl)isoxazol-5-yl)pyridin-2-amine

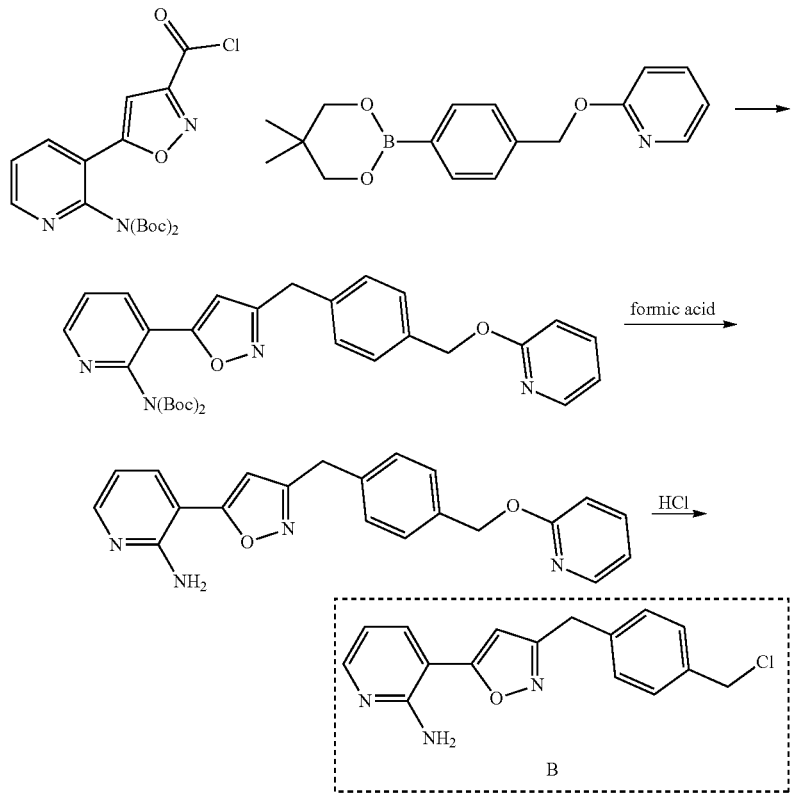

Di-tert-butyl [3-(3-(chloromethyl)-1,2-oxazol-5-yl)pyridin-2-yl]imidodicarbonate (Intermediate A, 1.00 g, 2.44 mmol) and 2-((4-(5,5-dimethyl-1,3,2-dioxaborinan-2-yl) benzyl)oxy)pyridine (0.87 g, 2.93 mmol) were mixed in DME (15 mL) in a sealable tube. A 2M solution of sodium carbonate in water (2.81 mL, 5.62 mmol) and palladium tetrakis triphenylphosphine (226 mg, 0.195 mmol) were added and the sealable tube was flushed with argon and sealed. The mixture was stirred for 4 h at 100° C. The cooled reaction mixture was poured into ethyl acetate (400 ml) and dried over Na$_2$SO$_4$, filtered and concentrated under reduced pressure. The residue was purified by column chromatography (SiO$_2$, hexane/ethyl acetate) to give the di-Boc protected coupling intermediate, to which was added formic acid (10 mL). The resulting mixture was stirred for 8 h at 21-25° C. to complete the di-Boc de-protection. The mixture was poured into ice-water (150 mL) containing K$_3$PO$_2$ (37 g) and then extracted with ethyl acetate (3×50 mL). The combined organic layers were washed with brine (30 mL), dried over Na$_2$SO$_4$, filtered and concentrated under reduced pressure to give the crude residue containing 3-(3-(4-((pyridin-2-yloxy)methyl)benzyl)isoxazol-5-yl)pyridin-2-amine. The residue was dissolved in dioxane (10 mL) and concentrated HCl (12M; 1 ml, 12 mmol) was added. The mixture was heated under reflux for 2 h. The cooled mixture was poured into an ice-cold pH 7 phosphate buffer solution (0.5M, 100 mL) containing an additional amount of NaOH (480 mg, 12 mmol) to neutralize the excess of HCl. The resulting mixture was extracted with ethyl acetate (3×50 mL). The combined organic layers were washed with brine (30 mL), dried over Na$_2$SO$_4$, filtered and concentrated under reduced pressure. The residue was purified by column chromatography (SiO$_2$, hexane/ethyl acetate) to yield 3-(3-(4-chloromethyl)benzyl)isoxazol-5-yl)pyridin-2-amine (280 mg, 0.93 mmol, 38% overall yield) as a white solid. 400 MHz $^1$H NMR (CDCl$_3$) δ 8.13 (dd, J=4.9, 1.8 Hz, 1H), 7.70 (dd, J=7.7, 1.8 Hz, 1H), 7.40-7.32 (m, 2H), 7.32-7.25 (m, 2H), 6.70 (dd, J=7.7, 4.9 Hz, 1H), 6.25 (s, 1H), 5.44 (s, 3H), 4.57 (s, 2H), 4.06 (s, 2H). MS: 300.4 [M+H]$^+$.

Intermediate C: Synthesis of 4-((5-(2-aminopyridin-3-yl)isoxazol-3-yl)methyl)phenol

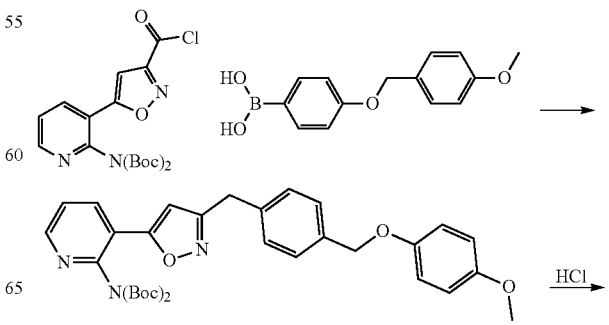

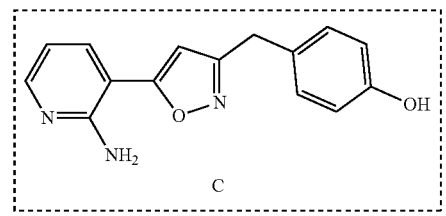

(4-((4-methoxybenzyl)oxy)phenyl)boronic acid (4.41 g, 17.08 mmol) was mixed with DME (70 mL) in a sealable tube. A 2M solution of sodium carbonate in water (14.64 mL, 29.28 mmol) was added followed by a solution of di-tert-butyl [3-(3-(chloromethyl)-1,2-oxazol-5-yl)pyridin-2-yl]imidodicarbonate (Intermediate A, 5.00 g, 12.20 mmol) in DME (10 mL). Palladium tetrakis triphenylphosphine (1.27 g, 1.10 mmol) was added and the sealable tube was flushed with argon and sealed. The mixture was stirred for 3 h at 90° C. The cooled reaction mixture was poured into a stirring mixture of water (300 mL) and warm ethyl acetate (500 mL). The layers were separated the aqueous phase was further extracted with ethyl acetate (3×100 mL). The combined organic layers were washed with brine (50 mL), dried over Na$_2$SO$_4$, filtered and concentrated under reduced pressure. The residue was purified by column chromatography (SiO$_2$, hexane/ethyl acetate) to give the di-Boc protected coupling intermediate (6.00 g, 10.21 mmol), which was dissolved in dioxane (60 mL). To the resulting solution was added HCl (4M; 10 mL, 40 mmol) and the mixture was stirred for 3 h at 50° C. THF (100 mL) and toluene (100 mL) were added and the pH was adjusted to 6-7 by the addition of an aqueous solution of K$_3$PO$_4$. The layers were separated the aqueous phase was further extracted with a mixture ethyl acetate/THF/toluene=1:1:1 (3×100 mL). The combined organic layers were dried over Na$_2$SO$_4$, filtered and concentrated under reduced pressure. The residue was purified by column chromatography (SiO$_2$, hexane/ethyl acetate) to yield 4-((5-(2-aminopyridin-3-yl)isoxazol-3-yl)methyl)phenol (2.30 g, 8.60 mmol, 84%) as a white solid. 400 MHz $^1$H NMR (DMSO-d6) δ 9.30 (s, 1H), 8.08 (dd, J=4.8, 1.8 Hz, 1H), 7.86 (dd, J=7.7, 1.9 Hz, 1H), 7.15-7.07 (m, 2H), 6.80-6.65 (m, 4H), 6.26 (s, 2H), 3.90 (s, 2H). MS: 268.4 [M+H]$^+$.

Intermediate D: Synthesis of 3-(3-(4-(aminomethyl)benzyl)isoxazol-5-yl)pyridin-2-amine

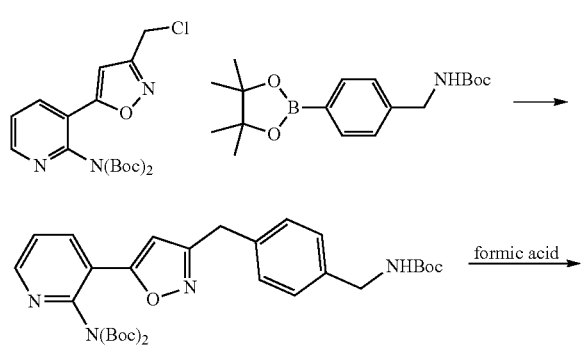

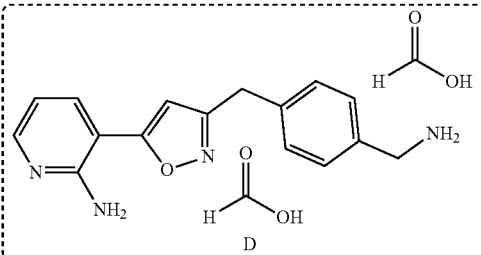

Di-tert-butyl [3-(3-(chloromethyl)-1,2-oxazol-5-yl)pyridin-2-yl]imidodicarbonate (Intermediate A, 1.35 g, 3.30 mmol) and tert-butyl (4-(4,4,5,5-tetramethyl-1,3,2-dioxaborolan-2-yl)benzyl)carbamate (1.00 g, 3.00 mmol) were mixed in DME (15 mL) in a sealable tube. A 2M solution of sodium carbonate in water (3.75 mL, 7.50 mmol) and palladium tetrakis triphenylphosphine (277 mg, 0.240 mmol) were added and the sealable tube was flushed with argon and sealed. The mixture was stirred for 4 h at 100° C. The cooled reaction mixture was poured into ethyl acetate (400 mL) and dried over Na$_2$SO$_4$, filtered and concentrated under reduced pressure. The residue was purified by column chromatograph (SiO$_2$, hexane/ethyl acetate) to give the Boc protected coupling intermediate to which was added formic acid (8 mL). The resulting mixture was stirred for 13 h at 21-25° C. to complete the global Boc de-protection, and then added dropwise to a rapidly stirring mixture of diethyl ether and hexane. The precipitated product in form of its formate salt was collected by filtration and dried under vacuum to yield 3-(3-(4-(aminomethyl)benzyl)isoxazol-5-yl)pyridin-2-amine formate (811 mg, 2.49 mmol, 83%) as a white solid. 500 MHz $^1$H NMR (DMSO-d6) δ 8.32 (s, 2H), 8.09 (dd, J=4.8, 1.8 Hz, 1H), 7.86 (dd, J=7.7, 1.8 Hz, 1H), 7.44-7.34 (m, 4H), 6.81 (s, 1H), 6.70 (dd, J=7.7, 4.8 Hz, 1H), 6.26 (s, 2H), 4.05 (s, 2H), 3.96 (s, 2H). MS: 281.4 [M+H]$^+$.

Intermediate E: Synthesis of 3-(3-((6-fluoropyridin-3-yl)methyl)isoxazol-5-yl)pyridin-2-amine

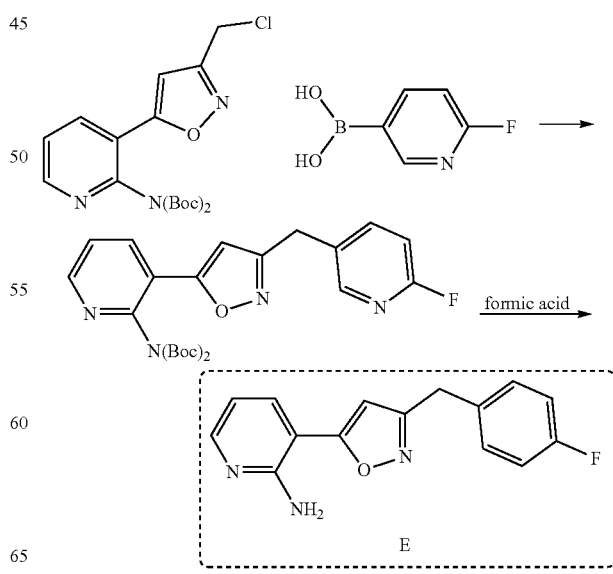

(6-fluoropyridin-3-yl)boronic acid (1.90 g, 13.48 mmol) was mixed with DME (50 mL) in a sealable tube. A 2M solution of sodium carbonate in water (11.24 mL, 22.48 mmol) was added followed by a solution of di-tert-butyl [3-(3-(chloromethyl)-1,2-oxazol-5-yl)pyridin-2-yl]imidodicarbonate (Intermediate A, 3.68 g, 8.99 mmol) in DME (6 mL). Palladium tetrakis triphenylphosphine (0.935 g, 0.809 mmol) was added and the sealable tube was flushed with argon and sealed. The mixture was stirred for 4 h at 90° C. The cooled reaction mixture was poured into ethyl acetate (500 mL), dried over Na$_2$SO$_4$, filtered and concentrated under reduced pressure. The residue was purified by column chromatography (SiO$_2$, hexane/ethyl acetate) to give the di-Boc protected coupling intermediate (2.10 g, 4.46 mmol), to which was added formic acid (10 mL). The resulting mixture was stirred for 13 h at 21-25° C. to complete the di-Boc de-protection. Ice-water (100 mL) and ethyl acetate (300 mL) were added and the pH was adjusted to 8-9 by the addition of 5N aqueous NaOH. The layers were separated and the aqueous phase was extracted with ethyl acetate (3×50 mL). The combined organic layers were washed with brine (30 mL), dried over Na$_2$SO$_4$, filtered and concentrated under reduced pressure. The residue was dissolved in ethyl acetate and the product was precipitated through the addition of hexane. The product was filtered and dried under vacuum to yield 3-(3-((6-fluoropyridin-3-yl)methyl)isoxazol-5-yl) pyridin-2-amine (1.06 g, 3.92 mmol, 44%) as a white solid. 500 MHz $^1$H NMR (DMSO-d6) δ 8.27-8.22 (m, 1H), 8.09 (dd, J=4.8, 1.9 Hz, 1H), 7.95 (td, J=8.2, 2.6 Hz, 1H), 7.87 (dd, J=7.7, 1.8 Hz, 1H), 7.16 (dd, J=8.4, 2.9 Hz, 1H), 6.85 (s, 1H), 6.70 (dd, J=7.7, 4.8 Hz, 1H), 6.27 (s, 2H), 4.11 (s, 2H). MS: 271.4 [M+H]$^+$.

Intermediate F: Synthesis of 4-((5-(2,6-diamino-pyridin-3-yl)isoxazol-3-yl)methyl)phenol

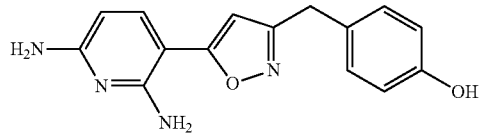 [SMILES: Nc1ccc(-c2cc(Cc3ccc(O)cc3)no2)c(N)n1]

3-(3-(4-(benzyloxy)benzyl)isoxazol-5-yl)pyridine-2,6 diamine (0.300 g, 0.806 mmol) and TFA (4.96 ml, 64.4 mmol) was added thioanisole (0.381 ml, 3.22 mmol) at room temperature and stirred for 2 hours. To the mixture was added a saturated sodium hydrogen carbon solution and was extracted with ethyl acetate. The organic phase was dried over sodium sulfate and concentrated under reduced pressure. The residue was purified by silica gel chromatography to give 4-((5-(2,6-diaminopyridin-3-yl)isoxazol-3-yl) methyl)phenol (0.170 g, 0.602 mmol, 74.8% yield). MS: 283.3 [M+H]$^+$.

Intermediate G: Synthesis of 3-(3-(4-(chloromethyl) benzyl)isoxazol-5-yl)pyridine-2,6-diamine

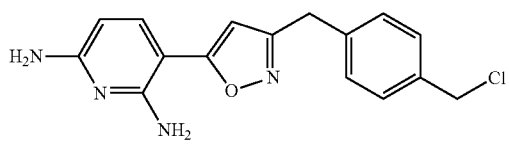 [SMILES: Nc1ccc(-c2cc(Cc3ccc(CCl)cc3)no2)c(N)n1]

3-(3-(4-((pyridin-2-yloxy)methyl)benzyl)isoxazol-5-yl) pyridine-2,6-diamine (0.100 g, 0.268 mmol) was dissolved in dioxane (1 mL) and added HCl (0.098 ml, 3.21 mmol). The mixture was heated at reflux for 2 hours. The cooled mixture was poured into ice cold buffer with pH 7 and neutralized with NaOH and then extracted with EtOAc. Organic solvents were removed under reduced pressure and the residue was purified using flash chromatography to give 3-(3-(4-(chloromethyl)benzyl)isoxazol-5-yl)pyridine-2,6-diamine (0.075 g, 0.238 mmol, 89% yield). MS: 315.7 [M+H]$^+$.

Intermediate H: Synthesis 3-(3-((2-fluoropyridin-4-yl)methyl)isoxazol-5-yl)pyridin-2-amine

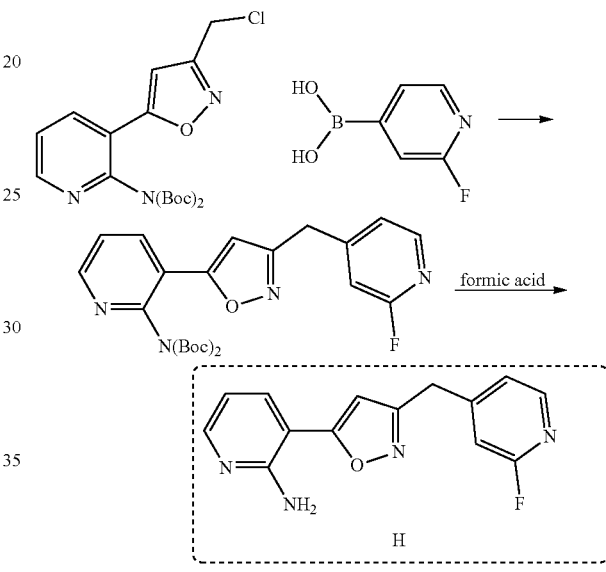

(2-fluoropyridin-4-yl)boronic acid (0.894 g, 6.34 mmol) was mixed with DME (25 mL) in a sealable tube. A 2M solution of sodium carbonate in water (7.32 mL, 14.64 mmol) was added followed by a solution of di-tert-butyl [3-(3-(chloromethyl)-1,2-oxazol-5-yl)pyridin-2-yl]imidodicarbonate (Intermediate A, 2.00 g, 4.88 mmol) in DME (4 mL). Palladium tetrakis triphenylphosphine (0.395 g, 0.342 mmol) was added and the sealable tube was flushed with argon and sealed. The mixture was stirred for 2 h at 90° C. The cooled reaction mixture was poured into ethyl acetate (200 mL), dried over Na$_2$SO$_4$, filtered and concentrated under reduced pressure. The residue was purified by column chromatography (SiO$_2$, hexane/ethyl acetate) to give the di-Boc protected coupling intermediate (1.050 g, 2.232 mmol), to which was added formic acid (6.1 mL). The resulting mixture was stirred for 18 h at 21-25° C. to complete the di-Boc de-protection. Ice-water (50 mL) and ethyl acetate (150 mL) were added and the pH was adjusted to 8-9 by the addition of 5N aqueous NaOH. The layers were separated and the aqueous phase was extracted with ethyl acetate (3×50 mL). The combined organic layers were washed with brine (30 mL), dried over Na$_2$SO$_4$, filtered and concentrated under reduced pressure. The residue was dissolved in ethyl acetate and the product was precipitated through the addition of hexane. The product was filtered and dried under vacuum to yield 3-(3-((6-fluoropyridin-3-yl) methyl)isoxazol-5-yl)pyridin-2-amine (0.515 g, 1.91 mmol, 41%) as a white solid. 500 MHz $^1$H NMR (DMSO-d6) δ 8.19 (d, J=5.1 Hz, 1H), 8.10 (dd, J=4.8, 1.8 Hz, 1H), 7.87 (dd, J=7.7, 1.8 Hz, 1H), 7.32 (dt, J=5.1, 1.7 Hz, 1H), 7.17 (s, 1H), 6.87 (s, 1H), 6.71 (dd, J=7.7, 4.8 Hz, 1H), 6.27 (s, 1H), 4.17 (s, 2H). MS 271.2 [M+H]$^+$.

Intermediate I: Synthesis of 3-(3-((6-fluoropyridin-2-yl)methyl)isoxazol-5-yl)pyridin-2-amine

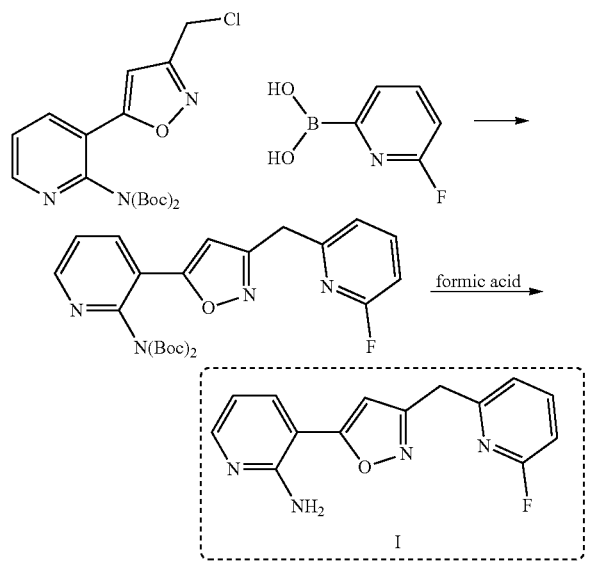

(6-fluoropyridin-2-yl)boronic acid (0.670 g, 4.76 mmol) was mixed with DME (20 mL) in a sealable tube. A 2M solution of sodium carbonate in water (5.49 mL, 10.98 mmol) was added followed by a solution of di-tert-butyl [3-(3-(chloromethyl)-1,2-oxazol-5-yl)pyridin-2-yl]imidodicarbonate (Intermediate A, 1.500 g, 3.66 mmol) in DME (2 mL). Palladium tetrakis triphenylphosphine (0.296 g, 0.256 mmol) was added and the sealable tube was flushed with argon and sealed. The mixture was stirred for 4 h at 90° C. The cooled reaction mixture was poured into ethyl acetate (200 mL), dried over Na$_2$SO$_4$, filtered and concentrated under reduced pressure. The residue was purified by column chromatography (SiO$_2$, hexane/ethyl acetate) to give the di-Boc protected coupling intermediate (0.900 g, 1.91 mmol), to which was added formic acid (5.5 mL). The resulting mixture was stirred for 18 h at 21-25° C. to complete the di-Boc de-protection. Ice-water (50 mL) and ethyl acetate (150 mL) were added and the pH was adjusted to 8-9 by the addition of 5N aqueous NaOH. The layers were separated and the aqueous phase was extracted with ethyl acetate (3×50 mL). The combined organic layers were washed with brine (30 mL), dried over Na$_2$SO$_4$, filtered and concentrated under reduced pressure. The residue was dissolved in ethyl acetate and the product was precipitated through the addition of hexane. The product was filtered and dried under vacuum to yield 3-(3-((6-fluoropyridin-2-yl)methyl)isoxazol-5-yl)pyridin-2-amine (0.440 g, 1.63 mmol, 44%) as a white solid. MS: 271.2 [M+H]$^+$.

Intermediate J: Synthesis of 3-(3-((5,6-difluoropyridin-3-yl)methyl)isoxazol-5-yl)pyridin-2-amine

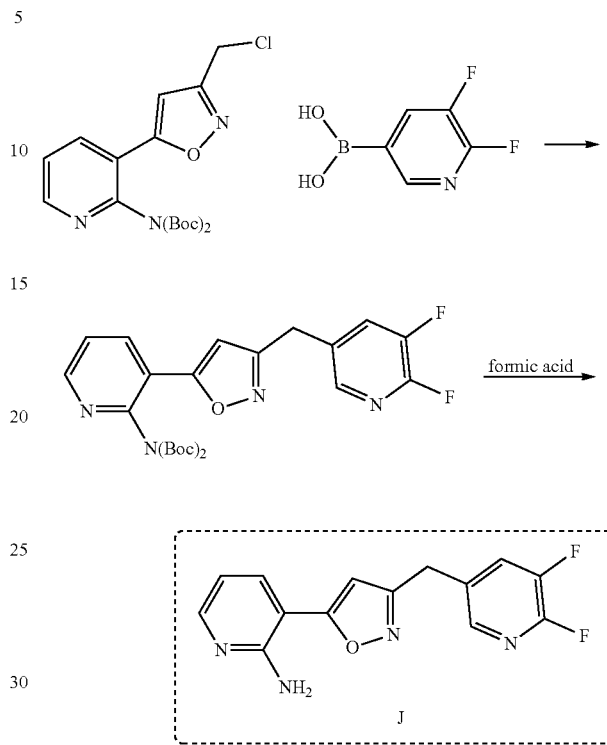

(5,6-difluoropyridin-3-yl)boronic acid (1.06 g, 6.65 mmol) and di-tert-butyl [3-(3-(chloromethyl)-1,2-oxazol-5-yl)pyridin-2-yl]imidodicarbonate (Intermediate A, 3.00 g, 7.32 mmol) were mixed with DME (25 mL) in a sealable tube. A 2M solution of sodium carbonate in water (8.32 mL, 16.64 mmol) was added followed by palladium tetrakis triphenylphosphine (0.54 g, 0.47 mmol). The sealable tube was flushed with argon and sealed. The mixture was stirred for 3 h at 90° C. The cooled reaction mixture was poured into ethyl acetate (500 mL), dried over Na$_2$SO$_4$, filtered and concentrated under reduced pressure. The residue was purified by column chromatography (SiO$_2$, hexane/ethyl acetate) to give the di-Boc protected coupling intermediate to which was added formic acid (8 mL). The resulting mixture was stirred for 13 h at 21-25° C. to complete the di-Boc de-protection. Toluene (100 mL) and acetonitrile (50 mL) were added and all volatiles were removed under reduced pressure. This addition/evaporation procedure was repeated three times to complete the removal of formic acid. Ethyl acetate was added and the precipitation of the product was completed by the addition of some hexane. The product was filtered off and dried under vacuum to yield 3-(3-((5,6-difluoropyridin-3-yl)methyl)isoxazol-5-yl)pyridin-2-amine (0.894 g, 3.10 mmol, 47% overall yield) as a white solid. 500 MHz $^1$H NMR (DMSO-d6) δ 8.12-8.01 (m, 3H), 7.86 (dd, J=7.6, 1.9 Hz, 1H), 6.87 (s, 1H), 6.70 (dd, J=7.7, 4.7 Hz, 1H), 6.28 (s, 2H), 4.15 (s, 2H). MS: 289.4 [M+H]$^+$.

Intermediate K: Synthesis of 4-((5-(2-aminopyridin-3-yl)isoxazol-3-yl)methyl)-2-fluorophenol

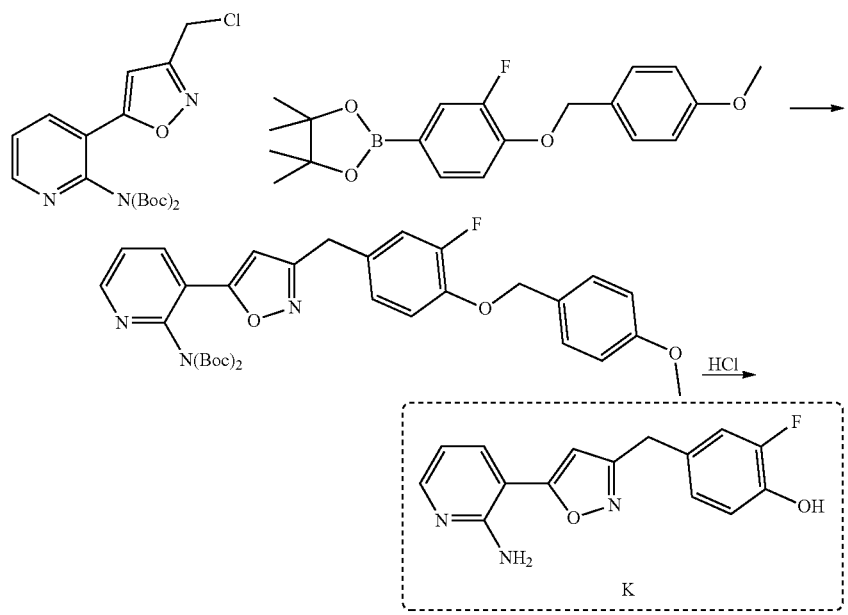

2-(3-fluoro-4-((4-methoxybenzyl)oxy)phenyl)-4,4,5,5-tetramethyl-1,3,2-dioxaborolane (6.29 g, 17.57 mmol) and di-tert-butyl [3-(3-(chloromethyl)-1,2-oxazol-5-yl)pyridin-2-yl]imidodicarbonate (Intermediate A, 6.00 g, 14.64 mmol) were mixed with DME (60 mL) in a sealable tube. A 2M solution of sodium carbonate in water (18.30 mL, 36.60 mmol) and palladium tetrakis triphenylphosphine (1.18 g, 1.03 mmol) were added and the sealable tube was flushed with argon and sealed. The mixture was stirred for 2 h at 90° C. The cooled reaction mixture was poured into a stirring mixture of water (300 mL) and warm ethyl acetate (500 mL). The layers were separated the aqueous phase was further extracted with ethyl acetate (3×100 mL). The combined organic layers were washed with brine (50 mL), dried over $Na_2SO_4$, filtered and concentrated under reduced pressure. The residue was purified by column chromatography ($SiO_2$, hexane/ethyl acetate) to give the di-Boc protected coupling intermediate, which was dissolved in dioxane (90 mL). To the resulting solution was added conc. HCl (12M; 6.28 mL, 75 mmol). The mixture was stirred at 55° C. for 2.5 h and then poured into a stirred mixture of a solution of sodium hydroxide (2.82 g, 70.6 mmol) in water (200 mL) and EtOAc (300 mL). Layers were separated and the aqueous phase was extracted with EtOAc (2×50 mL). The combined organic layers were dried over sodium sulfate and concentrated under reduced pressure. Before reaching complete dryness, the product started to precipitate out. At this point, ether (100 mL) was added and the product was collected by filtration to obtain 4-((5-(2-aminopyridin-3-yl)isoxazol-3-yl)methyl)-2-fluorophenol (2.18 g, 7.64 mmol, 52% overall yield) as a white powder. 500 MHz $^1$H NMR (DMSO-d6) δ 9.72 (s, 1H), 8.09 (dd, J=4.8, 1.8 Hz, 1H), 7.87 (dd, J=7.7, 1.8 Hz, 1H), 7.11 (dd, J=12.2, 2.0 Hz, 1H), 6.96-6.85 (m, 2H), 6.79 (s, 1H), 6.69 (dd, J=7.7, 4.8 Hz, 1H), 6.26 (s, 2H), 3.92 (s, 2H). MS: 296.4 [M+H]$^+$.

Intermediate L: Synthesis of 3-(3-((2-chloropyrimidin-5-yl)methyl)isoxazol-5-yl)pyridin-2-amine

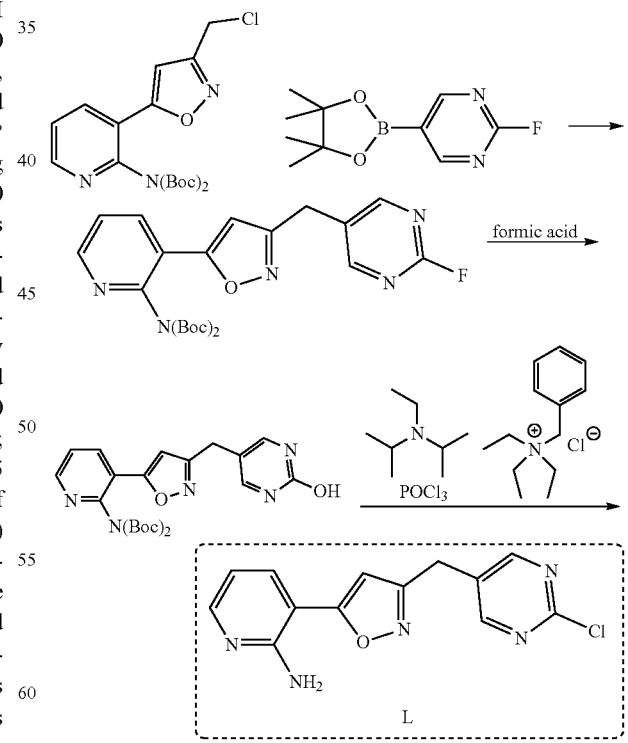

2-fluoro-5-(4,4,5,5-tetramethyl-1,3,2-dioxaborolan-2-yl)pyrimidine (1.00 g, 4.44 mmol) and di-tert-butyl [3-(3-(chloromethyl)-1,2-oxazol-5-yl)pyridin-2-yl]imidodicarbonate (Intermediate A, 2.00 g, 4.88 mmol) were mixed with DME (15 mL) in a sealable tube. A 2M solution of sodium carbonate in water (5.55 mL, 11.09 mmol) and palladium tetrakis triphenylphosphine (0.367 g, 0.31 mmol) were added and the sealable tube was flushed with argon and sealed. The mixture was stirred for 2 h at 95° C. The cooled reaction mixture was poured into ethyl acetate (500 mL), dried over Na₂SO₄, filtered and concentrated under reduced pressure. The residue was purified by column chromatography (SiO₂, hexane/ethyl acetate) to give the di-Boc protected coupling intermediate, to which was added formic acid (8 mL). The resulting mixture was stirred for 13 h at 21-25° C. to complete the di-Boc de-protection. During this step the fluoropyridine also completely hydrolyzed. Toluene (100 mL) and acetonitrile (50 mL) were added and all volatiles were removed under reduced pressure. This addition/evaporation procedure was repeated three times to complete the removal of formic acid and to obtain a solid residue of (5-((5-(2-aminopyridin-3-yl)isoxazol-3-yl)methyl)pyrimidin-2-ol (570 mg, 2.12 mmol). The residue was suspended in acetonitrile (2 mL). N-benzyl-N,N-diethylethanaminium chloride (237 mg, 1.04 mmol) and phosphoryl trichloride (0.58 mL, 6.24 mmol) were added, followed by the addition of N-ethyl-N-isopropylpropan-2-amine (0.71 mL, 4.16 mmol). The mixture was heated in a sealed tube at 90° C. for 20 h and then slowly added to a stirred solution of NaHCO₃ in water. Some ice was added to maintain a temperature around 30° C. After quenching was complete, the mixture was extracted with EtOAc. The combined organic layers were dried and concentrated under reduced pressure to obtain the crude product (3-(3-((2-chloropyrimidin-5-yl)methyl)isoxazol-5-yl)pyridin-2-amine (180 mg, 0.63 mmol, 13% overall yield)) as a solid, which was directly used in the following experiments without further purification. 500 MHz ¹H NMR (DMSO-d6) δ 8.80 (s, 2H), 8.10 (dd, J=4.8, 1.9 Hz, 1H), 7.86 (dd, J=7.7, 1.9 Hz, 1H), 6.89 (s, 1H), 6.71 (dd, J=7.7, 4.8 Hz, 1H), 6.28 (s, 2H), 4.15 (s, 2H). MS: 287.9 [M+H]⁺.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes.

Example 1: Synthesis 3-(3-(4-(1H-pyrazol-1-yl)methyl)benzyl)isoxazol-5-yl)pyridin-2-amine

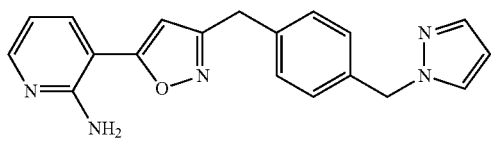 [SMILES: Nc1ncccc1-c1cc(Cc2ccc(Cn3cccn3)cc2)no1]

A solution of 1H-pyrazole (91 mg, 1.33 mmol) in NMP (0.5 mL) was added to a suspension of sodium hydride (60% w/mineral oil, 40 mg, 1.00 mmol) in NMP (1 mL). After stirring for 20 min at 21-25° C., a solution of 3-(3-(4-(chloromethyl)benzyl)isoxazol-5-yl)pyridin-2-amine (Intermediate B, 100 mg, 0.33 mmol) in NMP (1 ml) was added and the mixture was stirred for 4 min at 60° C. The cooled reaction mixture was directly purified by column chromatography (SiO₂, hexane/ethyl acetate). Fractions containing the product were concentrated under reduced pressure and further purified by HPLC to yield 3-(3-(4-((1H-pyrazol-1-yl)methyl)benzyl)isoxazol-5-yl)pyridin-2-amine (75 mg, 0.23 mmol, 68%) as a white solid. 400 MHz ¹H NMR (CDCl₃) δ 8.12 (dd, J=4.9, 1.8 Hz, 1H), 7.68 (dd, J=7.7, 1.8 Hz, 1H), 7.54 (d, J=1.8 Hz, 1H), 7.39 (dd, J=2.3, 0.7 Hz, 1H), 7.29-7.21 (m, 2H), 7.21-7.13 (m, 2H), 6.689 (dd, J=7.7, 4.9 Hz, 1H), 6.31-6.20 (m, 2H), 5.42 (s, 2H), 5.30 (s, 2H), 5.30 (s, 2H), 4.03 (s, 2H). MS: 332.2 [M+H]⁺.

Example 2: Synthesis of 2-(4-((5-(2-aminopyridin-3-yl)isoxazol-3-yl)methyl)phenyl)acetonitrile

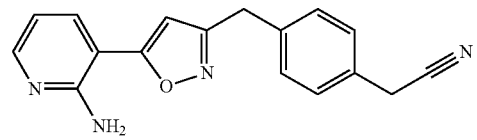 [SMILES: N#CCc1ccc(Cc2cc(-c3cccnc3N)on2)cc1]

Potassium cyanide (209 mg, 3.20 mmol) was added to PEG 400 (1.5 ml) and carefully ground to a fine suspension using a glass rod. 3-(3-(4-(chloromethyl)benzyl)isoxazol-5-yl)pyridin-2-amine (Intermediate B, 120 mg, 0.40 mmol) was added and the mixture was stirred for 30 min at 80° C. To the cooled reaction mixture was added to water (50 mL), and then extracted with ethyl acetate (3×30 mL). The combined organic layers were washed with brine (20 mL), dried over Na₂SO₄, filtered and concentrated under reduced pressure. The residue was purified by column chromatography (SiO₂, hexane/ethyl acetate) to yield 2-(4-((5-(2-aminopyridin-3-yl)isoxazol-3-yl)methyl)phenyl)acetonitrile (102 mg, 0.35 mmol, 88%) as a white solid. 400 MHz ¹H NMR (CDCl₃) δ 8.09 (dd, J=4.9, 1.8 Hz, 1H), 7.65 (dd, J=7.7, 1.8 Hz, 1H), 7.26 (m, 4H), 6.66 (dd, J=7.7, 4.9 Hz, 1H), 6.20 (s, 1H), 5.38 (s, 2H), 4.01 (s, 2H), 3.69 (s, 2H). MS: 291.2 [M+H]⁺.

Example 3: Synthesis of 1-(4-((5-(2-aminopyridin-3-yl)isoxazol-3-yl)methyl)benzyl)-1H-pyrazole-4-carbonitrile

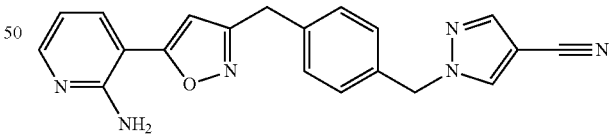

3-(3-(4-(chloromethyl)benzyl)isoxazol-5-yl)pyridin-2-amine (Intermediate B, 80 mg, 0.27 mmol) and 1H-pyrazole-4-carbonitrile (99 mg, 1.07 mmol) were dissolved in NMP (1 ml). Potassium 2-methylpropane-2-olate (1M in THF, 0.80 mL, 0.80 mmol) was added and the mixture was stirred for 5 min at 60° C. The cooled reaction mixture was directly purified by column chromatography (SiO₂, hexane/ethyl acetate). Fraction containing the product were concentrated under reduced pressure and further purified by HPLC to yield 1-(4-((5-(2-aminopyridin-3-yl)isoxazol-3-yl)methyl)benzyl)-1H-pyrazole-4-carbonitrile (66 mg, 0.19 mmol, 69%) as a white solid. 400 MHz ¹H NMR (CDCl₃)

δ 8.13 (dd, J=5.0, 1.8 Hz, 1H), 7.79 (dd, J=18.1, 0.7 Hz, 2H), 7.69 (dd, J=7.7, 1.8 Hz, 1H), 7.35-7.25 (m, 2H), 7.27-7.17 (m, 2H), 6.70 (dd, J=7.7, 4.8 Hz, 1H), 6.25 (s, 1H), 5.43 (s, 2H), 5.30 (s, 2H), 4.05 (s, 2H). MS: 357.3 [M+H]⁺.

Example 4: Synthesis 3-(3-(4-((4-fluoro-1H-pyrazol-1-yl)methyl)benzyl)isoxazol-5-yl)pyridin-2-amine

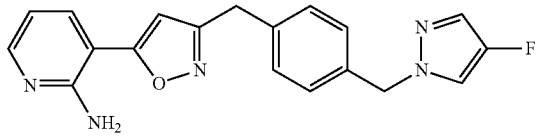 [SMILES: Nc1ncccc1-c1cc(Cc2ccc(Cn3cc(F)cn3)cc2)no1]

3-(3-(4-(chloromethyl)benzyl)isoxazol-5-yl)pyridin-2-amine (Intermediate B, 80 mg, 0.27 mmol) and 4-fluoro-1H-pyrazole (92 mg, 1.07 mmol) were dissolved in NMP (1 ml). Potassium 2-methylpropane-2-olate (1M in THF, 0.80 mL, 0.80 mmol) was added and the mixture was stirred for 5 min at 60° C. The cooled reaction mixture was directly purified by column chromatography (SiO₂, hexane/ethyl acetate). Fraction containing the product were concentrated under reduced pressure and further purified by HPLC to yield 3-(3-(4-((4-fluoro-1H-pyrazol-1-yl)methyl)benzyl)isoxazol-5-yl)pyridin-2-amine (75 mg, 0.22 mmol, 80%) as a white solid. 400 MHz ¹H NMR (CDCl₃) δ 8.14 (s, 1H), 7.79 (dd, J=7.7, 1.7 Hz, 1H), 7.35 (dd, J=4.3, 0.8 Hz, 1H), 7.31-7.13 (m, 5H), 6.70 (dd, J=7.7, 4.7 Hz, 1H), 6.24 (s, 1H), 5.43 (s, 2H), 5.18 (s, 2H), 4.04 (s, 2H). MS: 350.3 [M+H]⁺.

Example 5: Synthesis of 3-(3-(4-((4-(trifluoromethyl)-1H-pyrazol-1-yl)methyl)benzyl)isoxazol-5-yl)pyridin-2-amine

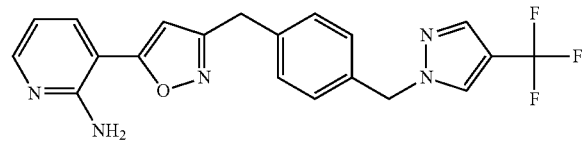 [SMILES: Nc1ncccc1-c1cc(Cc2ccc(Cn3cc(C(F)(F)F)cn3)cc2)no1]

3-(3-(4-(chloromethyl)benzyl)isoxazol-5-yl)pyridin-2-amine (Intermediate B, 80 mg, 0.27 mmol) and 4-(trifluoromethyl)-1H-pyrazole (145 mg, 1.07 mmol) were dissolved in NMP (1 ml). Potassium 2-methylpropane-2-olate (1M in THF, 0.80 mL, 0.80 mmol) was added and the mixture was stirred for 5 min at 60° C. The cooled reaction mixture was directly purified by column chromatography (SiO₂, hexane/ethyl acetate). Fraction containing the product were concentrated under reduced pressure and further purified by HPLC to yield 3-(3-(4-((4-(trifluoromethyl)-1H-pyrazol-1-yl)methyl)benzyl)isoxazol-5-yl)pyridin-2-amine (75 mg, 0.19 mmol, 70%) as a white solid. 400 MHz ¹H NMR (CDCl₃) δ 8.14 (d, J=3.7 Hz, 1H), 7.73 (s, 1H), 7.69 (dd, J=7.7, 1.8 Hz, 1H), 7.64 (s, 1H), 7.30 (d, J=8.2 Hz, 2H), 7.22 (d, J=8.2 Hz, 2H), 6.70 (dd, J=7.7, 4.9 Hz, 1H), 6.25 (s, 1H), 5.43 (s, 2H), 5.29 (s, 2H), 4.05 (s, 2H). MS: 400.3 [M+H]⁺.

Example 6: Synthesis of N-(4-((5-(2-aminopyridin-3-yl)isoxazol-3-yl)methyl)benzyl)-1,2,4-thiadiazol-5-amine

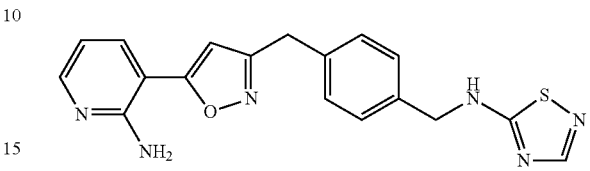

3-(3-(4-(Chloromethyl)benzyl)isoxazol-5-yl)pyridin-2-amine (Intermediate B, 0.10 g, 0.33 mmol) and 1,2,4-thiadiazol-5-amine (0.17 g, 1.7 mmol) were dissolved in tetrahydrofuran. Diisopropylethylamine (0.14 mL, 0.80 mmol) was added and the homogeneous amber-colored solution was stirred at room temperature. After 3 hours an additional 2 equivalents of 1,2,4-thiadiazol-5-amine (0.070 g, 0.66 mmol) and another 1.2 equivalents of diisopropylethylamine (0.070 mL, 0.40 mmol) were added. The mixture was heated at 60° C. for 72 hours. The mixture was cooled to room temperature and extracted three times with ethyl acetate. The organic phase was washed with brine, dried over sodium sulfate and evaporated under reduced pressure. The obtained residue was purified using Biotage reverse phase flash chromatography (12 g C18 SNAP, 5-95% acetonitrile in water with 0.1% formic acid). The desired fraction was lyophilized to give the title compound as a white solid (2.0 mg, 0.0051 mmol, 2%). MS: 365.2 [M+H]⁺.

Example 7: Synthesis of N-(4-((5-(2-aminopyridin-3-yl)isoxazol-3-yl)methyl)benzyl)-1H-pyrrolo[2,3-b]pyridin-5-amine

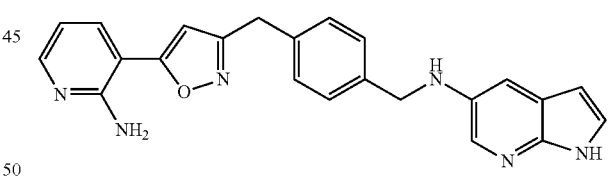

3-(3-(4-(Chloromethyl)benzyl)isoxazol-5-yl)pyridin-2-amine (Intermediate B, 0.10 g, 0.33 mmol) and 1H-pyrrolo[2,3-b]pyridin-5-amine (0.22 g, 1.7 mmol), were dissolved in tetrahydrofuran. Diisopropylethylamine (0.14 mL, 0.80 mmol) was added and the heterogenous mixture was stirred at room temperature for 3 hours, and then heated at 60° C. for 72 hours. The mixture was cooled to room temperature and extracted three times with ethyl acetate. The organic phase was washed with brine, dried over sodium sulfate and evaporated under reduced pressure. The obtained residue was purified using Biotage reverse phase flash chromatography (12 g C18 SNAP, 5-95% acetonitrile in water with 0.1% formic acid). The desired fraction was lyophilized to give the title compound as a white solid (20 mg, 0.051 mmol, 15%). MS: 397.3 [M+H]⁺.

Example 8: Synthesis of 3-(3-(4-benzylbenzyl) isoxazol-5-yl)pyridin-2-amine

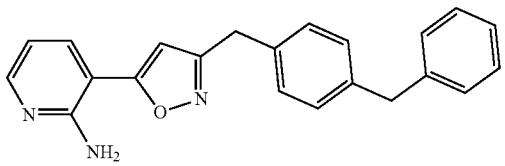

Phenylboronic acid (61 mg, 0.50 mmol) and 3-(3-(4-(chloromethyl)benzyl)isoxazol-5-yl)pyridin-2-amine (Intermediate B, 100 mg, 0.33 mmol) were mixed in DME (4 mL) in a sealable tube. A 2M solution of sodium carbonate in water (0.45 mL, 0.90 mmol) and palladium tetrakis triphenylphosphine (27 mg, 0.023 mmol) were added and the sealable tube was flushed with argon and sealed. The mixture was stirred for 2 h at 90° C. The cooled reaction mixture was poured into ethyl acetate and dried over $Na_2SO_4$, filtered and concentrated under reduced pressure. The residue was purified by column chromatography ($SiO_2$, hexane/ethyl acetate) to yield 3-(3-(4-benzylbenzyl)isoxazol-5-yl)pyridin-2-amine (84 mg, 0.25 mmol, 74%) as a white solid. 400 MHz $^1$H NMR (CDCl$_3$) δ 8.16-8.10 (m, 1H), 7.69 (dd, J=7.7, 1.7 Hz, 1H), 7.33-7.12 (m, 9H), 6.69 (dd, J=7.7, 4.8 Hz, 1H), 6.24 (s, 1H), 5.40 (s, 2H), 4.01 (s, 2H), 3.96 (s, 2H). MS: 342.2 [M+H]$^+$.

Example 9: Synthesis of 3-(3-(4-(pyridin-3-ylmethyl)benzyl)isoxazol-5-yl)pyridin-2-amine

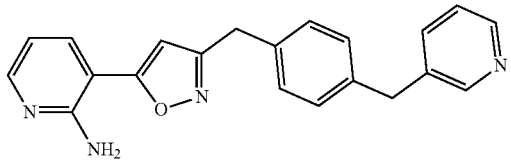

The title compound was prepared according to the procedure described in Example 8 using pyridin-3-ylboronoic acid (61.5 mg, 0.50 mmol) to yield 3-(3-(4-(pyridin-3-ylmethyl)benzyl)isoxazol-5-yl)pyridin-2-amine (64 mg, 0.19 mmol, 56%) as a white solid. 400 MHz $^1$H NMR (CDCl$_3$) δ 8.52 (s, 2H), 8.06 (d, J=4.1 Hz, 1H), 7.73 (dd, J=7.7, 1.7 Hz, 1H), 7.52 (d, J=7.7 Hz, 2H), 7.30-7.24 (m, 1H), 7.22 (d, J=8.1 Hz, 2H), 7.14 (d, J=8.1 Hz, 2H), 6.70 (dd, J=7.7, 4.9 Hz, 1H), 6.26 (s, 1H), 5.94 (s, 2H), 4.03 (s, 2H), 3.97 (s, 2H). MS: 343.2 [M+H]$^+$.

Example 10: Synthesis of 3-(3-(4-((1H-pyrazol-4-yl)methyl)benzyl)isoxazol-5-yl)pyridin-2-amine

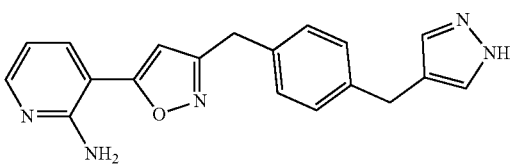 [SMILES: Nc1ncccc1-c1cc(Cc2ccc(Cc3cn[nH]c3)cc2)no1]

The title compound was prepared according to the procedure described in Example 8 using (1H-pyrazol-4-yl) boronic acid (56.0 mg, 0.50 mmol) and heating for 14 h at 90° C. to yield 3-(3-(4-((1H-pyrazol-4-yl)methyl)benzyl) isoxazol-5-yl)pyridin-2-amine (40 mg, 0.12 mmol, 36%) as a white solid. MS: 332.3 [M+H]$^+$.

Example 11: Synthesis of 3-(3-(4-((1-methyl-1H-pyrazol-4-yl)methyl)benzyl)isoxazol-5-yl)pyridin-2-amine

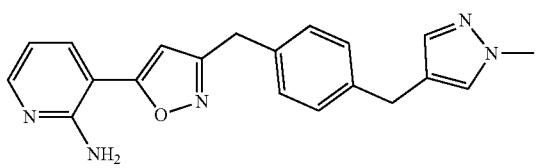 [SMILES: Cn1cc(Cc2ccc(Cc3cc(-c4cccnc4N)on3)cc2)cn1]

The title compound was prepared according to the procedure described in Example 8 using (1-methyl-1H-pyrazol-4-yl)boronic acid (633.0 mg, 0.50 mmol) to yield 3-(3-(4-((1-methyl-1H-pyrazol-4-yl)methyl)benzyl)isoxazol-5-yl) pyridin-2-amine (60 mg, 0.16 mmol, 52%) as a white solid. MS: 346.2 [M+H]$^+$.

Example 12: Synthesis of 3-(3-(4-((1-ethyl-1H-pyrazol-4-yl)methyl)benzyl)isoxazol-5-yl)pyridin-2-amine

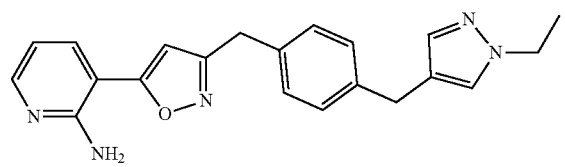

The title compound was prepared according to the procedure described in Example 8 using (1-ethyl-1H-pyrazol-4-yl)boronic acid (70.0 mg, 0.50 mmol) to yield 3-(3-(4-((1-ethyl-1H-pyrazol-4-yl)methyl)benzyl)isoxazol-5-yl) pyridin-2-amine (76 mg, 0.21 mmol, 63%) as a white solid. MS: 360.3 [M+H]$^+$.

Example 13: Synthesis of 3-(3-(4-([1,2,4]triazolol[1,5-a]pyridin-6-ylmethyl)benzyl)isoxazol-5-yl)pyridin-2-amine

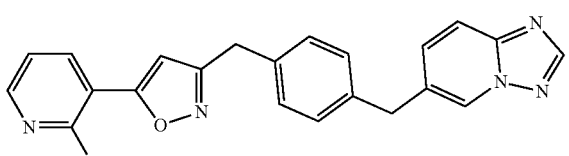

The title compound was prepared according to the procedure described in Example 8 using 6-(4,4,5,5-tetramethyl-1,3,2-dioxaborolan-2-yl)-[1,2,4]triazolo[1,5-a]pyridine (180 mg, 0.73 mmol) to yield 3-(3-(4-([1,2,4]triazolo[1,5-a]pyridin-6-ylmethyl)benzyl)isoxazol-5-yl)pyridin-2-amine (85 mg, 0.22 mmol, 61%) as a white solid. MS: 383.3 [M+H]⁺.

Example 14: Synthesis of 3-(3-(4-(isoxazol-4-ylmethyl)benzyl)isoxazol-5-yl)pyridin-2-amine

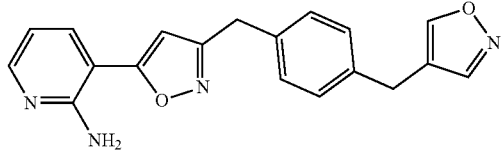 [SMILES: Nc1ncccc1-c1cc(Cc2ccc(Cc3cnoc3)cc2)no1]

The title compound was prepared according to the procedure described in Example 8 using isoxazol-4-yl)boronic acid (56.5 mg, 0.50 mmol) to yield 3-(3-(4-(isoxazol-4-ylmethyl)benzyl)isoxazol-5-yl)pyridin-2-amine (76 mg, 0.23 mmol, 69%) as a white solid. MS: 333.2 [M+H]⁺.

Example 15: Synthesis of 3-(3-(4-((6-fluoropyridin-2-yl)methyl)benzyl)isoxazol-5-yl)pyridin-2-amine

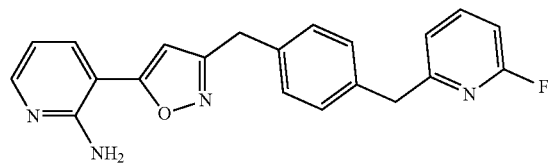

The title compound was prepared according to the procedure described in Example 8 using (6-fluoropyridin-2-yl) boronic acid (70.5 mg, 0.50 mmol) to yield 3-(3-(4-((6-fluoropyridin-2-yl)methyl)benzyl)isoxazol-5-yl)pyridin-2-amine (82 mg, 0.23 mmol, 68%) as a white solid. 500 MHz ¹H NMR (DMSO-d6) δ 8.08 (dd, J=4.8, 1.8 Hz, 1H), 7.93-7.83 (m, 2H), 7.29-7.20 (m, 5H), 6.97 (dd, J=8.1, 2.6 Hz, 1H), 6.80 (s, 1H), 6.69 (dd, J=7.7, 4.8 Hz, 1H), 6.24 (s, 2H), 4.01 (s, 2H), 3.99 (s, 2H). MS: 361.4 [M+H]⁺.

Example 16: Synthesis of 3-(3-(4-((1-isobutyl-1H-pyrazol-4-yl)methyl)benzyl)isoxazol-5-yl)pyridin-2-amine

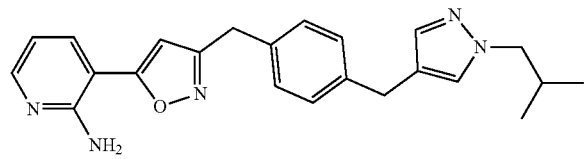 [SMILES: CC(C)Cn1cc(Cc2ccc(Cc3cc(-c4cccnc4N)on3)cc2)cn1]

The title compound was prepared according to the procedure described in Example 8 using (1-isobutyl-1H-pyrazol-4-yl)boronic acid (95.0 mg, 0.57 mmol) to yield 3-(3-(4-((1-isobutyl-1H-pyrazol-4-yl)methyl)benzyl)isoxazol-5-yl)pyridin-2-amine (72 mg, 0.19 mmol, 56%) as a white solid. MS: 388.3 [M+H]⁺.

Example 17: Synthesis of 3-(3-(4-(cyclopent-1-en-1-ylmethyl)benzyl)isoxazol-5-yl)pyridin-2-amine

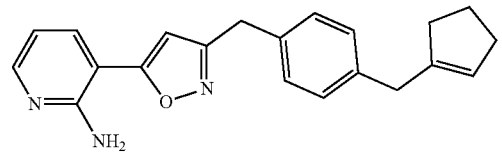 [SMILES: Nc1ncccc1-c1cc(Cc2ccc(CC3=CCCC3)cc2)no1]

The title compound was prepared according to the procedure described in Example 8 using cyclopent-1-en-1-yl) boronic acid (63.5 mg, 0.57 mmol) to yield 3-(3-(4-(cyclopent-1-en-1-ylmethyl)benzyl)isoxazol-5-yl)pyridin-2-amine (72 mg, 0.22 mmol, 65%) as a white solid. MS: 332.2 [M+H]⁺.

Example 18: Synthesis of 3-(3-(4-phenethylbenzyl)isoxazol-5-yl)pyridin-2-amine

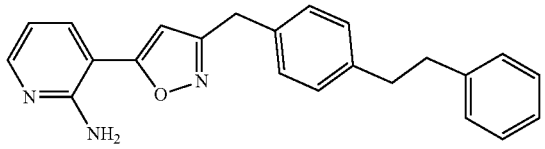 [SMILES: Nc1ncccc1-c1cc(Cc2ccc(CCc3ccccc3)cc2)no1]

The title compound was prepared according to the procedure described in Example 8 using (2-benzyl-4,4,5,5-tetramethyl-1,3,2-dioxaborolane (124 mg, 0.57 mmol) to yield 3-(3-(4-phenethylbenzyl)isoxazol-5-yl)pyridin-2-amine (41 mg, 0.12 mmol, 35%) as a white solid. MS: 356.2 [M+H]⁺.

Example 19: Synthesis of 3-(3-(4-((2-fluoropyridin-4-yl)methyl)benzyl)isoxazol-5-yl)pyridin-2-amine

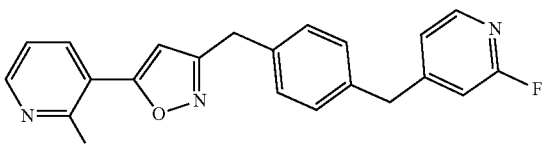

The title compound was prepared according to the procedure described in Example 8 using (2-fluoropyridin-4-yl) boronic acid (70.5 mg, 0.50 mmol) to yield 3-(3-(4-((2-fluoropyridin-4-yl)methyl)benzyl)isoxazol-5-yl)pyridin-2-amine (86 mg, 0.24 mmol, 72%) as a white solid. MS: 346.2 [M+H]⁺.

Example 20: Synthesis of 3-(3-(4-((2,3-difluoro-pyridin-4-yl)methyl)benzyl)isoxazol-5-yl)pyridin-2-amine

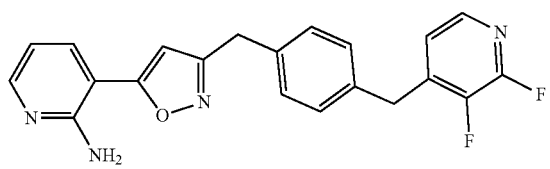 [SMILES: Nc1ncccc1-c1cc(Cc2ccc(Cc3ccnc(F)c3F)cc2)no1]

The title compound was prepared according to the procedure described in Example 8 using (2,3-difluoropyridin-4-yl)boronic acid (106 mg, 0.67 mmol) to yield 3-(3-(4-((2,3-difluoropyridin-4-yl)methyl)benzyl)isoxazol-5-yl)pyridin-2-amine (85 mg, 0.23 mmol, 67%) as a white solid. MS: 379.2 [M+H]$^+$.

Example 21: Synthesis of 3-(3-(4-(pyrimidin-5-ylmethyl)benzyl)isoxazol-5-yl)pyridin-2-amine

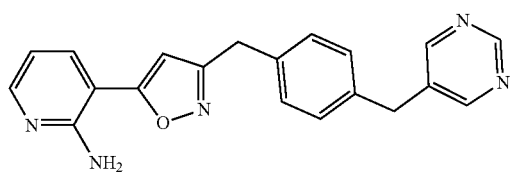 [SMILES: Nc1ncccc1-c1cc(Cc2ccc(Cc3cncnc3)cc2)no1]

The title compound was prepared according to the procedure described in Example 8 using pyrimidin-5-ylboronic acid (83.0 mg, 0.67 mmol) to yield 3-(3-(4-(pyrimidin-5-ylmethyl)benzyl)isoxazol-5-yl)pyridin-2-amine (78 mg, 0.23 mmol, 68%) as a white solid. MS: 344.3 [M+H]$^+$.

Example 22: Synthesis of (4-((5-(2-aminopyridin-3-yl)isoxazol-3-yl)methyl)phenyl)(phenyl)methanol

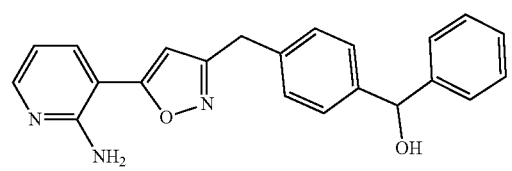 [SMILES: Nc1ncccc1-c1cc(Cc2ccc(C(O)c3ccccc3)cc2)no1]

Di-tert-butyl [3-(3-(chloromethyl)-1,2-oxazol-5-yl)pyridin-2-yl]imidodicarbonate (Intermediate A, 200 mg, 0.49 mmol) and (4-(hydroxy(phenyl)methyl)phenyl)boronic acid (122 mg, 0.54 mmol) were mixed in DME (4 mL) in a sealable tube. A 2M solution of sodium carbonate in water (0.56 mL, 1.12 mmol) and palladium tetrakis triphenylphosphine (45 mg, 0.039 mmol) were added and the sealable tube was flushed with argon and sealed. The mixture was stirred for 2 h at 100° C. The cooled reaction mixture was poured into ethyl acetate and dried over Na$_2$SO$_4$, filtered and concentrated under reduced pressure. The residue was purified by column chromatography (SiO$_2$, hexane/ethyl acetate) to give the di-Boc protected coupling product as a yellow oil to which was added formic acid (4 mL). This mixture was stirred for 3 h at 21-25° C. to complete the di-Boc de-protection. To this mixture was added dioxane (10 mL), ice and a 5M solution of NaOH in water until the pH of the resulting mixture was about 10-12. The mixture was stirred for 30 min at 21-25° C. to complete the hydrolysis of the formate ester on the hydroxyl group, which was formed during the di-Boc de-protection. The mixture was diluted with water (50 mL) and extracted with ethyl acetate (3×30 mL). The combined organic layers were washed with brine (20 mL), dried over Na$_2$SO$_4$, filtered and concentrated under reduced pressure. The residue was purified by column chromatography (SiO$_2$, hexane/ethyl acetate) to yield (4-((5-(2-aminopyridin-3-yl)isoxazol-3-yl)methyl)phenyl)(phenyl)methanol (75 mg, 0.21 mmol, 43%) as a white solid. MS: 358.2 [M+H]$^+$.

Example 23: Synthesis of 3-(3-(4-((cyclohexyloxy)methyl)benzyl)isoxazol-5-yl)pyridin-2-amine

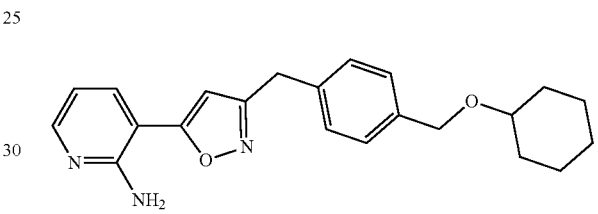

In a microwave vial was combined di-tert-butyl [3-(3-(chloromethyl)-1,2-oxazol-5-yl)pyridin-2-yl]imidodicarbonate (Intermediate A, 0.20 g, 0.48 mmol), (4-((cyclohexyloxy)methyl)phenyl)boronic acid (0.17 g, 0.73 mmol), cesium carbonate (0.48 g, 1.5 mmol), copper(I) iodide (0.0047 g, 0.024 mmol), [1,1'-bis(diphenylphosphino)ferrocene]dichloropalladium(II)dichloromethane complex (0.020 g, 0.024 mmol), and 1,2-dimethoxyethane (3 mL). The via was sealed and heated at 90° C. for 40 min under microwave irradiation. The mixture was filtered through Celite with ethyl acetate. The solvents were evaporated under reduced pressure and the residue was purified using Biotage flash chromatography (50 g SNAP, 2-75% acetone/hexane). Like fractions were combined and evaporated to give the desired di-BOC-protected intermediate. This material was dissolved in dichloromethane (10 mL) and treated with 4M hydrogen chloride in dioxane (3 mL). After stirring for 16 hours at room temperature, the mixture was diluted with water and basified with 5M aqueous sodium hydroxide solution to pH 13. The layers were separated, and the aqueous phase was extracted twice more with dichloromethane. The combined organic phase was washed with brine, dried over sodium sulfate, and evaporated under reduced pressure. The residue was purified using Biotage reverse phase flash chromatography (12 g C18 SNAP, 5-95% acetonitrile/water containing 0.1% Formic Acid). The desired fractions were combined and lyophilized to give the title compound as a white solid (0.055 g, 0.15 mmol, 31%). MS: 364.5 [M+H]$^+$.

Example 24: Synthesis of 3-(3-(4-((naphthalen-1-yloxy)methyl)benzyl)isoxazol-5-yl)pyridin-2-amine

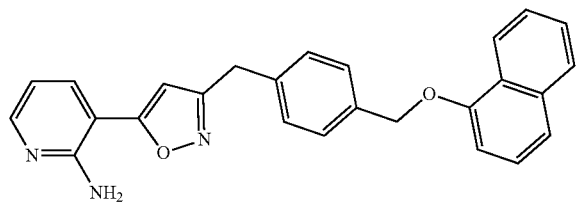 [SMILES: Nc1ncccc1-c1cc(Cc2ccc(COc3cccc4ccccc34)cc2)no1]

The title compound was prepared according to the procedure described in Example 23 using (4-((naphthalen-1-yloxy)methylphenyl)boronic acid (0.20 g, 0.73 mmol) to yield the title compound as a white solid. (0.056 g, 0.14 mmol, 29%). MS: 408.5 [M+H]$^+$.

Example 25: Synthesis of 3-(3-(4-(((4-chloronaphthalen-1-yl)oxy)methyl)benzyl)isoxazol-5-yl)pyridin-2-amine

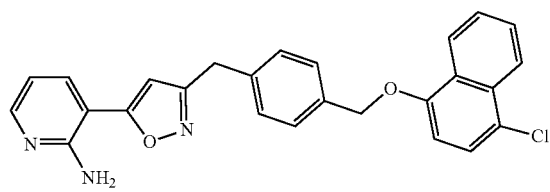 [SMILES: Nc1ncccc1-c1cc(Cc2ccc(COc3ccc(Cl)c4ccccc34)cc2)no1]

The title compound was prepared according to the procedure described in Example 23 using (4-(((4-chloronaphthalen-1-yl)oxy)methyl)phenyl)boronic acid (0.23 g, 0.73 mmol) to yield the title compound as a white solid (0.063 g, 0.14 mmol, 29%). MS: 442.4 [M+H]$^+$.

Example 26: Synthesis of 3-(3-(4-((5-methylisoxazol-3-yl)methoxy)benzyl)isoxazol-5-yl)pyridin-2-amine

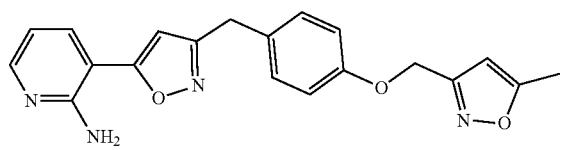 [SMILES: Cc1cc(COc2ccc(Cc3cc(-c4cccnc4N)on3)cc2)no1]

4-((5-(2-aminopyridin-3-yl)isoxazol-3-yl)methyl)phenol (Intermediate C, 80 mg, 0.30 mmol) was dissolved in DMF (1 mL) and potassium 2-methylpropane-2-olate (1M in THF, 0.33 mL, 0.33 mmol) was added dropwise. The mixture was stirred for 5 min and a solution of 3-(bromomethyl)-5-methylisoxazole (63.2 mg, 0.36 mmol) in DMF (0.5 mL) was added. The resulting mixture was stirred for 30 min and directly purified by column chromatography (SiO$_2$, hexane/ethyl acetate). Fraction containing the product were concentrated under reduced pressure and further purified by reversed phase flash chromatography (C18, acetonitrile/water) to yield 3-(3-(4-((1H-pyrazol-1-yl)methyl)benzyl)isoxazol-5-yl)pyridin-2-amine (71 mg, 0.20 mmol, 66%) as a white solid. 400 MHz $^1$H NMR (CDCl$_3$) δ 8.13 (s, 1H), 7.70 (dd, J=7.7, 1.8 Hz, 1H), 7.24-7.16 (m, 2H), 6.98-6.89 (m, 2H), 6.70 (dd, J=7.7, 4.8 Hz, 1H), 6.23 (s, 1H), 6.10 (d, J=1.1 Hz, 1H), 5.44 (s, 2H), 5.09 (s, 2H), 3.99 (s, 2H), 2.42 (d, J=0.9 Hz, 3H). MS: 363.3 [M+H]$^+$.

Example 27: Synthesis of 3-(3-(4-(quinolin-2-ylmethoxy)benzyl)isoxazol-5-yl)pyridin-2-amine

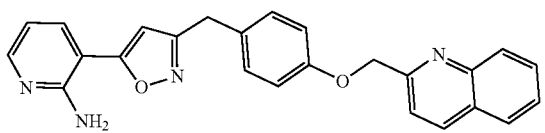 [SMILES: Nc1ncccc1-c1cc(Cc2ccc(OCc3ccc4ccccc4n3)cc2)no1]

The title compound was prepared according to the procedure described in Example 26 using (2-(chloromethyl)quinoline hydrochloride (83 mg, 0.39 mmol) and potassium 2-methylpropane-2-olate (1M in THF, 0.72 mL, 0.72 mmol) to yield 3-(3-(4-(quinolin-2-ylmethoxy)benzyl)isoxazol-5-yl)pyridin-2-amine (80 mg, 0.20 mmol, 66%) as a white solid. MS: 409.3 [M+H]$^+$.

Example 28: Synthesis of 3-(3-(4-(pyrimidin-2-ylmethoxy)benzyl)isoxazol-5-yl)pyridin-2-amine

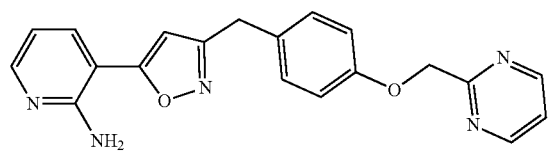 [SMILES: Nc1ncccc1-c1cc(Cc2ccc(OCc3ncccn3)cc2)no1]

The title compound was prepared according to the procedure described in Example 26 using 2-chloromethyl) pyrimidine hydrochloride (69 mg, 0.42 mmol) and potassium 2-methylpropane-2-olate (1M in THF, 0.75 mL, 0.75 mmol) to yield 3-(3-(4-(pyrimidin-2-ylmethoxy)benzyl)isoxazol-5-yl)pyridin-2-amine (56 mg, 0.16 mmol, 52%) as a white solid. MS: 360.3 [M+H]$^+$.

Example 29: Synthesis of 3-(3-(4-((5-methylpyrimidin-2-yl)methoxy)benzyl)isoxazol-5-yl)pyridin-2-amine

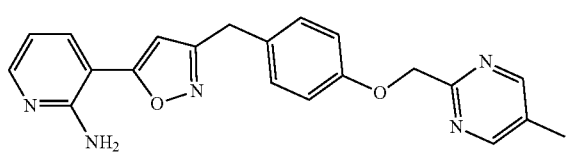 [SMILES: Cc1cnc(COc2ccc(Cc3cc(-c4cccnc4N)on3)cc2)nc1]

The title compound was prepared according to the procedure described in Example 26 using 2-chloromethyl)-5-methylpyrimidine hydrochloride (75 mg, 0.42 mmol) and potassium 2-methylpropane-2-olate (1M in THF, 0.75 mL, 0.75 mmol) to yield 3-(3-(4-((5-methylpyrimidin-2-yl)methoxy)benzyl)isoxazol-5-yl)pyridin-2-amine (79 mg, 0.21 mmol, 71%) as a white solid. MS: 374.3 [M+H]$^+$.

Example 30: Synthesis of 3-(3-(4-(quinoxalin-2-ylmethoxy)benzyl)isoxazol-5-yl)pyridin-2-amine

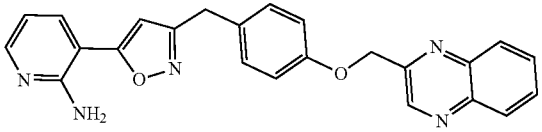 [SMILES: Nc1ncccc1-c1cc(Cc2ccc(OCc3cnc4ccccc4n3)cc2)no1]

The title compound was prepared according to the procedure described in Example 26 using 4-((5-(2-aminopyridin-3-yl)isoxazol-3-yl)methyl)phenol (Intermediate C, 90 mg, 0.34 mmol), 2-bromomethyl)quinoxaline (90 mg, 0.40 mmol) and potassium 2-methylpropane-2-olate (1M in THF, 0.34 mL, 0.34 mmol) to yield 3-(3-(4-(quinoxalin-2-ylmethoxy)benzyl)isoxazol-5-yl)pyridin-2-amine (73 mg, 0.18 mmol, 53%) as a white solid. MS: 410.3 [M+H]$^+$.

Example 31: Synthesis of N-(4-((5-(2-aminopyridin-3-yl)isoxazol-3-yl)methyl)benzyl-6-fluoropyridin-2-amine

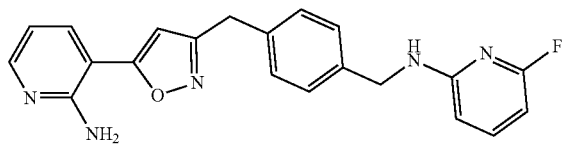

3-(3-(4-(aminomethyl)benzyl)isoxazol-5-yl)pyridin-2-amine diformate (Intermediate D, 80 mg, 0.22 mmol) was dissolved in DMSO (0.5 mL). N-ethyl-N-isopropylpropan-2-amine (83 mg, 0.65 mmol) and 2,6-difluoropyridine (148 mg, 1.29 mmol) were added and the mixture was stirred for 2 h at 120° C. The mixture was diluted with water (15 mL) and extracted with ethyl acetate (3×10 mL). The combined organic layers were washed with brine (10 mL), dried over Na$_2$SO$_4$, filtered and concentrated under reduced pressure. The residue was purified by column chromatography (SiO$_2$, hexane/ethyl acetate) to yield N-(4-((5-(2-aminopyridin-3-yl)isoxazol-3-yl)methyl)benzyl)-6-fluoropyridin-2-amine (47 mg, 0.13 mmol, 58%) as a white solid. 500 MHz $^1$H NMR (DMSO-d6) δ 8.08 (dd, J=4.8, 1.8 Hz, 1H), 7.86 (dd, J=7.7, 1.8 Hz, 1H), 7.52-7.40 (m, 2H), 7.28 (s, 4H), 6.79 (s, 1H), 6.69 (dd, J=7.7, 4.8 Hz, 1H), 6.35 (dd, J=8.0, 2.5 Hz, 1H), 6.25 (s, 2H), 6.08 (dd, J=7.6, 2.2 Hz, 1H), 4.38 (d, J=6.0 Hz, 2H), 4.00 (s, 2H). MS: 376.3 [M+H]$^+$.

Example 32: Synthesis of N-(4-((5-(2-aminopyridin-3-yl)isoxazol-3-yl)methyl)benzyl)pyrimidin-2-amine

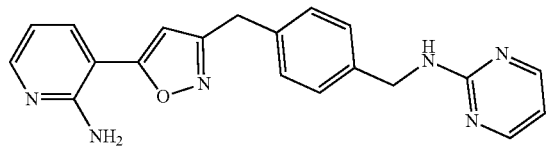 [SMILES: Nc1ncccc1-c1cc(Cc2ccc(CNc3ncccn3)cc2)no1]

The title compound was prepared according to the procedure described in Example 31 using 2-chloropyrimidine hydrochloride (148 mg, 1.29 mmol) to yield N-(4-((5-(2-aminopyridin-3-yl)isoxazol-3-yl)methyl)benzyl)pyrimidin-2-amine (45 mg, 0.17 mmol, 58%) as a white solid. MS: 359.2 [M+H]$^+$.

Example 33: Synthesis of N-(4-((5-(2-aminopyridin-3-yl)isoxazol-3-yl)methyl)benzyl)-2-methylpyrimidin-4-amine

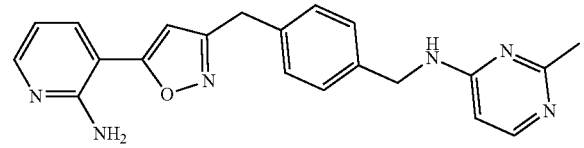 [SMILES: Cc1nccc(NCc2ccc(Cc3cc(-c4cccnc4N)on3)cc2)n1]

The title compound was prepared according to the procedure described in Example 31 using 4-chloro-2-methylpyrimidine (166 mg, 1.29 mmol) to yield N-(4-((5-(2-aminopyridin-3-yl)isoxazol-3-yl)methyl)benzyl)-2-methylpyrimidin-4-amine (41 mg, 0.11 mmol, 51%) as a slight yellow oil. MS: 373.2 [M+H]$^+$.

Example 34: Synthesis of N-(4-((5-(2-aminopyridin-3-yl)isoxazol-3-yl)methyl)benzyl)-4-chlorothiazol-2-amine

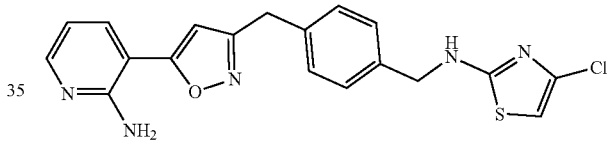

The title compound was prepared according to the procedure described in Example 31 using 2,4-dichlorothiazole (265 mg, 1.72 mmol) to yield N-(4-((5-(2-aminopyridin-3-yl)isoxazol-3-yl)methyl)benzyl)-4-chlorothiazol-2-amine (15 mg, 0.04 mmol, 18%) as a white solid. MS: 398.1 [M+H]$^+$.

Example 35: Synthesis of 3-(3-((6-(pyridin-2-ylmethoxy)pyridin-3-yl)methyl)isoxazol-5-yl)pyridin-2-amine

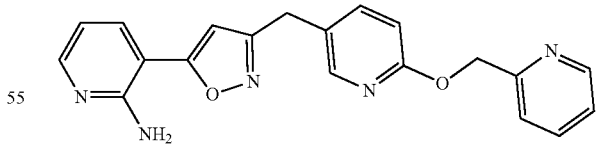

To a neat mixture of 3-(3-((6-fluoropyridin-3-yl)methyl)isoxazol-5-yl)pyridin-2-amine (Intermediate E, 50 mg, 0.19 mmol) and pyridin-2-ylmethanol (121 mg, 1.11 mmol) was added potassium 2-methylpropane-2-olate (1M in THF, 1.85 mL, 1.85 mmol) and the mixture was stirred for 30 min. The mixture was diluted with ice-water (15 mL) and the pH was adjusted to 8 using diluted HCl. The mixture was extracted with ethyl acetate (3×10 mL). The combined organic layers were washed with brine (10 mL), dried over Na$_2$SO$_4$, filtered and concentrated under reduced pressure. The residue was purified by column chromatography (SiO$_2$, hexane/ethyl acetate) to yield 3-(3-((6-(pyridin-2-ylmethoxy)pyridin-3-yl)methyl)isoxazol-5-yl)pyridin-2-amine (38 mg, 0.11 mmol, 57%) as a white solid. MS: 360.3 [M+H]$^+$.

Example 36: Synthesis of 3-(3-((6-(6-pyridin-3-ylmethoxy)pyridin-3-yl)methyl)isoxazol-5-yl)pyridin-2-amine

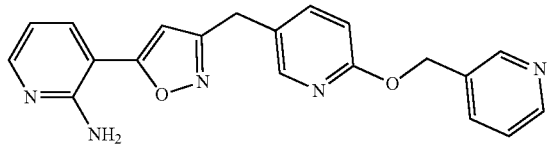 [SMILES: Nc1ncccc1-c1cc(Cc2ccc(OCc3cccnc3)nc2)no1]

To a neat mixture of 3-(3-((6-fluoropyridin-3-yl)methyl)isoxazol-5-yl)pyridin-2-amine (Intermediate E, 60 mg, 0.22 mmol) and pyridin-3-ylmethanol (242 mg, 2.22 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(pyridin-2-ylmethoxy)pyridin-3-yl)methyl)isoxazol-5-yl)pyridin-2-amine (19 mg, 0.052 mmol, 23%) as a white solid. MS: 360.2 [M+H]$^+$.

Example 37: Synthesis of 3-(3-((6-(pyridin-4-ylmethoxy)pyridin-3-yl)methyl)isoxazol-5-yl)pyridin-2-amine

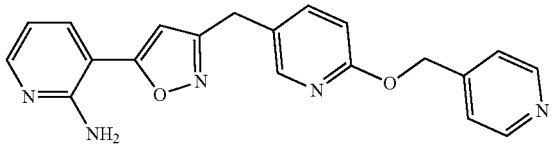

To a neat mixture of 3-(3-((6-fluoropyridin-3-yl)methyl)isoxazol-5-yl)pyridin-2-amine (Intermediate E, 60 mg, 0.22 mmol) and pyridin-3-ylmethanol (242 mg, 2.22 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(pyridin-4-ylmethoxy)pyridin-3-yl)methyl)isoxazol-5-yl)pyridin-2-amine (31 mg, 0.086 mmol, 39%) as a white solid. MS: 360.2 [M+H]$^+$.

Example 38: Synthesis of 3-(3-((6-((5-methylisoxazol-3-yl)methoxy)pyridin-3-yl)methyl)isoxazol-5-yl)pyridin-2-amine

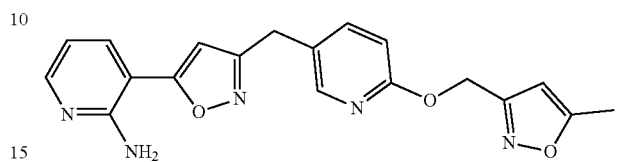

To a neat mixture of 3-(3-((6-fluoropyridin-3-yl)methyl)isoxazol-5-yl)pyridin-2-amine (Intermediate E, 60 mg, 0.22 mmol) and 5-methylisoxazol-3-yl)methanol (251 mg, 2.22 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((5-methylisoxazol-3-yl)methoxy)pyridin-3-yl)methyl)isoxazol-5-yl)pyridin-2-amine (62 mg, 0.171 mmol, 77%) as a white solid. MS: 364.1 [M+H]$^+$.

Example 39: Synthesis of 3-(3-((6-(2-(pyridin-2-yl)ethoxy)pyridin-3-yl)methyl)isoxazol-5-yl)pyridin-2-amine

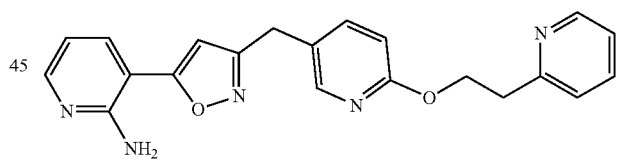

To a neat mixture of 3-(3-((6-fluoropyridin-3-yl)methyl)isoxazol-5-yl)pyridin-2-amine (Intermediate E, 60 mg, 0.22 mmol) and 2-(pyridin-2-yl)ethan-1-ol (273 mg, 2.22 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(2-(pyridin-2-yl)ethoxy)pyridin-3-yl)methyl)isoxazol-5-yl)pyridin-2-amine (6.4 mg, 0.017 mmol, 7.7%) as a white solid. MS: 374.1 [M+H]$^+$.

Example 40: Synthesis of 3-(3-((6-(thiophen-2-yl-methoxy)pyridin-3-yl)methyl)isoxazol-5-yl)pyridin-2-amine

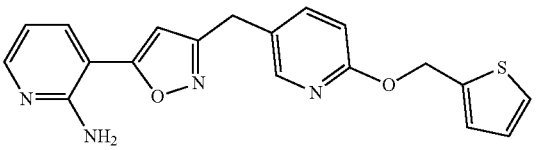 [SMILES: Nc1ncccc1-c1cc(Cc2ccc(OCc3cccs3)nc2)no1]

To a neat mixture of 3-(3-((6-fluoropyridin-3-yl)methyl)isoxazol-5-yl)pyridin-2-amine (Intermediate E, 50 mg, 0.19 mmol) and thiophen-2-ylmethanol (211 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(pyridin-2-ylmethoxy)pyridin-3-yl)methyl)isoxazol-5-yl)pyridin-2-amine (25 mg, 0.069 mmol, 37%) as a light yellow solid. MS: 365.1 [M+H]$^+$.

Example 41: Synthesis of 3-(3-((6-(thiazol-4-yl-methoxy)pyridin-3-yl)methyl)isoxazol-5-yl)pyridin-2-amine

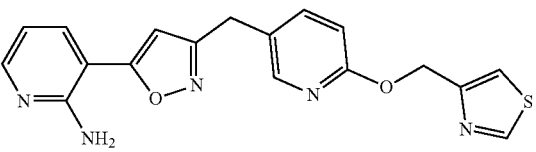 [SMILES: Nc1ncccc1-c1cc(Cc2ccc(OCc3cscn3)nc2)no1]

To a neat mixture of 3-(3-((6-fluoropyridin-3-yl)methyl)isoxazol-5-yl)pyridin-2-amine (Intermediate E, 50 mg, 0.19 mmol) and thiazol-4-ylmethanol (213 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(thiazol-4-ylmethoxy)pyridin-3-yl)methyl)isoxazol-5-yl)pyridin-2-amine (35 mg, 0.097 mmol, 52%) as a white solid. MS: 366.1 [M+H]$^+$.

Example 42: Synthesis of 3-(3-((6-(thiazol-2-yl-methoxy)pyridin-3-yl)methyl)isoxazol-5-yl)pyridin-2-amine

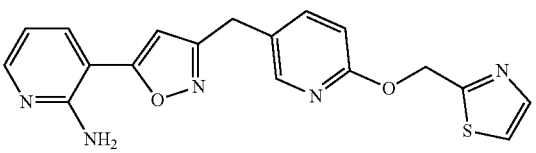 [SMILES: Nc1ncccc1-c1cc(Cc2ccc(OCc3nccs3)nc2)no1]

To a neat mixture of 3-(3-((6-fluoropyridin-3-yl)methyl)isoxazol-5-yl)pyridin-2-amine (Intermediate E, 50 mg, 0.19 mmol) and thiazol-2-ylmethanol (213 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(thiazol-2-ylmethoxy)pyridin-3-yl)methyl)isoxazol-5-yl)pyridin-2-amine (36 mg, 0.097 mmol, 53%) as a white solid. MS: 366.1 [M+H]$^+$.

Example 43: Synthesis of 3-(3-((6-(cyclopropyl-methoxy)pyridin-3-yl)methyl)isoxazol-5-yl)pyridin-2-amine

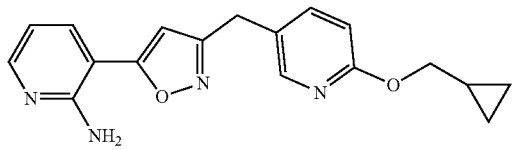 [SMILES: Nc1ncccc1-c1cc(Cc2ccc(OCC3CC3)nc2)no1]

To a neat mixture of 3-(3-((6-fluoropyridin-3-yl)methyl)isoxazol-5-yl)pyridin-2-amine (Intermediate E, 50 mg, 0.19 mmol) and cyclopropylmethanol (133 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(cyclopropylmethoxy)pyridin-3-yl)methyl)isoxazol-5-yl)pyridin-2-amine (38 mg, 0.097 mmol, 64%) as a white solid. 500 MHz $^1$H NMR (DMSO-d6) δ 8.12 (dd, J=2.5, 0.8 Hz, 1H), 8.09 (dd, J=4.8, 1.8 Hz, 1H), 7.86 (dd, J=7.7, 1.8 Hz, 1H), 7.64 (dd, J=8.5, 2.5 Hz, 1H), 6.92 (s, 1H), 6.78 (dd, J=8.5, 0.7 Hz, 1H), 6.69 (dd, J=7.7, 4.8 Hz, 1H), 6.26 (s, 2H), 4.06 (d, J=7.1 Hz, 2H), 3.98 (s, 2H), 1.27-1.18 (m, 1H), 0.58-0.48 (m, 2H), 0.35-0.24 (m, 2H). MS: 323.2 [M+H]$^+$.

Example 44: Synthesis of 3-(3-((6-(oxetan-3-yl-methoxy)pyridin-3-yl)methoyl)isoxazol-5-yl)pyridin-2-amine

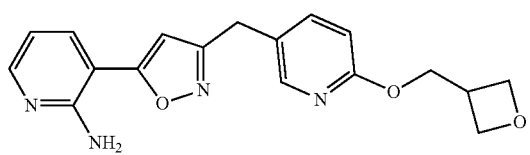 [SMILES: Nc1ncccc1-c1cc(Cc2ccc(OCC3COC3)nc2)no1]

To a neat mixture of 3-(3-((6-fluoropyridin-3-yl)methyl)isoxazol-5-yl)pyridin-2-amine (Intermediate E, 50 mg, 0.19 mmol) and pyridin-3-ylmethanol (196 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(oxetan-3-ylmethoxy)pyridin-3-yl)methyl)isoxazol-5-yl)pyridin-2-amine (11 mg, 0.031 mmol, 14%) as a white solid. MS: 339.3 [M+H]$^+$.

Example 45: Synthesis of 3-(3-((6-((1-methyl-1H-pyrazol-3-yl)methoxy)pyridin-3-yl)methyl)isoxazol-5-yl)pyridin-2-amine

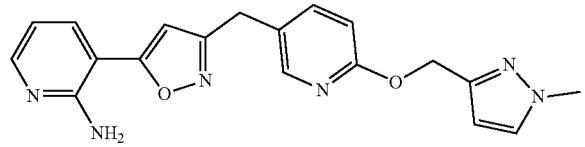 [SMILES: Cn1ccc(COc2ccc(Cc3cc(-c4cccnc4N)on3)cn2)n1]

To a neat mixture of 3-(3-((6-fluoropyridin-3-yl)methyl) isoxazol-5-yl)pyridin-2-amine (Intermediate E, 50 mg, 0.19 mmol) and 1-methyl-1H-pyrazol-3-yl-methanol (207 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((1-methyl-1H-pyrazol-3-yl)methoxy)pyridin-3-yl)methyl)isoxazol-5-yl)pyridin-2-amine (10 mg, 0.028 mmol, 15%) as a white solid. MS: 363.2 [M+H]$^+$.

Example 46: Synthesis of 3-(3-((6-(pyrimidin-2-ylmethoxy)pyridin-3-yl)methyl)isoxazol-5-yl)pyridin-2-amine

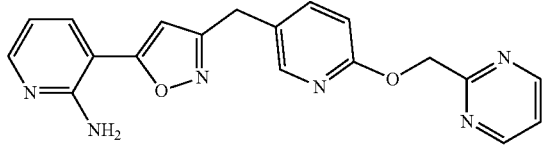 [SMILES: Nc1ncccc1-c1cc(Cc2ccc(OCc3ncccn3)nc2)no1]

To a neat mixture of 3-(3-((6-fluoropyridin-3-yl)methyl) isoxazol-5-yl)pyridin-2-amine (Intermediate E, 50 mg, 0.19 mmol) and pyrimidin-2-ylmethanol (204 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(pyrimidin-2-ylmethoxy)pyridin-3-yl)methyl)isoxazol-5-yl)pyridin-2-amine (21 mg, 0.058 mmol, 31%) as a white solid. MS: 361.2 [M+H]$^+$.

Example 47: Synthesis of 3-(3-((6-(pyrazin-2-ylmethoxy)pyridin-3-yl)methyl)isoxazol-5-yl)pyridin-2-amine

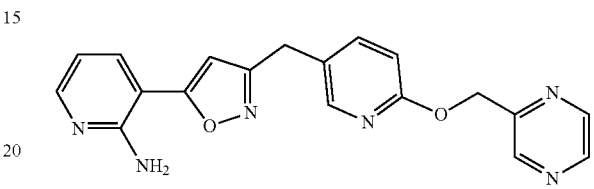

To a neat mixture of 3-(3-((6-fluoropyridin-3-yl)methyl) isoxazol-5-yl)pyridin-2-amine (Intermediate E, 50 mg, 0.19 mmol) and pyrazin-2-ylmethanol (204 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(pyrazin-2-ylmethoxy)pyridin-3-yl)methyl)isoxazol-5-yl)pyridin-2-amine (20 mg, 0.055 mmol, 30%) as a white solid. MS: 361.2 [M+H]$^+$.

Example 48: Synthesis of 3-(3-((6-(furan-3-ylmethoxy)pyridin-3-yl)methyl)isoxazol-5-yl)pyridin-2-amine

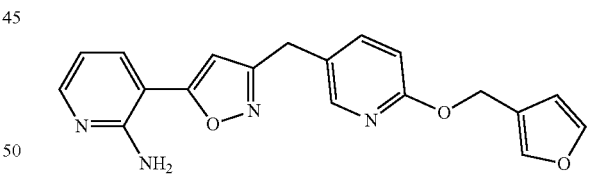

To a neat mixture of 3-(3-((6-fluoropyridin-3-yl)methyl) isoxazol-5-yl)pyridin-2-amine (Intermediate E, 50 mg, 0.19 mmol) and furan-3-ylmethanol (181 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(furan-3-ylmethoxy)pyridin-3-yl) methyl)isoxazol-5-yl)pyridin-2-amine (8.0 mg, 0.023 mmol, 12%) as a white solid. MS: 349.1 [M+H]$^+$.

Example 49: Synthesis of 3-(3-((6-((1-methyl-1H-pyrazol-4-yl)methoxy)pyridin-3-yl)methyl)isoxazol-5-yl)pyridin-2-amine

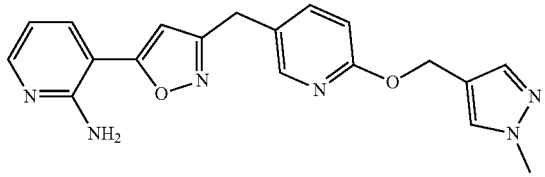 [SMILES: Cn1cc(COc2ccc(Cc3cc(-c4cccnc4N)on3)cn2)cn1]

To a neat mixture of 3-(3-((6-fluoropyridin-3-yl)methyl) isoxazol-5-yl)pyridin-2-amine (Intermediate E, 50 mg, 0.19 mmol) and 1-methyl-1H-pyrazol-4-yl-methanol (207 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((1-methyl-1H-pyrazol-4-yl)methoxy)pyridin-3-yl)methyl)isoxazol-5-yl)pyridin-2-amine (8.5 mg, 0.023 mmol, 13%) as a white solid. MS: 363.2 [M+H]$^+$.

Example 50: Synthesis of 3-(3-((6-((2-methylthiazol-4-yl)methoxy)pyridin-3-yl)methyl)isoxazol-5-yl)pyridin-2-amine

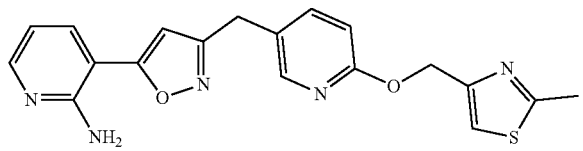

To a neat mixture of 3-(3-((6-fluoropyridin-3-yl)methyl) isoxazol-5-yl)pyridin-2-amine (Intermediate E, 50 mg, 0.19 mmol) and 2-methylthiazol-4-ylmethanol (213 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(2-methylthiazol-4-ylmethoxy) pyridin-3-yl)methyl)isoxazol-5-yl)pyridin-2-amine (25 mg, 0.67 mmol, 36%) as a white solid. MS: 380.1 [M+H]$^+$.

Example 51: Synthesis of 3-(3-((6-((5-fluoropyridin-2-yl)methoxy)pyridin-3-yl)methyl)isoxazol-5-yl)pyridin-2-amine

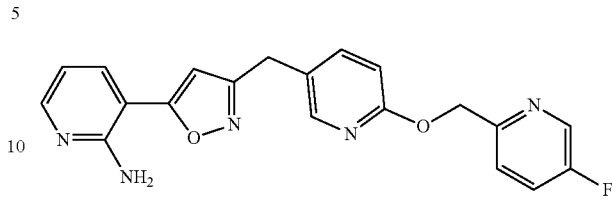

To a neat mixture of 3-(3-((6-fluoropyridin-3-yl)methyl) isoxazol-5-yl)pyridin-2-amine (Intermediate E, 50 mg, 0.19 mmol) and 5-fluoropyridin-2-yl)methanol (212 mg, 1.67 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((5-fluoropyridin-2-ylmethoxy) pyridin-3-yl)methyl)isoxazol-5-yl)pyridin-2-amine (21 mg, 0.056 mmol, 30%) as a white solid. MS: 378.0 [M+H]$^+$.

Example 52: Synthesis of 3-(3-((6-((2-methylfuran-3-yl)methoxy)pyridin-3-yl)methyl)isoxazol-5-yl)pyridin-2-amine

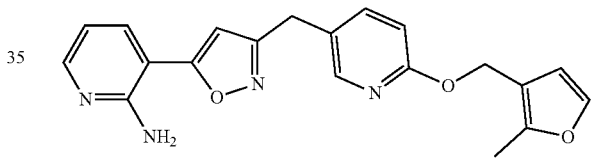

To a neat mixture of 3-(3-((6-fluoropyridin-3-yl)methyl) isoxazol-5-yl)pyridin-2-amine (Intermediate E, 50 mg, 0.19 mmol) and 2-methylfuran-3-ylmethanol (124 mg, 1.11 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(2-methylfuran-3-ylmethoxy) pyridin-3-yl)methyl)isoxazol-5-yl)pyridin-2-amine (15 mg, 0.040 mmol, 22%) as a white solid. MS: 362.8 [M+H]$^+$.

Example 53: Synthesis of 3-(3-((6-(oxazol-2-ylmethoxy)pyridin-3-yl)methyl)isoxazol-5-yl)pyridin-2-amine

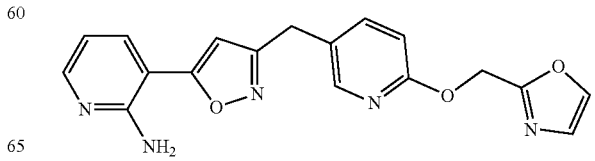

To a neat mixture of 3-(3-((6-fluoropyridin-3-yl)methyl)isoxazol-5-yl)pyridin-2-amine (Intermediate E, 50 mg, 0.19 mmol) and oxazol-2-ylmethanol (128 mg, 1.30 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(oxazol-2-ylmethoxy)pyridin-3-yl)methyl)isoxazol-5-yl)pyridin-2-amine (25 mg, 0.072 mmol, 39%) as a white solid. MS: 350.0 [M+H]$^+$.

Example 54: Synthesis of 3-(3-((6-((3-fluoropyridin-4-yl)methoxy)pyridin-3-yl)methyl)isoxazol-5-yl)pyridin-2-amine

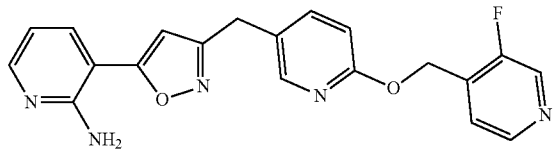 [SMILES: Nc1ncccc1-c1cc(Cc2ccc(OCc3ccncc3F)nc2)no1]

To a neat mixture of 3-(3-((6-fluoropyridin-3-yl)methyl)isoxazol-5-yl)pyridin-2-amine (Intermediate E, 50 mg, 0.19 mmol) and 3-fluoropyridin-2-yl)methanol (235 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3-fluoropyridin-2-ylmethoxy)pyridin-3-yl)methyl)isoxazol-5-yl)pyridin-2-amine (40 mg, 0.11 mmol, 57%) as a white solid. MS: 378.2 [M+H]$^+$.

Example 55: Synthesis of 3-(3-((6-(1-(pyridin-2-yl)ethoxy)pyridin-3-yl)methyl)isoxazol-5-yl)pyridin-2-amine

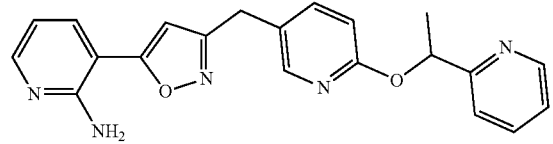 [SMILES: CC(Oc1ccc(Cc2cc(-c3cccnc3N)on2)cn1)c1ccccn1]

To a neat mixture of 3-(3-((6-fluoropyridin-3-yl)methyl)isoxazol-5-yl)pyridin-2-amine (Intermediate E, 60 mg, 0.1229 mmol) and 1-(pyridin-2-yl)ethan-1-ol (164 mg, 1.33 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(1-(pyridin-2-ethoxy)pyridin-3-yl)methyl)isoxazol-5-yl)pyridin-2-amine (32 mg, 0.086 mmol, 39%) as a white solid. MS: 374.1 [M+H]$^+$.

Example 56: Synthesis of 3-(3-((6-(1-(2-fluorophenyl)ethoxy)pyridin-3-yl)methyl)isoxazol-5-yl)pyridin-2-amine

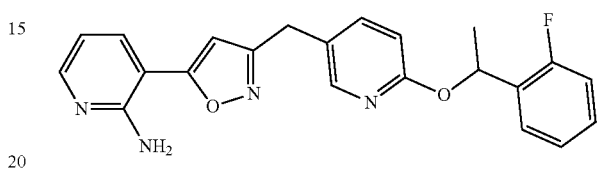

To a neat mixture of 3-(3-((6-fluoropyridin-3-yl)methyl)isoxazol-5-yl)pyridin-2-amine (Intermediate E, 50 mg, 0.19 mmol) and 1-(2-fluorophenyl)ethan-1-ol (207 mg, 1.48 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(1-(2-fluorophenyl)ethoxy)pyridin-3-yl)methyl)isoxazol-5-yl)pyridin-2-amine (30 mg, 0.078 mmol, 42%) as a white solid. MS: 391.3 [M+H]$^+$.

Example 57: Synthesis of 3-(3-((6-(cyclobutylmethoxy)pyridin-3-yl)methyl)isoxazol-5-yl)pyridin-2-amine

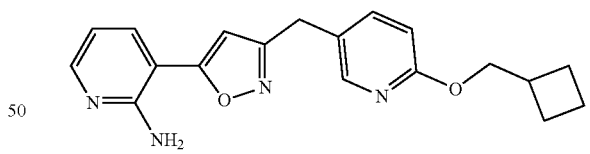

To a neat mixture of 3-(3-((6-fluoropyridin-3-yl)methyl)isoxazol-5-yl)pyridin-2-amine (Intermediate E, 50 mg, 0.19 mmol) and cyclobutylmethanol (159 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(cyclobutylmethoxy)pyridin-3-yl)methyl)isoxazol-5-yl)pyridin-2-amine (30 mg, 0.089 mmol, 48%) as a white solid. MS: 337.4 [M+H]$^+$.

Example 58: Synthesis of 5-((5-(2-aminopyridin-3-yl)isoxazol-3-yl)methyl)-N-phenylpyridin-2-amine

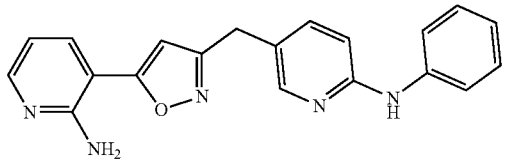

To a neat mixture of 3-(3-((6-fluoropyridin-3-yl)methyl)isoxazol-5-yl)pyridin-2-amine (Intermediate E, 50 mg, 0.19 mmol) and aniline (172 mg, 1.85 mmol) was added potassium 2-methylpropane-2-olate (1M in THF, 1.85 mL, 1.85 mmol) and the mixture was stirred for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 5-((5-(2-aminopyridin-3-yl)methyl)-N-phenylpyridin-2-amine (4.8 mg, 0.014 mmol, 7.6% as an orange solid. MS: 344.1 [M+H]$^+$.

Example 59: Synthesis of 5-((5-(2-aminopyridin-3-yl)isoxazol-3-yl)methyl)-N-(3-fluorophenyl)pyridin-2-amine

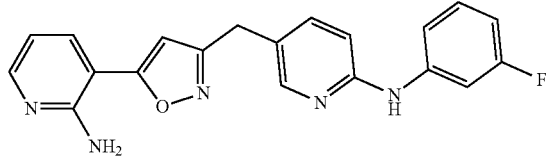

To a neat mixture of 3-(3-((6-fluoropyridin-3-yl)methyl)isoxazol-5-yl)pyridin-2-amine (Intermediate E, 50 mg, 0.19 mmol) and 3-fluoroaniline (206 mg, 1.85 mmol) was added potassium 2-methylpropane-2-olate (1M in THF, 1.85 mL, 1.85 mmol) and the mixture was stirred for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 5-((5-(2-aminopyridin-3-yl)isoxazol-3-yl)methyl)-N-(3-fluorophenyl)pyridin-2-amine (8.0 mg, 0.022 mmol, 12%) as a light orange solid. MS: 362.3 [M+H]$^+$.

Example 60: Synthesis of 5-((5-(2-aminopyridin-3-yl)isoxazol-3-yl)methyl)-N-(2-fluorophenyl)pyridin-2-amine

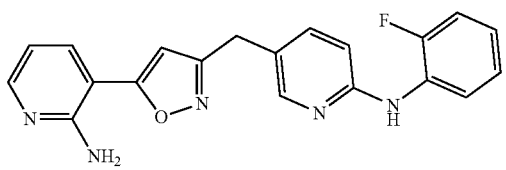

To a neat mixture of 3-(3-((6-fluoropyridin-3-yl)methyl)isoxazol-5-yl)pyridin-2-amine (Intermediate E, 50 mg, 0.19 mmol) and 2-fluoroaniline (206 mg, 1.85 mmol) was added potassium 2-methylpropane-2-olate (1M in THF, 1.85 mL, 1.85 mmol) and the mixture was stirred for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 5-((5-(2-aminopyridin-3-yl)isoxazol-3-yl)methyl)-N-(3-fluorophenyl)pyridin-2-amine (18 mg, 0.048 mmol, 26% as a pink solid. 500 MHz $^1$H NMR (formic acid-salt, DMSO-d6) δ 9.07 (s, 1H), 8.20 (dd, J=7.7, 1.7 Hz, 1H), 8.13 (dd, J=5.6, 1.7 Hz, 1H), 8.11 (d, J=2.4 Hz, 1H), 8.03 (td, J=8.3, 1.7 Hz, 1H), 7.64 (dd, J=8.7, 2.4 Hz, 1H), 7.25 (ddd, J=11.6, 8.1, 1.4 Hz, 1H), 7.16 (td, J=8.3, 1.7 Hz, 1H), 7.64 (dd, J=8.7, 2.4 Hz, 1H), 7.25 (ddd, J=11.6, 8.1, 1.4 Hz, 1H), 7.16 (td, J=7.8, 1.4 Hz, 1H), 7.10-7.03 (m, 1H), 7.00 (d, J=8.7 Hz, 1H), 6.96 (s, 1H), 6.93 (dd, J=7.6, 5.7 Hz, 1H), 4.00 (s, 2H) signal for —NH$_2$ not observed. MS: 362.3 [M+H]$^+$.

Example 61: Synthesis of 3-(3-((6-(benzylthio)pyridin-3-yl)methyl)isoxazol-5-yl)pyridin-2-amine

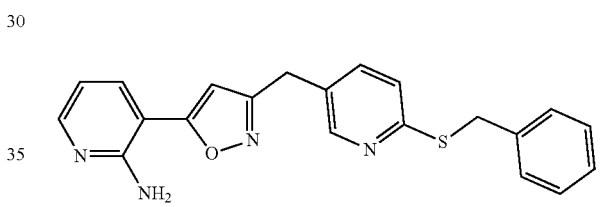

To a neat mixture of 3-(3-((6-fluoropyridin-3-yl)methyl)isoxazol-5-yl)pyridin-2-amine (Intermediate E, 60 mg, 0.22 mmol) and phenylmethanethiol (165 mg, 1.33 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(benzylthio)pyridin-3-yl)methyl)isoxazol-5-yl)pyridin-2-amine (5.8 mg, 0.015 mmol, 7%) as a white solid. MS: 375.2 [M+H]$^+$.

Example 62: Synthesis of 2-((4-((4-(pyridin-3-yl)-1H-pyrazol-1-yl)methyl)benzyl)oxy)pyridine

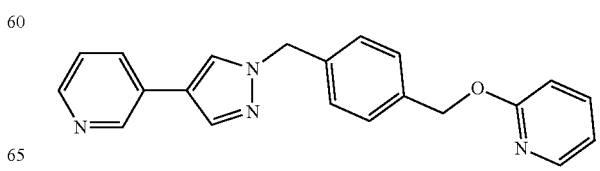

267
Step 1: (4-((pyridin-2-yloxy)ethyl)phenyl)methanol

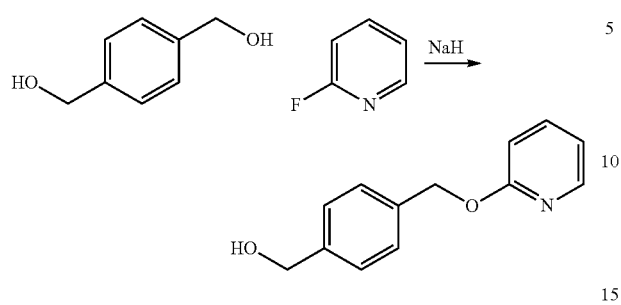

1,4-phenylenedimethanol (7.50 g, 54.3 mmol) and 2-fluoropyridine (1.76 g, 18.09 mmol) were dissolved in DMF (40 mL) and sodium hydride (60% w/mineral oil, 2.171 g, 54.3 mmol) was added at 0° C. in 10 portions over the course of 20 min. The resulting mixture was allowed to warm to 21-25° C. within 30 min and then warmed to 70° C. and stirred for 30 min at this temperature. The cooled reaction mixture was poured into a stirring mixture of ice-water (300 mL) and ethyl acetate (500 mL). The layers were separated and the aqueous phase was further extracted with ethyl acetate (3×100 mL). The combined organic layers were washed with brine (50 mL), dried over $Na_2SO_4$, filtered and concentrated under reduced pressure. The residue was purified by column chromatography ($SiO_2$, hexane/ethyl acetate) to give (4-((pyridin-2-yloxy)methyl)phenyl)methanol (2.6 g, 12.08 mmol, 67%).

Step 2: 2-((4-(bromomethyl)benzyl)oxy)pyridine

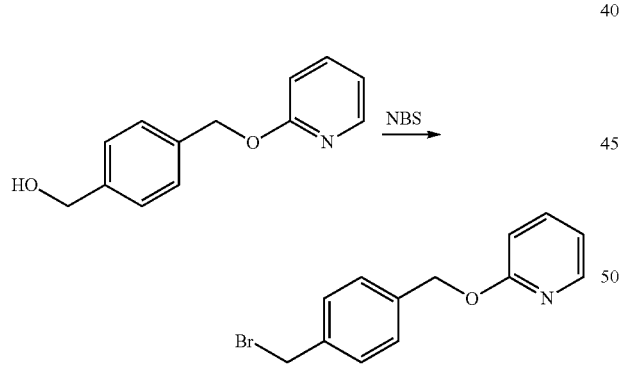

(4-((pyridin-2-yloxy)methyl)phenyl)methanol (500 mg, 2.32 mmol) and triphenylphosphane (914 mg, 3.48 mmol) were dissolved in THF (15 mL) and 2 g celite were added. To the stirred mixture was added a partial solution/suspension of 1-bromopyrrolidine-2,5-dione (NBS, 558 mg, 3.14 mmol) in THF at 0° C. The mixture was allowed to warm to 21-25° C. and stirred for 30 min. All volatiles were removed under reduced pressure and the residue was purified by flash chromatography to obtain 2-((4-(bromomethyl)benzyl)oxy)pyridine (250 mg, 0.90 mmol, 39%) as a colorless oil.

268
Step 3: 2-((4-((4-bromo-1H-pyrazol-1-yl)methyl)benzyl)oxy)pyridine

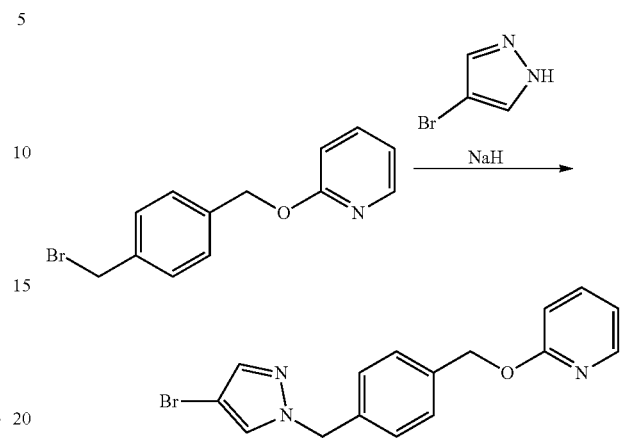

Sodium hydride (60% w/mineral oil, 48.3 mg, 1.21 mmol) was suspended in DMF (2 mL) and a solution of 4-bromo-1H-pyrazole (165 mg, 1.12 mmol) in DMF (1.5 mL) was added at 0° C. The mixture was allowed to warm to 23° C. and stirred for 15 min. A solution of 2-((4-(bromomethyl)benzyl)oxy)pyridine (240 mg, 0.86 mmol) in DMF (1.5 mL) was added at 0° C. and the mixture was stirred at 21-25° C. for 10 min. The mixture was warmed to 40° C. for 2 min. The cooled reaction mixture was then directly purified by flash chromatography to obtain 2-((4-((4-bromo-1H-pyrazol-1-yl)methyl)benzyl)oxy)pyridine (220 mg, 0.64 mmol, 74%) as a white solid.

Step 4: 2-((4-((4-(pyridin-3-yl)-1H-pyrazol-1-yl)methyl)benzyl)oxy)pyridine

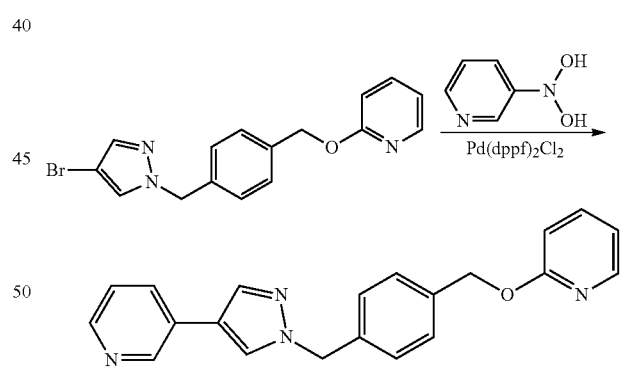

2-((4-((4-bromo-1H-pyrazol-1-yl)methyl)benzyl)oxy)pyridine (110 mg, 0.32 mmol) and pyridin-3-ylboronic acid (62.8 mg, 0.51 mmol) were mixed in a sealable tube with dioxane (3.5 mL). A 2M solution of sodium carbonate in water (511 μL, 1.02 mmol) was added followed by Pd(dppf)$_2$Cl$_2$ (CH$_2$Cl$_2$ adduct, 26 mg, 0.03 mmol) and the tube was flushed with argon and sealed. The mixture was heated in the MW at 100° C. for 10 min. The cooled reaction mixture was poured into a stirring mixture of water (30 mL) and ethyl acetate (50 mL). The layers were separated the aqueous phase was further extracted with ethyl acetate (3×20 mL). The combined organic layers were washed with brine (10 mL), dried over $Na_2SO_4$, filtered and concentrated under reduced pressure. The residue was purified by column chromatography (SiO$_2$, hexane/ethyl acetate).

Fractions containing the product also contained a small amount of inseparable impurities and were re-purified using RP flash chromatography (Biotage). Fractions containing the product were lyophilized to obtain 2-((4-((4-(pyridin-3-yl)-1H-pyrazol-1-yl)methyl)benzyl)oxy)pyridine (53 mg, 0.16 mmol, 49%) as a white solid. 400 MHz $^1$H NMR (TFA salt, CDCl$_3$) δ 9.00 (s, 1H), 8.57 (dd, J=5.6, 1.4 Hz, 1H), 8.29 (dt, J=8.2, 1.6 Hz, 1H), 8.23-8.16 (m, 1H), 7.93 (s, 1H), 7.87 (s, 1H), 7.77 (dd, J=8.2, 5.4 Hz, 1H), 7.63 (ddd, J=8.4, 7.1, 2.0 Hz, 1H), 7.48 (d, J=8.1 Hz, 1H), 7.32 (d, J=8.1 Hz, 2H), 6.93 (ddd, J=7.2, 5.2, 1.0 Hz, 1H), 6.83 (d5, J=8.3, 0.9 Hz, 1H), 5.38 (s, 2H), 5.37 (s, 2H). MS: 343.4 [M+H]$^+$.

The free base (RP chromatography solvent contained 0.05% TFA as modifier) was obtained as followed: The product was dissolved in DCM (2 mL) and MP-Carbonate resin from Biotage (600 mg) was added. The mixture was stirred for 30 min and filtered. The resin was washed multiple times with DCM and all solvents were removed under reduced pressure. The residue was dissolved in a small amount of acetonitrile, water was added and the final product obtained by lyophilization.

Example 63: Synthesis of 3-(1-((6-phenoxypyridin-3-yl)methyl)-1H-pyrazol-4-yl)pyridin-2-amine

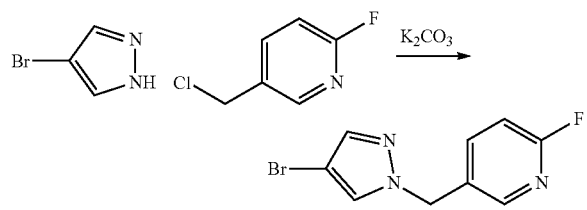

Step 1: 5-((4-bromo-1H-pyrazol-1-yl)methyl-2-fluoropyridine

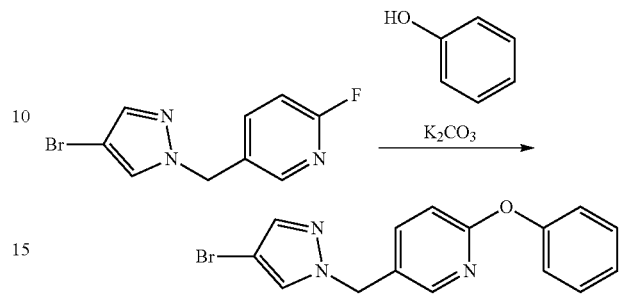

4-bromo-1H-pyrazole (2.02 g, 13.74 mmol) was dissolved in DMF (9 mL) and potassium carbonate (1.90 g, 13.74 mmol) was added. 5-(chloromethyl)-2-fluoropyridine (1 g, 6.87 mmol) was dissolved in DMF (1 mL) and added to the reaction mixture. The mixture was stirred for 4 h at 21-25° C. and directly purified by flash chromatography to give 5-((4-bromo-1H-pyrazol-1-yl)methyl)-2-fluoropyridine (1.66 g, 6.48 mmol, 94%).

Step 2: 5-((4-bromo-1H-pyrazol-1-yl)methyl)-2-phenoxypyridine

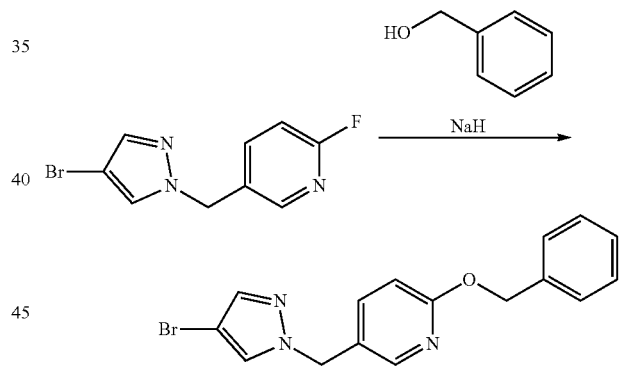

5-((4-bromo-1H-pyrazol-1-yl)methyl)-2-fluoropyridine (550 mg, 2.15 mmol) was dissolved in NMP (2.8 mL). Phenol (1.01 g, 10.75 mmol) and potassium carbonate (1.48 g, 10.75 mmol) were added and the mixture was heated in the MW at 120° C. for 20 min. The crude mixture was purified using flash chromatography to obtain 5-((4-bromo-1H-pyrazol-1-yl)methyl)-2-phenoxypyridine (260 mg, 0.79 mmol), 37%).

Step 3: 2-(benzyloxy)-5-((4-bromo-1H-pyrazol-1-yl)methyl)pyridine

Phenylmethanol (845 mg, 7.81 mmol) was added to a suspension of sodium hydride (60% w/mineral oil, 312 mg, 7.81 mmol) in DMF (4 mL). After no more gases evolved, a solution of 5-((4-bromo-1H-pyrazol-1-yl)methyl)-2-fluoropyridine (500 mg, 1.95 mmol) in DMF (2 mL) was added and the mixture was stirred at 21-25° C. for 1 h. The reaction mixture was poured into a stirring mixture of ice-water (50 mL) and ethyl acetate (150 mL). The layers were separated and the aqueous phase was further extracted with ethyl acetate (3×50 mL). The combined organic layers were washed with brine (30 mL), dried over Na$_2$SO$_4$, filtered and concentrated under reduced pressure. The residue was purified by column chromatography (SiO$_2$, hexane/ethyl acetate) to give 2-(benzyloxy)-5-((4-bromo-1H-pyrazol-1-yl)methyl)pyridine (440 mg, 1.28 mmol, 66%).

Step 4: 5-((4-bromo-1H-pyrazol-1-yl)methyl)-2-(phenylthio)pyridine

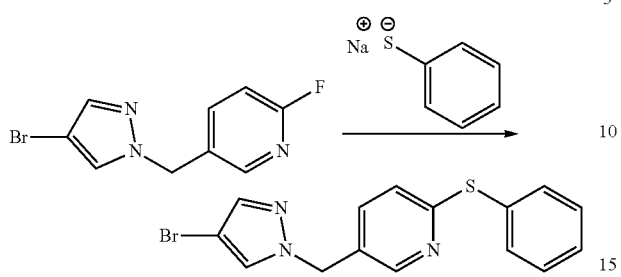

5-((4-bromo-1H-pyrazol-1-yl)methyl)-2-fluoropyridine (500 mg, 1.95 mmol) was dissolved in NMP (2.8 mL) and sodium benzenethiolate (516 mg, 3.91 mmol) was added. The mixture was heated in the MW at 100° C. for 15 min. The crude mixture was purified using flash chromatography to obtain 5-((4-bromo-1H-pyrazol-1-yl)methyl)-2-(phenylthio)pyridine (270 mg, 0.78 mmol, 40%).

Step 5: 3-(1-((6-phenyoxypyridin-3-yl)methyl)-1H-pyrazol-4-yl)pyridin-2-amine

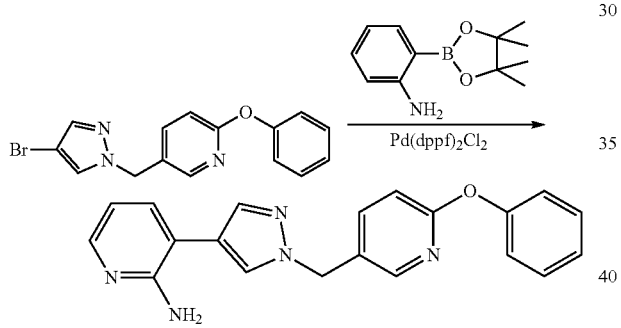

5-((4-bromo-1H-pyrazol-1-yl)methyl)-2-phenoxypyridine (130 mg, 0.39 mmol) and 3-(4,4,5,5-tetramethyl-1,3,2-dioxaborolan-2-yl)pyridin-2-amine (139 mg, 0.63 mmol) were mixed in a sealable tube with dioxane (3.5 mL). A 2M solution of sodium carbonate in water (492 μL, 0.98 mmol) was added followed by Pd(dppf)$_2$Cl$_2$ (CH$_2$Cl$_2$ adduct, 32 mg, 0.04 mmol) and the tube was flushed with argon and sealed. The mixture was heated in the MW at 100° C. for 20 min. The cooled reaction mixture was poured into a stirring mixture of water (30 mL) and ethyl acetate (50 mL). The layers were separated the aqueous phase was further extracted with ethyl acetate (3×20 mL). The combined organic layers were washed with brine (10 mL), dried over Na$_2$SO$_4$, filtered and concentrated under reduced pressure. The residue was purified by column chromatography (SiO$_2$, hexane/ethyl acetate).

Fractions containing the product also contained a small amount of inseparable impurities and were re-purified using RP flash chromatography (Biotage). Fractions containing the product were lyophilized to obtain 3-(1-((6-phenoxypyridin-3-yl)methyl)-1H-pyrazol-4-yl)pyridin-2-amine (80 mg, 0.23 mmol, 59%). 400 MHz $^1$H NMR (TFA-salt, DMSO-d6) δ 8.34 (s, 1H), 8.18 (d, J=2.3 Hz, 1H), 8.03-7.81 (m, 6H), 7.46-7.36 (m, 2H), 7.20 (t, J=7.4 Hz, 1H), 7.14-7.06 (m, 2H), 7.02 (d, J=8.4 Hz, 1H), 6.95 (t, J=6.8 Hz, 1H), 5.38 (s, 2H). MS: 344.4 [M+H]$^+$.

Example 64: Synthesis of 2-phenoxy-5-((4-(pyridin-3-yl)-1H-pyrazol-1-yl)methyl)pyridine

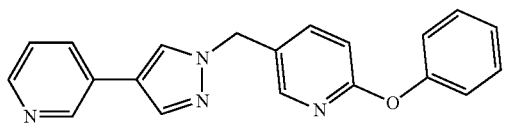

The title compound was prepared according to the procedure described fro Example 6 using pyridin-3-ylboronic acid (121 mg, 0.98 mmol) to yield 2-phenoxy-5-((4-(pyridin-3-yl)-1H-pryazol-1-yl)methyl)pyridine (78 mg, 0.24 mmol, 60%). 400 MHz $^1$H NMR (DMSO-d6) δ 9.21 (d, J=2.0 Hz, 1H), 8.81-8.65 (m, 3H), 8.26 (d, J=0.8 Hz, 1H), 8.18 (d, J=2.0 Hz, 1H), 8.04 (dd, J=8.2, 5.7 Hz, 1H), 7.83 (dd, J=8.5, 2.5 Hz, 1H), 7.47-7.36 (m, 2H), 7.28-7.16 (m, 1H), 7.15-7.07 (m, 2H), 7.03 (d, J=8.5 Hz, 1H), 5.40 (s, 2H). MS: 329.3 [M+H]$^+$.

Example 65: Synthesis of 2-(benzyloxy)-5-((4-(pyridin-3-yl)-1H-pyrazol-1-yl)methyl)pyridine

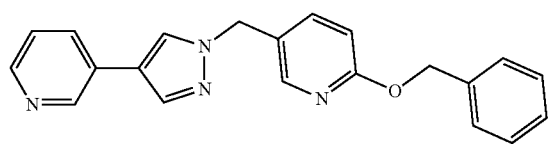

The title compound was prepared according to the procedure described for Example 63 using 2-(benzyloxy)-5-((4-bromo-1H-pyrazol-1-yl)methyl)pyridine (130 mg, 0.38 mmol) and pyridin-3-ylboronic acid (84 mg, 0.68 mmol) to yield 2-(benzyloxy)-5-((4-(pyridine-3-yl)-1H-pyrazol-1-yl)methyl)pyridine (75 mg, 0.22 mmol), 58%). MS: 343.3 [M+H]$^+$.

Example 66: Synthesis of 2-(phenylthio)-5-((4-(pyridin-3-yl)-1H-pyrazol-1-yl)methyl)pyridine

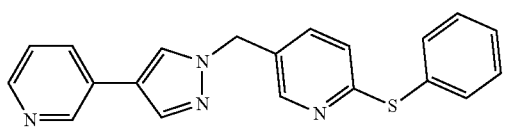 [SMILES: c1ccc(Oc2ccc(Cn3cc(-c4cccnc4)cn3)cn2)cc1]

The title compound was prepared according to the procedure described for Example 63 using 5-((4-bromo-1H-pyrazol-1-yl)methyl)-2-(phenylthio)pyridine (130 mg, 0.38 mmol) and pyridin-3-ylboronic acid (83 mg, 0.68 mmol) to yield 2-(phenylthio)-5-((4-(pyridine-3-yl)-1H-pyrazol-1-yl)methyl)pyridine (25 mg, 0.07 mmol, 19%). MS: 345.3 [M+H]$^+$.

Example 67: Synthesis of 3-(1-((6-(phenylthio)pyridin-3-yl)methyl)-1H-pyrazol-4-yl)pyridin-2-amine

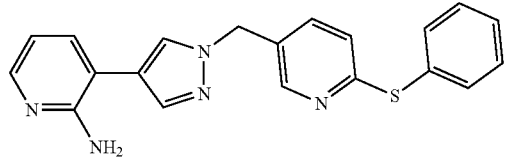 [SMILES: Nc1ncccc1-c1cnn(Cc2ccc(Sc3ccccc3)nc2)c1]

The title compound was prepared according to the procedure described for Example 63 using 5-((4-bromo-1H-pyrazol-1-yl)methyl)-2-(phenylthio)pyridine (130 mg, 0.38 mmol) and 3-(4,4,5,5-tetramethyl-1,3,2-dioxaborolan-2-yl)pyridin-2-amine (149 mg, 0.68 mmol) to yield 3-(1-((6-(phenylthio)pyridine-3-yl)methyl)-1H-pyrazol-4-yl)pyridin-2-amine (40 mg, 0.11 mmol), 30%). MS: 360.4 [M+H]+.

Example 68: Synthesis of 5-(1-((6-(benzyloxy)pyridin-3-yl)methyl)-1H-pyrazol-4-yl)pyridin-2-amine

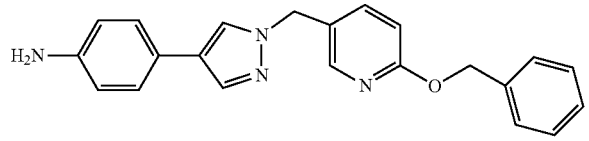 [SMILES: Nc1ccc(-c2cnn(Cc3ccc(OCc4ccccc4)nc3)c2)cc1]

The title compound was prepared according to the procedure described for Example 63 using 2-(benzyloxy)-5-((4-bromo-1H-pyrazol-1-yl)methyl)pyridine (170 mg, 0.49 mmol) and (6-aminopyridin-3-yl)boronic acid (123 mg, 0.89 mmol) to yield 5-(1-((6-(benzyloxy)pyridine-3-yl)-1H-pyrazol-4-yl)pyridin-2-amine (82 mg, 0.23 mmol), 47%). 400 MHz $^1$H NMR (DMSO-d6) δ 8.16 (m, 2H), 8.10 (s, 1H), 7.75 (s, 1H), 7.66 (dd, J=8.5, 2.5 Hz, 1H), 7.54 (d, J=8.7 Hz, 1H), 7.46-7.25 (m, 5H), 6.86 (d, J=8.6, 1H), 6.46 (d, J=7.5 Hz, 1H), 5.87 (s, 2H), 5.33 (s, 2H), 5.26 (s, 2H). MS: 358.4 [M+H]+.

Example 69: Synthesis of 3-(3-(4-((2-fluoropyridin-3-yl)methyl)benzyl)isoxazol-5-yl)pyridin-2-amine

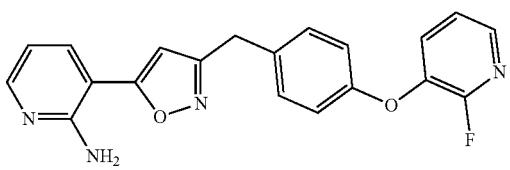

The title compound was prepared according to the procedure described for Example 8 using 6-fluoropyridin-2-yl)boronic acid (94.0 mg, 0.67 mmol) to yield 3-(3-(4-((2-fluoropyridin-3-yl)methyl)benzyl)isoxazol-5-yl)pyridin-2-amine (62 mg, 0.17 mmol, 52%) as a white solid. MS: 364.1 [M+H]+.

Example 70: Synthesis of 3-(3-(4-(((2-fluoropyridin-4-yl)amino)methyl)benzyl)isoxazol-5-yl)pyridin-2-amine

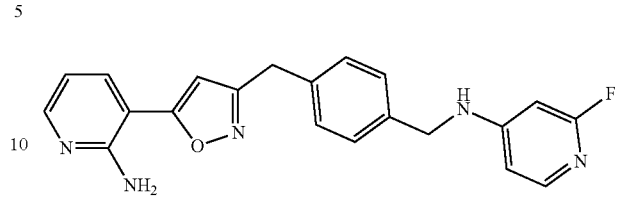

The title compound was prepared according to the procedure described for Example 31 using 2,4-difluoropyridine (185 mg, 1.61 mmol) to yield 3-(3-(4-(((2-fluoropyridin-4-yl)amino)methyl)benzyl)isoxazol-5-yl)pyridin-2-amine (36 mg, 0.10 mmol, 36%) as a white solid. MS: 376.4 [M+H]+.

Example 71: Synthesis of 4-((5-((5-(2-aminopyridin-3-yl)isoxazol-3-yl)methyl)pyridin-2-yl)oxy)-2,5-dimethylfuran-3(2H)-one

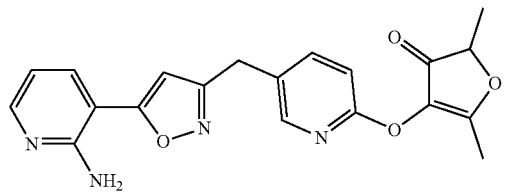 [SMILES: CC1=C(Oc2ccc(Cc3cc(-c4cccnc4N)on3)cn2)C(=O)C(C)O1]

To a neat mixture of 3-(3-((6-fluoropyridin-3-yl)methyl)isoxazol-5-yl)pyridin-2-amine (Intermediate E, 50 mg, 0.19 mmol) and 4-hydroxy-2,5-dimethylfuran-3(2H)-one (190 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO2, hexane/ethyl acetate). Combined fractions were concentrated under reduced pressure. Residue was dissolved in acetonitrile (5 mL) and water (10 mL), frozen and lyophilized to yield 4-((5-((5-(2-aminopyridin-3-yl)isoxazol-3-yl)methyl)pyridin-2-yl)oxy)-2,5-dimethylfuran-3(2H)-one (3.3 mg, 0.0087 mmol, 4.7%) as a white solid. MS: 379.3 [M+H]+.

Example 72: Synthesis of 5-((5-(2-aminopyridin-3-yl)isoxazol-3-yl)methyl)-N-(2,3-difluorophenyl)pyridin-2-amine

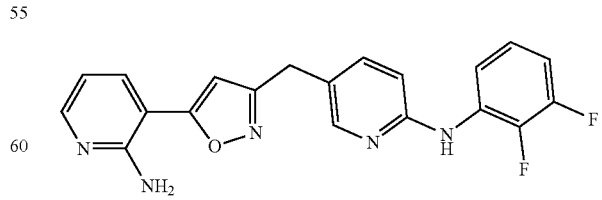

To a neat mixture of 3-(3-((6-fluoropyridin-3-yl)methyl)isoxazol-5-yl)pyridin-2-amine (Intermediate E, 50 mg, 0.19 mmol) and 2,3-difluoroaniline (191 mg, 1.48 mmol) was added potassium 2-methylpropane-2-olate (1M in THF, 1.85 mL, 1.85 mmol) and the mixture was heated to 90° C. for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 5-((5-(2-aminopyridin-3-yl)isoxazol-3-yl)methyl)-N-(2,3-difluorophenyl)pyridin-2-amine (21 mg, 0.055 mmol, 30%) as a white solid. MS: 380.3 [M+H]$^+$.

Example 73: Synthesis of 3-(3-((6-(furan-2-ylmethoxy)pyridin-3-yl)methyl)isoxazol-5-yl)pyridin-2-amine

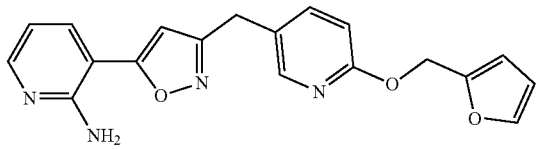 [SMILES: Nc1ncccc1-c1cc(Cc2ccc(OCc3ccco3)nc2)no1]

To a neat mixture of 3-(3-((6-fluoropyridin-3-yl)methyl)isoxazol-5-yl)pyridin-2-amine (Intermediate E, 50 mg, 0.19 mmol) and furan-2-ylmethanol (181 mg, 1.85 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(furan-2-ylmethoxy)pyridin-3-yl)methyl)isoxazol-5-yl)pyridin-2-amine (32 mg, 0.092 mmol, 50.%) as a white solid. MS: 349.3 [M+H]$^+$.

Example 74: Synthesis of 5-((5-(2-aminopyridin-3-yl)isoxazol-3-yl)methyl)-N-(2-fluorobenzyl)pyridin-2-amine

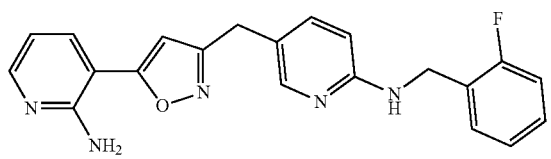

To a neat mixture of 3-(3-((6-fluoropyridin-3-yl)methyl)isoxazol-5-yl)pyridin-2-amine (Intermediate E, 50 mg, 0.19 mmol) 2-fluorobenzylamine (139 mg, 1.10 mmol) was added diisopropylethylamine (0.323 mL, 1.85 mmol), DMSO (1.0 mL), THF (1.0 mL) and the mixture was stirred for 16 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 5-((5-(2-aminopyridin-3-yl)isoxazol-3-yl)methyl)-N-(2-fluorobenzyl)pyridin-2-amine as a white solid. MS: 376.2 [M+H]$^+$.

Example 75: Synthesis of 3-(3-((6-(2,4-difluorophenoxy)pyridin-3-yl)methyl)isoxazol-5-yl)pyridin-2-amine

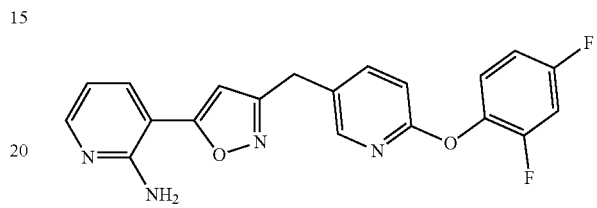

To a neat mixture of 3-(3-((6-fluoropyridin-3-yl)methyl)isoxazol-5-yl)pyridin-2-amine (Intermediate E, 50 mg, 0.19 mmol) 2,4-difluorophenol (144 mg, 1.10 mmol) was added potassium 2-methylpropane-2-olate (1M in THF, 1.85 mL, 1.85 mmol) and the mixture was stirred at 90° C. for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(2,4-difluorophenoxy)pyridin-3-yl)methyl)isoxazol-5-yl)pyridin-2-amine (29 mg, 0.075 mmol, 41%) as a white solid. MS: 381.3 [M+H]$^+$.

Example 76: Synthesis of 4-(((5-((5-(2-aminopyridin-3-yl)isoxazol-3-yl)methyl)pyridin-2-yl)oxy)methyl)benzonitrile

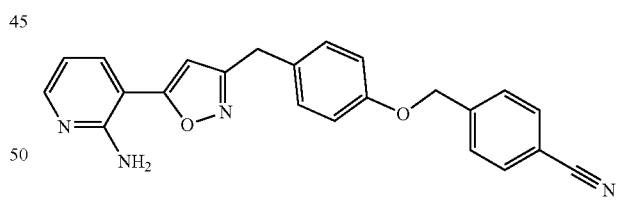

To a neat mixture of 3-(3-((6-fluoropyridin-3-yl)methyl)isoxazol-5-yl)pyridin-2-amine (Intermediate E, 50 mg, 0.19 mmol) and 4-(hydroxymethyl)benzonitrile (197 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 4-(((5-((5-(2-aminopyridin-3-yl)isoxazol-3-yl)methyl)pyridin-2-yl)oxy)methyl)benzonitrile (4.3 mg, 0.011 mmol, 6.0%) as a white solid. MS: 384.2 [M+H]$^+$.

Example 77: Synthesis of 3-(3-((6-(2-fluorophenethoxy)pyridin-3-yl)methyl)isoxazol-5-yl)pyridin-2-amine

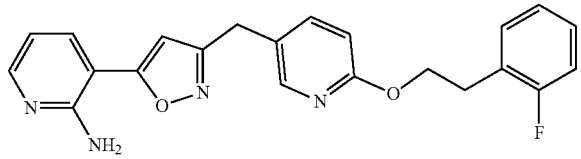 [SMILES: Nc1ncccc1-c1cc(Cc2ccc(OCCc3ccccc3F)nc2)no1]

To a neat mixture of 3-(3-((6-fluoropyridin-3-yl)methyl) isoxazol-5-yl)pyridin-2-amine (Intermediate E, 50 mg, 0.19 mmol) 2-(2-fluorophenyl)ethan-1-ol (156 mg, 1.10 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(2-fluorophenethoxy)pyridin-3-yl) methyl)isoxazol-5-yl)pyridin-2-amine (24 mg, 0.062 mmol, 33%) as a white solid. MS: 391.1 [M+H]$^+$.

Example 78: Synthesis of 3-(3-((6-phenethoxypyridin-3-yl)methyl)isoxazol-5-yl)pyridin-2-amine

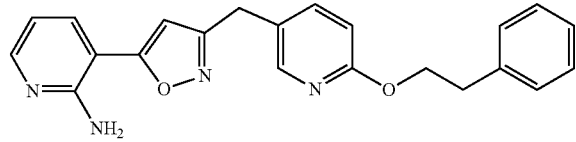 [SMILES: Nc1ncccc1-c1cc(Cc2ccc(OCCc3ccccc3)nc2)no1]

To a neat mixture of 3-(3-((6-fluoropyridin-3-yl)methyl) isoxazol-5-yl)pyridin-2-amine (Intermediate E, 50 mg, 0.19 mmol) 2-(2-fluorophenyl)ethan-1-ol (156 mg, 1.10 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-phenethoxy)pyridin-3-yl)methyl) isoxazol-5-yl)pyridin-2-amine (28 mg, 0.074 mmol, 40.%) as a white solid. MS: 37.0 [M+H]$^+$.

Example 79: Synthesis of 3-(3-((6-(4-fluorophenethoxy)pyridin-3-yl)methyl)isoxazol-5-yl)pyridin-2-amine

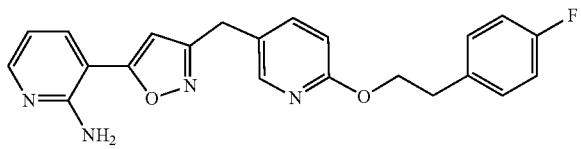 [SMILES: Nc1ncccc1-c1cc(Cc2ccc(OCCc3ccc(F)cc3)nc2)no1]

To a neat mixture of 3-(3-((6-fluoropyridin-3-yl)methyl) isoxazol-5-yl)pyridin-2-amine (Intermediate E, 50 mg, 0.19 mmol) 2-(4-fluorophenyl)ethan-1-ol (207 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-phenethoxy)pyridin-3-yl)methyl) isoxazol-5-yl)pyridin-2-amine (25 mg, 0.046 mmol, 25%) as a white solid. MS: 391.4 [M+H]$^+$.

Example 80: Synthesis of 3-(3-((6-((3-fluorobenzyl)oxy)pyridin-3-yl)methyl)isoxazol-5-yl)pyridin-2-amine

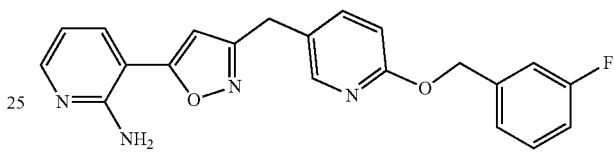

To a neat mixture of 3-(3-((6-fluoropyridin-3-yl)methyl) isoxazol-5-yl)pyridin-2-amine (Intermediate E, 50 mg, 0.19 mmol) (3-fluorophenyl)methanol (187 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3-fluorobenzyl)oxy)pyridin-3-yl)methyl)isoxazol-5-yl)pyridin-2-amine (45 mg, 0.12 mmol, 65%) as a white solid. MS: 377.3 [M+H]$^+$.

Example 81: Synthesis of 3-(3-((6-(3,5-difluorophenoxy)pyridin-3-yl)methyl)isoxazol-5-yl)pyridin-2-amine

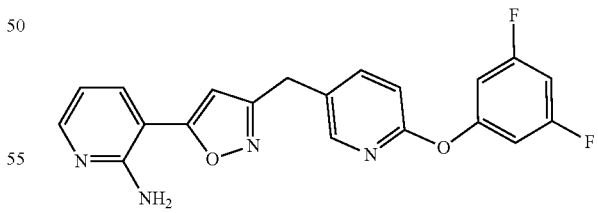

To a neat mixture of 3-(3-((6-fluoropyridin-3-yl)methyl) isoxazol-5-yl)pyridin-2-amine (Intermediate E, 50 mg, 0.19 mmol) 3,5-difluorophenol (193 mg, 1.48 mmol) was added potassium 2-methylpropane-2-olate (1M in THF, 1.85 mL, 1.85 mmol) and the mixture was stirred at 90° C. for 2 hours. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(3,5-difluorophenoxy)pyridin-3-yl)methyl)isoxazol-5-yl)pyridin-2-amine (7.4 mg, 0.019 mmol, 11%) as a white solid. 500 MHz $^1$H NMR (DMSO-d6) δ 8.21 (dt, J=2.4, 0.7 Hz, 1H), 8.09 (dd, J=4.9, 1.9 Hz, 1H), 7.90-7.83 (m, 2H), 7.13-7.05 (m, 2H), 7.00-6.91 (m, 2H), 6.86 (s, 1H), 6.70 (ddd, J=7.7, 4.7, 0.5 Hz, 1H), 6.27 (s, 2H), 4.06 (s, 2H). MS: 381.1 [M+H]$^+$.

Example 82: Synthesis of 3-(3-((6-((4-methylthiazol-2-yl)methoxy)pyridin-3-yl)methyl)isoxazol-5-yl)pyridin-2-amine

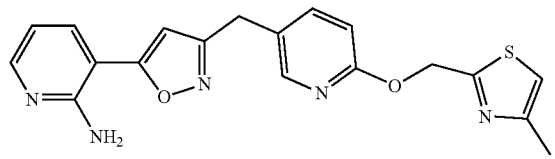 [SMILES: Cc1csc(COc2ccc(Cc3cc(-c4cccnc4N)on3)cn2)n1]

To a neat mixture of 3-(3-((6-fluoropyridin-3-yl)methyl)isoxazol-5-yl)pyridin-2-amine (Intermediate E, 50 mg, 0.19 mmol) 4-methylthiazol-2-yl)methanol (191 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((4-methylthiazol-2-yl)methoxy)pyridin-3-yl)methyl)isoxazol-5-yl)pyridin-2-amine (46 mg, 0.12 mmol, 66%) as a white solid. MS: 380.2 [M+H]$^+$.

Example 83: Synthesis of 3-(3-((6-((2-chloropyridin-4-yl)methoxy)pyridin-3-yl)methyl)isoxazol-5-yl)pyridin-2-amine

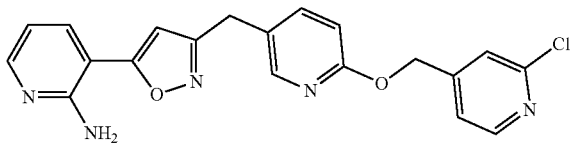

To a neat mixture of 3-(3-((6-fluoropyridin-3-yl)methyl)isoxazol-5-yl)pyridin-2-amine (Intermediate E, 50 mg, 0.19 mmol) 2-chloropyridin-4-yl)methanol (32 mg, 0.22 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((2-chloropyridin-4-yl)methoxy)pyridin-3-yl)methyl)isoxazol-5-yl)pyridin-2-amine (2.7 mg, 0.0068 mmol, 3.7%) as a white solid. MS: 394.2 [M+H]$^+$.

Example 84: Synthesis of 3-(3-((6-((3,5-difluorobenzyl)oxy)pyridin-3-yl)methyl)isoxazol-5-yl)pyridin-2-amine

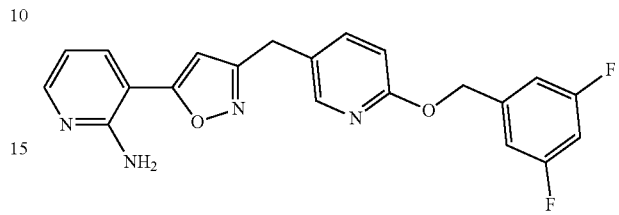

To a neat mixture of 3-(3-((6-fluoropyridin-3-yl)methyl)isoxazol-5-yl)pyridin-2-amine (Intermediate E, 50 mg, 0.19 mmol), (3,5-difluorophenyl)methanol (213 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3,5-difluorobenzyl)oxy)pyridin-3-yl)methyl)isoxazol-5-yl)pyridin-2-amine (49 mg, 0.12 mmol, 67%) as a white solid. MS: 395.2 [M+H]$^+$.

Example 85: Synthesis of 3-(3-((6-((3-chlorobenzyl)oxy)pyridin-3-yl)methyl)isoxazol-5-yl)pyridin-2-amine

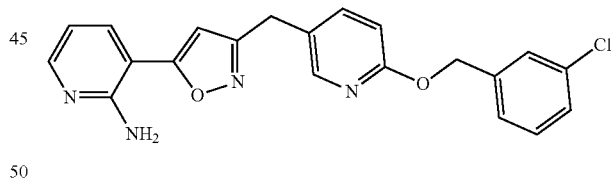

To a neat mixture of 3-(3-((6-fluoropyridin-3-yl)methyl)isoxazol-5-yl)pyridin-2-amine (Intermediate E, 50 mg, 0.19 mmol), (3-chlorophenyl)methanol (211 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3-chlorobenzyl)oxy)pyridin-3-yl)methyl)isoxazol-5-yl)pyridin-2-amine (40 mg, 0.10 mmol, 55%) as a white solid. MS: 393.2 [M+H]$^+$.

Example 86: Synthesis of 3-(3-((2-((3-fluorobenzyl)oxy)pyridin-4-yl)methyl)isoxazol-5-yl)pyridin-2-amine

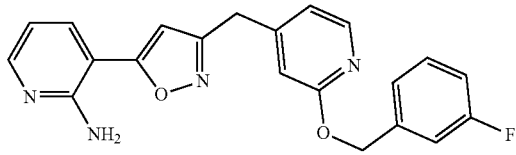

To a neat mixture of 3-(3-((2-fluoropyridin-4-yl)methyl)isoxazol-5-yl)pyridin-2-amine (40 mg, 0.15 mmol), (3-fluorophenyl)methanol (187 mg, 1.48 mmol) was added potassium 2-methylpropane-2-olate (1M in THF, 1.48 mL, 1.48 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((2-((3-fluorobenzyl)oxy)pyridin-4-yl)methyl)isoxazol-5-yl)pyridin-2-amine (23 mg, 0.061 mmol, 41%) as a white solid. 500 MHz $^1$H NMR (DMSO-d6) δ 8.11 (dd, J=5.2, 0.7 Hz, 1H), 8.09 (dd, J=4.8, 1.8 Hz, 1H), 7.87 (dd, J=7.7, 1.9 Hz, 1H), 7.43-7.38 (m, 1H), 7.29-7.24 (m, 2H), 7.16-7.11 (m, 1H), 6.98 (dd, J=5.2, 1.4 Hz, 1H), 6.88-6.85 (m, 2H), 6.70 (dd, J=7.7, 4.8 Hz, 1H), 6.26 (s, 2H), 5.35 (s, 2H), 4.05 (s, 2H). MS: 377.0 [M+H]$^+$.

Example 86: Synthesis of 3-(3-((6-((3-chloro-5-fluorobenzyl)oxy)pyridin-3-yl)methyl)isoxazol-5-yl)pyridin-2-amine

To a neat mixture of 3-(3-((6-fluoropyridin-3-yl)methyl)isoxazol-5-yl)pyridin-2-amine (Intermediate E, 50 mg, 0.19 mmol), (3-chloro-5-fluorophenyl)methanol (178 mg, 1.11 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3-chloro-5-fluorobenzyl)oxy)pyridin-3-yl)methyl)isoxazol-5-yl)pyrridin-2-amine (52 mg, 0.13 mmol, 69%) as a white solid. MS: 411.3 [M+H]$^+$.

Example 88: Synthesis of 3-(3-((2-((phenoxypyridin-4-yl)methyl)isoxazol-5-yl)pyridin-2-amine

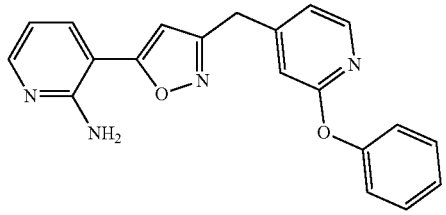 [SMILES: Nc1ncccc1-c1cc(Cc2ccnc(Oc3ccccc3)c2)no1]

To a neat mixture of 3-(3-((2-fluoropyridin-4-yl)methyl)isoxazol-5-yl)pyridin-2-amine (40 mg, 0.148 mmol), phenol (139 mg, 1.48 mmol) was added potassium 2-methylpropane-2-olate (1M in THF, 1.48 mL, 1.48 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((2-((phenoxypyridin-4-yl)methyl)isoxazol-5-yl)pyridin-2-amine (7.4 mg, 0.021 mmol, 15%) as a white solid. MS: 345.1 [M+H]$^+$.

Example 86: Synthesis of 3-(3-((6-((3-fluorobenzyl)oxy)pyridin-2-yl)methyl)isoxazol-5-yl)pyridin-2-amine

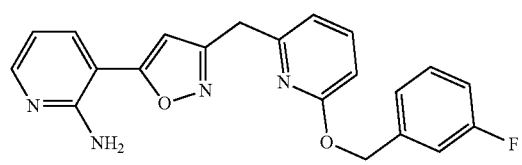

To a neat mixture of 3-(3-((6-fluoropyridin-2-yl)methyl)isoxazol-5-yl)pyridin-2-amine (40 mg, 0.15 mmol), (3-fluorophenyl)methanol (187 mg, 1.48 mmol) was added potassium 2-methylpropane-2-olate (1M in THF, 1.48 mL, 1.48 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((3-fluorobenzyl)oxy)pyridin-2-yl)methyl)isoxazol-5-yl)pyridin-2-amine (10 mg, 0.027 mmol, 18%) as a white solid. MS: 377.3 [M+H]$^+$.

Example 90: Synthesis of 3-(3-((6-((2-fluorobenzyl)oxy)pyridin-2-yl)methyl)isoxazol-5-yl)pyridin-2-amine

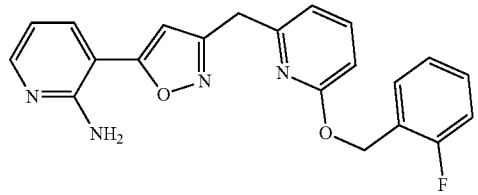 [SMILES: Nc1ncccc1-c1cc(Cc2cccc(OCc3ccccc3F)n2)no1]

To a neat mixture of 3-(3-((6-fluoropyridin-2-yl)methyl)isoxazol-5-yl)pyridin-2-amine (40 mg, 0.15 mmol), (2-fluorophenyl)methanol (187 mg, 1.48 mmol) was added potassium 2-methylpropane-2-olate (1M in THF, 1.48 mL, 1.48 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-((2-fluorobenzyl)oxy)pyridin-2-yl)methyl)isoxazol-5-yl)pyridin-2-amine (25 mg, 0.065 mmol, 44%) as a white solid. MS: 377.2 [M+H]$^+$.

Example 91: Synthesis of 3-(3-((6-(3-fluorophenethoxy)pyridin-3-yl)methyl)isoxazol-5-yl)pyridin-2-amine

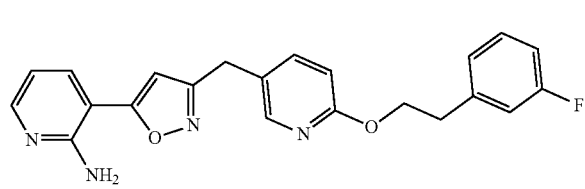 [SMILES: Nc1ncccc1-c1cc(Cc2ccc(OCCc3cccc(F)c3)nc2)no1]

To a neat mixture of 3-(3-((6-fluoropyridin-3-yl)methyl)isoxazol-5-yl)pyridin-2-amine (Intermediate E, 50 mg, 0.19 mmol), 2-(3-fluorophenyl)ethan-1-ol (207 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(3-fluorophenethoxy)pyridin-3-yl)methyl)isoxazol-5-yl)pyridin-2-amine (10 mg, 0.026 mmol, 14%) as a white solid. MS: 391.4 [M+H]$^+$.

Example 92: Synthesis of 3-(3-((6-((4-chloropyridin-2-yl)methoxy)pyridin-3-yl)methyl)isoxazol-5-yl)pyridin-2-amine

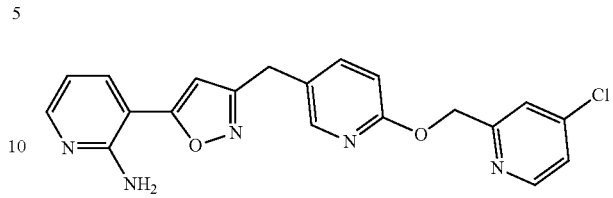

To a neat mixture of 3-(3-((6-fluoropyridin-3-yl)methyl)isoxazol-5-yl)pyridin-2-amine (Intermediate E, 50 mg, 0.19 mmol), (4-chloropyridin-2-yl)methanol (159 mg, 1.11 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-((6-(3-fluorophenethoxy)pyridin-3-yl)methyl)isoxazol-5-yl)pyridin-2-amine (10 mg, 0.025 mmol, 14%) as a white solid. MS: 394.2 [M+H]$^+$.

Example 93: Synthesis of 3-(3-(4-((((1H-pyrazol-5-yl)methyl)amino)methyl)benzyl)isoxazol-5-yl)pyridin-2-amine

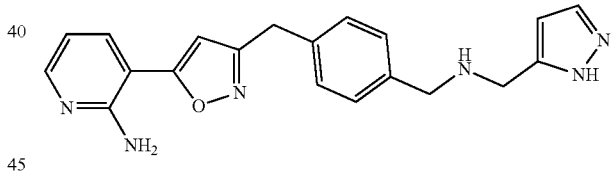

3-(3-(4-(chloromethyl)benzyl)isoxazol-5-yl)pyridin-2-amine (Intermediate B, 0.10 g, 0.33 mmol) and (1H-pyrazol-5-yl)methanamine (0.16 g, 1.7 mmol) were suspended in tetrahydrofuran (2 mL). Diisopropylethylamine (0.14 mL, 0.80 mmol) was added and the mixture was stirred at 60° C. for 18 h. The mixture was diluted with water and ethyl acetate, and the layers were partitioned. The aqueous phase was extracted twice more with ethyl acetate. The organic phase was washed with brine, dried over sodium sulfate and evaporated under reduced pressure. The residue was purified using Biotage reverse-phase flash chromatography (12 g C18 SNAP, 5-95% acetonitrile/water with 0.1% formic acid). The desired fractions were combined and lyophilized to give the title compound as a formate salt (0.0040 g, 0.010 mmol, 3%). MS: 361.2 [M+H]$^+$.

Example 94: Synthesis of 2-((4-((5-(2-aminopyridin-3-yl)isoxazol-3-yl)methyl)benzyl)amino)acetonitrile

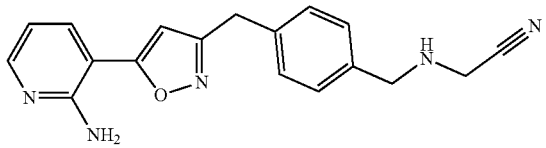

Prepared according to the procedure described in Example 93 using 2-aminoacetonitrile hydrochloride (0.15 g, 1.7 mmol). The title compound was obtained as a formate salt (0.0087 g, 0.024 mmol, 7%). MS: 320.2 [M+H]$^+$.

Example 95: Synthesis of 3-(3-(4-((((tetrahydro-2H-pyran-4-yl)methyl)amino)methyl)benzyl)isoxazol-5-yl)pyridin-2-amine

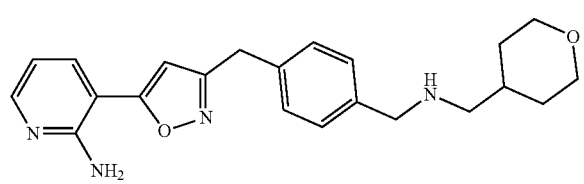 [SMILES: Nc1ncccc1-c1cc(Cc2ccc(CNCC3CCOCC3)cc2)no1]

3-(3-(4-(chloromethyl)benzyl)isoxazol-5-yl)pyridin-2-amine (Intermediate B, 0.10 g, 0.33 mmol) and (tetrahydro-2H-pyran-4-yl)methanamine (0.19 g, 1.7 mmol) were suspended in tetrahydrofuran (2 mL). Diisopropylethylamine (0.14 mL, 0.80 mmol) was added the heterogeneous mixture was stirred at room temperature for 3 hours. LCMS indicated a small peak with m/z corresponding to the desired product. The milky yellow mixture was heated at 60° C. for 72 h. Significant progress was noted, but the mixture was still mostly starting material. The mixture was diluted with water and ethyl acetate, and the layers were partitioned. The aqueous phase was extracted twice more with ethyl acetate. The organic phase was washed with brine, dried over sodium sulfate and evaporated under reduced pressure. The residue was purified using Biotage reverse phase flash chromatography (12 g C18 SNAP, 5-95% acetonitrile/water with 0.1% formic acid). The desired fractions were combined and lyophilized to give the title compound as a formate salt (0.0055 g, 0.013 mmol, 4%). MS: 379.3 [M+H]$^+$.

Example 96: Synthesis of 3-((4-((5-(2-aminopyridin-3-yl)isoxazol-3-yl)methyl)benzyl)amino)azepan-2-one

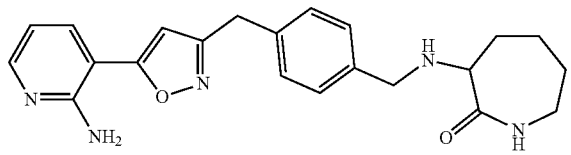 [SMILES: Nc1ncccc1-c1cc(Cc2ccc(CNC3CCCCNC3=O)cc2)no1]

Prepared according to the procedure described in Example 93 using 3-aminoazepan-2-one (0.21 g, 1.7 mmol) and a 2-day reaction time. The title compound was obtained as a formate salt (0.056 g, 0.13 mmol, 39%). MS: 392.3 [M+H]$^+$.

Example 97: Synthesis of 3-(3-(4-Vinylbenzyl)isoxazol-5-yl)pyridin-2-amine

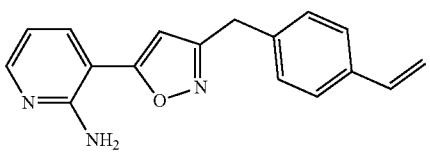 [SMILES: C=Cc1ccc(Cc2cc(-c3cccnc3N)on2)cc1]

Step 1: Synthesis of Di-tert-butyl [3-(3-(4-vinylbenzyl)isoxazol-5-yl)pyridin-2-yl]imidodicarbonate Di-tert-butyl [3-(3-(chloromethyl)-1,2-oxazol-5-yl)pyridin-2-yl]imidodicarbonate (Intermediate A, 1.7 g, 4.5 mmol), (4-vinylphenyl)boronic acid (0.82 g, 5.5 mmol), bis[(2-diphenylphosphino)phenyl]ether (0.11 g, 0.21 mmol), palladium(II) acetate (0.048 g, 0.21 mmol), potassium carbonate (0.76 g, 5.5 mmol), dimethylformamide (17 mL) and water (1.2 mL) were combined in a 50 mL sealed tube and heated at 60° C. for 18 hours. The mixture was cooled to ambient temperature, and then diluted with water and toluene. The layers were partitioned, and the aqueous phase was extracted twice more with toluene. The combined organic phase was washed with water, and then brine. The organic phase was dried over sodium sulfate and then the solvents were evaporated. The residue was purified in two portions, each using Biotage normal-phase flash chromatography (50 g SNAP Ultra, 5-65% ethyl acetate/hexane). The desired fractions from each purification were combined to give the title compound as a pale-yellow oil (1.3 g, 2.7 mmol, 65%). This material was taken forward without further purification.

Step 2: Synthesis of 3-(3-(4-Vinylbenzyl)isoxazol-5-yl)pyridin-2-amine

Di-tert-butyl [3-(3-(4-vinylbenzyl)isoxazol-5-yl)pyridin-2-yl]imidodicarbonate (0.017 g, 0.036 mmol) was dissolved in formic acid (3 mL). The mixture was stirred at room temperature for 4 days. The solution was treated with pH 7 buffer (3 mL), and then basified with 5N aqueous sodium hydroxide to pH 9-10. Ethyl acetate was added, and the layers were partitioned. The aqueous phase was extracted twice more with ethyl acetate. The combined organic phase was washed with water, and then brine. The organic phase was dried over sodium sulfate, and then the solvents were evaporated. The residue was purified using Biotage reverse-phase flash chromatography (12 g C18 SNAP, 5-95% acetonitrile/water with 0.1% formic acid). The desired fractions were combined and lyophilized to give the title compound as a white solid (0.0020 g, 0.0072 mmol, 20%). MS: 378.3 [M+H]$^+$.

Example 98: Synthesis of 2-((4-((5-(2-aminopyridin-3-yl)isoxazol-3-yl)methyl)phenethyl)thio)ethyl formate

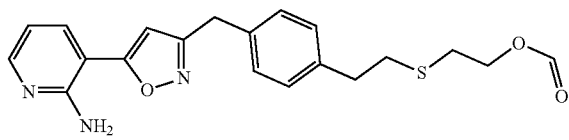 [SMILES: Nc1ncccc1-c1cc(Cc2ccc(CCSCCOC=O)cc2)no1]

Di-tert-butyl [3-(3-(4-vinylbenzyl)isoxazol-5-yl)pyridin-2-yl]imidodicarbonate (0.20 g, 0.42 mmol), 2,2-dimethoxy-2-phenylacetophenone (0.0054 g, 0.021 mmol), 2-mercaptoethanol (0.030 mL, 0.42 mmol), dichloromethane (0.7 mL) were combined in a 2 mL sealed tube and stirred under UV light (365 nm, 4 W) at ambient temperature for 4 h. The mixture was concentrated somewhat and then purified using Biotage normal-phase flash chromatography (25 g SNAP Ultra, 5-65% acetone/hexane). The desired fractions were combined and evaporated to give the di-BOC protected product. This material was dissolved in formic acid (6 mL) and stirred at room temperature for 13 hours. The mixture was treated with pH 7 buffer (20 mL), and then basified to pH 10 with 45% aqueous potassium hydroxide. The mixture was stirred for 15 minutes, then ethyl acetate was added and the mixture stirred for another 5 hours. The layers were partitioned. The aqueous phase was extracted twice more with ethyl acetate. The combined organic phase was washed with water, and then brine. The organic phase was dried over sodium sulfate, and then the solvents were evaporated. The residue was partially dissolved in methanol. The insoluble material was further (but not completely) dissolved in dimethyl sulfoxide. Both crude solutions were purified separately using Biotage reverse phase flash chromatography (12 g C18 SNAP, 5-95% acetonitrile/water with 0.1% formic acid). The like fractions from each purification were combined to give the title compound as a white solid (40 mg, 0.10 mmol, 25%). MS: 384.1 [M+H]$^+$.

Example 99: Synthesis of (E)-3-(3-(4-(2-cyclohexylvinyl)benzyl)isoxazol-5-yl)pyridin-2-amine

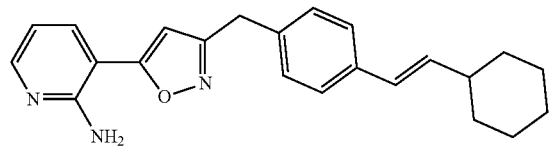

Di-tert-butyl [3-(3-(4-vinylbenzyl)isoxazol-5-yl)pyridin-2-yl]imidodicarbonate (0.50 g, 1.1 mmol), vinylcyclohexane (0.29 mL, 4.2 mmol), Grubbs catalyst 2$^{nd}$ generation (0.053 g, 0.0.064 mmol), and dichloromethane (7 mL) were combined in a sealed tube. The mixture was sparged with argon for 2 minutes, and then heated to 40° C. After 16 hours, another 2 equivalents of vinylcyclohexane (0.29 mL, 4.2 mmol) and another 0.03 equivalents of catalyst (0.026 g, 0.032) were added. The vial was sealed and sparged with argon for 2 min. The mixture was again heated to 40° C. and stirred for another 24 hours. After cooling to room temperature the reaction was quenched by addition of Isolute Si-Thiol resin (10 equivalents relative to Ru, 0.74 g, 0.96 mmol). The mixture was stirred for 3 hours before filtering through a plug of Celite. The filtrate was evaporated and the residue was purified using Biotage normal-phase flash chromatography (100 g SNAP Ultra, 5-60% ethyl acetate/hexane. The desired fractions were combined and evaporated to give di-tert-butyl [(E)-3-(3-(4-(2-cyclohexylvinyl)benzyl)isoxazol-5-yl)pyridin-2-yl]imidodicarbonate (0.17 g, 0.30 mmol, 28%). A portion of this material (0.10 g, 0.18 mmol) was dissolved in formic acid (5 mL) and stirred at room temperature for 4 hours. The solution was cooled to 0° C. and then basified to pH 10 with 50% aqueous sodium hydroxide solution. The mixture was further diluted with water and extracted three times with ethyl acetate. The combined organic phase was washed with water, and then brine. The organic phase was dried over sodium sulfate, and then the solvents were evaporated to give a solid residue. The solid was dissolved in 1,2-dimethoxyethane (5 mL), transferred through a 0.45µ syringe filter into a 50 mL conical tube, and then treated with 4M hydrogen chloride in dioxane (1.5 mL). No precipitate formed. The solvent was evaporated to give an off-white solid. The material was washed into a 50 mL conical tube using 1,2-dimethoxyethane (5 mL). The tube was centrifuged at 3200 rpm for 7 minutes. The supernatant was decanted, more 1,2-dimethoxyethane was added to the pellet. The suspension was vortexed, and then centrifuged at 3200 rpm for 7 min. The supernatant was decanted and the white pellet was dissolved with acetonitrile, transferred to a round bottom flask, and extensively dried under vacuum to give the title compound as a white solid hydrochloride salt (0.066 g, 0.17 mmol, 93%). MS: 360.2 [M+H]$^+$.

Example 100: Synthesis of 3-(3-(4-(2-cyclohexylethyl)benzyl)isoxazol-5-yl)pyridin-2-amine

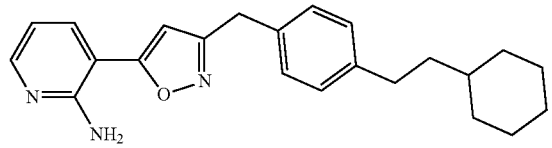

Palladium on carbon (10 wt %, 3 mg) was placed into a round bottom flask and covered with ethanol (0.5 mL). Di-tert-butyl [(E)-3-(3-(4-(2-cyclohexylvinyl)benzyl)isoxazol-5-yl)pyridin-2-yl]imidodicarbonate (0.070 g, 0.13 mmol) was transferred into the flask with more ethanol (0.5 mL). The head-space was purged with argon, and then with hydrogen. A balloon filled with hydrogen was affixed to the flask with a needle through a rubber septum. The mixture was stirred briskly for 3 hours before carefully filtering through a pad of Celite with methanol. The solvent was evaporated to give an oil which was purified using Biotage normal-phase flash chromatography (10 g SNAP Ultra, 5-60% ethyl acetate/hexane). The desired fractions were combined and evaporated to give di-tert-butyl [3-(3-(4-(2-cyclohexylethyl)benzyl)isoxazol-5-yl)pyridin-2-yl]imidodicarbonate (0.050 g, 0.089 mmol, 69%). This material was dissolved in formic acid (1 mL) and stirred at room temperature for 18 hours. The solution was cooled to 0° C. and then basified to pH 10 with 50% aqueous sodium hydroxide solution. The mixture was further diluted with water and extracted three times with ethyl acetate. The combined organic phase was washed with water, and then brine. The organic phase was dried over sodium sulfate, and then the solvents were evaporated. The residue was dissolved in 1,2-dimethoxyethane (5 mL), transferred through a 0.45μ syringe filter into a 50 mL conical tube, and then treated with 4M hydrogen chloride in dioxane (1.5 mL). A white precipitate formed. The tube was centrifuged at 3200 rpm for 7 minutes. The supernatant was decanted, more 1,2-dimethoxyethane was added to the pellet. The suspension was vortexed, and then centrifuged at 3200 rpm for 7 min. The centrifuge procedure was repeated for a third time. The supernatant was decanted and the white pellet was dissolved with acetonitrile, transferred to a round bottom flask, and extensively dried under vacuum to give the title compound as a white solid hydrochloride salt (0.030 g, 0.076 mmol, 85%). MS: 362.1 [M+H]⁺.

Example 101: Synthesis of 3-(1-((6-(benzyloxy) pyridin-3-yl)methyl)-1H-pyrazol-4-yl)pyridin-2-amine

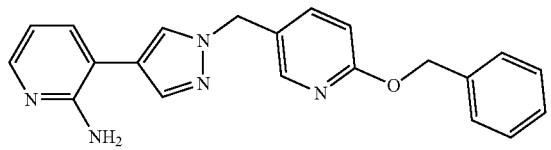

The title compound was prepared according to the procedure described for Example 63 using 2-(benzyloxy)-5-((4-bromo-1H-pyrazol-1-yl)methyl)pyridine (130 mg, 0.38 mmol) and 3-(4,4,5,5-tetramethyl-1,3,2-dioxaborolan-2-yl)pyridin-2-amine (150 mg, 0.68 mmol) to yield 3-(1-((6-(benzyloxy)pyridin-3-yl)methyl)-1H-pyrazol-4-yl)pyridin-2-amine (50 mg, 0.14 mmol, 37%). MS: 358.3 [M+H]⁺.

Example 102: Synthesis of (1-(4-((5-(2-aminopyridin-3-yl)isoxazol-3-yl)methyl)benzyl)-1H-pyrazol-4-yl)methanol

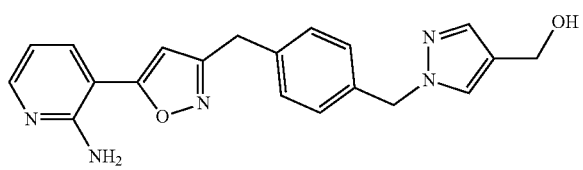

The title compound was prepared according to the procedure described for Example 4 using 1H-pyrazol-4-yl) methanol (105 mg, 1.07 mmol) to yield (1-(4-((5-(2-aminopyridin-3-yl)isoxazol-3-yl)methyl)benzyl)-1H-pyrazol-4-yl)methanol (59 mg, 0.16 mmol, 61%) as a white solid. MS: 362.4 [M+H]⁺.

Example 103: Synthesis of 3-(3-(4-((3-propylphenoxy)methyl)benzyl)isoxazol-5-yl)pyridin-2-amine

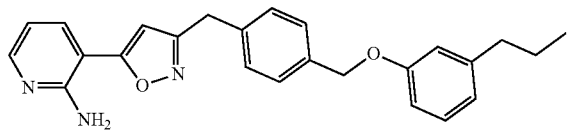 [SMILES: CCCc1cccc(OCc2ccc(Cc3cc(-c4cccnc4N)on3)cc2)c1]

A solution of 3-propylphenol (182 mg, 1.33 mmol) in NMP (0.5 mL) was added to a suspension of sodium hydride (60% w/mineral oil, 40 mg, 1.00 mmol) in NMP (1.5 mL). After stirring for 20 min at 21-25° C., a solution of 3-(3-(4-(chloromethyl)benzyl)isoxazol-5-yl)pyridin-2-amine (Intermediate B, 100 mg, 0.33 mmol) in NMP (1 ml) was added and the mixture was stirred for 4 min at 60° C. The cooled reaction mixture was directly purified by column chromatography (SiO₂, hexane/ethyl acetate). Fraction containing the product were concentrated under reduced pressure and further purified by HPLC to yield 3-(3-(4-((3-propylphenoxy)methyl)benzyl)isoxazol-5-yl)pyridin-2-amine (35 mg, 0.09 mmol, 26%). MS: 400.4 [M+H]⁺.

Example 104: Synthesis of 3-(3-(4-((3,4-dimethoxyphenoxy)methyl)benzyl)isoxazol-5-yl)pyridin-2-amine

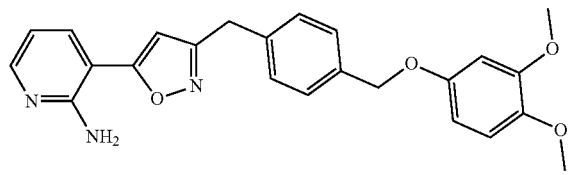 [SMILES: COc1ccc(OCc2ccc(Cc3cc(-c4cccnc4N)on3)cc2)cc1OC]

The title compound was prepared according to the procedure described for Example 103 using 3,4-dimethoxyphenol (206 mg, 1.33 mmol) to yield 3-(3-(4-((3,4-dimethoxyphenoxy)methyl)benzyl)isoxazol-5-yl)pyridin-2-amine (64 mg, 0.15 mmol, 46%) as a white solid. MS: 418.4 [M+H]⁺.

Example 105: Synthesis of 3-(3-(4-((pyridin-3-yloxy)methyl)benzyl)isoxazol-5-yl)pyridin-2-amine

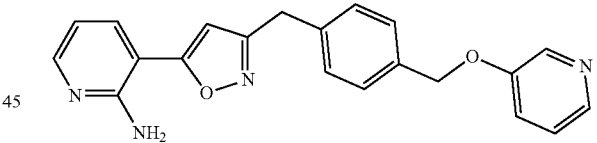

3-(3-(4-(chloromethyl)benzyl)isoxazol-5-yl)pyridin-2-amine (Intermediate B, 120 mg, 0.40 mmol), pyridine-3-ol (305 mg, 3.20 mmol) and potassium carbonate (443 mg, 3.20 mmol) were mixed in DMF (2 mL). The mixture was stirred for 1 h at 80° C. The cooled reaction mixture was directly purified by column chromatography (SiO₂, hexane/ ethyl acetate). Fraction containing the product were concentrated under reduced pressure and further purified by HPLC to yield 3-(3-(4-((pyridin-3-yloxy)methyl)benzyl)isoxazol-5-yl)pyridin-2-amine (12 mg, 0.03 mmol, 8%). 400 MHz ¹H NMR (CDCl₃) δ 8.38 (dd, J=2.8, 0.9 Hz, 1H), 8.23 (dd, J=4.4, 1.6 Hz, 1H), 8.14 (dd, J=4.9, 1.8 Hz, 1H), 7.70 (dd, J=7.7, 1.8 Hz, 1H), 7.41 (d, J=8.1 Hz, 2H), 7.32 (d, J=8.1 Hz, 2H), 7.28-7.19 (m, 2H), 6.71 (dd, J=7.7, 4.9 Hz, 1H), 6.26 (s, 1H), 5.41 (s, 2H), 5.10 (s, 2H), 4.08 (s, 2H). MS: 359.4 [M+H]⁺.

Example 106: Synthesis of 3-(3-(4-(((2-fluorophenyl)amino)methyl)benzyl)isoxazol-5-yl)pyridin-2-amine

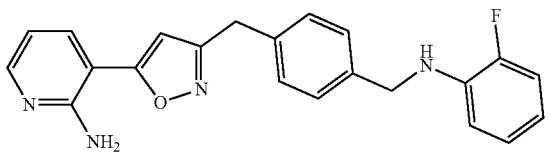

3-(3-(4-(chloromethyl)benzyl)isoxazol-5-yl)pyridin-2-amine (Intermediate B, 80 mg, 0.27 mmol) was dissolved in DMF (1.5 mL) and 2-fluoroaniline (297 mg, 2.67 mmol) was added. The mixture was stirred for 40 min at 90° C. The cooled reaction mixture was directly purified by column chromatography (SiO₂, hexane/ethyl acetate) to yield 3-(3-(4-((2-fluorophenyl)amino)methyl)benzyl)isoxazol-5-yl)pyridin-2-amine (54 mg, 0.14 mmol, 54%). MS: 375.3 [M+H]⁺.

Example 107: Synthesis of 3-(3-(4-(((3-fluorophenyl)amino)methyl)benzyl)isoxazol-5-yl)pyridin-2-amine

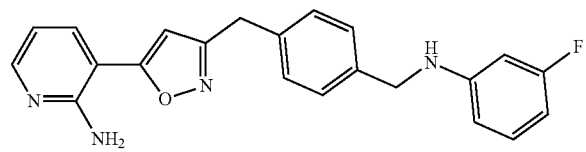

3-(3-(4-(chloromethyl)benzyl)isoxazol-5-yl)pyridin-2-amine (Intermediate B, 80 mg, 0.27 mmol) was dissolved in DMF (1.5 mL) and 3-fluoroaniline (297 mg, 2.67 mmol) was added. The mixture was stirred for 40 min at 90° C. The cooled reaction mixture was directly purified by column chromatography (SiO₂, hexane/ethyl acetate) to yield 3-(3-(4-(((3-fluorophenyl)amino)methyl)benzyl)isoxazol-5-yl)pyridin-2-amine (67 mg, 0.18 mmol, 67%). MS: 375. [M+H]⁺.

Example 108: Synthesis of 3-(3-(4-(((2,3-difluorophenyl)amino)methyl)benzyl)isoxazol-5-yl)pyridin-2-amine

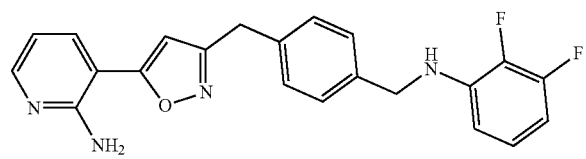 [SMILES: Nc1ncccc1-c1cc(Cc2ccc(CNc3cccc(F)c3F)cc2)no1]

3-(3-(4-chloromethyl)benzyl)isoxazol-5-yl)pyridin-2-amine (Intermediate B, 80 mg, 0.27 mmol) was dissolved in DMF (1.5 mL) and 2,3-difluoroaniline (345 mg, 2.67 mmol) was added. The mixture was stirred for 2 h at 110° C. The cooled reaction mixture was directly purified by column chromatography (SiO₂, hexane/ethyl acetate) to yield 3-(3-(4-(((2,3-difluorophenyl)amino)methyl)benzyl)isoxazol-5-yl)pyridin-2-amine (46 mg, 0.12 mmol, 44%). MS: 393.4 [M+H]⁺.

Example 109: Synthesis of 3-(3-(4-((4-methoxybenzyl)oxy)benzyl)isoxazol-5-yl)pyridin-2-amine

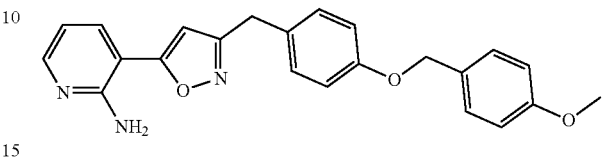

The title compound was prepared according to the procedure described for Example 26 using 1-(chloromethyl)-4-methoxybenzene (56 mg, 0.36 mmol) to yield 3-(3-(4-((4-methoxybenzyl)oxy)benzyl)isoxazol-5-yl)pyridin-2-amine (64 mg, 0.16 mmol, 55%) as a white solid. MS: 388.3 [M+H]⁺.

Example 110: Synthesis of 3-(3-(4-(pyridin-2-yloxy)benzyl)isoxazol-5-yl)pyridin-2-amine

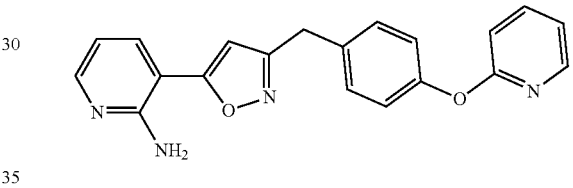

4-((5-(2-aminopyridin-3-yl)isoxazol-3-yl)methyl)phenol (100 mg, 0.37 mmol) was dissolved in DMF (1 mL) and potassium 2-methylpropane-2-olate (1M in THF, 0.33 mL, 0.33 mmol) was added dropwise. The mixture was stirred for 5 min and a solution of 2,6-difluoropyridine (51 mg, 0.52 mmol) in DMF (0.5 mL) was added. The resulting mixture was stirred for 6 h at 90° C. and directly purified by column chromatography (SiO₂, hexane/ethyl acetate). Fraction containing the product were concentrated under reduced pressure and further purified by reversed phase flash chromatography (C18, acetonitrile/water) to yield 3-(3-(4-(pyridin-2-yloxy)benzyl)isoxazol-5-yl)pyridin-2-amine (35 mg, 0.10 mmol, 27%) as a white solid. MS: 345.3 [M+H]⁺.

Example 111: Synthesis of 3-(3-(4-((6-fluoropridin-2-yl)oxy)benzyl)isoxazol-5-yl)pyridin-2-amine

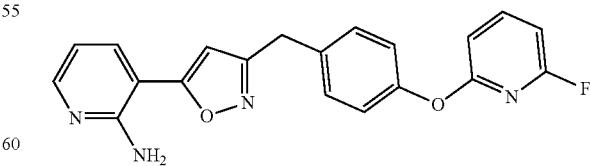

4-((5-(2-aminopyridin-3-yl)isoxazol-3-yl)methyl)phenol (80 mg, 0.30 mmol) was dissolved in DMF (1 mL) and potassium 2-methylpropane-2-olate (1M in THF, 0.33 mL, 0.33 mmol) was added dropwise. The mixture was stirred for 5 min and a solution of 2,6-difluoropyridine (48.2 mg, 0.42 mmol) in DMF (0.5 mL) was added. The resulting mixture was stirred for 3 min at 90° C. and directly purified by column chromatography (SiO₂, hexane/ethyl acetate). Fraction containing the product were concentrated under reduced pressure and further purified by reversed phase flash chromatography (C18, acetonitrile/water) to yield 3-(3-(4-((6-fluoropyridin-2-yl)oxy)benzyl)isoxazol-5-yl)pyridin-2-amine (65 mg, 0.18 mmol, 60%) as a white solid. 400 MHz ¹H NMR (CDCl₃) δ 8.14 (s, 1H), 7.80-7.69 (m, 2H), 7.31 (d, J=Hz, 2H), 7.11 (d, J=8.5 Hz, 2H), 6.77-6.68 (m, 2H), 6.60 (dd, J=7.8, 2.6 Hz, 1H), 6.30 (s, 1H), 5.43 (s, 2H), 4.07 (s, 2H). MS: 363.3 [M+H]⁺.

Example 112: Synthesis of 3-(3-(4-(thiazol-2-yl-methoxy)benzyl)isoxazol-5-yl)pyridin-2-amine

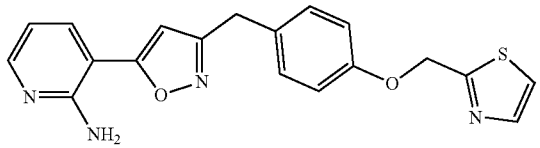

The title compound was prepared according to the procedure described for Example 26 using 2-(chloromethyl)-thiazole (48 mg, 0.36 mmol) to yield 3-(3-(4-(thiazol-2-ylmethoxy)benzyl)oxy)benzyl)isoxazol-5-yl)pyridin-2-amine (62 mg, 0.17 mmol, 57%) as a white solid. MS: 365.3 [M+H]⁺.

Example 113: Synthesis of 4-((4-((5-(2-aminopyridin-3-yl)isoxazol-3-yl)methyl)phenoxy)methyl)benzonitrile

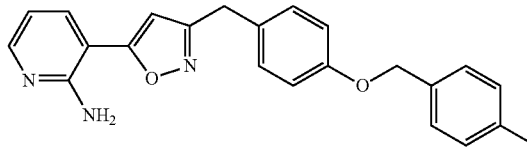

The title compound was prepared according to the procedure described for Example 26 using 4-(chloromethyl) benzonitrile (54 mg, 0.36 mmol) to yield 4-((4-((5-(2-aminopyridin-3-yl)isoxazol-3-yl)methyl)phenoxy)methyl) benzonitrile (69 mg, 0.18 mmol, 60%) as a white solid. MS: 383.3 [M+H]⁺.

Example 114: Synthesis of 3-(3-(4-((5-methylpyridin-3-yl)methoxy)benzyl)isoxazol-5-yl)pyridin-2-amine

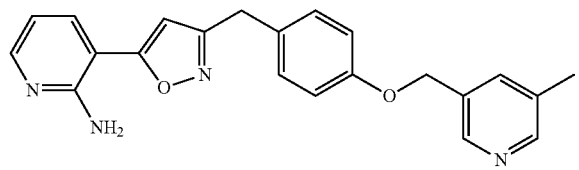 [SMILES: Cc1cncc(COc2ccc(Cc3cc(-c4cccnc4N)on3)cc2)c1]

The title compound was prepared according to the procedure described for Example 26 using 3-(chloromethyl)-5-methylpyridine hydrochloride (75 mg, 0.42 mmol) and potassium 2-methylpropane-2-olate (1M in THF, 0.75 mL, 0.75 mmol) to yield 3-(3-(4-((5-methylpyridin-3-yl)methoxy)benzyl)isoxazol-5-yl)pyridin-2-amine (87 mg, 0.23 mmol, 78%) as a white solid. MS: 373.3 [M+H]⁺.

Example 115: Synthesis of 3-(3-(4-((5-fluoropyridin-3-yl)methoxy)benzyl)isoxazol-5-yl)pyridin-2-amine

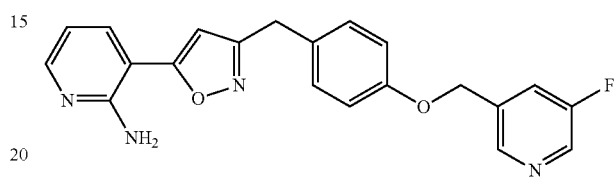

The title compound was prepared according to the procedure described for Example 26 using 3-(chloromethyl)-5-fluoropyridine hydrochloride (76 mg, 0.42 mmol) and potassium 2-methylpropane-2-olate (1M in THF, 0.75 mL, 0.75 mmol) to yield 3-((3-(4-((5-fluoropyridin-3-yl)methoxy) benzyl)isoxazol-5-yl)pyridin-2-amine (50 mg, 0.13 mmol, 44%) as a white solid. MS: 377.3 [M+H]⁺.

Example 116: Synthesis of 3-(3-(4-((6-fluoropyridin-3-yl)methoxy)benzyl)sioxazol-5-yl)pyridin-2-amine

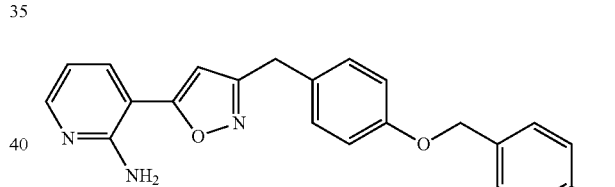

The title compound was prepared according to the procedure described for Example 26 using 5-(chloromethyl)-2-fluoropyridine (59 mg, 0.40 mmol) to yield 3-(3-(4-((6-fluoropyridin-(3-yl)methyoxy)benzyl)isoxazol-5-yl) pyridine-2-amine (56 mg, 0.15 mmol, 44%) as a white solid. MS: 377.4 [M+H]⁺.

Example 117: Synthesis of 3-(3-(4-((2-chloropyridin-4-yl)methoxy)benzyl)isoxazol-5-yl)pyridin-2-amine

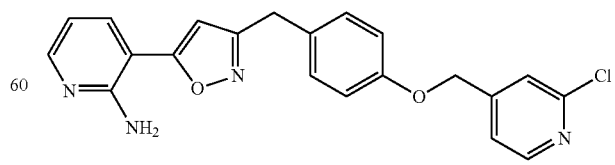

The title compound was prepared according to the procedure described for Example 26 using 2-(chloro-4-(chloromethyl)pyridine (66 mg, 0.40 mmol) to yield 3-(3-(4-((2- chloropyridin-4-yl)methoxy)benzyl)isoxazol-5-yl)pyridin-2-amine (54 mg, 0.14 mmol, 41%) as a white solid. MS: 393.5 [M+H]+.

Example 118: Synthesis of 6-((4-((5-(2-aminopyridin-3-yl)isoxazol-3-yl)methyl)phenoxy)methyl)picolinonitrile

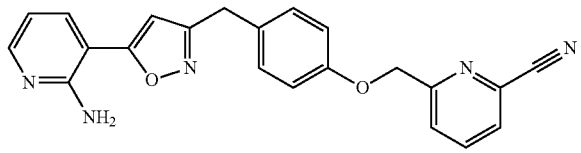 [SMILES: N#Cc1cccc(COc2ccc(Cc3cc(-c4cccnc4N)on3)cc2)n1]

The title compound was prepared according to the procedure described for Example 26 using 6-(chloromethyl)picolinonitrile (62 mg, 0.40 mmol) to yield 6-((4-((5-(2-aminopyridin-3-yl)isoxazol-3-yl)methyl)phenoxy)methyl)picolinonitrile (65 mg, 0.17 mmol, 50%) as a white solid. MS: 384.4 [M+H]+.

Example 119: Synthesis of 3-(4-((5-(2-aminopyridin-3-yl)isoxazol-3-yl)methyl)phenoxy)pyrazine 1-oxide

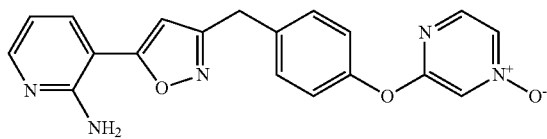 [SMILES: Nc1ncccc1-c1cc(Cc2ccc(Oc3c[n+]([O-])ccn3)cc2)no1]

The title compound was prepared according to the procedure described for Example 111 using 3-(chloropyrazine 1-oxide (55 mg, 0.42 mmol) to yield 3-(4-((5-(2-aminopyridin-3-yl)isoxazol-3-yl)methyl)phenoxy)pyrazine 1-oxide (64 mg, 0.18 mmol, 60%) as a white solid. MS: 362.4 [M+H]+.

Example 120: Synthesis of 3-(3-(4-(furan-3-ylmethyl)benzyl)isoxazol-5-yl)pyridin-2-amine

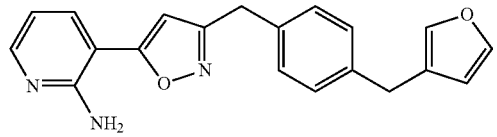 [SMILES: Nc1ncccc1-c1cc(Cc2ccc(Cc3ccoc3)cc2)no1]

The title compound was prepared according to the procedure described for Example 8 using furan-3-ylboronic acid (56 mg, 0.50 mmol) to yield 3-(3-(4-(furan-3-ylmethyl)benzyl)isoxazol-5-yl)pyridin-2-amine (69 mg, 0.21 mmol, 62%) as a white solid. MS: 332.2 [M+H]+.

Example 121: Synthesis of 3-(3-(4-(furan-2-ylmethyl)benzyl)isoxazol-5-yl)pyridin-2-amine

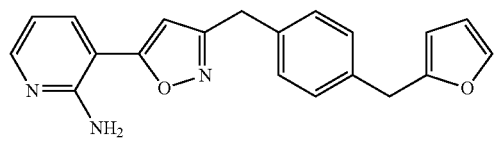

The title compound was prepared according to the procedure described for Example 8 using furan-2-ylboronic acid (56 mg, 0.50 mmol) to yield 3-(3-(4-(furan-2-ylmethyl)benzyl)isoxazol-5-yl)pyridin-2-amine (62 mg, 0.19 mmol, 56%) as a white solid. MS: 332.3 [M+H]+.

Example 122: Synthesis of 3-(3-(4-((5-methylfuran-2-yl)methyl)benzyl)isoxazol-5-yl)pyridin-2-amine

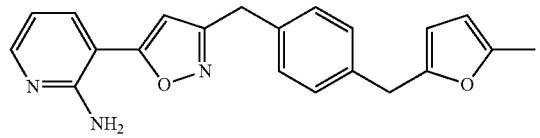 [SMILES: Cc1ccc(Cc2ccc(Cc3cc(-c4cccnc4N)on3)cc2)o1]

The title compound was prepared according to the procedure described for Example 8 using 4,4,5,5-tetramethyl-2-(5-methylfuran-2-yl)-1,3,2-dioxaborolane (104 mg, 0.50 mmol) to yield 3-(3-(4-((5-methylfuran-2-yl)methyl)benzyl)isoxazol-5-yl)pyridin-2-amine (73 mg, 0.21 mmol, 63%) as a white solid. MS: 346.3 [M+H]+.

Example 123: Synthesis of 3-(3-(4-((2,5-dihydrofuran-3-yl)methyl)benzyl)isoxazol-5-yl)pyridin-2-amine

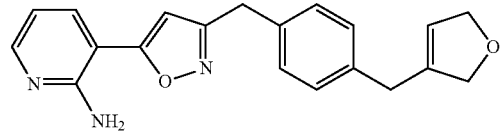 [SMILES: Nc1ncccc1-c1cc(Cc2ccc(CC3=CCOC3)cc2)no1]

The title compound was prepared according to the procedure described for Example 8 using 2-(2,5-dihydrofuran-3-yl)-4,4,5,5-tetramethyl-1,3,2-dioxaborolane (98 mg, 0.50 mmol) to yield 3-(3-(4-((2,5-dihydrofuran-3-yl)methyl)benzyl)isoxazol-5-yl)pyridin-2-amine (68 mg, 0.20 mmol, 61%) as a white solid. MS: 334.3 [M+H]+.

Example 124: Synthesis of 3-(3-(4-((5-fluorofuran-2-yl)methyl)benzyl)isoxazol-5-yl)pyridin-2-amine

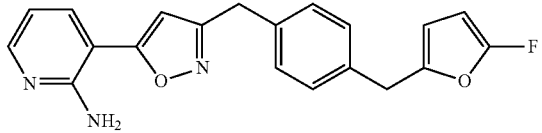

The title compound was prepared according to the procedure described for Example 8 using 2-(5-fluorofuran-2-yl)-4,4,5,5-tetramethyl-1,3,2-dioxaborolane (106 mg, 0.50 mmol) to yield 3-(3-(4-((5-fluorofuran-2-yl)methyl)benzyl)isoxazol-5-yl)pyridin-2-amine (84 mg, 0.24 mmol, 72%) as a white solid. MS: 350.3 [M+H]+.

Example 125: Synthesis of 3-(3-((2-(benzylthio)pyrimidin-3-yl)methyl)isoxazol-5-yl)pyridin-2-amine

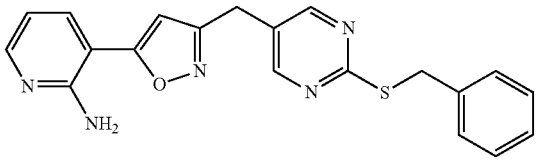 [SMILES: Nc1ncccc1-c1cc(Cc2cnc(SCc3ccccc3)nc2)no1]

Di-tert-butyl [3-(3-chloromethyl)-1,2-oxazol-5-yl)pyridin-2-yl]imidodicarbonate (1.67 g, 4.06 mmol) and (2-(benzylthio)pyrimidin-5-yl)boronic acid (1.00 g, 4.06 mmol) were mixed in DME (20 mL) in a sealable tube. A 2M solution of sodium carbonate in water (4.676 mL, 9.34 mmol) and palladium tetrakis triphenylphosphine (470 mg, 0.41 mmol) were added and the sealable tube was flushed with argon and sealed. The mixture was stirred for 5 h at 95° C. The cooled reaction mixture was poured into ethyl acetate (400 mL) and dried over Na₂SO₄, filtered and concentrated under reduced pressure. The residue was purified by column chromatography (SiO₂, hexane/ethyl acetate) to give the di-Boc protected coupling product as a yellow oil to which was added formic acid (8 mL). This mixture was stirred for 13 h at 21-25° C. to complete the di-Boc de-protection. To this mixture was added ice-water (80 mL) and ethyl acetate (160 mL). A 5M solution of NaOH in water was added until the pH of the aqueous layer was adjusted to 8-9. The layers were separated and the aqueous phase was extracted with ethyl acetate (3×30 mL). The combined organic layers were washed with brine (20 mL), dried over Na₂SO₄, filtered and concentrated under reduced pressure. The residue was purified by column chromatography (SiO₂, hexane/ethyl acetate) to yield 3-(3-((2-(benzylthio)pyrimidin-5-yl)methyl)isoxazol-5-yl)pyridin-2-amine (620 mg, 1.65 mmol, 41% as a white solid. MS: 376.4 [M+H]+.

Example 126: Synthesis of 1-(4-((5-(2-aminopyridin-3-yl)isoxazol-3-yl)methyl)benzyl)pyridin-2(1H)-one

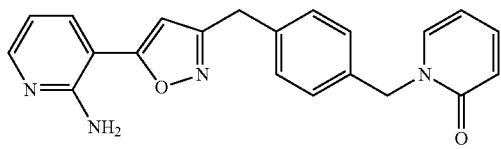 [SMILES: Nc1ncccc1-c1cc(Cc2ccc(Cn3ccccc3=O)cc2)no1]

3-(3-(4-((pyridin-2-yloxy)methyl)benzyl)isoxazol-5-yl)pyridin-2-amine (200 mg, 0.56 mmol) was dissolved in acetonitrile (2.5 mL) and lithium iodide (224 mg, 1.68 mmol) was added. The mixture was heated in the MW at 180° C. for 10 min. The cooled reaction mixture was poured into ethyl acetate (50 mL) and water (30 mL). The layers were separated and the aqueous phase was extracted with ethyl acetate (3×10 mL). The combined organic layers were washed with brine (10 mL), dried over Na₂SO₄, filtered and concentrated under reduced pressure. The residue was purified by column chromatography (SiO₂, hexane/ethyl acetate) to yield 1-(4-((5-(2-aminopyridin-3-yl)isoxazol-3-yl)methyl)benzyl)pyridin-2(1H)-one (46 mg, 0.13 mmol, 23%) as a white solid. MS: 359.4 [M+H]+.

Example 127: Synthesis of 3-(3-((6-((2-fluorobenzyl)oxy)pyridin-3-yl)methyl)isoxazol-5-yl)pyridin-2-amine

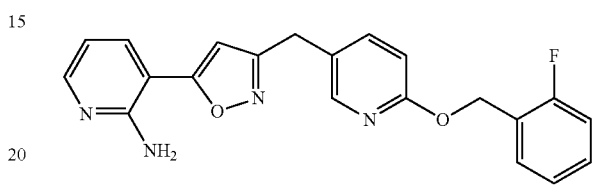

To a neat mixture of 3-(3-((6-fluoropyridin-4-yl)methyl)isoxazol-5-yl)pyridin-2-amine (60 mg, 0.22 mmol), (2-fluorophenyl)methanol (168 mg, 1.33 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO₂, hexane/ethyl acetate). Combined fractions were concentrated under reduced pressure. Residue was dissolved in acetonitrile (5 mL) and water (10 mL), frozen and lyophilized to yield 3-(3-((6-((2-fluorobenzyl)oxy)pyridin-3-yl)methyl)isoxazol-5-yl)pyridine-2-amine (27 mg, 0.073 mmol, 33%) as a white solid. MS: 377.0 [M+H]+.

Example 28: Synthesis of 3-(3-((6-((2-(trifluoromethyl)benzyl)oxy)pyridin-3-yl)methyl)isoxazol-5-yl)pyridin-2-amine

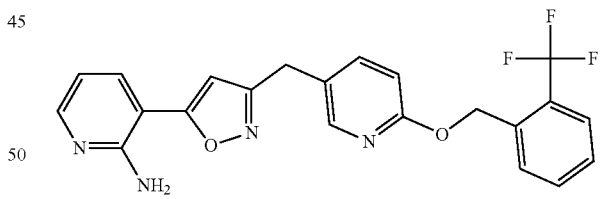

To a neat mixture of 3-(3-((6-fluoropyridin-4-yl)methyl)isoxazol-5-yl)pyridin-2-amine (50 mg, 0.19 mmol), (2-trifluoromethylphenyl)methanol (196 mg, 1.33 mmol) was added potassium 2-methylpropane-2-olate (1M in THF, 2.22 mL, 2.22 mmol) and the mixture was stirred for 30 min. The mixture was transferred to a silica gel samplet which was subsequently loaded on to a Biotage Snap column. The residue was purified by column chromatography (SiO₂, hexane/ethyl acetate). Combined fractions were concentrated under reduced pressure. Residue was dissolved in acetonitrile (5 mL) and water (10 mL), frozen and lyophilized to yield 3-(3-((6-((2-fluorobenzyl)oxy)pyridin-3-yl)methyl)isoxazol-5-yl)pyridine-2-amine (38 mg, 0.089 mmol, 48%) as a light pink solid. MS: 427.0 [M+H]+.

Example 129: Synthesis of 3-(3-((6-((5,6,7,8-tetrahydroquinolin-8-yl)oxy)pyridin-3-yl)methyl)isoxazol-5-yl)pyridin-2-amine

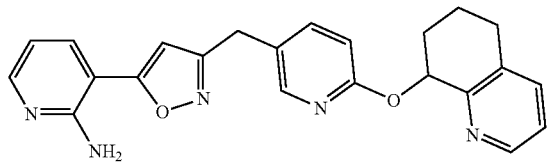

To a neat mixture of 3-(3-((6-fluoropyridin-4-yl)methyl)isoxazol-5-yl)pyridin-2-amine (50 mg, 0.19 mmol), 5,6,7,8-tetrahydroquinolin-8-ol (221 mg, 1.48 mmol) was added potassium 2-methylpropane-2-olate (1M in THF, 1.85 mL, 1.85 mmol) and the mixture was stirred for 30 min. The mixture was transferred to a silica gel samplet which was subsequently loaded on to a Biotage Snap column. The residue was purified by column chromatography (SiO₂, hexane/ethyl acetate). Combined fractions were concentrated under reduced pressure. Residue was dissolved in acetonitrile (5 mL) and water (10 mL), frozen and lyophilized to yield 3-(3-((6-((5,6,7,8-tetrahydroquinolin-8-yl)oxy)pyridin-3-yl)methyl)isoxazol-5-yl)pyridine-2-amine (30 mg, 0.076 mmol, 41%) as an orange glassy solid. MS: 400.3 [M+H]⁺.

Example 130: Synthesis of 3-(3-((6-(3-fluorophenoxy)pyridin-3-yl)methyl)isoxazol-5-yl)pyridin-2-amine

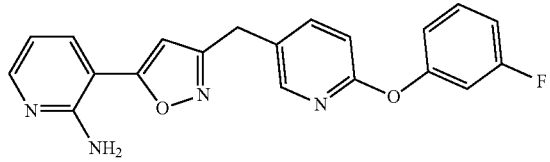

To a neat mixture of 3-(3-((6-fluoropyridin-4-yl)methyl)isoxazol-5-yl)pyridin-2-amine (50 mg, 0.19 mmol), 2-fluorophenol (207 mg, 1.85 mmol) was added potassium 2-methylpropane-2-olate (1M in THF, 1.85 mL, 1.85 mmol) and the mixture was stirred for 45 min at 140° C. in a sealed high pressure reaction vessel. The mixture was transferred to a silica gel samplet which was subsequently loaded on to a Biotage Snap column. The residue was purified by column chromatography (SiO₂, hexane/ethyl acetate). Combined fractions were concentrated under reduced pressure. Residue was dissolved in acetonitrile (5 mL) and water (10 mL), frozen and lyophilized to yield 3-(3-((6-((3-fluorophenoxy)pyridin-3-yl)methyl)isoxazol-5-yl)pyridine-2-amine (32 mg, 0.088 mmol, 48%) as a white solid. MS: 363.1 [M+H]⁺.

Example 131: Synthesis of 3-(3-((6-(2-fluorophenoxy)pyridin-3-yl)methyl)isoxazol-5-yl)pyridin-2-amine

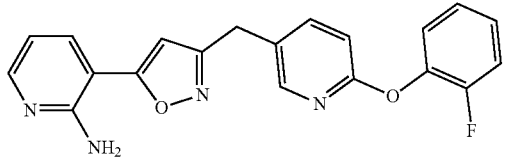 [SMILES: Nc1ncccc1-c1cc(Cc2ccc(Oc3ccccc3F)nc2)no1]

To a neat mixture of 3-(3-((6-fluoropyridin-4-yl)methyl)isoxazol-5-yl)pyridin-2-amine (50 mg, 0.19 mmol), 2-fluorophenol (207 mg, 1.85 mmol) was added potassium 2-methylpropane-2-olate (1M in THF, 1.85 mL, 1.85 mmol) and the mixture was stirred for 45 min at 140° C. in a sealed high pressure reaction mixture. The mixture was transferred to a silica gel samplet which was subsequently loaded on to a Biotage Snap column. The residue was purified by column chromatography (SiO₂, hexane/ethyl acetate). Combined fractions were concentrated under reduced pressure. Residue was dissolved in acetonitrile (5 mL) and water (10 mL), frozen and lyophilized to yield 3-(3-((6-((2-fluorobenzyl)oxy)pyridin-3-yl)methyl)isoxazol-5-yl)pyridine-2-amine (19 mg, 0.052 mmol, 28%) as a white solid. MS: 363.2 [M+H]⁺.

Example 132: Synthesis of 3-(3-(4-(benzyloxy)benzyl)isoxazol-5-yl)pyridine-2,6-diamine

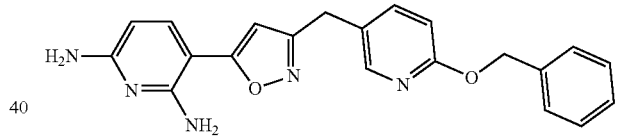

Step 1: Synthesis of 3-((trimethylsilyl)ethynyl)pyridine-2,6-diamine

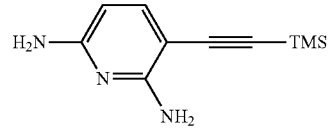

3-iodopyridine-2,6-diamine (2.640 g, 11.23 mmol), ethynyltrimethylsilane (2.207 g, 22.47 mmol), DIEA (4.90 ml, 28.1 mmol), and copper (I) iodide (0.214 g, 1.123 mmol) were combined in N-Methyl-2-pyrrolidinone (10 ml) under argon and was stirred for 2.5 hours at 45° C. The reaction mixture was poured into water and extracted with ethyl acetate three times. The organic phase was dried over sodium sulfate and concentrated under reduced pressure. The residue was purified by silica gel chromatography. Combined fractions were concentrated under reduced pressure to give 3-((trimethylsilyl)ethynyl)pyridine-2,6-diamine (1.20 g, 5.84 mmol, 52.0% yield). MS: 206.3 [M+H]⁺.

Step 1: Synthesis of 3-ethynylpyridine-2,6-diamine

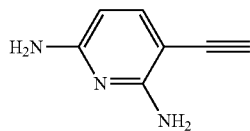

To a solution of 3-((trimethylsilyl)ethynyl)pyridine-2,6-diamine (1.200 g, 5.84 mmol) in THF (10 ml) was added TBAF (1.169 ml, 1.169 mmol) at 0° C. Reaction mixture was slowly brought up to room temperature and stirred at room temperature for 10 minutes. Water was added to the reaction mixture and then extracted with ethyl acetate three times. Combined organic phase was dried over sodium sulfate and the solvent was removed at reduced pressure. The residue was purified by silica gel chromatography to give 3-ethynylpyridine-2,6-diamine (0.724 g, 5.44 mmol, 93% yield). MS: 134.1 [M+H]$^+$.

Step 3: Synthesis of 1-(benzyloxy)-4-(2-nitroethyl)benzene

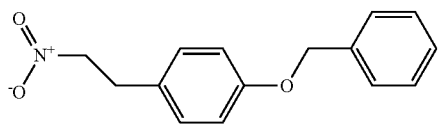

To a mixture of (E)-1-(benzyloxy)-4-(2-nitrovinyl)benzene (5.00 g, 19.59 mmol), acetic acid (5.000 ml, 87 mmol), and DMSO (60 ml) was added sodium borohydride (1.250 g, 33.0 mmol) at room temperature and stirred for 40 minutes. Water was added to the reaction mixture and organics were extracted with ethyl acetate. Solvents removed at reduced pressure. Residue was purified by silica gel column chromatography (ethyl acetate:hexane=1:3). Combined fractions were concentrated under reduced pressure to give 1-(benzyloxy)-4-(2-nitroethyl)benzene (1.500 g, 5.83 mmol, 29.8% yield). MS: 258.3 [M+H]$^+$.

Step 4: Synthesis of (Z)-2-(4-(benzyloxy)phenyl)-N-hydroxyacetimidoyl chloride

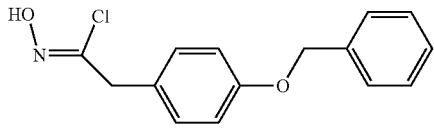 [SMILES: O/N=C(\Cl)Cc1ccc(OCc2ccccc2)cc1]

To a mixture of 1-(benzyloxy)-4-(2-nitroethyl)benzene (1.500 g, 5.83 mmol) in Methanol (15 ml) was added lithium methanolate (11.66 ml, 11.66 mmol) and was stirred for 15 minutes at room temperature. The reaction mixture was concentrated at reduced pressure. Dichloromethane (12 ml) and tetrahydrofuran (16 ml) were added to the residue. Reaction mixture was cooled to −78° C. and titanium tetrachloride (18.66 ml, 18.66 mmol) was added and stirred at 0° C. for 1 hour. The reaction mixture was cooled to −78° C. and water was added. Reaction mixture was gradually warmed to room temperature. Organics were dissolved in DCM and washed with brine. Residue was purified by normal phase chromatography to give (Z)-2-(4-benzyloxy)phenyl)-N-hydroxyacetimidoyl chloride (1.500 g, 5.44 mmol, 93% yield) MS: 276.7 [M+H]$^+$.

Step 5: Synthesis of 3-(3-(4-(benzyloxy)benzyl)isoxazol-5-yl)pyridine-2,6-diamine

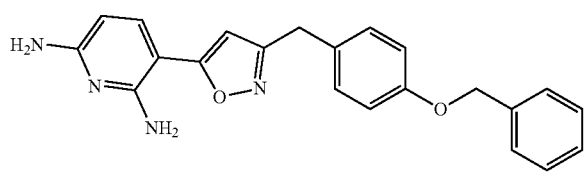 [SMILES: Nc1ccc(-c2cc(Cc3ccc(OCc4ccccc4)cc3)no2)c(N)n1]

To a mixture of (Z)-2-(4-(benzyloxy)phenyl)-N-hydroxyacetimidoyl chloride (1.500 g, 5.44 mmol) and 3-ethynylpyridine-2,6-diamine (0.724 g, 5.44 mmol) in THF was added triethylamine (1.517 ml, 10.88 mmol) and let stir overnight at room temperature. Reaction mixture was concentrated under reduced pressure. Residue was purified by silica gel chromatography. Combined fractions were concentrated under reduced pressure to give 3-(3-(4-(benzyloxy)benzyl)isoxazol-5-yl)pyridine-2,6-diamine (0.425 g, 1.141 mmol, 20.98% yield). MS: 373.3 [M+H]$^+$.

Example 133: Synthesis of 3-(3-(4-(thiazol-2-ylmethoxy)benzyl)isoxazol-5-yl)pyridine-2,6-diamine

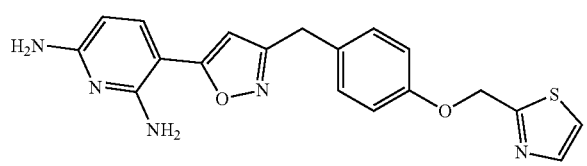 [SMILES: Nc1ccc(-c2cc(Cc3ccc(OCc4nccs4)cc3)no2)c(N)n1]

To a neat mixture of 4-((5-(2,6-diaminopyridin-3-yl)isoxazol-3-yl)methl)phenol (intermediate F, 55 mg, 0.20 mmol), 2-(chloromethyl)thiazole (31 mg, 0.23 mmol) was added potassium 2-methylpropane-2-olate (1M in THF, 0.21 mL, 0.21 mmol) and the mixture was stirred for 2 hours at room temperature. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-(4-(thiazol-2-ylmethoxy)benzyl)isoxazol-5-yl)pyridine-2,6-diamine (22 mg, 0.057 mmol, 30%) as a white solid. MS: 380.4 [M+H]$^+$.

Example 134: Synthesis of 3-(3-(4-((6-fluoropyridin-2-yl)oxy)benzyl)isoxazol-5-yl)pyridine-2,6-diamine

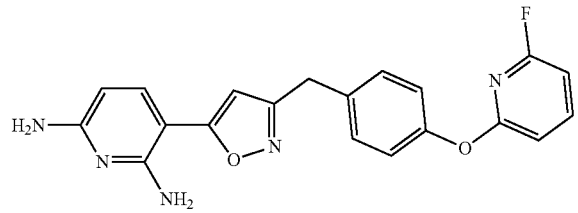 [SMILES: Nc1ccc(-c2cc(Cc3ccc(Oc4cccc(F)n4)cc3)no2)c(N)n1]

To a neat mixture of 4-((5-(2,6-diaminopyridin-3-yl)isoxazol-3-yl)methl)phenol (Intermediate F, (55 mg, 0.20 mmol), (2,6-difluoropyridine (31 mg, 0.27 mmol) was added potassium 2-methylpropane-2-olate (1M in THF, 0.21 mL, 0.21 mmol) and the mixture was stirred for 2 hours at room temperature. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-(4-((6-fluoropyridin-2-yl)oxy)benzyl)isoxazol-5-yl)pyridine-2,6-diamine (2.7 mg, 0.0072 mmol, 3.7%) as a white solid. MS: 378.4 [M+H]$^+$.

Example 135: Synthesis of 3-(3-(4-((3-methylbut-2-en-1-yl)oxy)benzyl)isoxazol-5-yl)pyridine-2,6-diamine

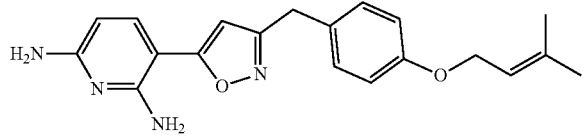

To a neat mixture of 4-((5-(2,6-diaminopyridin-3-yl)isoxazol-3-yl)methl)phenol (Intermediate F, (45 mg, 0.16 mmol), 1-bromo-3-methylbut-2-ene (29 mg, 0.19 mmol) was added potassium 2-methylpropane-2-olate (1M in THF, 0.35 mL, 0.35 mmol) and the mixture was stirred for 2 hours at room temperature. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-(4-((3-methylbut-2-en-1-yl)oxy)benzyl)isoxazol-5-yl)pyridine-2,6-diamine (17 mg, 0.049 mmol, 30%) as a white solid. MS: 351.4 [M+H]$^+$.

Example 136: Synthesis of 3-(3-(4-(((phenylamino)methyl)benzyl)isoxazol-5-yl)pyridine-2,6-diamine

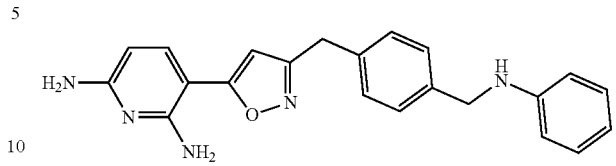

3-(3-(4-(chloromethyl)benzyl)isoxazol-5-yl)pyridine-2,6-diamine (Intermediate G, 75 mg, 0.24 mmol) and aniline (31 mg, 0.27 mmol) were dissolved in THF and the mixture was stirred for 18 hours at room temperature. The mixture was transferred to a silica gel samplet which was subsequently loaded on to a Biotage Snap column. The residue was purified by column chromatography (SiO$_2$, hexane/ethyl acetate). Combined fractions were concentrated under reduced pressure. Residue was dissolved in acetonitrile (5 mL) and water (10 mL), frozen and lyophilized to yield 3-(3-(4-((phenylamino)methyl)benzyl)isoxazol-5-yl)pyridin-2,6-diamine (36 mg, 0.098 mmol, 41%) as a white solid. MS: 372.5 [M+H]$^+$.

Example 137: Synthesis of 3-(3-(4-(((6-fluoropyridin-2-yl)oxy)methyl)benzyl)isoxazol-5-yl)pyridin-2-amine

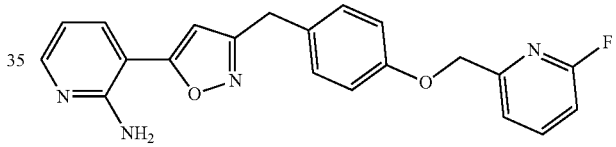

Step 1: Synthesis of (4-((5-(2-aminopyridin-3-yl)isoxazol-3-yl)methyl)phenyl)methanol

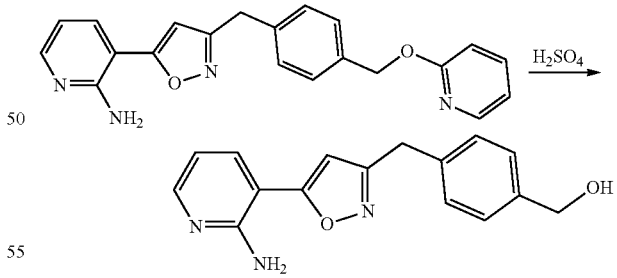

3-(3-(4-(pyridin-2-yloxy)methyl)benzyl)isoxazol-5-yl)pyridin-2-amine (1.5 g, 4.19 mmol) was dissolved in dioxane (20 mL) and water (20 mL) was added. Concentrated sulfuric acid (0.82 g, 8.37 mmol) was added and the mixture was heated to reflux for 6 h. The cooled mixture was poured into ice-cold pH 7 phosphate buffer (150 mL) containing 330 mg of NaOH (to neutralize excess of H$_2$SO$_4$) and was extracted with EtOAc (3×50 mL). The combined organic layers were washed with brine (50 mL), dried over Na$_2$SO$_4$, filtered and concentrated under reduced pressure.

The residue was purified using flash chromatography to give (4-((5-(2-aminopyridin-3-yl)isoxazol-3-yl)methyl)phenyl)methanol (1.09 g, 3.87 mmol, 93%) as a white solid. MS: 282.4 [M+H]$^+$.

Step 2: Synthesis of (4-((5-(2-(di-tert-butoxycarbonyl)-aminopyridin-3-yl)isoxazol-3-yl)methyl)phenyl)methanol tert-butyl carbonate

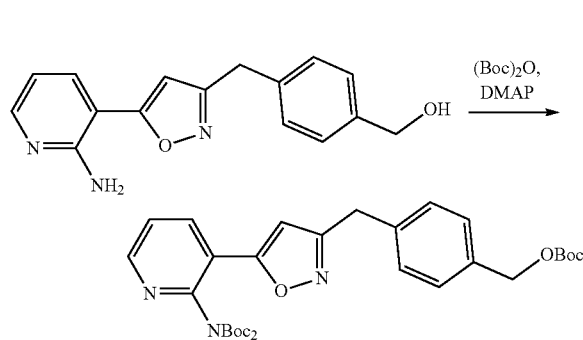

(4-((5-(2-aminopyridin-3-yl)isoxazol-3-yl)methyl)phenyl)methanol (1 g, 3.55 mmol) was dissolved in THF (8 mL) and N,N-dimethylpyridin-4-amine (DMAP, 0.043 g, 0.355 mmol) and di-tert-butyl dicarbonate (Boc)$_2$O, 2.72 g, 12.44 mol) were added. The mixture was stirred for 15 min at 21-25° C. and then for another 15 min at 50° C. The mixture was loaded directly onto celite and purified by flash chromatography to give (4-((5-(2-(di-tert-butoxycarbonyl)-aminopyridin-3-yl)isoxazol-3-yl)methyl)phenyl)methanol tert-butyl carbonate (1.21 g, 2.08 mmol, 58%). MS: 604.4 [M+Na]$^+$.

Step 3: Synthesis of (4-((5-(2-(di-tert-butoxycarbonyl)-aminopyridin-3-yl)isoxazol-3-yl)methyl)phenyl)methanol

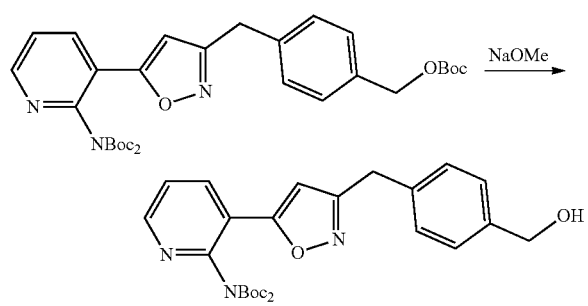

(4-((5-(2-(di-tert-butoxycarbonyl)-aminopyridin-3-yl)isoxazol-3-yl)methyl)phenyl)methanol tert-butyl carbonate (1 g, 1.72 mmol) was dissolved in MeOH (20 mL) and sodium methanolate (25% Wt in MeOH, 1.86 g, 8.60 mmol) was added. The mixture was stirred at 21-25° C. for 2 h. The reaction mixture was poured into a stirring mixture of water (100 mL) and ethyl acetate (100 mL). The layers were separated and the aqueous phase was further extracted with ethyl acetate (3×40 mL). The combined organic layers were washed with brine (40 mL), dried over Na$_2$SO$_4$, filtered and concentrated under reduced pressure. The residue was purified by column chromatography (SiO$_2$, hexane/ethyl acetate) to give (4-((5-(2-(di-tert-butoxycarbonyl)-aminopyridin-3-yl)isoxazol-3-yl)methyl)phenyl)methanol (320 mg, 0.66 mmol, 38%). MS: 482.5 [M+H]$^+$.

Step 4: Synthesis of di-tert-butyl [3-(3-(4-(((6-fluoropyridin-2-yl)oxy)methyl)benzyl)-1,2-oxazol-5-yl)pyridin-2-yl]imidodicarbonate

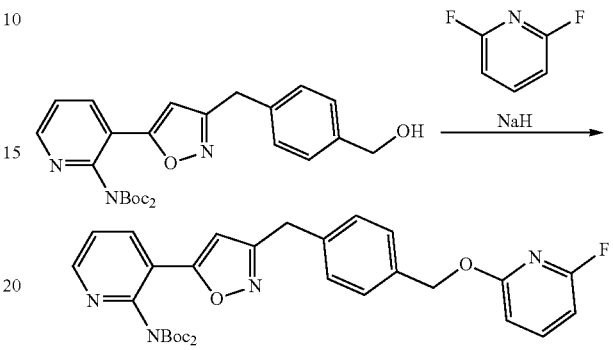

Sodium hydride (60% w/mineral oil, 13 mg, 0.32 mmol) was added to 0° C. to a solution of (4-((5-(2-(di-tert-butoxycabonyl)-aminopyridin-3-yl)isoxazol-3-yl)methyl)phenyl)methanol (130 mg, 0.27 mmol) and 2,6 difluoropyridine (155 mg, 1.35 mmol) in DMF (5 mL) and the mixture was stirred at 50° C. for 30 min. The cooled reaction mixture was poured into a stirring mixture of water (50 mL) and ethyl acetate (50 mL). The layers were separated and the aqueous phase was further extracted with ethyl acetate (3×20 mL). The combine organic layers were washed with brine (10 mL), dried over Na$_2$SO$_4$, filtered and concentrated under reduced pressure. The residue was purified by column chromatography (SiO$_2$, hexane/ethyl acetate) to obtain di-tert-butyl [3-(3-(4-(((6-fluoropyridin-2-yl)oxy)methyl)benzyl)-1,2-oxazol-5-yl)pyridin-2-yl]imidodicarbonate (116 mg, 0.20 mmol, 75%). MS: 577.5 [M+H]$^+$.

Step 5: Synthesis of 3-(3-(4-(((6-fluoropyridin-2-yl)oxy)methyl)benzyl)isoxazol-5-yl)pyridin-2-amine

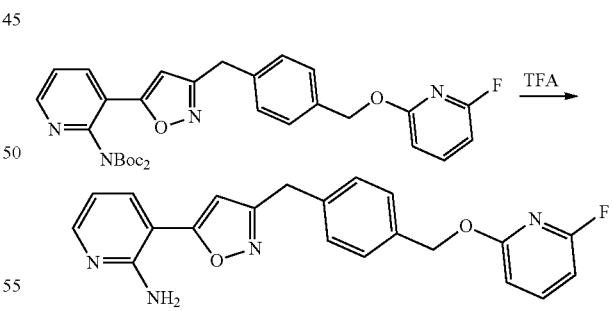

Di-tert-butyl [3-(3-(4-(((6-fluoropyridin-2-yl)oxy)methyl)benzyl)-1,2-oxazol-5-yl)pyridin-2-yl]imidodicarbonate (116 mg, 0.20 mmol) was dissolved in DCM (3 mL) and dioxane (3 mL). TFA (77 µL, 1.01 mmol) and HCl (4M in dioxane, 0.3 mL, 1.20 mmol) were added and the mixture was stirred for 3 days at 21-25° C. The mixture was poured into an ice-cold mixture of pH 7 phosphate buffer solution (0.5M, 50 mL) containing an additional amount of NaOH (89 mg, 2.22 mmol), to neutralize the excess of acids, and ethyl acetate (50 mL). The layers were separated and the aqueous phase was further extracted with ethyl acetate (3×50 mL). The combined organic layers were washed with brine (30 mL), dried over Na$_2$SO$_4$, filtered and concentrated under reduced pressure. The residue was purified by column chromatography (SiO$_2$, hexane/ethyl acetate) to yield 3-(3-(4-(((6-fluoropyridin-2-yl)oxy)methyl)benzyl)isoxazol-5-yl)pyridin-2-amine (48 mg, 0.13 mmol, 63%). MS: 377.2 [M+H]$^+$.

Examples 138-171 can be synthesized as described in any of the examples above.

Example 172: Synthesis of (2-amino-3-(3-(4-((6-fluoropyridin-2-yl)oxy)benzyl)isoxazol-5-yl)pyridin-1-ium-1-yl)methyl hydrogen phosphate

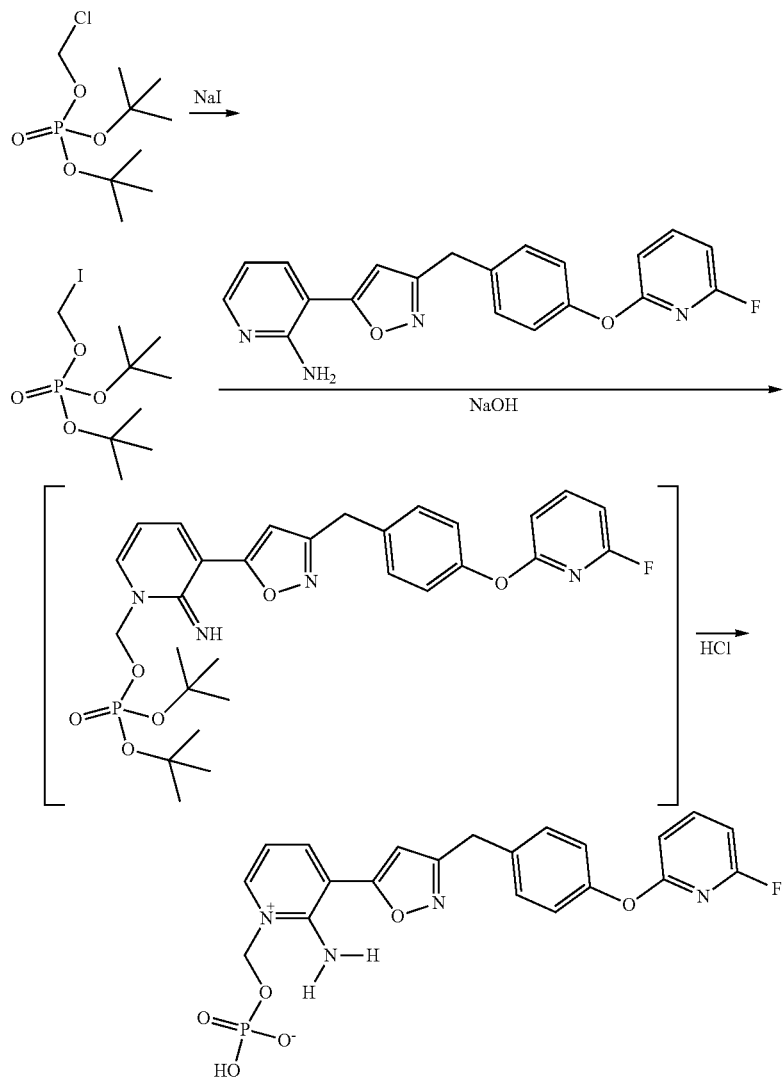

Sodium iodide (2.379 g, 15.87 mmol) and N-ethyl-N-isopropylpropan-2-amine (0.205 g, 1.587 mmol) were added to THF (7 mL). Di-tert-butyl (chloromethyl) phosphate (2.463 g, 9.52 mmol) was added and the mixture was stirred at 45° C. for 1.5 h. 3-(3-(4-(((6-fluoropyridin-2-yl)oxy)benzyl)isoxazol-5-yl)pryidin-2-amine (2.3 g, 6.35 mmol) and toluene (7 mL) were added followed by the addition of sodium hydroxide (5 N, 7 mL, 35 mmol). The mixture was stirred at 45° C. for 30 min and then for 1 h at 23° C. Another batch of freshly prepared iodomethyl phosphate (following the same procedure as described above, but using 1.2 g sodium iodide, 0.1 g N-ethyl-N-isopropylpropan-2-amine and 1.25 g di-tert-butyl (chloromethyl) phosphate in 4 mL of THF) was added and the mixture was stirred for 23° C. for 12 h. The organic layer was separated and the aq. phase extracted 3× with 5 mL of mixture of THF/toluene (1:1). The combined organic layers were cooled to 0° C. and 5N HCl (7 mL) was added. The mixture was stirred at 23° C. for 2 h. Water, ice and EtOAc were added and the pH of the aqueous phase was adjusted to 8-10. The aq. layer was extracted 3× with EtOAc and then its pH was adjusted to about 7 to 5.5. The mixture became slightly cloudy during this process, but no significant precipitation occurred. The mixture was now filtered through a plug of reversed phase C18 silica gel (or alternatively a 0.45 micrometer PTFE filter). The pH of the clear filtrate was adjusted slowly to 4-5, while precipitation of the product occurred. The mixture was stirred for about 1.5 h and the product collected by filtration. The filter cake was thoroughly washed with water and 1× with a small amount of MeOH and finally dried under vacuum to give (2-amino-3-(3-(4-(((6-fluoropyridin-2-yl)

oxy)benzyl)isoxazol-5-yl)pyridin-1-ium-1-yl)methyl hydrogen phosphate (1.45 g, 3.07 mmol, 48% yield). MS: 473.4 [M+H]$^+$. $^{31}$P NMR (200 MHz, DMOS-d$_6$/D$_2$O) δ 3.61. $^1$H NMR (400 MHz, DMOS-d$_6$/D$_2$O) δ 7.83 (q, J=8.1 Hz, 1H), 7.73 (d, J=7.0 Hz, 2H), 7.30 (m, 2H), 7.00 (m, 2H), 6.76 (s, 1H), 6.72 (m, 2H), 6.33 (t, J=7.0 Hz, 1H), 5.39 (d, J=7.4 Hz, 2H), 3.99 (s, 2H), signals for —NH$_2$ and —OH not observed.

Example 173: Synthesis of (2-amino-3-(3-(4-benzyloxy)benzyl)isoxazol-5-yl)pyridin-1-ium-1-yl) methyl hydrogen phosphate The title compound was prepared according to the procedure of Example 146 using sodium iodide (944 mg, 6.3 mmol), N-ethyl-N-isopropylpropan-2-amine (81 mg, 0.63 mmol), di-tert-butyl (chloromethyl) phosphate (977 mg, 3.78 mmol), 3-(3-(4-(benzyloxy)benzyl)isoxazol-5-yl)pyridin-2-amine (900 mg, 2.52 mmol) and sodium hydroxide (5N, 2.77 mL, 13.85 mmol) to give (2-amino-3-(3-(4-(benzyloxy)benzyl)isoxazol-5-yl)pyridin-1-ium-1-yl)methyl hydrogen phosphate (390 mg, 0.83 mmol, 33% yield). $^{31}$P NMR (200 MHz, DMOS-d$_6$/D$_2$O) δ 3.21 $^1$H NMR (500 MHz, DMOS-d$_6$/D$_2$O) δ 7.64-7.55 (m, 2H), 7.37-7.21 (m, 5H), 7.20-7.13 (m, 2H), 6.92-6.85 (m, 2H), 6.75-6.71 (m, 1H), 6.07 (t, J=7.0 Hz, 2H), 5.28 (d, J=6.9 Hz, 2H), 5.00 (s, 2H), 3.88 (s, 2H), signals for —NH$_2$ and —OH not observed. MS: 468.4[M+H]$^+$.

Example 174: Synthesis of (2-amino-3-(3-9(6-(benzyloxy)pyridin-3-yl)methyl)isoxazol-5-yl)pyridin-1-ium-1-yl)methyl hydrogen phosphate The title compound was prepared similarly to the procedure Example 146 using sodium iodide (1.5 g, 9.8 mmol), N-ethyl-N-isopropylpropan-2-amine (0.17 mL, 0.98 mmol), di-tert-butyl (chloromethyl) phosphate (1.4 mL, 5.9 mmol), 3-(3-((6-benzyloxy)pyridin-3-yl)methyl)isoxazol-5-yl)pyridin-2-amine (1.4 g, 3.9 mmol) and sodium hydroxide (5 N, 4.4 mL, 22 mmol) to give (2-amino-3-(3-((6-benzyloxy)pyridin-3-yl)methyl)isoxazol-5-yl)pyridin-1-ium-1-yl) methyl hydrogen phosphate (0.58 g, 1.2 mmol, 32% yield). MS: 469.4 [M+H]$^+$.

Example 175: Synthesis of (2-amino-3-(3-((6-(2-fluorophenoxy)pyridin-3-yl)methyl)isoxazol-5-yl) pyridin-1-ium-1-yl)methyl hydrogen phosphate The title compound was prepared according to the procedure of Example 146 using sodium iodide (2.64 g, 17.59 mmol), N-ethyl-N-isopropylpropan-2-amine (0.277 g, 1.76 mmol), di-tert-butyl (chloromethyl) phosphate (2.73 g, 10.56 mmol), 3-(3-((6-(2-fluorophenoxy)pyridin-3-yl) methyl)isoxazol-5-yl)pyridin-2-amine (2.55 g, 7.04 mmol) and sodium hydroxide (5N, 7.74 mL, 38.7 mmol) to give (2-amino-3-(3-((6-(2-fluorophenoxy)pyridin-3-yl)methyl) isoxazol-5-yl)pyridin-1-ium-1-yl)methyl hydrogen phosphate (340 mg, 0.72 mmol, 10% yield. MS: 473.4 [M+H]$^+$.

Example 176: (2-amino-3-(3-((6-(3,5-difluorophenoxy)pyridin-3-yl)methyl)isoxazol-5-yl)pyridin-1-ium-1-yl)methyl hydrogen phosphate The compound was synthesized from Example 81 according to methods described above. MS: 491.1 [M+H]$^+$.

Examples 177-184 can be synthesized as described in any of the above examples

Example 185: 3-(3-(4-(benzyloxy)benzyl)isoxazol-5-yl)pyridin-2-amine

The compound was synthesized from Intermediate A and (4-(benzyloxy)phenyl)boronic acid according to methods described above. 400 MHz $^1$H NMR (CDCl$_3$) δ 8.12 (dd, J=4.9, 1.8 Hz, 1H), 7.70 (dd, J=7.7, 1.8 Hz, 1H), 7.47-7.27 (m, 5H), 7.26-7.16 (m, 2H), 7.02-6.90 (m, 2H), 6.70 (dd, J=7.7, 4.9 Hz, 1H), 6.24 (s, 1H), 5.50 (s, 2H), 5.05 (s, 2H), 4.00 (s, 2H). MS: 358.3 [M+H]$^+$.

Example 186: 3-(3-((6-(phenylthio)pyridin-3-yl) methyl)isoxazol-5-yl)pyridin-2-amine The compound was synthesized from Intermediate E and benzenethiol according to methods described above. MS: 361.3 [M+H]$^+$.

Example 187: 3-(3-((6-((4-fluorobenzyl)oxy)pyridin-3-yl)methyl)isoxazol-5-yl)pyridin-2-amine The compound was synthesized from Intermediate E and (4-fluorophenyl)methanol according to methods described above. MS: 377.2 [M+H]$^+$.

Example 188: 3-(3-((6-((2-phenylazetidin-1-yl)pyridin-3-yl)methyl)isoxazol-5-yl)pyridin-2-amine The compound was synthesized from Intermediate E and 2-phenylazetidine according to methods described above. MS: 384.2 [M+H]$^+$.

Example 189: 3-(3-(4-((2,5-difluorophenoxy) methyl)benzyl)isoxazol-5-yl)pyridin-2-amine The compound was synthesized from Intermediate B and 2,5-difluorophenol according to methods described above. MS: 393.8 [M+H]$^+$.

Example 190: 3-(3-(4-((2,3,5-trifluorophenoxy) methyl)isoxazol-5-yl)pyridin-2-amine The compound was synthesized from Intermediate B and 2,3,5-trifluorophenyl according to methods described above. MS: 411.9 [M+H]$^+$.

Example 191: (4-((5-(2-aminopyridin-3-yl)isoxazol-3-yl)methyl)phenyl)(phenyl)methanone The compound was synthesized from Intermediate A and (4-benzoylphenyl)boronic acid according to methods described above. 500 MHz $^1$H NMR (DMSO-d6) δ 8.10 (dd, J=4.8, 1.8 Hz, 1H), 7.8 (dd, J=7.7, 1.8 Hz, 1H), 7.76-7.62 (m, 5H), 7.59-7.50 (m, 4H), 6.87 (s, 1H), 6.70 (dd, J=7.7, 4.7 Hz, 1H), 6.28 (s, 2H), 4.17 (s, 2H). MS: 356.1 [M+H]$^+$.

Example 192: 3-(3-(4-((5-fluoro-2-methoxyphenoxy)methyl)benzyl)isoxazol-5-yl)pyridin-2-amine The compound was synthesized from Intermediate B and 5-fluoro-2-methoxyphenol according to methods described above. MS: 406.0 [M+H]$^+$.

Example 193: 3-(3-(4-((2,3,4-trifluorophenyl)amino)methyl)benzylisoxazol-5-yl)pyridin-2-amine The compound was synthesized from Intermediate B and 2,3,4-trifluoroaniline according to methods described above. MS: 411.1 [M+H]⁺.

Example 194: (E)-3-(3-(4-(3-phenylprop-1-en-1-yl)benzylisoxazol-5-yl)pyridin-2-amine The compound was synthesized from Example 97 according to methods described for Example 99 but using allylbenzene. 500 MHz ¹H NMR (DMSO-d6) δ 8.08 (dd, J=4.8, 1.8 Hz, 1H), 7.86 (dd, J=7.7, 1.8 Hz, 1H), 7.40-7.16 (m, 9H), 6.79 (s, 1H), 6.69 (dd, J=7.7, 4.7 Hz, 1H), 6.50-6.36 (m, 2H), 6.25 (s, 2H), 4.00 (s, 2H), 3.51 (d, J=6.4 Hz, 2H). MS: 368.2 [M+H]⁺.

Example 195: 3-(3-((6-((2-bromopyridin-4-yl)methoxy)pyridin-3-yl)methyl)isoxazol-5-yl)pyridin-2-amine The compound was synthesized from Intermediate E and (2-bromopyridin-4-yl)methanol according to methods described above. MS: 440.2 [M+H]⁺.

Example 196: 3-(3-(4-(((2,5-difluorophenyl)amino)methyl)benzylisoxazol-5-yl)pyridin-2-amine The compound was synthesized from Intermediate B and 2,5-difluoroaniline according to methods described above. MS: 293.2 [M+H]⁺.

Example 197: (2-amino-3-(3-((6-(3-fluorophenoxy)pyridin-3-yl)methyl)isoxazol-5-yl)pyridin-2-ium-1-yl)methyl hydrogen phosphate The compound was synthesized from Example 130 according to methods described above. ³¹P NMR (200 MHz, DMOS-d₆/D₂O) δ 5.16. ¹H NMR (500 MHz, DMOS-d₆/D₂O) δ 8.15 (dd, J=7.15, 1.5 Hz, 2H), 8.10-8.04 (m, 2H), 7.79 (dd, J=8.5, 2.5 Hz, 1H), 7.38 (td, J=8.5, 6.9 Hz, 1H), 7.01-6.83 (m, 6H, 5.59 (d, J=8.0 Hz, 2H), 4.04 (s, 2H), signals for —NH₂ and —OH not observed. MS: 473.3 [M+H]⁺.

Example 198: 3-(3-(4-(((3,5-difluoro-2-methoxyphenyl)amino)methyl)benzyl)isoxazol-5-yl)pyridin-2-amine The compound was synthesized from Intermediate B and 3,5-difluoro-2-methoxyaniline according to methods described above. MS: 423.1 [M+H]⁺.

Example 199: 3-(3-(4-((1H-1,2,4-triazol-1-yl)methyl)benzyl)isoxazol-5-yl)pyridin-2-amine The compound was synthesized from Intermediate B and 1H-1,2,4-triazole according to methods described above. 500 MHz ¹H NMR (DMSO-d6) δ 8.64 (s, 1H), 8.08 (dd, J=4.8, 1.8 Hz, 1H), 7.96 (s, 1H), 7.85 (dd, J=7.7, 1.9 Hz, 1H), 7.34-7.28 (m, 2H), 7.28-7.22 (m, 2H), 6.79 (s, 1H), 6.69 (dd, J=7.7, 4.8 Hz, 1H), 6.24 (s, 2H), 5.39 (s, 2H), 4.01 (s, 2H). MS: 333.1 [M+H]⁺.

Example 200: 3-(3-(4-((4H-1,2,4-triazol-4-yl)methyl)benzyl)isoxazol-5-yl)pyridin-2-amine The compound was synthesized from Intermediate B and 1H-1,2,4-triazole according to methods described above. 500 MHz ¹H NMR (DMSO-d6) δ 8.59 (s, 2H), 8.08 (dd, J=4.8, 1.9 Hz, 1H), 7.85 (dd, J=7.7, 1.8 Hz, 1H), 7.37-7.24 (m, 4H), 6.79 (s, 1H), 6.69 (dd, J=7.7, 4.7 Hz, 1H), 6.24 (s, 2H), 5.25 (s, 2H), 4.02 (s, 2H). MS: 333.2 [M+H]⁺.

Example 201: 3-(3-(4-(((3-fluoro-5-methoxyphenyl)amino)methyl)benzylisoxazol-5-yl)pyridin-2-amine The compound was synthesized from Intermediate B and 3-fluoro-5-methoxyaniline according to methods described above. MS: 405.2 [M+H]⁺.

Example 202: 3-(3-((6-2-1H-1,2,4-triazol-1-yl)ethoxy)pyridin-3-yl)methyl)isoxazol-5-yl)pyridin-2-amine The compound was synthesized from Intermediate E and 2-(1H-1,2,4-triazol-1-yl)ethan)-1-ol according to methods described above. MS: 364.2 [M+H]⁺.

Example 203: 3-(3-(4-(pyridin-2-yl)benzyl)isoxazol-5-yl)pyridin-2-amine

The compound was synthesized from Intermediate A and 4-(2-Pyridinyl)phenylboronic acid pinacol ester according to methods described above. 500 MHz ¹H NMR (DMSO-d6) δ 8.79 (ddd, J=5.5, 1.8, 0.8 Hz, 1H), 8.44-8.33 (m, 2H), 8.31-8.19 (m, 4H), 8.15-8.09 (m, 2H), 7.81-7.74 (m 1H), 7.60-7.54 (m, 2H), 7.12 (s, 1H), 7.05 (dd, J=7.6, 6.2 Hz, 1H), 4.21 (s, 2H). MS: 329.1 [M+H]⁺.

Example 204: 3-(3-(4-(pyridin-4-yl)benzyl)isoxazol-5-yl)pyridin-2-amine

The compound was synthesized from Intermediate A and 4-(Pyridin-4-yl)phenylboronic acid pinacol ester according to methods described above. MS: 329.2 [M+H]⁺.

Example 205: 3-(3-((6-((4-fluorophenyl)pyridin-3-yl)methyl)isoxazol-5-yl)pyridin-2-amine The compound was synthesized from Intermediate A and 6-(4-Fluorophenyl)pyridine-3-boronic acid according to methods described above. 500 MHz ¹H NMR (DMSO-d6) δ 8.75 (dd, J=2.3, 1.0 Hz, 1H), 8.39 (dd, J=7.7, 1.6 Hz, 1H), 8.28-8.02 (m, 7H), 7.42-7.33 (m, 2H), 7.12 (s, 1H), 7.05 (dd, J=7.6, 6.1 Hz, 1H), 4.26 (s, 2H). MS: 347.1 [M+H]⁺.

Example 206: 3-(3-((6-(imidazo[1,2-a]pyridine-7-ylmethoxy)pyridin-3-yl)methyl)isoxazol-5-yl)pyridin-2-amine The compound was synthesized from Intermediate E and imidazo[1,2-a]pyridine-7-ylmethanol according to methods described above. MS: 399.2 [M+H]⁺.

Example 207: 3-(3-((6-((5-fluoro-2-methoxypyridin-4-yl)methoxy)pyridin-3-yl)methyl)isoxazol-5-yl)pyridin-2-amine The compound was synthesized from Intermediate E and (5-fluoro-2-methoxypyridin-4-yl)methanol according to methods described above. MS: 408.0 [M+H]⁺.

Example 208: 3-(3-(4-(3-fluorobenzyl)benzyl)isoxazol-5-yl)pyridin-2-amine

The compound was synthesized from Intermediate B and (3-fluorophenyl)boronic acid according to methods described above. 500 MHz $^1$H NMR (DMSO-d6) δ 8.08 (dd, J=4.8, 1.8 Hz, 1H), 7.86 (dd, J=7.7, 1.9 Hz, 1H), 7.34-7.28 (m, 1H), 7.25 (d, J=8.3 Hz, 2H), 7.21 (d, J=8.2 Hz, 2H), 7.09-7.03 (m, 2H), 7.02-6.96 (m, 1H), 6.79 (s, 1H), 6.69 (dd, J=7.7, 4.8 Hz, 1H), 6.24 (s, 2H), 3.98 (s, 2H), 3.93 (s, 2H). MS: 377.2 [M+H]$^+$.

Example 209: 2-(3-(4-((5-(2-aminopyridin-3-yl)isoxazol-3-yl)methyl)benzyl)phenyl)propan-2-ol The compound was synthesized from Intermediate B and (3-(2-hydroxypropan-2-yl)phenyl)boronic acid according to methods described above. MS: 400.3 [M+H]$^+$.

Example 210: 3-(3-((6-((2-chloro-3-fluoropyridin-3-yl)methoxy)pyridin-3-yl)methyl)isoxazol-5-yl)pyridin-2-amine The compound was synthesized from Intermediate E and (2-chloro-3-fluoropyridin-4-yl)methanol according to methods described above. MS: 412.2 [M+H]$^+$.

Example 211: N-(3-(4-((5-(2-aminopyridin-3-yl)isoxazol-3-yl)methyl)benzyl)phenyl)methanesulfonamide The compound was synthesized from Intermediate B and (3-(methylsulfonamido)phenyl)boronic acid according to methods described above. MS: 435.3 [M+H]$^+$.

Example 212: 3-(3-(4-(3,5-difluorobenzyl)benzyl)isoxazol-5-yl)pyridin-2-amine

The compound was synthesized from Intermediate B and (3,5-difluorophenyl)boronic acid according to methods described above. 500 MHz $^1$H NMR (DMSO-d6) δ 8.08 (dd, J=4.8, 1.9 Hz, 1H), 7.86 (dd, J=7.7, 1.9 Hz, 1H), 7.25 (q, J=8.3 Hz, 4H), 7.06-6.93 (m, 3H), 6.80 (s, 1H), 6.69 (dd, J=7.7, 4.7 Hz, 1H), 6.24 (s, 2H), 3.99 (s, 2H), 3.93 (s, 2H). MS: 377.9 [M+H]$^+$.

Example 213: 3-(3-((6-(3-phenylpropoxy)pyridin-3-yl)methyl)isoxazol-5-yl)pyridin-2-amine The compound was synthesized from Intermediate E and (3-phenylpropan-1-ol according to methods described above. MS: 387.2 [M+H]$^+$.

Example 214: 3-(3-((6-(3-(4-(benzyloxy)phenyl)propoxy)pyridin-3-yl)methyl)isoxazol-5-yl)pyridin-2-amine The compound was synthesized from Intermediate E and (3-(4-(benzyloxy)phenyl)propan-1-ol according to methods described above. MS: 493.1 [M+H]$^+$.

Example 215: 3-(3-((6-(2,2-diphenylethoxy)pyridin-3-yl)methyl)isoxazol-5-yl)pyridin-2-amine The compound was synthesized from Intermediate E and 2,2-diphenylethan-1-ol according to methods described above. MS: 449.3 [M+H]$^+$.

Example 216: 3-(3-(4-(3-fluoro-5-methoxybenzyl)benzyl)isoxazol-5-yl)pyridin-2-amine The compound was synthesized from Intermediate B and (3-fluoro-5-methoxyphenyl)boronic acid according to methods described above. MS: 390.0 [M+H]$^+$.

Example 217: 3-(3-((6-((3-methyl-4-(2,2,2-trifluoroethoxy)pyridin-2-yl)methoxy)pyridin-3-yl)methyl)isoxazol-5-yl)pyridin-2-amine The compound was synthesized from Intermediate E and (3-methyl-4-(2,2,2-trifluoroethoxy)pyridin-2-yl)methanol according to methods described above. MS: 472.3 [M+H]$^+$.

Example 218: 3-(3-((6-((3-chloropyridin-4-yl)methoxy)pyridin-3-yl)methyl)isoxazol-5-yl)pyridin-2-amine The compound was synthesized from Intermediate E and (3-chloropyridin-4-yl)methanol according to methods described above. MS: 394.1 [M+H]$^+$.

Example 219: 3-(3-((6-((2,6-dichloropyridin-4-yl)methoxy)pryidin-3-yl)methyl)isoxazol-5-yl)pyridin-2-amine The compound was synthesized from Intermediate E and (2,6-dichloropyridin-4-yl)methanol according to methods described above. MS: 428.1 [M+H]$^+$.

Example 220: 3-(3-((6-((2-chlorothiazol-4-yl)methoxy)pyridin-3-yl)methyl)isoxazol-5-yl)pyridin-2-amine The compound was synthesized from Intermediate E and (2-chlorothiazol-4-yl)methanol according to methods described above. MS: 399.9 [M+H]$^+$.

Example 221: 3-(3-((6-((5-chlorothiophen-2-yl)methoxy)pyridin-3-yl)methyl)isoxazol-5-yl)pyridin-2-amine The compound was synthesized from Intermediate E and (5-chlorothiophen-2-yl)methanol according to methods described above. MS: 398.9 [M+H]$^+$.

Example 222: 3-(3-((6-((6-chloropyridin-2-yl)methoxy)pryidin-3-yl)methyl)isoxazol-5-yl)pyridin-2-amine The compound was synthesized from Intermediate E and (6-chloropyridin-2-yl)methanol according to methods described above. MS: 393.8 [M+H]$^+$.

Example 223: 3-(3-((6-((6-bromopyridin-2-yl)methoxy)pryidin-3-yl)methyl)isoxazol-5-yl)pyridin-2-amine The compound was synthesized from Intermediate E and (6-bromopyridin-2-yl)methanol according to methods described above. MS: 440.2 [M+H]$^+$.

Example 224: 3-((5-((5-(2-aminopyridin-3-yl)isoxazol-3-yl)methyl)pyridin-2-yl)oxy)propanenitrile The compound was synthesized from Intermediate E and (3-hydroxypropanenitrile according to methods described above. MS: 322.2 [M+H]+.

Example 225: 3-(3-((6-(but-3-yn-1-yloxy)pyridin-3-yl)methyl)isoxazol-5-yl)pyridin-2-amine The compound was synthesized from Intermediate E and but-3-yn-1-ol according to methods described above. MS: 321.2 [M+H]+.

Example 226: 3-(3-((6-((6-fluoropyridin-2-yl)methoxy)pyridin-3-yl)methyl)isoxazol-5-yl)pyridin-2-amine The compound was synthesized from Intermediate E and (6-fluoropyridin-2-yl)methanol according to methods described above. MS: 377.8 [M+H]+.

Example 227: 3-(3-((6-morpholinopyridin-3-yl)methyl)isoxazol-5-yl)pyridin-2-amine The compound was synthesized from Intermediate A and 6-Morpholinopyridin-3-ylboronic acid according to methods described above. MS: 338.5 [M+H]+.

Example 228: 3-(3-(4-(morpholinosulfonyl)benzyl)isoxazol-5-yl)pyridin-2-amine The compound was synthesized from Intermediate A and 4-(4-(4,4,5,5-Tetramethyl-1,3,2-dioxaborolan-2-yl)phenylsulfonyl)morpholine according to methods described above. MS: 401.4 [M+H]+.

Example 229: 3-(3-((6-(2-phenylpyrrolidin-1-yl)pyridin-3-yl)methyl)isoxazol-5-yl)pyridin-2-amine The compound was synthesized from Intermediate E and (2-phenylpyrrolidine according to methods described above. MS: 398.2[M+H]+.

Example 230: 3-(3-((6-(piperidin-1-yl)pryidin-3-yl)methyl)isoxazol-5-yl)pyridin-2-amine The compound was synthesized from Intermediate A and 2-(Piperidin-1-yl)pyridine-5-boronic acid pinacol ester according to methods described above. 500 MHz $^1$H NMR (HCl-salt, DMSO-d6) δ 8.36 (dd, J=7.4, 1.5 Hz, 1H), 8.21 (dd, J=6.1, 1.6 Hz, 1H), 8.12 (bs, 2H), 8.01 (d, J=2.2 Hz, 1H), 7.94 (dd, J=9.4, 2.2 Hz, 1H), 7.42 (d, J=9.5 Hz, 1H), 7.08 (s, 1H), 7.05 (dd, J=7.6, 6.1 Hz, 1H), 4.10 (s, 2H), 3.73 (t, J=5.4 Hz, 4H), 1.70-1.57 (m, 6H). MS: 336.4 [M+H]+.

Example 231: 3-(3-(4-(((3-azidophenyl)amino)methyl)benzyl)isoxazol-5-yl)pyridin-2-amine The compound was synthesized from Intermediate B and 3-azidoaniline according to methods described above. 500 MHz $^1$H NMR (DMSO-d6) δ 8.14 (dd, J=4.9, 1.8 Hz, 1H), 7.70 (dd, J=7.7, 1.8 Hz, 1H), 7.35-7.29 (m, 2H), 7.30-7.23 (m, 2H), 7.12 (t, J=8.0 Hz, 1H), 6.70 (dd, J=7.7, 4.9 Hz, 1H), 6.43-6.37 (m, 2H), 6.28-6.21 (m, 2H), 5.39 (s, 2H), 4.30 (s, 2H), 4.16 (s, 1H), 4.05 (s, 2H). MS: 398.2 [M+H]+.

Example 232: 4-((4-((5-(2-aminopyridin-3-yl)isoxazol-3-yl)methyl)benzyl)amino)-5-fluoropyrimidin-2(1H)-one The compound was synthesized from Intermediate B and Flucytosine according to methods described above. MS: 393.3 [M+H]+.

Example 233: (E)-3-(3-(4-(3-fluorostyryl)benzyl)isoxazol-5-yl)pyridin-2-amine The compound was synthesized from Example 97 according to methods described for Example 99, but using 1-fluoro-3-vinylbenzene. MS: 371.9 [M+H]+.

Example 234: 3-(3-(4-((6-chloropyridin-2-yl)oxy)benzyl)isoxazol-5-yl)pyridin-2-amine The compound was synthesized from Intermediate C and 2,6-dichloropyridine according to methods described above. MS: 378.9 [M+H]+.

Example 235: 3-(3-(4-((3-fluoropyridin-2-yl)oxy)benzyl)isoxazol-5-yl)pyridin-2-amine The compound was synthesized from Intermediate C and 2,3-difluoropyridine according to methods described above. MS: 363.1 [M+H]+.

Example 236: 3-(3-(4-((5-chloro-3-fluoropyridin-2-yl)oxy)benzyl)isoxazol-5-yl)pyridin-2-amine The compound was synthesized from Intermediate C and (5-chloro-2,3-difluoropyridine according to methods described above. MS: 397.1 [M+H]+.

Example 237: 5-((5-(2-aminopyridin-2-yl)isoxazol-3-yl)methyl)-N-(2,6-difluorophenyl)pyridin-2-amine The compound was synthesized from Intermediate E and 2,6 difluoroaniline according to methods described above. MS: 380.2 [M+H]+.

Example 238: 5-((5-(2-aminopyridin-3-yl)isoxazol-3-yl)methyl)-N-(3,5-difluorophenyl)pyridin-2-amine The compound was synthesized from Intermediate E and 3,5-difluoroaniline according to methods described above. MS: 380.0 [M+H]+.

Example 239: 3-(3-(4-((4,6-difluoropyridin-2-yl)oxy)benzyl)isoxazol-5-yl)pyridin-2-amine The compound was synthesized from Intermediate C and 2,4,6-trifluoropyridine according to methods described above. MS: 380.9 [M+H]+.

Example 240: 3-(3-(4-((4-chlorothiazol-2-yl)oxy)benzyl)isoxazol-5-yl)pyridin-2-amine The compound was synthesized from Intermediate C and 2,4-dichlorothiazole according to methods described above. MS: 385.1 [M+H]+.

Example 241: 3-(3-(4-((3,5,6-trifluoropyridin-2-yl)oxy)benzyl)isoxazol-5-yl)pyridin-2-amine The compound was synthesized from Intermediate B and (3-fluorophenyl)boronic acid according to methods described above. MS: 398.9 [M+H]$^+$.

Example 242: 3-(3-(4-((3,5-difluoropyridin-2-yl)oxy)benzyl)isoxazol-5-yl)pyridin-2-amine The compound was synthesized from Intermediate C and 2,3,5-trifluoropyridine according to methods described above. MS: 380.9 [M+H]$^+$.

Example 243: 3-(3-(4-pyrimidin-2-yloxy)benzyl)isoxazol-5-yl)pyridin-2-amine

The compound was synthesized from Intermediate C and 2-chloroprimidine according to methods described above. MS: 346.0 [M+H]$^+$.

Example 244: 5-((5-(2-aminopyridin-2-yl)isoxazol-3-yl)methyl)-N-(2,5-difluorophenyl)pyridin-2-amine The compound was synthesized from Intermediate E and 2,5-difluoroaniline according to methods described above. MS: 380.1 [M+H]$^+$.

Example 245: 5-((3-(2-aminopyridin-3-yl)isoxazol-3-yl)methyl)-N-(2,3,4-trifluorphenyl)pyridin-2-amine The compound was synthesized from Intermediate E and 2,3,4-trifluoroaniline according to methods described above. MS: 398.0 [M+H]$^+$.

Example 246: 3-(3-(4-((6-fluoropyridin-2-yl)oxy)benzyl)isoxazol-5-yl)pyridin-2-amine The compound was synthesized from Intermediate C and 2,5-difluoropyridine according to methods described above. MS: 363.1 [M+H]$^+$.

Example 247: 3-(3-((6-(cyclopropylmethoxy)-5-fluoropyridin-3-yl)methyl)isoxazol-5-yl)pyridin-2-amine The compound was synthesized from Intermediate J and cyclopropylmethanol according to methods described above. MS: 340.7 [M+H]$^+$.

Example 248: 3-(3-((2-(3,5-difluorophenoxy)pyrimidin-5-yl)methyl)isoxazol-5-yl)pyridin-2-amine 3,5-difluorphenol (109 mg, 0.834 mmol) was dissolved in DMF (0.5 mL) and KOtBu (1M in THF, 730 μL, 0.730 mmol) was added dropwise. The mixture was stirred for 5 min and a solution of 3-(3-((2-chloropyrimidin-5-yl)methyl)isoxazol-5-yl)pyridin-2-amine (Intermediate L, 30 mg, 0.104 mmol) in DMF (0.5 mL) was added. The resulting mixture was stirred for 1 h at 60° C. and directly purified by flash chromatography to give 3-(3-((2-(3,5-difluorophenoxy)pyrimidin-3-yl)methyl)isoxazol-5-yl)pyridin-2-amine (17 mg, 0.045 mmol, 42.8% yield). 500 MHz $^1$H NMR (DMSO-d6) δ 8.70 (s, 2H), 8.10 (dd, J=4.8, 1.8 Hz, 1H), 7.86 (dd, J=7.7, 1.9 Hz, 1H), 7.21-7.06 (m, 3H), 6.89 (s, 1H), 6.71 (dd, J=7.7, 4.8 Hz, 1H), 6.28 (s, 2H), 4.10 (s, 2H). MS: 382.0 [M+H]$^+$.

Example 249: 3-(3-((2-((3-fluorobenzyl)oxy)pryidin-5-yl)methyl)isoxazol-5-yl)pyridin-2-amine The compound was synthesized from Intermediate L and according to methods described above. MS: 378.1 [M+H]$^+$.

Example 250: 5-((5-(2-aminopyridin-3-yl)isoxazol-3-yl)methyl)-3-fluoro-N-(2-fluorophenyl)pyridin-2-amine The compound was synthesized from Intermediate J and 2-fluoroaniline according to methods described above. MS: 380.0 [M+H]$^+$.

Example 251: 3-(3-((5-fluoro-6-((3-fluorobenzyl)oxy)pyridin-3-yl)methyl)isoxazol-5-yl)pyridin-2-amine The compound was synthesized from Intermediate J and (3-fluorophenyl)methanol according to methods described above. MS: 394.7 [M+H]$^+$.

Example 252: 3-(3-((6-(3,5-difluorophenoxy)-5-fluoropyridin-3-yl)methyl)isoxazol-5-yl)pyridin-2-amine The compound was synthesized from Intermediate J and 3,5-difluorophenol according to methods described above. MS: 398.5 [M+H]$^+$.

Example 253: 5-((5-(2-aminopyridin-3-yl)isoxazol-3-yl)methyl)-N-(2,6-difluorophenyl)-3-fluoropyridin-2-amine The compound was synthesized from Intermediate J and 2,6-difluoroaniline according to methods described above. MS: 398.0 [M+H]$^+$.

Example 254: 3-(3-((5-fluoro-6-(2-fluorophenoxy)pyridin-3-yl)methyl)isoxazol-5-yl)pyridin-2-amine The compound was synthesized from Intermediate J and 2-fluorophenol according to methods described above. MS: 380.9 [M+H]$^+$.

Example 255: 3-(3-((5-fluoro-6-phenoxypyridin-3-yl)methyl)isoxazol-5-yl)pyridin-2-amine The compound was synthesized from Intermediate J and phenol according to methods described above. MS: 362.7 [M+H]$^+$.

Example 256: 3-(3-((5-fluoro-6-(3-fluorophenoxy)pyridin-3-yl)methyl)isoxazol-5-yl)pyridin-2-amine The compound was synthesized from Intermediate J and 3-fluorophenol according to methods described above. MS: 380.8 [M+H]$^+$.

Example 257: 3-(3-((6-(benzyloxy)-5-fluoropyridin-3-yl)methyl)isoxazol-5-yl)pyridin-2-amine The compound was synthesized from Intermediate J and benzyl alcohol according to methods described above. MS: 376.6 [M+H]+.

Example 258: 3-(3-(3-fluoro-4-((6-fluoropyridin-2-yl)oxy)benzyl)isoxazol-5-yl)pyridin-2-amine 4-((5-(2-aminopyridin-3-yl)isoxazol-3-yl)methyl)-2-fluorophenol (Intermediate K, 100 mg, 0.351 mmol) was dissolved in DMF (1 mL) and potassium 2-methylpropan-2-olate (1M in THF, 421 μL, 0.421 mmol) was added dropwise. The mixture was stirred for 5 min and a solution of 2,6-difluoropyridine (81 mg, 0.701 mmol) in DMF (0.5 mL) was added. The resulting mixture was stirred for 16 h at 60° C. and directly purified by flash chromatography to give 3-(3-(3-fluoro-4-((6-fluoropyridin-2-yl)oxy)benzyl)isoxazol-5-yl)pyridin-2-amine. 500 MHz $^1$H NMR (DMSO-d6) δ 8.10 (dd, J=4.8, 1.8 Hz, 1H), 8.05 (q, 1H), 7.89 (dd, J=7.6, 1.8 Hz, 1H), 7.40 (dd, J=11.6, 2.0 Hz, 1H), 7.33 (t, 1H), 7.23 (ddd, J=8.3, 1.9, 0.8 Hz, 1H), 7.04 (dd, J=7.9, 1.5 Hz, 1H), 6.94-6.85 (m, 2H), 6.71 (dd, J=7.7, 4.8 Hz, 1H), 6.29 (s, 2H), 4.11 (s, 2H). MS: 380.9 [M+H]+.

Example 259: 3-(3-(3-fluoro-4-(pyrimidin-2-yloxy)benzyl)isoxazol-5-yl)pyridin-2-amine The compound was synthesized from Intermediate K and 2-chloropyrimidine according to methods described above. MS: 363.9 [M+H]+.

Example 260: 3-(3-((6-((2-fluorobenzyl)oxy)pyridin-3-yl)methyl)isoxazol-5-yl)pyridin-2-amine The compound was synthesized from Intermediate J and (2-fluorophenyl)methanol according to methods described above. MS: 394.7 [M+H]+.

Example 261: 3-(3-(4-((2,6-difluoropyridin-4-yl)methyl)benzyl)isoxazol-5-yl)pyridin-2-amine The compound was synthesized from Intermediate B and (2,6-difluoropyridin-4-yl)boronic acid according to methods described above. MS: 379.3 [M+H]+.

Examples 262-495 can be synthesized as described in any of the examples above.

Example 496: Evaluation of Compound Activity against *C. neoformans* and *C. gattii* isolates In this study, compound activity against *C. neoformans* and *C. gattii* isolates were evaluated. N-phosphonooxymethyl prodrugs of these molecules were synthesized and two of these prodrugs were evaluated in a disseminated *C. neoformans* infection model where 100 mg/kg ABT had been administered orally 2 h prior to therapy.

Cryptococcal meningitis (CM), caused primarily by *Cryptococcus neoformans*, is uniformly fatal if not treated. Treatment options are limited especially in resource-poor geographical regions, and mortality rates remain high despite current therapies. Here, the in vitro and in vivo activity of several compounds including Compound 2 and its prodrug Compound 1 were evaluated. These compounds target the conserved Gwt1 enzyme that is required for the localization of glycosylphosphatidyl inositol (GPI)-anchored cell wall mannoproteins in fungi.

Gwt1 inhibitors had low MIC values, ranging form 0.004 μg/mL to 0.5 μg/mL against both *C. neoformans* and *C. gattii*. Compound 2 and 3-(3-(4-(benzyloxy)benzyl)isoxazol-5-yl)pyridin-2-amine demonstrated in vitro synergy with fluconazole (FICI 0.37). In a CM model, Compound 1 and fluconazole each, alone, reduced $\log_{10}$ colony forming units (CFU)/g brain (0.78 and 1.04, respectively), whereas the combination resulted in a reduction of 3.52 $\log_{10}$ CFU/g brain.

Efficacy as measured by a reduction in brain and lung fungal burden was also observed for another Gwt1 inhibitor prodrug, (2-amino-3-(3-(4-((6-fluoropyridin-2-yl)oxy)benzyl)isoxazol-5-yl)pryidin-1-ium-1-yl)methyl hydrogen phosphate, where dose dependent reductions in fungal burden ranged between 5.91 and 1.79 $\log_{10}$ CFU/g lung and between 7.00 and 0.92 $\log_{10}$ CFU/g brain, representing near or complete sterilization of lung and brain tissue at the higher doses. These data support further clinical evaluation of this new class of antifungal agents for CM.

In Vitro Activity of Gwt1 inhibitors vs *Cryptococcus*

Antifungal susceptibility profile. Several compounds were highly active against all 4 fungal strains evaluated (Table 3), with MIC or MEC values ranging from 0.004 to 0.25 μg/mL against *C. neoformans, C. gattii, Candida albicans* and *Aspergillus fumigantus*. When compared to the MIC values of Compound 2 vs *Cryptococcus*. 3-(3-(4-(benzyloxy)benzyl)isoxazol-5-yl)pyridin-2-amine and 3-(3-((6-(benzyloxy)pyridin-3-yl)methyl)isoxazol-5-yl)pyridin-2-amine demonstrated to 4 to 8-fold lower MIC values, whereas 3-(3-(4-((6-fluoropyridin-2-yl)oxy)benzyl)isoxazol-5-yl)pyridin-2-amine demonstrated 32-fold lower MIC values. (Table 3).

TABLE 3

In vitro susceptibility profiles of Gwt1 Inhibitors

| Com-pound | Prodrug | MIC[2] (μg/mL) | | | MIC or MEC[2] (μg/mL) |
|---|---|---|---|---|---|
| | | *C. neoformans* H99 | *C. gattii* WM276 | *C. albicans* 90028 | *A. fumigatus* MYA3626 |
| Compound 2 | Compound 1 | 0.25 | 0.125 | 0.008 | 0.008 |
| Ex. 185 | Ex. 173 | 0.031 | 0.031 | 0.016 | 0.016 |
| Ex. 111 | Ex. 172 | 0.008 | 0.004 | 0.031 | 0.063 |
| Ex. 142 | Ex. 174 | 0.031 | 0.016 | 0.031 | 0.008 |
| AMB | — | 0.25 | 0.25 | 1 | 1 |
| FLC | — | 2 | 1 | 0.5 | >16 |
| CAS | — | ND[1] | ND | 0.5 | 0.25 |

Gwt1 inhibitors are synergistic with FLC. The synergy of Compound 2 and 3-(3-(4-benzyloxy)benzyl)isoxazol-5-yl)pyridin-2-amine in combination with FLC using standard microtiter dilution techniques was evaluated. Synergy (FICI values<0.5) was observed for both compounds vs. *C. neoformans* H99; FLC/Compound 2 (0.37), FLC/3-(3-(4-(benzyloxy)benzyl)isoxazol-5-yl)pyridin-2-amine (0.37). Importantly, no antagonism was observed.

The activity of Gwt1 inhibitors against susceptible and FLC non-susceptible/resistant strains. The activities of Compound 2, 3-(3-(4-(benzyloxy)benzyl)isoxazol-5-yl)pyridin-2-amine, 3-(3-(4-((6-fluoropyridin-2-yl)oxy)benzyl)isoxazol-5-yl)pyridin-2-amine, 3-(3-((6-(benzyloxy)pyridin-3-yl)methyl)isoxazol-5-yl)pyridin-2-amine, AMB and FLC were examined against a collection of susceptible and FLC nonsusceptible/resistant (MIC≥16 µg/mL) strains of C. neoformans and C. gattii 3-(3-(4-((6-fluoropyridin-2-yl)oxy)benzyl)isoxazol-5-yl)pyridin-2-amine was the most active compound tested with MCI values ranging between 0.004 to 0.031 µg/mL against all 18 strains tested, followed by 3-(3-((6-(benzyloxy)pyridin-3-yl)methyl)isoxazol-5-yl)pyridin-2-amine (range 0.016 to 0.125 µg/mL), 3-(3-(4-benzyloxy)benzyl)isoxazol-5-yl)pyridin-2-amine (range 0.031 to 0.25 µg/mL), and Compound 2 (range 0.125 to 0.5 µg/mL) (Table 2). Consistent with different mechanisms of action, the activities of the exemplary compounds as well as AMB were unchanged for FLC-resistant strains DUMC118 and RSA-MW-3615, relative to susceptible strains (Table 2). FLC-resistant C. neoformans DUMC158.03 demonstrated somewhat higher MIC values for the four exemplary compounds as well as AMB, suggesting that additional non-target-based mutations may be present in this strain.

In Vivo Activity of Gwt1 Inhibitors vs C. neoformans

Efficacy of Compound 1 alone and in combination with FLC in a murine model of cryptococcal meningitis. The efficacy of Compound 1 and FLC were evaluated in a well-established mouse CM model. Since *Cryptococcus* infections can be hematogenously disseminated to other organs, both lung and brain CFU were evaluated. Male CD-1 mice were infected with $5.9 \times 10^4$ CFU. *C. neoformans* strain H99 via lateral tail vein injection. Mice were assigned to four groups (n=10) consisting of a) treatment with Compound 1; b) treatment with Compound 1 plus FLC, 3) treatment with FLC, or d) no treatment control. Treatment was initiated within 1 h after infection. Compound 1 was administered by oral gavage at a dose of 390 mg/kg thrice daily, roughly eight hours apart. ABT was not used in this model, thus TID dosing of Compound 1 was necessitated by the short half-life of Compound 2 in mice (1.40 to 2.75 h) (34). FLC (2 mg/mL, Sagent Pharmaceuticals, Schaumburg, IL) was administered at a dose of 80 mg/kg/day intraperitoneally (IP).

The mean $\log_{10}$ CFU/g brain and lung counts in untreated control mice were 7.81±0.19 and 5.97±0.47, respectively. Significant differences (P=<0.05) in lung fungal burden were observed in all treatment groups (Compound 1, FLC, and Compound 1 plus FLC) as compared to the untreated control. In lung, the $\log_{10}$ CFU/g reductions in fungal burden were similar for all three treatments groups as compared to the untreated control: Compound 1 (1.50), FLC (1.30) and combined therapy (1.84), with no statistically significant differences between the treatment groups.

In brain, mice treated with Compound 1 demonstrated a reduction of 0.78 $\log_{10}$ CFU/g fungal burden versus the control group, which was not significantly different. However, significant reductions in $\log_{10}$ CFU/g fungal burden versus the control group were observed for FLC alone (1.04) and the combination of Compound 1 and FLC (3.51) (P<0.01 and P<0.001, respectively).

Effect of ABT on the Pharmacokinetics of Exemplary Compounds.

The PK of Compound 2, 3-(3-(4-((6-fluoropyridin-2-yl)oxy)benzyl)isoxazol-5-yl)pyridin-2-amine, 3-(3-(4-benzyloxy)benzyl)isoxazol-5-yl)pyridin-2-amine and 3-(3-((6-(benzyloxy)pyridin-3-yl)methyl)isoxazol-5-yl)pyridin-2-amine were compared in male CD-1 mice after the administration of 26 mg/kg of the corresponding prodrug (Compound 1, (2-amino-3-(3-(4-((6-fluoropyridin-2-yl)oxy)benzyl)isoxazol-5-yl)pyridin-1-ium-1-yl)methyl hydrogen phosphate, (2-amino-3-(3-(4-(benzyloxy)benzyl)isoxazol-5-yl)pyridin-1-ium-1-yl)methyl hydrogen phosphate, (2-amino-3-(3-((6-(benzyloxy)pyridin-3-yl)methyl)isoxazol-5-yl)pyridin-1-ium-1-yl)methyl hydrogen phosphate) either orally or by IP injection (Table 4). In half of the cohorts, 100 mg/kg ABT was administered 2 h prior to compound administration. Although the AUC values of the analytes differed up to 4-fold after oral administration of the four prodrugs, the addition of ABT resulted in similar exposures for Compound 2, 3-(3-(4-benzyloxy)benzyl)isoxazol-5-yl)pyridin-2-amine and 3-(3-((6-(benzyloxy)pyridin-3-yl)methyl)isoxazol-5-yl)pryidin-2-amine. The resulting exposure for 3-(3-(4-((6-fluoropyridin-2-yl)oxy)benzyl)isoxazol-5-yl)pyridin-2-amine was approximately 2-fold higher than the three other compounds evaluated. The addition of ABT resulted in 8.6 to 15-fold increased exposure after oral administration of the prodrugs.

TABLE 4

Exposures of Gwt1 Inhibitors Following Oral or IP Dosing of Prodrugs in the Presence or Absence of 100 mg/kg ABT Pre-Treatment

| Prodrug | Analyte | Average AUC[1] (µg · h/mL) resulting from 26 mg/kg dose | | | | Ratio +ABT/ −ABT (PO) | Ratio +ABT/ −ABT (IP) |
|---|---|---|---|---|---|---|---|
| | | PO | IP | PO + ABT | IP + ABT | | |
| Compd. 1 | Compd. 2 | 2.76 ± 0.23 | 4.36 ± 0.11 | 41.50 ± 8.09 | 24.28 ± 17.74 | 15.0 | 5.6 |
| Ex. 172 | Ex. 111 | 10.66 ± 0.48 | 11.75 ± 1.83 | 91.28 ± 20.75 | 97.25 ± 12.61 | 8.6 | 8.3 |
| Ex. 173 | Ex. 185 | 4.49 ± 2.32 | 4.31 ± 0.96 | 41.94 ± 6.41 | 35.61 ± 28.22 | 9.3 | 8.3 |
| Ex. 174 | Ex. 142 | 3.49 ± 0.27 | 4.68 + 0.73 | 49.92 ± 10.34 | 72.62 ± 9.07 | 14.3 | 15.5 |

When the prodrugs were administered IP, similar exposures were obtained for the analytes Compound 2, 3-(3-(4-(benzyloxy)benzyl)isoxazol-5-yl)pyridin-2-amine and 3-(3-((6-(benzyloxy)pyridin-3-yl)methyl)isoxazol-5-yl)pyridin-2-amine, while 3-(3-(4-((6-fluoropyridin-2-yl)oxy)benzyl)isoxazol-5-yl)pyridin-2-amine demonstrated an approximately 2-fold higher AUC than the other compounds evaluated (Table 4). The addition of ABT prior to IP drug administration increased exposures from 5.6 to 15.5-fold. IP dosing was chosen as the route of administration for Compound 1, (2-amino-3-(3-(4-((6-fluoropryidin-2-yl)oxy)benzyl)isoxazol-5-yl)pyridin-1-ium-1-yl)methyl hydrogen phosphate and (2-amino-3-(3-(4-benzyloxy)benzyl)isoxazol-5-yl)pryidin-1-ium-1-yl)methyl hydrogen phosphate in the CM model.

Efficacy of exemplary compounds in a murine model of cryptococcal meningitis when dosed in the presence of the pan-CYP inhibitor ABT. In a preliminary experiment, the efficacies of Compound 1, (2-amino-3-(3-(4-((6-fluoropyridin-2-yl)oxy)benzyl)isoxazol-5-yl)pyridin-1-ium-1-yl) methyl hydrogen phosphate and (2-amino-3-(3-(4-(benzyloxy)benzyl)isoxazol-5-yl)pyridin-1-ium-1-yl)methyl hydrogen phosphate were evaluated in the disseminated model of CM (n=5 mice/cohort). 100 mg/kg ABT was administered orally to male CD-1 mice 2 h prior to compound administration. Mice were injected with $6.9 \times 10^4$ CFU *C. neoformans* strain H99 per mouse via lateral tail vein at T=0 h. Treatment with each prodrug was initiated about 1 post-infection by IP administration and continued daily for 7 days with 100 mg/kg ABT administered orally 2 h prior to each dose of compound. The mean $\log_{10}$ CFU/g brain and lung counts in untreated control mice were 7.83±0.09 and 4.67±0.88, respectively (FIG. 1).

In lung, neither the 34 mg/kg or the 85 mg/kg dose of Compound 1 achieved a statistically significant reduction in $\log_{10}$ CFU/g tissue vs the untreated control. Of note is that 390 mg/kg Compound 1 dosed orally TID results in higher AUC values than 85 mg/kg Compound 1 dose IP QD with ABT (FIG. 2), thus better efficacy in lung was observed with Compound 1 monotherapy. In lung, administration of 60 mg/kg or 34 mg/kg (2-amino-3-(3-(4-((6-fluoropyridin-2-yl)oxy)benzyl)isoxazol-5-yl)pyridin-1-ium-1-yl)methyl hydrogen phosphate reduced tissue burdens below the limit of detection (approximately 4.67 $\log_{10}$ CFU/g lung tissue). For (2-amino-3-(3-(4-(benzyloxy)benzyl)isoxazol-5-yl)pyridin-1-ium-1-yl)methyl hydrogen phosphate, the reduction of CFU in lung was 3.28 $\log_{10}$ CFU/g (85 mg/kg QD) and 1.07 $\log_{10}$ CFU/g (34 mg/kg QD).

In brain, administration of 60 mg/kg or 34 mg/kg (2-amino-3-(3-(4-((6-fluoropyridin-2-yl)oxy)benzyl)isoxazol-5-yl)pyridin-1-ium-1-yl)methyl hydrogen phosphate resulted in a reduction of 7.13 and 7.05 $\log_{10}$ CFU/g brain tissue, respectively. For (2-amino-3-(3-(4-(benzyloxy)benzyl)isoxazol-5-yl)pyridin-1-ium-1-yl)methyl hydrogen phosphate, the reduction of CFU in brain was 2.72 $\log_{10}$ CFU/g (85 mg/kg QD) and 1.66 $\log_{10}$ CFU/g (34 mg/kg QD). Administration of 85 mg/kg Compound 1 demonstrated a modest reduction in $\log_{10}$ CFU/g (0.85), which did not, however, achieve statistical significance.

A dose response study was performed with (2-amino-3-(3-(4-((6-fluoropyridin-2-yl)oxy)benzyl)isoxazol-5-yl)pyridin-1-ium-1-yl)methyl hydrogen phosphate and (2-amino-3-(3-(4-(benzyloxy)benzyl)isoxazol-5-yl)pyridin-1-ium-1-yl)methyl hydrogen phosphate to confirm the observed activity. In this study, QD doses of 7.5, 20 and 60 mg/kg were evaluated in conjunction with the administration of ABT. A 60 mg/kg dose QD without ABT was also evaluated as a control.

Figure 2:
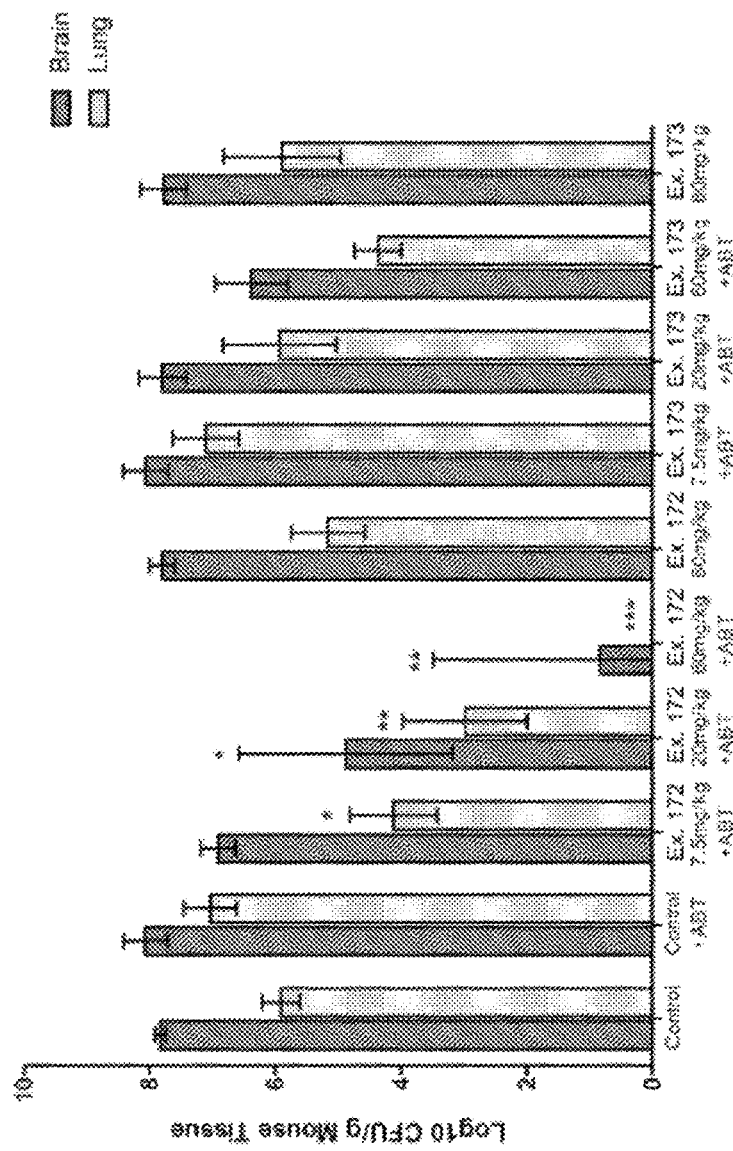
FIG. 2 shows a dose response study with (2-amino-3-(3-(4-((6-fluoropyridin-2-yl)oxy)benzyl)isoxazol-5-yl)pyridin-1-ium-1-yl)methyl hydrogen phosphate (Example 172) and (2-amino-3-(3-(4-(benzyloxy)benzyl)isoxazol-5-yl)pyridin-1-ium-1-yl)methyl hydrogen phosphate (Example 173).

The mean $\log_{10}$ CFU/g tissue counts in untreated control mice were 7.83±0.07 (brain) and 5.91±0.24 (lung) (FIG. 2). Control animals which received daily doses of 100 mg/kg ABT without compound had $\log_{10}$ CFU/g tissue values of 8.07±0.28 (brain) and 7.04±0.34 (lung).

Both (2-amino-3-(3-(4-((6-fluoropyridin-2-yl)oxy)benzyl)isoxazol-5-yl)pyridin-1-ium-1-yl)methyl hydrogen phosphate and (2-amino-3-(3-(4-(benzyloxy)benzyl)isoxazol-5-yl)pyridin-1-ium-1-yl)methyl hydrogen phosphate demonstrated a dose response in the reduction of $\log_{10}$ CFU/g brain and lung tissue when ABT was utilized. Cohorts which received 60 mg/kg/day of exemplary compounds without ABT showed either a numerical but non-significant reduction in lung burden of 0.74 $\log_{10}$ CFU/g ((2-amino-3-(3-(4-((6-fluoropyridin-2-yl)oxy)benzyl)isoxazol-5-yl)pyridin-1-ium-1-yl)methyl hydrogen phosphate) or no reductions in $\log_{10}$ CFU/g mouse tissue, consistent with a shorter half-life and lower exposure.

For (2-amino-3-(3-(4-((6-fluoropyridin-2-yl)oxy)benzyl) isoxazol-5-yl)pyridin-1-ium-1-yl)methyl hydrogen phosphate with ABT, dose dependent reductions in $\log_{10}$ CFU/g ranged between 5.91 to 1.79 for lung and between 7.00 to 0.92 for brain. All ABT plus (2-amino-3-(3-(4-(6-fluoropyridin-2-yl)oxy)benzyl)isoxazol-5-yl)pyridin-1-ium-1-yl) methyl hydrogen phosphate treatment cohorts demonstrated reductions in fungal lung burden that were statistically significant from the ABT-administered control group (P≤0.05). The two highest ABT plus (2-amino-3-(3-(4-((6-fluoropyridin-2-yl)oxy)benzyl)isoxazol-5-yl)pyridin-1-ium-1-yl)methyl hydrogen phosphate dosing levels also showed reductions in brain fungal burden, ranging from 6.99 to 2.95 $\log_{10}$ CFU/g (P≤0.05).

For (2-amino-3-(3-(4-(benzyloxy)benzyl)isoxazol-5-yl) pyridin-1-ium-1-yl)methyl hydrogen phosphate, dose dependent changes in $\log_{10}$ CFU/g ranged between a reduction of 1.55 $\log_{10}$ CFU/g to an increase of 1.20 for lung and between a reduction of 1.45 to an increase of 0.24 for brain. However, none of these reductions reached statistical significance vs the ABT-administered control group. Statistical significance was also not achieved when these cohorts were evaluated versus the no ABT vehicle control.

The results of the dose response experiment were consistent with the preliminary finding that (2-amino-3-(3-(4-((6-fluoropyridin-2-yl)oxy)benzyl)isoxazol-5-yl)pyridin-1-ium-1-yl)methyl hydrogen phosphate demonstrated near or complete sterilization of lung and brain tissue at doses of 34 and 60 mg/kg (plus ABT).

Analysis of AUC values vs change in $\log_{10}$ CFU/g tissue. The three compounds evaluated in the efficacy model had MIC values for the infection strain (*C. neoformans* H99) that differed by 8 to 32-fold: Compound 2 (0.25 µg/mL), 3-(3-(4-(benzyloxy)benzyl)isoxazol-5-yl)pyridin-2-amine (0.031 µg/mL), and 3-(3-(4-((6-fluoropyridin-2-yl)oxy)benzyl) isoxazol-5-yl)pyridin-2-amine (0.008 µg/mL) (Table 1). The data in Table 4 show that AUC show that AUC values after IP dosing (plus ABT) ranged from 24.3 to 97.3 µg·h/mL, representing a 4-fold difference. To understand the influence of AUC vs MIC differences, the magnitude of $\log_{10}$ CFU/g tissue changes across the three experiments were assessed.

AUC values across the three experiments for Compound 1 (with or without ABT) ranged from 7.0 µg·h/mL (7.5 mg/kg Compound 1 QD plus ABT) to 196.3 µg·h/mL (390 mg/kg TID). At an AUC of 196.3 µg·h/mL, a modest but significant reduction in lung burden was observed (1.5 $\log_{10}$ CFU/g). Lower AUC values were not efficacious. AUC values ranged from 10.0 to 116.4 µg·h/mL for (2-amino-3-(3-(4-(benzyloxy)benzyl)isoxazol-5-yl)pyridin-1-ium-1-yl) methyl hydrogen phosphate, and from 27 to 224.3 µg·h/mL for (2-amino-3-(3-(4-((6-fluoropyridin-2-yl)oxy)benzyl) isoxazol-5-yl)pyridin-1-ium-1-yl)methyl hydrogen phosphate. The efficacy of the three compounds at a dose that gave rise to similar AUC values were compared.

AUC values of approximately 80 µg·h/mL. In the presence of ABT, doses of 20 mg/kg (2-amino-3-(3-(4-((6-fluoropyridin-2-yl)oxy)benzyl)isoxazol-5-yl)pyridin-1-ium-1-yl)methyl hydrogen phosphate, 60 mg/kg (2-amino-3-(3-(4-(benzyloxy)benzyl)isoxazol-5-yl)pyridin-1-ium-1-yl) methyl hydrogen phosphate, and 80 mg/kg Compound 1 resulted in very similar AUC values of 74.8, 82.1, and 79.4 µg·h/mL respectively. However, $\log_{10}$ CFU/g brain reductions were 2.95, 1.45 and 0.85, respectively and $\log_{10}$ CFU/g lung reductions were 3.69, 1.55 and 0.9. Thus, despite the same AUC values for the 3 compounds, better efficacy was associated with lower MCI values (0.008 µg/mL, 0.031 µg/mL and 0.25 µg/mL, respectively) suggesting that improved microbiological activity largely accounts for improved efficacy.

Efficacy of (2-amino-3-(3-(4-((6-fluoropyridin-2-yl)oxy)benzyl)isoxazol-5-yl)pyridin-1-ium-1-yl)methyl hydrogen phosphate and AMB in a delayed model of cryptococcal meningitis. A delayed treatment model was used to compare the efficacy of once daily treatment using 60 mg/kg (IP) (2-amino)-3-(3-(4-((6-fluoropyridin-2-yl)oxy)benzyl)isoxazol-5-yl)pyridin-1-ium-1-yl)methyl hydrogen phosphate, 3 mg/kg (IP) AMB vs vehicle control (IP 5% dextrose). As in the previous mouse model, 100 mg/kg ABT (PO) was administered 2 h prior to each (2-amino-3-(3-(4-((6-fluoropyridin-2-yl)oxy)benzyl)isoxazol-5-yl)pyridin-1-ium-1-yl) methyl hydrogen phosphate dose (n=5 mice/cohort). Infection was initiated on Day 1 and treatment was initiated 24 f later (Day 2) rather than 1 h. Treatments were administered for 7 days (final dose on Day 8) and mice were sacrificed on Day 9 for CFU enumeration.

$MIC_{90}$ values were 0.5 µg/mL (Compound 2), 0.25 µg/mL (3-(3-(4-(benzyloxy)benzyl)isoxazol-5-yl)pyridin-2-amine) and 0.031 µg/mL (3-(3-(4-((6-fluoropyridin-2-yl)oxy)isoxazol-5-yl)pyridin-2-amine) (Table 4). These values compare favorably to other drugs in clinical use for CM. In a global study that evaluated antifungal activity versus 46 strains of *C. neoformans*. $MIC_{90}$ values for the azoles range from 0.06 µg/mL (isavuconazole) to 4 µg/mL (FLC), whereas the echinocandins were largely inactive with $MIC_{90}$ values≥16 µg/mL (35). Similarly, in a study of US isolates, $MIC_{90}$ values versus *C. neoformans* were: AMB (2 µg/mL), and 5-flucytosine (8 µg/mL), with only itraconazole (0.125 µg/mL) and keotconazole (0.06 µg/mL) demonstrating low $MIC_{90}$ values.

TABLE 4

Activity of Gwt1 Inhibitors vs Susceptible and FLC Non-Susceptible/Resistant Strains of *Cryptococcus*

| Species | Isolate | MIC (µg/mL) | | | | | |
|---|---|---|---|---|---|---|---|
| | | 001A | 2020 | 2039 | 2041 | AMB | FLC |
| *C. neoformans* | H99 | 0.125 | 0.031 | 0.004 | 0.031 | 0.25 | 1 |
| *C. neoformans* | DUMC 118.00 | 0.25 | 0.063 | 0.016 | 0.063 | 0.25 | 64 |
| *C. neoformans* | DUMC 158.03 | 0.25 | 0.25 | 0.031 | 0.125 | 1 | 32 |
| *C. neoformans* | MYA-4564 | 0.125 | 0.063 | 0.004 | 0.016 | 0.25 | 4 |
| *C. neoformans* | MYA-4565 | 0.5 | 0.25 | 0.031 | 0.125 | 0.125 | 1 |
| *C. neoformans* | MYA-4566 | 0.25 | 0.125 | 0.008 | 0.063 | 0.25 | 2 |
| *C. neoformans* | MYA-4567 | 0.25 | 0.063 | 0.016 | 0.031 | 0.25 | 1 |
| *C. neoformans* | 14116 | 0.125 | 0.031 | 0.004 | 0.016 | 0.25 | 4 |
| *C. neoformans* | 76484 | 0.125 | 0.063 | 0.004 | 0.016 | 0.25 | 4 |
| *C. gaitii* | RSA-MW-3615 | 0.125 | 0.031 | 0.004 | 0.016 | 0.25 | 64 |
| *C. gaitii* | MYA-4877 | 0.25 | 0.063 | 0.008 | 0.016 | 0.25 | 4 |
| *C. gaitii* | MYA-4093 | 0.5 | 0.125 | 0.016 | 0.125 | 0.25 | 2 |
| *C. gaitii* | MYA-4094 | 0.25 | 0.25 | 0.016 | 0.063 | 0.25 | 2 |
| *C. gaitii* | MYA-4560 | 0.25 | 0.063 | 0.008 | 0.016 | 0.063 | 1 |
| *C. gaitii* | MYA-4561 | 0.5 | 0.125 | 0.016 | 0.031 | 0.25 | 4 |
| *C. gaitii* | MYA-4562 | 0.25 | 0.125 | 0.016 | 0.031 | 0.25 | 2 |
| *C. gaitii* | MYA-4563 | 0.5 | 0.125 | 0.016 | 0.031 | 0.125 | 4 |
| *C. gaitii* | MYA-4560 | 0.25 | 0.063 | 0.008 | 0.016 | 0.063 | 1 |
| GEOMEAN | | 0.241 | 0.085 | 0.010 | 0.034 | 0.215 | 3.564 |
| $MIC_{90}$ | | 0.5 | 0.25 | 0.031 | 0.125 | 0.25 | 64 |

Figure 3:
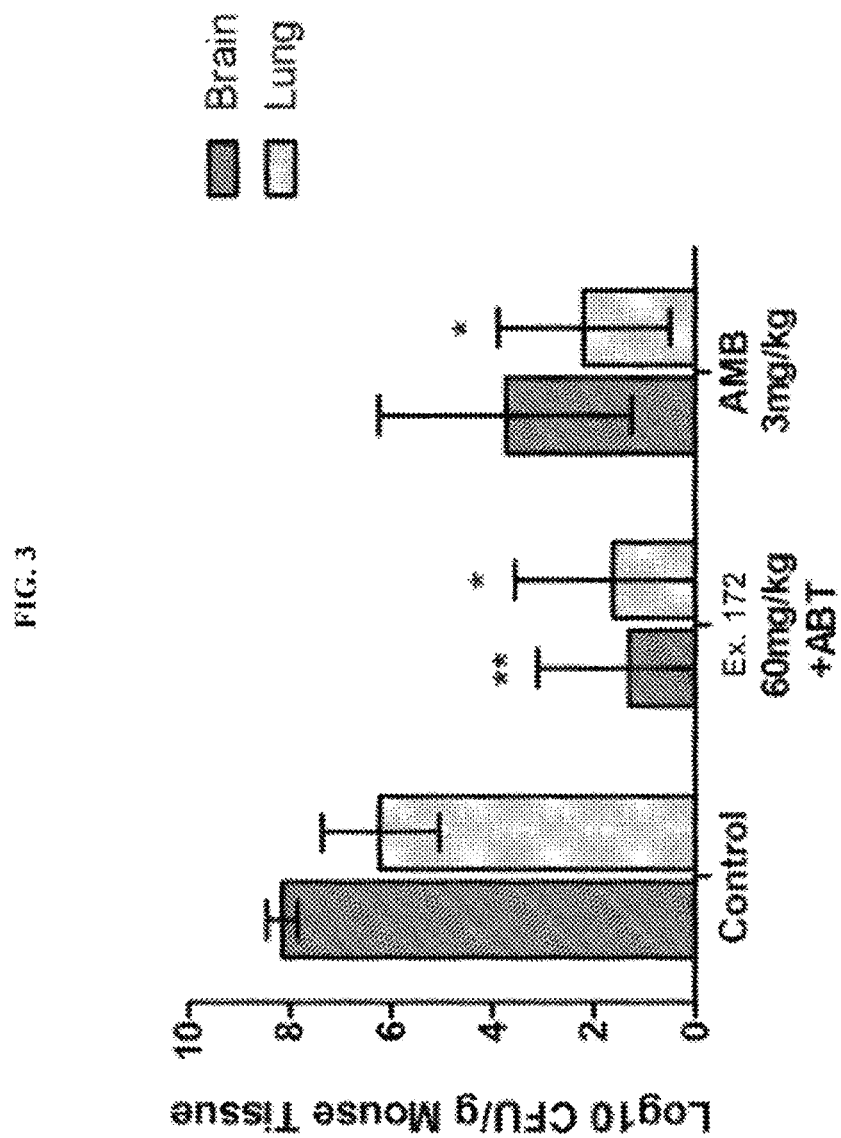
FIG. 3 shows the efficacy of (2-amino-3-(3-(4-((6-fluoropyridin-2-yl)oxy)benzyl)isoxazol-5-yl)pyridin-1-ium-1-yl)methyl hydrogen phosphate (Example 172) and amphotericin B (AMB) in a delayed model of cryptococcal meningitis.

The mean $log_{10}$ CFU/g tissue counts in untreated control mice were 8.15±0.24 (brain) and 6.22±0.93 (lung) (FIG. 3). Both (2-amino-3-(3-(4-((6-fluoropyridin-2-yl)oxy)benzyl)isoxazol-5-yl)pyridin-1-ium-1-yl)methyl hydrogen phosphate and AMB demonstrated a statistically significant reduction of $log_{10}$ CFU/g lung (4.59 and 4.02, respectively) vs the untreated control group (P≤0.05). (2-amino-3-(3-(4-((6-fluoropyridin-2-yl)oxy)benzyl)isoxazol-5-yl)pyridin-1-ium-1-yl)methyl hydrogen phosphate also showed a reduction of 6.84 $log_{10}$ CFU/g brain vs the untreated control, which was significant (P≤0.01). These data are very similar to the reductions observed in the 60 mg/kg (2-amino-3-(3-(4-((6-fluoropyridin-2-yl)oxy)benzyl)isoxazol-5-yl)pyridin-1-ium-1-yl)methyl hydrogen phosphate plus ABT cohort shown FIG. 2, demonstrating the reproducibility of these findings. Although AMB demonstrated a 4.40 $log_{10}$ CFU/g brain reduction, this did not meet statistical significance.

Two additional compounds, 3-(3-(4-(benzyloxy)benzyl)isoxazol-5-yl)pyridin-2-amine and 3-(3-(4-((6-fluoropyridin-2-yl)oxy)benzyl)isoxazol-5-yl)pyridin-2-amine, demonstrated 8 to 32-fold improved anti-*C. neoformans* H99 activity with MIC values of 0.031 and 0.008 µg/mL, respectively compared to Compound 2. This difference in activity was also seen against a larger panel of 18 isolates where In this study, a collection of clinically isolated FLC-susceptible and FLC-nonsusceptible/resistant strains of *C. neoformans* and *C. gattii* were examined. Consistent with a different mechanism of action, the potency of the four Gwt1 compounds relative to FLC was maintained, although one strain (DUMC 158.03) had higher MIC values for the exemplary compounds as well as AMB, suggesting that additional no-target-based mutations may be present in this strain. Despite the elevated MIC values for this strain, it is anticipated that appropriate clinical exposures may still be achieved for coverage of these types of strains.

Standard microtiter checkerboard dilution experiments demonstrated that both Compound 2 and 3-(3-(4-(benzyloxy)benzyl)isoxazol-5-yl)pyridin-2-amine are synergistic with FLC vs. *C. neoformans* H99. These data are consistent with previous reports of Compound 2 synergy with FLC against 9 of 10 *Candida tropicalis* strains and 2 of 20 strains of *C. albicans*. Importantly, no antagonism was observed. Improved activity in combination with FLC was also observed in the CM mouse model. Monotherapy of Compound 1 or FLC resulted in a reduction of 0.78 and 1.04 $log_{10}$ CFU/g brain tissue vs the untreated control, whereas the combination of Compound 1 and FLC resulted in a reduction of 3.52 $log_{10}$ CFU/g brain tissue as compared to control. This combination therapy was significantly more active in the reduction of fungal burden in the brain than monotherapy with Compound 1.

ABT has been used to increase exposure of drugs in other therapeutic animal modes; however, the use of ABT for improving efficacy in infectious disease models has not been widespread. Two studies utilized ABT in short-term models, where $\log_{10}$ CFU/g tissue were examined after 24 to 48 h. The antibacterial efficacy of experimental adenosine analogs targeting DNA ligase were evaluated at 24 h post-infection in a thigh model in which mice received a single dose of 100 mg/kg ABT 2 h prior to infection to reduce the high hepatic clearance. The efficacy of Compound 1 was examined after ABT administration in disseminated Candida infection models were C. albicans kidney burdens were reduced 6.0±0.1 $\log_{10}$ CFU/g kidney after 48 h. Since efficacy models can require treatments lasting 7 days or longer, the ability to maintain good drug exposures by administration of ABT over the treatment period is important. One study examined the pharmcokinetic parameters of antipyrine in mice administered as a 14-day continuous infusion of 20 or 60 mg ABT per ALZET osmotic pump. In that study AUC values increase 3 to 4-fold when antipyrine was dosed intravenously (IV) and 8 to 10-fold after oral administration, demonstrating the feasibility of long-term ABT administration. Here, it was shown that 7 days of daily administration of 100 mg/kg ABT 2 h prior to treatment with exemplary compounds dramatically increased the efficacy of three Gwt1 inhibitors. Pharmacokinetic studies demonstrated that ABT increased exposures 5.6 to 15.5-fold when exemplary molecules were dosed orally, and 8.6 to 15-fold, when exemplary molecules were dosed IP. These data support the use of ABT in infectious disease animal models for analysis of both clinical candidates and early discovery molecules, where proof-of-concept data are required.

Clinical studies have clearly shown that rapid killing of cryptococcal cells in the CNS is associated with an improved host outcome. The animal model data of the present disclosure provide evidence of effective brain penetration, one of the key factors in the choice of a drug for the treatment of CM. These data are consistent with $^{14}$C-Compound 1 distribution studies which demonstrated significant radioactivity in tissues associated with invasive fungal infections, including brain tissue; whereas poor CNS penetration has been observed for the echinocandins. Notably, (2-amino-3-(3-(4-((6-fluoropyridin-2-yl)oxy)benzyl) isoxazol-5-yl)pyridin-1-ium-1-yl)methyl hydrogen phosphate significantly reduced lung and brain tissue fungal burden in a murine CM model, where in past experience, only AMB has shown a similar reduction in CFU in this model. In the current study, (2-amino-3-(3-(4-((6-fluoropyridin-2-yl)oxy)benzyl)isoxazol-5-yl)pyridin-1-ium-1-yl) methyl hydrogen phosphate was at least comparable to or better than AMB in a delayed treatment model. Thus, an oral agent, with the potential to kill yeasts rapidly in the CNS of a host, such as (2-amino-3-(3-(4-((6-fluoropyridin-2-yl)oxy) benzyl)isoxazol-5-yl)pyridin-1-ium-1-yl)methyl hydrogen phosphate, is of significant interest. Further pharmacodynamics studies will be performed after the optimal Gwt1 inhibitor is identified.

Example 497: Materials and Methods

Isolates tested. C. neoformans strains H99, DUMC 118.00, DUMC 158.03 and C. gattii strains R272, and RSA-MW-3515 were obtained from Duke University. C. albicans 90028, A. fumigatus MYA3626, C. neoformans 14116, C. neoformans 14116, C. neoformans 76484 and the pathogenic Cryptococcus reference stains panel (ATCC MP-11) were obtained from America Type Culture Collection (ATCC, Manassas, VA, USA). The MP-11 panel consists of strains representing eight molecular types and three subtypes of C. neoformans and C. gattii.

Antifungal agents. All drug stock solutions were prepared at 10 mg/mL in 100% dimethyl sulfoxide (DMSO) and aliquots stored at −20° C.: AMB (VWR, Radnor, PA, USA), FLC (Alfa Aesar, Tewksbury, MA, USA or Sagent Pharmaceuticals, Schaumburg, IL), caspofungin (Sigma, St. Louis, MO, USA), Compound 2, 3-(3-(4-(benzyloxy)benzyl)isoxazol-5-yl)pyridin-2-amine 3-(3-(4-((6-fluoropyridin-2-yl) oxy)isoxazol-5-yl)pyridin-2-amine, 3-(3-((6-(benzyloxy) pyridin-3-yl)methyl)isoxazol-5-yl)pyridin-2-amine.

For pharmacokinetic and efficacy studies, the prodrugs Compound 1, (2 amino-3-(3-(4-((6-fluoropyridin-2-yl)oxy) benzyl)isoxazol-5-yl)pyridin-1-ium-1-yl)methyl hydrogen phosphate, (2-amino-3-(3-(4-(benzyloxy)benzyl)isoxazol-5-yl)pyridin-1-ium-1-yl)methyl hydrogen phosphate, (2-amino-3-(3-((6-(benzyloxy)pyridin-3-yl)methyl)isoxazol-5-yl)pyridin-1-ium-1-yl)methyl hydrogen phosphate were used. Compound 1, the N-phosphoooxymethyl prodrug, is soluble in water. On adding Compound 1 to water, the pH is less than 7.0. Sodium hydroxide was added to bring pH back to a neutral range, maintain solubility, and allow dosing of the formulated material. Prodrugs (2-amino-3-(3-(4-((6-fluoropyridin-2-yl)oxy)benzyl)isoxazol-5-yl)pyridin-1-ium-1-yl)methyl hydrogen phosphate, (2-amino-3-(3-(4-(benzyloxy)benzyl)isoxazol-5-yl)pyridin-1-ium-1-yl) methyl hydrogen phosphate and (2-amino-3-(3-((6-(benzyloxy)pyridin-3-yl)methyl)isoxazol-5-yl)pyridin-1-ium-1-yl)methyl hydrogen phosphate were formulated similarly to enable oral and IP dosing of compounds for pharmacokinetic and efficacy studies. Final prodrug solutions were 5% dextrose and dosed orally (PO) or IP on a per gram mouse body daily weight basis. A 10 mg/mL solution of ABT (Fisher Scientific, Hampton, NH) in water was administered orally 2 h prior to infection as 10 μL per gram mouse body weight resulting in a dose of 100 mg/kg.

Antifungal susceptibility testing. To establish antimicrobial activity, broth microdilution susceptibility testing was performed according to Clinical Laboratory Standards Institute (CLSI) guidelines M27-A3 for yeasts and M38-A2 for molds. Compound 2 and analogs were first diluted in DMSO to obtain intermediate dilutions. These were further diluted in microtiter plates to obtain a final concentration of 2 to 0.002 μg/mL. 1 μl of DMSO was added to "No drug" control wells. The solutions were mixed on a plate shaker for 10 mins and plates incubated at 35° C. for 40 to 48 h (C. albicans, A. fumigatus) and 72 h (C. neoformans). The minimum concentration that led to 50% reduction in fungal growth as compared to the control (with the aid of a reading mirror) was determined as the minimum inhibitory concentration (MIC) for C. albicans and C. neoformans. The minimum concentration that led to shortening of hyphae as compared to hyphal growth in DMSO control wells was determined as the minimum effective concentration (MEC) for A. fumigatus (as read for echinocandins). The use of the MIC and MEC endpoints for Compound 2 against yeasts and molds, respectively has been described previously. For the cryptococcal synergy studies, Compound 2 and 3-(3-(4-(benzyloxy)benzyl)isoxazol-5-yl)pyridin-2-amine MIC values were read at 50% inhibition.

Pharmacokinetic analysis. Single dose PK experiments were performed in healthy male CD-1 mice following IP or oral dosing of 26 mg/kg of the prodrugs Compound 1, (2-amino-3-(3-(4-((6-fluoropyridin-2-yl)oxy)benzyl)isoxazol-5-yl)pyridin-1-ium-1-yl)methyl hydrogen phosphate, (2-amino-3-(3-(4-(benzyloxy)benzyl)isoxazol-5-yl)pyridin-1-ium-1-yl)methyl hydrogen phosphate and (2-amino-3-(3-((6-(benzyloxy)pyridin-3-yl)methyl)isoxazol-5-yl)pyridin-1-ium-1-yl)methyl hydrogen phosphate. In half of the cohorts, mice received a single oral dose of 100 mg/kg ABT at 2 h prior to prodrug dosing. Plasma was collect at 0.083, 0.5, 2, 4, 8 and 24 h post-dose (n=3 per time point). UAC is the area under the curve, calculated from T=0 to the last measurable concentration. The active metabolite concentrations in plasma (Compound 2, 3-(3-(4-((6-fluoropyridin-2-yl)oxy)benzyl)isoxazol-5-yl)pyridin-2-amine, 3-(3-(4-(benzyloxy)benzyl)isoxazol-5-yl)pyridin-2-amine and 3-(3-((6-(benzyloxy)pryidin-3-yl)methyl)isoxazol-5-yl)pyridin-2-amine) were determined by LC-MS/MS. PK parameters were determined using Phoenix WinNonlin (v.7.0) and a non-compartmental model. Samples that were below the limit of quantification (0.5 or 1 ng/mL) were not used in the calculation of averages.

Cryptococcal meningitis model. *C. neoformans* strain H99 was grown in YPD broth at 30° C. on a shaker (220 rpm) for 24 h, centrifuged (1980 ref) and washed twice in PBS, resuspended in PBS, and quantified by hemacytometric count. CD-1 male mice were infected with ~$5 \times 10^4$ CFU per mouse via lateral tail vein injection of 100 μL. Mice were weighed, and treatment was within 1 h after infection. Treatments were administered daily for seven days. Mice were weighed daily and observed for acute and chronic adverse symptoms. Mice were sacrificed on day 8, and brain and left lung were homogenized and cultured for quantitative determination of tissue burden (CFU per gram of tissue). Tissues were homogenized for 25 seconds in 1 mL phosphate buffered saline suing two 6.5 mm steel beads and a Mini-Beadbeater 16 (Biospec Products, Inc., Bartlesville, OK), and serially diluted in 10-fold steps. Aliquots (100 μL) of homogenate were plated and incubated for 3 to 7 days at 37° C. Fungal burden data were $\log_{10}$ transformed and evaluated using Kruskal-Wallis tests with Dunn's Multiple Comparison Test for Post-hoc analysis (Prism 5: GraphPad Software, Inc., San Diego, CA). A P value of ≤0.05 is considered statistically significant.

Delayed treatment model. The delayed treatment model was similar to the cryptococcal meningitis model with the following exceptions: a) CD-1 male mice were infected with $5 \times 10^4$ CFU per mouse via lateral tail vein injection of 100 μL; b) treatment was initiated 24 h after infection and continued daily for seven days with 100 mg/kg ABT (PO) administered 2 h prior to each (2-amino-3-(3-(4-((6-fluoropyridin-2-yl)oxy)benzyl)isoxazol-5-yl)pyridin-1-ium-1-yl)methyl hydrogen phosphate dose; c) mice were sacrificed 24 h after the last dose, and brain and left lung were homogenized and cultured for quantitative determination of tissue burden (CFU per gram of tissue). Fungal burden data were $\log_{10}$ transformed and evaluated using Kruskal-Wallis tests with Dunn's Multiple Comparison Test for Post-hoc analysis (Prism 5; GraphPad Software, Inc., San Diego, CA). A P value of ≤0.05 is considered statistically significant.

Example II: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example III: Oral Solution To prepare a pharmaceutical composition for oral delivery, a sufficient amount of a compound described herein, or a pharmaceutically acceptable salt thereof, is added to water (with optional solubilizer(s), optional buffer(s) and taste making excipients) to provide a 20 mg/mL solution.

Example IV: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compound tablets is maintained at 100-500 mg.

Example V: Oral Capsule

To prepare a pharmaceutical composition for oral delivery, a 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example VI: Topical Gel Composition

To prepare a pharmaceutical topical gel composition, a compound described herein, or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example VII: Inhalation Composition

To prepare a pharmaceutical composition for inhalation delivery, a compound described herein, or a pharmaceutically acceptable salt thereof, is mixed with anhydrous citric acid and 0.9% sodium chloride solution. The mixture is incorporated into an inhalation delivery unit, such as a nebulizer, which is suitable for inhalation administration.

Example VIII: Ophthalmic Solution Composition

To prepare a pharmaceutical ophthalmic solution composition, a compound described herein, or a pharmaceutically acceptable salt thereof, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Biological Examples

Example IX: In Vitro Antifungal Assay

Measurement of antifungal activity: Antifungal activity of the compounds was evaluated in a microdilution broth assay as per Clinical and Laboratory Standard Instituted methodology for yeast (for Candida and Cryptococcus) (1) and molds (for Aspergillus and Rhizomucor) (2), Candida albicans 90028, Aspergillus fumigatus MYA3626, Rhizomucor pusillus 46342 and Crytococcus neoformans H99 strains were obtained from American Type Culture Collection (ATCC).

Preparation of Fungal Suspension: C. albicans 90028 and C. neoformans H99 strains were streaked from frozen stocks at −80° C. onto Sabouraud Dextrose Agar (SDA) plates. These were allowed to grow for 24 h (C. albicans) and 48 h (C. neoformans) at 35° C. before using them in the assay. 5-6 individual colonies were picked and diluted into sterile water to obtain a fungal suspension. The cell density of the suspension was determined and the culture diluted with RPMI1640 medium to obtain a fungal suspension of $2.5 \times 10^6$ cells/mL. The suspension was used in the MIC measurement as described below.

A. fumigatus and R. pusillus were spread onto Potato Dextrose Agar (PDA) plates spores from −80° C. frozen stocks and incubated for 3-6 days at 30° C. (A. fumigatus) and 35° C. (R. pusillus). Water containing 1% Tween was directly added to the agar plate and gently agitated to wet and remove the Aspergillus conidia. For R. pusillus, water as added to the surface and gently massaged to wet and remove the spores. For both species, the conidia or spores and mycelial fragments were collected, followed by removal of mycelium, conidiophores and large clumps of conidia/spores. The resulting spore suspension was counted and diluted into RPMI1640 medium to adjust to a final suspension of $1-2 \times 10^4$ spores/mL. The suspension was used in the MEC measurement as described below.

Preparation of Compound Stocks and Intermediate Dilutions: The compounds were weighed and DMSO was added to prepare a 10 mg/mL stock. The solutions were mixed by vortexing and sonication at 37° C. for 5-10 mins. The resulting solution were sterile filtered using a PTFE filter, and aliquoted (12 µL or as needed) and stored at −20° C. Intermediate compound dilutions were prepared in sterile polypropylene tubes in 100% DMSO. The compound stock solution was first diluted in DMSO to obtain a concentration of 1600 µg/mL. This was serially 2-fold diluted to obtain a dilution series from 1600 to 0.19 µg/mL.

MIC/MEC Measurement: 99 µL 1 of the fungal suspension in RPMI1640 prepared as above was added to each well of a 96-well round bottom assay plate. 1 µL of the intermediate compound dilutions (200-0.19 µg/mL) were added to wells of the plate. This led to a 100-fold dilution of the intermediate dilutions resulting in a final compound concentration of 2-0.0019 µg/mL in the plate. 1 µL of DMSO was added to "No drug" control wells. The solutions were mixed by shaking on a plate shaker for 10 mins and plates incubate at 35° C. for 40-48 h (C. albicans, A. fumigatus, R. pusillus) and 72 h (Cryptococcus). The minimum concentration that clearly inhibited fungal grown (≥50% inhibition) as compared to the control by visual inspection was determined as the minimum inhibitory concentration (MIC) for C. albicans and C. neoformans (as read for echinocandins). This was validated by thorough mixing and reading at 600 nm on a microplate reader. The minimum concentration that led to shortening of hyphae as compared to hyphal growth in DMSO control wells was determined as the minimum effective concentration (MEC) for A. fumigatus and R. pusillus (as read for echinocandins). The use of the MIC and MEC endpoints against yeasts and molds, respectively has been described by Pfaller M A, Duncanson F. Messer S A, Moet G J, Jones R N, Castanheira M. Antimicrob Agents Chemother. 2011. 55(11):5155-8. In vitro activity of a novel broad-spectrum antifungal, E1210, tested against Aspergillus spp. determined by CLSI and EUCAST broth microdilution methods. Results are shown in Table 2, and the letters indicate the following ranges in µg/mL:

A: MEC or MIC≤0.010; B: 0.010<MEC or MIC≤0.10; C: 0.10<MEC or MIC≤1.0; D: MEC or MIC>1.0; NT: Not tested

TABLE 2

| Ex. | Aspergillus fumigatus MEC | Candida albicans MIC | Rhizomucor pusillus MEC | Cryptococcus neoformans MIC | Cryptococcus gattii MIC |
| --- | --- | --- | --- | --- | --- |
| B | C | D | D | NT | NT |
| C | C | D | D | NT | NT |
| E | D | D | D | NT | NT |
| 1 | C | B | D | C | B |
| 2 | C | D | D | D | NT |
| 3 | C | C | D | NT | NT |
| 4 | B | C | C | C | C |
| 5 | C | C | C | C | C |
| 6 | D | D | D | NT | NT |
| 7 | C | C | D | NT | NT |
| 8 | C | C | C | B | A |
| 9 | C | B | C | C | B |
| 10 | C | C | D | C | C |
| 11 | B | C | D | C | C |
| 12 | B | C | D | C | C |
| 13 | C | C | D | NT | NT |
| 14 | B | C | C | C | C |
| 15 | A | B | C | B | B |
| 16 | C | C | C | NT | NT |
| 17 | B | B | C | B | B |
| 18 | B | B | C | C | C |
| 19 | B | B | C | B | B |
| 20 | B | C | C | B | B |
| 21 | C | C | D | NT | NT |
| 22 | C | C | D | C | B |
| 23 | C | C | C | C | B |
| 24 | D | D | D | NT | NT |
| 25 | D | D | D | NT | NT |
| 26 | B | C | D | C | C |
| 27 | D | C | D | C | C |
| 28 | C | C | D | C | C |
| 29 | C | C | D | NT | NT |
| 30 | D | C | C | D | D |
| 31 | B | B | C | C | C |
| 32 | B | B | C | C | C |
| 33 | D | D | D | NT | NT |
| 34 | C | B | C | D | C |
| 35 | B | B | D | B | B |
| 36 | B | B | D | B | B |
| 37 | B | B | D | A | A |
| 38 | B | C | C | A | C |
| 39 | C | C | D | C | C |
| 40 | B | C | C | B | B |
| 41 | B | B | C | B | B |
| 42 | B | B | C | B | B |
| 43 | B | C | C | B | B |
| 44 | D | C | D | NT | NT |
| 45 | C | C | D | NT | NT |
| 46 | C | C | D | C | C |
| 47 | C | B | C | C | C |
| 48 | B | B | C | B | B |
| 49 | D | D | D | NT | NT |
| 50 | C | C | D | C | C |

TABLE 2-continued

| Ex. | Aspergillus fumigatus MEC | Candida albicans MIC | Rhizomucor pusillus MEC | Cryptococcus neoformans MIC | Cryptococcus gattii MIC |
|---|---|---|---|---|---|
| 51 | B | C | C | C | C |
| 52 | C | C | D | NT | NT |
| 53 | C | C | C | C | C |
| 54 | B | B | D | B | A |
| 55 | C | C | D | C | C |
| 56 | C | C | D | NT | NT |
| 57 | B | B | C | B | A |
| 58 | C | B | C | C | B |
| 59 | C | C | D | NT | NT |
| 60 | C | B | D | B | B |
| 61 | B | B | D | C | B |
| 62 | B | C | D | D | D |
| 63 | NT | C | D | NT | NT |
| 64 | NT | C | D | NT | NT |
| 65 | B | C | D | C | C |
| 66 | C | C | D | NT | NT |
| 67 | C | C | D | NT | NT |
| 68 | C | C | D | NT | NT |
| 69 | B | B | C | B | B |
| 70 | B | C | D | C | C |
| 71 | D | D | D | NT | NT |
| 72 | C | B | C | B | C |
| 73 | C | B | D | D | D |
| 74 | C | B | D | B | B |
| 75 | B | B | C | B | C |
| 76 | C | D | C | NT | NT |
| 77 | C | B | C | B | B |
| 78 | C | B | C | B | B |
| 79 | C | B | C | B | C |
| 80 | A | A | C | B | B |
| 81 | B | B | C | A | B |
| 82 | B | C | D | B | B |
| 83 | B | B | D | A | B |
| 84 | B | B | C | B | C |
| 85 | B | B | C | NT | NT |
| 86 | B | B | D | NT | NT |
| 87 | B | C | D | NT | NT |
| 88 | C | C | D | NT | NT |
| 89 | D | D | D | NT | NT |
| 90 | D | C | D | NT | NT |
| 91 | NT | NT | D | NT | NT |
| 92 | NT | NT | C | NT | NT |
| 93 | D | D | D | NT | NT |
| 94 | D | D | D | NT | NT |
| 95 | D | D | D | NT | NT |
| 96 | D | D | D | NT | NT |
| 97 | C | D | D | NT | NT |
| 98 | C | C | D | NT | NT |
| 99 | C | D | D | C | C |
| 100 | C | C | D | C | C |
| 101 | C | C | D | B | B |
| 102 | D | D | D | NT | NT |
| 103 | C | C | D | NT | NT |
| 104 | D | D | D | D | NT |
| 105 | C | B | D | C | B |
| 106 | B | B | C | C | B |
| 107 | B | B | B | B | B |
| 108 | B | B | C | C | C |
| 109 | D | D | D | NT | NT |
| 110 | B | B | C | B | A |
| 111 | B | B | C | A | A |
| 112 | B | C | C | B | B |
| 113 | C | D | D | NT | NT |
| 114 | B | C | D | C | C |
| 115 | B | C | D | C | C |
| 116 | B | D | D | NT | NT |
| 117 | B | C | D | B | A |
| 118 | C | C | D | C | C |
| 119 | D | D | D | NT | NT |
| 120 | A | B | C | B | B |
| 121 | A | B | B | B | B |
| 122 | A | A | B | B | B |
| 123 | B | B | D | C | B |
| 124 | B | B | B | B | B |
| 125 | C | C | D | D | D |
| 126 | D | D | D | NT | NT |
| 127 | A | B | C | B | B |
| 128 | C | D | D | NT | NT |
| 129 | D | D | D | NT | NT |
| 130 | B | B | C | A | B |
| 131 | B | B | C | B | B |
| 132 | A | B | C | B | B |
| 133 | C | C | C | NT | NT |
| 134 | C | C | C | B | B |
| 135 | B | C | C | B | C |
| 136 | B | C | B | C | C |
| 137 | B | B | D | C | B |
| 138 | B | B | C | B | A |
| 139 | C | B | D | B | A |
| 140 | B | A | C | B | B |
| 141 | B | B | C | B | B |
| 142 | A | B | C | B | B |
| 143 | B | C | C | B | A |
| 144 | B | B | C | B | B |
| 145 | D | D | D | NT | NT |
| 146 | D | C | D | C | C |
| 147 | D | D | D | NT | NT |
| 148 | B | B | C | B | B |
| 149 | B | B | D | B | C |
| 150 | C | C | D | C | C |
| 151 | C | C | C | NT | NT |
| 152 | B | B | D | NT | NT |
| 153 | B | C | D | NT | NT |
| 154 | B | B | C | B | B |
| 155 | D | D | D | NT | NT |
| 156 | D | C | D | C | D |
| 157 | C | D | C | C | C |
| 158 | C | C | D | NT | NT |
| 159 | C | C | D | NT | NT |
| 160 | B | C | C | C | C |
| 161 | B | B | C | B | B |
| 162 | C | B | D | NT | NT |
| 163 | C | D | C | NT | NT |
| 164 | C | C | D | NT | NT |
| 165 | B | C | C | B | B |
| 166 | B | C | C | NT | NT |
| 167 | B | C | C | NT | NT |
| 168 | B | B | C | C | B |
| 169 | B | B | C | B | B |
| 170 | C | C | C | NT | NT |
| 171 | C | B | C | NT | NT |
| 172 | NT | NT | NT | NT | NT |
| 173 | NT | NT | NT | NT | NT |
| 174 | NT | NT | NT | NT | NT |
| 175 | NT | NT | NT | NT | NT |
| 176 | NT | NT | NT | NT | NT |
| 177 | NT | NT | NT | NT | NT |
| 178 | NT | NT | NT | NT | NT |
| 179 | NT | NT | NT | NT | NT |
| 180 | NT | NT | NT | NT | NT |
| 181 | NT | NT | NT | NT | NT |
| 182 | NT | NT | NT | NT | NT |
| 183 | NT | NT | NT | NT | NT |
| 184 | NT | NT | NT | NT | NT |
| 185 | C | C | C | B | B |
| 186 | B | B | D | C | B |
| 187 | C | C | C | C | B |
| 188 | B | D | C | D | D |
| 189 | B | B | D | B | C |
| 190 | C | C | D | C | C |
| 191 | B | C | C | C | C |
| 192 | C | C | D | NT | NT |
| 193 | C | C | C | C | C |
| 194 | C | D | D | NT | NT |
| 195 | C | C | D | B | B |
| 196 | C | B | C | B | C |
| 197 | NT | NT | NT | NT | NT |
| 198 | D | C | C | C | D |
| 199 | D | D | D | D | D |
| 200 | D | D | D | D | D |
| 201 | C | C | D | C | D |
| 202 | D | D | D | D | D |

TABLE 2-continued

| Ex. | Aspergillus fumigatus MEC | Candida albicans MIC | Rhizomucor pusillus MEC | Cryptococcus neoformans MIC | Cryptococcus gattii MIC |
|---|---|---|---|---|---|
| 203 | D | D | D | C | C |
| 204 | D | D | D | D | D |
| 205 | D | C | C | C | D |
| 206 | D | D | D | D | D |
| 207 | B | C | D | B | C |
| 208 | B | B | C | B | B |
| 209 | D | D | D | D | D |
| 210 | D | D | D | NT | NT |
| 211 | D | D | D | NT | NT |
| 212 | C | C | C | B | B |
| 213 | C | C | D | C | C |
| 214 | D | D | D | NT | NT |
| 215 | D | D | D | NT | NT |
| 216 | C | C | D | C | C |
| 217 | D | D | NT | D | D |
| 218 | C | C | D | D | D |
| 219 | C | D | NT | D | D |
| 220 | C | C | C | C | C |
| 221 | B | C | C | B | C |
| 222 | B | B | D | B | C |
| 223 | B | B | D | C | C |
| 224 | D | D | D | D | D |
| 225 | B | C | C | C | C |
| 226 | B | B | D | B | C |
| 227 | D | D | D | NT | NT |
| 228 | D | D | D | NT | NT |
| 229 | D | D | D | NT | NT |
| 230 | C | C | D | NT | NT |
| 231 | B | C | C | B | B |
| 232 | D | D | NT | NT | NT |
| 233 | C | D | NT | D | D |
| 234 | B | B | C | A | A |
| 235 | B | B | C | C | C |
| 236 | C | C | C | C | C |
| 237 | C | B | D | B | B |
| 238 | D | D | NT | C | C |
| 239 | C | C | C | B | B |
| 240 | C | C | C | B | B |
| 241 | B | C | C | B | B |
| 242 | B | B | C | B | A |
| 243 | C | C | D | C | C |
| 214 | C | C | D | C | C |
| 245 | C | C | D | C | C |
| 246 | B | C | C | B | C |
| 247 | B | B | NT | C | D |
| 248 | C | D | NT | D | D |
| 249 | B | C | NT | C | D |
| 250 | B | B | C | B | C |
| 251 | B | C | NT | C | C |
| 252 | C | C | NT | C | C |
| 253 | C | C | D | C | C |
| 254 | B | B | NT | C | D |
| 255 | B | B | NT | C | D |
| 256 | C | C | NT | C | D |
| 257 | B | B | C | C | D |
| 258 | B | C | C | B | C |
| 259 | B | D | NT | C | D |
| 260 | C | C | NT | C | D |
| 261 | C | C | C | C | C |

Example X: Systemic Candidal Infection Model in Mice

Preparation of Fungal Inoculant

*C. albicans* is subcultured in brain heart infusion broth and grown at 37° C. overnight. Cells are collected by centrifugation and washed three times with sterilized physiological saline and counted with a hemocytometer. The suspension is adjusted to $2 \times 10^7$ cells/mL with sterilized physiological saline to serve as the fungal inoculum.

Infection 8-week-old BALB/c mice weighing ~20 g are rendered neutropenic by receiving 150 mg/kg and 100 mg/kg of cyclophosphamide via IP injection on day −4 and day −1 prior to infection, respectively. The fungal inoculum is used in the amounts of 0.2 mL ($4 \times 10^4$ cells/mouse).

Treatment

From 0.5 to 1 hour after fungal inoculation, 0.2 mL of agent solution containing a compound described herein (dissolved or suspended in sterilized physiological saline containing 6.5% dimethyl sulfoxide and 3.5% Tween 80 or another appropriate vehicle) is administered into orally using a peroral probe, 3 times every 4 hours. The agent concentration ranges from 1 mg/kg to 500 mg/kg, and the number of animals in one group ranges from 5 to 10 animals.

Determination of Effects

Animals are sacrificed after 48 hrs and organs such as kidney and brain are harvested. Colony forming units/gram of tissue are determined in order to assess the protective effect of a compound vs a no drug (vehicle) control Example XI: Murine Model of Cryptococcal Meningitis Preparation of Fungal Inoculant

*Cryptococcus neoformans* strain H99 was grown in YPD broth at 30° C. on a shaker (220 rpm) for 24 hours, centrifuged (1980 ref) and washed twice in PBS, resuspended in PBS, and quantified by hemacytometric, count.

Infection and Treatment

CD-1 male mice are infected with ~$6 \times 10^4$ colony forming units (CFU) per mouse via lateral tail vein injection of 100 μL. Compounds are administered by oral, intraperitoneal or intravenous routes from 1 to 3 times daily. Treatments were given for seven days.

Determination of Effects

Mice are sacrificed on day 8, and brain and left lung are homogenized and cultured for quantitative determination of tissue burden (CFU per gram of tissue). Colony forming units/gram of tissue are determined in order to assess the protective effect of a compound vs a no drug (vehicle) control.

Example XII: Clinical Trial of a Compound Described herein in Patients with a Fungal Infection The purpose of this study is to investigate whether a compound described herein can treat patients with fungal infections. Another purpose of this study is to assess the safety, tolerability, pharmacokinetics, bioavailability and food effect of single doses of a compound described herein administered intravenously and orally, followed by an evaluation of the safety, tolerability, pharmacokinetics and drug-drug interaction potential of multiple doses of a compound described herein administered orally.

Study Type:
Interventional
Study Design:
　Allocation: Randomized
　Interventional Model: Crossover Assignment
　Masking: Double (Participant Investigator)
　Primary Purpose: Treatment
Primary Outcome Measures:
　Safety and tolerability of single and multiple oral doses of whether a compound described herein as measured by adverse events (AEs), physical examinations (PE), vital signs (VS), laboratory safety tests, urinalysis and 12-lead electrocardiograms (ECG). Time Frame: 21 days Secondary Outcome Measures
  Pharmacokinetics of single and multiple doses of a compound described herein as measured by maximum observed concentration (Cmax). Time Frame: 21 days
  Pharmacokinetics of single and multiple dose of a compound described herein as measured by area under the curve (AUC). Time Frame: 21 days
  Pharmacokinetics of single and multiple dose of a compound described herein as measured by terminal half life (t½). Time Frame: 21 days
  Pharmacokinetics of single and multiple dose of a compound described herein as measured by volume of distribution (Vd). Time Frame: 21 days
  Pharmacokinetics of single and multiple dose of a compound described herein as measured by elimination rate constant (Kel). Time Frame: 21 days
  Pharmacokinetics of single and multiple dose of a compound described herein as measured by accumulation ratio. Time Frame: 21 days
Eligibility:
Ages Eligible for Study: 18 Years to 55 Years (Adult)
Sexes Eligible for Study: All
Accepts Healthy Volunteers: Yes
Inclusion Criteria:
  Women of childbearing potential must agree to avoid pregnancy during the study and to use contraception at least 2 weeks before the start of the study until 3 months after the last dose of study drug.
  Males with partner(s) of childbearing potential must agree to use appropriate barrier contraception from the screening period until 3 months after the last dose of study drug.
  Screening hematology, clinical chemistry, coagulation and urinalysis consistent with overall good health.
  No significantly abnormal findings on physical examination, ECG and vital signs.
  Willing and able to provide written informed consent.
Exclusion Criteria:
  Any uncontrolled or active major system disease including, but not limited to: cardiovascular, pulmonary, gastrointestinal, metabolic, urogenital, neurological, immunological, psychiatric, or neoplastic disorder with metastatic potential.
  History or presence of malignancy within the past year. Subjects who have been successfully treated with no recurrence of basal cell carcinoma of the skin or carcinoma in-situ of the cervix may be enrolled.
  Use of prescription medication within 14 days prior to the first dose of study drug and throughout the study.
  use of non-prescription or over-the-counter medications within 7 days prior to the first dose of study drug and throughout the study.
Although the invention has been described with reference to the above example, it will be understood that modifications and variations are encompassed within the spirit and scope of the invention. Accordingly, the invention is limited only by the following claims.

What is claimed is:

1. A compound

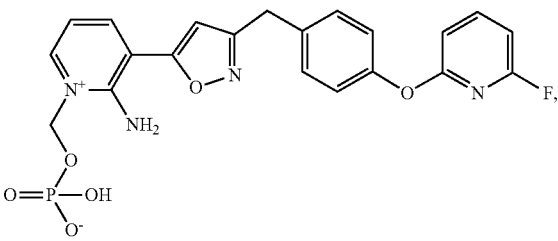 [SMILES: Nc1c(-c2cc(Cc3ccc(Oc4cccc(F)n4)cc3)no2)ccc[n+]1COP(=O)([O-])O]

or a pharmaceutically acceptable salt, solvate, hydrate, tautomer, stereoisomer, mixture of stereoisomers, or isotopic variant thereof.

2. A compound

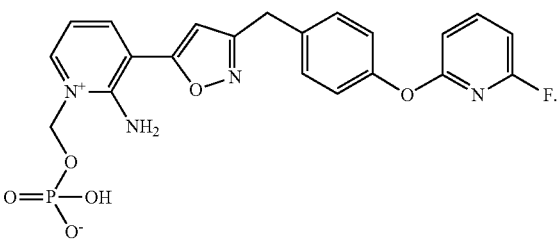 [SMILES: Nc1c(-c2cc(Cc3ccc(Oc4cccc(F)n4)cc3)no2)ccc[n+]1COP(=O)([O-])O]

3. A pharmaceutical composition, comprising:
  the compound of claim 1 or a pharmaceutically acceptable salt, solvate, hydrate, tautomer, stereoisomer, mixture of stereoisomers, or isotopic variant thereof; and
  at least one pharmaceutically acceptable excipient.

4. A pharmaceutical composition, comprising:
  the compound of claim 2; and
  at least one pharmaceutically acceptable excipient.

5. A method of treating a fungal disease in a subject in need thereof, the method comprising:
  administering to the subject a therapeutically effective amount of the compound of claim 1 or a pharmaceutically acceptable salt, solvate, hydrate, tautomer, stereoisomer, mixture of stereoisomers, or isotopic variant thereof.

6. A method of treating a fungal disease in a subject in need thereof, the method comprising:
  administering to the subject a therapeutically effective amount of the compound of claim 2.

7. A method of treating a fungal disease in a subject in need thereof, the method comprising:
  administering to the subject a therapeutically effective amount of the pharmaceutical composition of claim 3.

8. A method of treating a fungal disease in a subject in need thereof, the method comprising:
  administering to the subject a therapeutically effective amount of the pharmaceutical composition of claim 4.

* * * * *